US011584734B2

United States Patent
Yu et al.

(10) Patent No.: US 11,584,734 B2
(45) Date of Patent: *Feb. 21, 2023

(54) TRICYCLIC COMPOUNDS AS HISTONE METHYLTRANSFERASE INHIBITORS

(71) Applicant: GLOBAL BLOOD THERAPEUTICS, INC., South San Francisco, CA (US)

(72) Inventors: Ming Yu, Foster City, CA (US); Zhe Li, San Diego, CA (US); Qing Xu, Foster City, CA (US); Calvin Yee, Daly City, CA (US); Lina Setti, Fremont, CA (US); Hing Sham, Palo Alto, CA (US)

(73) Assignee: Global Blood Therapeutics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/639,047

(22) PCT Filed: Aug. 13, 2018

(86) PCT No.: PCT/US2018/046554
§ 371 (c)(1),
(2) Date: Feb. 13, 2020

(87) PCT Pub. No.: WO2019/036384
PCT Pub. Date: Feb. 21, 2019

(65) Prior Publication Data
US 2020/0361896 A1    Nov. 19, 2020

Related U.S. Application Data

(60) Provisional application No. 62/545,935, filed on Aug. 15, 2017.

(51) Int. Cl.
| C07D 401/12 | (2006.01) |
| C07D 221/06 | (2006.01) |
| C07D 221/22 | (2006.01) |
| C07D 401/14 | (2006.01) |
| C07D 471/04 | (2006.01) |

(52) U.S. Cl.
CPC ......... C07D 401/12 (2013.01); C07D 221/06 (2013.01); C07D 221/22 (2013.01); C07D 401/14 (2013.01); C07D 471/04 (2013.01)

(58) Field of Classification Search
CPC .. C07D 401/12; C07D 401/14; C07D 221/06; C07D 221/22; C07D 471/04
See application file for complete search history.

(56) References Cited

U.S. PATENT DOCUMENTS

| 4,107,288 A | 8/1978 | Oppenheim et al. |
| 5,145,684 A | 9/1992 | Liversidge et al. |
| 11,254,651 B2 * | 2/2022 | Yu .................. C07D 401/14 |
| 2015/0274660 A1 | 10/2015 | Pliushchev et al. |
| 2019/0047981 A1 * | 2/2019 | Yu .................. A61P 7/00 |

FOREIGN PATENT DOCUMENTS

| WO | WO 2015/085229 A1 | 6/2015 |
| WO | WO 2015/192981 A1 | 12/2015 |
| WO | WO 2017/102677 A1 | 6/2017 |
| WO | WO 2017/142947 A1 | 8/2017 |
| WO | WO 2019/036377 A1 | 2/2019 |

OTHER PUBLICATIONS

Hargarten, Frontiers in Immunology, Aug. 2018, vol. 9, article 1864, 1-10. (Year: 2018).*
Cao, E J Med CHem, vol. 179, 537-546, 2019. (Year: 2019).*
Agarwal et al., "G9a inhibition potentiates the anti-tumour activity of DNA double-strand break inducing agents by impairing DNA repair independent of p53 status," Cancer Letters, 280:467-475, (2016).
Antignano et al., "Methyltransferase G9A regulates T cell differentiation during murine intestinal inflammation," J. Clin. Invest., 124(5):1945-1955, (2014).
Casciello et al., "Functional role of G9a histone methyltransferase in cancer," Front. Immunol., 6:Article 487, 1-12, (2015).
Charache et al., "Hydroxyurea: Effects on Hemoglobin F Production in Patients With Sickle Cell Anemia," Blood, 79(10):2555-2265, (1992).
Galli et al., "Sodium-dependent Norepinephrine-Induced Currents in Norepinephrine-Transporter-Transfected HEK-293 Cells Blocked by Cocaine and Antidepressants," J. Exp. Biol., 198(Pt 10):2197-2212, (1995).
Gao et al., "Synthesis and biological evaluation of benzimidazole acridine derivatives as potential DNA binding and apoptosis inducing agents," Bioorganic and Medicinal Chemistry, 23(8):1800-1807, (2015).

(Continued)

*Primary Examiner* — D Margaret M Seaman
(74) *Attorney, Agent, or Firm* — Alston & Bird LLP

(57) ABSTRACT

The present disclosure provides tricyclic compounds of formula (I) that are histone methyltransferases G9a and/or GLP inhibitors and are therefore useful for the treatment of diseases treatable by inhibition of G9a and/or GLP such as cancers and hemoglobinopathies (e.g., beta-thalassemia and sickle cell disease). Also provided are pharmaceutical compositions containing such compounds and processes for preparing such compounds.

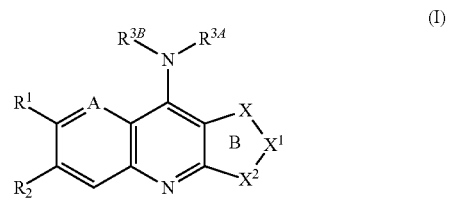

45 Claims, No Drawings

(56) References Cited

OTHER PUBLICATIONS

Imai et al., "Involvement of Histone H3 Lysine 9 (H3K9) Methyltransferase G9a in the Maintenance of HIV-1 Latency and Its Reactivation by BIX01294," J. Biol. Chem., 285(22):16538-16545, (2010).
Konshin et al., "2,3-Polymethylenequinolines," Chemistry of Heterocyclic Compounds, 9(4):490-492, (1973).
Korabecny et al., "Comparison of Novel Tacrine and 7-MEOTA Derivatives with Aromatic and Alicyclic Residues: Synthesis, Biological Evaluation and Docking Studies," Letters in Organic Chemistry, 10(4):291-297, (2013).
Krivega et al., "Inhibition of G9a methyltransferase stimulates fetal hemoglobin production by facilitating LCR/γ-globin looping," Blood, 126(5):665-672, (2015).
Ling et al., "Lysine methyltransferase G9a methylates the transcription factor MyoD and regulates skeletal muscle differentiation," Proc. Natl. Acad. Sci. USA, 109(3):841-846, (2012).
Liu et al., "Discovery of a 2,4-Diamino-7-aminoalkoxyquinazoline as a Potent and Selective Inhibitor of Histone Lysine Methyltransferase G9," J. Med. Chem., 52(24):7950-7953, (2009).
Liu et al., "Discovery of an in Vivo Chemical Probe of the Lysine Methyltransferases G9a and GLP," J. Med. Chem., 56(21):8931-8942, (2013).
Liu et al., "Optimization of Cellular Activity of G9a Inhibitors 7-Aminoalkoxy-quinazolines," J. Med. Chem., 54(17):6139-6150, (2011).
Liu et al., "Protein Lysine Methyltransferase G9a Inhibitors: Design, Synthesis, and Structure Activity Relationships of 2,4-Diamino-7-aminoalkoxy-quinazolines," J. Med. Chem., 53(15):5844-5857, (2010).
Merkling et al., "The Epigenetic Regulator G9a Mediates Tolerance to RNA Virus Infection in *Drosophila*," PLoS Pathog., 11(4):e1004692, 25 pages, (2015).
Michel et al., "Identification of a Single Alpha 1-adrenoceptor Corresponding to the Alpha 1A-subtype in Rat Submaxillary Gland," Br. J. Pharmacol., 98(3):883-889, (1989).
Nguyen et al., "Functionalized acridin-9-yl phenylamines protected neuronal HT22 cells from glutamate-induced cell death by reducing intracellular levels of free radical species," Bioorganic and Medicinal Chemistry Letters, 24(15):1830-1838, (2014).
Nickel et al., "Antimalarial 6-aminoquinolines. XI. Some 2-, 3-, and 4-alkyl-, aryl-, and arylalkyl derivatives (Abstract)," Arzneimittel-Forschung, 28(5):723-731, (1978).
Pitt et al., "Heteroaromatic Rings of the Future," J. Med. Chem., 52(9):2952-2963, (2009).
Pozharskii et al., Heterocycles in Life and Society Wiley, pp. 1-6, (1997).
PubChem SID 540857, Substance Record No. 5438-91-5, Aipha-[(dipropylamino)methyl]-5,6,7,8-tetrahydro-3-Acridinemethanol, Hydrochloride, Deposit Date: Mar. 26, 2005.
Renneville et al., "EHMT1 and EHMT2 inhibition induces fetal hemoglobin expression," Blood, 126(16):1930-1939, (2015).
San José-Enériz et al., "Discovery of first-in-class reversible dual small molecule inhibitors against G9a and DNMTs in hematological malignancies," Nature Communications, 8:15424, 60 pages, (2017).
Sankaran et al., "The Switch from Fetal to Adult Hemoglobin," Cold Spring Harb. Perspect. Med., 3(1):a011643, 14 pages, (2013).
Saucier et al., "Identification of an Endogenous 5-hydroxytryptamine2A Receptor in NIH-3T3 Cells: Agonist-Induced Down-Regulation Involves Decreases in Receptor RNA and Number," J. Neurochem., 68(5):1998-2011, (1997).
Shankar et al., "G9a, a multipotent regulator of gene expression," Epigenetics, 8(1):16-22, (2013).
Shinkai et al., "H3K9 methyltransferase G9a and the related molecule GLP," Genes Dev., 25(8):781-788, (2011).
Skripkina, "Methoxy derivatives of 7-sulfodimethylamidoacridine (Abstract)," Khimiya Geterotsiklicheskikh Soedinenii, 7(1):115-117, (1971).
Sondhi et al., "Synthesis, anti-inflammatory, and anticancer activity evaluation of some novel acridine derivatives," European Journal of Medicinal Chemistry, 45(2):555-563, (2009).
STN-Chemical Database Registry No. 5438-91-5, entry for alpha-[(dipropylamino)methyl]-5,6,7,8-tetrahydro-3-Acridinemethanol, Hydrochloride, Entered STN: Nov. 16, 1984.
Sweis et al., "Discovery and Development of Potent and Selective Inhibitors of Histone Methyltransferase G9a," ACS Med. Chem. Lett., 5(2):205-209, (2014).
Vedadi et al., "A chemical probe selectively inhibits G9a and GLP methyltransferase activity in cells," Nature Chemical Biology, 7(8):566-574, (2011).
Wang et al., "Histone H3K9 methyltransferase G9a represses PPARγ expression and adipogenesis," EMBO J., 32(1):45-59, (2013).
Wang et al., "Human Mu Opiate Receptor. cDNA and Genomic Clones, Pharmacologic Characterization and Chromosomal Assignment," FEBS Lett., 338(2):217-222, (1994).
Wang et al., "Synthesis of Improved Lysomotropic Autophagy Inhibitors," Journal of Medicinal Chemistry, 58(7):3025-3035, (2015).
Yang et al., "G9a coordinates with the RPA complex to promote DNA damage repair and cell survival," Proc. Natl. Acad. Sci. USA, 2017:1700694114, 10 pages, (2017).
You et al., "Cancer Genetics and Epigenetics: Two Sides of the Same Coin?," Cancer Cell., 22(1):9-20, (2012).
Zhang et al., "Down-regulation of G9a triggers DNA damage response and inhibits colorectal cancer cells proliferation," Oncotarget, 6(5):2917-2927, (2015).
Zhang et al., "Synthesis and biological evaluation of benzimidazole derivatives as the G9a Histone Methyltransferase inhibitors that induce autophagy and apoptosis of breast cancer cells," Bioorganic Chemistry, 72:168-181, (2017).
WIPO Application No. PCT/US2018/046541, PCT International Search Report and Written Opinion of the International Searching Authority dated Nov. 26, 2018.
WIPO Application No. PCT/US2018/046554, PCT International Search Report and Written Opinion of the International Searching Authority dated Nov. 23, 2018.
Petrow, V., "Some amino-derivatives of dihydro-β-quinindene and tetrahydroacridine," Journal of the Chemical Society (resumed), 634-637, (1947).
Indian Application No. 202017010779, Examination report dated Oct. 13, 2021.
Robin et al., "Spectral Assignments and Reference Data," Magnetic Resonance in Chemistry, 39:225-228, (2001).
Sanchez et al., "Synthesis and biological evaluation of modified acridines: the effect of N- and O-substitutent in the nitrogenated ring on antitumor activity," European Journal of Medicinal Chemistry, 41:340-352, (2006).
European Application No. 18762967.0, Article 94(3) Communication dated Nov. 8, 2021.

* cited by examiner

TRICYCLIC COMPOUNDS AS HISTONE METHYLTRANSFERASE INHIBITORS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Application No. 62/545,935, filed Aug. 15, 2017, and International Application No. PCT/US2018/046554 filed Aug. 13, 2018.

FIELD OF THE DISCLOSURE

The present disclosure provides certain tricyclic compounds that are histone methyltransferases G9a and/or GLP inhibitors, and are therefore useful for the treatment of diseases treatable by inhibition of G9a and/or GLP such as cancers and hemoglobinopathies (e.g., beta-thalassemia and sickle cell disease). Also provided are pharmaceutical compositions containing such compounds and processes for preparing such compounds.

BACKGROUND

Chromatin modification plays an essential role in transcriptional regulation. These modifications, including DNA methylation, histone acetylation and histone methylation, are important in a variety of biological processes including protein production and cellular differentiation, and are emerging as attractive drug targets in various human diseases. Two particular enzymes associated with histone methylation are G9a and GLP, also known as EHMT2 and EHMT1 (Euchromatic histone-lysine N-methyltransferase 2 and 1). G9a and GLP are the primary enzymes for mono- and dimethylation at Lys 9 of histone H3 (H3K9me1 and H3K9me2), and exist predominantly as a G9a-GLP heteromeric complex that appears to be a functional H3K9 methyltransferase in vivo. Structurally, either G9a or GLP is composed of a catalytic SET domain, a domain containing ankyrin repeats (involved in protein—protein interactions) and nuclear localization signals on the N-terminal region. The SET domain is responsible for the addition of methyl groups on H3, whereas the ankyrin repeats have been observed to represent mono- and dimethyl lysine binding regions. The G9a-GLP complex is thus not only able to both methylate histone tails but also able to recognize this modification, and can function as a scaffold for the recruitment of other target molecules on the chromatin. See Shinkai et al., *Genes Dev.* 2011; 25(8):781-8 and Shankar et al., *Epigenetics.* 2013; 8(1):16-22.

Many studies have reported that G9a and GLP play critical roles in various biological processes. Several reports have highlighted its link to a variety of cancers. See Cascielle et al., *Front Immunol.* 2015; 6:487. It is upregulated in hepatocellular carcinoma, B cell acute lymphoblastic leukemia and lung cancers. In addition, elevated expression of G9a in aggressive lung cancer correlates with poor prognosis, while its knockdown in highly invasive lung cancer cells suppressed metastasis in an in vivo mouse model. In prostate cancer cells (PC3), G9a knockdown caused significant morphological changes and inhibition of cell growth. See Liu et al., *J. Med. Chem.* 2013; 56(21):8931-42 and Sweis et al., *ACS Med. Chem. Lett.* 2014; 5(2):205-9. Loss of G9a has been demonstrated to impair DNA damage repair and enhance the sensitivity of cancer cells to radiation and chemotherapeutics. See Yang et al., *Proc. Natl. Acad. Sci. USA,* 2017, doi: 10.1073/pnas.1700694114.

Interestingly, recent studies have also shown that the inhibition of G9a and GLP by either genetic depletion or pharmacological intervention increased fetal hemoglobin (HbF) gene expression in erythroid cells. See Krivega et al., *Blood,* 2015; 126(5):665-72 and Renneville et al., *Blood,* 2015; 126(16):1930-9. Inducing fetal globin gene would be potentially therapeutically beneficial for the disease of hemoglobinopathies, including beta-thalassemia and sickle cell disease where the production of normal β-globin, a component of adult hemoglobin, is impaired. Similarly, induction of HbF would potentially be beneficial by diluting the concentration of hemoglobin S (HbS) molecules, thereby reducing polymerization of HbS. See Sankaran et al., *Cold Spring Harb. Perspect. Med.* 2013; 3(1):a011643. Moreover, G9a or GLP inhibitions may potentiate other clinically used therapies, such as hydroxyurea or HDAC inhibitors. These agents may act, at least in part, by increasing γ-globin gene expression through different mechanisms. See Charache et al., *Blood,* 1992; 79(10):2555-65. Thus, there is a need for the development of small molecules that are capable of inhibiting the activity of G9a and/or GLP.

SUMMARY

Compounds have now been developed that inhibit G9a and/or GLP. Some disclosed compounds may exhibit less off-target binding (such as reduced binding to G-protein coupled receptors), thus reducing off-target effects.

In one aspect provided is a compound of Formula (I):

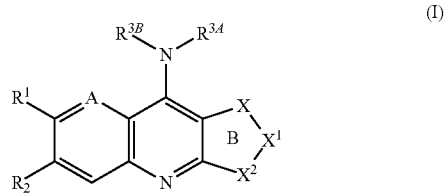

or a pharmaceutically acceptable salt thereof, wherein:

A can be CH or N;

$R^1$ can be hydroxy, alkoxy or haloalkoxy;

$R^2$ can be —$(CH_2)_{0-1}$—O-Alk-$R^{2A}$ or cycloalkoxy (optionally substituted with heterocyclylalkyl);

Alk can be an alkylene wherein one, two or three carbon atoms of the alkylene chain can be optionally and independently replaced by $NR_A$ or O, (where $R_A$ is hydrogen or alkyl) and the alkylene chain can be optionally substituted with one or two substituents independently selected from hydroxy, alkoxy, halogen and heterocyclylalkyl;

$R^{2A}$ can be (a) heterocyclyl, optionally substituted with one or more $R_B$, independently selected from hydroxy, alkyl, alkoxy, halogen, cyano, heterocyclylalkyl, haloalkyl and haloalkoxy, (b) spiroheterocycloamino, optionally substituted with one or more $R_C$, wherein $R_C$ can be alkyl, (c) heteroaryl, optionally substituted with one or more $R_D$, independently selected from alkyl, alkoxy, halogen and hydroxy, (d) cycloalkyl, optionally substituted with one or more $R_E$, independently selected from hydroxy and heterocyclylalkyl, (e) aryl, optionally substituted with one or more $R_E$, independently selected from hydroxy, halogen, alkoxy and alkyl, (f) sulfamido, (g) alkylcarbonyl, (h) N-sulfonamido, (i) S-sulfonamido (optionally substituted with one or two alkyl groups), (j) aminocarbonyl, (k) alkylamino, (l) haloalkyl, (m) alkoxy, (n) amino, or (o) hydroxy;

$R^{3A}$ can be (a) alkyl (optionally substituted with one or more $R_G$, independently selected from alkoxy, hydroxy and cyano), (b) heterocyclyl (optionally substituted with one or more $R_H$, independently selected from alkyl, aryl (optionally substituted with one or more halogens) and heteroaryl (optionally substituted with one or more halogens), (c) cycloalkylalkyl, (d) heteroaralkyl, (e) heterocyclylalkyl, or (f) cycloalkyl (optionally substituted with cyano);

$R_{3B}$ can be hydrogen, alkyl or —(C=O)NH$_2$;

X can be $(CR_{4A}R_{4B})_m$, $NR_{4C}$, O or

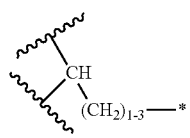

for which "*" indicates a point of attachment to another carbon atom in Ring B;

$X^1$ can be $CR^{5A}R^{5B}$, $NR_{5C}$ or O;

$X^2$ can be $(CR_{6A}R^{6B})_n$, $NR^{6C}$ or O;

wherein, X and $X^1$ cannot each be oxygen or nitrogen;

m can be 1, 2 or 3;

n can be 1, 2 or 3;

wherein the sum of m+n can be 2, 3, 4 or 5; and wherein Ring B is a monocyclic cycloalkyl, a bicyclic cycloalkyl, a monocyclic heterocyclyl or a bicyclic heterocyclyl; and each $R^{4A}$, $R^{4B}$, $R^{4C}$, $R^{5A}$, $R^{5B}$, $R^{5C}$, $R^{6A}$, $R^{6B}$ and $R^{6C}$ can be independently hydrogen or alkyl; except that when X is

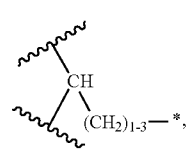 [SMILES: *C(*)CC]

then at least one of $X^1$ and $X^2$ is $CR^{5A}R^{5B}$ or $(CR^{6A}R^{6B})_n$, respectively, and one of $R^{5A}$, $R^{5B}$, $R^{6A}$ and $R^{6B}$ is replaced by a bond to the point of attachment of

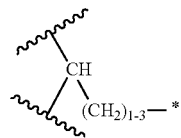

indicated by "*", such that Ring B is a 7- to 11-membered bridged ring system.

In a second aspect, this disclosure is directed to a pharmaceutical composition comprising a compound of Formula (I) (or any of the embodiments thereof described herein) or a pharmaceutically acceptable salt thereof; and a pharmaceutically acceptable excipient.

In a third aspect, this disclosure is directed to a method of treating a disease treatable by inhibition of G9a and/or GLP in a subject in need thereof, comprising administering a therapeutically effective amount of a compound of Formula (I) (or any of the embodiments thereof described herein) or a pharmaceutically acceptable salt thereof, or a pharmaceutical composition comprising a compound of Formula (I) (or any of the embodiments thereof described herein), or a pharmaceutically acceptable salt thereof, in a therapeutically effective amount, and a pharmaceutically acceptable excipient. In one embodiment, the disease can be a hemoglobinopathy, such as beta-thalassemia and sickle cell disease. See Krivega et al., Blood, 2015; 126(5):665-72 and Renneville et al., Blood. 2015 Oct. 15; 126(16):1930-9. In a second embodiment, the disease can be a cancer or tumor, for example, a cancer or tumor where G9a or GLP can be overexpressed. Examples of such cancers and tumors include, but are not limited to: Colorectal Cancer, Osteosarcoma Cancer, Acute Lymphoblastic Leukemia (ALL); Acute Myeloid Leukemia (AML); Adrenocortical Carcinoma, Kaposi Sarcoma (Soft Tissue Sarcoma); AIDS-Related Lymphoma (Lymphoma); Primary CNS Lymphoma; Anal Cancer; Gastrointestinal Carcinoid Tumors; Astrocytomas; Atypical Teratoid/Rhabdoid Tumor; Basal Cell Carcinoma of the Skin; Bile Duct Cancer; Bladder Cancer; Bone Cancer (includes Ewing Sarcoma and Osteosarcoma and Malignant Fibrous Histiocytoma); Brain Tumors; Breast Cancer; Bronchial Tumors—Burkitt Lymphoma; Cardiac Tumors; Embryonal Tumors (Brain Cancer); Germ Cell Tumor (Brain Cancer); Primary CNS Lymphoma; Cervical Cancer; Cholangiocarcinoma; Chordoma; Chronic Lymphocytic Leukemia (CLL); Chronic Myelogenous Leukemia (CML); Chronic Myeloproliferative Neoplasms; Colorectal Cancer; Craniopharyngioma (Brain Cancer); Cutaneous T-Cell Lymphoma; Ductal Carcinoma In Situ (DCIS); Endometrial Cancer (Uterine Cancer); Ependymoma (Brain Cancer); Esophageal Cancer; Esthesioneuroblastoma; Ewing Sarcoma (Bone Cancer); Extracranial Germ Cell Tumor; Extragonadal Germ Cell Tumor; Eye Cancer; Intraocular Melanoma; Retinoblastoma; Fallopian Tube Cancer; Fibrous Histiocytoma of Bone; Gallbladder Cancer; Gastric (Stomach) Gastrointestinal Stromal Tumors (GIST) (Soft Tissue Sarcoma); CNS Germ Cell Tumors (Brain Cancer); Extracranial Germ Cell Tumors; Extragonadal Germ Cell Tumors; Ovarian Germ Cell Tumors; Testicular Cancer; Gestational Trophoblastic Disease; Hairy Cell Leukemia; Head and Neck Cancer; Hepatocellular (Liver) Cancer; Histiocytosis, Langerhans Cell; Hodgkin Lymphoma; Hypopharyngeal Cancer (Head and Neck Cancer); Intraocular Melanoma; Islet Cell Tumors, Pancreatic Neuroendocrine Tumors; Kidney (Renal Cell) Cancer; Langerhans Cell Histiocytosis; Laryngeal Cancer (Head and Neck Cancer);

Leukemia; Lip and Oral Cavity Cancer (Head and Neck Cancer); Lung Cancer (Non-Small Cell and Small Cell); Lymphoma; Male Breast Cancer; Melanoma; Merkel Cell Carcinoma (Skin Cancer); Mesothelioma, Malignant Mesothelioma; Metastatic Squamous Neck Cancer with Occult Primary (Head and Neck Cancer); Midline Tract Carcinoma Involving NUT Gene; Mouth Cancer (Head and Neck Cancer); Multiple Endocrine Neoplasia Syndromes; Multiple Myeloma/Plasma Cell Neoplasms; Mycosis Fungoides (Lymphoma); Myelodysplastic Syndromes, Myelodysplastic/Myeloproliferative Neoplasms; Myelogenous Leukemia, Chronic (CML); Myeloproliferative Neoplasms, Chronic; Nasal Cavity and Paranasal Sinus Cancer (Head and Neck Cancer); Nasopharyngeal Cancer (Head and Neck Cancer); Nasopharyngeal Cancer—Neuroblastoma; Non-Hodgkin Lymphoma; Oral Cancer; Lip and Oral Cavity Cancer and Oropharyngeal Cancer (Head and Neck Cancer); Ovarian Cancer; Pancreatic Cancer; Papillomatosis; Paraganglioma; Paranasal Sinus and Nasal Cavity Cancer (Head and Neck Cancer); Parathyroid Cancer; Penile Cancer; Pharyngeal Cancer (Head and Neck Cancer); Pheochromocytoma; Pituitary Tumor; Plasma Cell Neoplasm/Multiple Myeloma; Pleuropulmonary Blastoma; Pregnancy and Breast Cancer; Primary CNS Lymphoma; Primary Peritoneal Cancer; Prostate Cancer; Rectal Cancer; Recurrent Cancer; Rhabdomyosarcoma (Soft Tissue Sarcoma); Salivary Gland Cancer (Head and Neck Cancer); Salivary Gland Tumors; Vascular Tumors (Soft Tissue Sarcoma); Uterine Sarcoma; Sézary Syndrome (Lymphoma); Small Intestine Cancer; Soft Tissue Sarcoma; Squamous Cell Carcinoma of the Skin; Skin Cancer; Squamous Neck Cancer with Occult Primary, Metastatic (Head and Neck Cancer); T-Cell Lymphoma, Cutaneous; Lymphoma (Mycosis Fungoides and Sezary Syndrome); Throat Cancer (Head and Neck Cancer); Nasopharyngeal Cancer; Oropharyngeal Cancer; Hypopharyngeal Cancer; Thymoma and Thymic Carcinoma; Thyroid Cancer; Urethral Cancer; Vaginal Cancer; Vascular Tumors (Soft Tissue Sarcoma); Vulvar Cancer; Myelodysplastic syndrome (MDS); and Wilms Tumor. Thus, the terms "cancerous cell," "cancer cell" or "tumor cell" as provided herein, includes a cell afflicted by any one of or related to the above identified conditions. See Cascielle et al., *Front. Immunol.* 2015; 6:487, Agarwal et al., *Cancer Letters* 2016: 467 and Zhang et al., *Oncotarget* 2015, 6(5): 2917. In a second embodiment, treating a cancer and/or tumor comprises increasing tumor free survival and/or reducing tumor mass and/or slowing tumor growth. In a third embodiment, the disease can be a cancer predisposition syndrome, such as Cowden syndrome. See You et al., *Cancer Cell.* 2012; 22(1):9-20. In a fourth embodiment, the disease can be an inflammatory and/or autoimmune disease, such as intestinal inflammation, arthritis, atherosclerosis, multiple sclerosis, myasthenia gravis, Crohn's disease, graft-versus-host disease, psoriasis, granulomatous colitis, lymphocyte colitis, collagenous colitis, ulcerative colitis, Coeliac Disease, subepidermal blistering disorders, systemic lupus erythematosus, discoid lupus erythematosus, cutaneous lupus, dermatomyositis, polymyositis, Sjogren's syndrome, primary biliary cirrhosis, active chronic hepatitis, chronic fatigue syndrome and vasculitis. See Antignano et al., *J. Clin. Invest.* 2014 4(5): 1945-55. In a fifth embodiment, the disease can be a metabolic disease, such as diabetes and/or obesity. See Wang et al., *EMBO J.* 2013; 32(1):45-59. In a sixth embodiment, the disease can be related to skeletal muscle development and regeneration. See Ling et al., *Proc. Natl. Acad. Sci. USA.* 2012; 109(3):841-6. In a seventh embodiment, the disease can be a viral disease, such as HIV-1 (human immunodeficiency virus 1) and HBV (Hepatitis B Virus). See Imai et al., *J. Biol. Chem.* 2010; 285(22): 16538-45 and Merkling et al., *PLoS Pathog.* 2015; 11(4). The compounds and compositions described herein can be administered with one or more additional therapeutic agents including, but not limited to, anticancer agents and antiviral agents. See, e.g., Front Immunol. 2015; 6:487; Agarwal et al., Cancer Lett. 2016:467 and Zhang et al., *Oncotarget.* 2015, 6(5):2917.

In a fourth aspect provided is the use of a compound of Formula (I) (or any of the embodiments thereof described herein) or a pharmaceutically acceptable salt thereof, in the treatment of the diseases provided in the third aspect herein.

In a fifth aspect, this disclosure is directed to a method of inhibiting G9a and/or GLP, comprising contacting a cell that contains G9a with a therapeutically effective amount of a compound of Formula (I) (or any of the embodiments thereof described herein) or a pharmaceutically acceptable salt thereof, thereby inhibiting the activity of G9a. In some embodiments, the cell suffers from one or more of the diseases provided in the third aspect herein.

DETAILED DESCRIPTION

Definitions

Unless otherwise stated, the following terms used in the specification and claims are defined for the purposes of this Application and have the following meaning:

"Alkyl" means a straight chained or branched saturated monovalent hydrocarbon radical of one to ten carbon atoms or a branched saturated monovalent hydrocarbon radical of three to ten carbon atoms, e.g., methyl, ethyl, propyl, 2-propyl (isopropyl), n-butyl, sec-butyl, iso-butyl, tert-butyl, pentyl (straight-chained or branched), hexyl (straight-chained or branched), heptyl (straight-chained or branched) and the like.

"Alkylene" means a straight chained or branched saturated divalent hydrocarbon radical of one to ten carbon atoms or a branched saturated divalent hydrocarbon radical of three to ten carbon atoms unless otherwise stated e.g., methylene, ethylene, propylene, 1-methylpropylene, 2-methylpropylene, butylene, pentylene and the like.

"Alkoxy" means a —OR radical where R is alkyl as defined above, e.g., methoxy, ethoxy, propoxy, or 2-propoxy, n-, iso-, or tert-butoxy and the like.

"Alkoxyalkyl" means alkyl as defined above which is substituted with one or two alkoxy groups as defined above, e.g., methoxyethyl, ethoxyethyl, methoxypropyl and the like.

"Alkylcarbonyl" or "Acyl" means a —COR radical where R is alkyl as defined above, e.g., methylcarbonyl, ethylcarbonyl and the like.

"Alkoxycarbonyl" means a —(C=O)OR radical where R is alkyl as defined above, e.g., tert-butyloxycarbonyl and the like.

"Alkoxycarbonylalkyl" means alkyl as defined above which is substituted with one or two alkoxycarbonyl groups as defined above, e.g., methoxycarbonylethyl, ethoxycarbonylethyl, methoxycarbonylpropyl and the like.

"Amino" means a —NH$_2$ group.

"Aminoalkyl" means an -(alkylene)-R radical where NR'R" where R' and R" are independently hydrogen or alkyl as defined above.

"Alkylamino" means a —NR'R" radical where R' and R" are independently hydrogen or alkyl as defined above and wherein at least one of R' and R" is alkyl.

"Aminocarbonyl" means a —(C=O)—NR'R" group, where R' and R" are independently hydrogen or alkyl as defined above.

"Aryl" means a monovalent monocyclic or bicyclic aromatic hydrocarbon radical of 6 to 10 ring atoms e.g., phenyl or naphthyl.

"Aralkyl" means a -(alkylene)-R radical where R is aryl as defined above, e.g., benzyl, phenethyl and the like.

"Aryloxy" means a —OR radical where R is aryl as defined above, e.g., phenoxy, naphthyloxy and the like.

"Cyano" means a —CN group.

"Cyanoalkyl" means an alkyl group as defined above, substituted with one or more cyano groups, e.g., cyanomethyl, cyanoethyl, 2-cyanopropyl, 2,3-dicyanobutyl and the like.

"Cycloalkyl" means a saturated monovalent monocyclic hydrocarbon radical of three to ten carbon atoms, or a saturated monovalent bicyclic hydrocarbon radical of five to ten carbon atoms, unless stated otherwise. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Examples of monocyclic cycloalkyl groups includes, for example, cyclopropyl, cyclobutyl, cyclopentyl, or cyclohexyl and the like. Examples of bicyclic cycloalkyl groups include, for example, decalinyl, norbornanyl, decahydronaphthalenyl, dodecahydro-1H-phenalenyl, adamantly, bicyclo[3.3.0]octanyl, spiro[3.3]heptanyl, spiro[3.4]octanyl, spiro[3.4]octanyl, spiro[3.5]nonanyl, spiro[4.4]nonanyl, spiro[3.6]decanyl, spiro[4.5]decanyl and the like.

"Cycloalkoxy" means a —OR radical where R is cycloalkyl as defined above, e.g., cyclopropyl, cyclobutyl, cyclopentyl, cyclohexyl, cycloheptyl, cyclooctyl and the like.

"Cycloalkylalkyl" means a -(alkylene)-R radical where R is cycloalkyl as defined above, e.g., cyclopropylmethyl, cyclohexylmethyl and the like.

"Cycloalkenyl" means a cyclic hydrocarbon radical of three to ten carbon atoms containing a double bond, unless stated otherwise, e.g., cyclopropenyl, cyclobutenyl, cyclopentenyl, cyclohexenyl and the like.

"Carboxyalkyl" means an alkyl radical as defined above that is substituted with a carboxy (—COOH) group.

"5- or 6-membered cycloalkenyl" means a cyclic hydrocarbon radical of five or six carbon atoms containing a double bond "Deuterated alkyl" means an alkyl radical as defined above that is substituted with one, two or three deuterium atoms.

"Halo" or "halogen" means fluoro, chloro, bromo, or iodo, preferably fluoro or chloro.

"Haloalkyl" means alkyl radical as defined above, which is substituted with one or more halogen atoms, such as one to five halogen atoms, such as fluorine or chlorine, including those substituted with different halogens, e.g., —CH$_2$C$_1$, —CF$_3$, —CHF$_2$, —CH$_2$CF$_3$, —CF$_2$CF$_3$, —CF(CH$_3$)$_2$ and the like. When the alkyl is substituted with only fluoro, it can be referred to in this Application as fluoroalkyl.

"Haloalkoxy" means a —OR radical where R is haloalkyl as defined above e.g., —OCF$_3$, —OCHF$_2$, —OCH$_2$F and the like. When R is haloalkyl where the alkyl is substituted with only fluoro, it is referred to in this Application as fluoroalkoxy.

"Haloalkoxyalkyl" means alkyl as defined above which is substituted with one or two haloalkoxy groups as defined above, e.g., trifluormethoxyethyl, 3,3,3-trifluoroethoxyethyl and the like.

"Haloalkylcarbonyl" means a —COR radical where R is haloalkyl as defined above, e.g., trifluoromethylcarbonyl, pentafluoroethylcarbonyl and the like.

"Hydroxyalkyl" means alkyl as defined above which is substituted with one or two hydroxy groups as defined above, e.g., hydroxymethyl, hydroxyethyl, 1,3-dihydroxypropyl and the like.

"Halocycloalkyl" means cycloalkyl group as defined above which is substituted with one, two or three halogen as defined above, e.g., 2,2-difluorocyclopropyl and the like.

"Heterocyclyl" means a saturated or unsaturated monovalent group of 3 to 10 ring atoms in which one, two, or three ring atoms are heteroatoms independently selected from N, O and S(O)$_n$, where n is an integer from 0 to 2 and the remaining ring atoms are C, unless stated otherwise. Additionally, one or two ring carbon atoms in the heterocyclyl ring can optionally be replaced by a (C=O)— group. Heterocyclyl groups can be monocyclic or bicyclic. More specifically the term heterocyclyl includes, but is not limited to, pyrrolidino, piperidino, homopiperidino, 2-oxopyrrolidinyl, 2-oxopiperidinyl, morpholino, piperazino, dihydropyranyl, thiomorpholino, 1,3-dioxinyl, 1,3-dioxanyl, 1,4-dioxanyl, 1,2-dioxolanyl, 1,3-dioxolanyl, 1,4-dioxolanyl, 2H-1,2-oxazinyl, maleimido, succinimido, barbituric acid, thiobarbituric acid, dioxopiperazino, hydantoino, dihydrouracilyl, hexahydro-1,3,5-triazinyl, imidazolino, imidazolidino, isoxazolino, isoxazolidino, oxazolino, oxazolidino, oxazolidinono, thiazolino, thiazolidino, oxiranyl, pyrrolidonyl, pyrrolidionyl, 4-piperidonyl, pyrazolino, pyrazolidino, 2-oxopyrrolidino, tetrahydropyranyl, 4H-pyranyl, tetrahydrothiopyranyl, azepanyl and the like. Heterocyclic groups can be monocyclic, for example, pyrrolidine, piperidine and piperazine, or bicyclic, for example, hexahydro-1H-pyrrolizine. Bicyclic heterocyclyl groups include bridged and fused ring systems, for example, indoline, 7-azabicyclo[2.2.1]heptane, hexahydro-1H-pyrrolizine, 8-azabicyclo[3.2.1]octane and the like. When the heterocyclyl ring is unsaturated it can contain one or two ring double bonds provided that the ring is not aromatic. When the heterocyclyl ring has no double bond, it can be referred to herein as saturated heterocyclyl.

"Heterocyclylalkyl" or "heterocycloalkyl" means a -(alkylene)-R radical where R is heterocyclyl ring as defined above e.g., tetrahydrofuranylmethyl, piperazinylmethyl, morpholinylethyl and the like. When a heterocyclylalkyl group contains a secondary amino group (i.e., —NH—), the alkyl portion of the heterocyclylalkyl may replace the hydrogen on the nitrogen in the heterocyclyl ring, such that the heterocyclyl ring is linked to the alkyl portion of the heterocyclylalkyl group via the nitrogen atom.

"Heteroaryl" means a monovalent monocyclic or bicyclic aromatic radical of 5 to 10 ring atoms, unless otherwise stated, where one or more, (in one embodiment, one, two, or three), ring atoms are heteroatom selected from N, O and S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl and the like. When the heteroaryl ring contains 5- or 6 ring atoms, it is also referred to herein as 5- or 6-membered heteroaryl.

"Heteroaralkyl" means a -(alkylene)-R radical where R is heteroaryl as defined above, e.g., pyridinylmethyl and the like. The heteroaryl ring in heteroaralkyl can contain from 5- to 10 ring atoms. When the heteroaryl ring in heteroaralkyl contains 5- or 6 ring atoms, it is also referred to herein as 5- or 6-membered heteroaralkyl. When a heteroaralkyl group contains a secondary amino group (i.e., —NH—), the alkyl portion of the heteroaralkyl may replace the hydrogen on the nitrogen in the heteroaryl ring, such that the heteroaryl ring is linked to the alkyl portion of the heteroaralkyl group via the nitrogen atom.

"Heteroaryloxy" means a —OR radical where R is heteroaryl as defined above, e.g., pyridinoxy, pyrazinoxy, pyrimidinoxy, quinolinoxy and the like.

"Hydroxy" means —OH group.

"Hydroxyalkoxy" means a —OR radical where R is alkyl as defined above, e.g., methoxy, ethoxy, propoxy, or 2-propoxy, n-, iso-, or tert-butoxy and the like, where R is substituted with one or more hydroxyl groups.

"Cyanoalkoxy" means a —OR radical where R is alkyl as defined above, e.g., methoxy, ethoxy, propoxy, or 2-propoxy, n-, iso-, or tert-butoxy and the like, where R is substituted with a cyano group. For example, cyanomethoxy, 2-cyanoethoxy, 2-cyanopropoxy and the like.

"N-sulfonamido" means "$R_x$—SO$_2$NH—" group in which $R_x$ can hydrogen, hydroxy, deuterium, alkyl, cycloalkyl, aryl, heteroaryl, heterocyclyl, aralkyl, heteroaralkyl or heterocyclylalkyl, each as defined above.

Oxo" means a =(O) radical. As would be readily apparent to one of skill in the art, "carbonyl" refers to an oxo radical attached to a carbon atom, i.e., —C(=O)—.

"S-sulfonamido" means a "—SO$_2$NH$_2$" group.

"Sulfamido" means a "—NH—SO$_2$NH$_2$ group.

"Spiroheterocycloamino" means a saturated bicyclic ring having 7 to 10 ring atoms in which one, two, or three ring atoms are heteroatoms selected from N, NH, N-oxide, O and S(O)$_n$, where n is an integer from 0 to 2, the remaining ring atoms being C, provided that at least one ring atom is N and the rings are connected through only one atom. The connecting atom is also called the spiroatom and is most often a quaternary carbon ("spiro carbon"). Representative examples include, but are not limited to, 2-azaspiro[3.3] heptane, 2-oxaspiro[3.3]heptane, 1-azaspiro[3.3]heptane, 1-oxaspiro[3.3]heptane, 5-oxaspiro[3.4]octane, 5-azaspiro [3.4]octane, 2-oxaspiro[3.4]octane, 2-azaspiro[3.4]octane, 1-oxa-4-azaspiro[4.4]nonane, 1,4-dioxaspiro[4.4]nonane, 2-azaspiro[3.5]nonane, 2-oxaspiro[3.5]nonane, 4-azaspiro [2.5]octane, 4-oxaspiro[2.5]octane, 1,4-dioxaspiro[4.5]decane, 1-thiaspiro[4.5]decane 1,1-dioxide, 2-oxa-1-azaspiro [4.5]decane and the like.

It will be well recognized by a person skilled in the art that when Ring B is cycloalkyl (including monocyclic, and bicyclic bridged, fused, or spiro cycloalkyls) or heterocyclyl, the carbon atoms in these rings that are shared with the adjacent ring (i.e., ring substituted with—NR$^{3A}$R$^{3B}$ in Formula I) are sp$^2$ carbons.

The present disclosure also includes protected derivatives of compounds of the present disclosure. For example, when compounds of the present disclosure contain groups such as hydroxy, carboxy, thiol or any group containing a nitrogen atom(s), these groups can be protected with a suitable protecting group. A comprehensive list of suitable protective groups can be found in T. W. Greene, *Protective Groups in Organic Synthesis*, John Wiley & Sons, Inc. (1999), the disclosure of which is incorporated herein by reference in its entirety. The protected derivatives of compounds of the present disclosure can be prepared by methods well known in the art.

It is to be understood that where compounds disclosed herein have unfilled valencies, then the valencies are to be filled with hydrogen.

The present disclosure also includes deuterated forms of the compound of the present disclosure, or a pharmaceutically acceptable salt thereof. Indeed, also provided herein are isotopologues (isotopically labeled analogues) of the compounds described herein. Substitution with isotopes such as deuterium may afford certain therapeutic advantages resulting from greater metabolic stability, such as, for example, increased in vivo half-life or reduced dosage requirements. In some embodiments, at any position of a compound described herein, or a pharmaceutically acceptable salt thereof, that has a hydrogen, the hydrogen atom can be replaced with hydrogen-2 (deuterium) or hydrogen-3 (tritium).

A "pharmaceutically acceptable salt" of a compound means a salt that is pharmaceutically acceptable and that possesses the desired pharmacological activity of the parent compound. Such salts include: acid addition salts, formed with inorganic acids such as hydrochloric acid, hydrobromic acid, sulfuric acid, nitric acid, phosphoric acid and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine and the like. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference in its entirety.

The compounds of the present disclosure may have asymmetric centers. Compounds of the present disclosure containing an asymmetrically substituted atom may be isolated in optically active or racemic forms. It is well known in the art how to prepare optically active forms, such as by resolution of materials. All chiral, diastereomeric, all mixtures of chiral or diastereomeric forms and racemic forms are within the scope of this disclosure, unless the specific stereochemistry or isomeric form is specifically indicated. It will also be well recognized by a person skilled in the art that when a bond is drawn from an optically active center, that a "flat" bond ( ———— ) represents and encompasses both the "wedge" bond ( ◀━━ ) and the "dashed" bond ( ꜱꜱꜱꜱꜱꜱ ) each representing the (R) or (S) stereoisomer. It will also be understood by a person of ordinary skill in the art that when a compound is denoted as (R) stereoisomer, it may contain the corresponding (S) stereoisomer as an impurity i.e., the (S) stereoisomer in less than about 5%, preferably 2% by wt. and then it is denoted as a mixture of R and S isomers, the amounts of R or S isomer in the mixture is greater than about 5%, preferably 2% w/w.

Certain compounds of the present disclosure can exist as tautomers and/or geometric isomers. All possible tautomers and cis and trans isomers, as individual forms and mixtures thereof are within the scope of this disclosure. Additionally, as used herein the term alkyl includes all the possible isomeric forms of said alkyl group albeit only a few examples are set forth. Furthermore, when the cyclic groups such as aryl, heteroaryl, heterocyclyl are substituted, they include all the positional isomers albeit only a few examples are set forth. Furthermore, all hydrates of a compound of the present disclosure are within the scope of this disclosure.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with alkyl.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

A "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees and apes, and, in particular, humans. In some embodiments, the subject can be human. In some embodiments, the subject can be a human child and/or a human infant, for example, a child or infant with a fever. In other embodiments, the subject can be a human adult.

"Treating" or "treatment" of a disease includes:

(1) preventing the disease, i.e. causing the clinical symptoms of the disease not to develop in a subject that may be exposed to or predisposed to the disease but does not yet experience or display symptoms of the disease;

(2) inhibiting the disease, i.e., arresting or reducing the development of the disease or its clinical symptoms; or (3) relieving the disease, i.e., causing regression of the disease or its clinical symptoms.

A "therapeutically effective amount" means the amount of a compound of the present disclosure or a pharmaceutically acceptable salt thereof that, elicits the biological or medicinal response indicated. For example, when administered to a subject for treating a disease, the therapeutically effective amount of a compound is sufficient to prevent, alleviate or ameliorate symptoms of disease or prolong the survival of the subject being treated. This response may occur in a tissue, system, animal or human and includes alleviation of the signs or symptoms of the disease being treated. Determination of an effective amount is well within the capability of those skilled in the art, in view of the disclosure provided herein. The "therapeutically effective amount" of the compounds disclosed herein will vary depending on the compound, the disease and its severity and the age, weight, etc., of the subject to be treated.

EMBODIMENTS

In further embodiments 1-180 below, the present disclosure includes:

1. In embodiment 1, the compounds of Formula (I), or a pharmaceutically acceptable salt thereof, are as defined in the Summary.
2. In embodiment 2, the compounds of embodiment 1, or a pharmaceutically acceptable salt thereof, are those wherein A can be CH.
3. In embodiment 3, the compounds of embodiment 1, or a pharmaceutically acceptable salt thereof, are those wherein A can be N.
4. In embodiment 4, the compounds of any one of embodiments 1-3, or a pharmaceutically acceptable salt thereof, are those wherein $R^{3B}$ can be hydrogen.
5. In embodiment 5, the compounds of any one of embodiments 1-3, or a pharmaceutically acceptable salt thereof, are those wherein $R^{3B}$ can be alkyl, for example, a $C_1$-$C_6$ alkyl such as methyl, ethyl, n-propyl, isopropyl, n-butyl, sec-butyl, isobutyl, t-butyl, pentyl (straight-chained or branched) or hexyl (straight-chained or branched).
6. In embodiment 6, the compounds of any one of embodiments 1-3, or a pharmaceutically acceptable salt thereof, are those wherein $R^{3B}$ can be —(C=O)NH$_2$.
7. In embodiment 7, the compounds of any one of embodiments 1-6, or a pharmaceutically acceptable salt thereof, are those wherein X can be $(CR^{4A}R^{4B})_m$.
8. In embodiment 8, the compounds of any one of embodiments 1-7, or a pharmaceutically acceptable salt thereof, are those wherein m can be 1.
9. In embodiment 9, the compounds of any one of embodiments 1-8, or a pharmaceutically acceptable salt thereof, are those wherein $R^{4A}$ and $R^{4B}$ can each independently be alkyl. For example, in some aspects of embodiment 9, $R^{4A}$ and $R^{4B}$ can each independently be a $C_1$-$C_6$ alkyl such as methyl, ethyl, n-propyl, isopropyl, n-butyl, sec-butyl, isobutyl, t-butyl, pentyl (straight-chained or branched) or hexyl (straight-chained or branched).
10. In embodiment 10, the compounds of any one of embodiments 1-8, or a pharmaceutically acceptable salt thereof, are those wherein one of $R^{4A}$ and $R^{4B}$ can be hydrogen; and the other of $R^{4A}$ and $R^{4B}$ can be alkyl, for example, a $C_1$-$C_6$ alkyl such as methyl, ethyl, n-propyl, isopropyl, n-butyl, sec-butyl, isobutyl, t-butyl, pentyl (straight-chained or branched) or hexyl (straight-chained or branched).
11. In embodiment 11, the compounds of any one of embodiments 9-10, or a pharmaceutically acceptable salt thereof, are those wherein the alkyl of $R^{4A}$ and $R^{4B}$ can be methyl.
12. In embodiment 12, the compounds of any one of embodiments 1-7, or a pharmaceutically acceptable salt thereof, are those wherein m can be 2.
13. In embodiment 13, the compounds of any one of embodiments 1-7, or a pharmaceutically acceptable salt thereof, are those wherein m can be 3.
14. In embodiment 14, the compounds of any one of embodiments 1-8 and 12-13, or a pharmaceutically acceptable salt thereof, are those wherein $R^{4A}$ and $R^{4B}$ can each be hydrogen.

15. In embodiment 15, the compounds of any one of embodiments 1-6, or a pharmaceutically acceptable salt thereof, are those wherein X can be O (oxygen).
16. In embodiment 16, the compounds of any one of embodiments 1-6, or a pharmaceutically acceptable salt thereof, are those wherein X can be $NR^{4C}$.
17. In embodiment 17, the compounds of embodiment 16, or a pharmaceutically acceptable salt thereof, are those wherein $R^{4C}$ can be alkyl, for example, a $C_1$-$C_6$ alkyl such as methyl, ethyl, n-propyl, isopropyl, n-butyl, sec-butyl, isobutyl, t-butyl, pentyl (straight-chained or branched) or hexyl (straight-chained or branched).
18. In embodiment 18, the compounds of any one of embodiments 16-17, or a pharmaceutically acceptable salt thereof, are those wherein Roc can be methyl.
19. In embodiment 19, the compounds of embodiment 16, or a pharmaceutically acceptable salt thereof, are those wherein $R^{4C}$ can be hydrogen.
20. In embodiment 20, the compounds of any one of embodiments 1-6, or a pharmaceutically acceptable salt thereof, are those wherein (i) X is

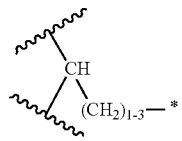

for which "*" represents the point of attachment to another carbon atom in Ring B, (ii) at least one of $X^1$ and $X^2$ is $CR^{5A}R^{5B}$ or $(CR^{6A}R^{6B})_n$, respectively, and (iii) one of $R^{5A}$, $R^{5B}$, $R^{6A}$ and $R^{6B}$ is replaced by a bond to "*", such that (iv) Ring B is a 7- to 11-membered bridged ring system. In some aspects of embodiment 20, X can be —CH—$(CH_2)_1$—*, and Ring B can be a 7-membered bridged ring system. In some aspects of embodiment 20, X can be —CH—$(CH_2)_1$—*, and Ring B can be an 8-membered bridged ring system. In some aspects of embodiment 20, X can be —CH—$(CH_2)_1$—*, and Ring B can be a 9-membered bridged ring system. In some aspects of embodiment 20, X can be —CH—$(CH_2)_2$—*, and Ring B can be a 7-membered bridged ring system. In some aspects of embodiment 20, X can be —CH—$(CH_2)_2$—*, and Ring B can be an 8-membered bridged ring system. In some aspects of embodiment 20, X can be —CH—$(CH_2)_2$—*, and Ring B can be a 9-membered bridged ring system. In some aspects of embodiment 20, X can be —CH—$(CH_2)_2$—*, and Ring B can be a 10-membered bridged ring system. In some aspects of embodiment 20, X can be —CH—$(CH_2)_3$—*, and Ring B can be an 8-membered bridged ring system. In some aspects of embodiment 20, X can be —CH—$(CH_2)_3$—*, and Ring B can be a 9-membered bridged ring system. In some aspects of embodiment 20, X can be —CH—$(CH_2)_3$—*, and Ring B can be a 10-membered bridged ring system. In some aspects of embodiment 20, X can be —CH—$(CH_2)_3$—*, and Ring B can be an 11-membered bridged ring system. In some aspects of embodiment 20, X can be —CH—$(CH_2)_1$—* and "*" can bond to $X^1$, replacing one of $R^{5A}$ or $R^{5B}$. In some aspects of embodiment 20, X can be —CH—$(CH_2)_2$—* and "*" can bond to $X^1$, replacing one of $R^{5A}$ or $R^{5B}$. In some aspects of embodiment 20, X can be —CH—$(CH_2)_3$—* and "*" can bond to $X^1$, replacing one of $R^{5A}$ or $R^{5B}$. In some aspects of embodiment 20, X can be —CH—$(CH_2)_1$—* and "*" can bond to $X^2$, replacing one of $R^{6A}$ or $R^{6B}$. In some aspects of embodiment 20, X can be —CH—$(CH_2)_2$—* and "*" can bond to $X^2$, replacing one of $R^{6A}$ or $R^{6B}$. In some aspects of embodiment 20, X can be —CH—$(CH_2)_3$—* and "*" can bond to $X^2$, replacing one of $R^{6A}$ or $R^{6B}$.

21. In embodiment 21, the compounds of embodiment 20, or a pharmaceutically acceptable salt thereof, are those wherein Ring B can be selected from:

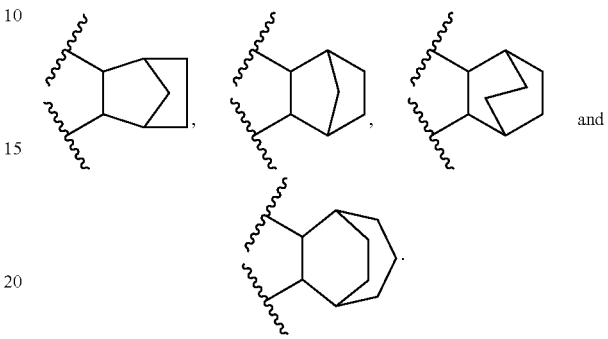

22. In embodiment 22, the compounds of any one of embodiments 1-19, or a pharmaceutically acceptable salt thereof, are those wherein $X^1$ can be $CR^{5A}R^{5B}$. In some aspects of embodiment 22, one of $R^{5A}$ or $R^{5B}$ can be replaced by a bond to "*" as described herein.
23. In embodiment 23, the compounds of embodiment 22, or a pharmaceutically acceptable salt thereof, are those wherein $R^{5A}$ and $R^{5B}$ can each independently be alkyl. For example, in some aspects of embodiment 23, $R^{5A}$ and $R^{5B}$ can each independently be a $C_1$-$C_6$ alkyl such as methyl, ethyl, n-propyl, isopropyl, n-butyl, sec-butyl, isobutyl, t-butyl, pentyl (straight-chained or branched) or hexyl (straight-chained or branched).
24. In embodiment 24, the compounds of embodiment 22, or a pharmaceutically acceptable salt thereof, are those wherein one of $R^{5A}$ and $R^{5B}$ can be hydrogen; and the other of $R^{5A}$ and $R^{5B}$ can be alkyl, for example, a $C_1$-$C_6$ alkyl such as methyl, ethyl, n-propyl, isopropyl, n-butyl, sec-butyl, isobutyl, t-butyl, pentyl (straight-chained or branched) or hexyl (straight-chained or branched).
25. In embodiment 25, the compounds of any one of embodiments 23-24, or a pharmaceutically acceptable salt thereof, are those wherein the alkyl of $R^{5A}$ and $R^{5B}$ can be methyl.
26. In embodiment 26, the compounds of embodiment 22, or a pharmaceutically acceptable salt thereof, are those wherein $R^{5A}$ and $R^{5B}$ can each be hydrogen.
27. In embodiment 27, the compounds of any one of embodiments 1-19, or a pharmaceutically acceptable salt thereof, are those wherein $X^1$ can be O (oxygen).
28. In embodiment 28, the compounds of any one of embodiments 1-19, or a pharmaceutically acceptable salt thereof, are those wherein $X^1$ can be $NR^{5C}$.
29. In embodiment 29, the compounds of embodiment 28, or a pharmaceutically acceptable salt thereof, are those wherein $R^{5C}$ can be alkyl, for example, a $C_1$-$C_6$ alkyl such as methyl, ethyl, n-propyl, isopropyl, n-butyl, sec-butyl, isobutyl, t-butyl, pentyl (straight-chained or branched) or hexyl (straight-chained or branched).
30. In embodiment 30, the compounds of any one of embodiments 28-29, or a pharmaceutically acceptable salt thereof, are those wherein $R^{5C}$ can be methyl.

31. In embodiment 31, the compounds of embodiment 30, or a pharmaceutically acceptable salt thereof, are those wherein $R^{5C}$ can be hydrogen.

32. In embodiment 32, the compounds of any one of embodiments 1-20 or 22-31, or a pharmaceutically acceptable salt thereof, are those wherein $X^2$ can be $(CR^{6A}R^{6B})_n$. In some aspects of embodiment 32, one of $R_{6A}$ or $R_{6B}$ can be replaced by a bond to "*" as described herein.

33. In embodiment 33, the compounds of embodiment 32, or a pharmaceutically acceptable salt thereof, are those wherein n can be 1.

34. In embodiment 34, the compounds of any one of embodiments 32-33, or a pharmaceutically acceptable salt thereof, are those wherein $R^{6A}$ and $R^{6B}$ can each independently be alkyl. For example, in some aspects of embodiment 34, $R^{6A}$ and $R^{6B}$ can each independently be a $C_1$-$C_6$ alkyl such as methyl, ethyl, n-propyl, isopropyl, n-butyl, sec-butyl, isobutyl, t-butyl, pentyl (straight-chained or branched) or hexyl (straight-chained or branched).

35. In embodiment 35, the compounds of any one of embodiments 32-33, or a pharmaceutically acceptable salt thereof, are those wherein one of $R^{6A}$ and $R^{6B}$ can be hydrogen; and the other of $R^{6A}$ and $R^{6B}$ can be alkyl, for example, a $C_1$-$C_6$ alkyl such as methyl, ethyl, n-propyl, isopropyl, n-butyl, sec-butyl, isobutyl, t-butyl, pentyl (straight-chained or branched) or hexyl (straight-chained or branched).

36. In embodiment 36, the compounds of any one of embodiments 34-35, or a pharmaceutically acceptable salt thereof, are those wherein the alkyl can be methyl.

37. In embodiment 37, the compounds of embodiment 32, or a pharmaceutically acceptable salt thereof, are those wherein n can be 2.

38. In embodiment 38, the compounds of embodiment 32, or a pharmaceutically acceptable salt thereof, are those wherein n can be 3.

39. In embodiment 39, the compounds of any one of embodiments 32-33 and 37-38, or a pharmaceutically acceptable salt thereof, are those wherein $R^{6A}$ and $R^{6B}$ can each be hydrogen.

40. In embodiment 40, the compounds of any one of embodiments 1-19, or a pharmaceutically acceptable salt thereof, are those wherein $X^2$ can be O (oxygen).

41. In embodiment 41, the compounds of any one of embodiments 1-19, or a pharmaceutically acceptable salt thereof, are those wherein $X^2$ can be $NR^{6C}$ 42. In embodiment 42, the compounds of embodiment 41, or a pharmaceutically acceptable salt thereof, are those wherein $R^{6C}$ can be alkyl, for example, a $C_1$-$C_6$ alkyl such as methyl, ethyl, n-propyl, isopropyl, n-butyl, sec-butyl, isobutyl, t-butyl, pentyl (straight-chained or branched) or hexyl (straight-chained or branched).

43. In embodiment 43, the compounds of any one of embodiments 41-42, or a pharmaceutically acceptable salt thereof, are those wherein $R^{6C}$ can be methyl.

44. In embodiment 44, the compounds of embodiment 41, or a pharmaceutically acceptable salt thereof, are those wherein $R^{6C}$ can be hydrogen.

45. In embodiment 45, the compounds of any one of embodiments 1-6, or a pharmaceutically acceptable salt thereof, are those wherein Ring B can be selected from:

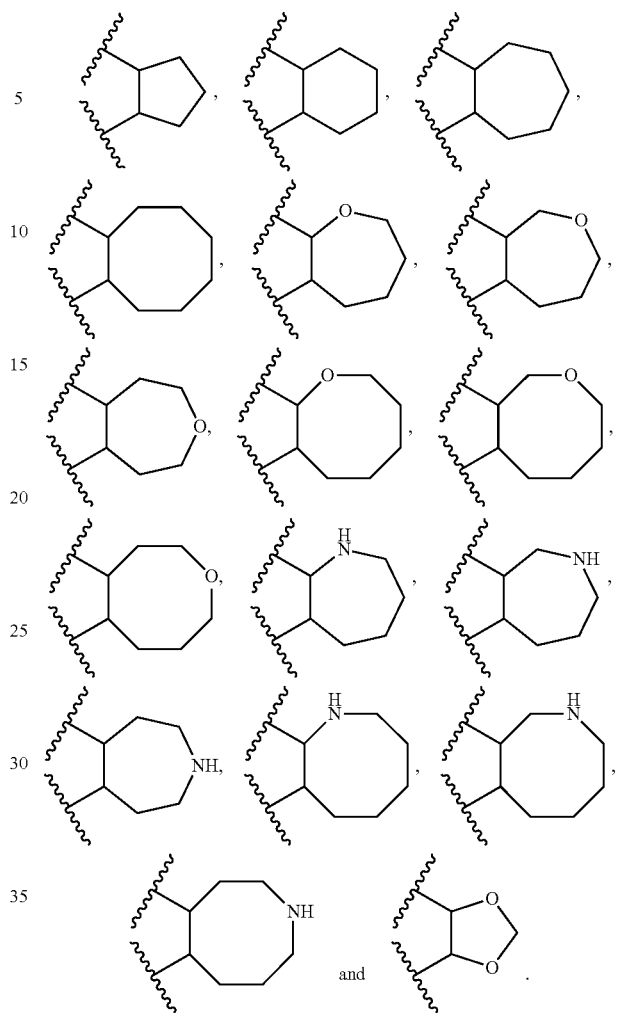

46. In embodiment 46, the compounds of any one of embodiments 1-45, or a pharmaceutically acceptable salt thereof, are those wherein $R^1$ can be alkoxy. For example, in some aspects of embodiment 46, $R^1$ can be a $C_1$-$C_6$ alkoxy such as methoxy, ethoxy, n-propoxy, isopropoxy, n-butoxy, isobutoxy, sec-butoxy, t-butoxy, pentoxy (straight-chained or branched) or hexoxy (straight-chained or branched).

47. In embodiment 47, the compounds of any one of embodiments 1-46, or a pharmaceutically acceptable salt thereof, are those wherein $R^1$ can be selected from —OCH₃, —OCH₂CH₃ and —OCH(CH₃)₂.

48. In embodiment 48, the compounds of any one of embodiments 1-47, or a pharmaceutically acceptable salt thereof, are those wherein $R^1$ can be —OCH₃.

49. In embodiment 49, the compounds of any one of embodiments 1-45, or a pharmaceutically acceptable salt thereof, are those wherein $R^1$ can be hydroxy.

50. In embodiment 50, the compounds of any one of embodiments 1-45, or a pharmaceutically acceptable salt thereof, are those wherein $R^1$ can be haloalkoxy. For example, in some aspects of embodiment 50, $R^1$ can be a $C_1$-$C_6$ haloalkoxy such as halomethoxy, haloethoxy, halo-n-propoxy, haloisopropoxy, halo-n-butoxy, halo-sec-butoxy, halo-isobutoxy, halo-t-butoxy, halo-pentoxy (straight-chained or branched) or halo-hexoxy (straight-chained or branched). In some aspects of embodiment 50, $R^1$ can be a $C_1$-$C_6$ fluoroalkoxy. In some aspects of embodiment 50, $R^1$ can be a $C_1$-$C_6$ chloroalkoxy. In some aspects of embodiment 50, $R^1$ can be a $C_1$-$C_6$ haloalkoxy, wherein the haloalkoxy includes chlorine and fluorine.

51. In embodiment 51, the compounds of embodiment 50, or a pharmaceutically acceptable salt thereof, are those wherein $R^1$ can be selected from —OCH$_2$F, —OCHF$_2$, —OCF$_3$, —OCH$_2$CH$_2$F, —OCH$_2$CHF$_2$, —OCH$_2$CF$_3$ and —OCF$_2$CF$_3$.

52. In embodiment 52, the compounds of any one of embodiments 1-51, or a pharmaceutically acceptable salt thereof, are those wherein $R^2$ can be —O-Alk-$R^{2A}$.

53. In embodiment 53 the compounds of any one of embodiments 1-51, or a pharmaceutically acceptable salt thereof, are those wherein $R^2$ can be —CH$_2$O-Alk-$R^{2A}$.

54. In embodiment 54, the compounds of any one of embodiments 1-53, or a pharmaceutically acceptable salt thereof, are those wherein Alk can be

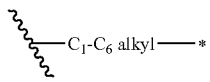

for which "*" represents the point of attachment of $R^{2A}$; wherein the alkylene chain can be optionally substituted with one or two substituents independently selected from hydroxy, alkoxy (for example, a $C_1$-$C_6$ alkoxy such as methoxy, ethoxy, n-propoxy, isopropoxy, n-butoxy, sec-butoxy, isobutoxy, t-butoxy, pentoxy (straight-chained or branched) or hexoxy (straight-chained or branched)), halogen (for example fluoro or chloro) and heterocyclylalkyl (for example a 5- or 6-membered heterocyclyl($C_1$-$C_3$ alkyl) group, such as those described herein); and wherein the $C_1$-$C_6$ alkyl of Alk can be straight-chained or branched. For example, in some aspects of embodiment 54, Alk can be an unsubstituted

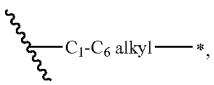

such as methylene, ethylene, n-propylene, isopropylene, n-butylene, sec-butylene, isobutylene, t-butylene, pentylene (straight-chained or branched) or hexylene (straight-chained or branched). In some aspects of embodiment 54, Alk can be an unsubstituted

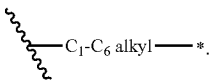

In some aspects of embodiment 54, Alk can be

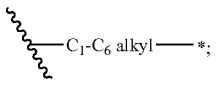

wherein the alkylene chain can be substituted with one substituent selected from hydroxy, fluoro, chloro, methoxy, ethoxy, n-propoxy, isopropoxy and methylpyrrolidino.

55. In embodiment 55, the compounds of any one of embodiments 1-54, or a pharmaceutically acceptable salt thereof, are those wherein Alk can be

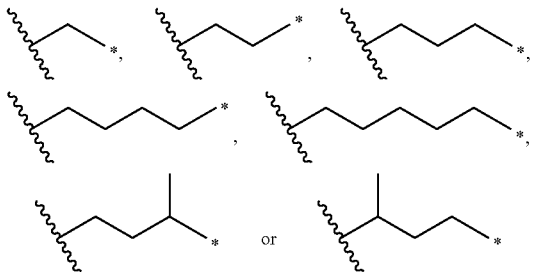

for which "*" represents the point of attachment of $R^{2A}$; and wherein the alkylene chain can be optionally substituted with one or two substituents independently selected from hydroxy, alkoxy (for example, a $C_1$-$C_6$ alkoxy such as methoxy, ethoxy, n-propoxy, isopropoxy, n-butoxy, t-butoxy, pentoxy (straight-chained or branched) or hexoxy (straight-chained or branched)), halogen (for example fluoro or chloro) and heterocyclylalkyl (for example a 5- or 6-membered heterocyclyl($C_1$-$C_3$ alkyl) group, such as those described herein). In some aspects of embodiment 55, the alkylene chain can be substituted with one substituent selected from hydroxy, fluoro, chloro, methoxy, ethoxy, n-propoxy, isopropoxy and methylpyrrolidino.

56. In embodiment 56, the compounds of any one of embodiments 1-55, or a pharmaceutically acceptable salt thereof, are those wherein Alk can be

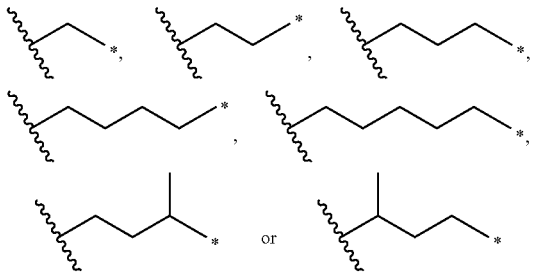

for which "*" represents the point of attachment of $R^{2A}$.

57. In embodiment 57, the compounds of any one of embodiments 1-53, or a pharmaceutically acceptable salt thereof, are those wherein Alk can be

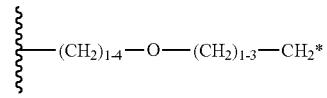

for which "*" represents the point of attachment of $R^{2A}$; and wherein the alkylene chain can be optionally substituted with one or two substituents independently selected from hydroxy, alkoxy (for example, a $C_1$-$C_6$ alkoxy such as methoxy, ethoxy, n-propoxy, isopropoxy, n-butoxy, t-butoxy, pentoxy (straight-chained or branched) or hexoxy (straight-chained or branched)), halogen (for example fluoro or chloro) and heterocyclylalkyl (for example a 5- or 6-membered heterocyclyl($C_1$-$C_3$ alkyl) group, such as those described herein). For example, in some aspects of embodiment 57, Alk can be

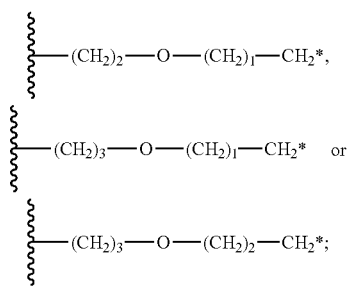

wherein the alkylene chain can be optionally substituted with one or two substituents independently selected from hydroxy, alkoxy (for example, a $C_1$-$C_6$ alkoxy such as methoxy, ethoxy, n-propoxy, isopropoxy, n-butoxy, t-butoxy, pentoxy (straight-chained or branched) or hexoxy (straight-chained or branched)), halogen (for example fluoro or chloro) and heterocyclylalkyl (for example a 5- or 6-membered heterocyclyl($C_1$-$C_3$ alkyl) group, such as those described herein). In some aspects of embodiment 57, the alkylene chain can be substituted with one substituent selected from hydroxy, fluoro, chloro, methoxy, ethoxy, n-propoxy, isopropoxy and methylpyrrolidino.

58. In embodiment 58, the compounds of embodiment 57, or a pharmaceutically acceptable salt thereof, are those wherein Alk can be

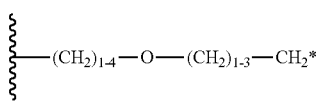

for which "*" represents the point of attachment of $R^{2A}$. For example, in some aspects of embodiment 57, Alk can be

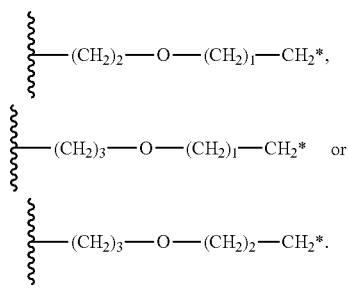

59. In embodiment 59 the compounds of embodiment 58, or a pharmaceutically acceptable salt thereof, are those wherein Alk can be

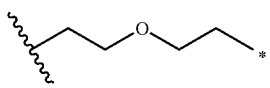 [SMILES: *CCOCCC]

for which "*" represents the point of attachment of $R^{2A}$.

60. In embodiment 60, the compounds of any one of embodiments 1-53, or a pharmaceutically acceptable salt thereof, are those wherein Alk can be

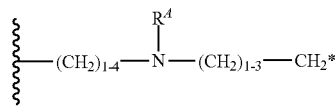

for which "*" represents the point of attachment of $R^{2A}$; wherein the alkylene chain can be optionally substituted with one or two substituents independently selected from hydroxy, alkoxy (for example, a $C_1$-$C_6$ alkoxy such as methoxy, ethoxy, n-propoxy, isopropoxy, n-butoxy, t-butoxy, pentoxy (straight-chained or branched) or hexoxy (straight-chained or branched)), halogen (for example fluoro or chloro) and heterocyclylalkyl (for example a 5- or 6-membered heterocyclyl($C_1$-$C_3$ alkyl) group, such as those described herein); and wherein $R^A$ can be hydrogen or a $C_1$-$C_6$ alkyl, for example, methyl, ethyl, n-propyl, isopropyl, n-butyl, sec-butyl, isobutyl, t-butyl, pentyl (straight-chained or branched) or hexyl (straight-chained or branched). In some aspects of embodiment 60, the alkylene chain can be substituted with one substituent selected from hydroxy, fluoro, chloro, methoxy, ethoxy, n-propoxy, isopropoxy and methylpyrrolidino.

61. In embodiment 61, the compounds of embodiment 60, or a pharmaceutically acceptable salt thereof, are those wherein Alk can be

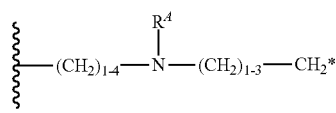

for which "*" represents the point of attachment of $R^{2A}$; and wherein $R^A$ can be hydrogen or a $C_1$-$C_3$ alkyl, such as those described herein, including methyl, ethyl, n-propyl or isopropyl.

62. In embodiment 62, the compounds of embodiment 61, or a pharmaceutically acceptable salt thereof, are those wherein Alk can be

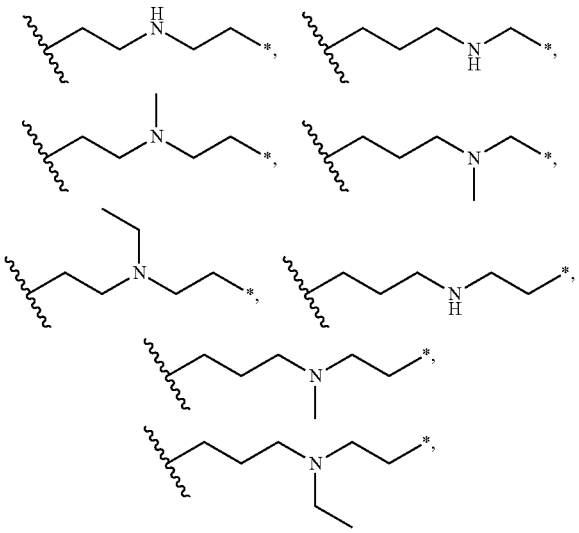

-continued

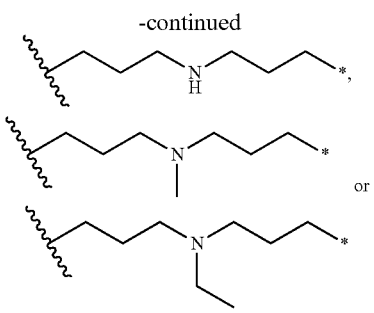

for which "*" represents the point of attachment of $R^{2A}$.
63. In embodiment 63, the compounds of any one of embodiments 1-53, or a pharmaceutically acceptable salt thereof, are those wherein Alk can be

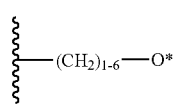

for which "*" represents the point of attachment of $R^{2A}$; and wherein the alkylene chain can be optionally substituted with one or two substituents independently selected from hydroxy, alkoxy (for example, a $C_1$-$C_6$ alkoxy such as methoxy, ethoxy, n-propoxy, isopropoxy, n-butoxy, t-butoxy, pentoxy (straight-chained or branched) or hexoxy (straight-chained or branched)), halogen (for example fluoro or chloro) and heterocyclylalkyl (for example a 5- or 6-membered heterocyclyl($C_1$-$C_3$ alkyl) group, such as those described herein). In some aspects of embodiment 63, Alk can be

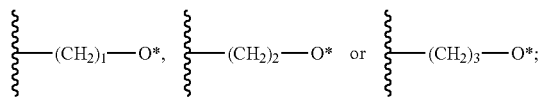

wherein the alkylene chain can be optionally substituted with one or two substituents independently selected from hydroxy, alkoxy (for example, a $C_1$-$C_6$ alkoxy such as methoxy, ethoxy, n-propoxy, isopropoxy, n-butoxy, t-butoxy, pentoxy (straight-chained or branched) or hexoxy (straight-chained or branched)), halogen (for example fluoro or chloro) and heterocyclylalkyl (for example a 5- or 6-membered heterocyclyl($C_1$-$C_3$ alkyl) group, such as those described herein). In some aspects of embodiment 63, the alkylene chain can be substituted with one substituent selected from hydroxy, fluoro, chloro, methoxy, ethoxy, n-propoxy, isopropoxy and methylpyrrolidino.
64. In embodiment 64, the compounds of embodiment 63, or a pharmaceutically acceptable salt thereof, are those wherein Alk can be selected from:

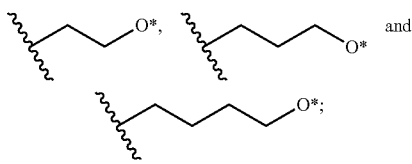

wherein the alkylene chain can be optionally substituted with one or two substituents independently selected from hydroxy, alkoxy (for example, a $C_1$-$C_6$ alkoxy such as methoxy, ethoxy, n-propoxy, isopropoxy, n-butoxy, t-butoxy, pentoxy (straight-chained or branched) or hexoxy (straight-chained or branched)), halogen (for example fluoro or chloro) and heterocyclylalkyl (for example a 5- or 6-membered heterocyclyl($C_1$-$C_3$ alkyl) group, such as those described herein). In some aspects of embodiment 64, the alkylene chain can be substituted with one substituent selected from hydroxy, fluoro, chloro, methoxy, ethoxy, n-propoxy, isopropoxy and methylpyrrolidino.
65. In embodiment 65, the compounds of embodiment 64, or a pharmaceutically acceptable salt thereof, are those wherein Alk can be selected from:

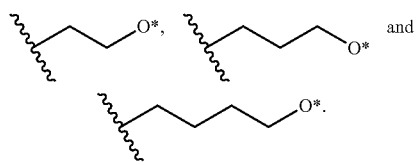

66. In embodiment 66, the compounds of any one of embodiments 1-53, or a pharmaceutically acceptable salt thereof, are those wherein Alk can be

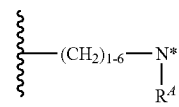

for which "*" represents the point of attachment of $R^{2A}$; wherein $R^A$ can be hydrogen or a $C_1$-$C_6$ alkyl (such as those described herein, for example, methyl, ethyl, n-propyl and isopropyl); and wherein the alkylene chain can be optionally substituted with one or two substituents independently selected from hydroxy, alkoxy (for example, a $C_1$-$C_6$ alkoxy such as methoxy, ethoxy, n-propoxy, isopropoxy, n-butoxy, t-butoxy, pentoxy (straight-chained or branched) or hexoxy (straight-chained or branched)), halogen (for example fluoro or chloro) and heterocyclylalkyl (for example a 5- or 6-membered heterocyclyl($C_1$-$C_3$ alkyl) group, such as those described herein). In some aspects of embodiment 66, Alk can be

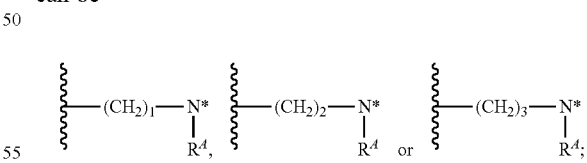

wherein the alkylene chain can be optionally substituted with one or two substituents independently selected from hydroxy, alkoxy, halogen and heterocyclylalkyl. In some aspects of embodiment 66, the alkylene chain can be substituted with one substituent selected from hydroxy, fluoro, chloro, methoxy, ethoxy, n-propoxy, isopropoxy and methylpyrrolidino.
67. In embodiment 67, the compounds of embodiment 66, or a pharmaceutically acceptable salt thereof, are those wherein Alk can be selected from:

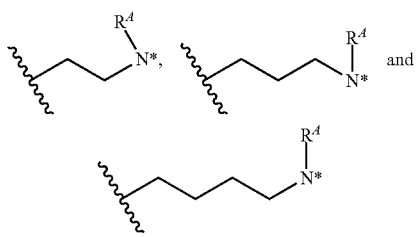

for which "*" represents the point of attachment of $R^{2A}$; wherein $R^A$ can be hydrogen or a $C_1$-$C_3$ alkyl; and wherein the alkylene chain can be optionally substituted with one or two substituents independently selected from hydroxy, alkoxy (for example, a $C_1$-$C_6$ alkoxy such as methoxy, ethoxy, n-propoxy, isopropoxy, n-butoxy, t-butoxy, pentoxy (straight-chained or branched) or hexoxy (straight-chained or branched)), halogen (for example fluoro or chloro) and heterocyclylalkyl (for example a 5- or 6-membered heterocyclyl($C_1$-$C_3$ alkyl) group, such as those described herein). In some aspects of embodiment 67, the alkylene chain can be substituted with one substituent selected from hydroxy, fluoro, chloro, methoxy, ethoxy, n-propoxy, isopropoxy and methylpyrrolidino.

68. In embodiment 68, the compounds of embodiment 67, or a pharmaceutically acceptable salt thereof, are those wherein Alk can be selected from:

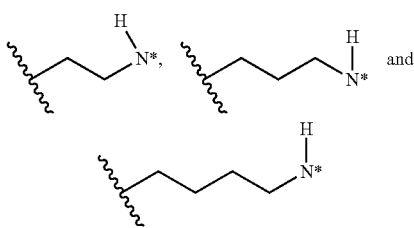

for which "*" represents the point of attachment of $R^{2A}$.

69. In embodiment 69, the compounds of any one of embodiments 1-53, or a pharmaceutically acceptable salt thereof, are those wherein Alk can be

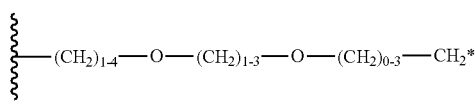

for which "*" represents the point of attachment of $R^{2A}$; and wherein the alkylene chain can be optionally substituted with one or two substituents independently selected from hydroxy, alkoxy (for example, a $C_1$-$C_6$ alkoxy such as methoxy, ethoxy, n-propoxy, isopropoxy, n-butoxy, t-butoxy, pentoxy (straight-chained or branched) or hexoxy (straight-chained or branched)), halogen (for example fluoro or chloro) and heterocyclylalkyl (for example a 5- or 6-membered heterocyclyl($C_1$-$C_3$ alkyl) group, such as those described herein). In some aspects of embodiment 69, Alk can be

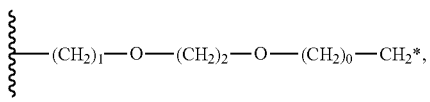

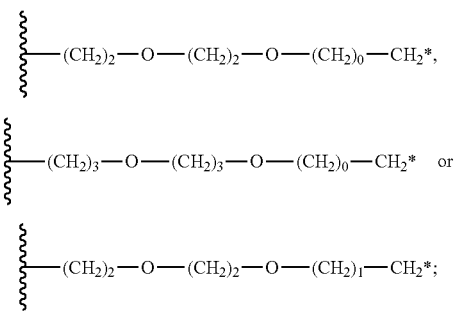

wherein the alkylene chain can be optionally substituted with one or two substituents independently selected from hydroxy, alkoxy, halogen and heterocyclylalkyl. In some aspects of embodiment 69, the alkylene chain can be substituted with one substituent selected from hydroxy, fluoro, chloro, methoxy, ethoxy, n-propoxy, isopropoxy and methylpyrrolidino.

70. In embodiment 70, the compounds of embodiment 69, or a pharmaceutically acceptable salt thereof, are those wherein Alk can be selected from:

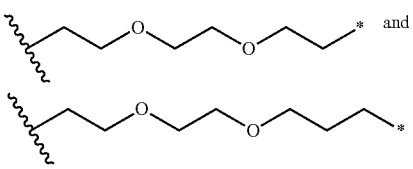

for which "*" represents the point of attachment of $R^{2A}$; and wherein the alkylene chain can be optionally substituted with one or two substituents independently selected from hydroxy, alkoxy (for example, a $C_1$-$C_6$ alkoxy such as methoxy, ethoxy, n-propoxy, isopropoxy, n-butoxy, t-butoxy, pentoxy (straight-chained or branched) or hexoxy (straight-chained or branched)), halogen (for example fluoro or chloro) and heterocyclylalkyl (for example a 5- or 6-membered heterocyclyl($C_1$-$C_3$ alkyl) group, such as those described herein). In some aspects of embodiment 70, the alkylene chain can be substituted with one substituent selected from hydroxy, fluoro, chloro, methoxy, ethoxy, n-propoxy, isopropoxy and methylpyrrolidino.

71. In embodiment 71, the compounds of embodiment 70, or a pharmaceutically acceptable salt thereof, are those wherein Alk can be selected from:

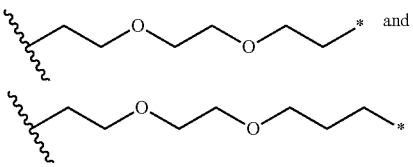

for which "*" represents the point of attachment of $R^{2A}$.

72. In embodiment 72, the compounds of any one of embodiments 1-53, or a pharmaceutically acceptable salt thereof, are those wherein Alk can be selected from:

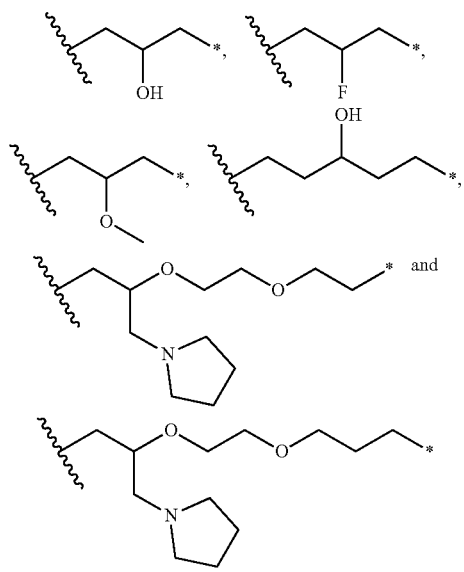

for which "*" represents the point of attachment of $R^{2A}$.

73. In embodiment 73, the compounds of any one of embodiments 1-72, or a pharmaceutically acceptable salt thereof, are those wherein $R^{2A}$ can be heterocyclyl, optionally substituted with one or more $R^B$, independently selected from hydroxy, alkyl (for example, a $C_1$-$C_6$ alkyl as described herein, and including methyl, ethyl, n-propyl and isopropyl), alkoxy (for example, a $C_1$-$C_6$ alkoxy as described herein, and including methoxy, ethoxy, n-propoxy and isopropoxy), halogen (for example, fluoro or chloro), cyano, heterocyclylalkyl (for example a 5- or 6-membered heterocyclyl group, such as those described herein), haloalkyl (for example, a $C_1$-$C_3$ haloalkyl such, as those described herein, including —$CF_3$, —$CHF_2$ and —$CH_2F$), and haloalkoxy (for example, a $C_1$-$C_6$ haloalkoxy as described herein, and including —$OCF_3$, —$OCHF_2$ and —$OCH_2F$). In some aspects of embodiment 73, $R^{2A}$ can be, for example, a 4- to 6-membered monocyclic heterocyclyl or a 6- to 10-membered bicyclic heterocyclyl. In some aspects of embodiment 73, $R^{2A}$ can be, for example, a nitrogen-containing 4- to 6-membered monocyclic heterocyclyl. In some aspects of embodiment 73, $R^{2A}$ can be, for example, a 4- to 6-membered monocyclic heterocyclyl containing one nitrogen atom or a 5- to 6-membered monocyclic heterocyclyl containing one nitrogen atom and one oxygen atom. Exemplary heterocyclyl groups include, but are not limited to: 1,3 dioxole, 2,3-dihydroimidazole, 2,3-dihydrofuran, pyrrolidine, 1,4 dioxine and 3,4-dihydro-1,4-oxazine.

74. In embodiment 74, the compounds of any one of embodiments 1-73, or a pharmaceutically acceptable salt thereof, are those wherein $R^{2A}$ can be an unsubstituted heterocyclyl, for example, a 4- to 6-membered monocyclic heterocyclyl such as: 1,3 dioxole, 2,3-dihydroimidazole, 2,3-dihydrofuran, pyrrolidine, 1,4 dioxine and 3,4-dihydro-1,4-oxazine.

75. In embodiment 75, the compounds of any one of embodiments 1-74, or a pharmaceutically acceptable salt thereof, are those wherein $R^{2A}$ can be an unsubstituted heterocyclyl selected from:

76. In embodiment 76, the compounds of any one of embodiments 1-75, or a pharmaceutically acceptable salt thereof, are those wherein $R^{2A}$ can be

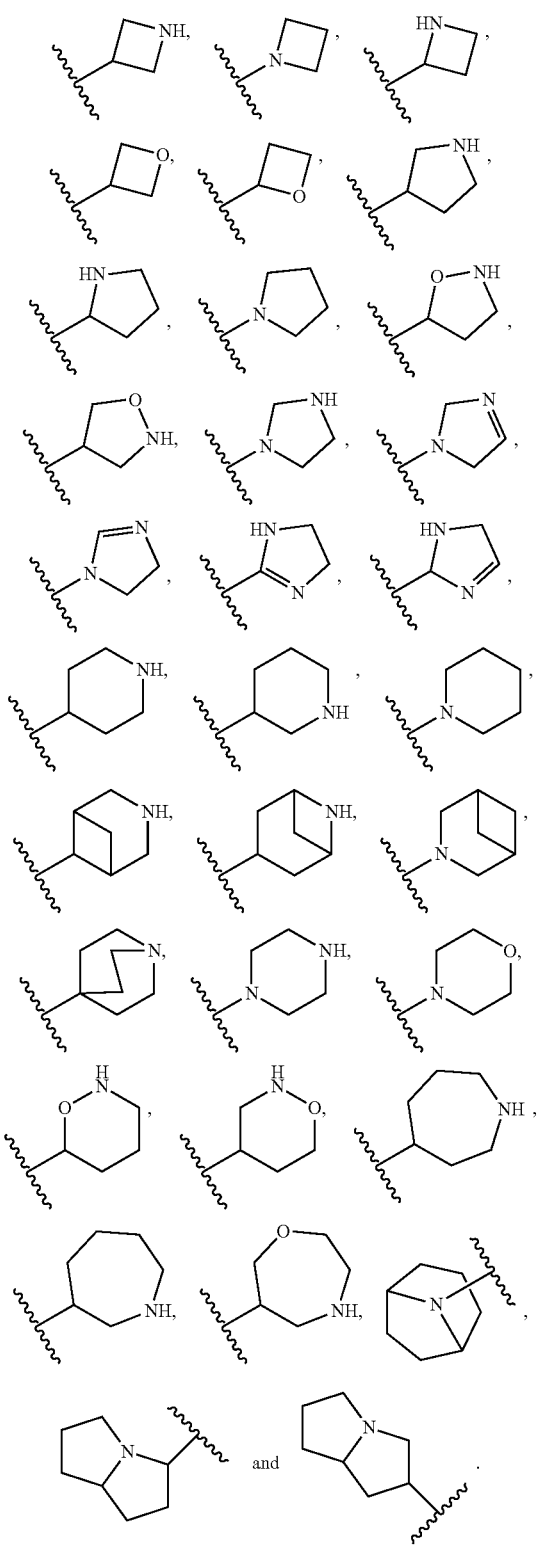

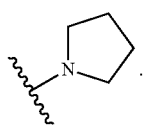 [SMILES: *N1CCCC1]

77. In embodiment 77, the compounds of any one of embodiments 1-73, or a pharmaceutically acceptable salt thereof, are those wherein $R^{2A}$ can be heterocyclyl substituted with one or two $R^B$, independently selected from hydroxy, alkyl (for example, a $C_1$-$C_6$ alkyl, such as those described herein, including methyl, ethyl, n-propyl and isopropyl), alkoxy (for example, a $C_1$-$C_6$ alkoxy, such as those described herein, including methoxy, ethoxy, n-propoxy and isopropoxy), halogen (for example, fluoro or chloro), cyano, heterocyclylalkyl (for example, a 5- to 6-membered nitrogen-containing monocyclic heterocyclyl as described herein, and a $C_1$-$C_3$ alkyl), haloalkyl (for example, a $C_1$-$C_3$ haloalkyl such as those described herein, including —$CF_3$, —$CHF_2$ and —$CH_2F$), and haloalkoxy (for example, a $C_1$-$C_6$ haloalkoxy, such as those described herein, including —$OCF_3$, —$OCHF_2$ and —$OCH_2F$).

78. In embodiment 78, the compounds of embodiment 77, or a pharmaceutically acceptable salt thereof, are those wherein each $R^{2A}$ can be substituted with one $R^B$, independently selected from hydroxy, alkyl (for example, a $C_1$-$C_6$ alkyl, such as those described herein, including methyl, ethyl, n-propyl and isopropyl), alkoxy (for example, a $C_1$-$C_6$ alkoxy, such as those described herein, including methoxy, ethoxy, n-propoxy and isopropoxy), halogen (for example, fluoro or chloro), cyano, haloalkyl (for example, a $C_1$-$C_3$ haloalkyl, such as those described herein, including —$CF_3$, —$CHF_2$ and —$CH_2F$), and haloalkoxy (for example, a $C_1$-$C_6$ haloalkoxy, such as those described herein, including —$OCF_3$, —$OCHF_2$ and —$OCH_2F$).

79. In embodiment 79, the compounds of embodiment 78, or a pharmaceutically acceptable salt thereof, are those wherein $R^{2A}$ can be selected from:

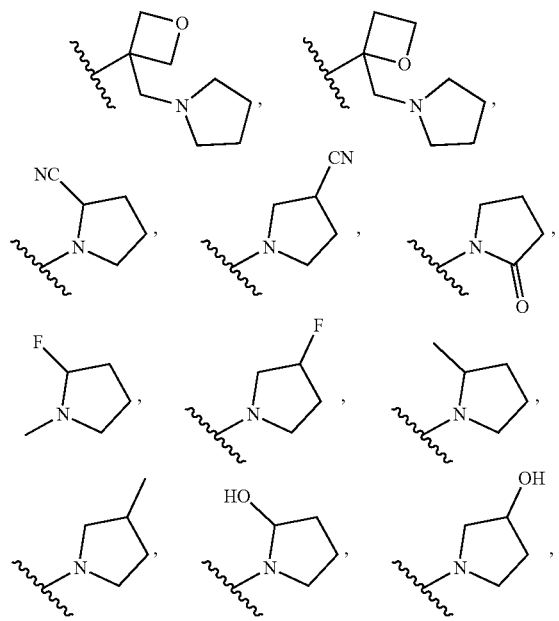

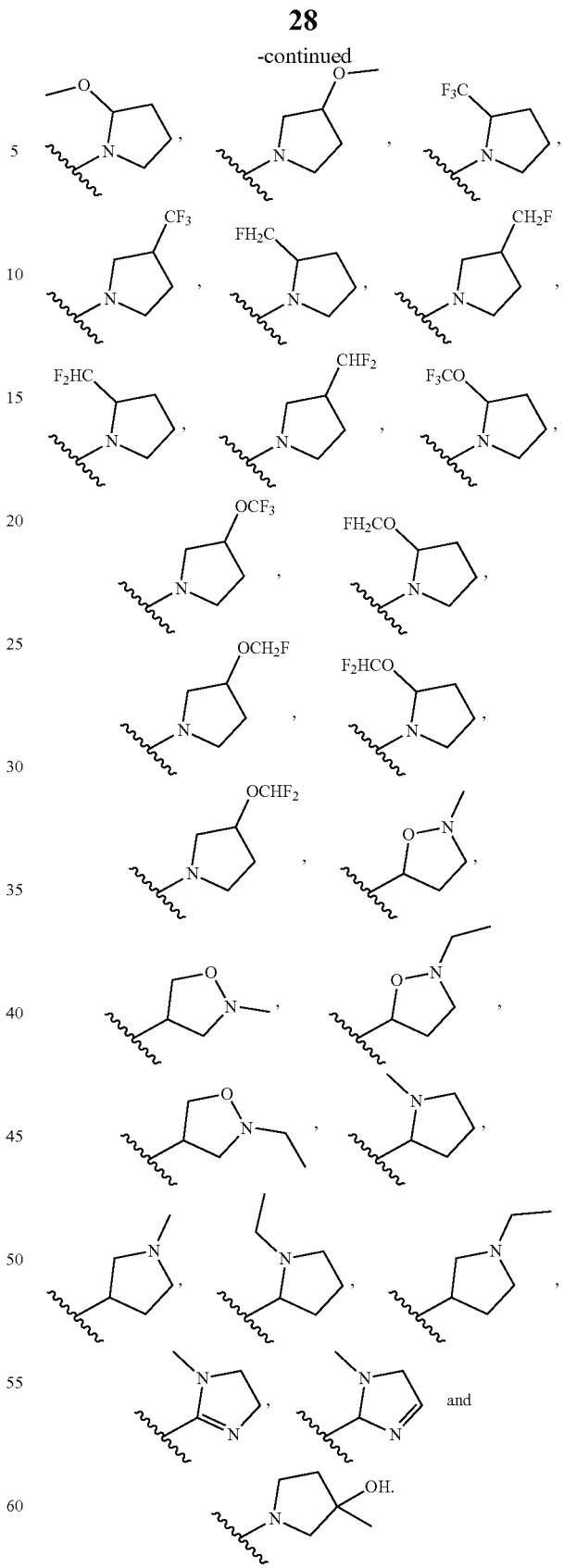

80. In embodiment 80, the compounds of any one of embodiments 1-72, or a pharmaceutically acceptable salt thereof, are those wherein $R^{2A}$ can be aminocarbonyl.

81. In embodiment 81, the compounds of embodiment 80, or a pharmaceutically acceptable salt thereof, are those wherein $R^{2A}$ can be selected from:

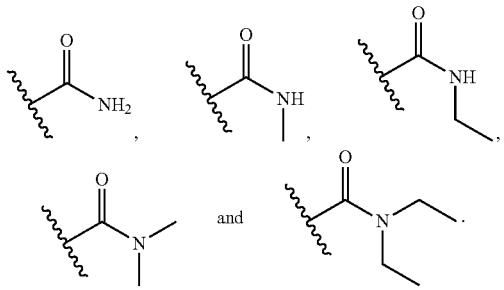

82. In embodiment 82, the compounds of any one of embodiments 1-72, or a pharmaceutically acceptable salt thereof, are those wherein $R^{2A}$ can be sulfamido.
83. In embodiment 83, the compounds of any one of embodiments 1-72, or a pharmaceutically acceptable salt thereof, are those wherein $R^{2A}$ can be alkylcarbonyl.
84. In embodiment 84, the compounds of embodiment 83, or a pharmaceutically acceptable salt thereof, are those wherein $R^{2A}$ can be acetyl.
85. In embodiment 85, the compounds of any one of embodiments 83-84, or a pharmaceutically acceptable salt thereof, are those wherein $R^{2A}$ can be acetyl bonded to a nitrogen atom in Alk.
86. In embodiment 86, the compounds of any one of embodiments 1-72, or a pharmaceutically acceptable salt thereof, are those wherein $R^{2A}$ can be S-sulfonamido (optionally substituted with one or two alkyl groups, for example, $C_1$-$C_6$ alkyl groups such as methyl, ethyl, n-propyl, isopropyl, n-butyl, sec-butyl, isobutyl, t-butyl, pentyl (straight-chained or branched) and hexyl (straight-chained or branched)).
87. In embodiment 87, the compounds of embodiment 86, or a pharmaceutically acceptable salt thereof, are those wherein $R^{2A}$ can be an unsubstituted S-sulfonamido.
88. In embodiment 88, the compounds of embodiment 86, or a pharmaceutically acceptable salt thereof, are those wherein $R^{2A}$ can be S-sulfonamido substituted with two alkyl groups, such as $C_1$-$C_6$ alkyl groups described herein.
89. In embodiment 89, the compounds of any one of embodiments 1-72, or a pharmaceutically acceptable salt thereof, are those wherein $R^{2A}$ can be N-sulfonamido.
90. In embodiment 90, the compounds of any one of embodiments 1-72, or a pharmaceutically acceptable salt thereof, are those wherein $R^{2A}$ can be alkylamino. In some aspects of embodiment 90, $R^{2A}$ can be a $C_1$-$C_6$ alkylamino, such as methylamino, dimethylamino, isopropylethylamino, diiso-butylamino or pentyl (straight-chained or branched)amino.
91. In embodiment 91, the compounds of embodiment 90, or a pharmaceutically acceptable salt thereof, are those wherein $R^{2A}$ can be selected from —$NHCH_3$, —$NHCH_2CH_3$, —$NHC(CH_3)_2$, —$N(CH_3)(CH_2CH_3)$, —$N(CH_3)_2$, —$N(CH_2CH_3)_2$ and —$N[CH(CH_3)]_2$.
92. In embodiment 92, the compounds of any one of embodiments 1-72, or a pharmaceutically acceptable salt thereof, are those wherein $R^{2A}$ can be haloalkyl, for example a $C_1$-$C_6$ haloalkyl.
93. In embodiment 93, the compounds of embodiment 92, or a pharmaceutically acceptable salt thereof, are those wherein $R^{2A}$ can be selected from —$CH_2F$, —$CHF_2$, —$CF_3$, —$CH_2CH_2F$, —$CH_2CHF_2$, —$CH_2CF_3$ and —$CF_2CF_3$.
94. In embodiment 94 the compounds of any one of embodiments 1-72, or a pharmaceutically acceptable salt thereof, are those wherein $R^{2A}$ can be alkoxy, for example, a $C_1$-$C_6$ alkoxy, such as methoxy, ethoxy, isopropoxy, n-propoxy, n-butoxy, isobutoxy, sec-butoxy, t-butoxy, pentoxy (straight chained or branched) or hexoxy (straight chained or branched).
95. In embodiment 95 the compounds of embodiment 94, or a pharmaceutically acceptable salt thereof, are those wherein $R^{2A}$ can be selected from —$OCH_3$, —$OCH_2CH_3$ and —$OC(CH_3)_2$.
96. In embodiment 96, the compounds of any one of embodiments 1-72, or a pharmaceutically acceptable salt thereof, are those wherein $R^{2A}$ can be amino.
97. In embodiment 97, the compounds of any one of embodiments 1-72, or a pharmaceutically acceptable salt thereof, are those wherein $R^{2A}$ can be hydroxy.
98. In embodiment 98, the compounds of any one of embodiments 1-72, or a pharmaceutically acceptable salt thereof, are those wherein $R^{2A}$ can be spiroheterocycloamino, optionally substituted with one or more $R_C$, independently selected from alkyl (for example, a $C_1$-$C_6$ alkyl, such as methyl, ethyl, n-propyl, isopropyl, n-butyl, sec-butyl, isobutyl, t-butyl, pentyl (straight-chained or branched) and hexyl (straight-chained or branched)). In some aspects of embodiment 98, the spiroheterocycloamino can be a nitrogen-containing 7- to 10-membered ring system. In some aspects of embodiment 98, the spiroheterocycloamino can be a 7- to 10-membered ring system containing nitrogen and oxygen. In some aspects of embodiment 98, the spiroheterocycloamino can be 2-azaspiro[3.3]heptane, 2-oxaspiro[3.3]heptane, 1-azaspiro[3.3]heptane, 1-oxaspiro[3.3]heptane, 5-oxaspiro[3.4]octane, 5-azaspiro[3.4]octane, 2-oxaspiro[3.4]octane, 2-azaspiro[3.4]octane, 1-oxa-4-azaspiro[4.4]nonane, 1,4-dioxaspiro[4.4]nonane, 2-azaspiro[3.5]nonane, 2-oxaspiro[3.5]nonane, 4-azaspiro[2.5]octane, 4-oxaspiro[2.5]octane, 1,4-dioxaspiro[4.5]decane, 1-thiaspiro[4.5]decane 1,1-dioxide or 2-oxa-1-azaspiro[4.5]decane.
99. In embodiment 99, the compounds of embodiment 98, or a pharmaceutically acceptable salt thereof, are those wherein $R^{2A}$ can be selected from:

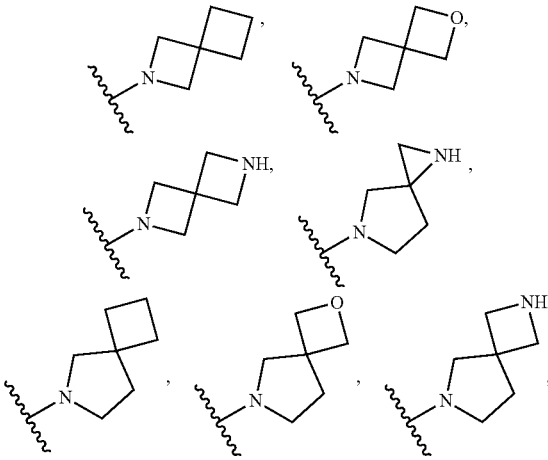

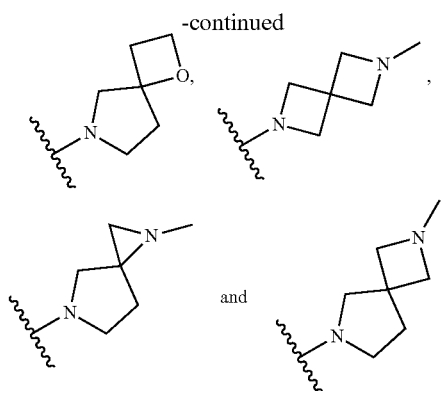

100. In embodiment 100, the compounds of any one of embodiments 1-72, or a pharmaceutically acceptable salt thereof, are those wherein $R^{2A}$ can be heteroaryl, optionally substituted with one or more $R^D$, independently selected from alky, alkoxy, halogen (for example, fluoro and chloro) and hydroxy. In some aspects of embodiment 100, the heteroaryl group can be a 5-membered heteroaryl group, a 6-membered heteroaryl group or a 10-membered heteroaryl group. In some aspects of embodiment 100, the heteroaryl group can be a monocyclic 5- or 6-membered heteroaryl. In some aspects of embodiment 100, the heteroaryl group can be a nitrogen-containing 5- or 6-membered monocyclic heteroaryl group. In some aspects of embodiment 102, the heteroaryl group can be a 5- or 6-membered heteroaryl group containing nitrogen and oxygen. In some aspects of embodiment 100, the heteroaryl group can be, for example, pyrrole, pyrazole, imidazole, 1,2,4-triazole, furan, thiophene, oxazole, isoxazole, thiazole, isothiazole, 1,2,5-oxadiazole, 1,2,3-oxadiazole, 1,3,4-thiadiazole, pyridine, pyridazine, pyrimidine, pyrazine, 1,2,4-triazine or 1,3,5-traizine.

101. In embodiment 101, the compounds of embodiment 100, or a pharmaceutically acceptable salt thereof, are those wherein $R^{2A}$ can be a 5- or 6-membered heteroaryl, optionally substituted with one or two $R^D$, independently selected from alky (for example, a $C_1$-$C_6$ alkyl, such as methyl, ethyl, n-propyl, isopropyl, n-butyl, sec-butyl, isobutyl, t-butyl, pentyl (straight-chained or branched) and hexyl (straight-chained or branched)), alkoxy (for example, a $C_1$-$C_6$ alkoxy, such as methoxy, ethoxy, n-propoxy, isopropoxy, n-butoxy, pentoxy (straight-chained or branched) and hexoxy (straight-chained or branched)), halogen (for example fluoro and chloro) and hydroxy. In some aspects of embodiment 101, when $R^{2A}$ is a 6-membered heteroaryl substituted with one $R^D$, the $R^D$ can be at the ortho, meta or para position relative to the point of attachment of the heteroaryl ring to the rest of the compound of Formula (I). In some aspects of embodiment 101, when $R^{2A}$ is a 6-membered heteroaryl substituted with two $R^D$, one $R^D$ can be at the ortho position and the other $R^D$ can be at the meta position relative to the point of attachment of the heteroaryl ring to the rest of the compound of Formula (I). In some aspects of embodiment 101, when $R^{2A}$ is a 6-membered heteroaryl substituted with two $R^D$, one $R^D$ can be at the ortho position and the other $R^D$ can be at the para position relative to the point of attachment of the heteroaryl ring to the rest of the compound of Formula (I). In some aspects of embodiment 101, when $R^{2A}$ is a 6-membered heteroaryl substituted with two $R^D$, one $R^D$ can be at one meta position and the other $R^D$ can be at the other meta position relative to the point of attachment of the heteroaryl ring to the rest of the compound of Formula (I). In some aspects of embodiment 101, when $R^{2A}$ is a 6-membered heteroaryl substituted with two $R^D$, one $R^D$ can be at one ortho position and the other $R^D$ can be at the other ortho position relative to the point of attachment of the heteroaryl ring to the rest of the compound of Formula (I). In some aspects of embodiment 101, when $R^{2A}$ is a 6-membered heteroaryl substituted with two $R^D$, one $R^D$ can be at the meta position and the other $R^D$ can be at the para position relative to the point of attachment of the heteroaryl ring to the rest of the compound of Formula (I).

102. In embodiment 102, the compounds of any one of embodiments 100-101, or a pharmaceutically acceptable salt thereof, are those wherein $R^{2A}$ can be selected from:

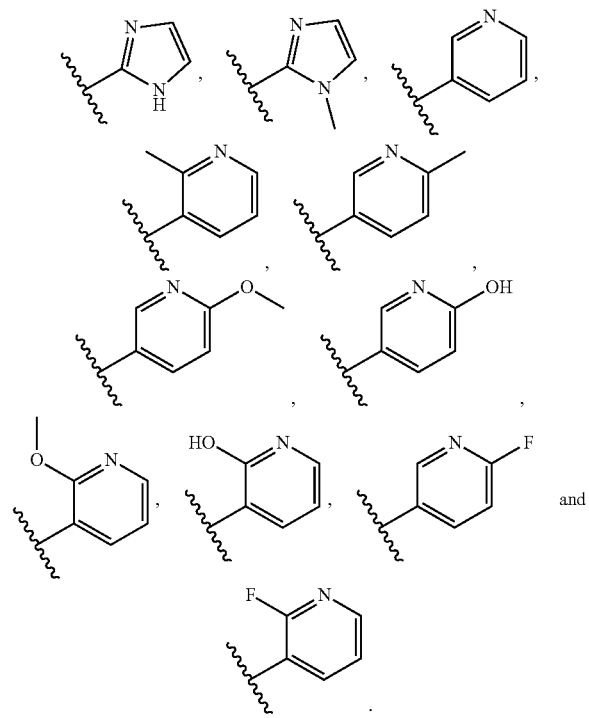

103. In embodiment 103, the compounds of any one of embodiments 1-72, or a pharmaceutically acceptable salt thereof, are those wherein $R^{2A}$ can be cycloalkyl, optionally substituted with one or more $R^E$, independently selected from hydroxy and heterocyclylalkyl (for example, a 5- or 6-membered nitrogen-containing monocyclic heterocyclyl($C_1$-$C_3$ alkyl)). In some aspects of embodiment 103, the cycloalkyl can be a monocyclic $C_3$-$C_8$ cycloalkyl. In some aspects of embodiment 103, the cycloalkyl can be a bicyclic $C_6$-$C_{10}$ cycloalkyl.

104. In embodiment 104, the compounds of embodiment 103, or a pharmaceutically acceptable salt thereof, are those wherein $R^{2A}$ can be cycloalkyl, optionally substituted with one or two $R^E$, independently selected from hydroxy and heterocyclylalkyl (for example, a 5- or 6-membered nitrogen-containing monocyclic heterocyclyl($C_1$-$C_3$ alkyl)). In some aspects of embodiment 104, the cycloalkyl can be a monocyclic $C_3$-$C_8$ cycloalkyl. In some aspects of embodiment 104, the cycloalkyl can be a bicyclic $C_6$-$C_{10}$ cycloalkyl. In some aspects of embodiment 104, at least one $R^E$ is attached to the same carbon atom connecting the cycloalkyl group to the rest of the compound of Formula (I).

105. In embodiment 105, the compounds of any one of embodiments 103-104, or a pharmaceutically acceptable salt thereof, are those wherein $R^{2A}$ can be selected from:

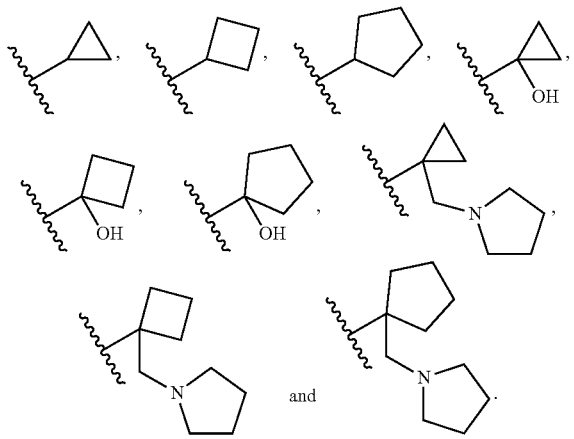

106. In embodiment 106, the compounds of any one of embodiments 1-72, or a pharmaceutically acceptable salt thereof, are those wherein $R^{2A}$ can be aryl (for example a $C_6$ aryl or a $C_{10}$ aryl), optionally substituted with one or more $R^E$, independently selected from hydroxy, halogen (for example, fluoro or chloro), alkoxy (for example, a $C_1$-$C_6$ alkoxy, such as methoxy, ethoxy, n-propoxy, isopropoxy, n-butoxy, pentoxy (straight-chained or branched) and hexoxy (straight-chained or branched)) and alkyl (for example, a $C_1$-$C_6$ alkyl, such as methyl, ethyl, n-propyl, isopropyl, n-butyl, sec-butyl, isobutyl, t-butyl, pentyl (straight-chained or branched) and hexyl (straight-chained or branched)).

107. In embodiment 107, the compounds of embodiment 106, or a pharmaceutically acceptable salt thereof, are those wherein $R^{2A}$ can be a $C_6$ aryl, optionally substituted with one, two or three $R^E$, independently selected from hydroxy, halogen (for example, fluoro or chloro), alkoxy (for example, a $C_1$-$C_6$ alkoxy, such as methoxy, ethoxy, n-propoxy, isopropoxy, n-butoxy, pentoxy (straight-chained or branched) and hexoxy (straight-chained or branched)) and alkyl (for example, a $C_1$-$C_6$ alkyl, such as methyl, ethyl, n-propyl, isopropyl, n-butyl, sec-butyl, isobutyl, t-butyl, pentyl (straight-chained or branched) and hexyl (straight-chained or branched)). In some aspects of embodiment 107, when $R^{2A}$ can be substituted with one $R^E$, the $R^E$ can be in the ortho, meta or para position relative to the point of attachment of the aryl ring to the rest of the compound of Formula (I). In some aspects of embodiment 107, when $R^{2A}$ is an aryl substituted with two $R^F$, one $R^F$ can be at the ortho position and the other $R^F$ can be at the meta position relative to the point of attachment of the aryl ring to the rest of the compound of Formula (I). In some aspects of embodiment 107, one $R^F$ can be at the ortho position and the other $R^F$ can be at the para position relative to the point of attachment of the aryl ring to the rest of the compound of Formula (I). In some aspects of embodiment 107, one $R^F$ can be at one meta position and the other $R^F$ can be at the other meta position relative to the point of attachment of the aryl ring to the rest of the compound of Formula (I).

In some aspects of embodiment 107, one $R^F$ can be at one ortho position and the other $R^F$ can be at the other ortho position relative to the point of attachment of the aryl ring to the rest of the compound of Formula (I). In some aspects of embodiment 107, one $R^F$ can be at the meta position and the other $R^F$ can be at the para position relative to the point of attachment of the aryl ring to the rest of the compound of Formula (I).

108. In embodiment 108, the compounds of any one of embodiments 106-107, or a pharmaceutically acceptable salt thereof, are those wherein $R^{2A}$ can be selected from:

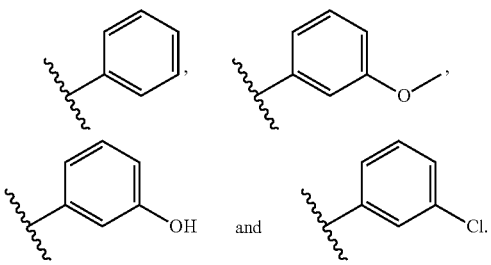

109. In embodiment 109, the compounds of any one of embodiments 1-51, or a pharmaceutically acceptable salt thereof, are those wherein $R^2$ can be cycloalkoxy (optionally substituted with heterocyclylalkyl, for example, a 4- to 7-membered nitrogen-containing monocyclic heterocyclyl($C_1$-$C_3$ alkyl)). In some aspects of embodiment 109, the cycloalkoxy group can be a monocyclic $C_3$-$C_8$ cycloalkoxy such as cyclopropoxy, cyclobutoxy, cyclopentoxy, cycloheptoxy or cyclooctoxy. In some aspects of embodiment 109, the cycloalkoxy group can be a $C_6$-$C_{10}$ bicyclic cycloalkoxy, for example, a fused, spiro or bridged cycloalkoxy, for example, octahydropentalenoxy, bicyclo[3.1.1]heptanoxy or bicyclo[2.2.1]heptanoxy.

110. In embodiment 110, the compounds of embodiment 109, or a pharmaceutically acceptable salt thereof, are those wherein $R^2$ can be an unsubstituted cycloalkoxy, for example, a monocyclic $C_3$-$C_8$ cycloalkoxy such as cyclopropoxy, cyclobutoxy, cyclopentoxy, cycloheptoxy or cyclooctoxy.

111. In embodiment 111, the compounds of any one of embodiments 109-110, or a pharmaceutically acceptable salt thereof, are those wherein $R^2$ can be selected from cyclopropoxy, cyclobutoxy, cyclopentoxy and cyclohexoxy.

112. In embodiment 112, the compounds of embodiment 109, or a pharmaceutically acceptable salt thereof, are those wherein $R^2$ can be selected from:

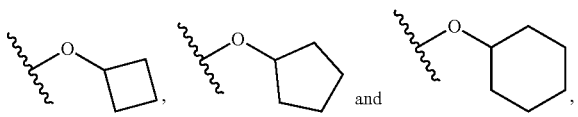

each substituted with heterocyclylalkyl, for example, a 4- to 7-membered nitrogen-containing monocyclic heterocyclyl ($C_1$-$C_3$ alkyl), such as azetidinylmethyl, pyrrolidinylmethyl, piperidinylmethyl, azepanylmethyl and 1,4-oxazepanylmethyl.

113. In embodiment 113, the compounds of embodiment 112, or a pharmaceutically acceptable salt thereof, are those wherein R² can be cycloalkoxy substituted with heterocyclylalkyl selected from

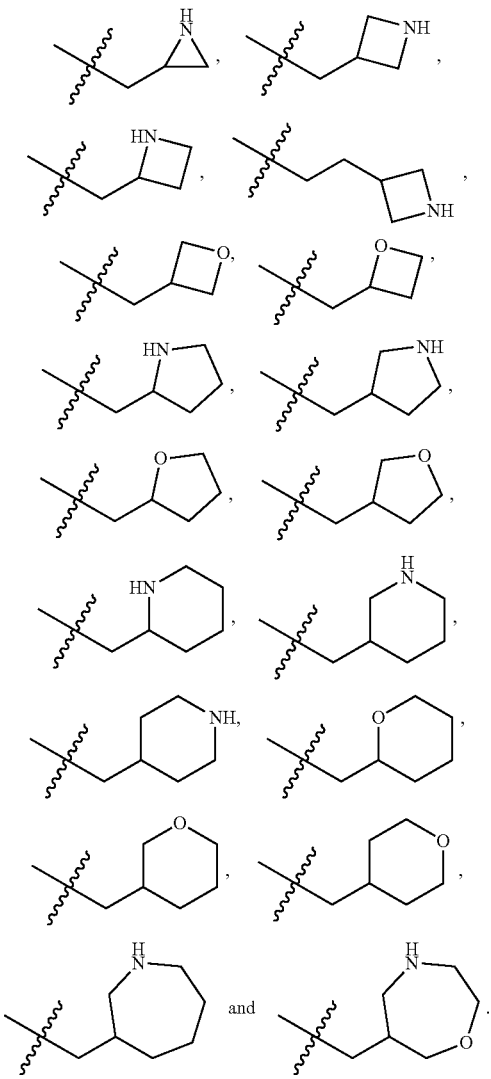

114. In embodiment 114, the compounds of embodiment 112, or a pharmaceutically acceptable salt thereof, are those wherein R² can be selected from:

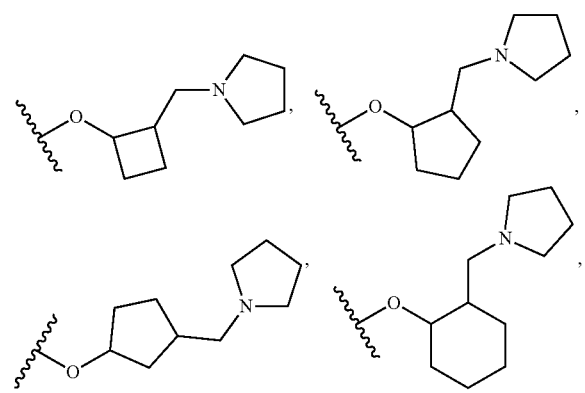

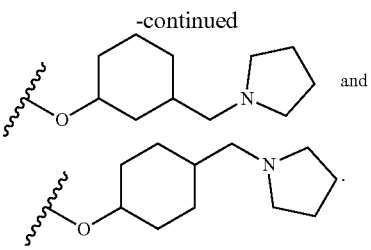

115. In embodiment 115, the compounds of any one of embodiments 1-114, or a pharmaceutically acceptable salt thereof, are those wherein $R^{3A}$ can be alkyl (optionally substituted with one or more $R^G$, independently selected from alkoxy (for example, a $C_1$-$C_6$ alkoxy, such as methoxy, ethoxy, n-propoxy, isopropoxy, n-butoxy, pentoxy (straight-chained or branched) and hexoxy (straight-chained or branched)), hydroxy and cyano). In some aspects of embodiment 115, the alkyl is a $C_1$-$C_8$ alkyl, for example, methyl, ethyl, n-propyl, isopropyl, n-butyl, sec-butyl, isobutyl, t-butyl, pentyl (straight-chained or branched), hexyl (straight-chained or branched), heptyl (straight-chained or branched) and octyl (straight-chained or branched).

116. In embodiment 116, the compounds of embodiment 115, or a pharmaceutically acceptable salt thereof, are those wherein $R^{3A}$ can be an unsubstituted alkyl, for example, a $C_1$-$C_8$ alkyl, for example, methyl, ethyl, n-propyl, isopropyl, n-butyl, sec-butyl, isobutyl, t-butyl, pentyl (straight-chained or branched), hexyl (straight-chained or branched), heptyl (straight-chained or branched) and octyl (straight-chained or branched).

117. In embodiment 117, the compounds of any one of embodiments 115-116, or a pharmaceutically acceptable salt thereof, are those wherein $R^{3A}$ can be —$CH_3$, —$CH_2CH_3$, —$CH_2CH_2CH_3$, —$CH(CH_3)_2$ or —$CH_2CH_2CH_2CH_3$.

118. In embodiment 118, the compounds of embodiment 115, or a pharmaceutically acceptable salt thereof, are those wherein $R^{3A}$ can be alkyl (for example, a $C_1$-$C_8$ alkyl, such as methyl, ethyl, n-propyl, isopropyl, n-butyl, sec-butyl, isobutyl, t-butyl, pentyl (straight-chained or branched), hexyl (straight-chained or branched), heptyl (straight-chained or branched) and octyl (straight-chained or branched)) substituted with one or more $R^G$, independently selected from alkoxy (for example, a $C_1$-$C_6$ alkoxy, such as methoxy, ethoxy, n-propoxy, isopropoxy, n-butoxy, pentoxy (straight-chained or branched) and hexoxy (straight-chained or branched)), hydroxy and cyano.

119. In embodiment 119, the compounds of embodiment 118, or a pharmaceutically acceptable salt thereof, are those wherein $R^{3A}$ can be alkyl substituted with one $R^G$, independently selected from alkoxy (for example, a $C_1$-$C_6$ alkoxy, such as methoxy, ethoxy, n-propoxy, isopropoxy, n-butoxy, pentoxy (straight-chained or branched) and hexoxy (straight-chained or branched)), hydroxy and cyano. In some aspects of embodiment 119, the alkyl is a $C_1$-$C_8$ alkyl, for example, methyl, ethyl, n-propyl, isopropyl, n-butyl, sec-butyl, isobutyl, t-butyl, pentyl (straight-chained or branched), hexyl (straight-chained or branched), heptyl (straight-chained or branched) and octyl (straight-chained or branched).

120. In embodiment 120, the compounds of any one of embodiments 118-119, or a pharmaceutically acceptable salt thereof, are those wherein $R^{3A}$ can be selected from:

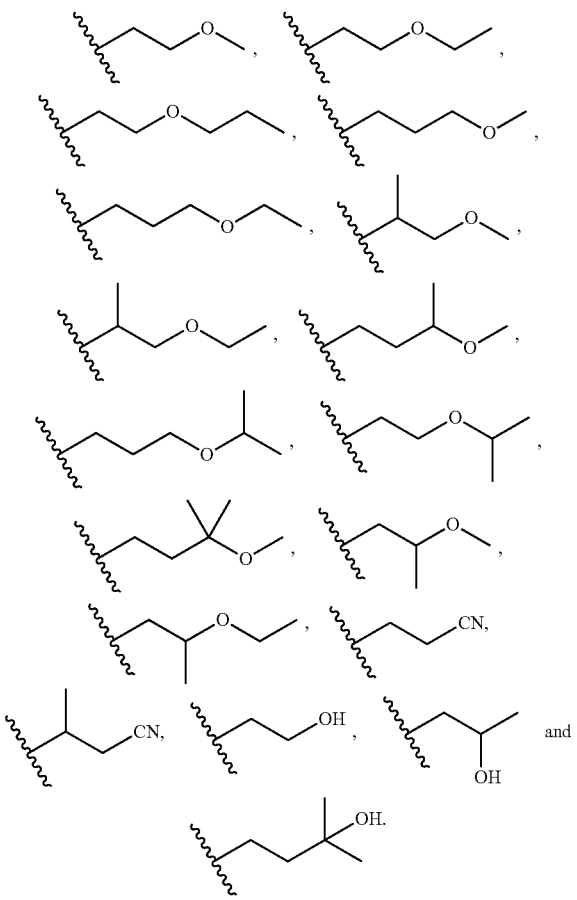

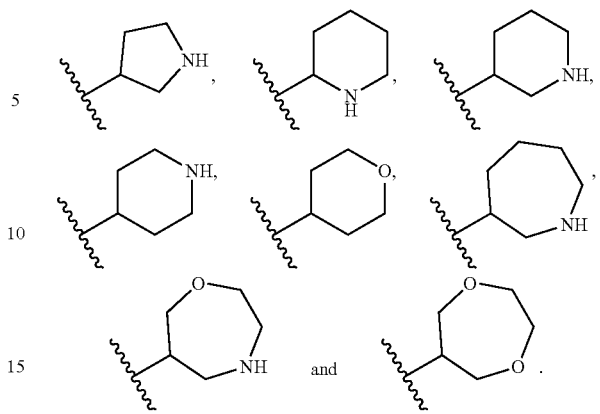

121. In embodiment 121, the compounds of any one of embodiments 1-114, or a pharmaceutically acceptable salt thereof, are those wherein $R^{3A}$ can be heterocyclyl (for example, a 4- to 7-membered nitrogen-containing monocyclic heterocyclyl such as azetidinyl, pyrrolidinyl, piperidinyl, piperazinyl, azepanyl and oxepanyl) (optionally substituted with one or more $R_H$, independently selected from alkyl (for example, a $C_1$-$C_6$ alkyl such as methyl, ethyl, n-propyl, isopropyl, n-butyl, sec-butyl, isobutyl, t-butyl, pentyl (straight-chained or branched) and hexyl (straight-chained or branched)), aryl (for example, a $C_6$ aryl or a Cm aryl) (optionally substituted with one or more halogens, such as fluoro and chloro) and heteroaryl (for example, a 5- or 6-membered nitrogen-containing monocyclic heteroaryl such as pyrrolo, imidazolyl, oxazolyl, thiazolyl, pyridinyl, pyrazinyl and pyrimidinyl) (optionally substituted with one or more halogens, such as fluoro and chloro).

122. In embodiment 122, the compounds of embodiment 121, or a pharmaceutically acceptable salt thereof, are those wherein $R^{3A}$ can be an unsubstituted heterocyclyl. In some aspects of embodiment 122, the substituted heterocyclyl can be, for example, a 4- to 7-membered nitrogen-containing monocyclic heterocyclyl such as azetidinyl, pyrrolidinyl, piperidinyl, piperazinyl, azepanyl and oxepanyl.

123. In embodiment 123, the compounds of any one of embodiments 121-122, or a pharmaceutically acceptable salt thereof, are those wherein $R^{3A}$ can be selected from:

124. In embodiment 124, the compounds of embodiment 121, or a pharmaceutically acceptable salt thereof, are those wherein $R^{3A}$ can be heterocyclyl (for example, a 4- to 7-membered nitrogen-containing monocyclic heterocyclyl such as azetidinyl, pyrrolidinyl, piperidinyl, piperazinyl, azepanyl and oxepanyl) substituted with one $R^H$, independently selected from alkyl (for example, a $C_1$-$C_6$ alkyl such as methyl, ethyl, n-propyl, isopropyl, n-butyl, sec-butyl, isobutyl, t-butyl, pentyl (straight-chained or branched) and hexyl (straight-chained or branched)), aryl (for example, a $C_6$ aryl or a $C_{10}$ aryl) (optionally substituted with one or more halogens, such as fluoro and chloro) and heteroaryl (for example, a 5- or 6-membered nitrogen-containing monocyclic heteroaryl) (optionally substituted with one or more halogens, such as fluoro and chloro).

125. In embodiment 125, the compounds of embodiment 124, or a pharmaceutically acceptable salt thereof, are those wherein $R^{3A}$ can be heterocyclyl (for example, a 4- to 7-membered nitrogen-containing monocyclic heterocyclyl such as azetidinyl, pyrrolidinyl, piperidinyl, piperazinyl, azepanyl and oxepanyl) substituted with one $R^H$, which can be alkyl (for example, a $C_1$-$C_6$ alkyl such as methyl, ethyl, n-propyl, isopropyl, n-butyl, sec-butyl, isobutyl, t-butyl, pentyl (straight-chained or branched) and hexyl (straight-chained or branched)).

126. In embodiment 126, the compounds of embodiment 125, or a pharmaceutically acceptable salt thereof, are those wherein $R^{3A}$ can be selected from:

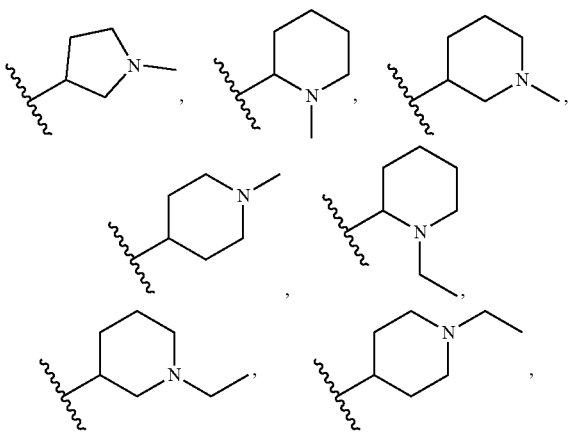

-continued

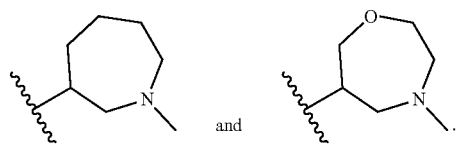
and

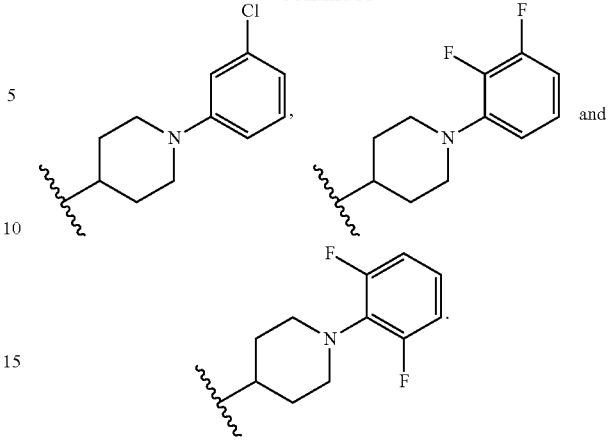
and

127. In embodiment 127, the compounds of embodiment 124, or a pharmaceutically acceptable salt thereof, are those wherein $R^{3A}$ can be heterocyclyl (for example, a 4- to 7-membered nitrogen-containing monocyclic heterocyclyl such as azetidinyl, pyrrolidinyl, piperidinyl, piperazinyl, azepanyl and oxepanyl) substituted with one $R^H$, which can be aryl (for example, a $C_6$ aryl or a $C_{10}$ aryl) (optionally substituted with one or more halogens, such as fluoro and chloro). In some aspects of embodiment 127, when $R^H$ can be a $C_6$ aryl substituted with one halogen, the halogen can be in the ortho, meta or para position relative to the point of attachment of the aryl ring to $R^{3A}$. In some aspects of embodiment 127, when $R^H$ can be an aryl substituted with two halogens, one halogen can be at the ortho position and the other halogen can be at the meta position relative to the point of attachment of the aryl ring to $R^{3A}$. In some aspects of embodiment 127, one halogen can be at the ortho position and the other halogen can be at the para position relative to the point of attachment of the aryl ring to $R^{3A}$. In some aspects of embodiment 127, one halogen can be at one meta position and the other halogen can be at the other meta position relative to the point of attachment of the aryl ring to $R^{3A}$. In some aspects of embodiment 127, one halogen can be at one ortho position and the other halogen can be at the other ortho position relative to the point of attachment of the aryl ring to $R^{3A}$. In some aspects of embodiment 127, one halogen can be at the meta position and the other halogen can be at the para position relative to the point of attachment of the aryl ring to $R^{3A}$.

128. In embodiment 128, the compounds of embodiment 127, or a pharmaceutically acceptable salt thereof, are those wherein $R^{3A}$ can be selected from:

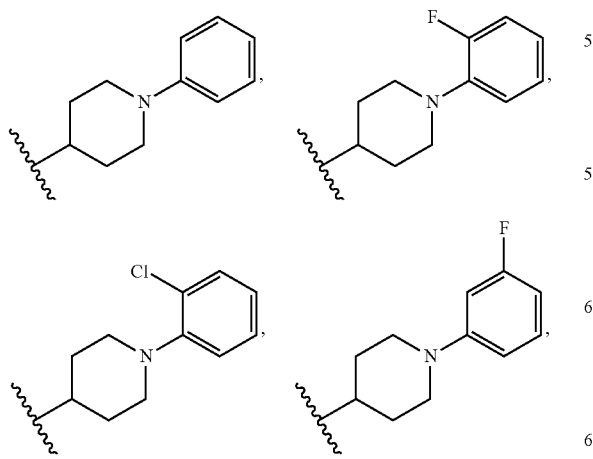

129. In embodiment 129, the compounds of embodiment 124, or a pharmaceutically acceptable salt thereof, are those wherein $R^{3A}$ can be heterocyclyl (for example, a 4- to 7-membered nitrogen-containing monocyclic heterocyclyl such as azetidinyl, pyrrolidinyl, piperidinyl, piperazinyl, azepanyl and oxepanyl) substituted with one $R^H$, which can be heteroaryl (for example, a 5- or 6-membered nitrogen-containing monocyclic heteroaryl) (optionally substituted with one or more halogens, such as fluoro and chloro).

130. In embodiment 130, the compounds of embodiment 129, or a pharmaceutically acceptable salt thereof, are those wherein $R^{3A}$ can be selected from:

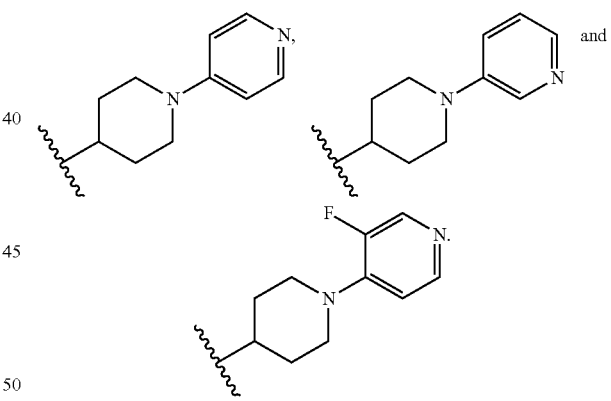

131. In embodiment 131, the compounds of any one of embodiments 1-114, or a pharmaceutically acceptable salt thereof, are those wherein $R^{3A}$ can be cycloalkylalkyl. In some aspects of embodiment 131, the cycloalkyl of the cycloalkylalkyl can be a monocyclic $C_3$-$C_8$ cycloalkyl. In some aspects of embodiment 131, the cycloalkyl of the cycloalkylalkyl can be a bicyclic $C_6$-$C_{10}$ cycloalkyl. In some aspects of embodiment 131, the alkyl of the cycloalkylalkyl can be —(CH$_2$)—, —(CH$_2$)$_2$— or —(CH$_2$)$_3$—. In some aspects of embodiment 131, the alkyl group in cycloalkylalkyl can be a methylene (—CH$_2$—) group.

132. In embodiment 132, the compounds of embodiment 131, or a pharmaceutically acceptable salt thereof, are those wherein $R^{3A}$ can be

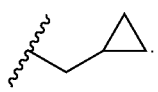

133. In embodiment 133, the compounds of any one of embodiments 1-114, or a pharmaceutically acceptable salt thereof, are those wherein $R^{3A}$ can be heteroaralkyl. In some aspects of embodiment 133, the heteroaryl group in heteroaralkyl can be a 5-membered heteroaryl group, a 6-membered heteroaryl group or a 10-membered heteroaryl group. In some aspects of embodiment 133, the heteroaryl group in heteroaralkyl can be a monocyclic heteroaryl. In some aspects of embodiment 133, the heteroaryl group in heteroaralkyl can be a 5- or 6-membered heteroaryl group. In some aspects of embodiment 133, the heteroaryl group in heteroaralkyl can be a nitrogen-containing 5- or 6-membered heteroaryl group. In some aspects of embodiment 133, the heteroaryl group in heteroaralkyl can be a 5- or 6-membered heteroaryl group containing nitrogen and oxygen. In some aspects of embodiment 133, the heteroaryl group in heteroaralkyl can be, for example, pyrrole, pyrazole, imidazole, 1,2,4-triazole, furan, thiophene, oxazole, isoxazole, thiazole, isothiazole, 1,2,5-oxadiazole, 1,2,3-oxadiazole, 1,3,4-thiadiazole, pyridine, pyridazine, pyrimidine, pyrazine, 1,2,4-triazine or 1,3,5-traizine. In some aspects of embodiment 133, the alkyl group in heteroaralkyl can be a $C_1$-$C_6$ alkyl group, for example, —$(CH_2)_{1-6}$—. In some aspects of embodiment 133, the alkyl group in heteroaralkyl can be a methylene (—$CH_2$—) group. For example, in some aspects of embodiment 133, the heteroaryl portion of the heteroaralkyl group can be pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl or tetrazolyl and the alkyl portion of the heteroaralkyl group can be a $C_1$-$C_4$ alkyl such as methyl, ethyl, n-propyl, n-butyl, sec-butyl, isobutyl, or t-butyl. Exemplary heteroaralkyl groups include, but are not limited to: pyrrolylmethyl, thienylmethyl, thiazolylmethyl, imidazolylmethyl, furanylmethyl, indolylmethyl, isoindolylmethyl, oxazolylmethyl, isoxazolylmethyl, benzothiazolylmethyl, benzoxazolylmethyl, quinolinylmethyl, isoquinolinylmethyl, pyridinylmethyl, pyrimidinylmethyl, pyrazinylmethyl, pyridazinylmethyl, triazolylmethyl, tetrazolylmethyl, pyrrolylethyl, thienylethyl, thiazolylethyl, imidazolylethyl, furanylethyl, indolylethyl, isoindolylethyl, oxazolylethyl, isoxazolylethyl, benzothiazolylethyl, benzoxazolylethyl, quinolinylethyl, isoquinolinylethyl, pyridinylethyl, pyrimidinylethyl, pyrazinylethyl, pyridazinylethyl, triazolylethyl and tetrazolylethyl.

134. In embodiment 134, the compounds of embodiment 133, or a pharmaceutically acceptable salt thereof, are those wherein $R^{3A}$ can be

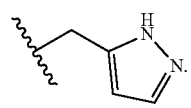

135. In embodiment 135, the compounds of any one of embodiments 1-114, or a pharmaceutically acceptable salt thereof, are those wherein $R^{3A}$ can be heterocyclylalkyl. In some aspects of embodiment 135, the heterocyclyl of the heterocyclylalkyl can be a 4- to 8-membered monocyclic heterocyclyl. In some aspects of embodiment 135, the heterocyclyl of the heterocyclylalkyl can be a 6- to 10-membered fused or bridged bicyclic heterocyclyl. In some aspects of embodiment 135, the heterocyclyl of the heterocyclylalkyl can be a nitrogen-containing heterocyclyl. In some aspects of embodiment 135, the heterocyclyl of the heterocyclylalkyl can be a nitrogen- and an oxygen-containing heterocyclyl. In some aspects of embodiment 135, the alkyl of the heterocyclylalkyl can be a $C_1$-$C_3$ alkyl such as —$(CH_2)$—, —$(CH_2)_2$— or —$(CH_2)_3$—. In some aspects of embodiment 135, the alkyl group in heterocyclylalkyl can be a methylene (—$CH_2$—) group.

136. In embodiment 136, the compounds of embodiment 135, or a pharmaceutically acceptable salt thereof, are those wherein $R^{3A}$ can be selected from:

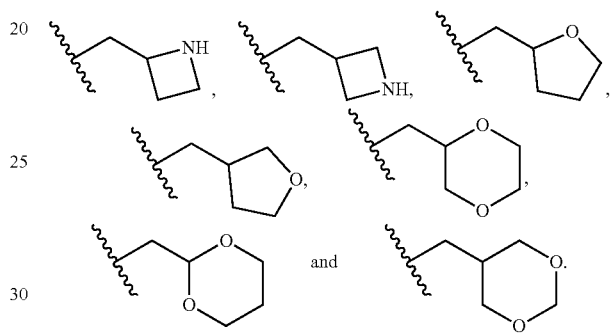

137. In embodiment 137, the compounds of any one of embodiments 1-114, or a pharmaceutically acceptable salt thereof, are those wherein $R^{3A}$ can be cycloalkyl (for example, a $C_3$-$C_8$ monocyclic cycloalkyl such as cyclopropyl, cyclobutyl, cyclopentyl or cyclohexyl), optionally substituted with cyano.

138. In embodiment 138, the compounds of embodiment 137, or a pharmaceutically acceptable salt thereof, are those wherein $R^{3A}$ can be an unsubstituted cycloalkyl, for example, an unsubstituted monocyclic $C_3$-$C_8$ cycloalkyl.

139. In embodiment 139, the compounds of any one of embodiments 137-138, or a pharmaceutically acceptable salt thereof, are those wherein $R^{3A}$ can be selected from an unsubstituted cyclopropyl, an unsubstituted cyclobutyl and an unsubstituted cyclopentyl.

140. In embodiment 140, the compounds of embodiment 137, or a pharmaceutically acceptable salt thereof, are those wherein $R^{3A}$ can be cycloalkyl (for example, a monocyclic $C_3$-$C_8$ cycloalkyl such as cyclopropyl, cyclobutyl, cyclopentyl or cyclohexyl) substituted with cyano.

141. In embodiment 141, the compounds of embodiment 140, or a pharmaceutically acceptable salt thereof, are those wherein $R^{3A}$ can be

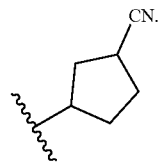 [SMILES: *C1CCC(C#N)C1]

142. In embodiment 142, the compounds of embodiment 1, or a pharmaceutically acceptable salt thereof, are those having structural Formula (Ia):

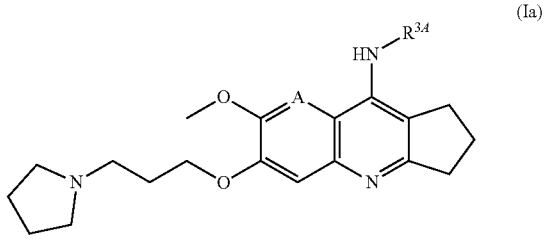

or a pharmaceutically acceptable salt thereof, wherein:
A can be CH or N; and
$R^{3A}$ can be (a) alkyl, for example, a $C_1$-$C_6$ alkyl such as methyl, ethyl, n-propyl, isopropyl, n-butyl, sec-butyl, isobutyl, t-butyl, pentyl (straight-chained or branched) and hexyl (straight-chained or branched), (optionally substituted with one or more $R^G$, independently selected from alkoxy, hydroxy and cyano), (b) heterocyclyl (optionally substituted with one or more $R^H$, independently selected from alkyl (for example, a $C_1$-$C_6$ alkyl such as methyl, ethyl, n-propyl, isopropyl, n-butyl, sec-butyl, isobutyl, t-butyl, pentyl (straight-chained or branched) and hexyl (straight-chained or branched)), aryl (optionally substituted with one or more halogens, such as fluoro and chloro) and heteroaryl (optionally substituted with one or more halogens, such as fluoro and chloro), (c) cycloalkylalkyl (for example, a $C_3$-$C_8$ monocyclic cycloalkyl and a $C_1$-$C_3$ alkyl), (d) heteroaralkyl (for example, a 5- or 6-membered nitrogen-containing monocyclic heteroaryl and a $C_1$-$C_3$ alkyl), (e) heterocyclylalkyl (for example, a 4- to 7-membered nitrogen-containing monocyclic heterocyclyl and a $C_1$-$C_3$ alkyl), or (f) cycloalkyl (for example, a $C_3$-$C_8$ monocyclic cycloalkyl) (optionally substituted with cyano).

143. In embodiment 143, the compounds of embodiment 1, or a pharmaceutically acceptable salt thereof, are those having structural Formula (Ib):

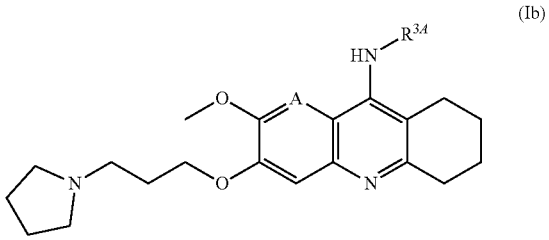

or a pharmaceutically acceptable salt thereof, wherein:
A can be CH or N; and
$R^{3A}$ can be (a) alkyl, for example, a $C_1$-$C_6$ alkyl such as methyl, ethyl, n-propyl, isopropyl, n-butyl, sec-butyl, isobutyl, t-butyl, pentyl (straight-chained or branched) and hexyl (straight-chained or branched), (optionally substituted with one or more $R^G$, independently selected from alkoxy, hydroxy and cyano), (b) heterocyclyl (optionally substituted with one or more $R^H$, independently selected from alkyl (for example, a $C_1$-$C_6$ alkyl such as methyl, ethyl, n-propyl, isopropyl, n-butyl, sec-butyl, isobutyl, t-butyl, pentyl (straight-chained or branched) and hexyl (straight-chained or branched)), aryl (optionally substituted with one or more halogens, such as fluoro and chloro) and heteroaryl (optionally substituted with one or more halogens, such as fluoro and chloro), (c) cycloalkylalkyl (for example, a $C_3$-$C_8$ monocyclic cycloalkyl and a $C_1$-$C_3$ alkyl), (d) heteroaralkyl (for example, a 5- or 6-membered nitrogen-containing monocyclic heteroaryl and a $C_1$-$C_3$ alkyl), (e) heterocyclylalkyl (for example, a 4- to 7-membered nitrogen-containing monocyclic heterocyclyl and a $C_1$-$C_3$ alkyl), or (f) cycloalkyl (for example, a $C_3$-$C_8$ monocyclic cycloalkyl) (optionally substituted with cyano).

144. In embodiment 144, the compounds of embodiment 1, or a pharmaceutically acceptable salt thereof, are those having structural Formula (Ic):

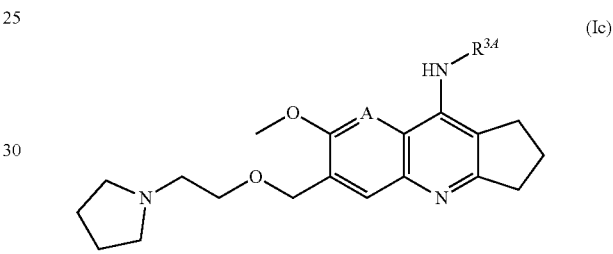

or a pharmaceutically acceptable salt thereof, wherein:
A can be CH or N; and
$R^{3A}$ can be (a) alkyl, for example, a $C_1$-$C_6$ alkyl such as methyl, ethyl, n-propyl, isopropyl, n-butyl, sec-butyl, isobutyl, t-butyl, pentyl (straight-chained or branched) and hexyl (straight-chained or branched), (optionally substituted with one or more $R^G$, independently selected from alkoxy, hydroxy and cyano), (b) heterocyclyl (optionally substituted with one or more $R^H$, independently selected from alkyl (for example, a $C_1$-$C_6$ alkyl such as methyl, ethyl, n-propyl, isopropyl, n-butyl, sec-butyl, isobutyl, t-butyl, pentyl (straight-chained or branched) and hexyl (straight-chained or branched)), aryl (optionally substituted with one or more halogens, such as fluoro and chloro) and heteroaryl (optionally substituted with one or more halogens, such as fluoro and chloro), (c) cycloalkylalkyl (for example, a $C_3$-$C_8$ monocyclic cycloalkyl and a $C_1$-$C_3$ alkyl), (d) heteroaralkyl (for example, a 5- or 6-membered nitrogen-containing monocyclic heteroaryl and a $C_1$-$C_3$ alkyl), (e) heterocyclylalkyl (for example, a 4- to 7-membered nitrogen-containing monocyclic heterocyclyl and a $C_1$-$C_3$ alkyl), or (f) cycloalkyl (for example, a $C_3$-$C_8$ monocyclic cycloalkyl) (optionally substituted with cyano).

145. In embodiment 145, the compounds of embodiment 1, or a pharmaceutically acceptable salt thereof, are those having structural Formula (Id):

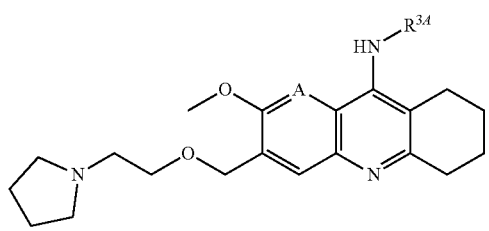

(Id)

or a pharmaceutically acceptable salt thereof, wherein:
A can be CH or N; and
$R^{3A}$ can be (a) alkyl, for example, a $C_1$-$C_6$ alkyl such as methyl, ethyl, n-propyl, isopropyl, n-butyl, sec-butyl, isobutyl, t-butyl, pentyl (straight-chained or branched) and hexyl (straight-chained or branched), (optionally substituted with one or more $R^G$, independently selected from alkoxy, hydroxy and cyano), (b) heterocyclyl (optionally substituted with one or more $R^H$, independently selected from alkyl (for example, a $C_1$-$C_6$ alkyl such as methyl, ethyl, n-propyl, isopropyl, n-butyl, sec-butyl, isobutyl, t-butyl, pentyl (straight-chained or branched) and hexyl (straight-chained or branched)), aryl (optionally substituted with one or more halogens, such as fluoro and chloro) and heteroaryl (optionally substituted with one or more halogens, such as fluoro and chloro), (c) cycloalkylalkyl (for example, a $C_3$-$C_8$ monocyclic cycloalkyl and a $C_1$-$C_3$ alkyl), (d) heteroaralkyl (for example, a 5- or 6-membered nitrogen-containing monocyclic heteroaryl and a $C_1$-$C_3$ alkyl), (e) heterocyclylalkyl (for example, a 4- to 7-membered nitrogen-containing monocyclic heterocyclyl and a $C_1$-$C_3$ alkyl), or (f) cycloalkyl (for example, a $C_3$-$C_8$ monocyclic cycloalkyl) (optionally substituted with cyano).

146. In embodiment 146, the compounds of any one of embodiments 142-145, or a pharmaceutically acceptable salt thereof, are those wherein A can be CH.

147. In embodiment 147, the compounds of any one of embodiments 142-145, or a pharmaceutically acceptable salt thereof, are those wherein A can be N (nitrogen).

148. In embodiment 148, the compounds of any one of embodiments 142-147, or a pharmaceutically acceptable salt thereof, are those wherein $R^{3A}$ can be selected from:

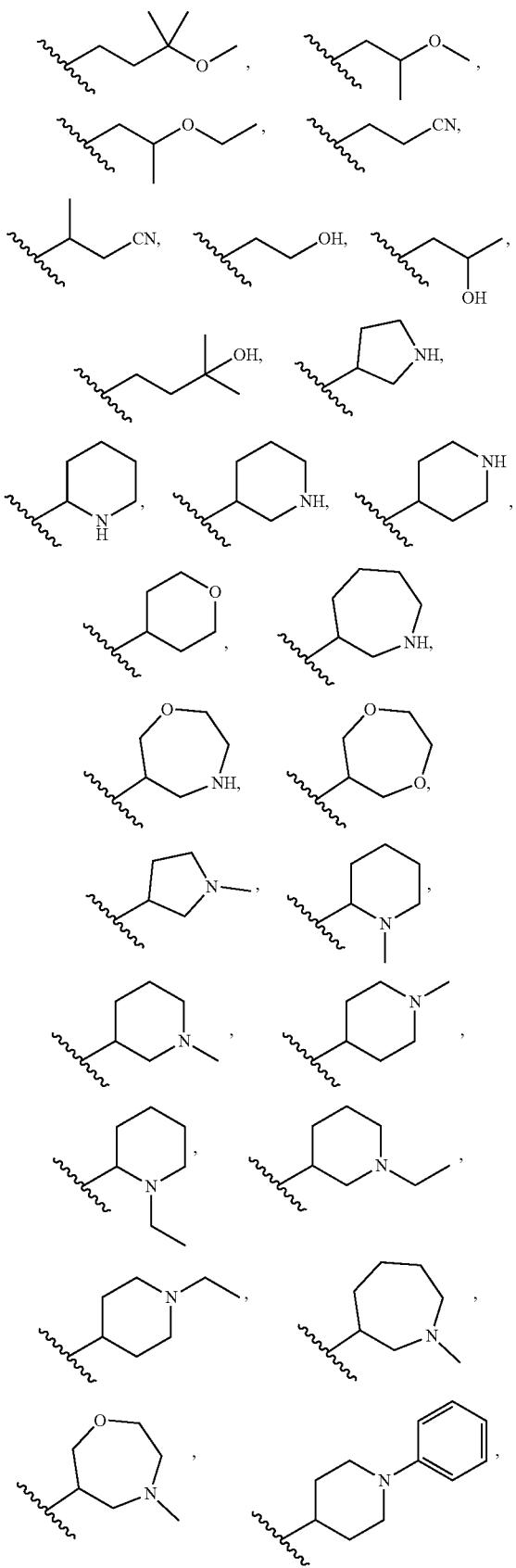

-continued

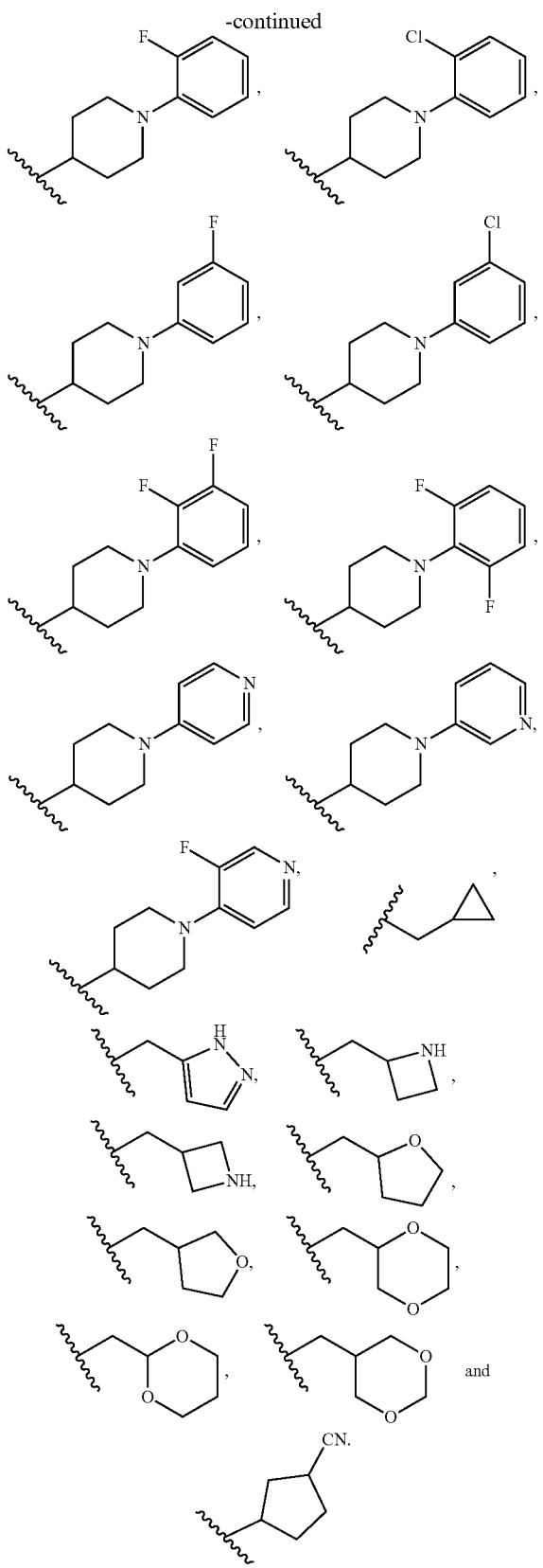

149. In embodiment 149 the compounds of any one of embodiments 142-148, or a pharmaceutically acceptable salt thereof, are those wherein $R_H$ can be selected from alkyl (for example, a $C_1$-$C_6$ alkyl such as methyl, ethyl, n-propyl, isopropyl, n-butyl, sec-butyl, isobutyl, t-butyl, pentyl (straight-chained or branched) and hexyl (straight-chained or branched)), unsubstituted heteroaryl (for example a 5- or 6-membered monocyclic heteroaryl), unsubstituted phenyl, heteroaryl (for example a 5- or 6-membered monocyclic heteroaryl) substituted with one or two halogens (for example, fluoro and chloro) and phenyl substituted with one or two halogens (for example, fluoro and chloro).

150. In embodiment 150, the compounds of any one of embodiments 1-149, or a pharmaceutically acceptable salt thereof, are not compounds of Formula (Q):

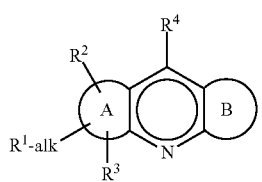

(Q)

wherein:

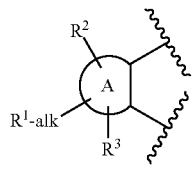

is a ring of formula (i), (ii), (iii), or (iv):

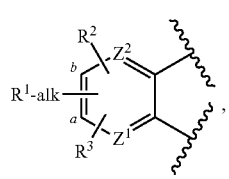

(i)

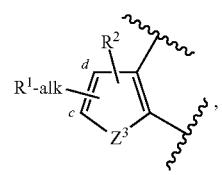

(ii)

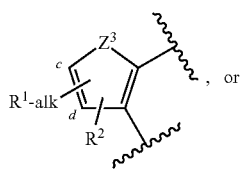

(iii)

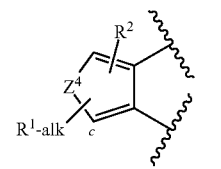

(iv)

wherein:

Z¹ and Z² are independently C (when R² or R³ is attached thereto), CH, or N;

Z³ is NH, N-alkyl, O, or S;

Z⁴ is N (when -alk-R¹ is attached thereto), NH, N-alkyl, O, or S;

alk is alkylene wherein one or two carbon atoms of the alkylene chain are optionally replaced by NR, O, S, or SO₂ (where R is hydrogen or alkyl) and the alkylene chain is optionally substituted with one or two substituents independently selected from halo, haloalkyl, haloalkoxy, hydroxyl, and alkoxy; wherein -alk-R¹ is attached to carbon (a) or (b) of ring (i), carbon (c) or (d) of rings (ii) or (iii), or Z⁴ or carbon (c) of ring (iv);

R¹ is —NR⁶R⁷ (where R⁶ and R⁷ are independently hydrogen, alkyl, hydroxyalkyl, alkoxyalkyl, haloalkyl, or haloalkoxyalkyl), heterocyclyl (optionally substituted with W, R$^b$, or R$_C$ independently selected from alkyl, hydroxyl, alkoxy, halo, haloalkyl, alkylcarbonyl, and haloalkylcarbonyl), or spiroheterocycloamino wherein a nitrogen atom of the spiroheterocycloamino is attached to alk;

R² is hydrogen, alkyl, cycloalkyl, halo, hydroxyl, alkoxy, haloalkoxy, or cyano;

R³ is hydrogen, alkyl, halo, alkoxy, or cyano or R³ is absent in rings of formula (ii), (iii) and (iv);

R⁴ is hydrogen, alkyl (optionally substituted with one, two, or three deuterium), —OR$^d$ (where R$^d$ is hydrogen, alkyl, haloalkyl, hydroxyalkyl, alkoxyalkyl, cycloalkyl, halocycloalkyl, cycloalkylalkyl, aryl, aralkyl, heteroaryl, heteroaralkyl, heterocyclyl, or heterocyclylalkyl), or NR$^e$R$^f$ (where W is hydrogen or alkyl and R$^f$ is hydrogen, alkyl, aminoalkyl, cyanoalkyl, carboxyalkyl, alkoxycarbonylalkyl, haloalkyl, hydroxyalkyl, alkoxyalkyl, cycloalkyl, cycloalkylalkyl, dicycloalkylalkyl, aryl, aralkyl, heteroaryl, heteroaralkyl, heterocyclyl, bridged heterocyclyl, heterocyclylalkyl, alkylsulfonyl, cycloalkylsulfonyl, cycloalkylalkylsulfonyl, arylsulfonyl, aralkylsulfonyl, heteroarylsulfonyl, heteroaralkylsulfonyl, heterocyclylsulfonyl, or heterocyclylalkylsulfonyl) wherein cycloalkyl, aryl, heteroaryl, and heterocyclyl either alone or in cycloalkylalkyl, aralkyl, heteroaralkyl or heterocyclylalkyl in R$^d$ are optionally substituted with R$^g$, R$^h$, or R$^i$ independently selected from alkyl, hydroxyl, alkoxy, halo, haloalkyl, and haloalkoxy, and wherein cycloalkyl, aryl, heteroaryl, and heterocyclyl either alone or in cycloalkylalkyl, aralkyl, heteroaralkyl, heterocyclylalkyl, cycloalkylsulfonyl, heteroaralkylsulfonyl, or heterocyclylalkylsulfonyl in R$^f$ are optionally substituted with R$^g$, R$^h$, or R$^i$ independently selected from alkyl, cycloalkyl, hydroxyl, alkoxy, alkoxycarbonyl, halo, haloalkyl, and haloalkoxy and further wherein alkylene in aralkyl, heteroaralkyl, heterocyclylalkyl, and cycloalkylalkyl is optionally substituted with one, two, or three deuterium;

Ring B is phenyl, 5- or 6-membered heteroaryl containing one or two heteroatoms independently selected from nitrogen, oxygen and sulfur, 5- or 6- or 7-membered cycloalkyl, or 5- or 6- or 7-membered saturated heterocyclyl, each optionally substituted with R$^j$, R$^k$, or R$^l$ independently selected from alkyl, hydroxyl, alkoxy, halo, haloalkyl, and haloalkoxy; and wherein each of the definitions used in embodiment 150 (including, but not limited to R, R¹, R², R³, R⁴, R⁶, R⁷, Z¹, Z², Z³, Z⁴, alk, R$^a$, R$^b$, R$^C$, R$^d$, R$^e$, R$^f$, R$^g$, R$^h$, R$^i$, R$^j$, R$^k$, R$^l$, Ring A and Ring B) refer to only embodiment 150 and not to any other embodiment described herein.

151. In embodiment 151, the compounds of any one of embodiments 1-149, or a pharmaceutically acceptable salt thereof, are not any of the compounds listed below:

2-methoxy-N-methyl-3-[3-(pyrrolidin-1-yl)propoxy]acridin-9-amine
2-methoxy-N-(propan-2-yl)-3-[3-(pyrrolidin-1-yl)propoxy]-acridin-9-amine
2-methoxy-N-(oxan-4-yl)-3-[3-(pyrrolidin-1-yl)propoxy]-acridin-9-amine
2-methoxy-N-(1-methylpiperidin-4-yl)-3-[3-(pyrrolidin-1-yl)propoxy]acridin-9-amine
2-methoxy-N-[1-(propan-2-yl)piperidin-4-yl]-3-[3-(pyrrolidin-1-yl)propoxy]acridin-9-amine
2-methoxy-3-[3-(pyrrolidin-1-yl)propoxy]acridin-9-ol
9-ethoxy-2-methoxy-3-[3-(pyrrolidin-1-yl)propoxy]acridine
3-[3-(pyrrolidin-1-yl)propoxy]acridin-9-ol
2-chloro-N-methyl-3-[3-(pyrrolidin-1-yl)propoxy]acridin-9-amine
N-methyl-3-[3-(pyrrolidin-1-yl)propoxy]acridin-9-amine
N,2-dimethyl-3-[3-(pyrrolidin-1-yl)propoxy]acridin-9-amine
N-ethyl-2-methyl-3-[3-(pyrrolidin-1-yl)propoxy]acridin-9-amine
2-methyl-N-(propan-2-yl)-3-[3-(pyrrolidin-1-yl)propoxy]acridin-9-amine
3-[3-(diethylamino)propoxy]-2-methoxy-N-methylacridin-9-amine
2-methoxy-N-methyl-3-[3-(piperidin-1-yl)propoxy]acridin-9-amine
7-methoxy-N-[1-(propan-2-yl)piperidin-4-yl]-6-[3-(pyrrolidin-1-yl)propoxy]-1,2,3,4-tetrahydroacridin-9-amine
7-methoxy-6-[3-(pyrrolidin-1-yl)propoxy}-1,2,3,4-tetrahydroacridine
7-methoxy-N-(1-methylpiperidin-4-yl)-6-[3-(pyrrolidin-1-yl)propoxy]-1,2,3,4-tetrahydroacridin-9-amine
7-methoxy-N-(propan-2-yl)-6-[3-(pyrrolidin-1-yl)propoxy}-1H,2H,3H-cyclopent4b]quinolin-9-amine
7-methoxy-N-(oxan-4-yl)-6-[3-(pyrrolidin-1-yl)propoxy]-1H,2H,3H-cyclopenta[b]quinolin-9-amine
N-{7-methoxy-6-[3-(pyrrolidin-1-yl)propoxy}-1H,2H,3H-cyclopenta[b]quinolin-9-yl}-1-methylpiperidin-4-amine
7-methoxy-N-(propan-2-yl)-6-[3-(pyrrolidin-1-yl)propoxy]-1,2,3,4-tetrahydroacridin-9-amine
7-methoxy-N-(oxan-4-yl)-6-[3-(pyrrolidin-1-yl)propoxy]-1,2,3,4-tetrahydroacridin-9-amine
N-{7-methoxy-6-[3-(pyrrolidin-1-yl)propoxy}-1H,2H,3H-cyclopenta[b]quinolin-9-yl}-1-(propan-2-yl)piperidin-4-amine
7-methoxy-N-methyl-6-[3-(pyrrolidin-1-yl)propoxy]-1,2,3,4-tetrahydroacridin-9-amine
7-methoxy-N-methyl-6-[3-(pyrrolidin-1-yl)propoxy]-1H,2H,3H-cyclopenta[b]quinolin-9-amine
7-methoxy-N-ethyl-6-[3-(pyrrolidin-1-yl)propoxy]-1H,2H,3H-cyclopenta[b]quinolin-9-amine
7-methoxy-N-ethyl-6-[3-(pyrrolidin-1-yl)propoxy]-1,2,3,4-tetrahydroacridin-9-amine
6-[3-(3-fluoropyrrolidin-1-yl)propoxy]-7-methoxy-N-methyl-1H,2H,3H-cyclopenta[b]quinolin-9-amine -continued 2-methoxy-3-[3-(morpholin-4-yl)propoxy]-N-(propan-2-yl)acridin-9-amine
N-cyclopropyl-7-methoxy-6-[3-(pyrrolidin-1-yl)propoxy]-1H,2H,3H-cyclopenta[b]quinolin-9-amine
N-(cyclopropylmethyl)-7-methoxy-6-[3-(pyrrolidin-1-yl)propoxy]-1H,2H,3H-cyclopenta[b]quinolin-9-amine
7-methoxy-6-[3-(pyrrolidin-1-yl)propoxy]-1H,2H,3H-cyclopenta[b]quinolin-9-amine
2-({7-methoxy-6-[3-(pyrrolidin-1-yl)propoxy]-1H,2H,3H-cyclopenta[b]quinolin-9-yl}amino)ethan-1-ol
N-cyclobutyl-7-methoxy-6-[3-(pyrrolidin-1-yl)propoxy]-1H,2H,3H-cyclopenta[b]quinolin-9-amine
N-cyclopentyl-7-methoxy-6-[3-(pyrrolidin-1-yl)propoxy}-1H,2H,3H-cyclopenta[b]quinolin-9-amine
7-methoxy-N-propyl-6-[3-(pyrrolidin-1-yl)propoxy]-1H,2H,3H-cyclopenta[b]quinolin-9-amine
7-methoxy-N-(2-methoxyethyl)-6-[3-(pyrrolidin-1-yl)propoxy}-1H,2H,3H-cyclopenta[b]quinolin-9-amine
7-methoxy-N-[(oxetan-3-yl)methyl]-6-[3-(pyrrolidin-1-yl)propoxy]-1H,2H,3H-cyclopenta[b]quinolin-9-amine
N-{7-methoxy-6-[3-(pyrrolidin-1-yl)propoxy}-1H,2H,3H-cyclopenta[b]quinolin-9-yl}pyridin-2-amine
N-(cyclobutylmethyl)-7-methoxy-6-[3-(pyrrolidin-1-yl)propoxy]-1H,2H,3H-cyclopenta[b]quinolin-9-amine
7-methoxy-N-(2-methylpropyl)-6-[3-(pyrrolidin-1-yl)propoxy]-1H,2H,3H-cyclopenta[b]quinolin-9-amine
N-(2,2-dimethylpropyl)-7-methoxy-6-[3-(pyrrolidin-1-yl)propoxy]-1H,2H,3H-cyclopenta[b]quinolin-9-amine
7-methoxy-N-[(1-methylcyclopropypmethyl]-6-[3-(pyrrolidin-1-yl)propoxy]-1H,2H,3H-cyclopenta[b]quinolin-9-amine
N-tert-butyl-7-methoxy-6-[3-(pyrrolidin-1-yl)propoxy]-1H,2H,3H-cyclopenta[b]quinolin-9-amine
N-benzyl-7-methoxy-6-[3-(pyrrolidin-1-yl)propoxy]-1H,2H,3H-cyclopenta[b]quinolin-9-amine
N-{7-methoxy-6-[3-(pyrrolidin-1-yl)propoxy}-1H,2H,3H-cyclopenta[b]quinolin-9-yl}methanesulfonamide
N-[(3,3-difluorocyclobutyl)methyl]-7-methoxy-6-[3-(pyrrolidin-1-yl)propoxy]-1H,2H,3H-cyclopenta[b]quinolin-9-amine
N-(3,3-difluorocyclobutyl)-7-methoxy-6-[3-(pyrrolidin-1-yl)propoxy]-1H,2H,3H-cyclopenta[b]quinolin-9-amine
7-methoxy-6-[3-(pyrrolidin-1-yl)propoxy]-N-(2,2,2-trifluoroethyl)-1H,2H,3H-cyclopenta[b]quinolin-9-amine
7-methoxy-6-[3-(pyrrolidin-1-yl)propoxy]-N-(3,3,3-trifluoropropyl)-1H,2H,3H-cyclopenta[b]quinolin-9-amine
N-(cyclopropylmethyl)-7-methoxy-6-[(1-methylpyrrolidin-3-yl)methoxy]-1H,2H,3H-cyclopenta[b]quinolin-9-amine
N-(2,6-dimethyloxan-4-yl)-7-methoxy-6-[3-(pyrrolidin-1-yl)propoxy]-1H,2H,3H-cyclopenta[b]quinolin-9-amine
7-methoxy-N-[(pyridin-2-yl)methyl]-6-[3-(pyrrolidin-1-yl)propoxy]-1H,2H,3H-cyclopenta[b]quinolin-9-amine
7-methoxy-N-[(pyridin-3-yl)methyl]-6-[3-(pyrrolidin-1-yl)propoxy]-1H,2H,3H-cyclopenta[b]quinolin-9-amine
7-methoxy-N-(3-methoxycyclobutyl)-6-[3-(pyrrolidin-1-yl)propoxy]-1H,2H,3H-cyclopenta[b]quinolin-9-amine
(1s,3s)-3-({7-methoxy-6-[3-(pyrrolidin-1-yl)propoxy}-1H,2H,3H-cyclopenta[b]quinolin-9-yl}amino)cyclobutan-1-ol
5-({7-methoxy-6-[3-(pyrrolidin-1-yl)propoxy]-1H,2H,3H-cyclopenta[b]quinolin-9-yl}amino)-1-methylpiperidin-2-one
2-({7-methoxy-6-[3-(pyrrolidin-1-yl)propoxy]-1H,2H,3H-cyclopenta[b]quinolin-9-yl}amino)propane-1,3-diol
4-({7-methoxy-6-[3-(pyrrolidin-1-yl)propoxy]-1H,2H,3H-cyclopenta[b]quinolin-9-yl}amino)pyrrolidin-2-one
4-({7-methoxy-6-[3-(pyrrolidin-1-yl)propoxy]-1H,2H,3H-cyclopenta[b]quinolin-9-yl}amino)-1-methylpyrrolidin-2-one
5-({7-methoxy-6-[3-(pyrrolidin-1-yl)propoxy]-1H,2H,3H-cyclopenta[b]quinolin-9-yl}amino)piperidin-2-one
4-({7-methoxy-6-[3-(pyrrolidin-1-yl)propoxy]-1H,2H,3H-cyclopenta[b]quinolin-9-yl}amino)-1-methylpiperidin-2-one
4-({7-methoxy-6-[3-(pyrrolidin-1-yl)propoxy]-1H,2H,3H-cyclopenta[b]quinolin-9-yl}amino)piperidin-2-one
N-(dicyclopropylmethyl)-7-methoxy-6-[3-(pyrrolidin-1-yl)propoxy}-1H,2H,3H-cyclopenta[b]quinolin-9-amine
N-[{7-methoxy-6-[3-(pyrrolidin-1-yl)propoxy]-1H,2H,3H-cyclopenta[b]quinolin-9-yl}hexane-1,6-diamine
7-methoxy-N-[2-(morpholin-4-yl)ethyl]-6-[3-(pyrrolidin-1-yl)propoxy}-1H,2H,3H-cyclopenta[b]quinolin-9-amine
7-methoxy-N-(oxetan-3-yl)-6-[3-(pyrrolidin-1-yl)propoxy]-1H,2H,3H-cyclopenta[b]quinolin-9-amine
1-({7-methoxy-6-[3-(pyrrolidin-1-yl)propoxy]-1H,2H,3H-cyclopent4b]quinolin-9-yl}amino)-2-methylpropan-2-ol
N-[7-methoxy-6-[3-(pyrrolidin-1-yl)propoxy]-1H,2H,3H-cyclopenta[b]quinolin-9-yl}-1-methyl-1H-pyrazol-3-amine
methyl 3-[({7-methoxy-6-[3-(pyrrolidin-1-yl)propoxy]-1H,2H,3H-cyclopenta[b]quinolin-9-yl}amino)methyl]azetidine-1-carboxylate
1-({7-methoxy-6-[3-(pyrrolidin-1-yl)propoxy]-1H,2H,3H-cyclopenta[b]quinolin-9- yl}amino)propan-2-ol
7-methoxy-N-(3-methoxypropyl)-6-[3-(pyrrolidin-1-yl)propoxy]-1H,2H,3H-cyclopenta[b]quinolin-9-amine
3-({7-methoxy-6-[3-(pyrrolidin-1-yl)propoxy]-1H,2H,3H-cyclopenta[b]quinolin-9-yl}amino)propan-1-ol
3-({7-methoxy-6-[3-(pyrrolidin-1-yl)propoxy]-1H,2H,3H-cyclopenta[b]quinolin-9-yl}amino)-1-methylpyrrolidin-2-one
N-cyclopropyl-2-methoxy-3-[3-(pyrrolidin-1-yl)propoxy]acridin-9-amine
2-methoxy-N-[(3S)-oxolan-3-yl]-3-[3-(pyrrolidin-1-yl)propoxy]acridin-9-amine
2-methoxy-N-[(3R)-oxolan-3-yl]-3-[3-(pyrrolidin-1-yl)propoxy]acridin-9-amine
2-methoxy-N-(oxetan-3-yl)-3-[3-(pyrrolidin-1-yl)propoxy]acridin-9-amine
2-methoxy-N-{8-oxabicyclo[3.2.1]octan-3-yl}-3-[3-(pyrrolidin-1-yl)propoxy]acridin-9-amine
5-({2-methoxy-3-[3-(pyrrolidin-1-yl)propoxy]acridin-9-yl}amino)-1-methylpiperidin-2-one
(1S,3R)-3-({2-methoxy-3-[3-(pyrrolidin-1-yl)propoxy]acridin-9-yl}amino)cyclopentan-1-ol
(1R,3R)-3-({2-methoxy-3-[3-(pyrrolidin-1-yl)propoxy]acridin-9-yl}amino)cyclopentan-1-ol
4-({2-methoxy-3-[3-(pyrrolidin-1-yl)propoxy]acridin-9-yl}amino)piperidin-2-one
1-ethyl-4-{2-methoxy-3-[3-(pyrrolidin-1-yl)propoxy]acridin-9-yl}amino)pyrrolidin-2-one
3-({2-methoxy-3-[3-(pyrrolidin-1-yl)propoxy]acridin-9-yl}amino)-1-(propan-2-yl)pyrrolidin-2-one
1-cyclobutyl-4-({2-methoxy-3-[3-(pyrrolidin-1-yl)propoxy]acridin-9-yl}amino)pyrrolidin-2-one
1-ethyl-4-{2-methoxy-3-[3-(pyrrolidin-1-yl)propoxy]acridin-9-yl}amino)piperidin-2-one
4-({2-methoxy-3-[3-(pyrrolidin-1-yl)propoxy]acridin-9-yl}amino)-1-(propan-2-yl)piperidin-2-one
5-({2-methoxy-3-[3-(pyrrolidin-1-yl)propoxy]acridin-9-yl}amino)piperidin-2-one
N-[(2S)-butan-2-yl]-2-methoxy-3-[3-(pyrrolidin-1-yl)propoxy]acridin-9-amine
N-[(2R)-butan-2-yl]-2-methoxy-3-[3-(pyrrolidin-1-yl)propoxy]acridin-9-amine
2-({2-methoxy-3-[3-(pyrrolidin-1-yl)propoxy]acridin-9-yl}amino)ethan-1-ol
3-({2-methoxy-3-[3-(pyrrolidin-1-yl)propoxy]acridin-9-yl}amino)propan-1-ol
2-methoxy-N-(2-methoxypropyl)-3-[3-(pyrrolidin-1-yl)propoxy]acridin-9-amine
2-methoxy-N-[(oxolan-3-yl)methyl]-3-[3-(pyrrolidin-1-yl)propoxy]acridin-9-amine
2-methoxy-N-[(oxan-2-yl)methyl]-3-[3-(pyrrolidin-1-yl)propoxy]acridin-9-amine
3-({2-methoxy-3-[3-(pyrrolidin-1-yl)propoxy]acridin-9-yl}amino)propanenitrile
(1R,4R)-4-({2-methoxy-3-[3-(pyrrolidin-1-yl)propoxy]acridin-9-yl}amino)-1-methylcyclohexan-1-ol
(1S,4S)-4-({2-methoxy-3-[3-(pyrrolidin-1-yl)propoxy]acridin-9-yl}amino)-1-methylcyclohexan-1-ol
N-(cyclopropylmethyl)-2-methoxy-3-[3-(pyrrolidin-1-yl)propoxy]acridin-9-amine
4-({2-methoxy-3-[3-(pyrrolidin-1-yl)propoxy]acridin-9-yl}amino)-2-methylbutan-2-ol
1-({2-methoxy-3-[3-(pyrrolidin-1-yl)propoxy]acridin-9-yl}amino)-2-methylpropan-2-ol
2-({2-methoxy-3-[3-(pyrrolidin-1-yl)propoxy]acridin-9-yl}amino)acetic acid
methyl 2-([2-methoxy-3-[3-(pyrrolidin-1-yl)propoxy]acridin-9-yl}amino)acetate
4-({2-methoxy-3-[3-(pyrrolidin-1-yl)propoxy]acridin-9-yl}amino)butanenitrile
N-(2,6-dimethyloxan-4-yl)-2-methoxy-3-[3-(pyrrolidin-1-yl)propoxy]acridin-9-amine
3-({2-methoxy-3-[3-(pyrrolidin-1-yl)propoxy]acridin-9-yl}amino)-1-methylpyrrolidin-2-one
2-methoxy-N-methyl-3-[(1-methylpyrrolidin-3-yl)methoxy]acridin-9-amine
2-methoxy-N-methyl-3-[(1-methylpiperidin-3-yl)methoxy]acridin-9-amine
1-fluoro-7-methoxy-N-(2-methoxyethyl)-6-[3-(pyrrolidin-1-yl)propoxy]acridin-9-amine
(1S,3R)-3-([2-methyl-3-[3-(pyrrolidin-1-yl)propoxy]acridin-9-yl]amino)cyclopentan-1-ol
2-chloro-N-(propan-2-yl)-3-[3-(pyrrolidin-1-yl)propoxy]acridin-9-amine
2-methoxy-7-methyl-N-(oxan-4-yl)-3-[3-(pyrrolidin-1-yl)propoxy]acridin-9-amine
2,7-dimethoxy-N-(oxan-4-yl)-3-[3-(pyrrolidin-1-yl)propoxy]acridin-9-amine
2-methoxy-3-[(1-methylpyrrolidin-3-yl)methoxy]-N-(oxan-4-yl)acridin-9-amine
3-[3-(3-fluoropyrrolidin-1-yl)propoxy]-2-methoxy-N-methylacridin-9-amine
2-ethoxy-N-methyl-3-[3-(pyrrolidin-1-yl)propoxy]acridin-9-amine and 3-ethoxy-N-methyl-2-[3-(pyrrolidin-1-yl)propoxy]acridin-9-amine
3-[3-(dimethylamino)propoxy]-2-methoxy-N-methylacridin-9-amine
5-fluoro-2-methoxy-N-(propan-2-yl)-3-[3-(pyrrolidin-1-yl)propoxy]acridin-9-amine
8-methoxy-N-(propan-2-yl)-7-[3-(pyrrolidin-1-yl)propoxy]benzo[b]1,6-naphthyridin-10-amine
8-methoxy-N-(propan-2-yl)-7-[3-(pyrrolidin-1-yl)propoxy]benzo[b]1,5-naphthyridin-10-amine
1-({7-methoxy-8-[3-(pyrrolidin-1-yl)propoxy]benzo[b]1,8-naphthyridin-5-yl}amino)-2-methylpropan-2-ol
7-methoxy-N-(oxan-4-yl)-6-[3-(pyrrolidin-1-yl)propoxy]-1,2,3,4-tetrahydroacridin-9-amine
N-cyclopropyl-7-methoxy-6-[3-(pyrrolidin-1-yl)propoxy]-1,2,3,4-tetrahydroacridin-9-amine
2-({7-methoxy-6-[3-(pyrrolidin-1-yl)propoxy]-1,2,3,4-tetrahydroacridin-9-yl}amino)ethan-1-ol
3-({7-methoxy-6-[3-(pyrrolidin-1-yl)propoxy]-1,2,3,4-tetrahydroacridin-9-yl}amino)cyclobutan-1-ol
7-methoxy-6-[3-(pyrrolidin-1-yl)propoxy]-1H,2H,3H-cyclopenta[b]quinolin-9-ol
7-methoxy-6-[3-(pyrrolidin-1-yl)propoxy]-1,2,3,4-tetrahydroacridin-9-ol
1-[3-({7-methoxy-1H,2H,3H-cyclopenta[b]quinolin-6-yl}oxy)propyl]pyrrolidine
1-(3-{[2-methoxy-9-(methylamino)acridin-3-yl]oxy}propyl)-3-methylpyrrolidin-3-ol
1-(3-{[2-methoxy-9-(methylamino)-5,6,7,8-tetrahydroacridin-3-yl]oxy}propyl)-3-methylpyrrolidin-3-ol
1-(3-{[7-methoxy-9-(methylamino)-1H,2H,3H-cyclopenta[b]quinolin-6-yl]oxy}propyl)-3-methylpyrrolidin-3-ol
1-(3-{[2-methoxy-9-(methylamino)acridin-3-yl]oxy}propyl)-3-methylazetidin-3-ol
1-(3-{[2-methoxy-9-(methylamino)-5,6,7,8-tetrahydroacridin-3-yl]oxy}propyl)-3-methylazetidin-3-ol
1-(3-{[7-methoxy-9-(methylamino)-1H,2H,3H-cyclopenta[b]quinolin-6-yl]oxy}propyl)-3-methylazetidin-3-ol
3-[3-(3-fluoropyrrolidin-1-yl)propoxy]-2-methoxy-N-methylacridin-9-amine
6-[3-(3-fluoropyrrolidin-1-yl)propoxy]-7-methoxy-N-methyl-1,2,3,4-tetrahydroacridin-9-amine 3-[3-(3-fluoroazetidin-1-yl)propoxy]-2-methoxy-N-methylacridin-9-amine
6-[3-(3-fluoroazetidin-1-yl)propoxy]-7-methoxy-N-methyl-1,2,3,4-tetrahydroacridin-9-amine
6-[3-(3-fluoroazetidin-1-yl)propoxy]-7-methoxy-N-methyl-1H,2H,3H-cyclopenta[b]quinolin-9-amine
3-{3-[(3R)-3-fluoropyrrolidin-1-yl]propoxy}-2-methoxy-N-methylacridin-9-amine
6-{3-[(3R)-3-fluoropyrrolidin-1-yl]propoxy}-7-methoxy-N-methyl-1,2,3,4-tetrahydroacridin-9-amine
6-{3-[(3R)-3-fluoropyrrolidin-1-yl]propoxy}-7-methoxy-N-methyl-1H,2H,3H-cyclopenta[b]quinolin-9-amine
3-{3-[(3S)-3-fluoropyrrolidin-1-yl]propoxy}-2-methoxy-N-methylacridin-9-amine
6-{3-[(3S)-3-fluoropyrrolidin-1-yl]propoxy}-7-methoxy-N-methyl-1,2,3,4-tetrahydroacridin-9-amine
6-{3-[(3S)-3-fluoropyrrolidin-1-yl]propoxy}-7-methoxy-N-methyl-1H,2H,3H-cyclopenta[b]quinolin-9-amine
1-[3-({7-methoxy-9-[(propan-2-yl)amino]-1H,2H,3H-cyclopenta[b]quinolin-6-yl}oxy)propyl]-3-methylpyrrolidin-3-ol
1-[3-({7-methoxy-9-[(propan-2-yl)amino]-1H,2H,3H-cyclopenta[b]quinolin-6-yl}oxy)propyl]-3-methylazetidin-3-ol
N-ethyl-3-{3-[(3R)-3-fluoropyrrolidin-1-yl]propoxy}-2-methoxyacridin-9-amine
N-ethyl-6-{3-[(3R)-3-fluoropyrrolidin-1-yl]propoxy}-7-methoxy-1,2,3,4-tetrahydroacridin-9-amine
N-ethyl-6-{3-[(3R)-3-fluoropyrrolidin-1-yl]propoxy}-7-methoxy-1H,2H,3H-cyclopenta[b]quinolin-9-amine
N-ethyl-3-{3-[(3S)-3-fluoropyrrolidin-1-yl]propoxy}-2-methoxyacridin-9-amine
N-ethyl-6-{3-[(3S)-3-fluoropyrrolidin-1-yl]propoxy}-7-methoxy-1,2,3,4-tetrahydroacridin-9-amine
N-ethyl-6-{3-[(3S)-3-fluoropyrrolidin-1-yl]propoxy}-7-methoxy-1H,2H,3H-cyclopenta[b]quinolin-9-amine
3-{3-[(3R)-3-fluoropyrrolidin-1-yl]propoxy}-2-methoxy-N-(propan-2-yl)acridin-9-amine
6-{3-[(3R)-3-fluoropyrrolidin-1-yl]propoxy}-7-methoxy-N-(propan-2-yl)-1,2,3,4-tetrahydroacridin-9-amine
6-{3-[(3R)-3-fluoropyrrolidin-1-yl]propoxy}-7-methoxy-N-(propan-2-yl)-1H,2H,3H-cyclopenta[b]quinolin-9-amine
3-{3-[(3S)-3-fluoropyrrolidin-1-yl]propoxy}-2-methoxy-N-(propan-2-yl)acridin-9-amine
6-{3-[(3S)-3-fluoropyrrolidin-1-yl]propoxy}-7-methoxy-N-(propan-2-yl)-1,2,3,4-tetrahydroacridin-9-amine
6-{3-[(3S)-3-fluoropyrrolidin-1-yl]propoxy}-7-methoxy-N-(propan-2-yl)-1H,2H,3H-cyclopenta[b]quinolin-9-amine
N-cyclopropyl-3-{3-[(3R)-3-fluoropyrrolidin-1-yl]propoxy}-2-methoxyacridin-9-amine
N-cyclopropyl-6-{3-[(3R)-3-fluoropyrrolidin-1-yl]propoxy}-7-methoxy-1,2,3,4-tetrahydroacridin-9-amine
N-cyclopropyl-6-{3-[(3R)-3-fluoropyrrolidin-1-yl]propoxy}-7-methoxy-1H,2H,3H-cyclopenta[b]quinolin-9-amine
N-cyclopropyl-3-{3-[(3S)-3-fluoropyrrolidin-1-yl]propoxy}-2-methoxyacridin-9-amine
N-cyclopropyl-6-{3-[(3S)-3-fluoropyrrolidin-1-yl]propoxy}-7-methoxy-1,2,3,4-tetrahydroacridin-9-amine
N-cyclopropyl-6-{3-[(3S)-3-fluoropyrrolidin-1-yl]propoxy}-7-methoxy-1H,2H,3H-cyclopenta[b]quinolin-9-amine
2-methoxy-N-methyl-3-[3-(morpholin-4-yl)propoxy]acridin-9-amine
7-methoxy-N-methyl-6-[3-(morpholin-4-yl)propoxy]-1,2,3,4-tetrahydroacridin-9-amine
7-methoxy-N-methyl-6-[3-(morpholin-4-yl)propoxy]-1H,2H,3H-cyclopenta[b]quinolin-9-amine
N-ethyl-2-methoxy-3-[3-(morpholin-4-yl)propoxy]acridin-9-amine
N-ethyl-7-methoxy-6-[3-(morpholin-4-yl)propoxy]-1,2,3,4-tetrahydroacridin-9-amine
N-ethyl-7-methoxy-6-[3-(morpholin-4-yl)propoxy]-1H,2H,3H-cyclopenta[b]quinolin-9-amine
7-methoxy-6-[3-(morpholin-4-yl)propoxy]-N-(propan-2-yl)-1,2,3,4-tetrahydroacridin-9-amine
7-methoxy-6-[3-(morpholin-4-yl)propoxy]-N-(propan-2-yl)-1H,2H,3H-cyclopenta[b]quinolin-9-amine
N-cyclopropyl-2-methoxy-3-[3-(morpholin-4-yl)propoxy]acridin-9-amine
N-cyclopropyl-7-methoxy-6-[3-(morpholin-4-yl)propoxy]-1,2,3,4-tetrahydroacridin-9-amine
N-cyclopropyl-7-methoxy-6-[3-(morpholin-4-yl)propoxy]-1H,2H,3H-cyclopenta[b]quinolin-9-amine
7-methoxy-N-[(1-methylcyclobutyl)methyl]-6-[3-(pyrrolidin-1-yl)propoxy]-1H,2H,3H-cyclopenta[b]quinolin-9-amine
N-[(3,3-dimethylcyclobutyl)methyl]-7-methoxy-6-[3-(pyrrolidin-1-yl)propoxy]-1H,2H,3H-cyclopenta[b]quinolin-9-amine
N-[(3-fluorocyclobutyl)methyl]-7-methoxy-6-[3-(pyrrolidin-1-yl)propoxy]-1H,2H,3H-cyclopenta[b]quinolin-9-amine
N-(3-fluorocyclobutyl)-7-methoxy-6-[3-(pyrrolidin-1-yl)propoxy]-1H,2H,3H-cyclopenta[b]quinolin-9-amine
N-(2-fluoroethyl)-7-methoxy-6-[3-(pyrrolidin-1-yl)propoxy]-1H,2H,3H-cyclopenta[b]quinolin-9-amine
N-(2,2-difluoroethyl)-7-methoxy-6-[3-(pyrrolidin-1-yl)propoxy]-1H,2H,3H-cyclopenta[b]quinolin-9-amine
N-(3-fluoropropyl)-7-methoxy-6-[3-(pyrrolidin-1-yl)propoxy]-1H,2H,3H-cyclopenta[b]quinolin-9-amine
N-(3,3-difluoropropyl)-7-methoxy-6-[3-(pyrrolidin-1-yl)propoxy]-1H,2H,3H-cyclopenta[b]quinolin-9-amine
7-methoxy-N-(pentan-3-yl)-6-[3-(pyrrolidin-1-yl)propoxy]-1H,2H,3H-cyclopenta[b]quinolin-9-amine N-(butan-2-yl)-7-methoxy-6-[3-(pyrrolidin-1-yl)propoxy]-1H,2H,3H-cyclopenta[b]quinolin-9-amine
7-methoxy-N-(pentan-2-yl)-6-[3-(pyrrolidin-1-yl)propoxy]-1H,2H,3H-cyclopenta[b]quinolin-9-amine
7-methoxy-N-(2-methylbutyl)-6-[3-(pyrrolidin-1-yl)propoxy]-1H,2H,3H-cyclopenta[b]quinolin-9-amine
N-(2-ethylbutyl)-7-methoxy-6-[3-(pyrrolidin-1-yl)propoxy]-1H,2H,3H-cyclopenta[b]quinolin-9-amine
N-(2-cyclobutylethyl)-7-methoxy-6-[3-(pyrrolidin-1-yl)propoxy]-1H,2H,3H-cyclopenta[b]quinolin-9-amine
N-(2-cyclopropylethyl)-7-methoxy-6-[3-(pyrrolidin-1-yl)propoxy]-1H,2H,3H-cyclopenta[b]quinolin-9-amine
N-(2-cyclopentylethyl)-7-methoxy-6-[3-(pyrrolidin-1-yl)propoxy]-1H,2H,3H-cyclopenta[b]quinolin-9-amine
N-(2-cyclohexylethyl)-7-methoxy-6-[3-(pyrrolidin-1-yl)propoxy]-1H,2H,3H-cyclopenta[b]quinolin-9-amine
N-(cyclohexylmethyl)-7-methoxy-6-[3-(pyrrolidin-1-yl)propoxy]-1H,2H,3H-cyclopenta[b]quinolin-9-amine
7-methoxy-N-[(pyridin-4-yl)methyl]-6-[3-(pyrrolidin-1-yl)propoxy]-1H,2H,3H-cyclopenta[b]quinolin-9-amine
4-({7-methoxy-6-[3-(pyrrolidin-1-yl)propoxy]-1H,2H,3H-cyclopenta[b]quinolin-9-yl}amino)-2-methylbutan-2-ol
7-methoxy-N-(3-methoxy-3-methylbutyl)-6-[3-(pyrrolidin-1-yl)propoxy]-1H,2H,3H-cyclopenta[b]quinolin-9-amine
4-({7-methoxy-6-[3-(pyrrolidin-1-yl)propoxy]-1H,2H,3H-cyclopenta[b]quinolin-9-yl}amino)butan-2-ol
7-methoxy-N-(3-methoxybutyl)-6-[3-(pyrrolidin-1-yl)propoxy]-1H,2H,3H-cyclopenta[b]quinolin-9-amine
N-butyl-7-methoxy-6-[3-(pyrrolidin-1-yl)propoxy]-1H,2H,3H-cyclopenta[b]quinolin-9-amine or a pharmaceutically acceptable salt of any of the foregoing.

152. In embodiment 152, the compounds of any one of embodiments 1-149 are not compounds disclosed in International PCT Application No. PCT/US2017/017977, which is hereby incorporated by reference in its entirety for the express purpose of describing compounds which are not compounds of any one of embodiments 1-149, or a pharmaceutically acceptable salt thereof. Each of the definitions used in embodiment 152 with respect to PCT Application No. PCT/US2017/017977 refer to only the compounds described therein.
153. In embodiment 153, the compounds of embodiment 1, or a pharmaceutically acceptable salt thereof, are those compounds listed in Table 1.
154. In embodiment 154, the compounds of embodiment 1, or a pharmaceutically acceptable salt thereof, are those compounds listed in Table 2.
155. In embodiment 155, the compounds of any of embodiments 1-154, or a pharmaceutically acceptable salt thereof, wherein when $R^1$ is methoxy; $R^2$ is

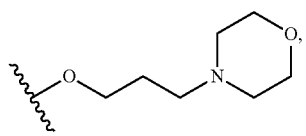

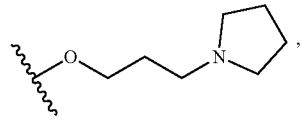 [SMILES: *OCCCN1CCCC1]

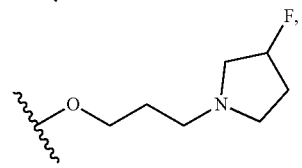

-continued

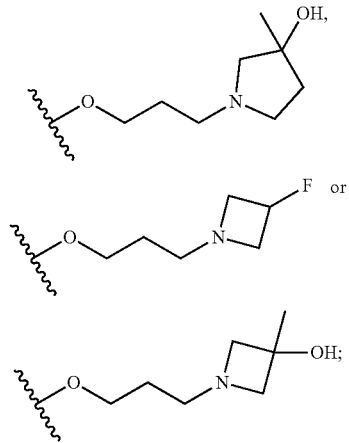

$R^{3A}$ is an unsubstituted $C_1$-$C_6$ alkyl; and $R^{3B}$ is hydrogen; then (a1) at least one of X, $X^1$ and $X^2$ is not $(CR^{4A}R^{4B})_m$, $CR^{5A}R^{5B}$ and $(CR^{6A}R^{6B})_n$, respectively; (b1) the sum of m+n is 4 or 5; (c1) A is N; (d1) at least one of $R^{4A}$, $R^{4B}$, $R^{4C}$, $R^{5A}$, $R^{5B}$, $R^{5C}$, $R^{6A}$, $R^{6B}$ and $R^{6C}$ is independently alkyl; or (e1) any two, any three, or all four of said (a1), (b1), (c1) and (d1) apply.

156. In embodiment 156, the compounds of any of embodiments 1-155, or a pharmaceutically acceptable salt thereof, wherein when $R^1$ is methoxy; $R^2$ is

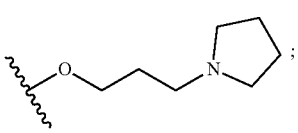 [SMILES: *OCCCN1CCCC1]

$R^{3A}$ is

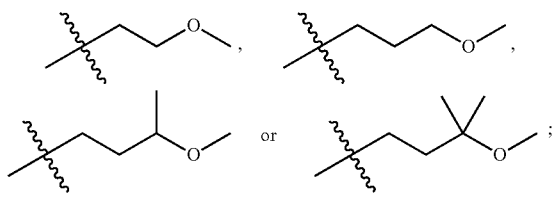

and $R_{3B}$ is hydrogen; then (f1) at least one of X, $X^1$ and $X^2$ is not $(CR^{4A}R^{4B})_m$, $CR^{5A}R^{5B}$ and $(CR^{6A}R^{6B})_m$, respectively; (g1) the sum of m+n is 4 or 5; (h1) A is N; (i1) at least one of $R^{4A}$, $R^{4B}$, $R^{4C}$, $R^{5A}$, $R^{5B}$, $R^{5C}$, $R^{6A}$, $R^{6B}$ and $R^{6C}$ is alkyl; or (j1) any two, any three, or all four of said (f1), (g1), (h1) and (i1) apply.

157. In embodiment 157, the compounds of any of embodiments 1-156, or a pharmaceutically acceptable salt thereof, wherein when $R^1$ is methoxy; $R^{3A}$ is an unsubstituted cyclopropylmethyl, an unsubstituted cyclopropylethyl, an unsubstituted cyclobutylmethyl, an unsubstituted cyclobutylethyl, an unsubstituted cyclopentylethyl, an unsubstituted cyclohexylmethyl, or an unsubstituted cyclohexylethyl; and $R^{3B}$ is hydrogen; then $R^2$ is not

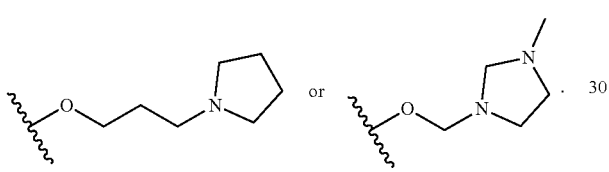

158. In embodiment 158, the compounds of any of embodiments 1-157, or a pharmaceutically acceptable salt thereof, wherein when $R^1$ is methoxy; $R^2$ is

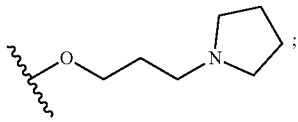

Ring B is

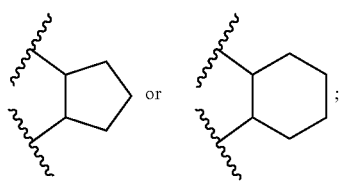 [SMILES: *C1CCCC1* ; *C1CCCCC1*]

$R^{3B}$ is hydrogen; and A is CH; then (k1) $R^{3A}$ is not a 4- to 6-membered unsubstituted heterocyclyl group having 1 oxygen and 0 nitrogen atoms; (l1) $R^{3A}$ is not a 4- to 6-membered heterocyclyl group having 1 oxygen and 0 nitrogen atoms and substituted with one or two $C_1$-$C_3$ alkyl groups; (m1) $R^{3A}$ is not unsubstituted or N—$C_1$-$C_6$ alkyl-substituted 2-pyrrolidinone; (n1) $R^{3A}$ is not unsubstituted or N—$C_1$-$C_6$ alkyl-substituted 2-piperidone; (o1) $R^{3A}$ is not N—$C_1$-$C_6$ alkyl-substituted 4-piperidine or; or (p1) any two, any three, any four, or all five of said (k1), (l1), (m1), (n1) and (o1) apply.

159. In embodiment 159, the compounds of any of embodiments 1-158, or a pharmaceutically acceptable salt thereof, wherein when $R^1$ is methoxy; $R^2$ is

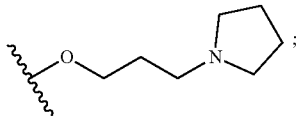 [SMILES: *OCCCN1CCCC1]

$R^{3B}$ is hydrogen; A is CH; and Ring B is

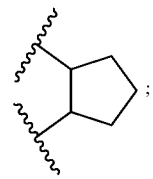 [SMILES: *C1CCCC1*]

then $R^{3A}$ is not pyridinylmethyl.

160. In embodiment 160, the compounds of any of embodiments 1-159, or a pharmaceutically acceptable salt thereof, wherein when $R^1$ is methoxy; $R^2$ is

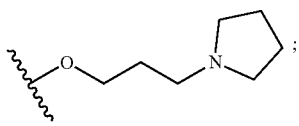 [SMILES: *OCCCN1CCCC1]

$R^{3A}$ is a $C_1$-$C_6$ alkyl, mono-substituted with hydroxy or

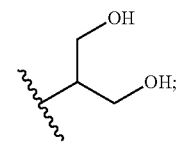 [SMILES: *C(CO)CO]

$R^{3B}$ is hydrogen; and A is CH; then (q1) at least one of X, $X^1$ and $X^2$ is not $(CR^{4A}R^{4B})_m$, $CR^{5A}R^{5B}$ and $(CR^{6A}R^{6B})_n$, respectively; (r1) the sum of m+n is 4 or 5; (s1) at least one of $R^{4A}$, $R^{4B}$, $R^{4C}$, $R^{5A}$, $R^{5B}$, $R^{5C}$, $R^{6A}$, $R^{6B}$ and $R^{6C}$ is independently alkyl; or (t1) any two, or all three of said (q1), (r1) and (s1) apply.

161. In embodiment 161, the compounds of any of embodiments 1-160, or a pharmaceutically acceptable salt thereof, wherein when $R^1$ is methoxy; $R^2$ is

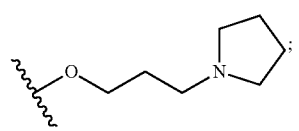 [SMILES: *OCCCN1CCCC1]

$R_{3B}$ is hydrogen; A is CH; and Ring B is

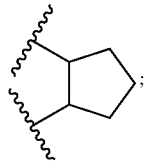 [SMILES: *C1CCCC1*]

then $R^{3A}$ is not selected from: 3-oxetanylmethyl, 3-azetidyl-methyl, 3-(N-methylcarbamoyl)-azetidylmethyl, 3-(N-methylcarbamoyl)-azetidylethyl and

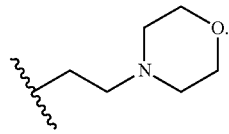 [SMILES: *CCN1CCOCC1]

162. In embodiment 162, the compounds of any of embodiments 1-161, or a pharmaceutically acceptable salt thereof, wherein when $R^1$ is methoxy; $R^2$ is

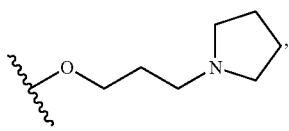

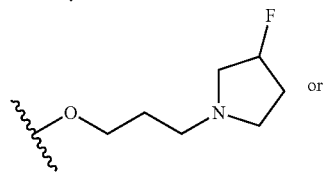

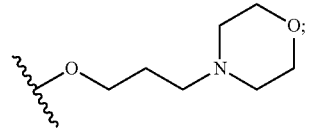

$R^{3A}$ is an unsubstituted $C_3$-$C_6$ cycloalkyl; and $R^{3B}$ is hydrogen; then A is N.

163. In embodiment 163, the compounds of any of embodiments 1-162, or a pharmaceutically acceptable salt thereof, wherein the compound of Formula (I) is not selected from:

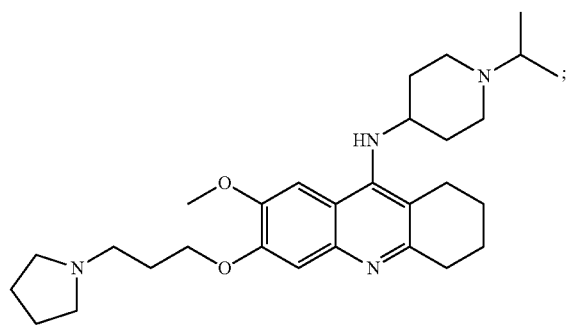

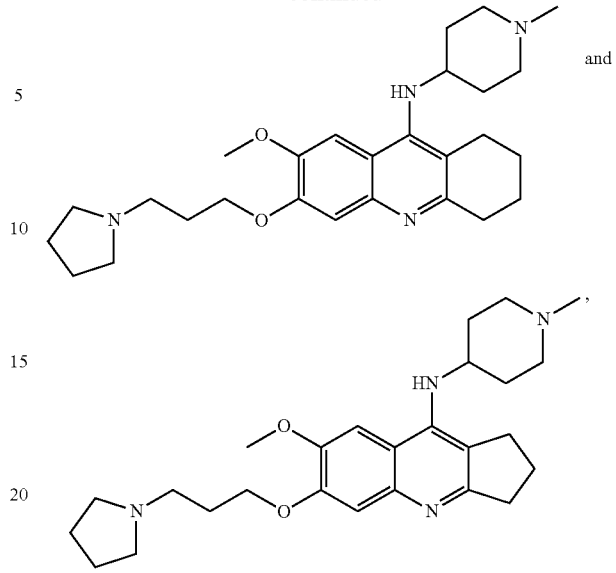

or a pharmaceutically acceptable salt of any of the foregoing.

164. In embodiment 164, the compounds of embodiment 155, or a pharmaceutically acceptable salt thereof, wherein: when $R^1$ is methoxy; $R^2$ is

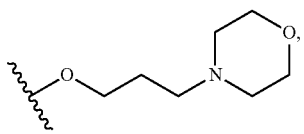

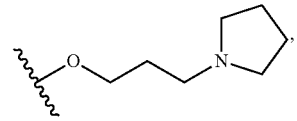

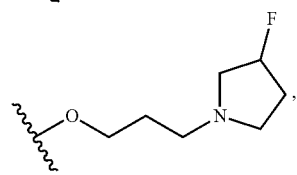

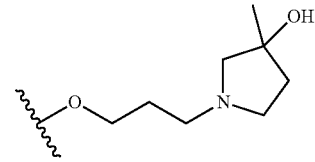

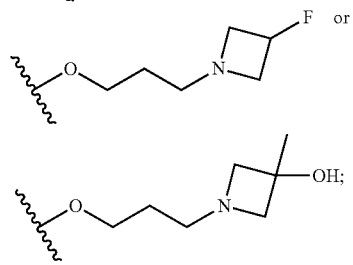

$R^{3A}$ is an unsubstituted $C_1$-$C_6$ alkyl; and $R^{3B}$ is hydrogen; then (a1) at least one of X, $X^1$ and $X^2$ is not $(CR^{4A}R^{4B})_m$, $CR^{5A}R^{5B}$ and $(CR^{6A}R^{6B})_n$, respectively; (b1) the sum of m+n is 4 or 5; (c1) A is N; (d1) at least one of $R^{4A}$, $R^{4B}$, $R^{4C}$, $R^{5A}$, $R^{5B}$, $R^{5C}$, $R^{6A}$, $R^{6B}$, and $R^{6C}$ is alkyl; or (e1) any two, any three, or all four of said (a1), (b1), (c1) and (d1) apply.

165. In embodiment 165, the compound of embodiment 155, or a pharmaceutically acceptable salt thereof, wherein one of $R^{4A}$, $R^{4B}$, $R^{4C}$, $R^{5A}$, $R^{5B}$, $R^{5C}$, $R^{6A}$, $R^{6B}$ and $R^{6C}$ is independently alkyl, for example, a $C_1$-$C_6$ alkyl, such as methyl, ethyl, n-propyl, isopropyl, n-butyl, sec-butyl, isobutyl, t-butyl, pentyl (straight-chained or branched) or hexyl (straight-chained or branched).

166. In embodiment 166, the compound of embodiment 155, or a pharmaceutically acceptable salt thereof, wherein two of $R^{4A}$, $R^{4B}$, $R^{4C}$, $R^{5A}$, $R^{5B}$, $R^{5C}$, $R^{6A}$, $R^{6B}$ and $R^{6C}$ are independently alkyl, for example, a $C_1$-$C_6$ alkyl, such as methyl, ethyl, n-propyl, isopropyl, n-butyl, sec-butyl, isobutyl, t-butyl, pentyl (straight-chained or branched) or hexyl (straight-chained or branched).

167. In embodiment 167, the compound of embodiment 156, or a pharmaceutically acceptable salt thereof, wherein $R^{4A}$, $R^{4B}$, $R^{4C}$, $R^{5A}$, $R^{5B}$, $R^{5C}$, $R^{6A}$, $R^{6B}$ and $R^{6C}$ is independently alkyl, for example, a $C_1$-$C_6$ alkyl, such as methyl, ethyl, n-propyl, isopropyl, n-butyl, sec-butyl, isobutyl, t-butyl, pentyl (straight-chained or branched) or hexyl (straight-chained or branched).

168. In embodiment 168, the compound of embodiment 156, or a pharmaceutically acceptable salt thereof, wherein two of $R^{4A}$, $R^{4B}$, $R^{4C}$, $R^{5A}$, $R^{5B}$, $R^{5C}$, $R^{6A}$, $R^{6B}$ and $R^{6C}$ are independently alkyl, for example, a $C_1$-$C_6$ alkyl, such as methyl, ethyl, n-propyl, isopropyl, n-butyl, sec-butyl, isobutyl, t-butyl, pentyl (straight-chained or branched) or hexyl (straight-chained or branched).

169. In embodiment 169, the compound of embodiment 160, or a pharmaceutically acceptable salt thereof, wherein one of $R^{4A}$, $R^{4B}$, $R^{4C}$, $R^{5A}$, $R^{5B}$, $R^{5C}$, $R^{6A}$, $R^{6B}$ and $R^{6C}$ is independently alkyl, for example, a $C_1$-$C_6$ alkyl, such as methyl, ethyl, n-propyl, isopropyl, n-butyl, sec-butyl, isobutyl, t-butyl, pentyl (straight-chained or branched) or hexyl (straight-chained or branched).

170. In embodiment 170, the compound of embodiment 160, or a pharmaceutically acceptable salt thereof, wherein two of $R^{4A}$, $R^{4B}$, $R^{4C}$, $R^{5A}$, $R^{5B}$, $R^{5C}$, $R^{6A}$, $R^{6B}$ and $R^{6C}$ are independently alkyl, for example, a $C_1$-$C_6$ alkyl, such as methyl, ethyl, n-propyl, isopropyl, n-butyl, sec-butyl, isobutyl, t-butyl, pentyl (straight-chained or branched) or hexyl (straight-chained or branched).

171. Embodiment 171 provides a pharmaceutical composition comprising a compound of any one of embodiments 1-170, or a pharmaceutically acceptable salt thereof, and a pharmaceutically acceptable excipient.

172. Embodiment 172 provides a method of inhibiting G9a in a cell containing G9a, comprising contacting a cell with a therapeutically effective amount of a compound of any one embodiments 1-170, or a pharmaceutically acceptable salt thereof, thereby inhibiting the activity of G9a.

173. In embodiment 173, the cell of embodiment 172 can be a cancer cell.

174. Embodiment 174, provides a method of ameliorating and/or treating a hemoglobinopathy, comprising administering a therapeutically effective amount of a compound of any one of embodiments 1-170, or a pharmaceutically acceptable salt thereof, or the pharmaceutical composition of embodiment 171 to a subject in need thereof.

175. In embodiment 175, the hemoglobinopathy of embodiment 174 can be sickle cell disease or beta-thalassemia.

176. Embodiment 176, provides a method of ameliorating and/or treating a cancer, comprising administering a therapeutically effective amount of a compound of any one of embodiments 1-170, or a pharmaceutically acceptable salt thereof, or the pharmaceutical composition of embodiment 171 to a subject in need thereof.

177. In embodiment 177, the cancer of embodiment 176 can be selected from: a Colorectal Cancer; a Osteosarcoma Cancer; an Acute Lymphoblastic Leukemia (ALL); an Acute Myeloid Leukemia (AML); an Adrenocortical Carcinoma; a Kaposi Sarcoma (Soft Tissue Sarcoma); an AIDS-Related Lymphoma (Lymphoma); a Primary CNS Lymphoma; an Anal Cancer; a Gastrointestinal Carcinoid Tumor; an Astrocytoma; an Atypical Teratoid/Rhabdoid Tumor; a Basal Cell Carcinoma of the Skin; a Bile Duct Cancer; a Bladder Cancer; a Bone Cancer (includes Ewing Sarcoma and Osteosarcoma and Malignant Fibrous Histiocytoma); a Brain Tumor; a Breast Cancer; a Bronchial Tumor; a Burkitt Lymphoma; a Cardiac Tumor; an Embryonal Tumor (Brain Cancer); a Germ Cell Tumor (Brain Cancer); a Primary CNS Lymphoma; a Cervical Cancer; a Cholangiocarcinoma; a Chordoma; a Chronic Lymphocytic Leukemia (CLL); a Chronic Myelogenous Leukemia (CML); a Chronic Myeloproliferative Neoplasm; a Craniopharyngioma (Brain Cancer); a Cutaneous T-Cell Lymphoma; a Ductal Carcinoma In Situ (DCIS); an Endometrial Cancer (Uterine Cancer); an Ependymoma (Brain Cancer); an Esophageal Cancer; an Esthesioneuroblastoma; an Ewing Sarcoma (Bone Cancer); Extracranial Germ Cell Tumor; Extragonadal Germ Cell Tumor; Eye Cancer; Intraocular Melanoma; a Retinoblastoma; a Fallopian Tube Cancer; a Fibrous Histiocytoma of Bone; a Gallbladder Cancer; a Gastric (Stomach) Gastrointestinal Stromal Tumor (GIST) (Soft Tissue Sarcoma); a CNS Germ Cell Tumors (Brain Cancer); an Extracranial Germ Cell Tumor; an Extragonadal Germ Cell Tumor; an Ovarian Germ Cell Tumor; a Testicular Cancer; a Gestational Trophoblastic Disease; a Hairy Cell Leukemia; a Head and Neck Cancer; a Hepatocellular (Liver) Cancer; a Histiocytosis, a Langerhans Cell; Hodgkin Lymphoma; a Hypopharyngeal Cancer (Head and Neck Cancer); an Intraocular Melanoma; an Islet Cell Tumor; a Pancreatic Neuroendocrine Tumor; a Kidney (Renal Cell) Cancer; a Langerhans Cell Histiocytosis; a Laryngeal Cancer (Head and Neck Cancer); a Leukemia; a Lip and Oral Cavity Cancer (Head and Neck Cancer); a Lung Cancer (Non-Small Cell and Small Cell); a Lymphoma; a Male Breast Cancer; a Melanoma; a Merkel Cell Carcinoma (Skin Cancer); a Mesothelioma; a Malignant Mesothelioma; a Metastatic Squamous Neck Cancer with Occult Primary (Head and Neck Cancer); a Midline Tract Carcinoma involving NUT Gene; a Mouth Cancer (Head and Neck Cancer); Multiple Endocrine Neoplasia Syndromes; Multiple Myeloma/Plasma Cell Neoplasms; a Mycosis Fungoides (Lymphoma); a Myelodysplastic Syndrome, a Myelodysplastic/Myeloproliferative Neoplasm; a Nasal Cavity and Paranasal Sinus Cancer (Head and Neck Cancer); a Nasopharyngeal Cancer (Head and Neck Cancer); a Nasopharyngeal Cancer—Neuroblastoma; a Non-Hodgkin Lymphoma; an Oral Cancer; Lip and Oral Cavity Cancer and Oropharyngeal Cancer (Head and Neck Cancer); an Ovarian Cancer; a Pancreatic Cancer; a Papillomatosis; a Paraganglioma; a Paranasal Sinus and Nasal Cavity Cancer (Head and Neck Cancer); a Parathyroid Cancer; a Penile Cancer; a Pharyngeal Cancer (Head and Neck Cancer); a Pheochromocytoma; a Pituitary Tumor; a Pleuropulmonary Blastoma; a Primary CNS Lymphoma; a Primary Peritoneal Cancer; a Prostate Cancer; a Rectal Cancer; a Rhabdomyosarcoma (Soft Tissue Sarcoma); a Salivary Gland Cancer (Head and Neck Cancer); a Salivary Gland Tumor; a Vascular Tumor (Soft Tissue Sarcoma); an Uterine Sarcoma; a Sézary Syndrome (Lymphoma); a Small Intestine Cancer; a Squamous Cell Carcinoma; a Skin Cancer; a Squamous Neck Cancer with Occult Primary, Metastatic (Head and Neck Cancer); a Cutaneous T-Cell Lymphoma; a Throat Cancer (Head and Neck Cancer); a Nasopharyngeal Cancer; an Oropharyngeal Cancer; a Hypopharyngeal Cancer; a Thymoma and Thymic Carcinoma; a Thyroid Cancer; an Urethral Cancer; a Vaginal Cancer; a Vascular Tumor (Soft Tissue Sarcoma); a Vulvar Cancer; a Myelodysplastic syndrome (MDS); and a Wilms Tumor.

178. In embodiment 178, the cancer of any one of embodiments 176-177 can be selected from: a Myelodysplastic Syndrome (MDS); an Acute Myeloid Leukemia (AML); an Ovarian Cancer; a Colon Cancer; and a Non-Small Cell Lung Cancer (NSCLC).

179. Embodiment 179, provides a method of ameliorating and/or treating an autoimmune or inflammatory disease in, comprising administering a therapeutically effective amount of a compound of any one of embodiments 1-170, or a pharmaceutically acceptable salt thereof, or the pharmaceutical composition of embodiment 171 to a subject in need thereof.

180. In embodiment 180, the autoimmune or inflammatory disease of embodiment 179 can be selected from: arthritis, atherosclerosis, multiple sclerosis, myasthenia gravis, Crohn's disease, graft-versus-host disease, psoriasis, granulomatous colitis, lymphocyte colitis, collagenous colitis, ulcerative colitis, Coeliac Disease, subepidermal blistering disorders, systemic lupus erythematosus, discoid lupus erythematosus, cutaneous lupus, dermatomyositis, polymyositis, Sjogren's syndrome, primary biliary cirrhosis, active chronic hepatitis, chronic fatigue syndrome and vasculitis.

181. In embodiment 181, the autoimmune or inflammatory disease of any one of embodiments 179-180 can be Crohn's disease, rheumatoid arthritis, systemic lupus erythematosus, systemic sclerosis, primary biliary cirrhosis and graft-versus-host disease.

182. Embodiment 182, provides for the use of an effective amount of a compound of any one embodiments 1-170, or a pharmaceutically acceptable salt thereof, in the manufacture of a medicament for inhibiting the activity of G9a in a cell.

183. In embodiment 183, the cell of embodiment 182 can be a cancer cell.

184. Embodiment 184, provides an effective amount of a compound of any one embodiments 1-170, or a pharmaceutically acceptable salt thereof, for inhibiting the activity of G9a in a cell.

185. In embodiment 185, the cell of embodiment 184 can be a cancer cell.

186. Embodiment 186, provides for the use of an effective amount of a compound of any one embodiments 1-170, or a pharmaceutically acceptable salt thereof, or the pharmaceutical composition of embodiment 171, in the manufacture of a medicament for ameliorating and/or treating a hemoglobinopathy.

187. In embodiment 187, the hemoglobinopathy of embodiment 186 can be sickle cell disease or beta-thalassemia.

188. Embodiment 188, provides an effective amount of a compound of any one embodiments 1-170, or a pharmaceutically acceptable salt thereof, or the pharmaceutical composition of embodiment 171, for ameliorating and/or treating a hemoglobinopathy.

189. In embodiment 189, the hemoglobinopathy of embodiment 188 can be sickle cell disease or beta-thalassemia.

190. Embodiment 190, provides for the use of an effective amount of a compound of any one embodiments 1-170, or a pharmaceutically acceptable salt thereof, or the pharmaceutical composition of embodiment 171, in the manufacture of a medicament for ameliorating and/or treating a cancer.

191. In embodiment 191, the cancer of embodiment 190 can be selected from: a Colorectal Cancer; a Osteosarcoma Cancer; an Acute Lymphoblastic Leukemia (ALL); an Acute Myeloid Leukemia (AML); an Adrenocortical Carcinoma; a Kaposi Sarcoma (Soft Tissue Sarcoma); an AIDS-Related Lymphoma (Lymphoma); a Primary CNS Lymphoma; an Anal Cancer; a Gastrointestinal Carcinoid Tumor; an Astrocytoma; an Atypical Teratoid/Rhabdoid Tumor; a Basal Cell Carcinoma of the Skin; a Bile Duct Cancer; a Bladder Cancer; a Bone Cancer (includes Ewing Sarcoma and Osteosarcoma and Malignant Fibrous Histiocytoma); a Brain Tumor; a Breast Cancer; a Bronchial Tumor; a Burkitt Lymphoma; a Cardiac Tumor; an Embryonal Tumor (Brain Cancer); a Germ Cell Tumor (Brain Cancer); a Primary CNS Lymphoma; a Cervical Cancer; a Cholangiocarcinoma; a Chordoma; a Chronic Lymphocytic Leukemia (CLL); a Chronic Myelogenous Leukemia (CML); a Chronic Myeloproliferative Neoplasm; a Craniopharyngioma (Brain Cancer); a Cutaneous T-Cell Lymphoma; a Ductal Carcinoma In Situ (DCIS); an Endometrial Cancer (Uterine Cancer); an Ependymoma (Brain Cancer); an Esophageal Cancer; an Esthesioneuroblastoma; an Ewing Sarcoma (Bone Cancer); Extracranial Germ Cell Tumor; Extragonadal Germ Cell Tumor; Eye Cancer; Intraocular Melanoma; a Retinoblastoma; a Fallopian Tube Cancer; a Fibrous Histiocytoma of Bone; a Gallbladder Cancer; a Gastric (Stomach) Gastrointestinal Stromal Tumor (GIST) (Soft Tissue Sarcoma); a CNS Germ Cell Tumors (Brain Cancer); an Extracranial Germ Cell Tumor; an Extragonadal Germ Cell Tumor; an Ovarian Germ Cell Tumor; a Testicular Cancer; a Gestational Trophoblastic Disease; a Hairy Cell Leukemia; a Head and Neck Cancer; a Hepatocellular (Liver) Cancer; a Histiocytosis, a Langerhans Cell; Hodgkin Lymphoma; a Hypopharyngeal Cancer (Head and Neck Cancer); an Intraocular Melanoma; an Islet Cell Tumor; a Pancreatic Neuroendocrine Tumor; a Kidney (Renal Cell) Cancer; a Langerhans Cell Histiocytosis; a Laryngeal Cancer (Head and Neck Cancer); a Leukemia; a Lip and Oral Cavity Cancer (Head and Neck Cancer); a Lung Cancer (Non-Small Cell and Small Cell); a Lymphoma; a Male Breast Cancer; a Melanoma; a Merkel Cell Carcinoma (Skin Cancer); a Mesothelioma; a Malignant Mesothelioma; a Metastatic Squamous Neck Cancer with Occult Primary (Head and Neck Cancer); a Midline Tract Carcinoma involving NUT Gene; a Mouth Cancer (Head and Neck Cancer); Multiple Endocrine Neoplasia Syndromes; Multiple Myeloma/Plasma Cell Neoplasms; a Mycosis Fungoides (Lymphoma); a Myelodysplastic Syndrome, a Myelodysplastic/Myeloproliferative Neoplasm; a Nasal Cavity and Paranasal Sinus Cancer (Head and Neck Cancer); a Nasopharyngeal Cancer (Head and Neck Cancer); a Nasopharyngeal Cancer—Neuroblastoma; a Non-Hodgkin Lymphoma; an Oral Cancer; Lip and Oral Cavity Cancer and Oropharyngeal Cancer (Head and Neck Cancer); an Ovarian Cancer; a Pancreatic Cancer; a Papillomatosis; a Paraganglioma; a Paranasal Sinus and Nasal Cavity Cancer (Head and Neck Cancer); a Parathyroid Cancer; a Penile Cancer; a Pharyngeal Cancer (Head and Neck Cancer); a Pheochromocytoma; a Pituitary Tumor; a Pleuropulmonary Blastoma; a Primary CNS Lymphoma; a Primary Peritoneal Cancer; a Prostate Cancer; a Rectal Cancer; a Rhabdomyosarcoma (Soft Tissue Sarcoma); a Salivary Gland Cancer (Head and Neck Cancer); a Salivary Gland Tumor; a Vascular Tumor (Soft Tissue Sarcoma); an Uterine Sarcoma; a Sézary Syndrome (Lymphoma); a Small Intestine Cancer; a Squamous Cell Carcinoma; a Skin Cancer; a Squamous Neck Cancer with Occult Primary, Metastatic (Head and Neck Cancer); a Cutaneous T-Cell Lymphoma; a Throat Cancer (Head and Neck Cancer); a Nasopharyngeal Cancer; an Oropharyngeal Cancer; a Hypopharyngeal Cancer; a Thymoma and Thymic Carcinoma; a Thyroid Cancer; an Urethral Cancer; a Vaginal Cancer; a Vascular Tumor (Soft Tissue Sarcoma); a Vulvar Cancer; a Myelodysplastic syndrome (MDS); and a Wilms Tumor.

192. In embodiment 192, the cancer of any one of embodiments 190-191 can be selected from: a Myelodysplastic Syndrome (MDS); an Acute Myeloid Leukemia (AML); an Ovarian Cancer; a Colon Cancer; and a Non-Small Cell Lung Cancer (NSCLC).

193. Embodiment 193, provides an effective amount of a compound of any one embodiments 1-170, or a pharmaceutically acceptable salt thereof, or the pharmaceutical composition of embodiment 171, for ameliorating and/or treating a cancer.

194. In embodiment 194, the cancer of embodiment 193 can be selected from: a Colorectal Cancer; a Osteosarcoma Cancer; an Acute Lymphoblastic Leukemia (ALL); an Acute Myeloid Leukemia (AML); an Adrenocortical Carcinoma; a Kaposi Sarcoma (Soft Tissue Sarcoma); an AIDS-Related Lymphoma (Lymphoma); a Primary CNS Lymphoma; an Anal Cancer; a Gastrointestinal Carcinoid Tumor; an Astrocytoma; an Atypical Teratoid/Rhabdoid Tumor; a Basal Cell Carcinoma of the Skin; a Bile Duct Cancer; a Bladder Cancer; a Bone Cancer (includes Ewing Sarcoma and Osteosarcoma and Malignant Fibrous Histiocytoma); a Brain Tumor; a Breast Cancer; a Bronchial Tumor; a Burkitt Lymphoma; a Cardiac Tumor; an Embryonal Tumor (Brain Cancer); a Germ Cell Tumor (Brain Cancer); a Primary CNS Lymphoma; a Cervical Cancer; a Cholangiocarcinoma; a Chordoma; a Chronic Lymphocytic Leukemia (CLL); a Chronic Myelogenous Leukemia (CML); a Chronic Myeloproliferative Neoplasm; a Craniopharyngioma (Brain Cancer); a Cutaneous T-Cell Lymphoma; a Ductal Carcinoma In Situ (DCIS); an Endometrial Cancer (Uterine Cancer); an Ependymoma (Brain Cancer); an Esophageal Cancer; an Esthesioneuroblastoma; an Ewing Sarcoma (Bone Cancer); Extracranial Germ Cell Tumor; Extragonadal Germ Cell Tumor; Eye Cancer; Intraocular Melanoma; a Retinoblastoma; a Fallopian Tube Cancer; a Fibrous Histiocytoma of Bone; a Gallbladder Cancer; a Gastric (Stomach) Gastrointestinal Stromal Tumor (GIST) (Soft Tissue Sarcoma); a CNS Germ Cell Tumors (Brain Cancer); an Extracranial Germ Cell Tumor; an Extragonadal Germ Cell Tumor; an Ovarian Germ Cell Tumor; a Testicular Cancer; a Gestational Trophoblastic Disease; a Hairy Cell Leukemia; a Head and Neck Cancer; a Hepatocellular (Liver) Cancer; a Histiocytosis, a Langerhans Cell; Hodgkin Lymphoma; a Hypopharyngeal Cancer (Head and Neck Cancer); an Intraocular Melanoma; an Islet Cell Tumor; a Pancreatic Neuroendocrine Tumor; a Kidney (Renal Cell) Cancer; a Langerhans Cell Histiocytosis; a Laryngeal Cancer (Head and Neck Cancer); a Leukemia; a Lip and Oral Cavity Cancer (Head and Neck Cancer); a Lung Cancer (Non-Small Cell and Small Cell); a Lymphoma; a Male Breast Cancer; a Melanoma; a Merkel Cell Carcinoma (Skin Cancer); a Mesothelioma; a Malignant Mesothelioma; a Metastatic Squamous Neck Cancer with Occult Primary (Head and Neck Cancer); a Midline Tract Carcinoma involving NUT Gene; a Mouth Cancer (Head and Neck Cancer); Multiple Endocrine Neoplasia Syndromes; Multiple Myeloma/Plasma Cell Neoplasms; a Mycosis Fungoides (Lymphoma); a Myelodysplastic Syndrome, a Myelodysplastic/Myeloproliferative Neoplasm; a Nasal Cavity and Paranasal Sinus Cancer (Head and Neck Cancer); a Nasopharyngeal Cancer (Head and Neck Cancer); a Nasopharyngeal Cancer—Neuroblastoma; a Non-Hodgkin Lymphoma; an Oral Cancer; Lip and Oral Cavity Cancer and Oropharyngeal Cancer (Head and Neck Cancer); an Ovarian Cancer; a Pancreatic Cancer; a Papillomatosis; a Paraganglioma; a Paranasal Sinus and Nasal Cavity Cancer (Head and Neck Cancer); a Parathyroid Cancer; a Penile Cancer; a Pharyngeal Cancer (Head and Neck Cancer); a Pheochromocytoma; a Pituitary Tumor; a Pleuropulmonary Blastoma; a Primary CNS Lymphoma; a Primary Peritoneal Cancer; a Prostate Cancer; a Rectal Cancer; a Rhabdomyosarcoma (Soft Tissue Sarcoma); a Salivary Gland Cancer (Head and Neck Cancer); a Salivary Gland Tumor; a Vascular Tumor (Soft Tissue Sarcoma); an Uterine Sarcoma; a Sézary Syndrome (Lymphoma); a Small Intestine Cancer; a Squamous Cell Carcinoma; a Skin Cancer; a Squamous Neck Cancer with Occult Primary, Metastatic (Head and Neck Cancer); a Cutaneous T-Cell Lymphoma; a Throat Cancer (Head and Neck Cancer); a Nasopharyngeal Cancer; an Oropharyngeal Cancer; a Hypopharyngeal Cancer; a Thymoma and Thymic Carcinoma; a Thyroid Cancer; an Urethral Cancer; a Vaginal Cancer; a Vascular Tumor (Soft Tissue Sarcoma); a Vulvar Cancer; a Myelodysplastic syndrome (MDS); and a Wilms Tumor.

195. In embodiment 195, the cancer of any one of embodiments 193-194 can be selected from: a Myelodysplastic Syndrome (MDS); an Acute Myeloid Leukemia (AML); an Ovarian Cancer; a Colon Cancer; and a Non-Small Cell Lung Cancer (NSCLC).

196. Embodiment 196, provides for the use of an effective amount of a compound of any one embodiments 1-170, or a pharmaceutically acceptable salt thereof, or the pharmaceutical composition of embodiment 171, in the manufacture of a medicament for ameliorating and/or treating an autoimmune or inflammatory disease.

197. In embodiment 197, the autoimmune or inflammatory disease of embodiment 196 can be selected from: arthritis, atherosclerosis, multiple sclerosis, myasthenia gravis, Crohn's disease, graft-versus-host disease, psoriasis, granulomatous colitis, lymphocyte colitis, collagenous colitis, ulcerative colitis, Coeliac Disease, subepidermal blistering disorders, systemic lupus erythematosus, discoid lupus erythematosus, cutaneous lupus, dermatomyositis, polymyositis, Sjogren's syndrome, primary biliary cirrhosis, active chronic hepatitis, chronic fatigue syndrome and vasculitis.

198. In embodiment 198, the autoimmune or inflammatory disease of any one of embodiments 196-197 can be selected from: Crohn's disease, rheumatoid arthritis, systemic lupus erythematosus, systemic sclerosis, primary biliary cirrhosis and graft-versus-host disease.

199. Embodiment 199, provides an effective amount of a compound of any one embodiments 1-170, or a pharmaceutically acceptable salt thereof, or the pharmaceutical composition of embodiment 171, for ameliorating and/or treating an autoimmune or inflammatory disease.

200. In embodiment 200, the autoimmune or inflammatory disease of embodiment 199 can be selected from: arthritis, atherosclerosis, multiple sclerosis, myasthenia gravis, Crohn's disease, graft-versus-host disease, psoriasis, granulomatous colitis, lymphocyte colitis, collagenous colitis, ulcerative colitis, Coeliac Disease, subepidermal blistering disorders, systemic lupus erythematosus, discoid lupus erythematosus, cutaneous lupus, dermatomyositis, polymyositis, Sjogren's syndrome, primary biliary cirrhosis, active chronic hepatitis, chronic fatigue syndrome and vasculitis.

201. In embodiment 201, the autoimmune or inflammatory disease of any one of embodiments 199-200 can be selected from: Crohn's disease, rheumatoid arthritis, systemic lupus erythematosus, systemic sclerosis, primary biliary cirrhosis and graft-versus-host disease.

Representative compounds of Formula (I), or pharmaceutically acceptable salts therein, are disclosed in Tables 1 and 2 below. Compounds in Table 1 were prepared either as a free base, or in salt form, for example, with formic acid, HCl or trifluoroacetic acid.

TABLE 1

| No | Structure | IUPAC Name | MS found |
|---|---|---|---|
| 1 | 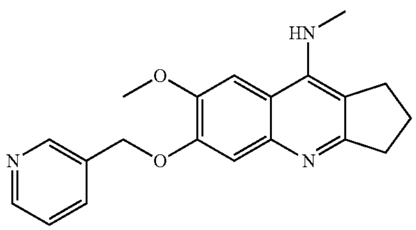 [SMILES: CNc1c2c(nc3cc(OCc4cccnc4)c(OC)cc13)CCC2] | 7-methoxy-N-methyl-6-(pyridin-3-ylmethoxy)-2,3-dihydro-1H-cyclopenta[b]quinolin-9-amine | 336.3 |
| 2 | 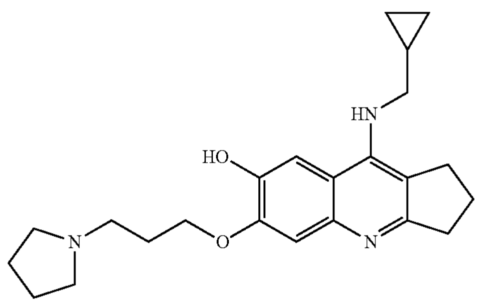 [SMILES: Oc1cc2c(NCC3CC3)c3c(nc2cc1OCCCN1CCCC1)CCC3] | 9-[(cyclopropylmethyl)amino]-6-[3-(pyrrolidin-1-yl)propoxy]-1H,2H,3H-cyclopenta[b]quinolin-7-ol | 381.52 |
| 3 | 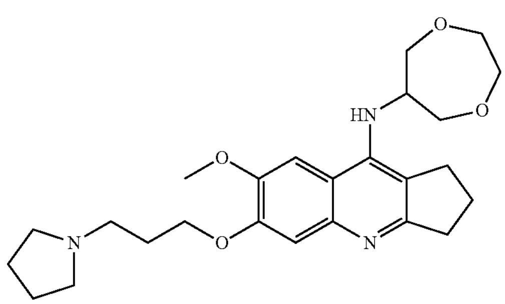 [SMILES: COc1cc2c(NC3COCCOC3)c3c(nc2cc1OCCCN1CCCC1)CCC3] | N-(1,4-dioxepan-6-yl)-7-methoxy-6-[3-(pyrrolidin-1-yl)propoxy]-1H,2H,3H-cyclopenta[b]quinolin-9-amine | 441.57 |
| 4 | 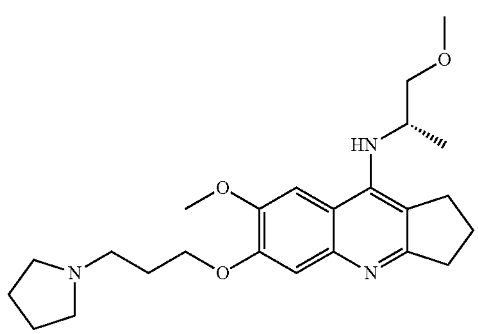 [SMILES: COC[C@H](C)Nc1c2c(nc3cc(OCCCN4CCCC4)c(OC)cc13)CCC2] | 7-methoxy-N-[(2S)-1-methoxypropan-2-yl]-6-[3-(pyrrolidin-1-yl)propoxy]-1H,2H,3H-cyclopenta[b]quinolin-9-amine | 413.56 |

TABLE 1-continued

| No | Structure | IUPAC Name | MS found |
|---|---|---|---|
| 5 | 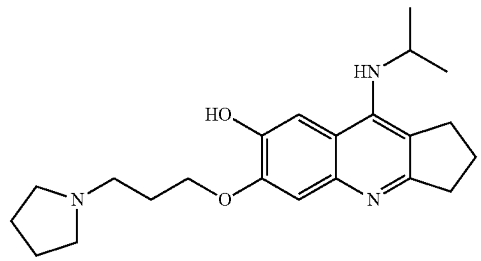 [SMILES: CC(C)Nc1c2c(nc3cc(OCCCN4CCCC4)c(O)cc13)CCC2] | 9-[(propan-2-yl)amino]-6-[3-(pyrrolidin-1-yl)propoxy]-1H,2H,3H-cyclopenta[b]quinolin-7-ol | 369.51 |
| 6 | 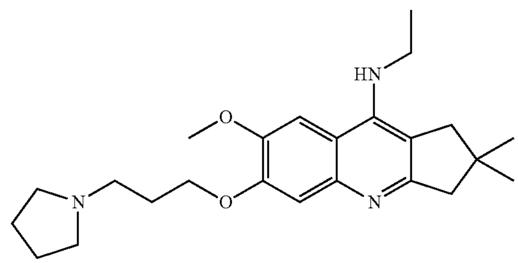 [SMILES: CCNc1c2c(nc3cc(OCCCN4CCCC4)c(OC)cc13)CC(C)(C)C2] | N-ethyl-7-methoxy-2,2-dimethyl-6-[3-(pyrrolidin-1-yl)propoxy]-1H,2H,3H-cyclopenta[b]quinolin-9-amine | 397.56 |
| 7 | 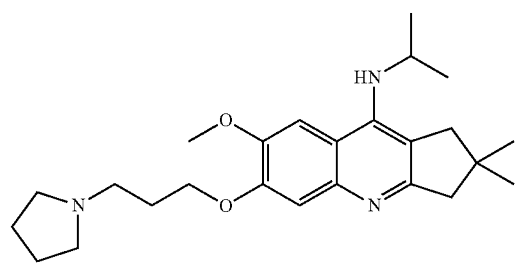 [SMILES: COc1cc2c(NC(C)C)c3c(nc2cc1OCCCN1CCCC1)CC(C)(C)C3] | 7-methoxy-2,2-dimethyl-N-(propan-2-yl)-6-[3-(pyrrolidin-1-yl)propoxy]-1H,2H,3H-cyclopenta[b]quinolin-9-amine | 411.59 |
| 8 | 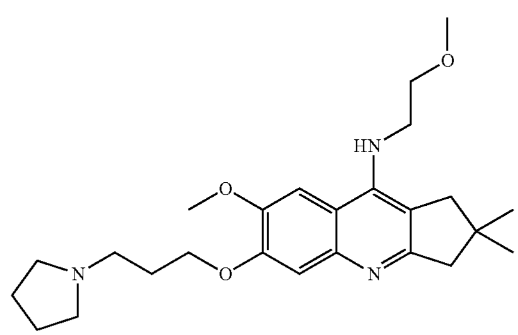 [SMILES: COCCNc1c2c(nc3cc(OCCCN4CCCC4)c(OC)cc13)CC(C)(C)C2] | 7-methoxy-N-(2-methoxyethyl)-2,2-dimethyl-6-[3-(pyrrolidin-1-yl)propoxy]-1H,2H,3H-cyclopenta[b]quinolin-9-amine | 427.59 |
| 9 | 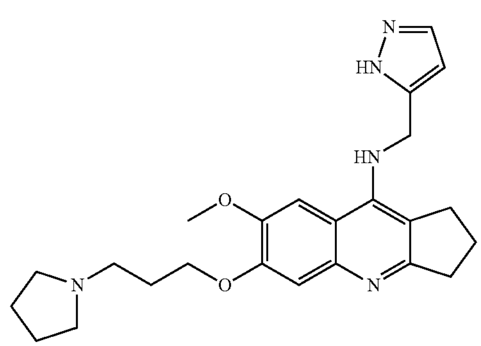 [SMILES: COc1cc2c(NCc3ccn[nH]3)c3c(nc2cc1OCCCN1CCCC1)CCC3] | 7-methoxy-N-[(1H-pyrazol-5-yl)methyl]-6-[3-(pyrrolidin-1-yl)propoxy]-1H,2H,3H-cyclopenta[b]quinolin-9-amine | 421.55 |

TABLE 1-continued

| No | Structure | IUPAC Name | MS found |
|---|---|---|---|
| 10 | 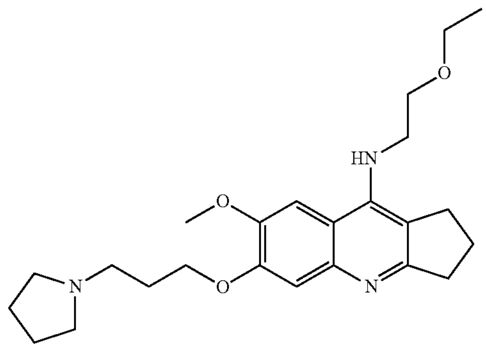 [SMILES: CCOCCNc1c2c(nc3cc(OCCCN4CCCC4)c(OC)cc13)CCC2] | N-(2-ethoxyethyl)-7-methoxy-6-[3-(pyrrolidin-1-yl)propoxy]-1H,2H,3H-cyclopenta[b]quinolin-9-amine | 413.56 |
| 11 | 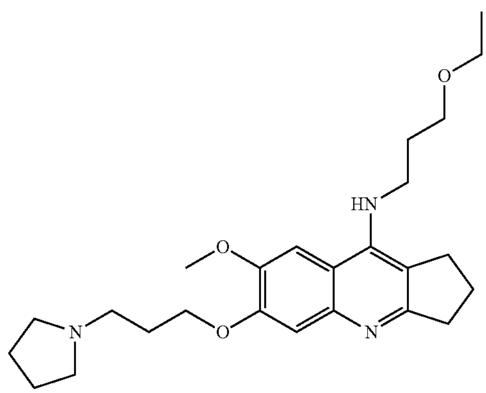 [SMILES: CCOCCCNc1c2c(nc3cc(OCCCN4CCCC4)c(OC)cc13)CCC2] | N-(3-ethoxypropyl)-7-methoxy-6-[3-(pyrrolidin-1-yl)propoxy]-1H,2H,3H-cyclopenta[b]quinolin-9-amine | 427.59 |
| 12 | 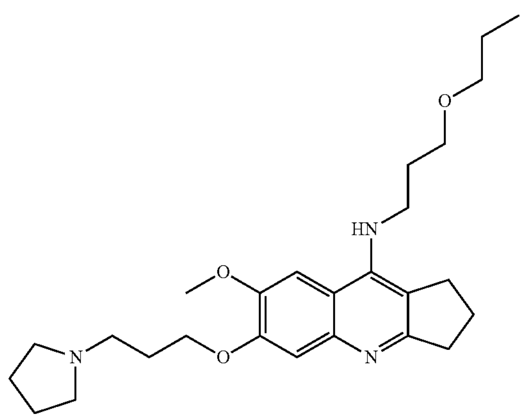 [SMILES: CCCOCCCNc1c2c(nc3cc(OCCCN4CCCC4)c(OC)cc13)CCC2] | 7-methoxy-N-(3-propoxypropyl)-6-[3-(pyrrolidin-1-yl)propoxy]-1H,2H,3H-cyclopenta[b]quinolin-9-amine | 441.62 |
| 13 | 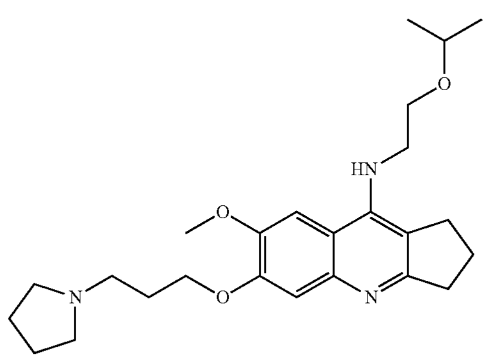 [SMILES: COc1cc2c(NCCOC(C)C)c3c(nc2cc1OCCCN1CCCC1)CCC3] | 7-methoxy-N-[2-(propan-2-yloxy)ethyl]-6-[3-(pyrrolidin-1-yl)propoxy]-1H,2H,3H-cyclopenta[b]quinolin-9-amine | 427.59 |

TABLE 1-continued

| No | Structure | IUPAC Name | MS found |
|---|---|---|---|
| 14 | 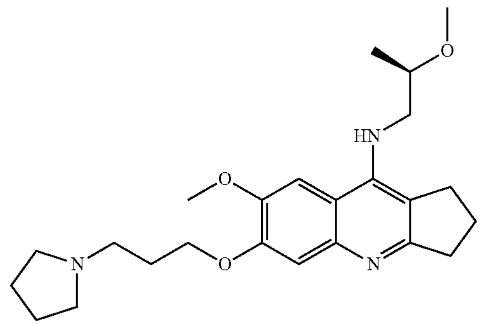 [SMILES: COc1cc2c(NC[C@@H](C)OC)c3c(nc2cc1OCCCN1CCCC1)CCC3] | 7-methoxy-N-[(2R)-2-methoxypropyl]-6-[3-(pyrrolidin-1-yl)propoxy]-1H,2H,3H-cyclopenta[b]quinolin-9-amine | 413.56 |
| 15 | 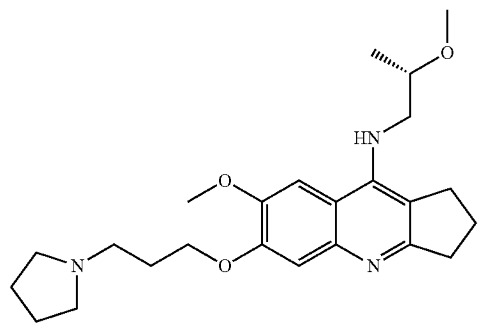 [SMILES: COc1cc2c(NC[C@H](C)OC)c3c(nc2cc1OCCCN1CCCC1)CCC3] | 7-methoxy-N-[(2S)-2-methoxypropyl]-6-[3-(pyrrolidin-1-yl)propoxy]-1H,2H,3H-cyclopenta[b]quinolin-9-amine | 413.56 |
| 16 | 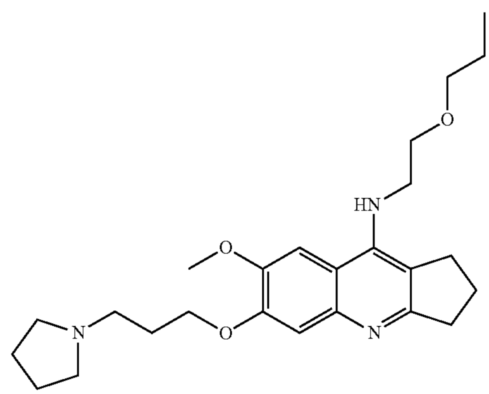 [SMILES: CCCOCCNc1c2c(nc3cc(OCCCN4CCCC4)c(OC)cc13)CCC2] | 7-methoxy-N-(2-propoxyethyl)-6-[3-(pyrrolidin-1-yl)propoxy]-1H,2H,3H-cyclopenta[b]quinolin-9-amine | 427.59 |
| 17 | 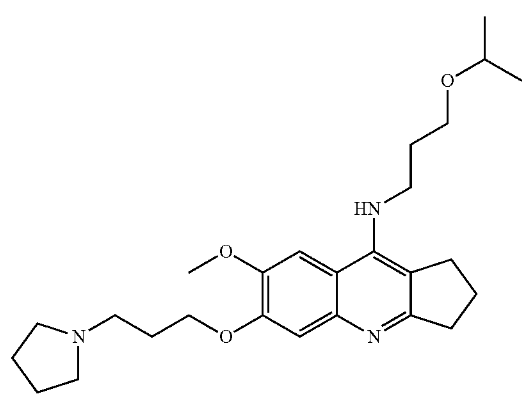 [SMILES: COc1cc2c(NCCCOC(C)C)c3c(nc2cc1OCCCN1CCCC1)CCC3] | 7-methoxy-N-[3-(propan-2-yloxy)propyl]-6-[3-(pyrrolidin-1-yl)propoxy]-1H,2H,3H-cyclopenta[b]quinolin-9-amine | 441.62 |

TABLE 1-continued

| No | Structure | IUPAC Name | MS found |
|---|---|---|---|
| 18 | 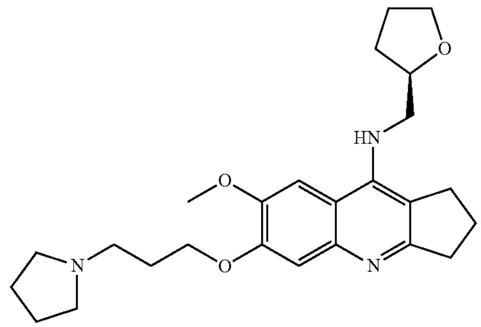 [SMILES: COc1cc2c(NC[C@H]3CCCO3)c3c(nc2cc1OCCCN1CCCC1)CCC3] | 7-methoxy-N-{[(2R)-oxolan-2-yl]methyl}-6-[3-(pyrrolidin-1-yl)propoxy]-1H,2H,3H-cyclopenta[b]quinolin-9-amine | 425.57 |
| 19 | 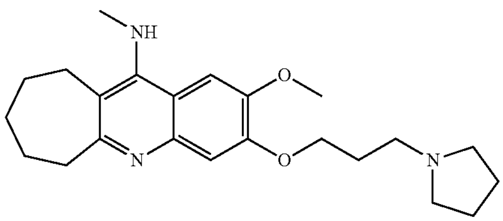 [SMILES: CNc1c2c(nc3cc(OCCCN4CCCC4)c(OC)cc13)CCCCC2] | 2-methoxy-N-methyl-3-[3-(pyrrolidin-1-yl)propoxy]-6H,7H,8H,9H,10H-cyclohepta[b]quinolin-11-amine | 383.54 |
| 20 | 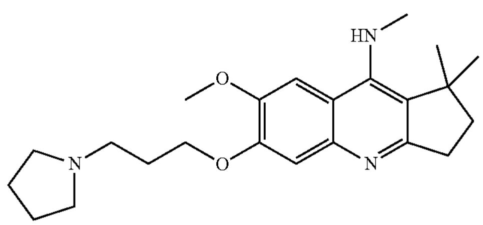 [SMILES: CNc1c2c(nc3cc(OCCCN4CCCC4)c(OC)cc13)CCC2(C)C] | 7-methoxy-N,1,1-trimethyl-6-[3-(pyrrolidin-1-yl)propoxy]-1H,2H,3H-cyclopenta[b]quinolin-9-amine | 383.54 |
| 21 | 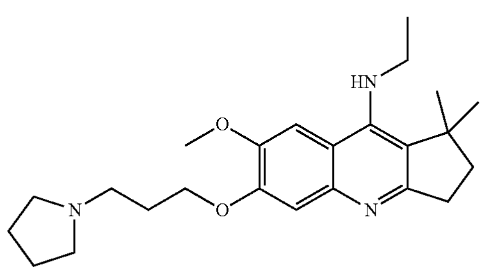 [SMILES: CCNc1c2c(nc3cc(OCCCN4CCCC4)c(OC)cc13)CCC2(C)C] | N-ethyl-7-methoxy-1,1-dimethyl-6-[3-(pyrrolidin-1-yl)propoxy]-1H,2H,3H-cyclopenta[b]quinolin-9-amine | 397.56 |
| 22 | 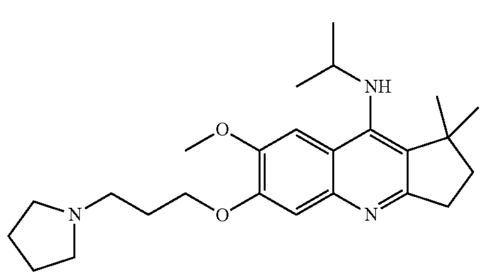 [SMILES: COc1cc2c(NC(C)C)c3c(nc2cc1OCCCN1CCCC1)CCC3(C)C] | 7-methoxy-1,1-dimethyl-N-(propan-2-yl)-6-[3-(pyrrolidin-1-yl)propoxy]-1H,2H,3H-cyclopenta[b]quinolin-9-amine | 411.59 |

TABLE 1-continued

| No | Structure | IUPAC Name | MS found |
|---|---|---|---|
| 23 | 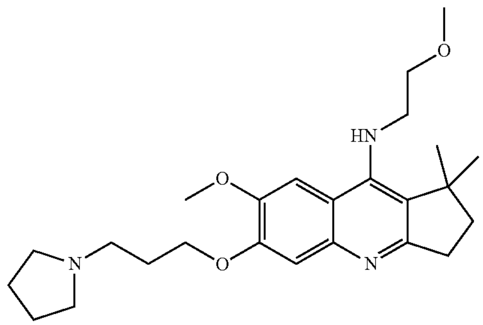 [SMILES: COCCNc1c2c(nc3cc(OCCCN4CCCC4)c(OC)cc13)CCC2(C)C] | 7-methoxy-N-(2-methoxyethyl)-1,1-dimethyl-6-[3-(pyrrolidin-1-yl)propoxy]-1H,2H,3H-cyclopenta[b]quinolin-9-amine | 427.59 |
| 24 | 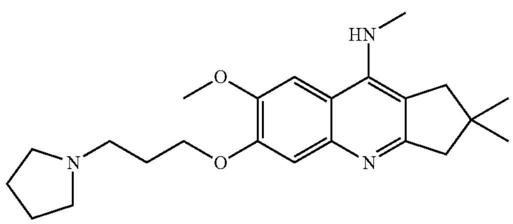 [SMILES: CNc1c2c(nc3cc(OCCCN4CCCC4)c(OC)cc13)CC(C)(C)C2] | 7-methoxy-N,2,2-trimethyl-6-[3-(pyrrolidin-1-yl)propoxy]-1H,2H,3H-cyclopenta[b]quinolin-9-amine | 383.54 |
| 25 | 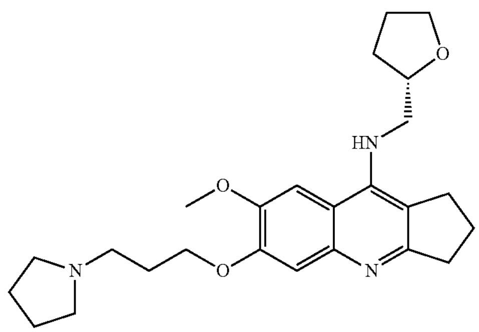 [SMILES: COc1cc2c(NC[C@@H]3CCCO3)c3c(nc2cc1OCCCN1CCCC1)CCC3] | 7-methoxy-N-{[(2S)-oxolan-2-yl]methyl}-6-[3-(pyrrolidin-1-yl)propoxy]-1H,2H,3H-cyclopenta[b]quinolin-9-amine | 425.57 |
| 26 | 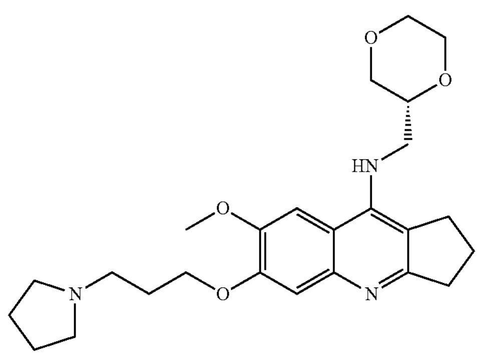 [SMILES: COc1cc2c(NC[C@@H]3COCCO3)c3c(nc2cc1OCCCN1CCCC1)CCC3] | N-{[(2R)-1,4-dioxan-2-yl]methyl}-7-methoxy-6-[3-(pyrrolidin-1-yl)propoxy]-1H,2H,3H-cyclopenta[b]quinolin-9-amine | 441.57 |
| 27 | 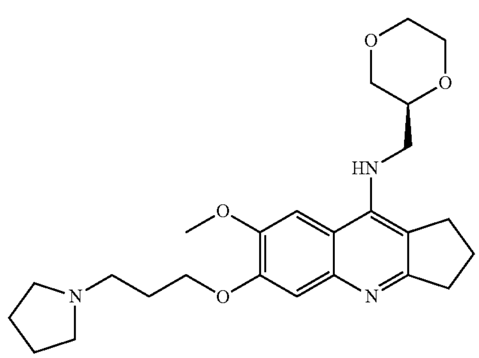 [SMILES: COc1cc2c(NC[C@H]3COCCO3)c3c(nc2cc1OCCCN1CCCC1)CCC3] | N-{[(2S)-1,4-dioxan-2-yl]methyl}-7-methoxy-6-[3-(pyrrolidin-1-yl)propoxy]-1H,2H,3H-cyclopenta[b]quinolin-9-amine | 441.57 |

TABLE 1-continued

| No | Structure | IUPAC Name | MS found |
|---|---|---|---|
| 28 | 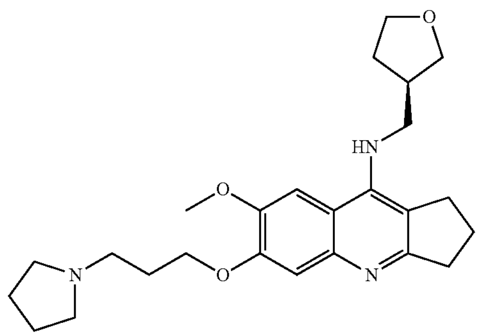 | 7-methoxy-N-{[(3R)-oxolan-3-yl]methyl}-6-[3-(pyrrolidin-1-yl)propoxy]-1H,2H,3H-cyclopenta[b]quinolin-9-amine | 425.57 |
| 29 | 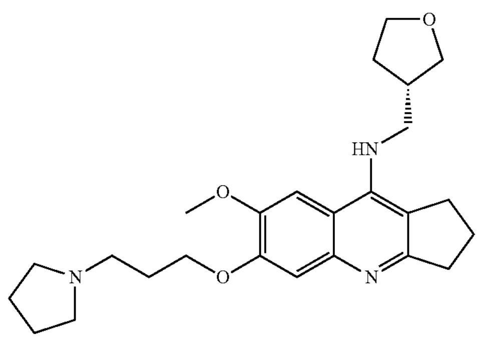 | 7-methoxy-N-{[(3S)-oxolan-3-yl]methyl}-6-[3-(pyrrolidin-1-yl)propoxy]-1H,2H,3H-cyclopenta[b]quinolin-9-amine | 425.57 |
| 30 | 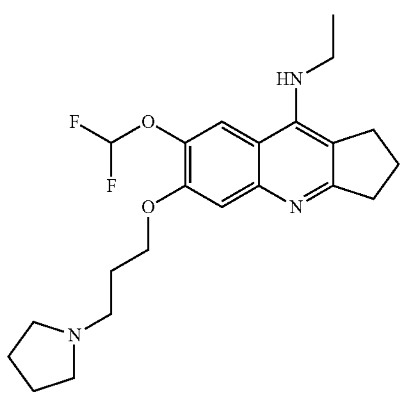 [SMILES: CCNc1c2c(nc3cc(OCCCN4CCCC4)c(OC(F)F)cc13)CCC2] | 7-(difluoromethoxy)-N-ethyl-6-[3-(pyrrolidin-1-yl)propoxy]-1H,2H,3H-cyclopenta[b]quinolin-9-amine | 405.49 |
| 31 | 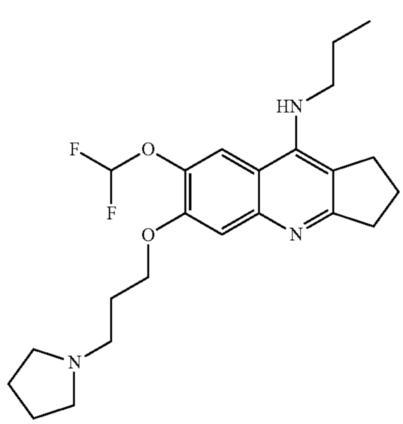 [SMILES: CCCNc1c2c(nc3cc(OCCCN4CCCC4)c(OC(F)F)cc13)CCC2] | 7-(difluoromethoxy)-N-propyl-6-[3-(pyrrolidin-1-yl)propoxy]-1H,2H,3H-cyclopenta[b]quinolin-9-amine | 419.52 |

TABLE 1-continued

| No | Structure | IUPAC Name | MS found |
|----|-----------|------------|----------|
| 32 | 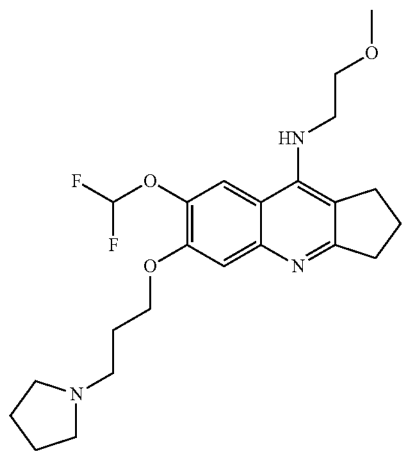 [SMILES: COCCNc1c2c(nc3cc(OCCCN4CCCC4)c(OC(F)F)cc13)CCC2] | 7-(difluoromethoxy)-N-(2-methoxyethyl)-6-[3-(pyrrolidin-1-yl)propoxy]-1H,2H,3H-cyclopenta[b]quinolin-9-amine | 435.52 |
| 33 | 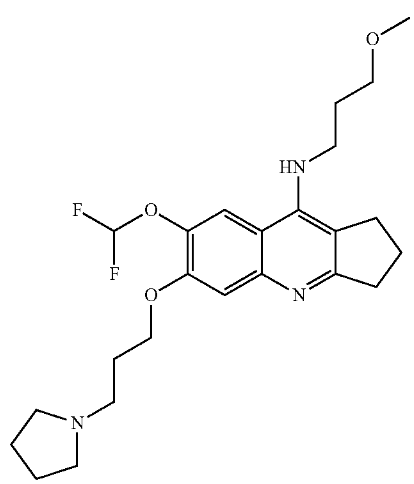 [SMILES: COCCCNc1c2c(nc3cc(OCCCN4CCCC4)c(OC(F)F)cc13)CCC2] | 7-(difluoromethoxy)-N-(3-methoxypropyl)-6-[3-(pyrrolidin-1-yl)propoxy]-1H,2H,3H-cyclopenta[b]quinolin-9-amine | 449.54 |
| 34 | 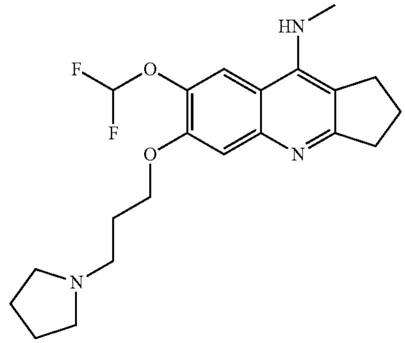 [SMILES: CNc1c2c(nc3cc(OCCCN4CCCC4)c(OC(F)F)cc13)CCC2] | 7-(difluoromethoxy)-N-methyl-6-[3-(pyrrolidin-1-yl)propoxy]-1H,2H,3H-cyclopenta[b]quinolin-9-amine | 391.46 |

TABLE 1-continued

| No | Structure | IUPAC Name | MS found |
|---|---|---|---|
| 35 | 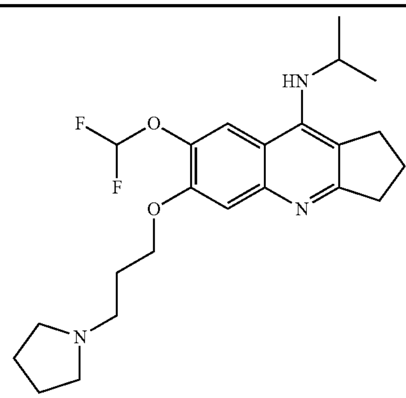 | 7-(difluoromethoxy)-N-(propan-2-yl)-6-[3-(pyrrolidin-1-yl)propoxy]-1H,2H,3H-cyclopenta[b]quinolin-9-amine | 419.52 |
| 36 | 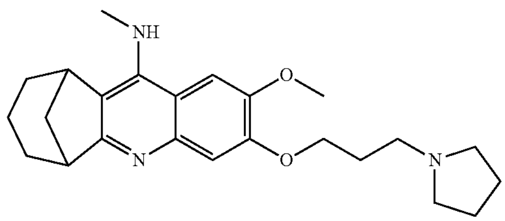 [SMILES: CNc1c2c(nc3cc(OCCCN4CCCC4)c(OC)cc13)C1CCCC2C1] | 7-methoxy-N-methyl-6-[3-(pyrrolidin-1-yl)propoxy]-3-azatetracyclo[10.3.1.0^{2,11}.0^{4,9}]hexadeca-2,4,6,8,10-pentaen-10-amine | 395.55 |
| 37 | 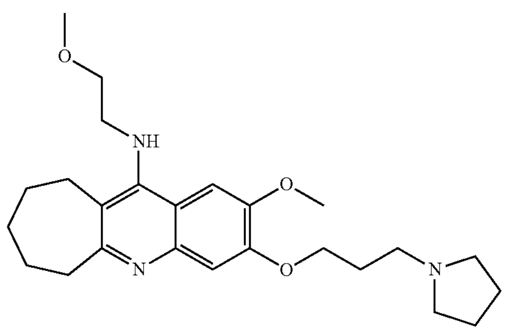 [SMILES: COCCNc1c2c(nc3cc(OCCCN4CCCC4)c(OC)cc13)CCCCC2] | 2-methoxy-N-(2-methoxyethyl)-3-[3-(pyrrolidin-1-yl)propoxy]-6H,7H,8H,9H,10H-cyclohepta[b]quinolin-11-amine | 427.59 |
| 38 | 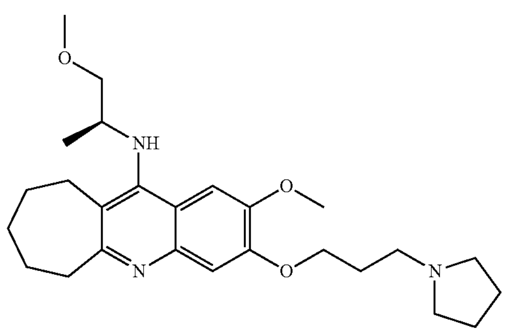 [SMILES: COC[C@H](C)Nc1c2c(nc3cc(OCCCN4CCCC4)c(OC)cc13)CCCCC2] | 2-methoxy-N-[(2S)-1-methoxypropan-2-yl]-3-[3-(pyrrolidin-1-yl)propoxy]-6H,7H,8H,9H,10H-cyclohepta[b]quinolin-11-amine | 441.62 |
| 39 | 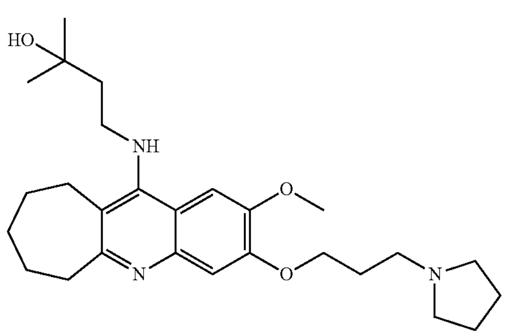 [SMILES: COc1cc2c(NCCC(C)(C)O)c3c(nc2cc1OCCCN1CCCC1)CCCCC3] | 4-({2-methoxy-3-[3-(pyrrolidin-1-yl)propoxy]-6H,7H,8H,9H,10H-cyclohepta[b]quinolin-11-yl}amino)-2-methylbutan-2-ol | 455.64 |

TABLE 1-continued

| No | Structure | IUPAC Name | MS found |
|---|---|---|---|
| 40 | 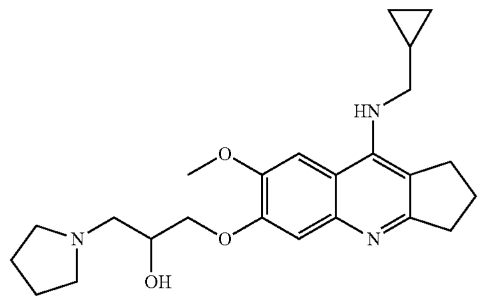 [SMILES: COc1cc2c(NCC3CC3)c3c(nc2cc1OCC(O)CN1CCCC1)CCC3] | 1-({9-[(cyclopropylmethyl)amino]-7-methoxy-1H,2H,3H-cyclopenta[b]quinolin-6-yl}oxy)-3-(pyrrolidin-1-yl)propan-2-ol | 411.55 |
| 41 | 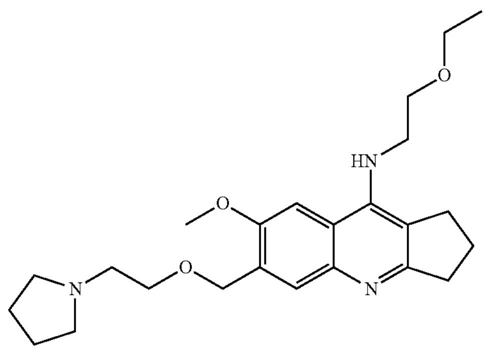 [SMILES: CCOCCNc1c2c(nc3cc(COCCN4CCCC4)c(OC)cc13)CCC2] | N-(2-ethoxyethyl)-7-methoxy-6-{[2-(pyrrolidin-1-yl)ethoxy]methyl}-1H,2H,3H-cyclopenta[b]quinolin-9-amine | 413.56 |
| 42 | 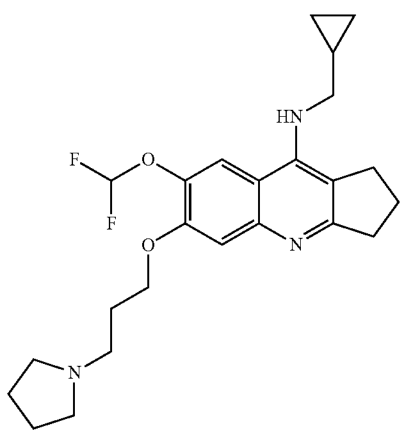 [SMILES: FC(F)Oc1cc2c(NCC3CC3)c3c(nc2cc1OCCCN1CCCC1)CCC3] | N-(cyclopropylmethyl)-7-(difluoromethoxy)-6-[3-(pyrrolidin-1-yl)propoxy]-1H,2H,3H-cyclopenta[b]quinolin-9-amine | 431.53 |
| 43 | 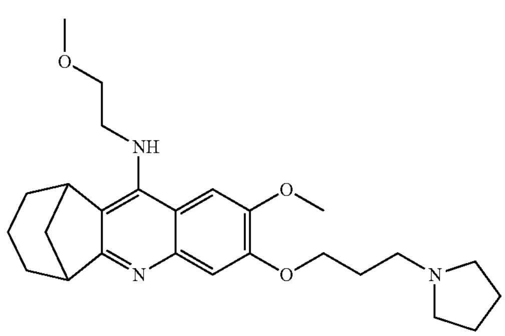 [SMILES: COCCNc1c2c(nc3cc(OCCCN4CCCC4)c(OC)cc13)C1CCCC2C1] | 7-methoxy-N-(2-methoxyethyl)-6-[3-(pyrrolidin-1-yl)propoxy]-3-azatetracyclo[10.3.1.0^{2,11}.0^{4,9}]hexadeca-2,4,6,8,10-pentaen-10-amine | 439.6 |

TABLE 1-continued

| No | Structure | IUPAC Name | MS found |
|---|---|---|---|
| 44 | 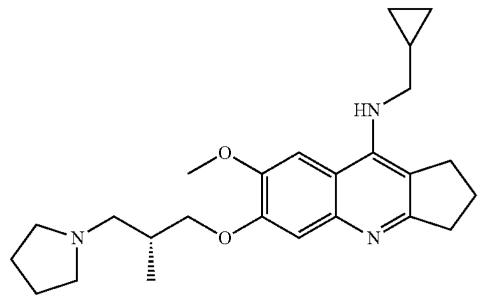 [SMILES: COc1cc2c(NCC3CC3)c3c(nc2cc1OC[C@H](C)CN1CCCC1)CCC3] | N-(cyclopropylmethyl)-7-methoxy-6-[(2R)-2-[(pyrrolidin-1-yl)methyl]propoxy]-1H,2H,3H-cyclopenta[b]quinolin-9-amine | 409.57 |
| 45 | 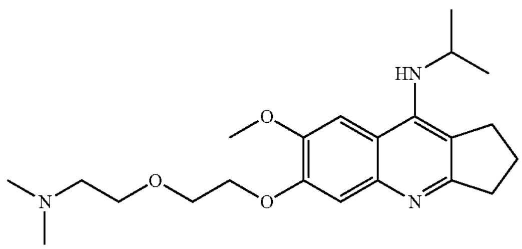 [SMILES: COc1cc2c(NC(C)C)c3c(nc2cc1OCCOCCN(C)C)CCC3] | 6-{2-[2-(dimethylamino)ethoxy]ethoxy}-7-methoxy-N-(propan-2-yl)-1H,2H,3H-cyclopenta[b]quinolin-9-amine | 387.52 |
| 46 | 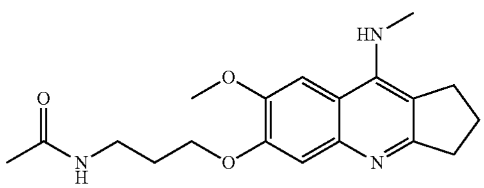 [SMILES: CNc1c2c(nc3cc(OCCCNC(C)=O)c(OC)cc13)CCC2] | N-(3-{[7-methoxy-9-(methylamino)-1H,2H,3H-cyclopenta[b]quinolin-6-yl]oxy}propyl)acetamide | 343.43 |
| 47 | 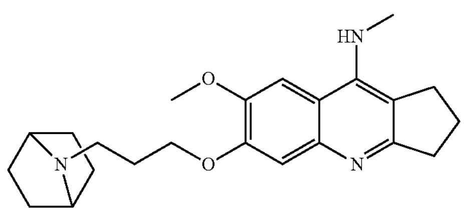 [SMILES: CNc1c2c(nc3cc(OCCCN4C5CCC4CC5)c(OC)cc13)CCC2] | 6-(3-{7-azabicyclo[2.2.1]heptan-7-yl}propoxy)-7-methoxy-N-methyl-1H,2H,3H-cyclopenta[b]quinolin-9-amine | 381.52 |
| 48 | 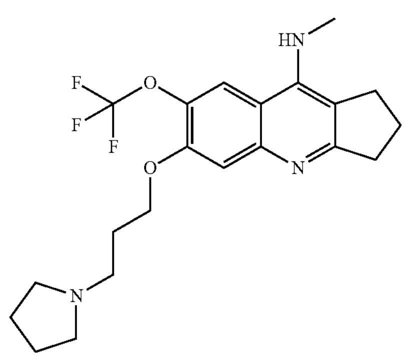 [SMILES: CNc1c2c(nc3cc(OCCCN4CCCC4)c(OC(F)(F)F)cc13)CCC2] | N-methyl-6-[3-(pyrrolidin-1-yl)propoxy]-7-(trifluoromethoxy)-1H,2H,3H-cyclopenta[b]quinolin-9-amine | 409.45 |

TABLE 1-continued

| No | Structure | IUPAC Name | MS found |
|---|---|---|---|
| 49 | 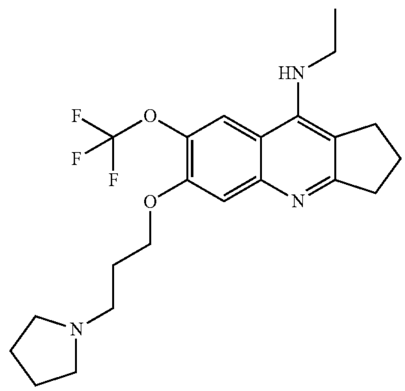 [SMILES: CCNc1c2c(nc3cc(OCCCN4CCCC4)c(OC(F)(F)F)cc13)CCC2] | N-ethyl-6-[3-(pyrrolidin-1-yl)propoxy]-7-(trifluoromethoxy)-1H,2H,3H-cyclopenta[b]quinolin-9-amine | 423.48 |
| 50 | 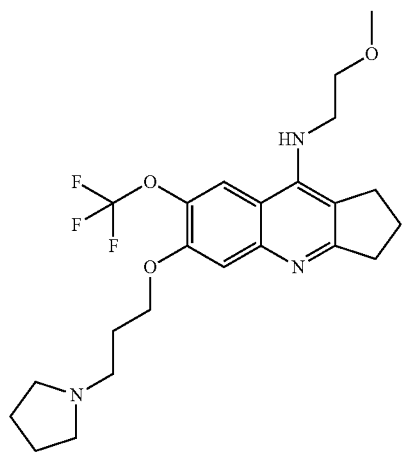 [SMILES: COCCNc1c2c(nc3cc(OCCCN4CCCC4)c(OC(F)(F)F)cc13)CCC2] | N-(2-methoxyethyl)-6-[3-(pyrrolidin-1-yl)propoxy]-7-(trifluoromethoxy)-1H,2H,3H-cyclopenta[b]quinolin-9-amine | 453.51 |
| 51 | 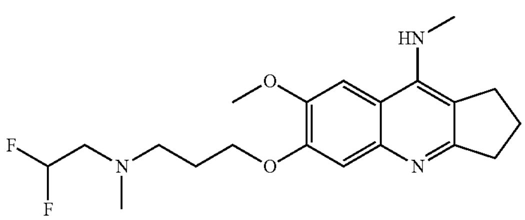 [SMILES: CNc1c2c(nc3cc(OCCCN(C)CC(F)F)c(OC)cc13)CCC2] | 6-{3-[(2,2-difluoroethyl)(methyl)amino]propoxy}-7-methoxy-N-methyl-1H,2H,3H-cyclopenta[b]quinolin-9-amine | 379.45 |
| 52 | 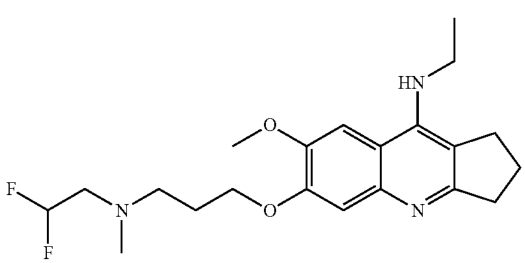 [SMILES: CCNc1c2c(nc3cc(OCCCN(C)CC(F)F)c(OC)cc13)CCC2] | 6-{3-[(2,2-difluoroethyl)(methyl)amino]propoxy}-N-ethyl-7-methoxy-1H,2H,3H-cyclopenta[b]quinolin-9-amine | 393.48 |

TABLE 1-continued

| No | Structure | IUPAC Name | MS found |
|---|---|---|---|
| 53 | 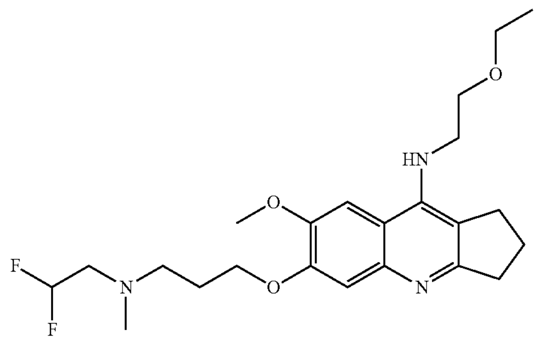 [SMILES: CCOCCNc1c2c(nc3cc(OCCCN(C)CC(F)F)c(OC)cc13)CCC2] | 6-{3-[(2,2-difluoroethyl)(methyl)amino]propoxy}-N-(2-ethoxyethyl)-7-methoxy-1H,2H,3H-cyclopenta[b]quinolin-9-amine | 437.53 |
| 54 | 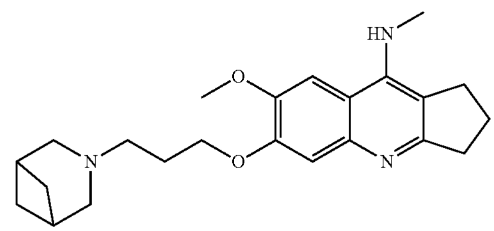 [SMILES: CNc1c2c(nc3cc(OCCCN4CC5CC(C5)C4)c(OC)cc13)CCC2] | 6-(3-{3-azabicyclo[3.1.1]heptan-3-yl}propoxy)-7-methoxy-N-methyl-1H,2H,3H-cyclopenta[b]quinolin-9-amine | 381.52 |
| 55 | 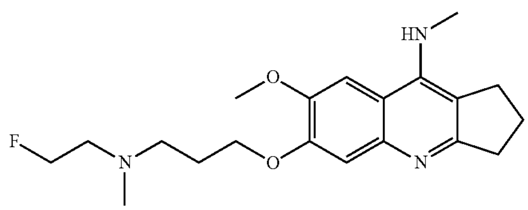 [SMILES: CNc1c2c(nc3cc(OCCCN(C)CCF)c(OC)cc13)CCC2] | 6-{3-[(2-fluoroethyl)(methyl)amino]propoxy}-7-methoxy-N-methyl-1H,2H,3H-cyclopenta[b]quinolin-9-amine | 361.46 |
| 56 | 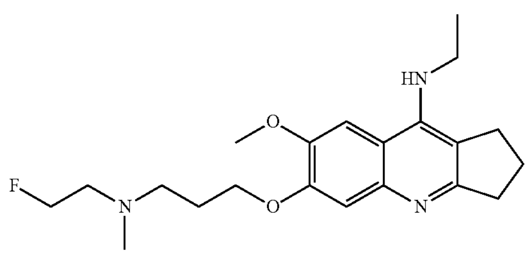 [SMILES: CCNc1c2c(nc3cc(OCCCN(C)CCF)c(OC)cc13)CCC2] | N-ethyl-6-{3-[(2-fluoroethyl)(methyl)amino]propoxy}-7-methoxy-1H,2H,3H-cyclopenta[b]quinolin-9-amine | 375.49 |
| 57 | 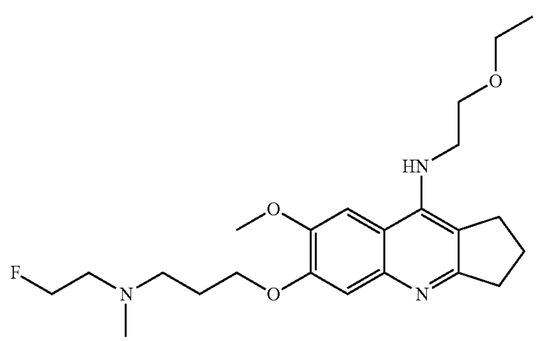 [SMILES: CCOCCNc1c2c(nc3cc(OCCCN(C)CCF)c(OC)cc13)CCC2] | N-(2-ethoxyethyl)-6-{3-[(2-fluoroethyl)(methyl)amino]propoxy}-7-methoxy-1H,2H,3H-cyclopenta[b]quinolin-9-amine | 419.54 |

TABLE 1-continued

| No | Structure | IUPAC Name | MS found |
|---|---|---|---|
| 58 | 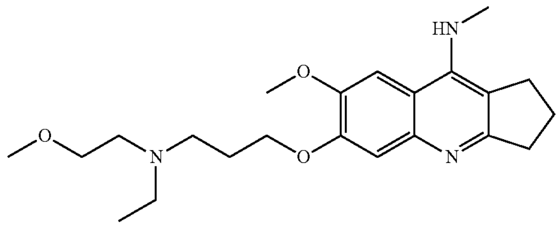 [SMILES: CCN(CCCOc1cc2nc3c(c(NC)c2cc1OC)CCC3)CCOC] | 6-{3-[ethyl(2-methoxyethyl)amino]propoxy}-7-methoxy-N-methyl-1H,2H,3H-cyclopenta[b]quinolin-9-amine | 387.52 |
| 59 | 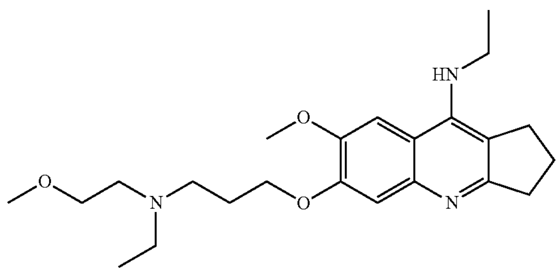 [SMILES: CCNc1c2c(nc3cc(OCCCN(CC)CCOC)c(OC)cc13)CCC2] | N-ethyl-6-{3-[ethyl(2-methoxyethyl)amino]propoxy}-7-methoxy-1H,2H,3H-cyclopenta[b]quinolin-9-amine | 401.55 |
| 60 | 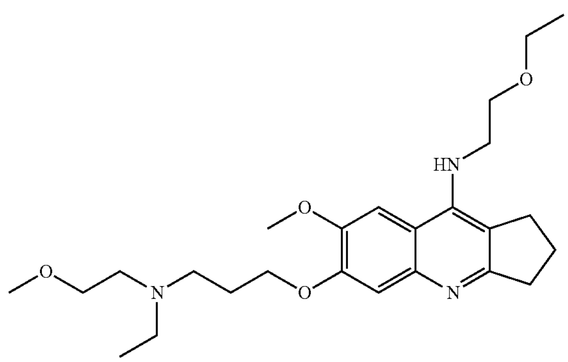 [SMILES: CCOCCNc1c2c(nc3cc(OCCCN(CC)CCOC)c(OC)cc13)CCC2] | N-(2-ethoxyethyl)-6-{3-[ethyl(2-methoxyethyl)amino]propoxy}-7-methoxy-1H,2H,3H-cyclopenta[b]quinolin-9-amine | 445.6 |
| 61 | 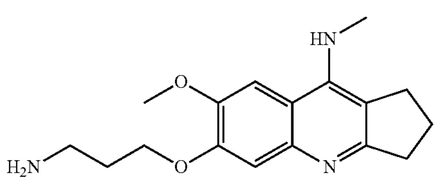 [SMILES: CNc1c2c(nc3cc(OCCCN)c(OC)cc13)CCC2] | 6-(3-aminopropoxy)-7-methoxy-N-methyl-1H,2H,3H-cyclopenta[b]quinolin-9-amine | 301.39 |
| 62 | 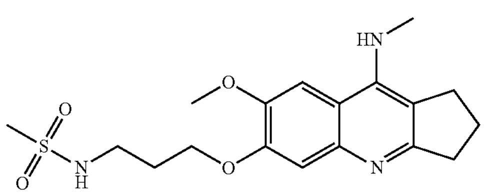 [SMILES: CNc1c2c(nc3cc(OCCCNS(C)(=O)=O)c(OC)cc13)CCC2] | N-(3-{[7-methoxy-9-(methylamino)-1H,2H,3H-cyclopenta[b]quinolin-6-yl]oxy}propyl)methanesulfonamide | 379.48 |
| 63 | 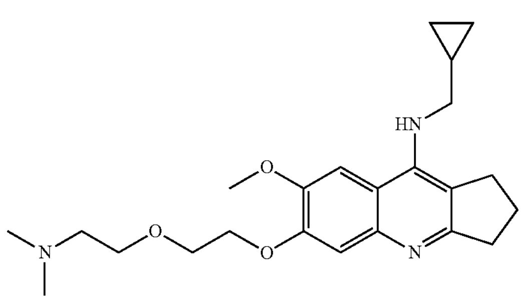 [SMILES: COc1cc2c(NCC3CC3)c3c(nc2cc1OCCOCCN(C)C)CCC3] | N-(cyclopropylmethyl)-6-{2-[2-(dimethylamino)ethoxy]ethoxy}-7-methoxy-1H,2H,3H-cyclopenta[b]quinolin-9-amine | 399.54 |

TABLE 1-continued

| No | Structure | IUPAC Name | MS found |
|---|---|---|---|
| 64 | 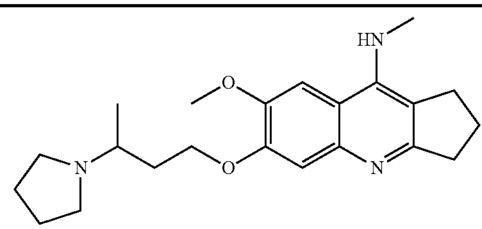 | 7-methoxy-N-methyl-6-[3-(pyrrolidin-1-yl)butoxy]-1H,2H,3H-cyclopenta[b]quinolin-9-amine | 369.51 |
| 65 | 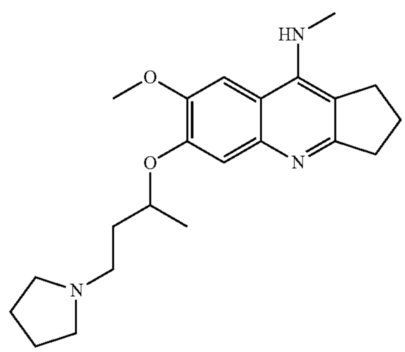 [SMILES: CNc1c2c(nc3cc(OC(C)CCN4CCCC4)c(OC)cc13)CCC2] | 7-methoxy-N-methyl-6-{[4-(pyrrolidin-1-yl)butan-2-yl]oxy}-1H,2H,3H-cyclopenta[b]quinolin-9-amine | 369.51 |
| 66 | 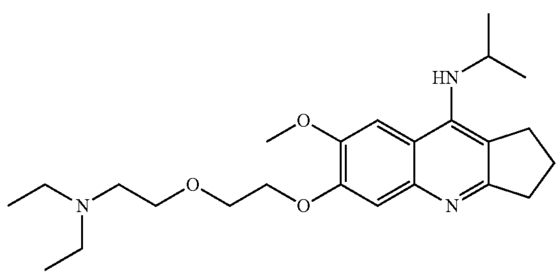 [SMILES: CCN(CC)CCOCCOc1cc2nc3c(c(NC(C)C)c2cc1OC)CCC3] | 6-{2-[2-(diethylamino)ethoxy]ethoxy}-7-methoxy-N-(propan-2-yl)-1H,2H,3H-cyclopenta[b]quinolin-9-amine | 415.58 |
| 67 | 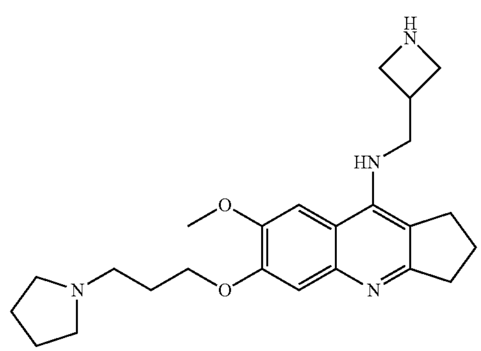 [SMILES: COc1cc2c(NCC3CNC3)c3c(nc2cc1OCCCN1CCCC1)CCC3] | N-[(azetidin-3-yl)methyl]-7-methoxy-6-[3-(pyrrolidin-1-yl)propoxy]-1H,2H,3H-cyclopenta[b]quinolin-9-amine | 410.56 |
| 68 | 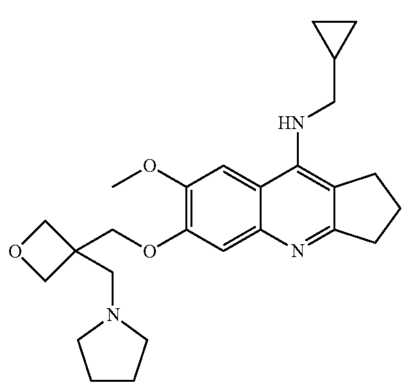 [SMILES: COc1cc2c(NCC3CC3)c3c(nc2cc1OCC1(CN2CCCC2)COC1)CCC3] | N-(cyclopropylmethyl)-7-methoxy-6-({3-[(pyrrolidin-1-yl)methyl]oxetan-3-yl}methoxy)-1H,2H,3H-cyclopenta[b]quinolin-9-amine | 437.58 |

TABLE 1-continued

| No | Structure | IUPAC Name | MS found |
|----|-----------|------------|----------|
| 69 | 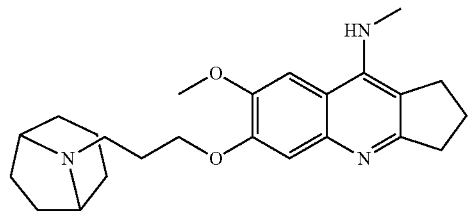 [SMILES: CNc1c2c(nc3cc(OCCCN4C5CCCC4CC5)c(OC)cc13)CCC2] | 6-(3-{8-azabicyclo[3.2.1]octan-8-yl}propoxy)-7-methoxy-N-methyl-1H,2H,3H-cyclopenta[b]quinolin-9-amine | 395.55 |
| 70 | 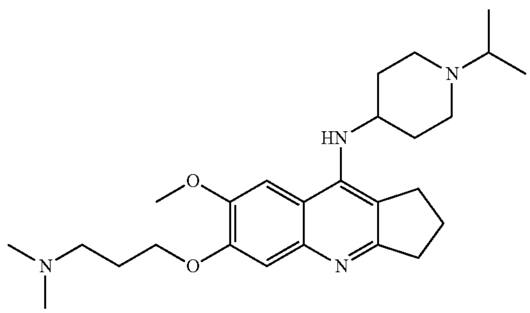 [SMILES: COc1cc2c(NC3CCN(C(C)C)CC3)c3c(nc2cc1OCCCN(C)C)CCC3] | N-{6-[3-(dimethylamino)propoxy]-7-methoxy-1H,2H,3H-cyclopenta[b]quinolin-9-yl}-1-(propan-2-yl)piperidin-4-amine | 440.63 |
| 71 | 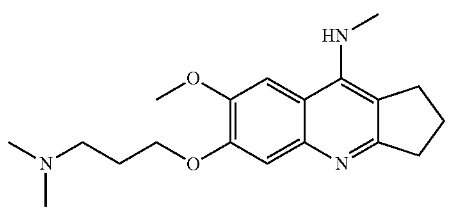 [SMILES: CNc1c2c(nc3cc(OCCCN(C)C)c(OC)cc13)CCC2] | 6-[3-(dimethylamino)propoxy]-7-methoxy-N-methyl-1H,2H,3H-cyclopenta[b]quinolin-9-amine | 329.44 |
| 72 | 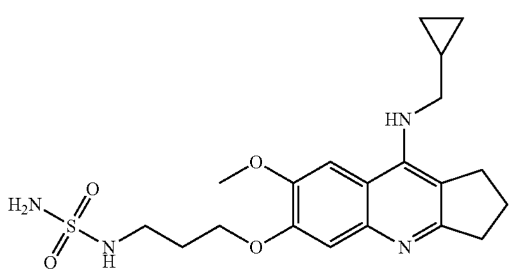 [SMILES: COc1cc2c(NCC3CC3)c3c(nc2cc1OCCCNS(N)(=O)=O)CCC3] | N-[3-({9-[(cyclopropylmethyl)amino]-7-methoxy-1H,2H,3H-cyclopenta[b]quinolin-6-yl}oxy)propyl]aminosulfonamide | 420.53 |
| 73 | 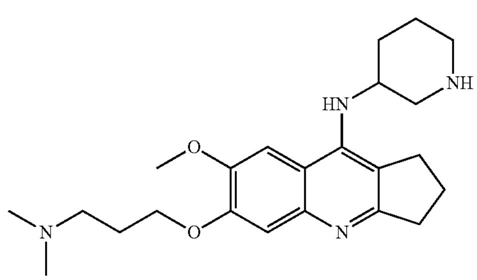 [SMILES: COc1cc2c(NC3CCCNC3)c3c(nc2cc1OCCCN(C)C)CCC3] | N-{6-[3-(dimethylamino)propoxy]-7-methoxy-1H,2H,3H-cyclopenta[b]quinolin-9-yl}piperidin-3-amine | 398.55 |

TABLE 1-continued

| No | Structure | IUPAC Name | MS found |
|---|---|---|---|
| 74 | 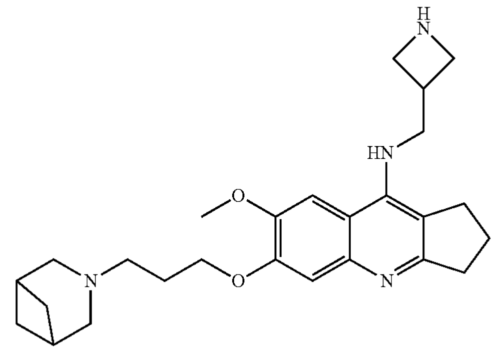 [SMILES: COc1cc2c(NCC3CNC3)c3c(nc2cc1OCCCN1CC2CC(C2)C1)CCC3] | 6-(3-{3-azabicyclo[3.1.1]heptan-3-yl}propoxy)-N-[(azetidin-3-yl)methyl]-7-methoxy-1H,2H,3H-cyclopenta[b]quinolin-9-amine | 436.6 |
| 75 | 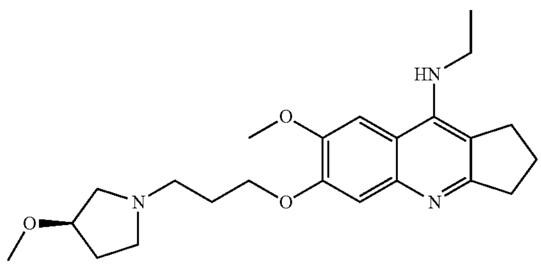 [SMILES: CCNc1c2c(nc3cc(OCCCN4CC[C@@H](OC)C4)c(OC)cc13)CCC2] | N-ethyl-7-methoxy-6-{3-[(3R)-3-methoxypyrrolidin-1-yl]propoxy}-1H,2H,3H-cyclopenta[b]quinolin-9-amine | 399.54 |
| 76 | 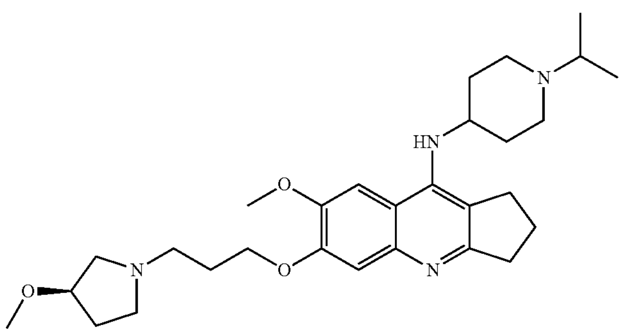 [SMILES: COc1cc2c(NC3CCN(C(C)C)CC3)c3c(nc2cc1OCCCN1CC[C@@H](OC)C1)CCC3] | N-(7-methoxy-6-{3-[(3R)-3-methoxypyrrolidin-1-yl]propoxy}-1H,2H,3H-cyclopenta[b]quinolin-9-yl)-1-(propan-2-yl)piperidin-4-amine | 496.7 |
| 77 | 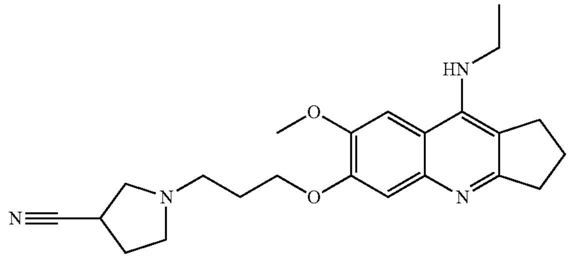 [SMILES: CCNc1c2c(nc3cc(OCCCN4CCC(C#N)C4)c(OC)cc13)CCC2] | 1-(3-{[9-(ethylamino)-7-methoxy-1H,2H,3H-cyclopenta[b]quinolin-6-yl]oxy}propyl)pyrrolidine-3-carbonitrile | 394.52 |

TABLE 2

| No. | Structure | IUPAC Name |
|---|---|---|
| 78 | 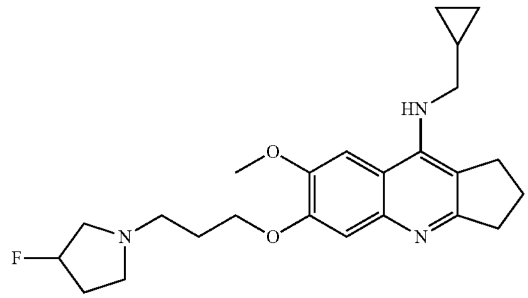 [SMILES: COc1cc2c(NCC3CC3)c3c(nc2cc1OCCCN1CCC(F)C1)CCC3] | N-(cyclopropylmethyl)-6-[3-(3-fluoropyrrolidin-1-yl)propoxy]-7-methoxy-1H,2H,3H-cyclopenta[b]quinolin-9-amine |
| 79 | 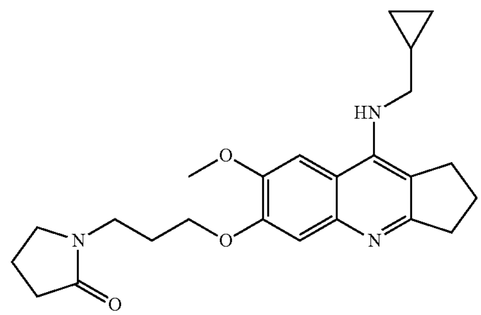 [SMILES: COc1cc2c(NCC3CC3)c3c(nc2cc1OCCCN1CCCC1=O)CCC3] | 1-[3-({9-[(cyclopropylmethyl)amino]-7-methoxy-1H,2H,3H-cyclopenta[b]quinolin-6-yl}oxy)propyl]pyrrolidin-2-one |
| 80 | 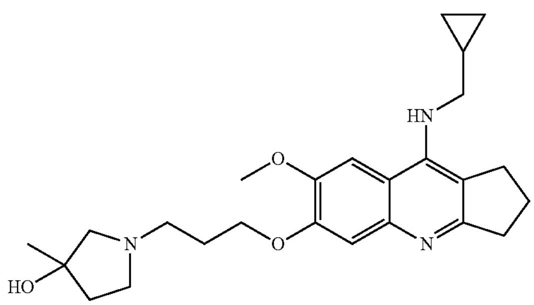 [SMILES: COc1cc2c(NCC3CC3)c3c(nc2cc1OCCCN1CCC(C)(O)C1)CCC3] | 1-[3-({9-[(cyclopropylmethyl)amino]-7-methoxy-1H,2H,3H-cyclopenta[b]quinolin-6-yl}oxy)propyl]-3-methylpyrrolidin-3-ol |
| 81 | 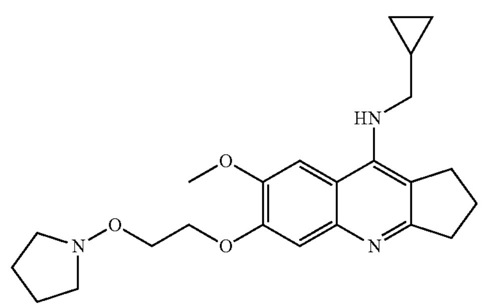 [SMILES: COc1cc2c(NCC3CC3)c3c(nc2cc1OCCON1CCCC1)CCC3] | N-(cyclopropylmethyl)-7-methoxy-6-[2-(pyrrolidin-1-yloxy)ethoxy]-1H,2H,3H-cyclopenta[b]quinolin-9-amine |
| 82 | 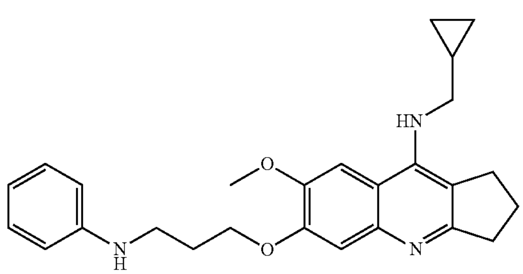 [SMILES: COc1cc2c(NCC3CC3)c3c(nc2cc1OCCCNc1ccccc1)CCC3] | N-(cyclopropylmethyl)-7-methoxy-6-[3-(phenylamino)propoxy]-1H,2H,3H-cyclopenta[b]quinolin-9-amine |

| No. | Structure | IUPAC Name |
|-----|-----------|------------|
| 83 | 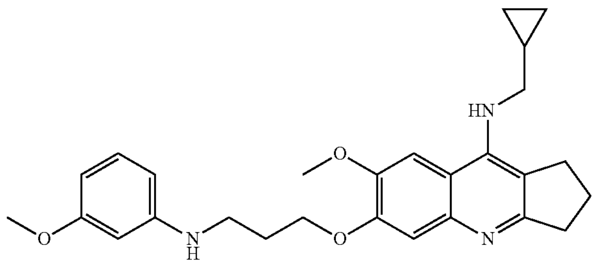 [SMILES: COc1cccc(NCCCOc2cc3nc4c(c(NCC5CC5)c3cc2OC)CCC4)c1] | N-(cyclopropylmethyl)-7-methoxy-6-{3-[(3-methoxyphenyl)amino]propoxy}-1H,2H,3H-cyclopenta[b]quinolin-9-amine |
| 84 | 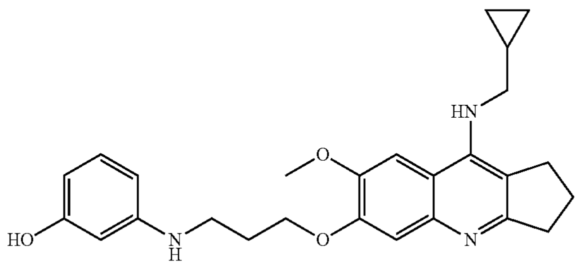 [SMILES: COc1cc2c(NCC3CC3)c3c(nc2cc1OCCCNc1cccc(O)c1)CCC3] | 3-{[3-({9-[(cyclopropylmethyl)amino]-7-methoxy-1H,2H,3H-cyclopenta[b]quinolin-6-yl}oxy)propyl]amino}phenol |
| 85 | 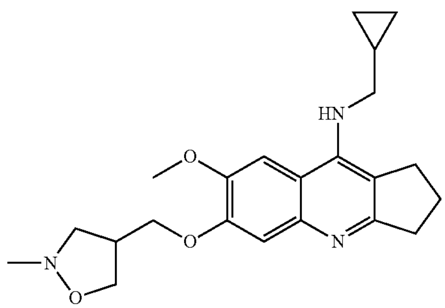 [SMILES: COc1cc2c(NCC3CC3)c3c(nc2cc1OCC1CON(C)C1)CCC3] | N-(cyclopropylmethyl)-7-methoxy-6-[(2-methyl-1,2-oxazolidin-4-yl)methoxy]-1H,2H,3H-cyclopenta[b]quinolin-9-amine |
| 86 | 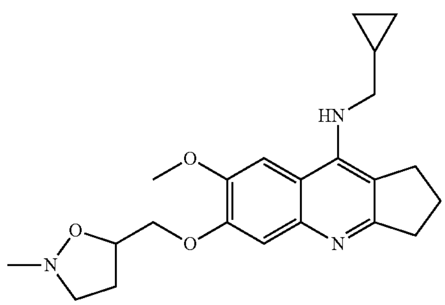 [SMILES: COc1cc2c(NCC3CC3)c3c(nc2cc1OCC1CCN(C)O1)CCC3] | N-(cyclopropylmethyl)-7-methoxy-6-[(2-methyl-1,2-oxazolidin-5-yl)methoxy]-1H,2H,3H-cyclopenta[b]quinolin-9-amine |
| 87 | 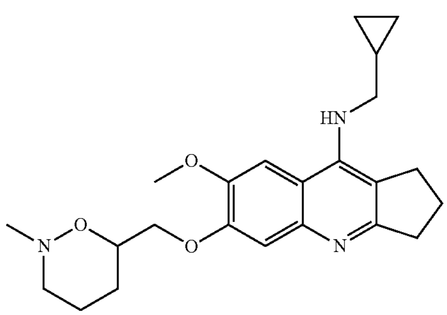 [SMILES: COc1cc2c(NCC3CC3)c3c(nc2cc1OCC1CCCN(C)O1)CCC3] | N-(cyclopropylmethyl)-7-methoxy-6-[(2-methyl-1,2-oxazinan-6-yl)methoxy]-1H,2H,3H-cyclopenta[b]quinolin-9-amine |

TABLE 2-continued

| No. | Structure | IUPAC Name |
|---|---|---|
| 88 | 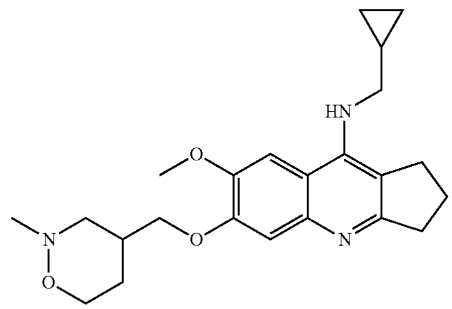 [SMILES: COc1cc2c(NCC3CC3)c3c(nc2cc1OCC1CCON(C)C1)CCC3] | N-(cyclopropylmethyl)-7-methoxy-6-[(2-methyl-1,2-oxazinan-4-yl)methoxy]-1H,2H,3H-cyclopenta[b]quinolin-9-amine |
| 89 | 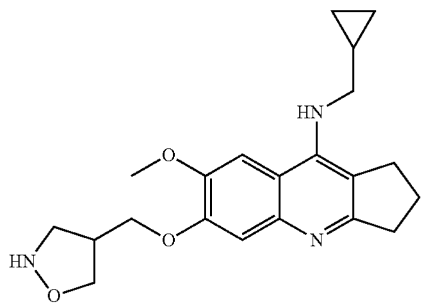 [SMILES: COc1cc2c(NCC3CC3)c3c(nc2cc1OCC1CNOC1)CCC3] | N-(cyclopropylmethyl)-7-methoxy-6-[(1,2-oxazolidin-4-yl)methoxy]-1H,2H,3H-cyclopenta[b]quinolin-9-amine |
| 90 | 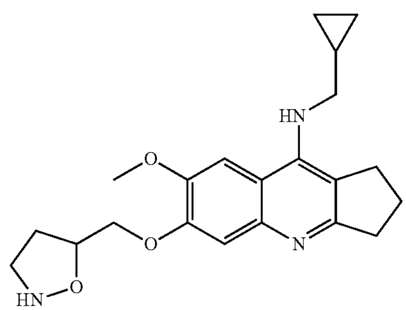 [SMILES: COc1cc2c(NCC3CC3)c3c(nc2cc1OCC1CCNO1)CCC3] | N-(cyclopropylmethyl)-7-methoxy-6-[(1,2-oxazolidin-5-yl)methoxy]-1H,2H,3H-cyclopenta[b]quinolin-9-amine |
| 91 | 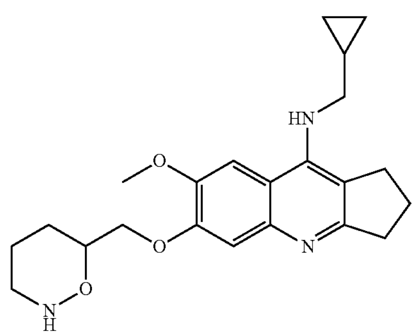 [SMILES: COc1cc2c(NCC3CC3)c3c(nc2cc1OCC1CCCNO1)CCC3] | N-(cyclopropylmethyl)-7-methoxy-6-[(1,2-oxazinan-6-yl)methoxy]-1H,2H,3H-cyclopenta[b]quinolin-9-amine |
| 92 | 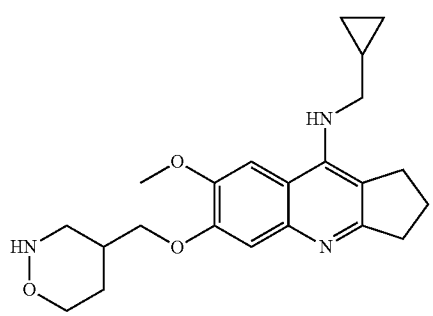 [SMILES: COc1cc2c(NCC3CC3)c3c(nc2cc1OCC1CCONC1)CCC3] | N-(cyclopropylmethyl)-7-methoxy-6-[(1,2-oxazinan-4-yl)methoxy]-1H,2H,3H-cyclopenta[b]quinolin-9-amine |

TABLE 2-continued

| No. | Structure | IUPAC Name |
|---|---|---|
| 93 | 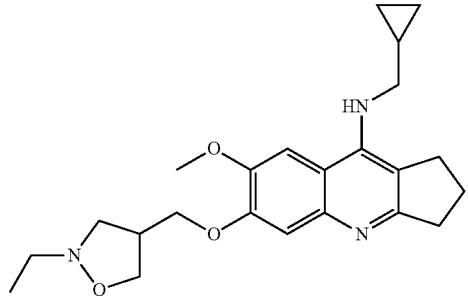 [SMILES: CCN1CC(COc2cc3nc4c(c(NCC5CC5)c3cc2OC)CCC4)CO1] | N-(cyclopropylmethyl)-6-[(2-ethyl-1,2-oxazolidin-4-yl)methoxy]-7-methoxy-1H,2H,3H-cyclopenta[b]quinolin-9-amine |
| 94 | 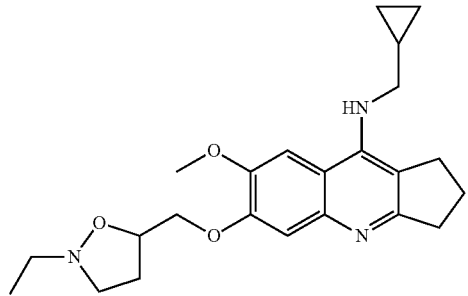 [SMILES: CCN1CCC(COc2cc3nc4c(c(NCC5CC5)c3cc2OC)CCC4)O1] | N-(cyclopropylmethyl)-6-[(2-ethyl-1,2-oxazolidin-5-yl)methoxy]-7-methoxy-1H,2H,3H-cyclopenta[b]quinolin-9-amine |
| 95 | 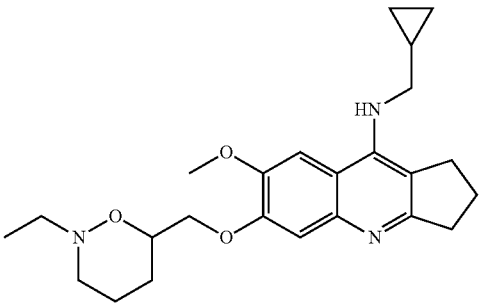 [SMILES: CCN1CCCC(COc2cc3nc4c(c(NCC5CC5)c3cc2OC)CCC4)O1] | N-(cyclopropylmethyl)-6-[(2-ethyl-1,2-oxazinan-6-yl)methoxy]-7-methoxy-1H,2H,3H-cyclopenta[b]quinolin-9-amine |
| 96 | 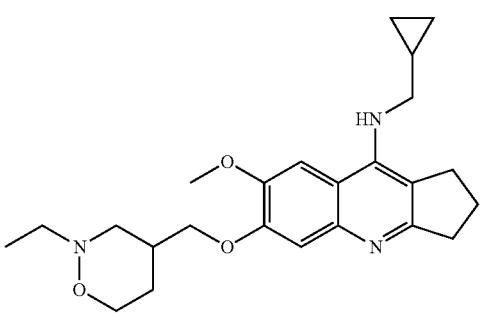 [SMILES: CCN1CC(COc2cc3nc4c(c(NCC5CC5)c3cc2OC)CCC4)CCO1] | N-(cyclopropylmethyl)-6-[(2-ethyl-1,2-oxazinan-4-yl)methoxy]-7-methoxy-1H,2H,3H-cyclopenta[b]quinolin-9-amine |
| 97 | 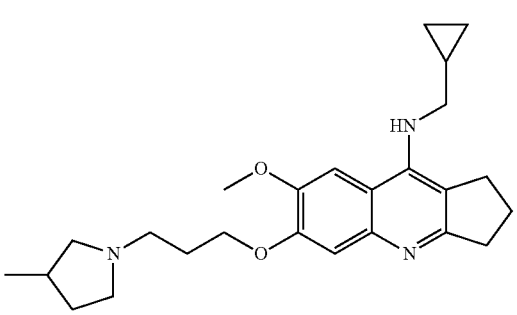 [SMILES: COc1cc2c(NCC3CC3)c3c(nc2cc1OCCCN1CCC(C)C1)CCC3] | N-(cyclopropylmethyl)-7-methoxy-6-[3-(3-methylpyrrolidin-1-yl)propoxy]-1H,2H,3H-cyclopenta[b]quinolin-9-amine |

TABLE 2-continued

| No. | Structure | IUPAC Name |
|---|---|---|
| 98 | 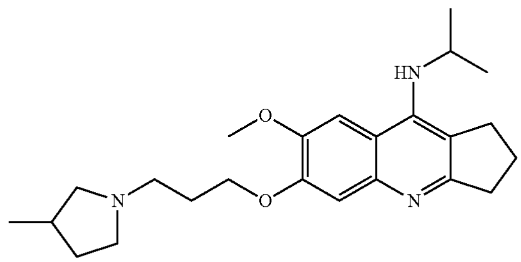 [SMILES: COc1cc2c(NC(C)C)c3c(nc2cc1OCCCN1CCC(C)C1)CCC3] | 7-methoxy-6-[3-(3-methylpyrrolidin-1-yl)propoxy]-N-(propan-2-yl)-1H,2H,3H-cyclopenta[b]quinolin-9-amine |
| 99 | 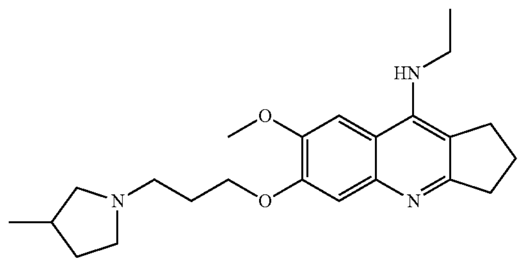 [SMILES: CCNc1c2c(nc3cc(OCCCN4CCC(C)C4)c(OC)cc13)CCC2] | N-ethyl-7-methoxy-6-[3-(3-methylpyrrolidin-1-yl)propoxy]-1H,2H,3H-cyclopenta[b]quinolin-9-amine |
| 100 | 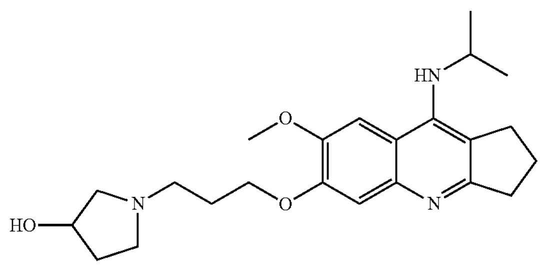 [SMILES: COc1cc2c(NC(C)C)c3c(nc2cc1OCCCN1CCC(O)C1)CCC3] | 1-[3-({7-methoxy-9-[(propan-2-yl)amino]-1H,2H,3H-cyclopenta[b]quinolin-6-yl}oxy)propyl]pyrrolidin-3-ol |
| 101 | 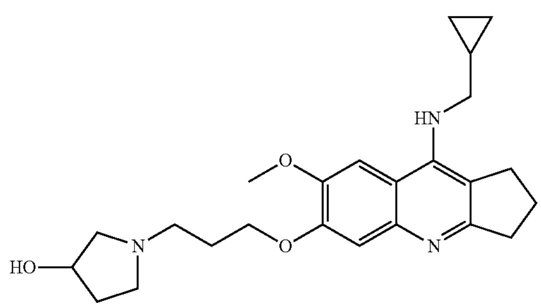 [SMILES: COc1cc2c(NCC3CC3)c3c(nc2cc1OCCCN1CCC(O)C1)CCC3] | 1-[3-({9-[(cyclopropylmethyl)amino]-7-methoxy-1H,2H,3H-cyclopenta[b]quinolin-6-yl}oxy)propyl]pyrrolidin-3-ol |
| 102 | 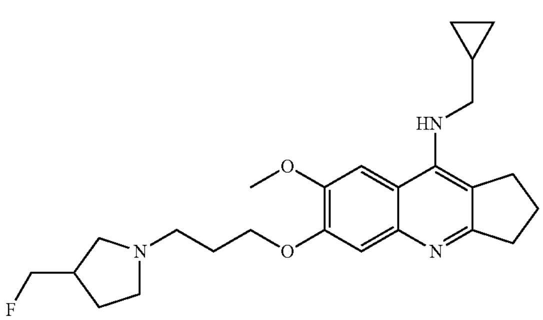 [SMILES: COc1cc2c(NCC3CC3)c3c(nc2cc1OCCCN1CCC(CF)C1)CCC3] | N-(cyclopropylmethyl)-6-{3-[3-(fluoromethyl)pyrrolidin-1-yl]propoxy}-7-methoxy-1H,2H,3H-cyclopenta[b]quinolin-9-amine |

TABLE 2-continued

| No. | Structure | IUPAC Name |
|---|---|---|
| 103 | 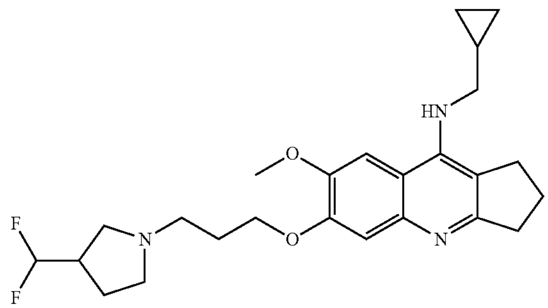 [SMILES: COc1cc2c(NCC3CC3)c3c(nc2cc1OCCCN1CCC(C(F)F)C1)CCC3] | N-(cyclopropylmethyl)-6-{3-[3-(difluoromethyl)pyrrolidin-1-yl]propoxy}-7-methoxy-1H,2H,3H-cyclopenta[b]quinolin-9-amine |
| 104 | 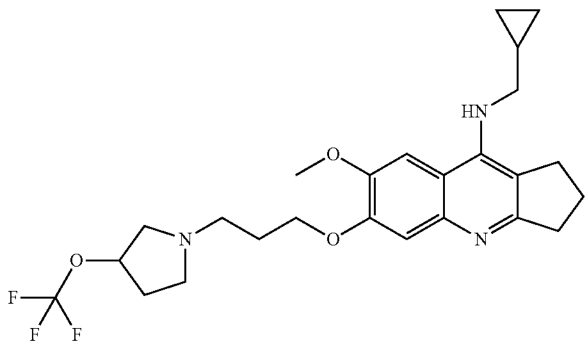 [SMILES: COc1cc2c(NCC3CC3)c3c(nc2cc1OCCCN1CCC(OC(F)(F)F)C1)CCC3] | N-(cyclopropylmethyl)-7-methoxy-6-{3-[3-(trifluoromethoxy)pyrrolidin-1-yl]propoxy}-1H,2H,3H-cyclopenta[b]quinolin-9-amine |
| 105 | 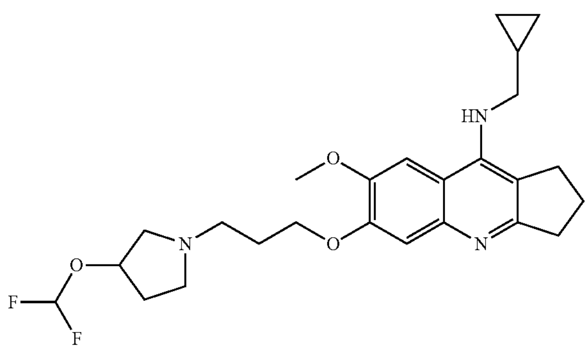 [SMILES: COc1cc2c(NCC3CC3)c3c(nc2cc1OCCCN1CCC(OC(F)F)C1)CCC3] | N-(cyclopropylmethyl)-6-{3-[3-(difluoromethoxy)pyrrolidin-1-yl]propoxy}-7-methoxy-1H,2H,3H-cyclopenta[b]quinolin-9-amine |
| 106 | 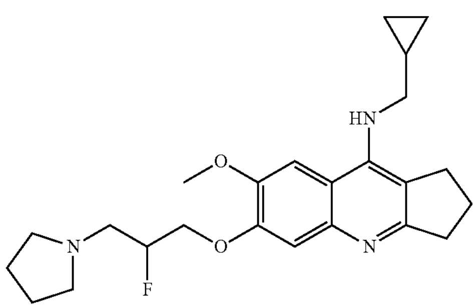 [SMILES: COc1cc2c(NCC3CC3)c3c(nc2cc1OCC(F)CN1CCCC1)CCC3] | N-(cyclopropylmethyl)-6-[2-fluoro-3-(pyrrolidin-1-yl)propoxy]-7-methoxy-1H,2H,3H-cyclopenta[b]quinolin-9-amine |
| 107 | 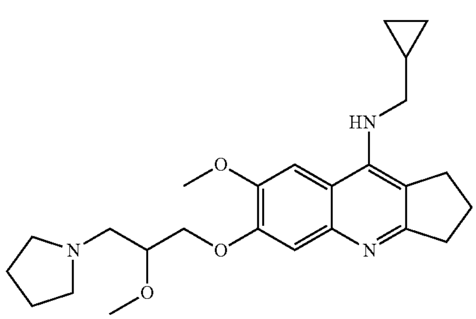 [SMILES: COc1cc2c(NCC3CC3)c3c(nc2cc1OCC(CN1CCCC1)OC)CCC3] | N-(cyclopropylmethyl)-7-methoxy-6-[2-methoxy-3-(pyrrolidin-1-yl)propoxy]-1H,2H,3H-cyclopenta[b]quinolin-9-amine |

TABLE 2-continued

| No. | Structure | IUPAC Name |
|---|---|---|
| 108 | 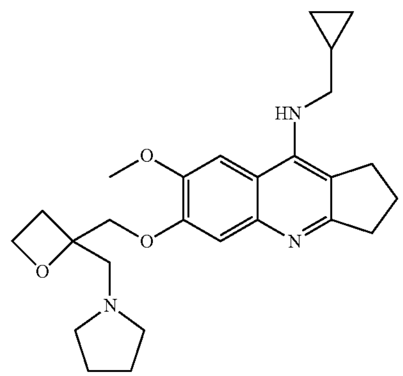 [SMILES: COc1cc2c(NCC3CC3)c3c(nc2cc1OCC1(CN2CCCC2)CCC1)CCC3] | N-(cyclopropylmethyl)-7-methoxy-6-({2-[(pyrrolidin-1-yl)methyl]oxetan-2-yl}methoxy)-1H,2H,3H-cyclopenta[b]quinolin-9-amine |
| 109 | 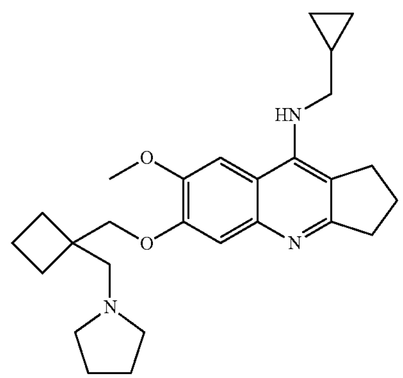 | N-(cyclopropylmethyl)-7-methoxy-6-({1-[(pyrrolidin-1-yl)methyl]cyclobutyl}methoxy)-1H,2H,3H-cyclopenta[b]quinolin-9-amine |
| 110 | 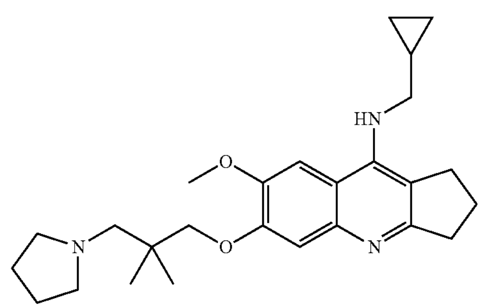 [SMILES: COc1cc2c(NCC3CC3)c3c(nc2cc1OCC(C)(C)CN1CCCC1)CCC3] | N-(cyclopropylmethyl)-7-methoxy-6-{2-methyl-2-[(pyrrolidin-1-yl)methyl]propoxy}-1H,2H,3H-cyclopenta[b]quinolin-9-amine |
| 111 | 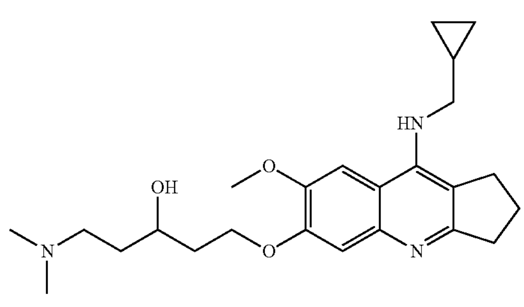 [SMILES: COc1cc2c(NCC3CC3)c3c(nc2cc1OCCC(O)CCN(C)C)CCC3] | 1-({9-[(cyclopropylmethyl)amino]-7-methoxy-1H,2H,3H-cyclopenta[b]quinolin-6-yl}oxy)-5-(dimethylamino)pentan-3-ol |

| No. | Structure | IUPAC Name |
|---|---|---|
| 112 | 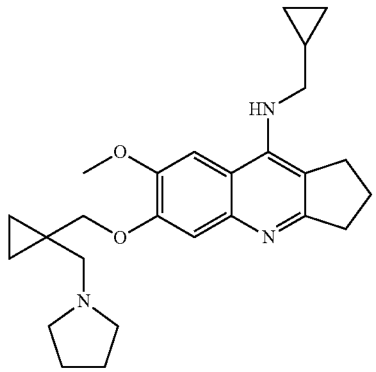 [SMILES: COc1cc2c(NCC3CC3)c3c(nc2cc1OCC1(CN2CCCC2)CC1)CCC3] | N-(cyclopropylmethyl)-7-methoxy-6-({1-[(pyrrolidin-1-yl)methyl]cyclopropyl}methoxy)-1H,2H,3H-cyclopenta[b]quinolin-9-amine |
| 113 | 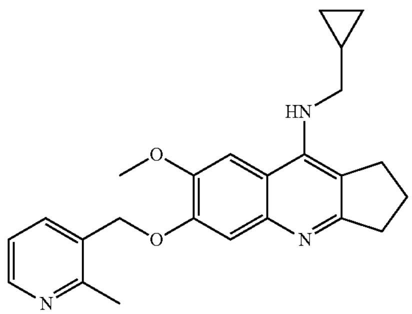 [SMILES: COc1cc2c(NCC3CC3)c3c(nc2cc1OCc1cccnc1C)CCC3] | N-(cyclopropylmethyl)-7-methoxy-6-[(2-methylpyridin-3-yl)methoxy]-1H,2H,3H-cyclopenta[b]quinolin-9-amine |
| 114 | 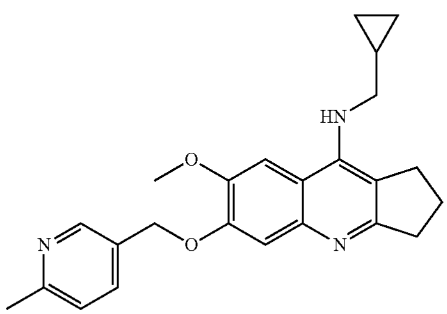 [SMILES: COc1cc2c(NCC3CC3)c3c(nc2cc1OCc1ccc(C)nc1)CCC3] | N-(cyclopropylmethyl)-7-methoxy-6-[(6-methylpyridin-3-yl)methoxy]-1H,2H,3H-cyclopenta[b]quinolin-9-amine |
| 115 | 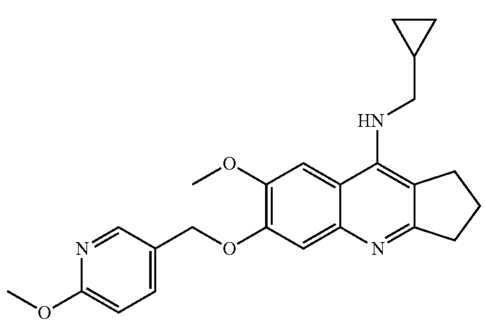 [SMILES: COc1ccc(COc2cc3nc4c(c(NCC5CC5)c3cc2OC)CCC4)cn1] | N-(cyclopropylmethyl)-7-methoxy-6-[(6-methoxypyridin-3-yl)methoxy]-1H,2H,3H-cyclopenta[b]quinolin-9-amine |

TABLE 2-continued

| No. | Structure | IUPAC Name |
| --- | --- | --- |
| 116 | 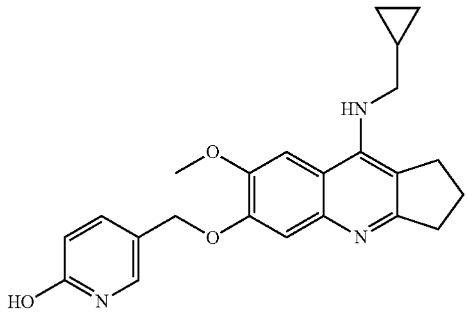 [SMILES: COc1cc2c(NCC3CC3)c3c(nc2cc1OCc1ccc(O)nc1)CCC3] | 5-[({9-[(cyclopropylmethyl)amino]-7-methoxy-1H,2H,3H-cyclopenta[b]quinolin-6-yl}oxy)methyl]pyridin-2-ol |
| 117 | 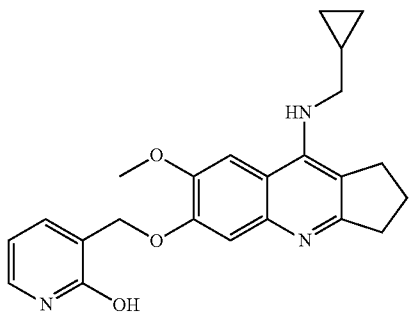 [SMILES: COc1cc2c(NCC3CC3)c3c(nc2cc1OCc1cccnc1O)CCC3] | 3-[({9-[(cyclopropylmethyl)amino]-7-methoxy-1H,2H,3H-cyclopenta[b]quinolin-6-yl}oxy)methyl]pyridin-2-ol |
| 118 | 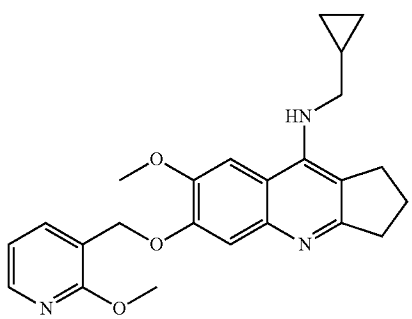 [SMILES: COc1cc2c(NCC3CC3)c3c(nc2cc1OCc1cccnc1OC)CCC3] | N-(cyclopropylmethyl)-7-methoxy-6-[(2-methoxypyridin-3-yl)methoxy]-1H,2H,3H-cyclopenta[b]quinolin-9-amine |
| 119 | 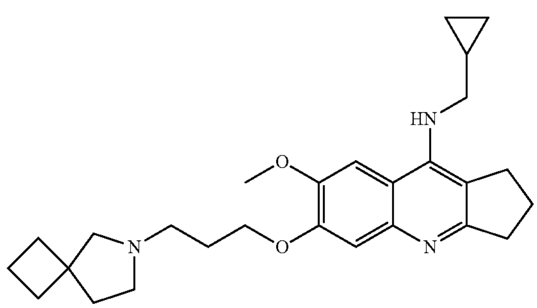 [SMILES: COc1cc2c(NCC3CC3)c3c(nc2cc1OCCCN1CCC2(CCC2)C1)CCC3] | 6-(3-{6-azaspiro[3.4]octan-6-yl}propoxy)-N-(cyclopropylmethyl)-7-methoxy-1H,2H,3H-cyclopenta[b]quinolin-9-amine |
| 120 | 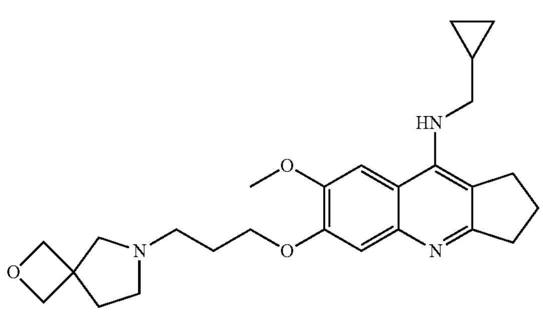 [SMILES: COc1cc2c(NCC3CC3)c3c(nc2cc1OCCCN1CCC2(COC2)C1)CCC3] | N-(cyclopropylmethyl)-7-methoxy-6-(3-{2-oxa-6-azaspiro[3.4]octan-6-yl}propoxy)-1H,2H,3H-cyclopenta[b]quinolin-9-amine |

TABLE 2-continued

| No. | Structure | IUPAC Name |
| --- | --- | --- |
| 121 | 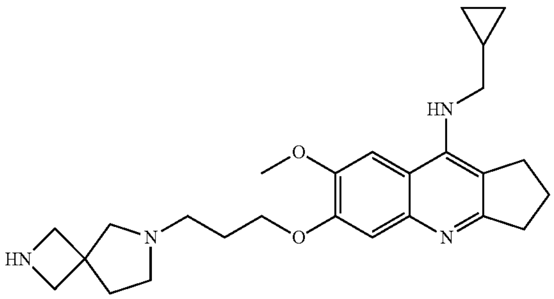 [SMILES: COc1cc2c(NCC3CC3)c3c(nc2cc1OCCCN1CCC2(CNC2)C1)CCC3] | N-(cyclopropylmethyl)-6-(3-{2,6-diazaspiro[3.4]octan-6-yl}propoxy)-7-methoxy-1H,2H,3H-cyclopenta[b]quinolin-9-amine |
| 122 | 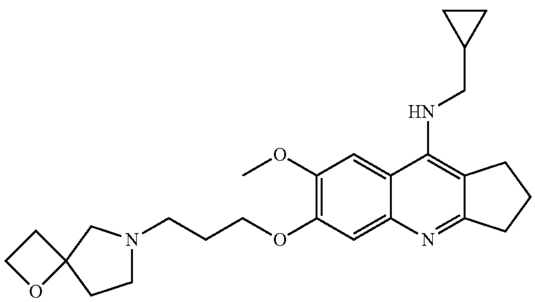 [SMILES: COc1cc2c(NCC3CC3)c3c(nc2cc1OCCCN1CCC2(CCO2)C1)CCC3] | N-(cyclopropylmethyl)-7-methoxy-6-(3-{1-oxa-6-azaspiro[3.4]octan-6-yl}propoxy)-1H,2H,3H-cyclopenta[b]quinolin-9-amine |
| 123 | 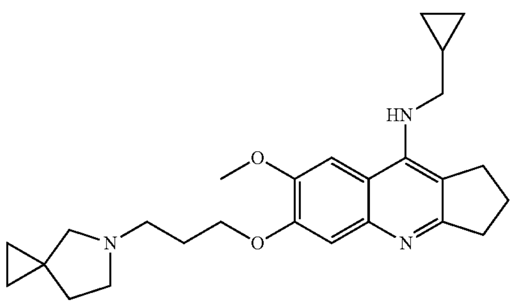 [SMILES: COc1cc2c(NCC3CC3)c3c(nc2cc1OCCCN1CCC2(CC2)C1)CCC3] | 6-(3-{5-azaspiro[2.4]heptan-5-yl}propoxy)-N-(cyclopropylmethyl)-7-methoxy-1H,2H,3H-cyclopenta[b]quinolin-9-amine |
| 124 | 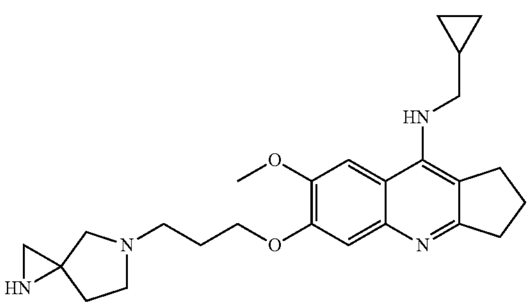 [SMILES: COc1cc2c(NCC3CC3)c3c(nc2cc1OCCCN1CCC2(CN2)C1)CCC3] | N-(cyclopropylmethyl)-6-(3-{1,5-diazaspiro[2.4]heptan-5-yl}propoxy)-7-methoxy-1H,2H,3H-cyclopenta[b]quinolin-9-amine |
| 125 | 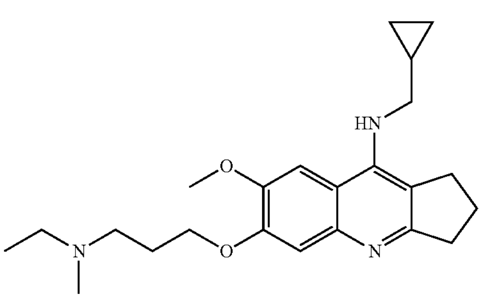 [SMILES: CCN(C)CCCOc1cc2nc3c(c(NCC4CC4)c2cc1OC)CCC3] | N-(cyclopropylmethyl)-6-{3-[ethyl(methyl)amino]propoxy}-7-methoxy-1H,2H,3H-cyclopenta[b]quinolin-9-amine |

TABLE 2-continued

| No. | Structure | IUPAC Name |
|---|---|---|
| 126 | 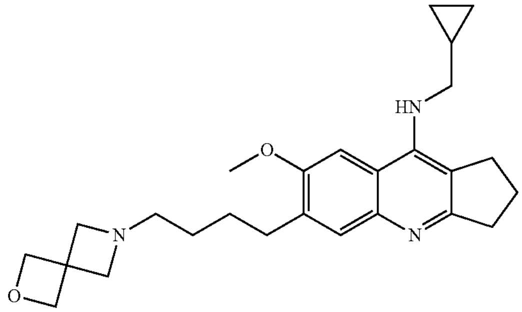 [SMILES: COc1cc2c(NCC3CC3)c3c(nc2cc1CCCCN1CC2(COC2)C1)CCC3] | N-(cyclopropylmethyl)-7-methoxy-6-(4-{2-oxa-6-azaspiro[3.3]heptan-6-yl}butyl)-1H,2H,3H-cyclopenta[b]quinolin-9-amine |
| 127 | 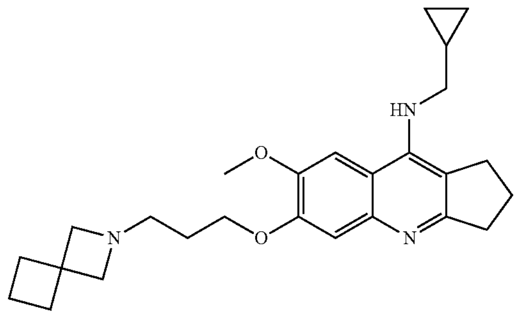 [SMILES: COc1cc2c(NCC3CC3)c3c(nc2cc1OCCCN1CC2(CCC2)C1)CCC3] | 6-(3-{2-azaspiro[3.3]heptan-2-yl}propoxy)-N-(cyclopropylmethyl)-7-methoxy-1H,2H,3H-cyclopenta[b]quinolin-9-amine |
| 128 | 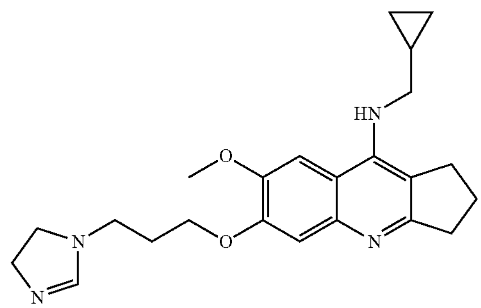 [SMILES: COc1cc2c(NCC3CC3)c3c(nc2cc1OCCCN1C=NCC1)CCC3] | N-(cyclopropylmethyl)-6-[3-(4,5-dihydro-1H-imidazol-1-yl)propoxy]-7-methoxy-1H,2H,3H-cyclopenta[b]quinolin-9-amine |
| 129 | 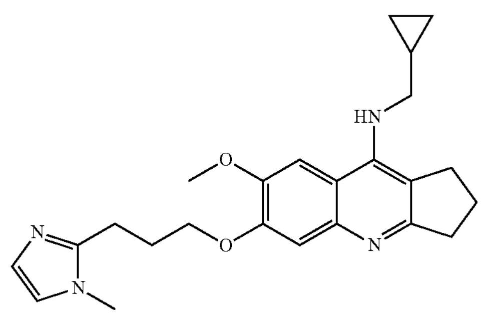 [SMILES: COc1cc2c(NCC3CC3)c3c(nc2cc1OCCCc1nccn1C)CCC3] | N-(cyclopropylmethyl)-7-methoxy-6-[3-(1-methyl-1H-imidazol-2-yl)propoxy]-1H,2H,3H-cyclopenta[b]quinolin-9-amine |
| 130 | 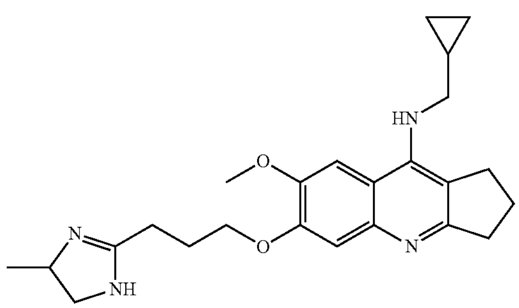 [SMILES: COc1cc2c(NCC3CC3)c3c(nc2cc1OCCCC1=NC(C)CN1)CCC3] | N-(cyclopropylmethyl)-7-methoxy-6-[3-(4-methyl-4,5-dihydro-1H-imidazol-2-yl)propoxy]-1H,2H,3H-cyclopenta[b]quinolin-9-amine |

TABLE 2-continued

| No. | Structure | IUPAC Name |
|---|---|---|
| 131 | 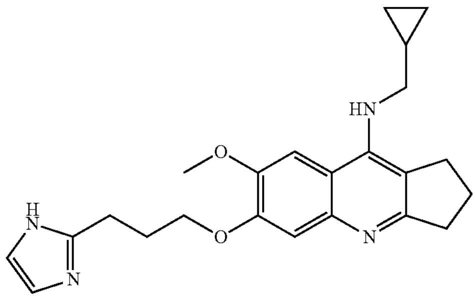 [SMILES: COc1cc2c(NCC3CC3)c3c(nc2cc1OCCCc1ncc[nH]1)CCC3] | N-(cyclopropylmethyl)-6-[3-(1H-imidazol-2-yl)propoxy]-7-methoxy-1H,2H,3H-cyclopenta[b]quinolin-9-amine |
| 132 | 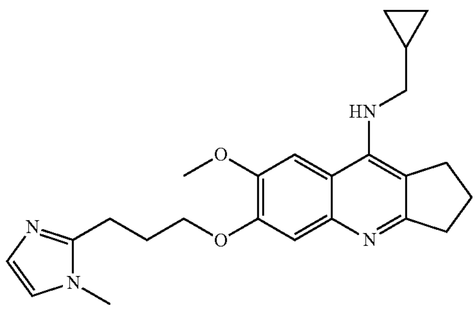 [SMILES: COc1cc2c(NCC3CC3)c3c(nc2cc1OCCCc1nccn1C)CCC3] | N-(cyclopropylmethyl)-7-methoxy-6-[3-(1-methyl-1H-imidazol-2-yl)propoxy]-1H,2H,3H-cyclopenta[b]quinolin-9-amine |
| 133 | 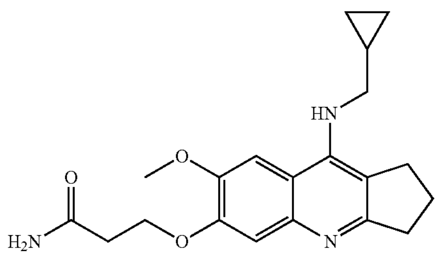 [SMILES: COc1cc2c(NCC3CC3)c3c(nc2cc1OCCC(N)=O)CCC3] | 3-({9-[(cyclopropylmethyl)amino]-7-methoxy-1H,2H,3H-cyclopenta[b]quinolin-6-yl}oxy)propanamide |
| 134 | 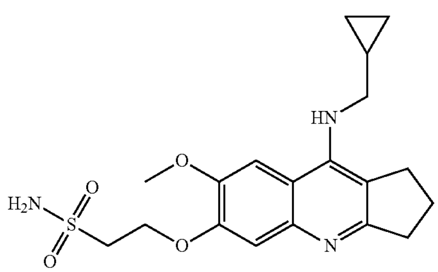 [SMILES: COc1cc2c(NCC3CC3)c3c(nc2cc1OCCS(N)(=O)=O)CCC3] | 2-({9-[(cyclopropylmethyl)amino]-7-methoxy-1H,2H,3H-cyclopenta[b]quinolin-6-yl}oxy)ethane-1-sulfonamide |
| 135 | 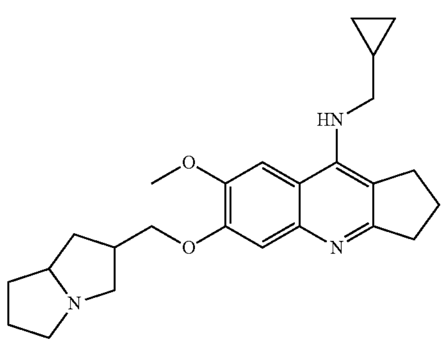 [SMILES: COc1cc2c(NCC3CC3)c3c(nc2cc1OCC1CC2CCCN2C1)CCC3] | N-(cyclopropylmethyl)-6-[(hexahydro-1H-pyrrolizin-2-yl)methoxy]-7-methoxy-1H,2H,3H-cyclopenta[b]quinolin-9-amine |

TABLE 2-continued

| No. | Structure | IUPAC Name |
|---|---|---|
| 136 | 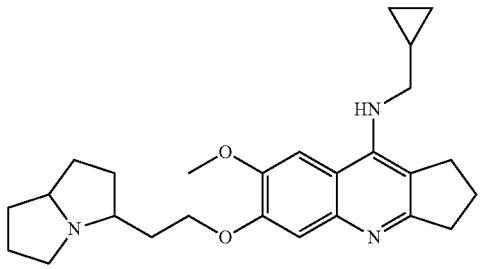 [SMILES: COc1cc2c(NCC3CC3)c3c(nc2cc1OCCC1CCC2CCCN21)CCC3] | N-(cyclopropylmethyl)-6-[2-(hexahydro-1H-pyrrolizin-3-yl)ethoxy]-7-methoxy-1H,2H,3H-cyclopenta[b]quinolin-9-amine |
| 137 | 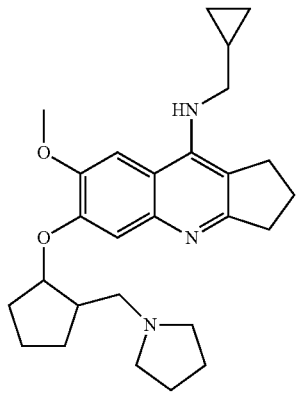 [SMILES: COc1cc2c(NCC3CC3)c3c(nc2cc1OC1CCCC1CN1CCCC1)CCC3] | N-(cyclopropylmethyl)-7-methoxy-6-({2-[(pyrrolidin-1-yl)methyl]cyclopentyl}oxy)-1H,2H,3H-cyclopenta[b]quinolin-9-amine |
| 138 | 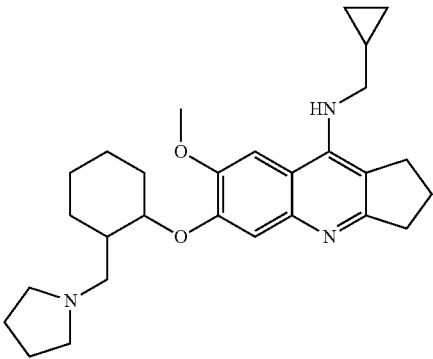 [SMILES: COc1cc2c(NCC3CC3)c3c(nc2cc1OC1CCCCC1CN1CCCC1)CCC3] | N-(cyclopropylmethyl)-7-methoxy-6-({2-[(pyrrolidin-1-yl)methyl]cyclohexyl}oxy)-1H,2H,3H-cyclopenta[b]quinolin-9-amine |
| 139 | 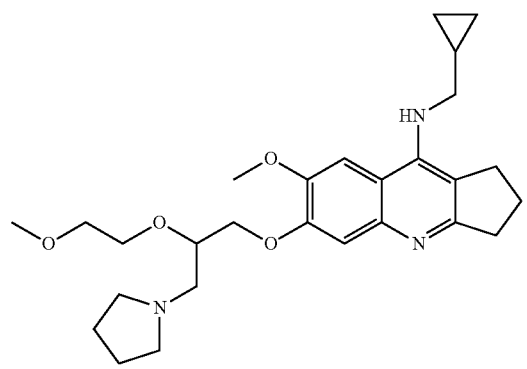 [SMILES: COCCOC(COc1cc2nc3c(c(NCC4CC4)c2cc1OC)CCC3)CN1CCCC1] | N-(cyclopropylmethyl)-7-methoxy-6-[2-(2-methoxyethoxy)-3-(pyrrolidin-1-yl)propoxy]-1H,2H,3H-cyclopenta[b]quinolin-9-amine |

TABLE 2-continued

| No. | Structure | IUPAC Name |
|---|---|---|
| 140 | 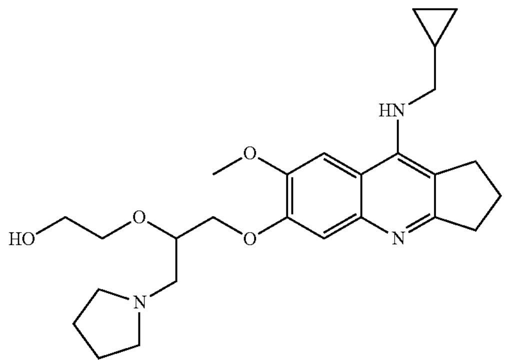 [SMILES: COc1cc2c(NCC3CC3)c3c(nc2cc1OCC(CN1CCCC1)OCCO)CCC3] | 2-{[1-({9-[(cyclopropylmethyl)amino]-7-methoxy-1H,2H,3H-cyclopenta[b]quinolin-6-yl}oxy)-3-(pyrrolidin-1-yl)propan-2-yl]oxy}ethan-1-ol |
| 141 | 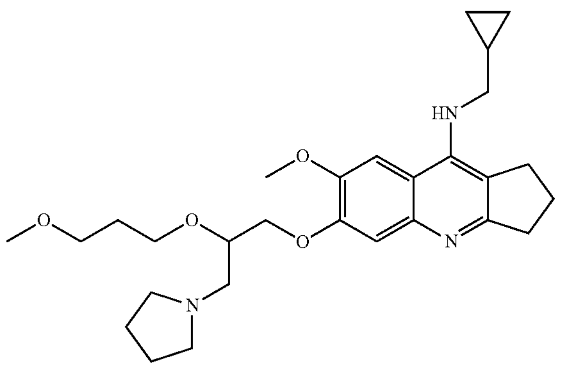 [SMILES: COCCCOC(COc1cc2nc3c(c(NCC4CC4)c2cc1OC)CCC3)CN1CCCC1] | N-(cyclopropylmethyl)-7-methoxy-6-[2-(3-methoxypropoxy)-3-(pyrrolidin-1-yl)propoxy]-1H,2H,3H-cyclopenta[b]quinolin-9-amine |
| 142 | 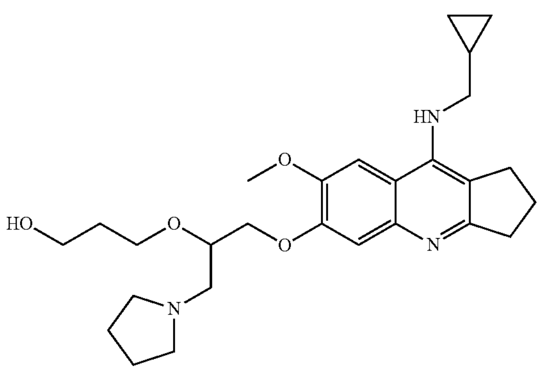 [SMILES: COc1cc2c(NCC3CC3)c3c(nc2cc1OCC(CN1CCCC1)OCCCO)CCC3] | 3-{[1-({9-[(cyclopropylmethyl)amino]-7-methoxy-1H,2H,3H-cyclopenta[b]quinolin-6-yl}oxy)-3-(pyrrolidin-1-yl)propan-2-yl]oxy}propan-1-ol |
| 143 | 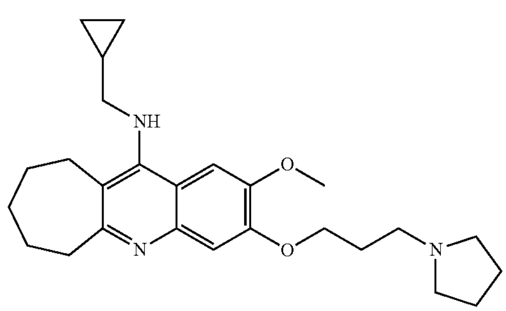 [SMILES: COc1cc2c(NCC3CC3)c3c(nc2cc1OCCCN1CCCC1)CCCCC3] | N-(cyclopropylmethyl)-2-methoxy-3-[3-(pyrrolidin-1-yl)propoxy]-6H,7H,8H,9H,10H-cyclohepta[b]quinolin-11-amine |

TABLE 2-continued

| No. | Structure | IUPAC Name |
|---|---|---|
| 144 | 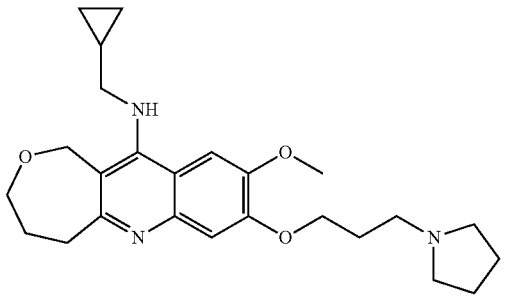 | N-(cyclopropylmethyl)-9-methoxy-8-[3-(pyrrolidin-1-yl)propoxy]-1H,3H,4H,5H-oxepino[4,3-b]quinolin-11-amine |
| 145 | 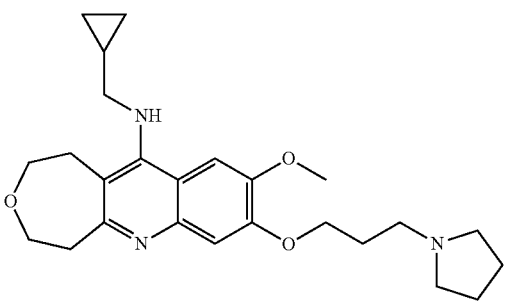 [SMILES: COc1cc2c(NCC3CC3)c3c(nc2cc1OCCCN1CCCC1)CCOCC3] | N-(cyclopropylmethyl)-9-methoxy-8-[3-(pyrrolidin-1-yl)propoxy]-1H,2H,4H,5H-oxepino[4,5-b]quinolin-11-amine |
| 146 | 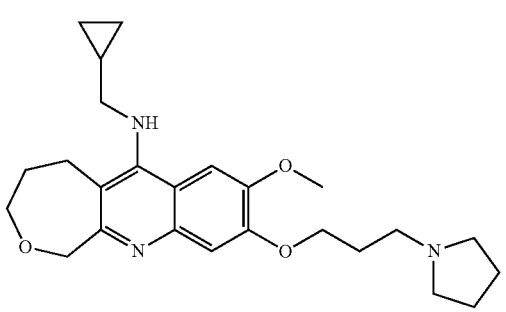 [SMILES: COc1cc2c(NCC3CC3)c3c(nc2cc1OCCCN1CCCC1)COCCC3] | N-(cyclopropylmethyl)-8-methoxy-9-[3-(pyrrolidin-1-yl)propoxy]-1H,3H,4H,5H-oxepino[3,4-b]quinolin-6-amine |
| 147 | 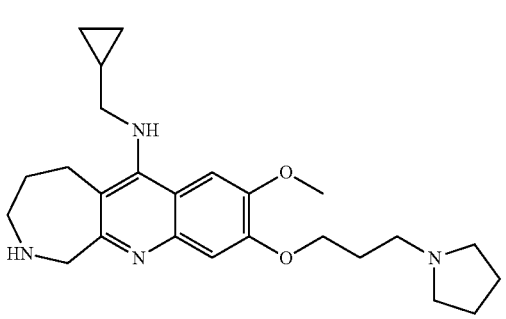 | N-(cyclopropylmethyl)-8-methoxy-9-[3-(pyrrolidin-1-yl)propoxy]-1H,2H,3H,4H,5H-azepino[3,4-b]quinolin-6-amine |
| 148 | 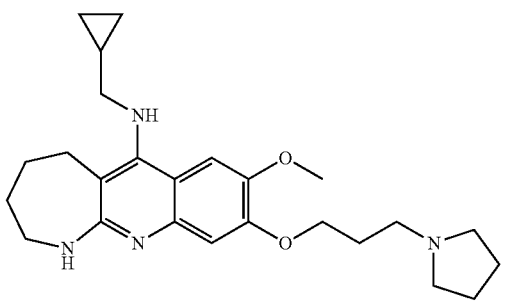 [SMILES: COc1cc2c(NCC3CC3)c3c(nc2cc1OCCCN1CCCC1)NCCCC3] | N-(cyclopropylmethyl)-8-methoxy-9-[3-(pyrrolidin-1-yl)propoxy]-1H,2H,3H,4H,5H-azepino[2,3-b]quinolin-6-amine |

TABLE 2-continued

| No. | Structure | IUPAC Name |
|-----|-----------|------------|
| 149 | 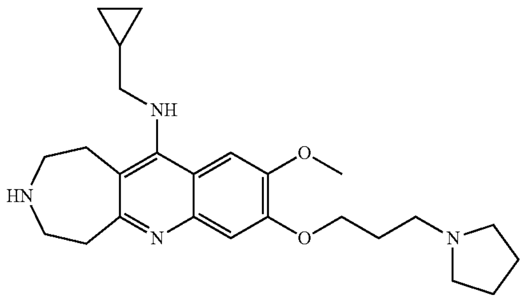 [SMILES: COc1cc2c(NCC3CC3)c3c(nc2cc1OCCCN1CCCC1)CCNCC3] | N-(cyclopropylmethyl)-9-methoxy-8-[3-(pyrrolidin-1-yl)propoxy]-1H,2H,3H,4H,5H-azepino[4,5-b]quinolin-11-amine |
| 150 | 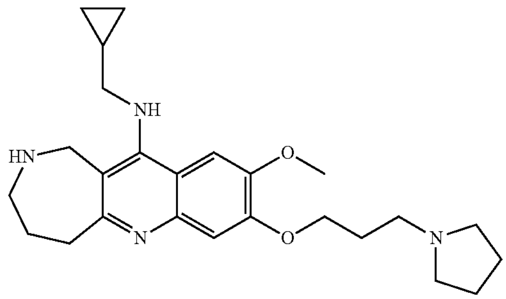 [SMILES: COc1cc2c(NCC3CC3)c3c(nc2cc1OCCCN1CCCC1)CCCNC3] | N-(cyclopropylmethyl)-9-methoxy-8-[3-(pyrrolidin-1-yl)propoxy]-1H,2H,3H,4H,5H-azepino[4,3-b]quinolin-11-amine |
| 151 | 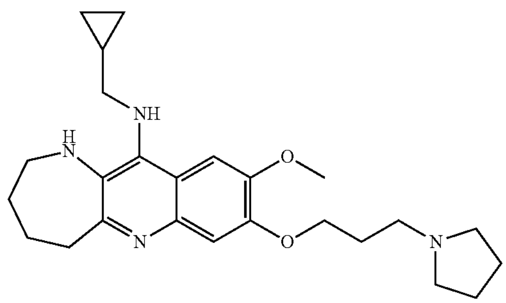 [SMILES: COc1cc2c(NCC3CC3)c3c(nc2cc1OCCCN1CCCC1)CCCCN3] | N-(cyclopropylmethyl)-9-methoxy-8-[3-(pyrrolidin-1-yl)propoxy]-1H,2H,3H,4H,5H-azepino[3,2-b]quinolin-11-amine |
| 152 | 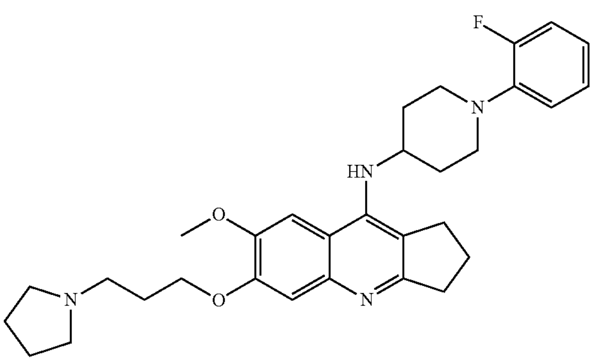 [SMILES: COc1cc2c(NC3CCN(c4ccccc4F)CC3)c3c(nc2cc1OCCCN1CCCC1)CCC3] | 1-(2-fluorophenyl)-N-{7-methoxy-6-[3-(pyrrolidin-1-yl)propoxy]-1H,2H,3H-cyclopenta[b]quinolin-9-yl}piperidin-4-amine |
| 153 | 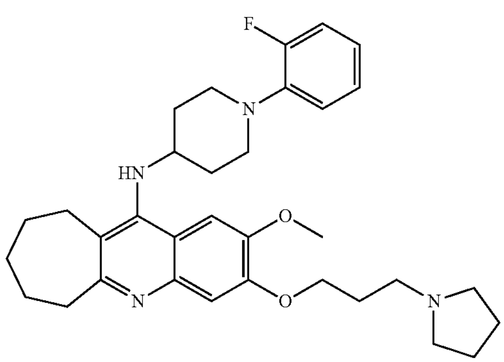 | 1-(2-fluorophenyl)-N-{2-methoxy-3-[3-(pyrrolidin-1-yl)propoxy]-6H,7H,8H,9H,10H-cyclohepta[b]quinolin-11-yl}piperidin-4-amine |

TABLE 2-continued

| No. | Structure | IUPAC Name |
| --- | --- | --- |
| 154 | 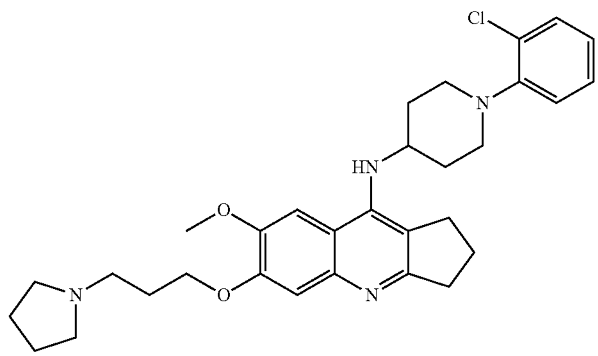 | 1-(2-chlorophenyl)-N-{7-methoxy-6-[3-(pyrrolidin-1-yl)propoxy]-1H,2H,3H-cyclopenta[b]quinolin-9-yl}piperidin-4-amine |
| 155 | 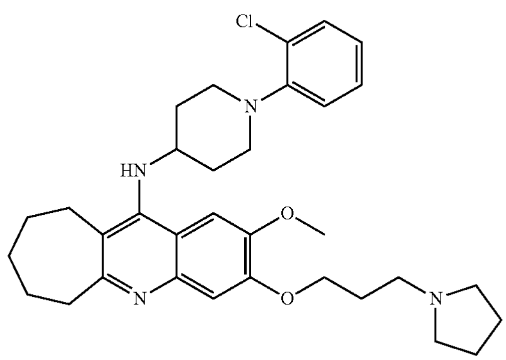 [SMILES: COc1cc2c(NC3CCN(c4ccccc4Cl)CC3)c3c(nc2cc1OCCCN1CCCC1)CCCCC3] | 1-(2-chlorophenyl)-N-{2-methoxy-3-[3-(pyrrolidin-1-yl)propoxy]-6H,7H,8H,9H,10H-cyclohepta[b]quinolin-11-yl}piperidin-4-amine |
| 156 | 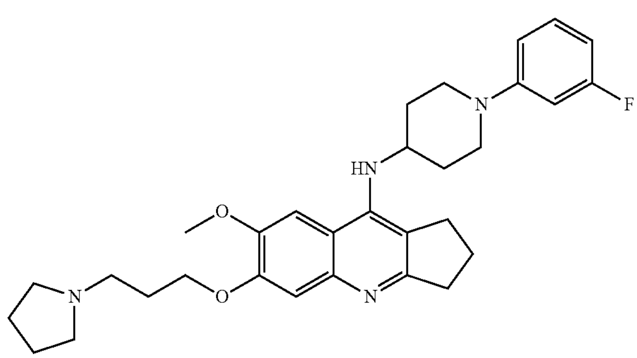 [SMILES: COc1cc2c(NC3CCN(c4cccc(F)c4)CC3)c3c(nc2cc1OCCCN1CCCC1)CCC3] | 1-(3-fluorophenyl)-N-{7-methoxy-6-[3-(pyrrolidin-1-yl)propoxy]-1H,2H,3H-cyclopenta[b]quinolin-9-yl}piperidin-4-amine |
| 157 | 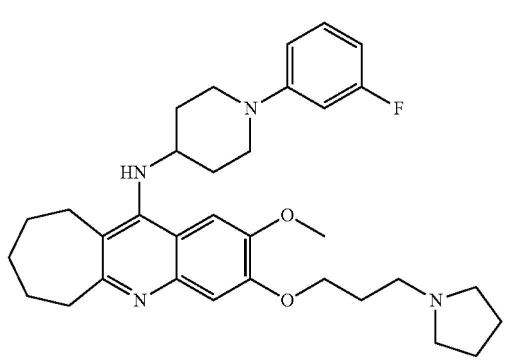 | 1-(3-fluorophenyl)-N-{2-methoxy-3-[3-(pyrrolidin-1-yl)propoxy]-6H,7H,8H,9H,10H-cyclohepta[b]quinolin-11-yl}piperidin-4-amine |

| No. | Structure | IUPAC Name |
| --- | --- | --- |
| 158 | 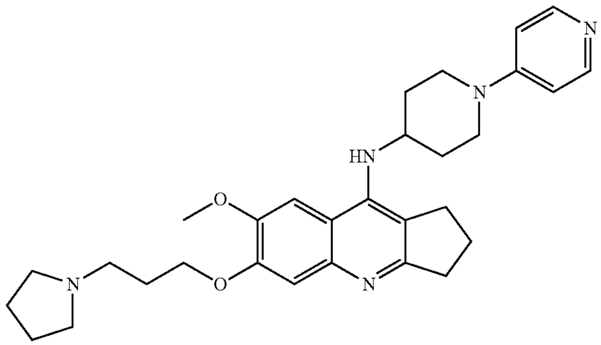 [SMILES: COc1cc2c(NC3CCN(c4ccncc4)CC3)c3c(nc2cc1OCCCN1CCCC1)CCC3] | N-{7-methoxy-6-[3-(pyrrolidin-1-yl)propoxy]-1H,2H,3H-cyclopenta[b]quinolin-9-yl}-1-(pyridin-4-yl)piperidin-4-amine |
| 159 | 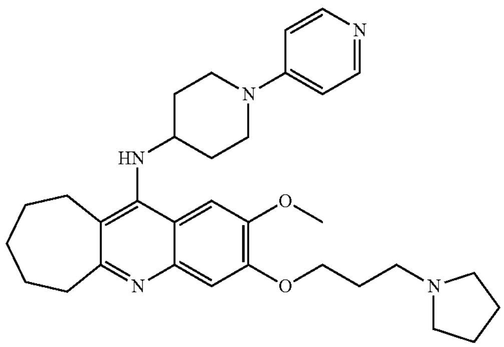 [SMILES: COc1cc2c(NC3CCN(c4ccncc4)CC3)c3c(nc2cc1OCCCN1CCCC1)CCCCC3] | N-{2-methoxy-3-[3-(pyrrolidin-1-yl)propoxy]-6H,7H,8H,9H,10H-cyclohepta[b]quinolin-11-yl}-1-(pyridin-4-yl)piperidin-4-amine |
| 160 | 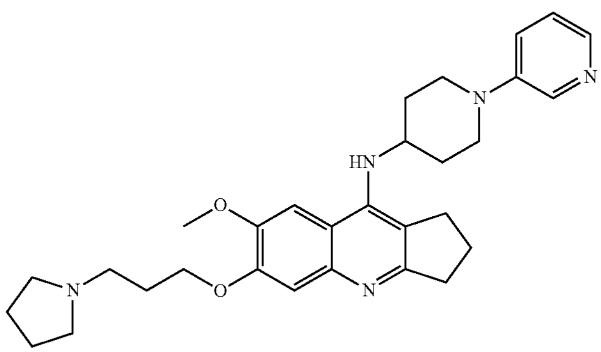 [SMILES: COc1cc2c(NC3CCN(c4cccnc4)CC3)c3c(nc2cc1OCCCN1CCCC1)CCC3] | N-{7-methoxy-6-[3-(pyrrolidin-1-yl)propoxy]-1H,2H,3H-cyclopenta[b]quinolin-9-yl}-1-(pyridin-3-yl)piperidin-4-amine |
| 161 | 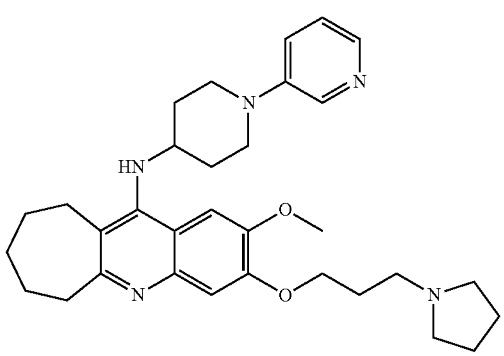 [SMILES: COc1cc2c(NC3CCN(c4cccnc4)CC3)c3c(nc2cc1OCCCN1CCCC1)CCCCC3] | N-{2-methoxy-3-[3-(pyrrolidin-1-yl)propoxy]-6H,7H,8H,9H,10H-cyclohepta[b]quinolin-11-yl}-1-(pyridin-3-yl)piperidin-4-amine |

TABLE 2-continued

| No. | Structure | IUPAC Name |
|---|---|---|
| 162 | 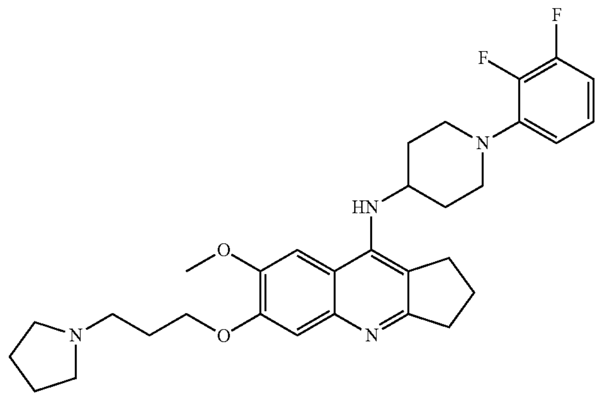 [SMILES: COc1cc2c(NC3CCN(c4cccc(F)c4F)CC3)c3c(nc2cc1OCCCN1CCCC1)CCC3] | 1-(2,3-difluorophenyl)-N-{7-methoxy-6-[3-(pyrrolidin-1-yl)propoxy]-1H,2H,3H-cyclopenta[b]quinolin-9-yl}piperidin-4-amine |
| 163 | 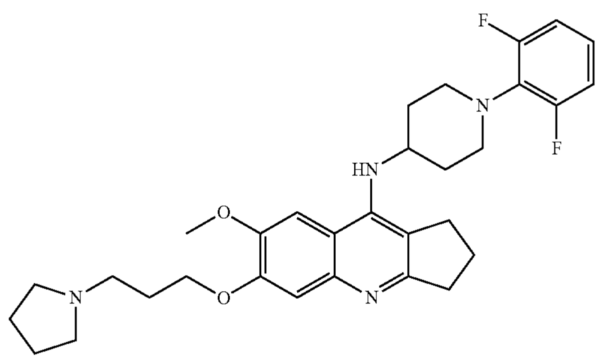 [SMILES: COc1cc2c(NC3CCN(c4c(F)cccc4F)CC3)c3c(nc2cc1OCCCN1CCCC1)CCC3] | 1-(2,6-difluorophenyl)-N-{7-methoxy-6-[3-(pyrrolidin-1-yl)propoxy]-1H,2H,3H-cyclopenta[b]quinolin-9-yl}piperidin-4-amine |
| 164 | 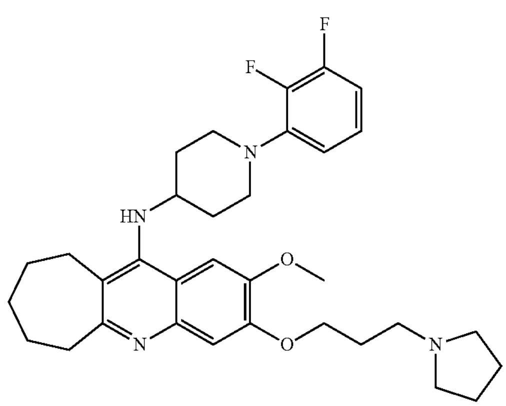 | 1-(2,3-difluorophenyl)-N-{2-methoxy-3-[3-(pyrrolidin-1-yl)propoxy]-6H,7H,8H,9H,10H-cyclohepta[b]quinolin-11-yl}piperidin-4-amine |
| 165 | 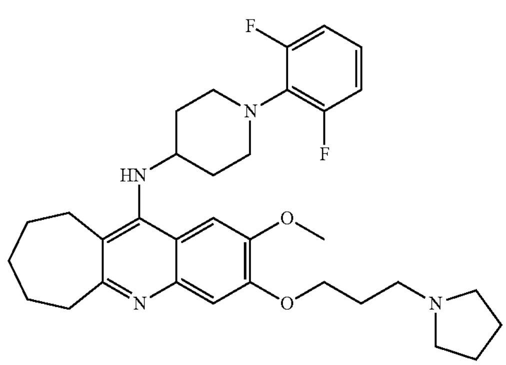 [SMILES: COc1cc2c(NC3CCN(c4c(F)cccc4F)CC3)c3c(nc2cc1OCCCN1CCCC1)CCCCC3] | 1-(2,6-difluorophenyl)-N-{2-methoxy-3-[3-(pyrrolidin-1-yl)propoxy]-6H,7H,8H,9H,10H-cyclohepta[b]quinolin-11-yl}piperidin-4-amine |

TABLE 2-continued

| No. | Structure | IUPAC Name |
|---|---|---|
| 166 | 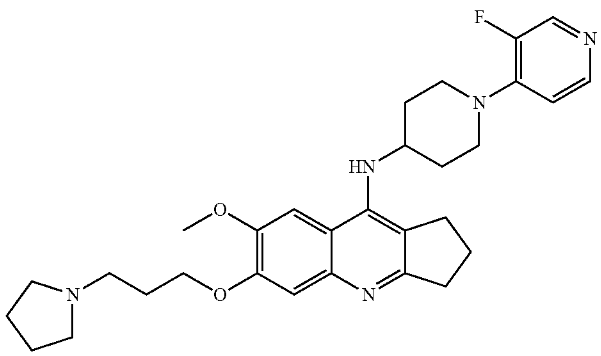 | 1-(3-fluoropyridin-4-yl)-N-{7-methoxy-6-[3-(pyrrolidin-1-yl)propoxy]-1H,2H,3H-cyclopenta[b]quinolin-9-yl}piperidin-4-amine |
| 167 | 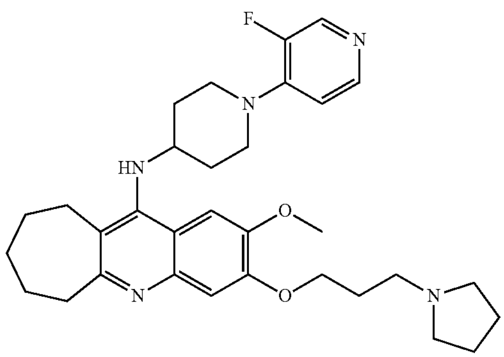 [SMILES: COc1cc2c(NC3CCN(c4ccncc4F)CC3)c3c(nc2cc1OCCCN1CCCC1)CCCCC3] | 1-(3-fluoropyridin-4-yl)-N-{2-methoxy-3-[3-(pyrrolidin-1-yl)propoxy]-6H,7H,8H,9H,10H-cyclohepta[b]quinolin-11-yl}piperidin-4-amine |
| 168 | 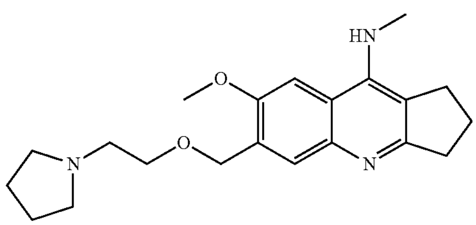 [SMILES: CNc1c2c(nc3cc(COCCN4CCCC4)c(OC)cc13)CCC2] | 7-methoxy-N-methyl-6-{[2-(pyrrolidin-1-yl)ethoxy]methyl}-1H,2H,3H-cyclopenta[b]quinolin-9-amine |
| 169 | 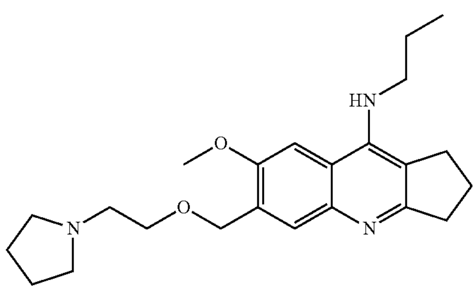 [SMILES: CCCNc1c2c(nc3cc(COCCN4CCCC4)c(OC)cc13)CCC2] | 7-methoxy-N-propyl-6-{[2-(pyrrolidin-1-yl)ethoxy]methyl}-1H,2H,3H-cyclopenta[b]quinolin-9-amine |
| 170 | 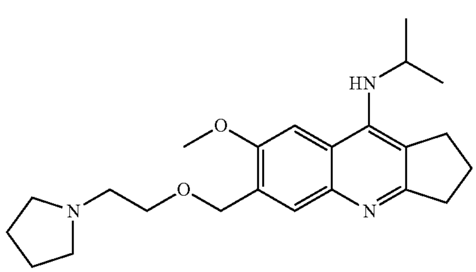 [SMILES: COc1cc2c(NC(C)C)c3c(nc2cc1COCCN1CCCC1)CCC3] | 7-methoxy-N-(propan-2-yl)-6-{[2-(pyrrolidin-1-yl)ethoxy]methyl}-1H,2H,3H-cyclopenta[b]quinolin-9-amine |

TABLE 2-continued

| No. | Structure | IUPAC Name |
|---|---|---|
| 171 | 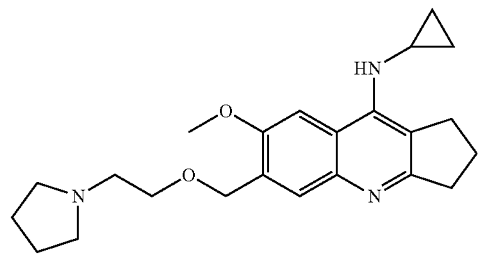 [SMILES: COc1cc2c(NC3CC3)c3c(nc2cc1COCCN1CCCC1)CCC3] | N-cyclopropyl-7-methoxy-6-{[2-(pyrrolidin-1-yl)ethoxy]methyl}-1H,2H,3H-cyclopenta[b]quinolin-9-amine |
| 172 | 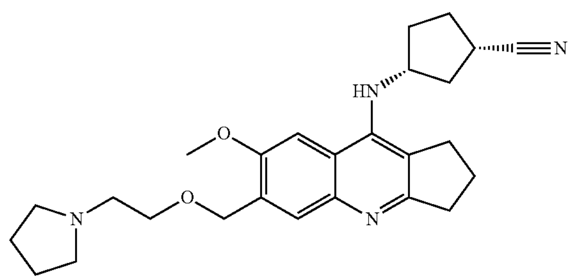 [SMILES: COc1cc2c(N[C@@H]3CC[C@H](C#N)C3)c3c(nc2cc1COCCN1CCCC1)CCC3] | (1S,3R)-3-[(7-methoxy-6-{[2-(pyrrolidin-1-yl)ethoxy]methyl}-1H,2H,3H-cyclopenta[b]quinolin-9-yl)amino]cyclopentane-1-carbonitrile |
| 173 | 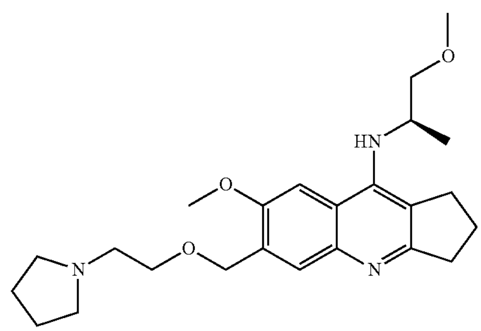 [SMILES: COC[C@@H](C)Nc1c2c(nc3cc(COCCN4CCCC4)c(OC)cc13)CCC2] | 7-methoxy-N-[(2R)-1-methoxypropan-2-yl]-6-{[2-(pyrrolidin-1-yl)ethoxy]methyl}-1H,2H,3H-cyclopenta[b]quinolin-9-amine |
| 174 | 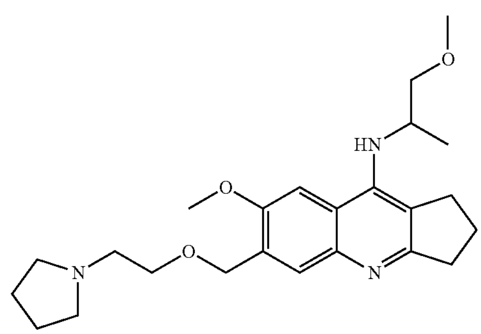 [SMILES: COCC(C)Nc1c2c(nc3cc(COCCN4CCCC4)c(OC)cc13)CCC2] | 7-methoxy-N-(1-methoxypropan-2-yl)-6-{[2-(pyrrolidin-1-yl)ethoxy]methyl}-1H,2H,3H-cyclopenta[b]quinolin-9-amine |
| 175 | 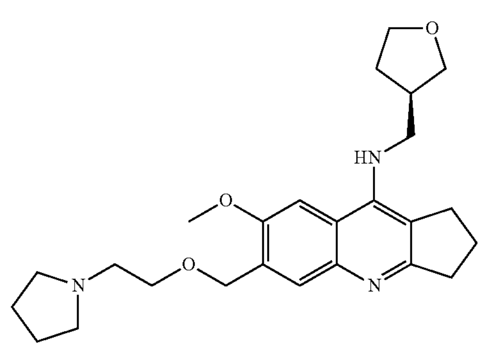 [SMILES: COc1cc2c(NC[C@H]3CCOC3)c3c(nc2cc1COCCN1CCCC1)CCC3] | 7-methoxy-N-{[(3R)-oxolan-3-yl]methyl}-6-{[2-(pyrrolidin-1-yl)ethoxy]methyl}-1H,2H,3H-cyclopenta[b]quinolin-9-amine |

TABLE 2-continued

| No. | Structure | IUPAC Name |
|-----|-----------|------------|
| 176 | 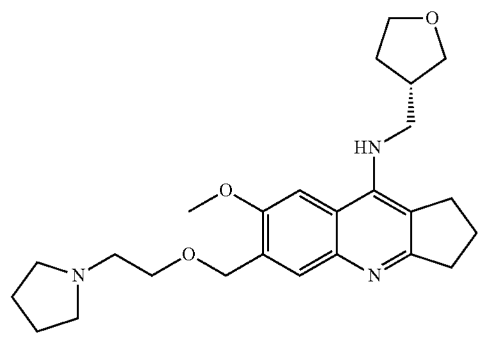 [SMILES: COc1cc2c(NC[C@@H]3CCOC3)c3c(nc2cc1COCCN1CCCC1)CCC3] | 7-methoxy-N-{[(3S)-oxolan-3-yl]methyl}-6-{[2-(pyrrolidin-1-yl)ethoxy]methyl}-1H,2H,3H-cyclopenta[b]quinolin-9-amine |
| 177 | 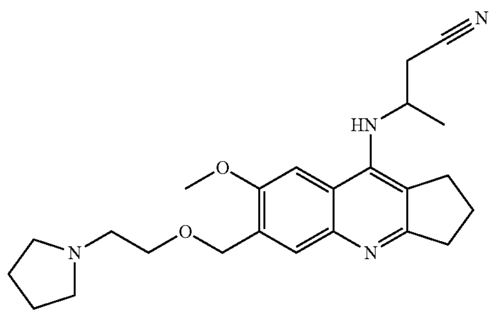 [SMILES: COc1cc2c(NC(C)CC#N)c3c(nc2cc1COCCN1CCCC1)CCC3] | 3-[(7-methoxy-6-{[2-(pyrrolidin-1-yl)ethoxy]methyl}-1H,2H,3H-cyclopenta[b]quinolin-9-yl)amino]butanenitrile |
| 178 | 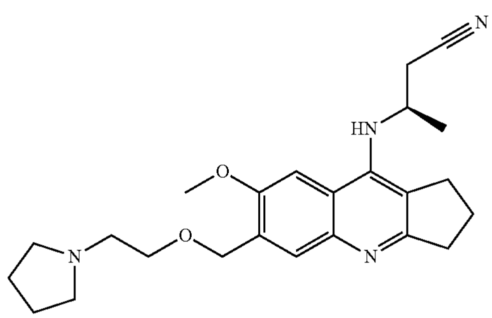 [SMILES: COc1cc2c(N[C@H](C)CC#N)c3c(nc2cc1COCCN1CCCC1)CCC3] | (3R)-3-[(7-methoxy-6-{[2-(pyrrolidin-1-yl)ethoxy]methyl}-1H,2H,3H-cyclopenta[b]quinolin-9-yl)amino]butanenitrile |
| 179 | 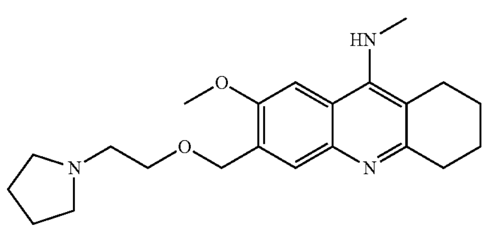 [SMILES: CNc1c2c(nc3cc(COCCN4CCCC4)c(OC)cc13)CCCC2] | 7-methoxy-N-methyl-6-{[2-(pyrrolidin-1-yl)ethoxy]methyl}-1,2,3,4-tetrahydroacridin-9-amine |
| 180 | 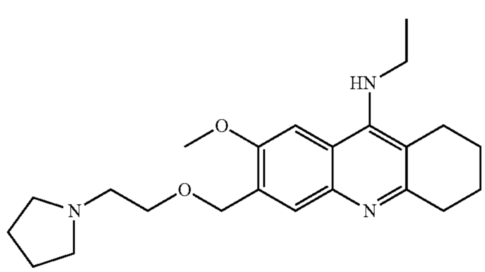 [SMILES: CCNc1c2c(nc3cc(COCCN4CCCC4)c(OC)cc13)CCCC2] | N-ethyl-7-methoxy-6-{[2-(pyrrolidin-1-yl)ethoxy]methyl}-1,2,3,4-tetrahydroacridin-9-amine |

TABLE 2-continued

| No. | Structure | IUPAC Name |
| --- | --- | --- |
| 181 | 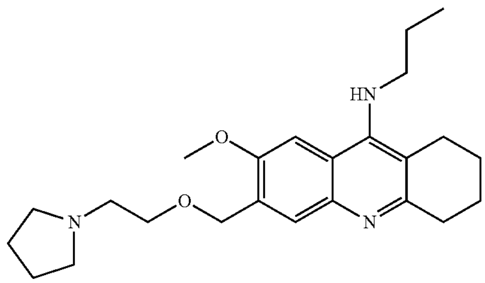 [SMILES: CCCNc1c2c(nc3cc(COCCN4CCCC4)c(OC)cc13)CCCC2] | 7-methoxy-N-propyl-6-{[2-(pyrrolidin-1-yl)ethoxy]methyl}-1,2,3,4-tetrahydroacridin-9-amine |
| 182 | 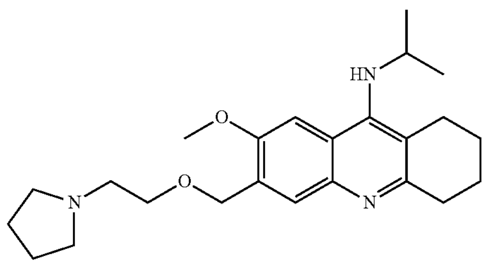 [SMILES: COc1cc2c(NC(C)C)c3c(nc2cc1COCCN1CCCC1)CCCC3] | 7-methoxy-N-(propan-2-yl)-6-{[2-(pyrrolidin-1-yl)ethoxy]methyl}-1,2,3,4-tetrahydroacridin-9-amine |
| 183 | 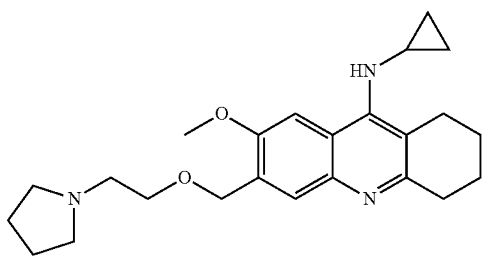 [SMILES: COc1cc2c(NC3CC3)c3c(nc2cc1COCCN1CCCC1)CCCC3] | N-cyclopropyl-7-methoxy-6-{[2-(pyrrolidin-1-yl)ethoxy]methyl}-1,2,3,4-tetrahydroacridin-9-amine |
| 184 | 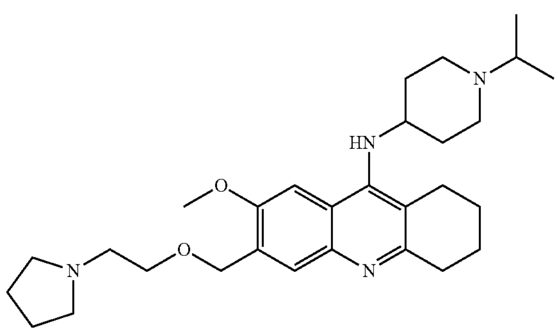 [SMILES: COc1cc2c(NC3CCN(C(C)C)CC3)c3c(nc2cc1COCCN1CCCC1)CCCC3] | 7-methoxy-N-[1-(propan-2-yl)piperidin-4-yl]-6-{[2-(pyrrolidin-1-yl)ethoxy]methyl}-1,2,3,4-tetrahydroacridin-9-amine |
| 185 | 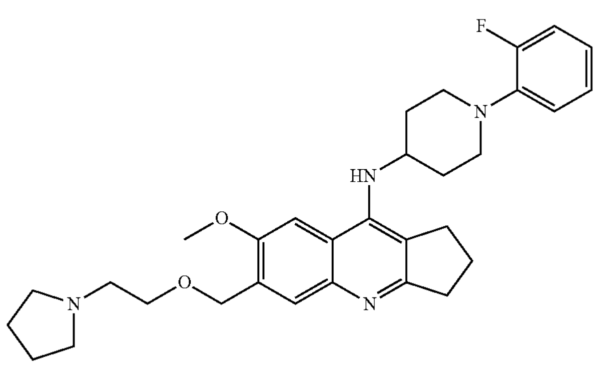 [SMILES: COc1cc2c(NC3CCN(c4ccccc4F)CC3)c3c(nc2cc1COCCN1CCCC1)CCC3] | 1-(2-fluorophenyl)-N-(7-methoxy-6-{[2-(pyrrolidin-1-yl)ethoxy]methyl}-1H,2H,3H-cyclopenta[b]quinolin-9-yl)piperidin-4-amine |

TABLE 2-continued

| No. | Structure | IUPAC Name |
|---|---|---|
| 186 | 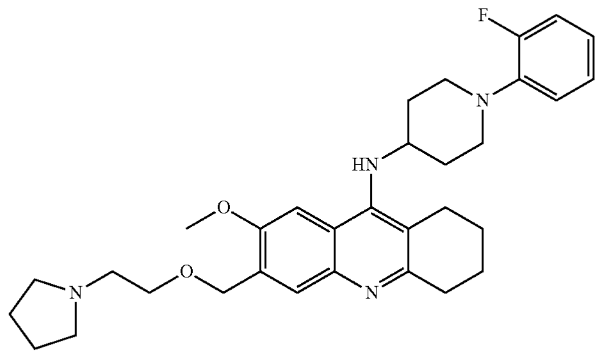 [SMILES: COc1cc2c(NC3CCN(c4ccccc4F)CC3)c3c(nc2cc1COCCN1CCCC1)CCCC3] | N-[1-(2-fluorophenyl)piperidin-4-yl]-7-methoxy-6-{[2-(pyrrolidin-1-yl)ethoxy]methyl}-1,2,3,4-tetrahydroacridin-9-amine |
| 187 | 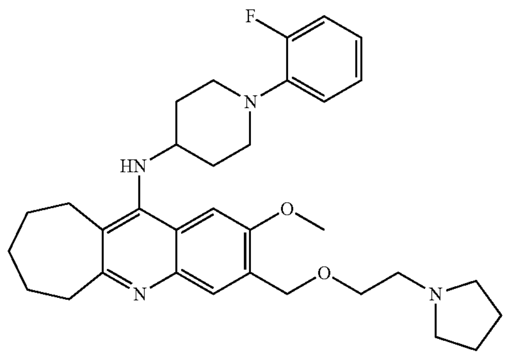 [SMILES: COc1cc2c(NC3CCN(c4ccccc4F)CC3)c3c(nc2cc1COCCN1CCCC1)CCCCC3] | 1-(2-fluorophenyl)-N-(2-methoxy-3-{[2-(pyrrolidin-1-yl)ethoxy]methyl}-6H,7H,8H,9H,10H-cyclohepta[b]quinolin-11-yl)piperidin-4-amine |
| 188 | 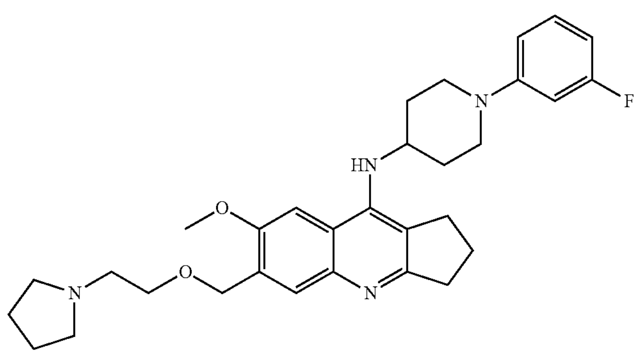 [SMILES: COc1cc2c(NC3CCN(c4cccc(F)c4)CC3)c3c(nc2cc1COCCN1CCCC1)CCC3] | 1-(3-fluorophenyl)-N-(7-methoxy-6-{[2-(pyrrolidin-1-yl)ethoxy]methyl}-1H,2H,3H-cyclopenta[b]quinolin-9-yl)piperidin-4-amine |
| 189 | 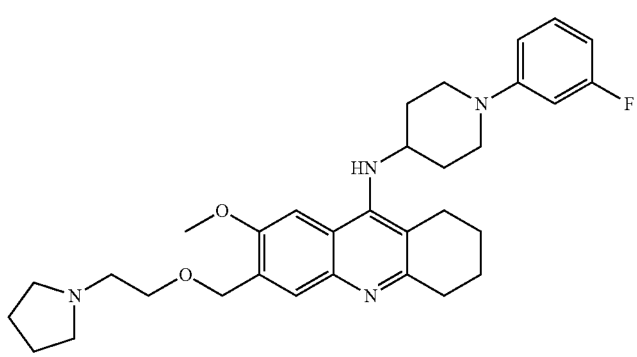 [SMILES: COc1cc2c(NC3CCN(c4cccc(F)c4)CC3)c3c(nc2cc1COCCN1CCCC1)CCCC3] | N-[1-(3-fluorophenyl)piperidin-4-yl]-7-methoxy-6-{[2-(pyrrolidin-1-yl)ethoxy]methyl}-1,2,3,4-tetrahydroacridin-9-amine |

TABLE 2-continued

| No. | Structure | IUPAC Name |
|---|---|---|
| 190 | 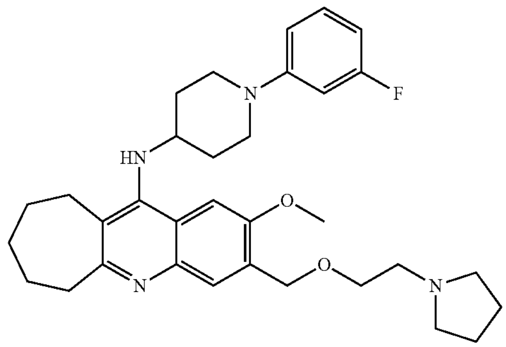 [SMILES: COc1cc2c(NC3CCN(c4cccc(F)c4)CC3)c3c(nc2cc1COCCN1CCCC1)CCCCC3] | 1-(3-fluorophenyl)-N-(2-methoxy-3-{[2-(pyrrolidin-1-yl)ethoxy]methyl}-6H,7H,8H,9H,10H-cyclohepta[b]quinolin-11-yl)piperidin-4-amine |
| 191 | 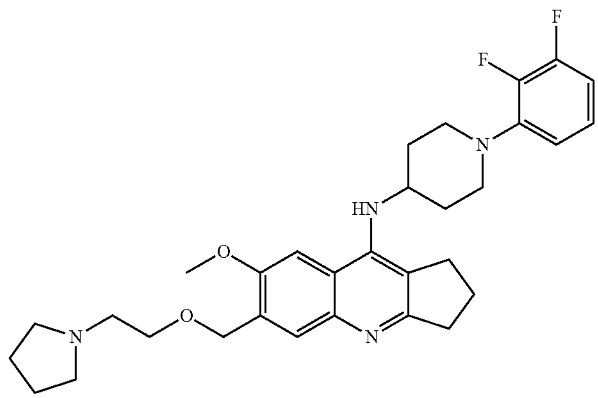 [SMILES: COc1cc2c(NC3CCN(c4cccc(F)c4F)CC3)c3c(nc2cc1COCCN1CCCC1)CCC3] | 1-(2,3-difluorophenyl)-N-(7-methoxy-6-{[2-(pyrrolidin-1-yl)ethoxy]methyl}-1H,2H,3H-cyclopenta[b]quinolin-9-yl)piperidin-4-amine |
| 192 | 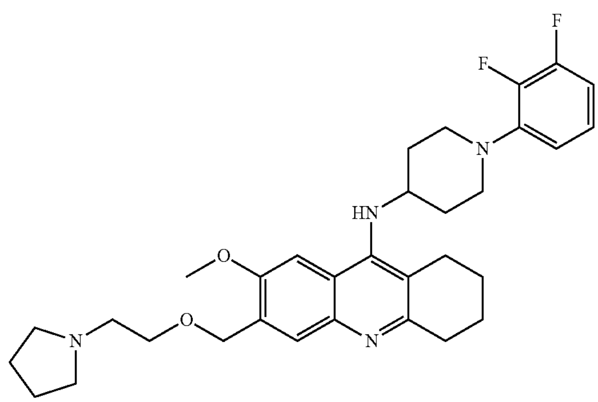 [SMILES: COc1cc2c(NC3CCN(c4cccc(F)c4F)CC3)c3c(nc2cc1COCCN1CCCC1)CCCC3] | N-[1-(2,3-difluorophenyl)piperidin-4-yl]-7-methoxy-6-{[2-(pyrrolidin-1-yl)ethoxy]methyl}-1,2,3,4-tetrahydroacridin-9-amine |
| 193 | 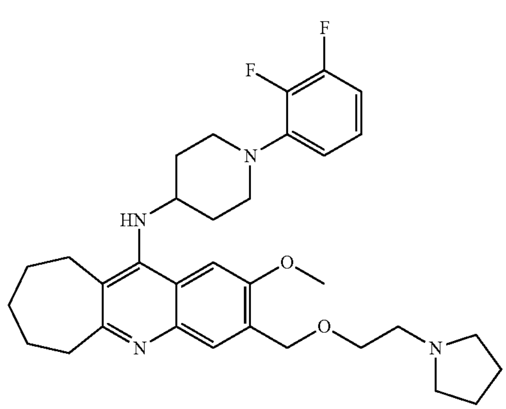 [SMILES: COc1cc2c(NC3CCN(c4cccc(F)c4F)CC3)c3c(nc2cc1COCCN1CCCC1)CCCCC3] | 1-(2,3-difluorophenyl)-N-(2-methoxy-3-{[2-(pyrrolidin-1-yl)ethoxy]methyl}-6H,7H,8H,9H,10H-cyclohepta[b]quinolin-11-yl)piperidin-4-amine |

TABLE 2-continued

| No. | Structure | IUPAC Name |
|---|---|---|
| 194 | 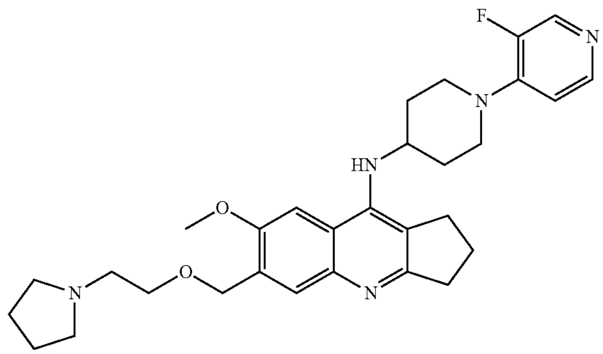 [SMILES: COc1cc2c(NC3CCN(c4ccncc4F)CC3)c3c(nc2cc1COCCN1CCCC1)CCC3] | 1-(3-fluoropyridin-4-yl)-N-(7-methoxy-6-{[2-(pyrrolidin-1-yl)ethoxy]methyl}-1H,2H,3H-cyclopenta[b]quinolin-9-yl)piperidin-4-amine |
| 195 | 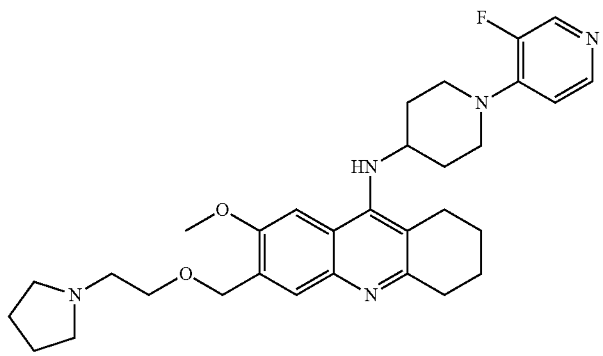 | N-[1-(3-fluoropyridin-4-yl)piperidin-4-yl]-7-methoxy-6-{[2-(pyrrolidin-1-yl)ethoxy]methyl}-1,2,3,4-tetrahydroacridin-9-amine |
| 196 | 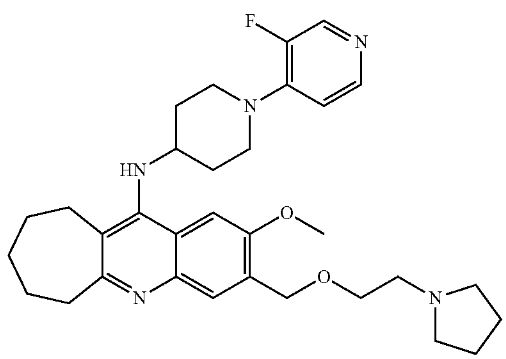 [SMILES: COc1cc2c(NC3CCN(c4ccncc4F)CC3)c3c(nc2cc1COCCN1CCCC1)CCCCC3] | 1-(3-fluoropyridin-4-yl)-N-(2-methoxy-3-{[2-(pyrrolidin-1-yl)ethoxy]methyl}-6H,7H,8H,9H,10H-cyclohepta[b]quinolin-11-yl)piperidin-4-amine |
| 197 | 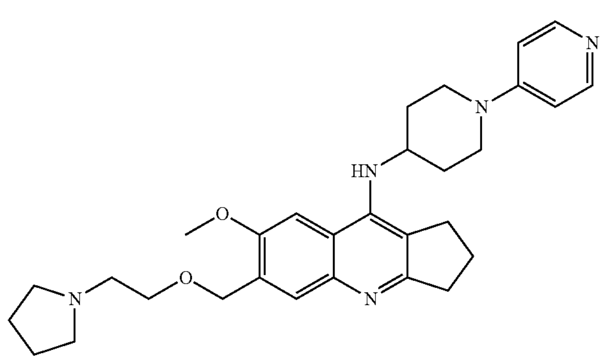 | N-(7-methoxy-6-{[2-(pyrrolidin-1-yl)ethoxy]methyl}-1H,2H,3H-cyclopenta[b]quinolin-9-yl)-1-(pyridin-4-yl)piperidin-4-amine |

TABLE 2-continued

| No. | Structure | IUPAC Name |
|---|---|---|
| 198 | 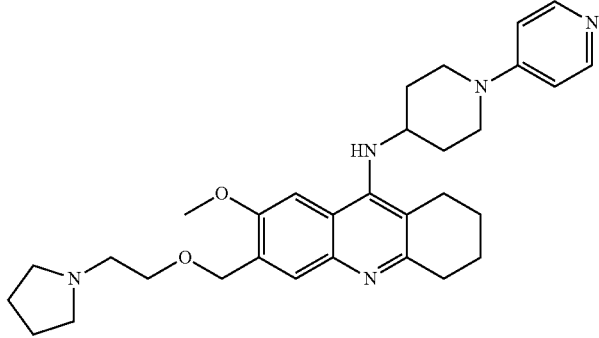 [SMILES: COc1cc2c(NC3CCN(c4ccncc4)CC3)c3c(nc2cc1COCCN1CCCC1)CCCC3] | 7-methoxy-N-[1-(pyridin-4-yl)piperidin-4-yl]-6-{[2-(pyrrolidin-1-yl)ethoxy]methyl}-1,2,3,4-tetrahydroacridin-9-amine |
| 199 | 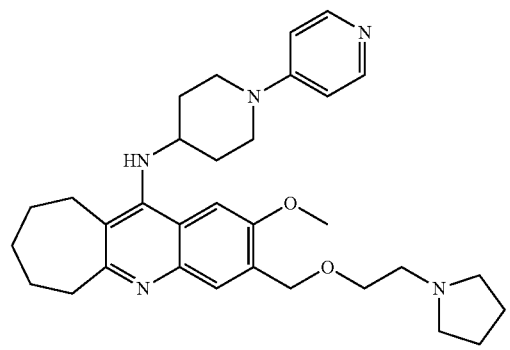 | N-(2-methoxy-3-{[2-(pyrrolidin-1-yl)ethoxy]methyl}-6H,7H,8H,9H,10H-cyclohepta[b]quinolin-11-yl)-1-(pyridin-4-yl)piperidin-4-amine |
| 200 | 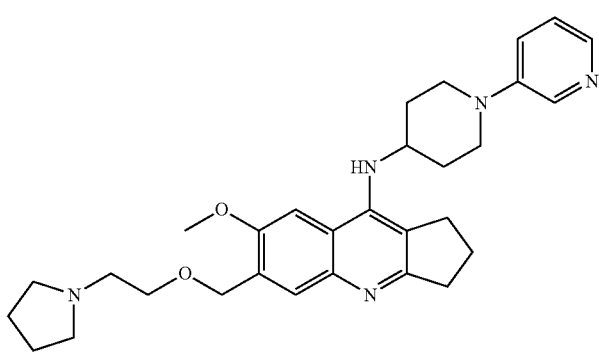 | N-(7-methoxy-6-{[2-(pyrrolidin-1-yl)ethoxy]methyl}-1H,2H,3H-cyclopenta[b]quinolin-9-yl)-1-(pyridin-3-yl)piperidin-4-amine |
| 201 | 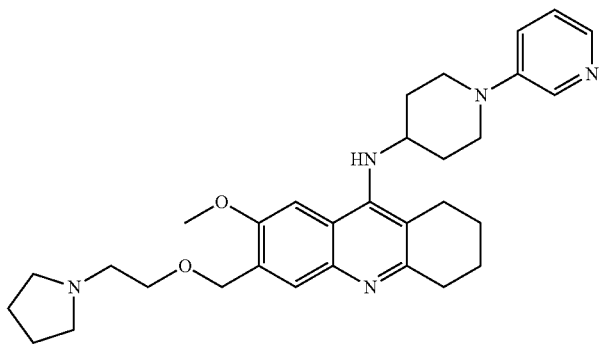 | 7-methoxy-N-[1-(pyridin-3-yl)piperidin-4-yl]-6-{[2-(pyrrolidin-1-yl)ethoxy]methyl}-1,2,3,4-tetrahydroacridin-9-amine |

TABLE 2-continued

| No. | Structure | IUPAC Name |
|-----|-----------|------------|
| 202 | 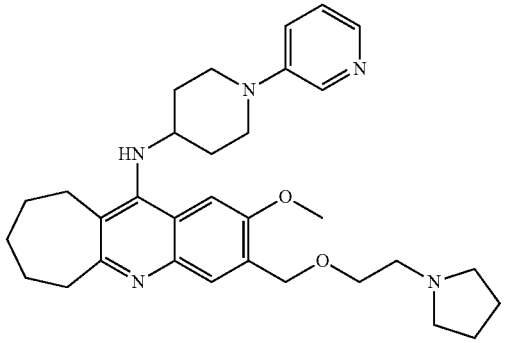 [SMILES: COc1cc2c(NC3CCN(c4cccnc4)CC3)c3c(nc2cc1COCCN1CCCC1)CCCCC3] | N-(2-methoxy-3-{[2-(pyrrolidin-1-yl)ethoxy]methyl}-6H,7H,8H,9H,10H-cyclohepta[b]quinolin-11-yl)-1-(pyridin-3-yl)piperidin-4-amine |
| 203 | 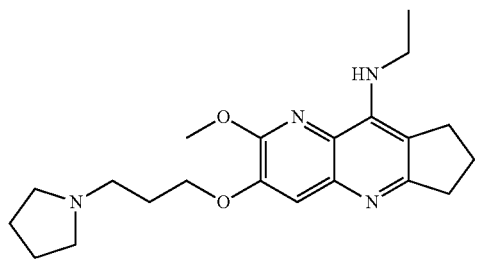 | N-ethyl-2-methoxy-3-[3-(pyrrolidin-1-yl)propoxy]-6H,7H,8H-cyclopenta[b]1,5-naphthyridin-9-amine |
| 204 | 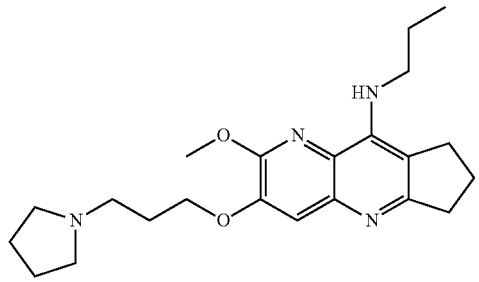 | 2-methoxy-N-propyl-3-[3-(pyrrolidin-1-yl)propoxy]-6H,7H,8H-cyclopenta[b]1,5-naphthyridin-9-amine |
| 205 | 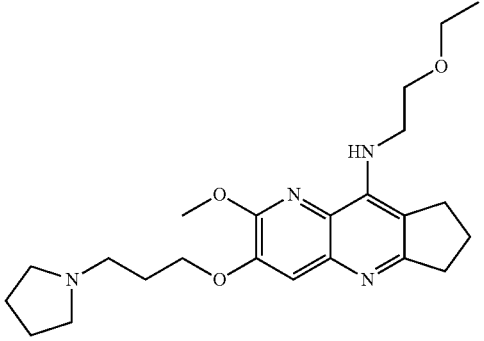 [SMILES: CCOCCNc1c2c(nc3cc(OCCCN4CCCC4)c(OC)nc13)CCC2] | N-(2-ethoxyethyl)-2-methoxy-3-[3-(pyrrolidin-1-yl)propoxy]-6H,7H,8H-cyclopenta[b]1,5-naphthyridin-9-amine |
| 206 | 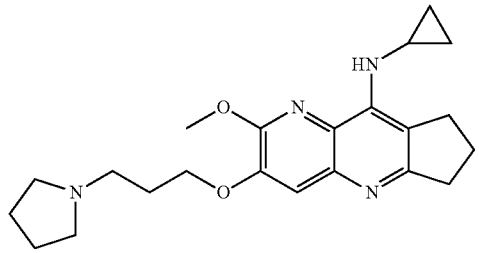 [SMILES: COc1nc2c(NC3CC3)c3c(nc2cc1OCCCN1CCCC1)CCC3] | N-cyclopropyl-2-methoxy-3-[3-(pyrrolidin-1-yl)propoxy]-6H,7H,8H-cyclopenta[b]1,5-naphthyridin-9-amine |

TABLE 2-continued

| No. | Structure | IUPAC Name |
|---|---|---|
| 207 | 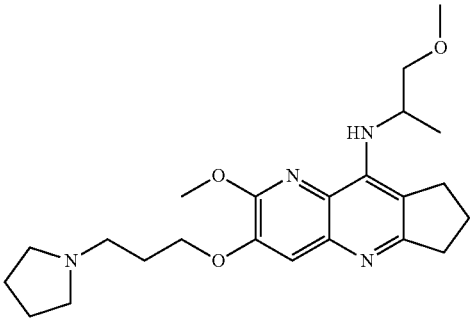 [SMILES: COCC(C)Nc1c2c(nc3cc(OCCCN4CCCC4)c(OC)nc13)CCC2] | 2-methoxy-N-(1-methoxypropan-2-yl)-3-[3-(pyrrolidin-1-yl)propoxy]-6H,7H,8H-cyclopenta[b]1,5-naphthyridin-9-amine |
| 208 | 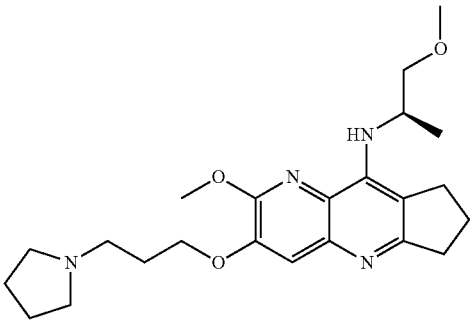 [SMILES: COC[C@@H](C)Nc1c2c(nc3cc(OCCCN4CCCC4)c(OC)nc13)CCC2] | 2-methoxy-N-[(2R)-1-methoxypropan-2-yl]-3-[3-(pyrrolidin-1-yl)propoxy]-6H,7H,8H-cyclopenta[b]1,5-naphthyridin-9-amine |
| 209 | 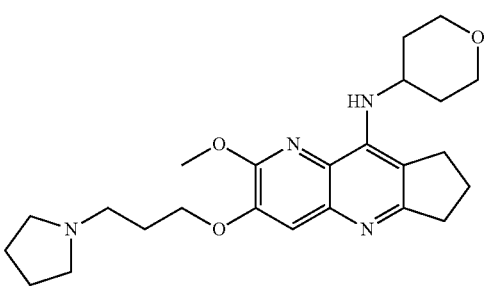 [SMILES: COc1nc2c(NC3CCOCC3)c3c(nc2cc1OCCCN1CCCC1)CCC3] | 2-methoxy-N-(oxan-4-yl)-3-[3-(pyrrolidin-1-yl)propoxy]-6H,7H,8H-cyclopenta[b]1,5-naphthyridin-9-amine |
| 210 | 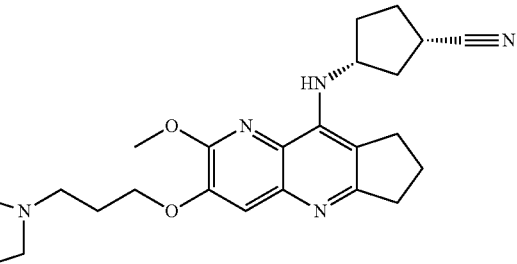 | (1S,3R)-3-({2-methoxy-3-[3-(pyrrolidin-1-yl)propoxy]-6H,7H,8H-cyclopenta[b]1,5-naphthyridin-9-yl}amino)cyclopentane-1-carbonitrile |
| 211 | 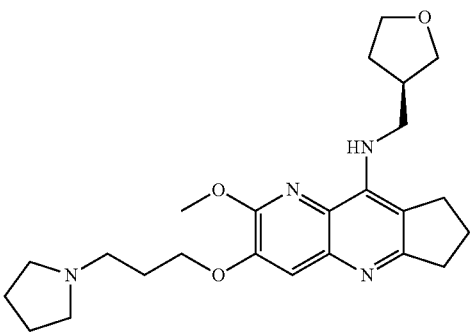 [SMILES: COc1nc2c(NC[C@H]3CCOC3)c3c(nc2cc1OCCCN1CCCC1)CCC3] | 2-methoxy-N-{[(3R)-oxolan-3-yl]methyl}-3-[3-(pyrrolidin-1-yl)propoxy]-6H,7H,8H-cyclopenta[b]1,5-naphthyridin-9-amine |

TABLE 2-continued

| No. | Structure | IUPAC Name |
|---|---|---|
| 212 | 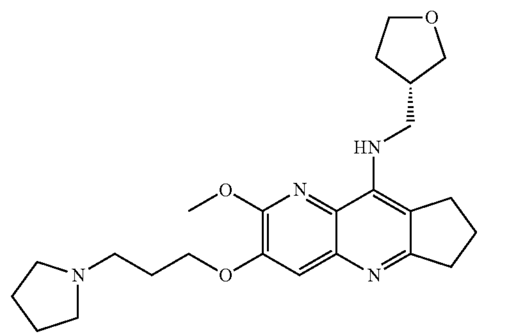 | 2-methoxy-N-{[(3S)-oxolan-3-yl]methyl}-3-[3-(pyrrolidin-1-yl)propoxy]-6H,7H,8H-cyclopenta[b]1,5-naphthyridin-9-amine |
| 213 | 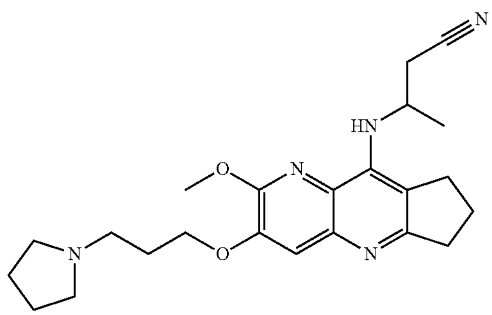 [SMILES: COc1nc2c(NC(C)CC#N)c3c(nc2cc1OCCCN1CCCC1)CCC3] | 3-({2-methoxy-3-[3-(pyrrolidin-1-yl)propoxy]-6H,7H,8H-cyclopenta[b]1,5-naphthyridin-9-yl}amino)butanenitrile |
| 214 | 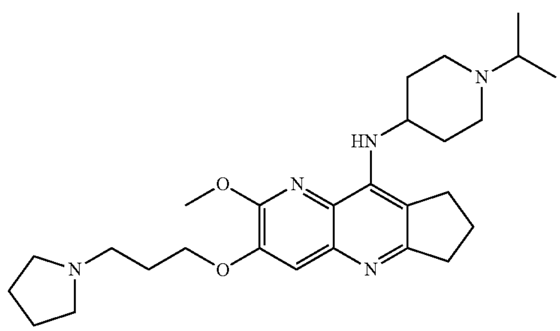 [SMILES: COc1nc2c(NC3CCN(C(C)C)CC3)c3c(nc2cc1OCCCN1CCCC1)CCC3] | N-{2-methoxy-3-[3-(pyrrolidin-1-yl)propoxy]-6H,7H,8H-cyclopenta[b]1,5-naphthyridin-9-yl}-1-(propan-2-yl)piperidin-4-amine |
| 215 | 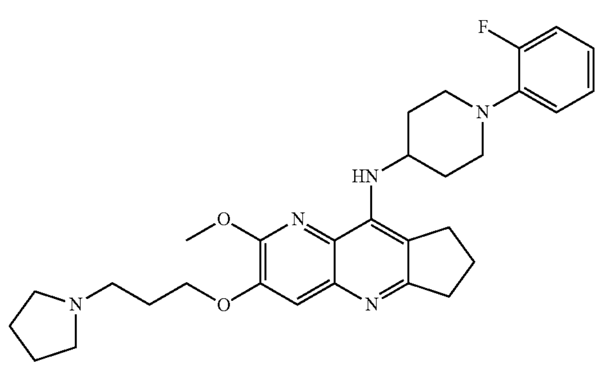 | 1-(2-fluorophenyl)-N-{2-methoxy-3-[3-(pyrrolidin-1-yl)propoxy]-6H,7H,8H-cyclopenta[b]1,5-naphthyridin-9-yl}piperidin-4-amine |

TABLE 2-continued

| No. | Structure | IUPAC Name |
|---|---|---|
| 216 | 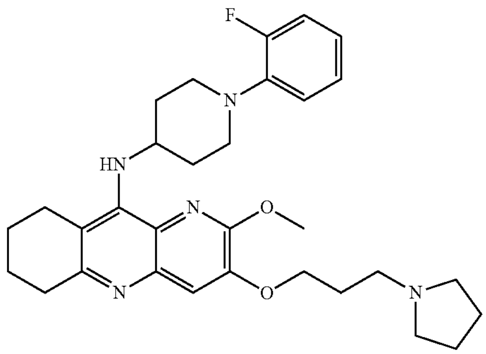 | 1-(2-fluorophenyl)-N-{2-methoxy-3-[3-(pyrrolidin-1-yl)propoxy]-6H,7H,8H,9H-cyclohexa[b]1,5-naphthyridin-10-yl}piperidin-4-amine |
| 217 | 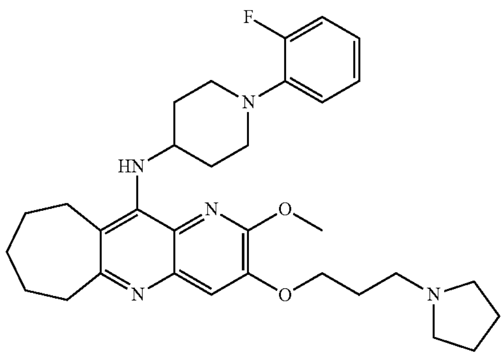 [SMILES: COc1nc2c(NC3CCN(c4ccccc4F)CC3)c3c(nc2cc1OCCCN1CCCC1)CCCCC3] | 1-(2-fluorophenyl)-N-{2-methoxy-3-[3-(pyrrolidin-1-yl)propoxy]-6H,7H,8H,9H,10H-cyclohepta[b]1,5-naphthyridin-11-yl}piperidin-4-amine |
| 218 | 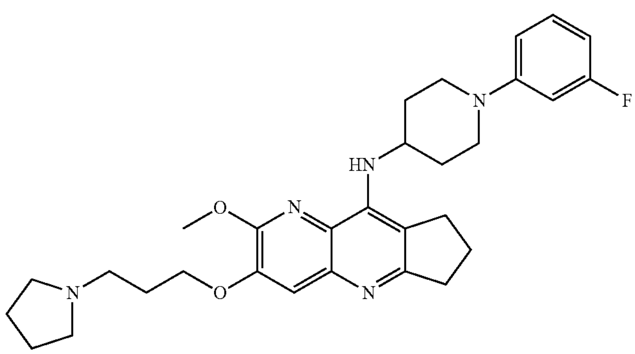 [SMILES: COc1nc2c(NC3CCN(c4cccc(F)c4)CC3)c3c(nc2cc1OCCCN1CCCC1)CCC3] | 1-(3-fluorophenyl)-N-{2-methoxy-3-[3-(pyrrolidin-1-yl)propoxy]-6H,7H,8H-cyclopenta[b]1,5-naphthyridin-9-yl}piperidin-4-amine |
| 219 | 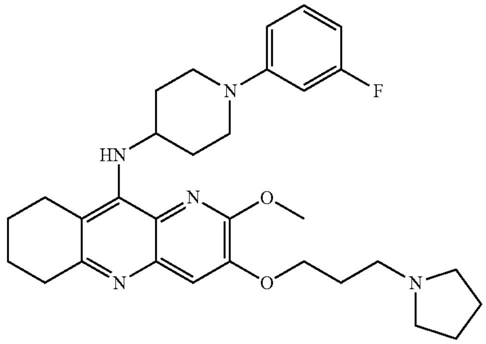 | 1-(3-fluorophenyl)-N-{2-methoxy-3-[3-(pyrrolidin-1-yl)propoxy]-6H,7H,8H,9H-cyclohexa[b]1,5-naphthyridin-10-yl}piperidin-4-amine |

TABLE 2-continued

| No. | Structure | IUPAC Name |
|---|---|---|
| 220 | 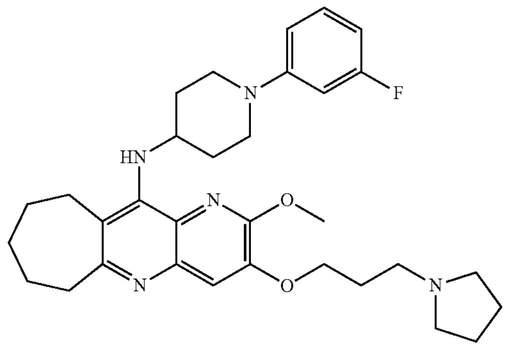 [SMILES: COc1nc2c(NC3CCN(c4cccc(F)c4)CC3)c3c(nc2cc1OCCCN1CCCC1)CCCCC3] | 1-(3-fluorophenyl)-N-{2-methoxy-3-[3-(pyrrolidin-1-yl)propoxy]-6H,7H,8H,9H,10H-cyclohepta[b]1,5-naphthyridin-11-yl}piperidin-4-amine |
| 221 | 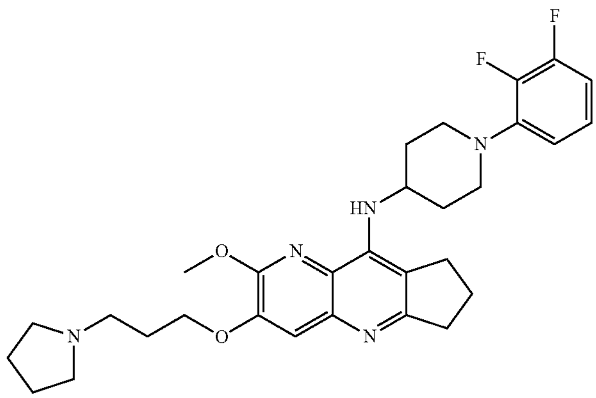 [SMILES: COc1nc2c(NC3CCN(c4cccc(F)c4F)CC3)c3c(nc2cc1OCCCN1CCCC1)CCC3] | 1-(2,3-difluorophenyl)-N-{2-methoxy-3-[3-(pyrrolidin-1-yl)propoxy]-6H,7H,8H-cyclopenta[b]1,5-naphthyridin-9-yl}piperidin-4-amine |
| 222 | 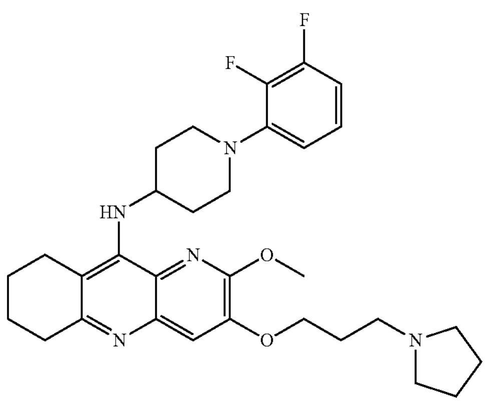 [SMILES: COc1nc2c(NC3CCN(c4cccc(F)c4F)CC3)c3c(nc2cc1OCCCN1CCCC1)CCCC3] | 1-(2,3-difluorophenyl)-N-{2-methoxy-3-[3-(pyrrolidin-1-yl)propoxy]-6H,7H,8H,9H-cyclohexa[b]1,5-naphthyridin-10-yl}piperidin-4-amine |
| 223 | 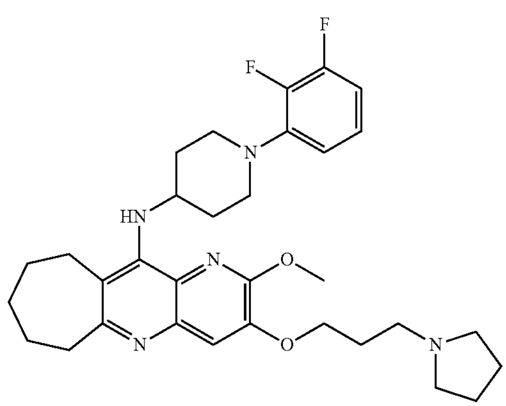 [SMILES: COc1nc2c(NC3CCN(c4cccc(F)c4F)CC3)c3c(nc2cc1OCCCN1CCCC1)CCCCC3] | 1-(2,3-difluorophenyl)-N-{2-methoxy-3-[3-(pyrrolidin-1-yl)propoxy]-6H,7H,8H,9H,10H-cyclohepta[b]1,5-naphthyridin-11-yl}piperidin-4-amine |

TABLE 2-continued

| No. | Structure | IUPAC Name |
| --- | --- | --- |
| 224 | 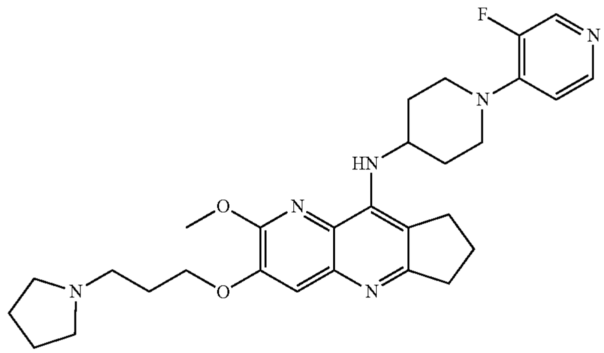 | 1-(3-fluoropyridin-4-yl)-N-{2-methoxy-3-[3-(pyrrolidin-1-yl)propoxy]-6H,7H,8H-cyclopenta[b]1,5-naphthyridin-9-yl}piperidin-4-amine |
| 225 | 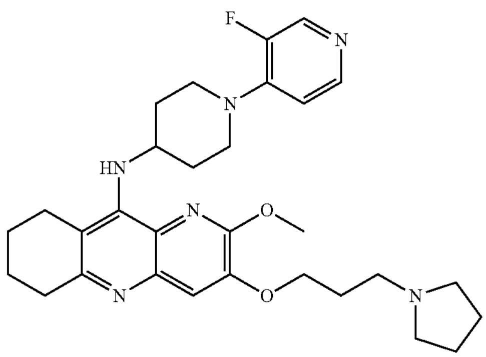 [SMILES: COc1nc2c(NC3CCN(c4ccncc4F)CC3)c3c(nc2cc1OCCCN1CCCC1)CCCC3] | 1-(3-fluoropyridin-4-yl)-N-{2-methoxy-3-[3-(pyrrolidin-1-yl)propoxy]-6H,7H,8H,9H-cyclohexa[b]1,5-naphthyridin-10-yl}piperidin-4-amine |
| 226 | 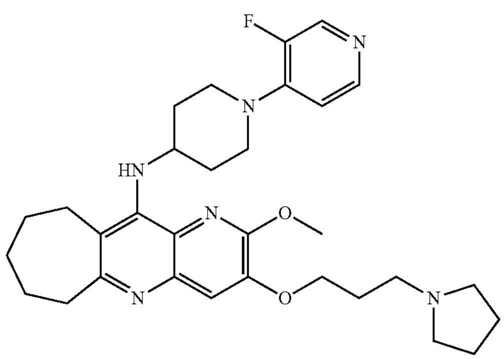 [SMILES: COc1nc2c(NC3CCN(c4ccncc4F)CC3)c3c(nc2cc1OCCCN1CCCC1)CCCCC3] | 1-(3-fluoropyridin-4-yl)-N-{2-methoxy-3-[3-(pyrrolidin-1-yl)propoxy]-6H,7H,8H,9H,10H-cyclohepta[b]1,5-naphthyridin-11-yl}piperidin-4-amine |
| 227 | 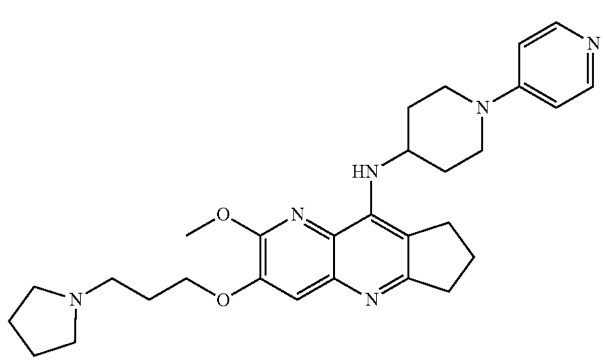 [SMILES: COc1nc2c(NC3CCN(c4ccncc4)CC3)c3c(nc2cc1OCCCN1CCCC1)CCC3] | N-{2-methoxy-3-[3-(pyrrolidin-1-yl)propoxy]-6H,7H,8H-cyclopenta[b]1,5-naphthyridin-9-yl}-1-(pyridin-4-yl)piperidin-4-amine |

TABLE 2-continued

| No. | Structure | IUPAC Name |
|---|---|---|
| 228 | 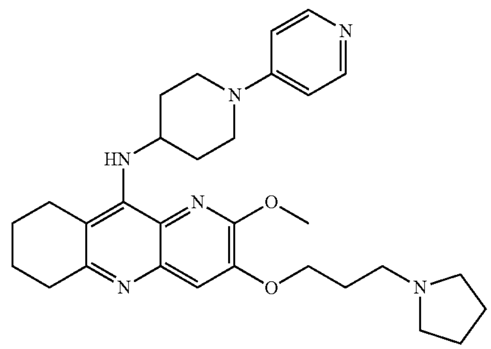 | N-{2-methoxy-3-[3-(pyrrolidin-1-yl)propoxy]-6H,7H,8H,9H-cyclohexa[b]1,5-naphthyridin-10-yl}-1-(pyridin-4-yl)piperidin-4-amine |
| 229 | 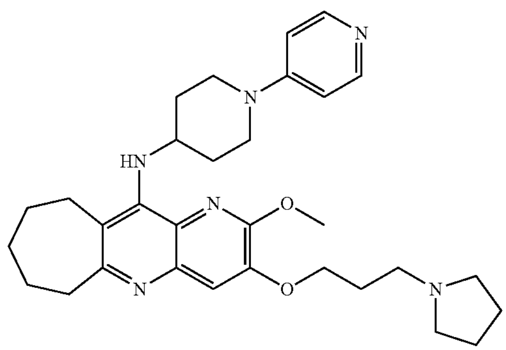 [SMILES: COc1nc2c(NC3CCN(c4ccncc4)CC3)c3c(nc2cc1OCCCN1CCCC1)CCCCC3] | N-{2-methoxy-3-[3-(pyrrolidin-1-yl)propoxy]-6H,7H,8H,9H,10H-cyclohepta[b]1,5-naphthyridin-11-yl}-1-(pyridin-4-yl)piperidin-4-amine |
| 230 | 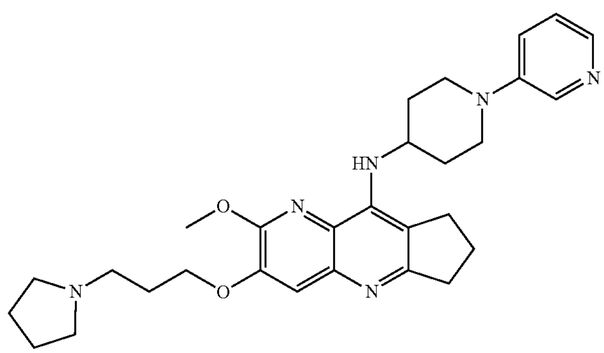 [SMILES: COc1nc2c(NC3CCN(c4cccnc4)CC3)c3c(nc2cc1OCCCN1CCCC1)CCC3] | N-{2-methoxy-3-[3-(pyrrolidin-1-yl)propoxy]-6H,7H,8H-cyclopenta[b]1,5-naphthyridin-9-yl}-1-(pyridin-3-yl)piperidin-4-amine |
| 231 | 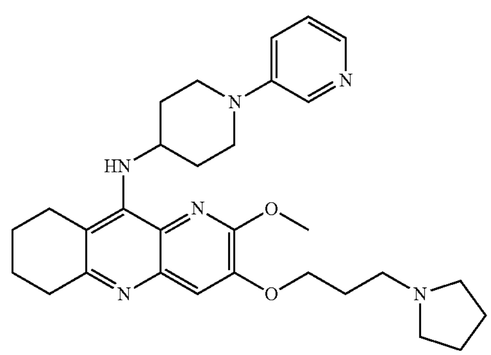 [SMILES: COc1nc2c(NC3CCN(c4cccnc4)CC3)c3c(nc2cc1OCCCN1CCCC1)CCCC3] | N-{2-methoxy-3-[3-(pyrrolidin-1-yl)propoxy]-6H,7H,8H,9H-cyclohexa[b]1,5-naphthyridin-10-yl}-1-(pyridin-3-yl)piperidin-4-amine |

TABLE 2-continued

| No. | Structure | IUPAC Name |
|---|---|---|
| 232 | 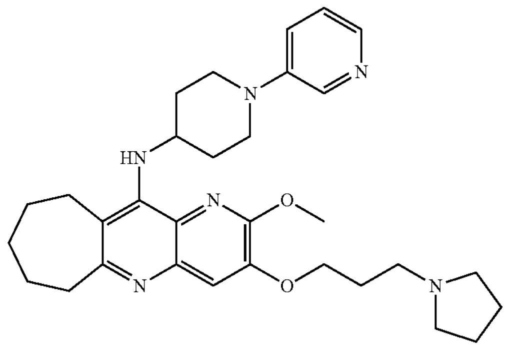 [SMILES: COc1nc2c(NC3CCN(c4cccnc4)CC3)c3c(nc2cc1OCCCN1CCCC1)CCCCC3] | N-{2-methoxy-3-[3-(pyrrolidin-1-yl)propoxy]-6H,7H,8H,9H,10H-cyclohepta[b]1,5-naphthyridin-11-yl}-1-(pyridin-3-yl)piperidin-4-amine |
| 233 | 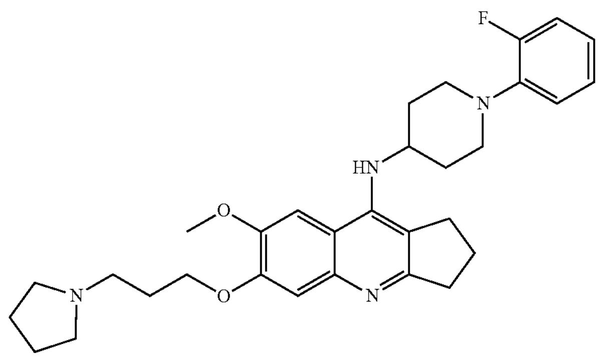 [SMILES: COc1cc2c(NC3CCN(c4ccccc4F)CC3)c3c(nc2cc1OCCCN1CCCC1)CCC3] | 1-(2-fluorophenyl)-N-{7-methoxy-6-[3-(pyrrolidin-1-yl)propoxy]-1H,2H,3H-cyclopenta[b]quinolin-9-yl}piperidin-4-amine |
| 234 | 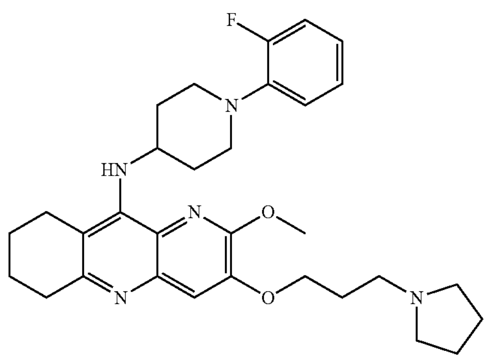 | 1-(2-fluorophenyl)-N-{2-methoxy-3-[3-(pyrrolidin-1-yl)propoxy]-6H,7H,8H,9H-cyclohexa[b]1,5-naphthyridin-10-yl}piperidin-4-amine |
| 235 | 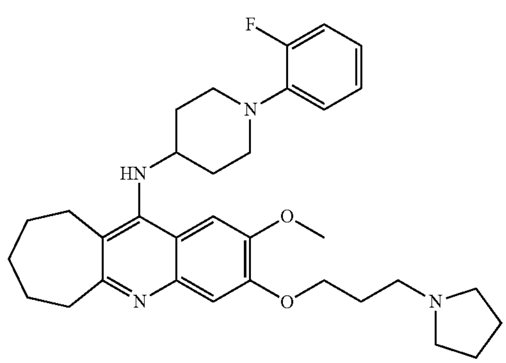 | 1-(2-fluorophenyl)-N-{2-methoxy-3-[3-(pyrrolidin-1-yl)propoxy]-6H,7H,8H,9H,10H-cyclohepta[b]quinolin-11-yl}piperidin-4-amine |

TABLE 2-continued

| No. | Structure | IUPAC Name |
|---|---|---|
| 236 | 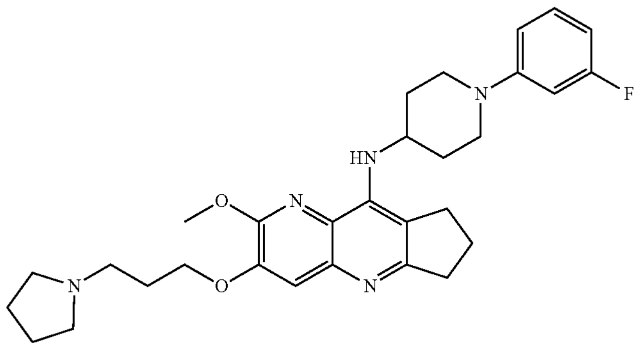 [SMILES: COc1nc2c(NC3CCN(c4cccc(F)c4)CC3)c3c(nc2cc1OCCCN1CCCC1)CCC3] | 1-(3-fluorophenyl)-N-{7-methoxy-6-[3-(pyrrolidin-1-yl)propoxy]-1H,2H,3H-cyclopenta[b]quinolin-9-yl}piperidin-4-amine |
| 237 | 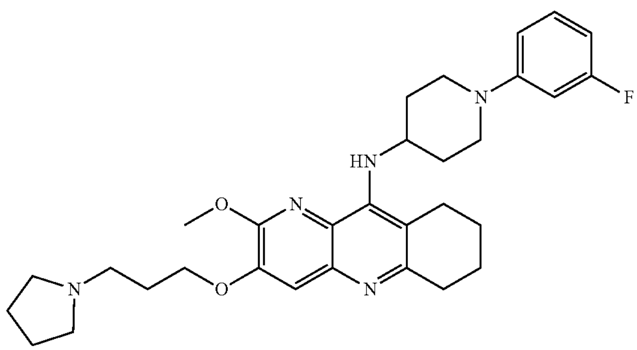 [SMILES: COc1nc2c(NC3CCN(c4cccc(F)c4)CC3)c3c(nc2cc1OCCCN1CCCC1)CCCC3] | N-[1-(3-fluorophenyl)piperidin-4-yl]-7-methoxy-6-[3-(pyrrolidin-1-yl)propoxy]-1,2,3,4-tetrahydroacridin-9-amine |
| 238 | 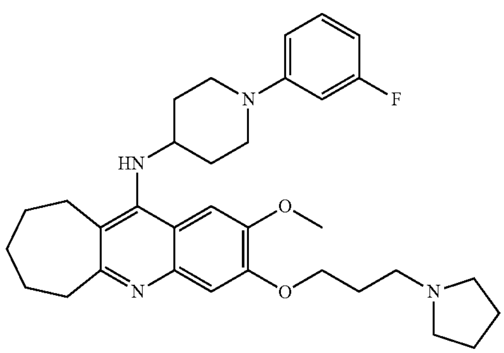 [SMILES: COc1cc2c(NC3CCN(c4cccc(F)c4)CC3)c3c(nc2cc1OCCCN1CCCC1)CCCCC3] | 1-(3-fluorophenyl)-N-{2-methoxy-3-[3-(pyrrolidin-1-yl)propoxy]-6H,7H,8H,9H,10H-cyclohepta[b]quinolin-11-yl}piperidin-4-amine |
| 239 | 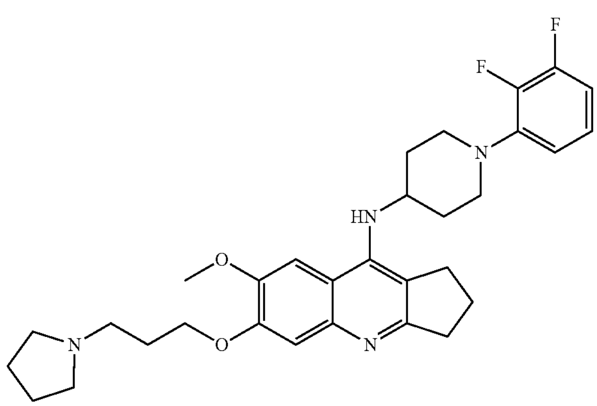 [SMILES: COc1cc2c(NC3CCN(c4cccc(F)c4F)CC3)c3c(nc2cc1OCCCN1CCCC1)CCC3] | 1-(2,3-difluorophenyl)-N-{7-methoxy-6-[3-(pyrrolidin-1-yl)propoxy]-1H,2H,3H-cyclopenta[b]quinolin-9-yl}piperidin-4-amine |

TABLE 2-continued

| No. | Structure | IUPAC Name |
|---|---|---|
| 240 | 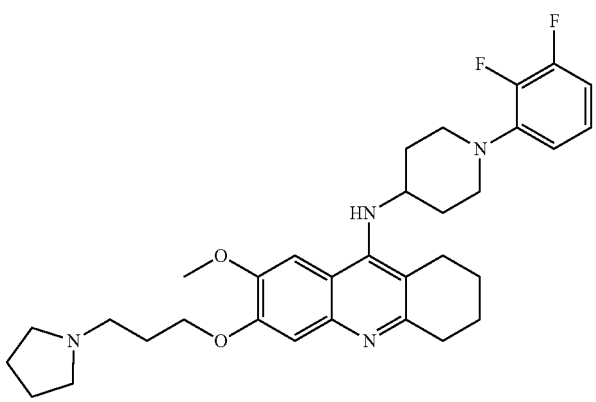 [SMILES: COc1cc2c(NC3CCN(c4cccc(F)c4F)CC3)c3c(nc2cc1OCCCN1CCCC1)CCCC3] | N-[1-(2,3-difluorophenyl)piperidin-4-yl]-7-methoxy-6-[3-(pyrrolidin-1-yl)propoxy]-1,2,3,4-tetrahydroacridin-9-amine |
| 241 | 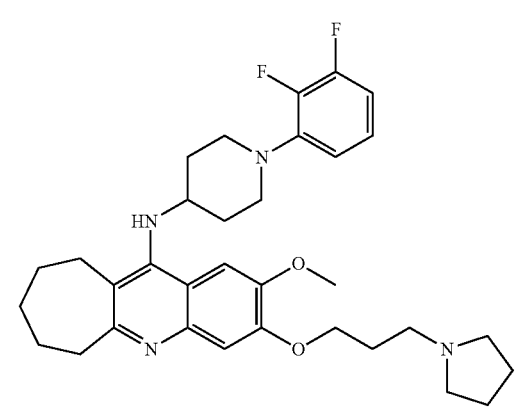 [SMILES: COc1cc2c(NC3CCN(c4cccc(F)c4F)CC3)c3c(nc2cc1OCCCN1CCCC1)CCCCC3] | 1-(2,3-difluorophenyl)-N-{2-methoxy-3-[3-(pyrrolidin-1-yl)propoxy]-6H,7H,8H,9H,10H-cyclohepta[b]quinolin-11-yl}piperidin-4-amine |
| 242 | 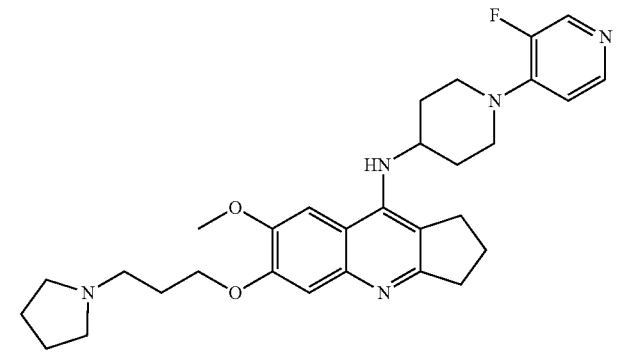 [SMILES: COc1cc2c(NC3CCN(c4ccncc4F)CC3)c3c(nc2cc1OCCCN1CCCC1)CCC3] | 1-(3-fluoropyridin-4-yl)-N-{7-methoxy-6-[3-(pyrrolidin-1-yl)propoxy]-1H,2H,3H-cyclopenta[b]quinolin-9-yl}piperidin-4-amine |
| 243 | 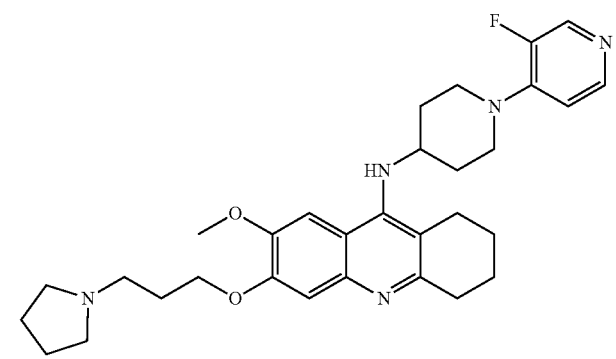 [SMILES: COc1cc2c(NC3CCN(c4ccncc4F)CC3)c3c(nc2cc1OCCCN1CCCC1)CCCC3] | N-[1-(3-fluoropyridin-4-yl)piperidin-4-yl]-7-methoxy-6-[3-(pyrrolidin-1-yl)propoxy]-1,2,3,4-tetrahydroacridin-9-amine |

TABLE 2-continued

| No. | Structure | IUPAC Name |
|---|---|---|
| 244 | 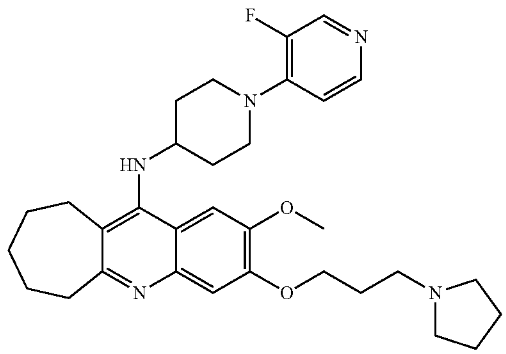 | 1-(3-fluoropyridin-4-yl)-N-{2-methoxy-3-[3-(pyrrolidin-1-yl)propoxy]-6H,7H,8H,9H,10H-cyclohepta[b]quinolin-11-yl}piperidin-4-amine |
| 245 | 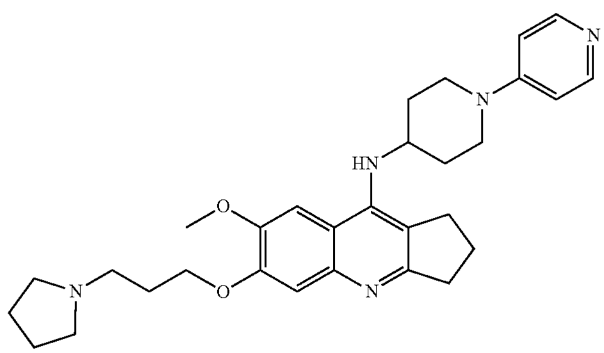 [SMILES: COc1cc2c(NC3CCN(c4ccncc4)CC3)c3c(nc2cc1OCCCN1CCCC1)CCC3] | N-{7-methoxy-6-[3-(pyrrolidin-1-yl)propoxy]-1H,2H,3H-cyclopenta[b]quinolin-9-yl}-1-(pyridin-4-yl)piperidin-4-amine |
| 246 | 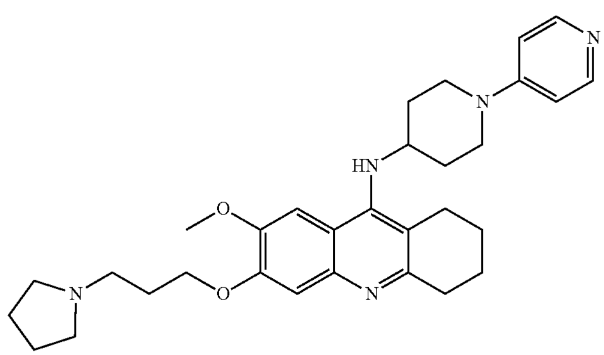 | 7-methoxy-N-[1-(pyridin-4-yl)piperidin-4-yl]-6-[3-(pyrrolidin-1-yl)propoxy]-1,2,3,4-tetrahydroacridin-9-amine |
| 247 | 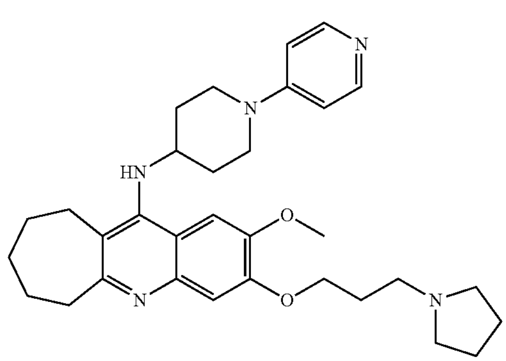 [SMILES: COc1cc2c(NC3CCN(c4ccncc4)CC3)c3c(nc2cc1OCCCN1CCCC1)CCCCC3] | N-{2-methoxy-3-[3-(pyrrolidin-1-yl)propoxy]-6H,7H,8H,9H,10H-cyclohepta[b]quinolin-11-yl}-1-(pyridin-4-yl)piperidin-4-amine |

TABLE 2-continued

| No. | Structure | IUPAC Name |
|---|---|---|
| 248 | 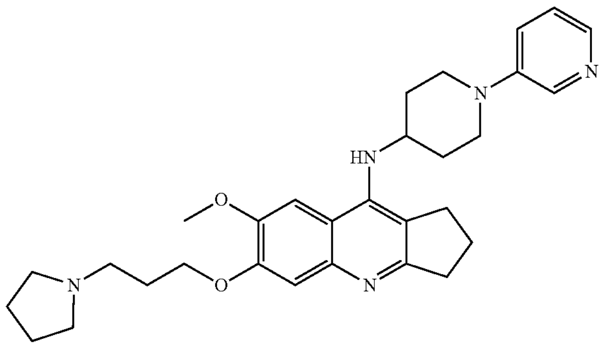 | N-{7-methoxy-6-[3-(pyrrolidin-1-yl)propoxy]-1H,2H,3H-cyclopenta[b]quinolin-9-yl}-1-(pyridin-3-yl)piperidin-4-amine |
| 249 | 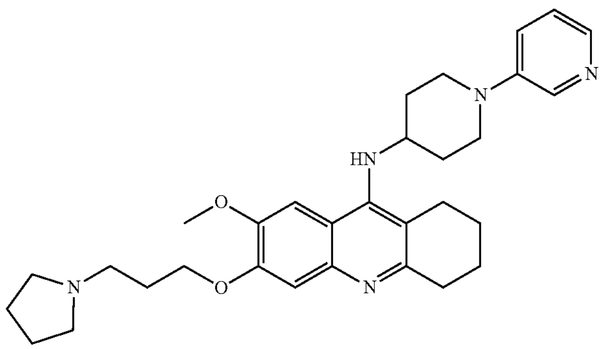 [SMILES: COc1cc2c(NC3CCN(c4cccnc4)CC3)c3c(nc2cc1OCCCN1CCCC1)CCCC3] | 7-methoxy-N-[1-(pyridin-3-yl)piperidin-4-yl]-6-[3-(pyrrolidin-1-yl)propoxy]-1,2,3,4-tetrahydroacridin-9-amine |
| 250 | 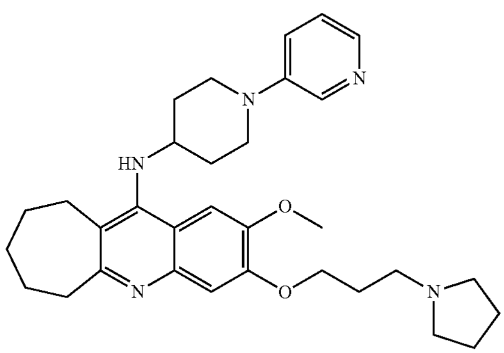 [SMILES: COc1cc2c(NC3CCN(c4cccnc4)CC3)c3c(nc2cc1OCCCN1CCCC1)CCCCC3] | N-{2-methoxy-3-[3-(pyrrolidin-1-yl)propoxy]-6H,7H,8H,9H,10H-cyclohepta[b]quinolin-11-yl}-1-(pyridin-3-yl)piperidin-4-amine |
| 251 | 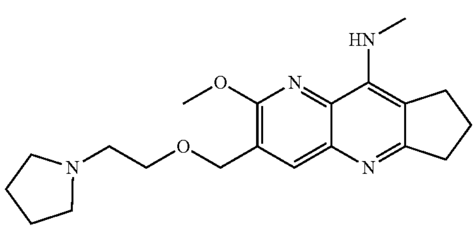 [SMILES: CNc1c2c(nc3cc(COCCN4CCCC4)c(OC)nc13)CCC2] | 2-methoxy-N-methyl-3-{[2-(pyrrolidin-1-yl)ethoxy]methyl}-6H,7H,8H-cyclopenta[b]1,5-naphthyridin-9-amine |
| 252 | 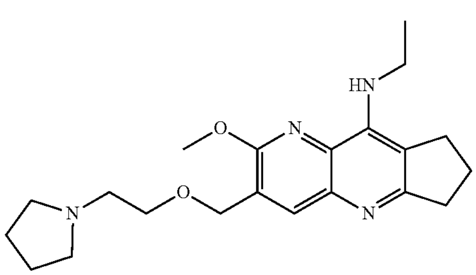 [SMILES: CCNc1c2c(nc3cc(COCCN4CCCC4)c(OC)nc13)CCC2] | N-ethyl-2-methoxy-3-{[2-(pyrrolidin-1-yl)ethoxy]methyl}-6H,7H,8H-cyclopenta[b]1,5-naphthyridin-9-amine |

TABLE 2-continued

| No. | Structure | IUPAC Name |
|---|---|---|
| 253 | 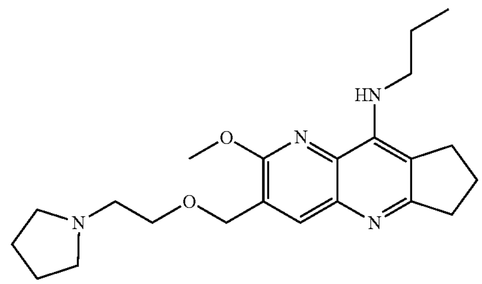 [SMILES: CCCNc1c2c(nc3cc(COCCN4CCCC4)c(OC)nc13)CCC2] | 2-methoxy-N-propyl-3-{[2-(pyrrolidin-1-yl)ethoxy]methyl}-6H,7H,8H-cyclopenta[b]1,5-naphthyridin-9-amine |
| 254 | 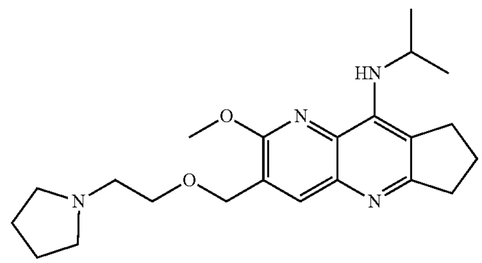 [SMILES: COc1nc2c(NC(C)C)c3c(nc2cc1COCCN1CCCC1)CCC3] | 2-methoxy-N-(propan-2-yl)-3-{[2-(pyrrolidin-1-yl)ethoxy]methyl}-6H,7H,8H-cyclopenta[b]1,5-naphthyridin-9-amine |
| 255 | 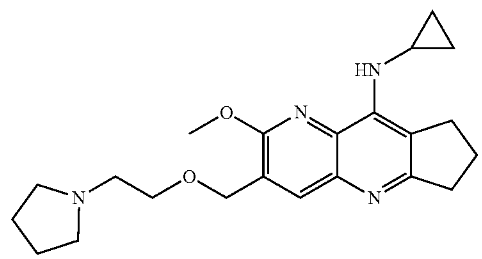 [SMILES: COc1nc2c(NC3CC3)c3c(nc2cc1COCCN1CCCC1)CCC3] | N-cyclopropyl-2-methoxy-3-{[2-(pyrrolidin-1-yl)ethoxy]methyl}-6H,7H,8H-cyclopenta[b]1,5-naphthyridin-9-amine |
| 256 | 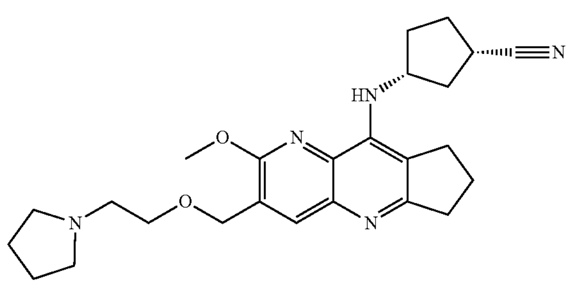 [SMILES: COc1nc2c(N[C@@H]3CC[C@H](C#N)C3)c3c(nc2cc1COCCN1CCCC1)CCC3] | (1S,3R)-3-[(2-methoxy-3-{[2-(pyrrolidin-1-yl)ethoxy]methyl}-6H,7H,8H-cyclopenta[b]1,5-naphthyridin-9-yl)amino]cyclopentane-1-carbonitrile |
| 257 | 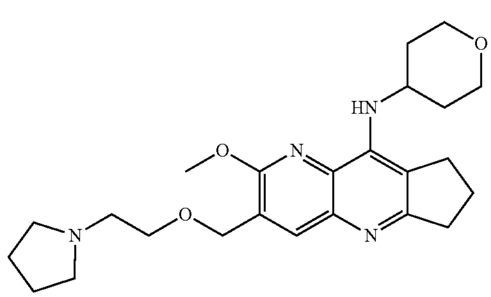 | 2-methoxy-N-(oxan-4-yl)-3-{[2-(pyrrolidin-1-yl)ethoxy]methyl}-6H,7H,8H-cyclopenta[b]1,5-naphthyridin-9-amine |

TABLE 2-continued

| No. | Structure | IUPAC Name |
|---|---|---|
| 258 | 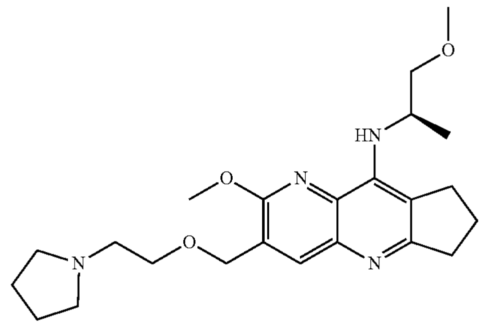 | 2-methoxy-N-[(2R)-1-methoxypropan-2-yl]-3-{[2-(pyrrolidin-1-yl)ethoxy]methyl}-6H,7H,8H-cyclopenta[b]1,5-naphthyridin-9-amine |
| 259 | 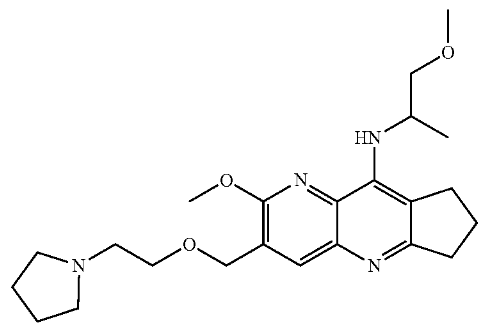 [SMILES: COCC(C)Nc1c2c(nc3cc(COCCN4CCCC4)c(OC)nc13)CCC2] | 2-methoxy-N-(1-methoxypropan-2-yl)-3-{[2-(pyrrolidin-1-yl)ethoxy]methyl}-6H,7H,8H-cyclopenta[b]1,5-naphthyridin-9-amine |
| 260 | 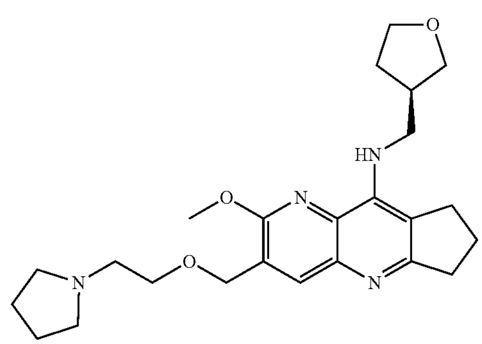 [SMILES: COc1nc2c(NC[C@H]3CCOC3)c3c(nc2cc1COCCN1CCCC1)CCC3] | 2-methoxy-N-{[(3R)-oxolan-3-yl]methyl}-3-{[2-(pyrrolidin-1-yl)ethoxy]methyl}-6H,7H,8H-cyclopenta[b]1,5-naphthyridin-9-amine |
| 261 | 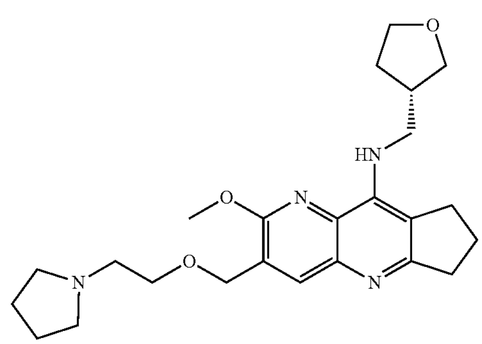 [SMILES: COc1nc2c(NC[C@@H]3CCOC3)c3c(nc2cc1COCCN1CCCC1)CCC3] | 2-methoxy-N-{[(3S)-oxolan-3-yl]methyl}-3-{[2-(pyrrolidin-1-yl)ethoxy]methyl}-6H,7H,8H-cyclopenta[b]1,5-naphthyridin-9-amine |

TABLE 2-continued

| No. | Structure | IUPAC Name |
|---|---|---|
| 262 | 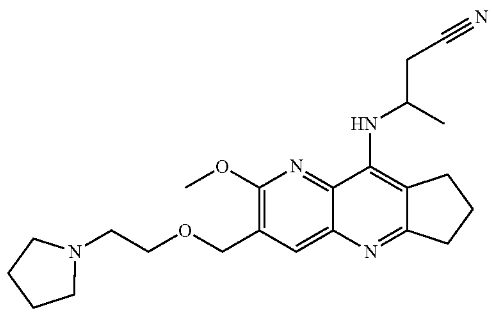 [SMILES: COc1nc2c(NC(C)CC#N)c3c(nc2cc1COCCN1CCCC1)CCC3] | 3-[(2-methoxy-3-{[2-(pyrrolidin-1-yl)ethoxy]methyl}-6H,7H,8H-cyclopenta[b]1,5-naphthyridin-9-yl)amino]butanenitrile |
| 263 | 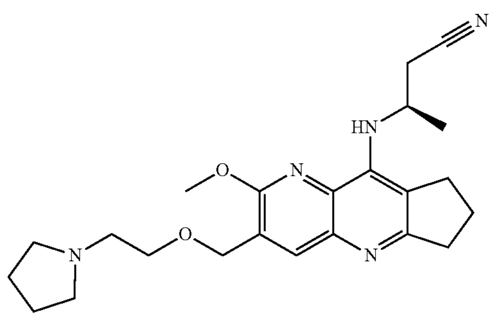 [SMILES: COc1nc2c(N[C@H](C)CC#N)c3c(nc2cc1COCCN1CCCC1)CCC3] | (3R)-3-[(2-methoxy-3-{[2-(pyrrolidin-1-yl)ethoxy]methyl}-6H,7H,8H-cyclopenta[b]1,5-naphthyridin-9-yl)amino]butanenitrile |
| 264 | 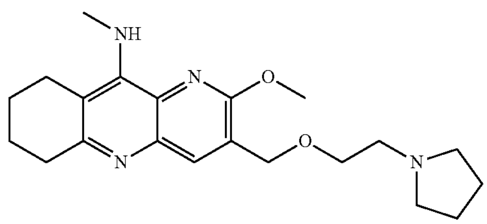 [SMILES: CNc1c2c(nc3cc(COCCN4CCCC4)c(OC)nc13)CCCC2] | 2-methoxy-N-methyl-3-{[2-(pyrrolidin-1-yl)ethoxy]methyl}-6H,7H,8H,9H-cyclohexa[b]1,5-naphthyridin-10-amine |
| 265 | 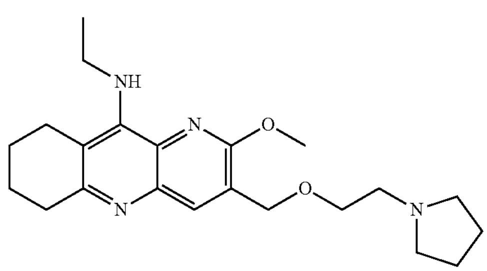 [SMILES: CCNc1c2c(nc3cc(COCCN4CCCC4)c(OC)nc13)CCCC2] | N-ethyl-2-methoxy-3-{[2-(pyrrolidin-1-yl)ethoxy]methyl}-6H,7H,8H,9H-cyclohexa[b]1,5-naphthyridin-10-amine |
| 266 | 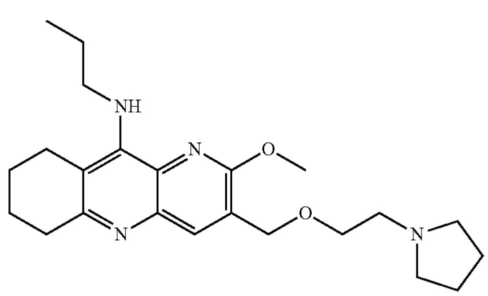 [SMILES: CCCNc1c2c(nc3cc(COCCN4CCCC4)c(OC)nc13)CCCC2] | 2-methoxy-N-propyl-3-{[2-(pyrrolidin-1-yl)ethoxy]methyl}-6H,7H,8H,9H-cyclohexa[b]1,5-naphthyridin-10-amine |

TABLE 2-continued

| No. | Structure | IUPAC Name |
|---|---|---|
| 267 | 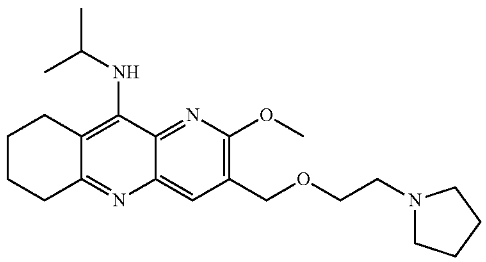 [SMILES: COc1nc2c(NC(C)C)c3c(nc2cc1COCCN1CCCC1)CCCC3] | 2-methoxy-N-(propan-2-yl)-3-{[2-(pyrrolidin-1-yl)ethoxy]methyl}-6H,7H,8H,9H-cyclohexa[b]1,5-naphthyridin-10-amine |
| 268 | 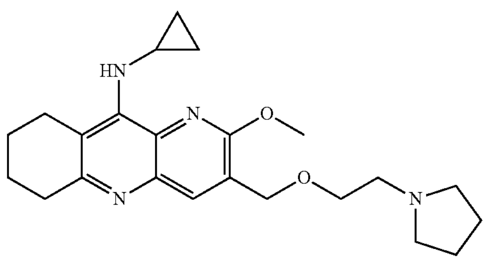 [SMILES: COc1nc2c(NC3CC3)c3c(nc2cc1COCCN1CCCC1)CCCC3] | N-cyclopropyl-2-methoxy-3-{[2-(pyrrolidin-1-yl)ethoxy]methyl}-6H,7H,8H,9H-cyclohexa[b]1,5-naphthyridin-10-amine |
| 269 | 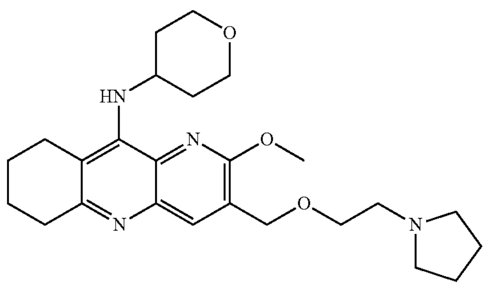 [SMILES: COc1nc2c(NC3CCOCC3)c3c(nc2cc1COCCN1CCCC1)CCCC3] | 2-methoxy-N-(oxan-4-yl)-3-{[2-(pyrrolidin-1-yl)ethoxy]methyl}-6H,7H,8H,9H-cyclohexa[b]1,5-naphthyridin-10-amine |
| 270 | 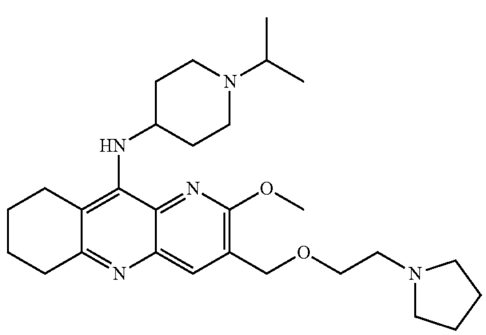 [SMILES: COc1nc2c(NC3CCN(C(C)C)CC3)c3c(nc2cc1COCCN1CCCC1)CCCC3] | N-(2-methoxy-3-{[2-(pyrrolidin-1-yl)ethoxy]methyl}-6H,7H,8H,9H-cyclohexa[b]1,5-naphthyridin-10-yl)-1-(propan-2-yl)piperidin-4-amine |
| 271 | 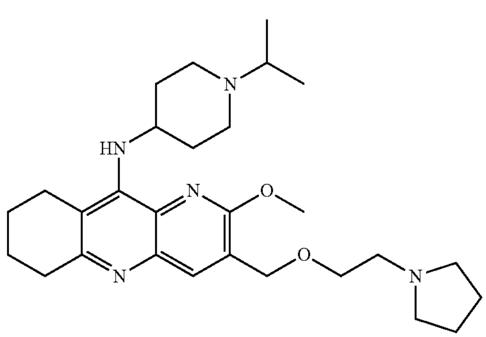 [SMILES: COc1nc2c(NC3CCN(C(C)C)CC3)c3c(nc2cc1COCCN1CCCC1)CCCC3] | N-(2-methoxy-3-{[2-(pyrrolidin-1-yl)ethoxy]methyl}-6H,7H,8H,9H-cyclohexa[b]1,5-naphthyridin-10-yl)-1-(propan-2-yl)piperidin-4-amine |

TABLE 2-continued

| No. | Structure | IUPAC Name |
|---|---|---|
| 272 | 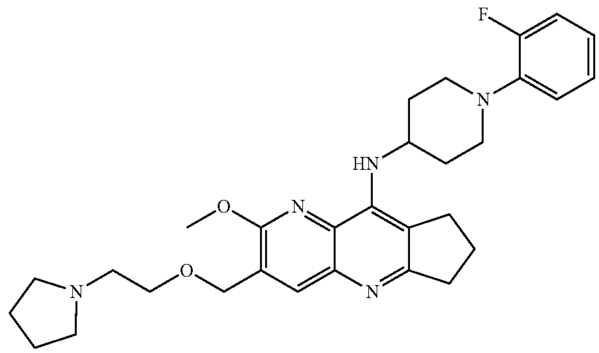 [SMILES: COc1nc2c(NC3CCN(c4ccccc4F)CC3)c3c(nc2cc1COCCN1CCCC1)CCC3] | 1-(2-fluorophenyl)-N-(2-methoxy-3-{[2-(pyrrolidin-1-yl)ethoxy]methyl}-6H,7H,8H-cyclopenta[b]1,5-naphthyridin-9-yl)piperidin-4-amine |
| 273 | 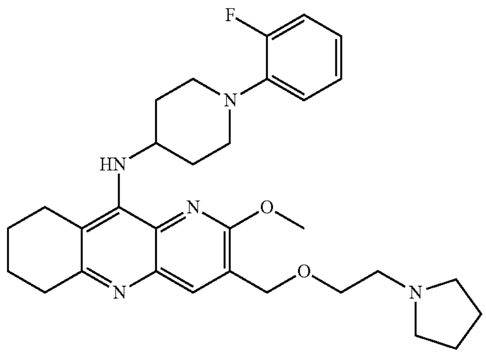 [SMILES: COc1nc2c(NC3CCN(c4ccccc4F)CC3)c3c(nc2cc1COCCN1CCCC1)CCCC3] | 1-(2-fluorophenyl)-N-(2-methoxy-3-{[2-(pyrrolidin-1-yl)ethoxy]methyl}-6H,7H,8H,9H-cyclohexa[b]1,5-naphthyridin-10-yl)piperidin-4-amine |
| 274 | 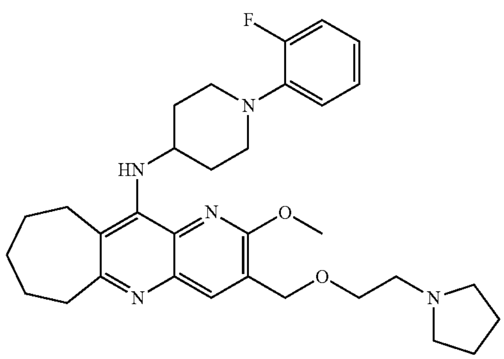 [SMILES: COc1nc2c(NC3CCN(c4ccccc4F)CC3)c3c(nc2cc1COCCN1CCCC1)CCCCC3] | 1-(2-fluorophenyl)-N-(2-methoxy-3-{[2-(pyrrolidin-1-yl)ethoxy]methyl}-6H,7H,8H,9H,10H-cyclohepta[b]1,5-naphthyridin-11-yl)piperidin-4-amine |
| 275 | 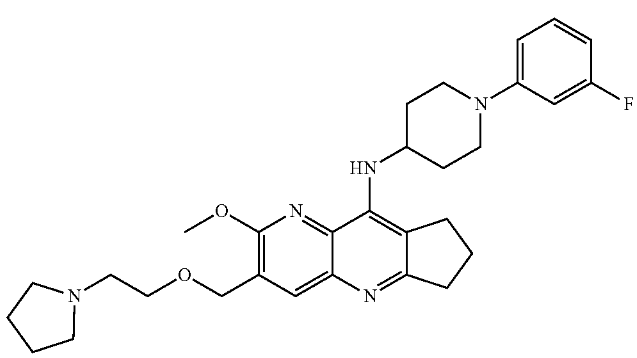 [SMILES: COc1nc2c(NC3CCN(c4cccc(F)c4)CC3)c3c(nc2cc1COCCN1CCCC1)CCC3] | 1-(3-fluorophenyl)-N-(2-methoxy-3-{[2-(pyrrolidin-1-yl)ethoxy]methyl}-6H,7H,8H-cyclopenta[b]1,5-naphthyridin-9-yl)piperidin-4-amine |

TABLE 2-continued

| No. | Structure | IUPAC Name |
|---|---|---|
| 276 | 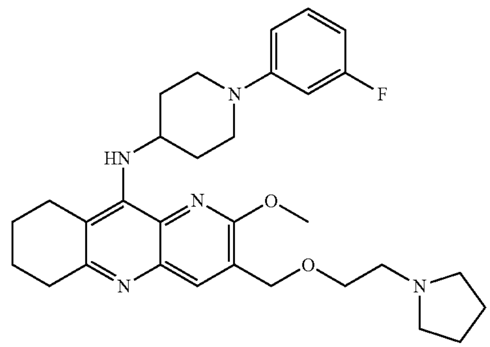 [SMILES: COc1nc2c(NC3CCN(c4cccc(F)c4)CC3)c3c(nc2cc1COCCN1CCCC1)CCCC3] | 1-(3-fluorophenyl)-N-(2-methoxy-3-{[2-(pyrrolidin-1-yl)ethoxy]methyl}-6H,7H,8H,9H-cyclohexa[b]1,5-naphthyridin-10-yl)piperidin-4-amine |
| 277 | 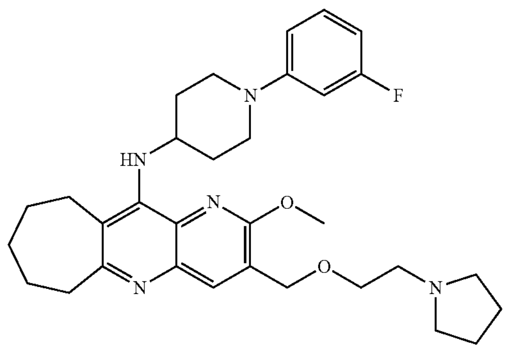 [SMILES: COc1nc2c(NC3CCN(c4cccc(F)c4)CC3)c3c(nc2cc1COCCN1CCCC1)CCCCC3] | 1-(3-fluorophenyl)-N-(2-methoxy-3-{[2-(pyrrolidin-1-yl)ethoxy]methyl}-6H,7H,8H,9H,10H-cyclohepta[b]1,5-naphthyridin-11-yl)piperidin-4-amine |
| 278 | 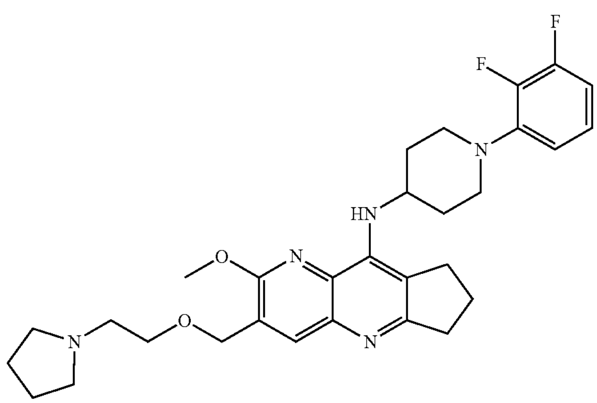 [SMILES: COc1nc2c(NC3CCN(c4cccc(F)c4F)CC3)c3c(nc2cc1COCCN1CCCC1)CCC3] | 1-(2,3-difluorophenyl)-N-(2-methoxy-3-{[2-(pyrrolidin-1-yl)ethoxy]methyl}-6H,7H,8H-cyclopenta[b]1,5-naphthyridin-9-yl)piperidin-4-amine |
| 279 | 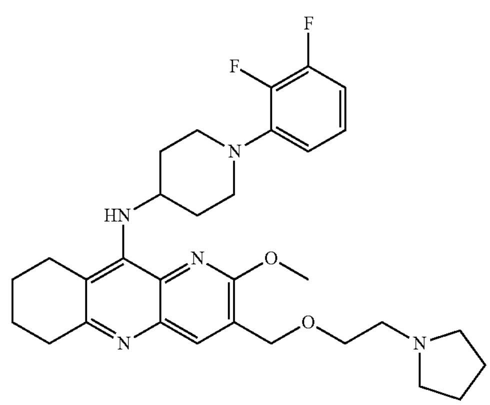 | 1-(2,3-difluorophenyl)-N-(2-methoxy-3-{[2-(pyrrolidin-1-yl)ethoxy]methyl}-6H,7H,8H,9H-cyclohexa[b]1,5-naphthyridin-10-yl)piperidin-4-amine |

TABLE 2-continued

| No. | Structure | IUPAC Name |
|---|---|---|
| 280 | 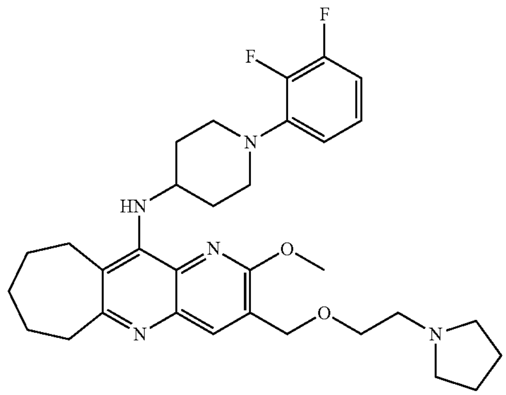 [SMILES: COc1nc2c(NC3CCN(c4cccc(F)c4F)CC3)c3c(nc2cc1COCCN1CCCC1)CCCCC3] | 1-(2,3-difluorophenyl)-N-(2-methoxy-3-{[2-(pyrrolidin-1-yl)ethoxy]methyl}-6H,7H,8H,9H,10H-cyclohepta[b]1,5-naphthyridin-11-yl)piperidin-4-amine |
| 281 | 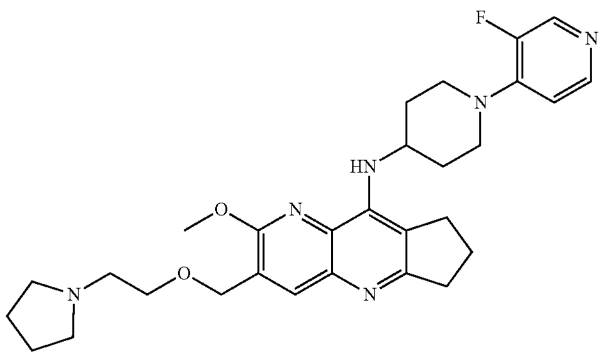 [SMILES: COc1nc2c(NC3CCN(c4ccncc4F)CC3)c3c(nc2cc1COCCN1CCCC1)CCC3] | 1-(3-fluoropyridin-4-yl)-N-(2-methoxy-3-{[2-(pyrrolidin-1-yl)ethoxy]methyl}-6H,7H,8H-cyclopenta[b]1,5-naphthyridin-9-yl)piperidin-4-amine |
| 282 | 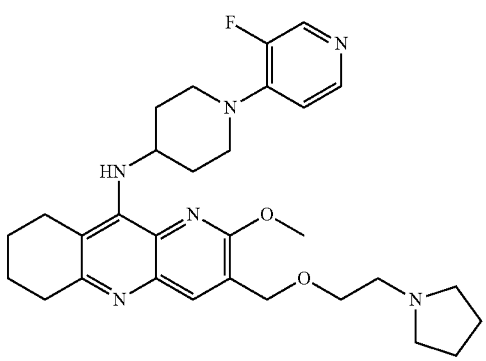 [SMILES: COc1nc2c(NC3CCN(c4ccncc4F)CC3)c3c(nc2cc1COCCN1CCCC1)CCCC3] | 1-(3-fluoropyridin-4-yl)-N-(2-methoxy-3-{[2-(pyrrolidin-1-yl)ethoxy]methyl}-6H,7H,8H,9H-cyclohexa[b]1,5-naphthyridin-10-yl)piperidin-4-amine |
| 283 | 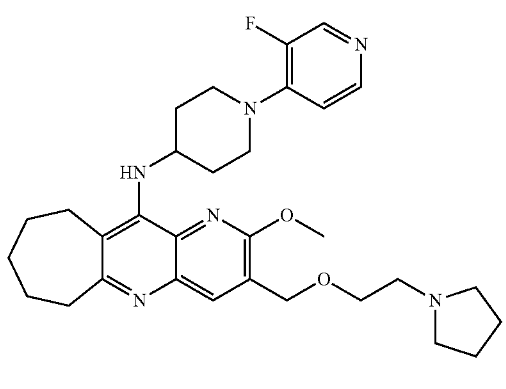 [SMILES: COc1nc2c(NC3CCN(c4ccncc4F)CC3)c3c(nc2cc1COCCN1CCCC1)CCCCC3] | 1-(3-fluoropyridin-4-yl)-N-(2-methoxy-3-{[2-(pyrrolidin-1-yl)ethoxy]methyl}-6H,7H,8H,9H,10H-cyclohepta[b]1,5-naphthyridin-11-yl)piperidin-4-amine |

TABLE 2-continued

| No. | Structure | IUPAC Name |
|---|---|---|
| 284 | 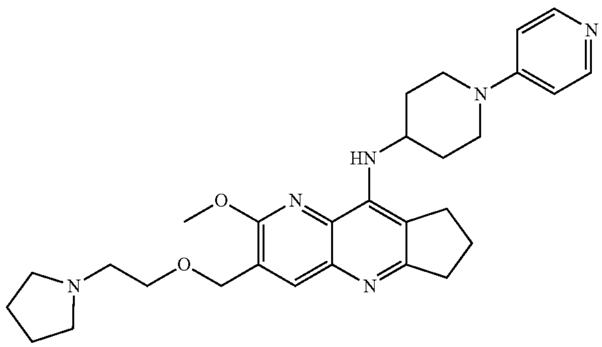 [SMILES: COc1nc2c(NC3CCN(c4ccncc4)CC3)c3c(nc2cc1COCCN1CCCC1)CCC3] | N-(2-methoxy-3-{[2-(pyrrolidin-1-yl)ethoxy]methyl}-6H,7H,8H-cyclopenta[b]1,5-naphthyridin-9-yl)-1-(pyridin-4-yl)piperidin-4-amine |
| 285 | 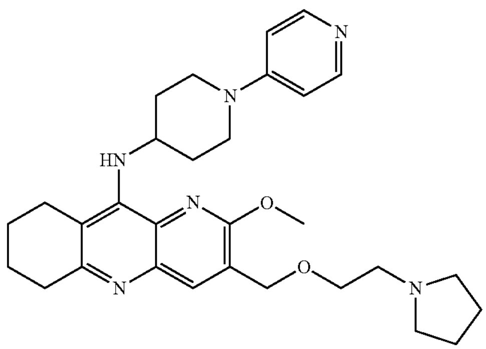 | N-(2-methoxy-3-{[2-(pyrrolidin-1-yl)ethoxy]methyl}-6H,7H,8H,9H-cyclohexa[b]1,5-naphthyridin-10-yl)-1-(pyridin-4-yl)piperidin-4-amine |
| 286 | 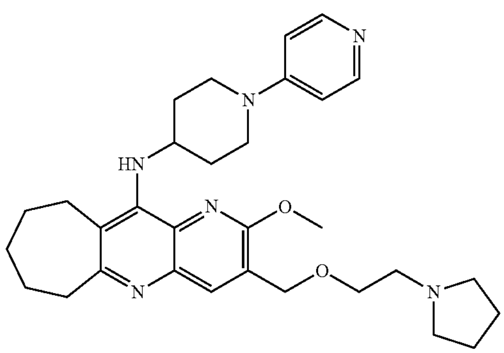 [SMILES: COc1nc2c(NC3CCN(c4ccncc4)CC3)c3c(nc2cc1COCCN1CCCC1)CCCCC3] | N-(2-methoxy-3-{[2-(pyrrolidin-1-yl)ethoxy]methyl}-6H,7H,8H,9H,10H-cyclohepta[b]1,5-naphthyridin-11-yl)-1-(pyridin-4-yl)piperidin-4-amine |
| 287 | 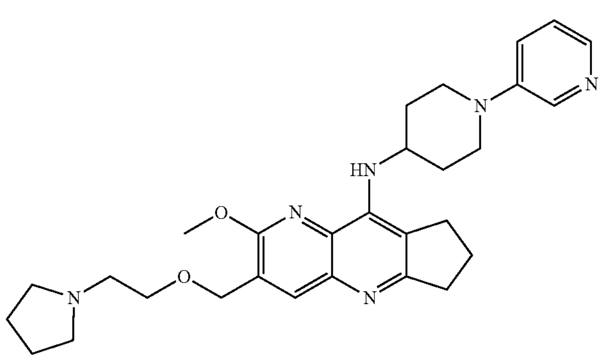 | N-(2-methoxy-3-{[2-(pyrrolidin-1-yl)ethoxy]methyl}-6H,7H,8H-cyclopenta[b]1,5-naphthyridin-9-yl)-1-(pyridin-3-yl)piperidin-4-amine |

TABLE 2-continued

| No. | Structure | IUPAC Name |
|---|---|---|
| 288 | 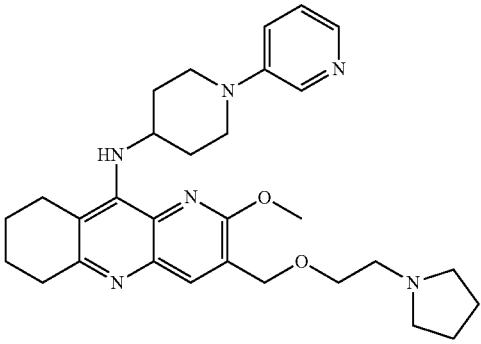 [SMILES: COc1nc2c(NC3CCN(c4cccnc4)CC3)c3c(nc2cc1COCCN1CCCC1)CCCC3] | N-(2-methoxy-3-{[2-(pyrrolidin-1-yl)ethoxy]methyl}-6H,7H,8H,9H-cyclohexa[b]1,5-naphthyridin-10-yl)-1-(pyridin-3-yl)piperidin-4-amine |
| 289 | 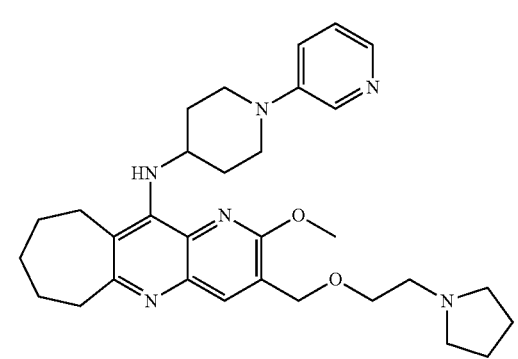 [SMILES: COc1nc2c(NC3CCN(c4cccnc4)CC3)c3c(nc2cc1COCCN1CCCC1)CCCCC3] | N-(2-methoxy-3-{[2-(pyrrolidin-1-yl)ethoxy]methyl}-6H,7H,8H,9H,10H-cyclohepta[b]1,5-naphthyridin-11-yl)-1-(pyridin-3-yl)piperidin-4-amine |
| 290 | 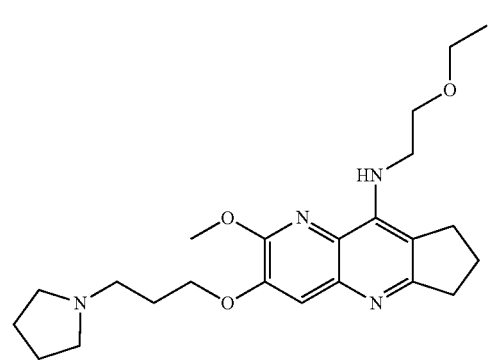 [SMILES: CCOCCNc1c2c(nc3cc(OCCCN4CCCC4)c(OC)nc13)CCC2] | N-(2-ethoxyethyl)-2-methoxy-3-[3-(pyrrolidin-1-yl)propoxy]-6H,7H,8H-cyclopenta[b]1,5-naphthyridin-9-amine |
| 291 | 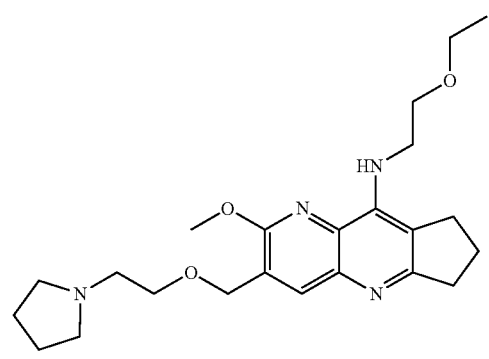 | N-(2-ethoxyethyl)-2-methoxy-3-{[2-(pyrrolidin-1-yl)ethoxy]methyl}-6H,7H,8H-cyclopenta[b]1,5-naphthyridin-9-amine |

TABLE 2-continued

| No. | Structure | IUPAC Name |
|---|---|---|
| 292 | 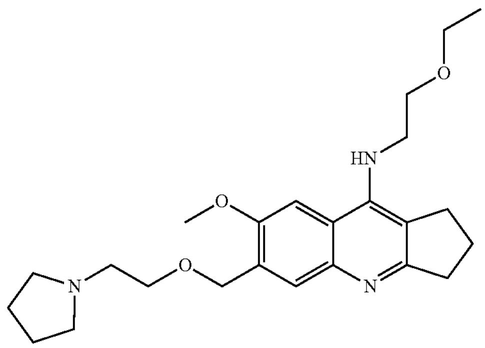 [SMILES: CCOCCNc1c2c(nc3cc(COCCN4CCCC4)c(OC)cc13)CCC2] | N-(2-ethoxyethyl)-7-methoxy-6-{[2-(pyrrolidin-1-yl)ethoxy]methyl}-1H,2H,3H-cyclopenta[b]quinolin-9-amine |
| 293 | 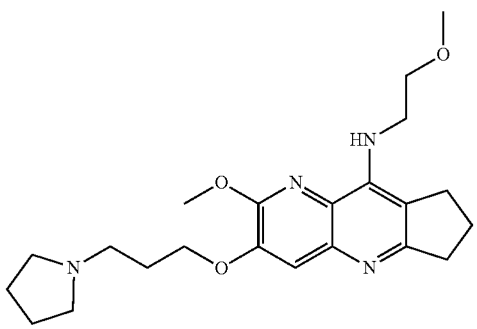 [SMILES: COCCNc1c2c(nc3cc(OCCCN4CCCC4)c(OC)nc13)CCC2] | 2-methoxy-N-(2-methoxyethyl)-3-[3-(pyrrolidin-1-yl)propoxy]-6H,7H,8H-cyclopenta[b]1,5-naphthyridin-9-amine |
| 294 | 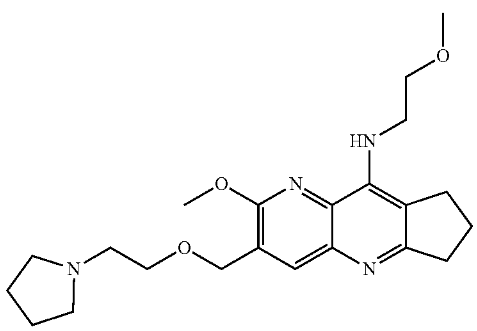 [SMILES: COCCNc1c2c(nc3cc(COCCN4CCCC4)c(OC)nc13)CCC2] | 2-methoxy-N-(2-methoxyethyl)-3-{[2-(pyrrolidin-1-yl)ethoxy]methyl}-6H,7H,8H-cyclopenta[b]1,5-naphthyridin-9-amine |
| 295 | 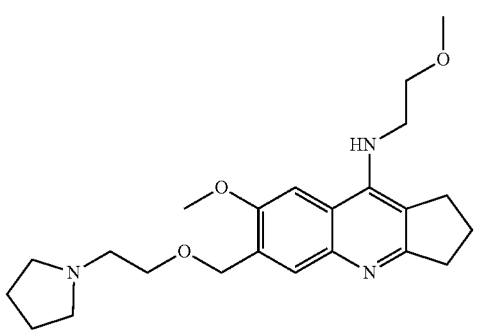 [SMILES: COCCNc1c2c(nc3cc(COCCN4CCCC4)c(OC)cc13)CCC2] | 7-methoxy-N-(2-methoxyethyl)-6-{[2-(pyrrolidin-1-yl)ethoxy]methyl}-1H,2H,3H-cyclopenta[b]quinolin-9-amine |

TABLE 2-continued

| No. | Structure | IUPAC Name |
| --- | --- | --- |
| 296 | 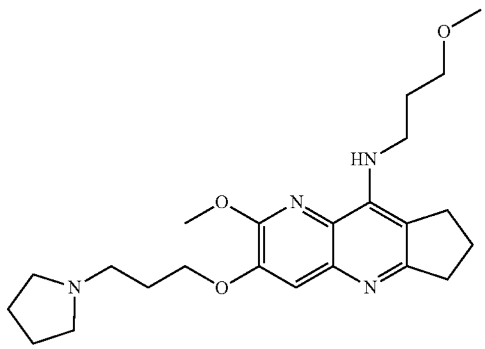 | 2-methoxy-N-(3-methoxypropyl)-3-[3-(pyrrolidin-1-yl)propoxy]-6H,7H,8H-cyclopenta[b]1,5-naphthyridin-9-amine |
| 297 | 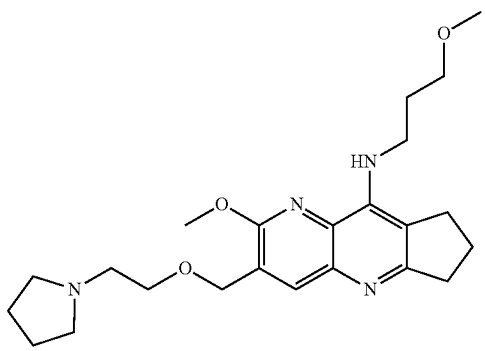 [SMILES: COCCCNc1c2c(nc3cc(COCCN4CCCC4)c(OC)nc13)CCC2] | 2-methoxy-N-(3-methoxypropyl)-3-{[2-(pyrrolidin-1-yl)ethoxy]methyl}-6H,7H,8H-cyclopenta[b]1,5-naphthyridin-9-amine |
| 298 | 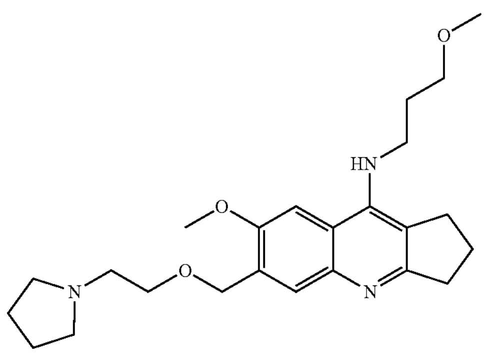 [SMILES: COCCCNc1c2c(nc3cc(COCCN4CCCC4)c(OC)cc13)CCC2] | 7-methoxy-N-(3-methoxypropyl)-6-{[2-(pyrrolidin-1-yl)ethoxy]methyl}-1H,2H,3H-cyclopenta[b]quinolin-9-amine |
| 299 | 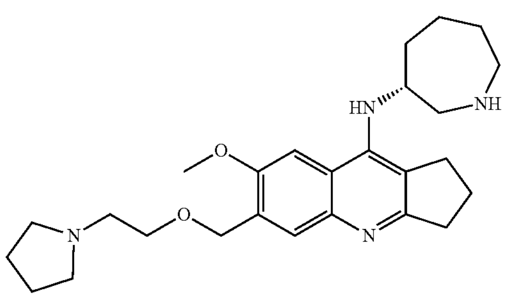 [SMILES: COc1cc2c(N[C@@H]3CCCCNC3)c3c(nc2cc1COCCN1CCCC1)CCC3] | (3R)-N-(7-methoxy-6-{[2-(pyrrolidin-1-yl)ethoxy]methyl}-1H,2H,3H-cyclopenta[b]quinolin-9-yl)azepan-3-amine |

TABLE 2-continued

| No. | Structure | IUPAC Name |
|---|---|---|
| 300 | 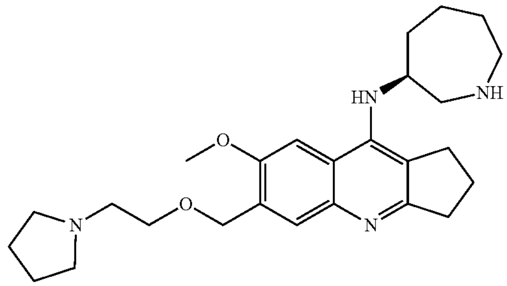 [SMILES: COc1cc2c(N[C@H]3CCCCNC3)c3c(nc2cc1COCCN1CCCC1)CCC3] | (3S)-N-(7-methoxy-6-{[2-(pyrrolidin-1-yl)ethoxy]methyl}-1H,2H,3H-cyclopenta[b]quinolin-9-yl)azepan-3-amine |
| 301 | 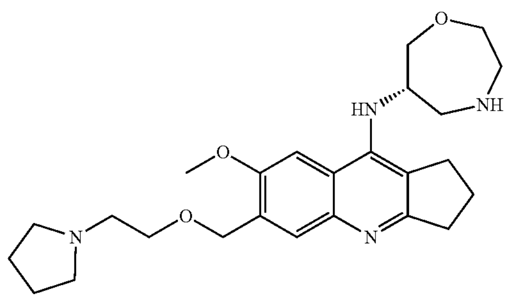 [SMILES: COc1cc2c(N[C@H]3CNCCOC3)c3c(nc2cc1COCCN1CCCC1)CCC3] | (6S)-N-(7-methoxy-6-{[2-(pyrrolidin-1-yl)ethoxy]methyl}-1H,2H,3H-cyclopenta[b]quinolin-9-yl)-1,4-oxazepan-6-amine |
| 302 | 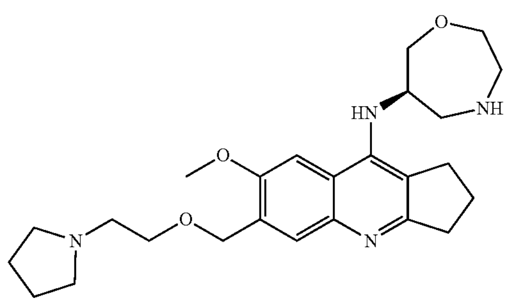 [SMILES: COc1cc2c(N[C@@H]3CNCCOC3)c3c(nc2cc1COCCN1CCCC1)CCC3] | (6R)-N-(7-methoxy-6-{[2-(pyrrolidin-1-yl)ethoxy]methyl}-1H,2H,3H-cyclopenta[b]quinolin-9-yl)-1,4-oxazepan-6-amine |
| 303 | 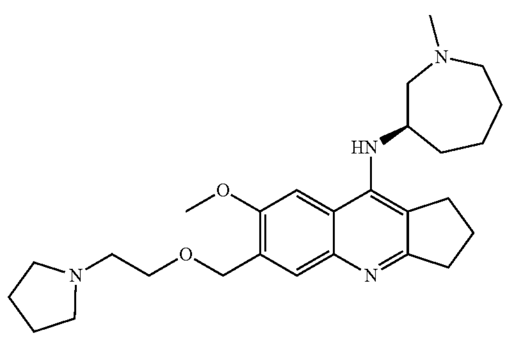 [SMILES: COc1cc2c(N[C@@H]3CCCCN(C)C3)c3c(nc2cc1COCCN1CCCC1)CCC3] | (3R)-N-(7-methoxy-6-{[2-(pyrrolidin-1-yl)ethoxy]methyl}-1H,2H,3H-cyclopenta[b]quinolin-9-yl)-1-methylazepan-3-amine |
| 304 | 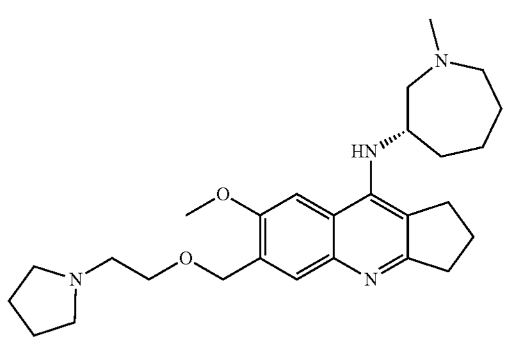 | (3S)-N-(7-methoxy-6-{[2-(pyrrolidin-1-yl)ethoxy]methyl}-1H,2H,3H-cyclopenta[b]quinolin-9-yl)-1-methylazepan-3-amine |

TABLE 2-continued

| No. | Structure | IUPAC Name |
|---|---|---|
| 305 | 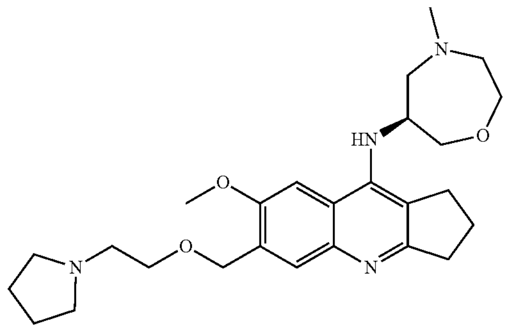 [SMILES: COc1cc2c(N[C@@H]3COCCN(C)C3)c3c(nc2cc1COCCN1CCCC1)CCC3] | (6S)-N-(7-methoxy-6-{[2-(pyrrolidin-1-yl)ethoxy]methyl}-1H,2H,3H-cyclopenta[b]quinolin-9-yl)-4-methyl-1,4-oxazepan-6-amine |
| 306 | 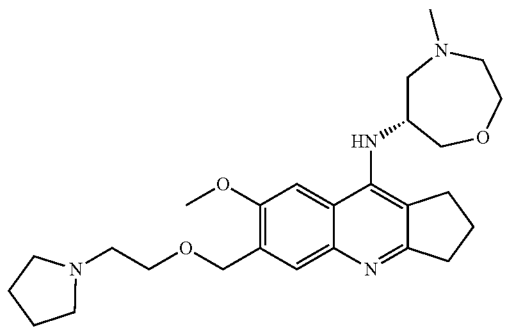 [SMILES: COc1cc2c(N[C@H]3COCCN(C)C3)c3c(nc2cc1COCCN1CCCC1)CCC3] | (6R)-N-(7-methoxy-6-{[2-(pyrrolidin-1-yl)ethoxy]methyl}-1H,2H,3H-cyclopenta[b]quinolin-9-yl)-4-methyl-1,4-oxazepan-6-amine |
| 307 | 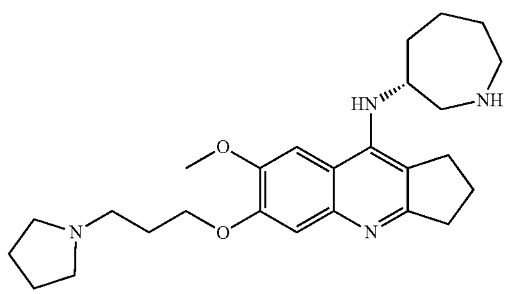 [SMILES: COc1cc2c(N[C@@H]3CCCCNC3)c3c(nc2cc1OCCCN1CCCC1)CCC3] | (3R)-N-{7-methoxy-6-[3-(pyrrolidin-1-yl)propoxy]-1H,2H,3H-cyclopenta[b]quinolin-9-yl}azepan-3-amine |
| 308 | 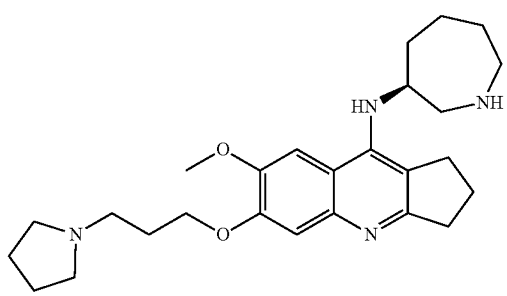 [SMILES: COc1cc2c(N[C@H]3CCCCNC3)c3c(nc2cc1OCCCN1CCCC1)CCC3] | (3S)-N-{7-methoxy-6-[3-(pyrrolidin-1-yl)propoxy]-1H,2H,3H-cyclopenta[b]quinolin-9-yl}azepan-3-amine |
| 309 | 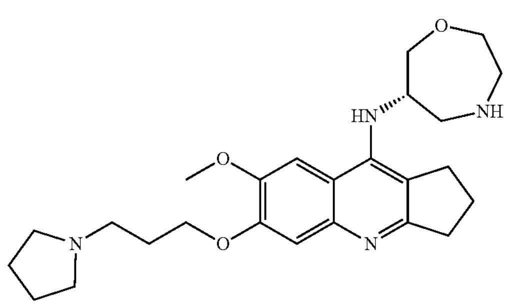 [SMILES: COc1cc2c(N[C@H]3CNCCOC3)c3c(nc2cc1OCCCN1CCCC1)CCC3] | (6S)-N-{7-methoxy-6-[3-(pyrrolidin-1-yl)propoxy]-1H,2H,3H-cyclopenta[b]quinolin-9-yl}-1,4-oxazepan-6-amine |

TABLE 2-continued

| No. | Structure | IUPAC Name |
|---|---|---|
| 310 | 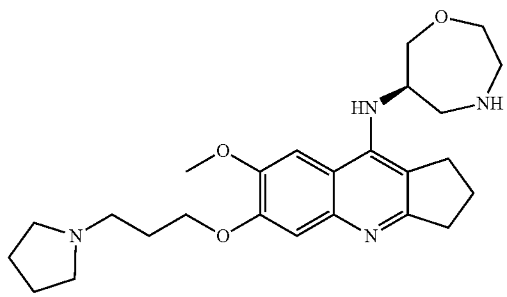 [SMILES: COc1cc2c(N[C@@H]3CNCCOC3)c3c(nc2cc1OCCCN1CCCC1)CCC3] | (6R)-N-{7-methoxy-6-[3-(pyrrolidin-1-yl)propoxy]-1H,2H,3H-cyclopenta[b]quinolin-9-yl}-1,4-oxazepan-6-amine |
| 311 | 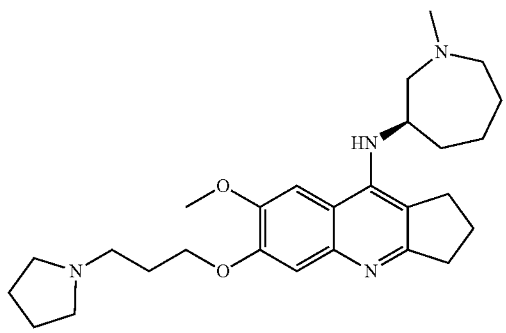 [SMILES: COc1cc2c(N[C@@H]3CCCCN(C)C3)c3c(nc2cc1OCCCN1CCCC1)CCC3] | (3R)-N-{7-methoxy-6-[3-(pyrrolidin-1-yl)propoxy]-1H,2H,3H-cyclopenta[b]quinolin-9-yl}-1-methylazepan-3-amine |
| 312 | 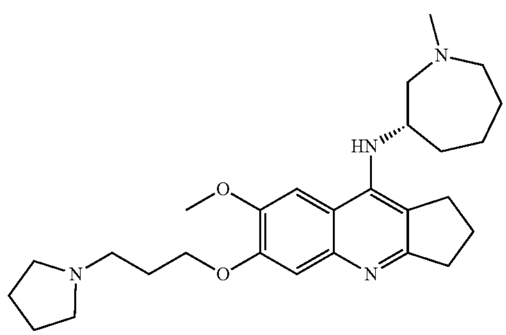 [SMILES: COc1cc2c(N[C@H]3CCCCN(C)C3)c3c(nc2cc1OCCCN1CCCC1)CCC3] | (3S)-N-{7-methoxy-6-[3-(pyrrolidin-1-yl)propoxy]-1H,2H,3H-cyclopenta[b]quinolin-9-yl}-1-methylazepan-3-amine |
| 313 | 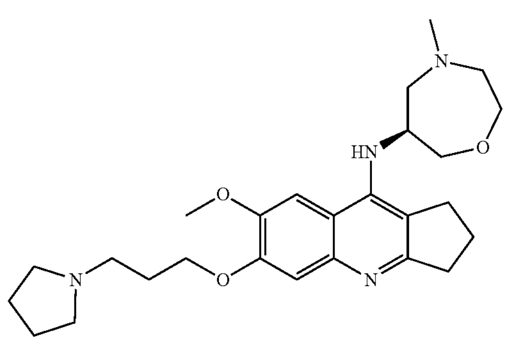 | (6S)-N-{7-methoxy-6-[3-(pyrrolidin-1-yl)propoxy]-1H,2H,3H-cyclopenta[b]quinolin-9-yl}-4-methyl-1,4-oxazepan-6-amine |

TABLE 2-continued

| No. | Structure | IUPAC Name |
| --- | --- | --- |
| 314 | 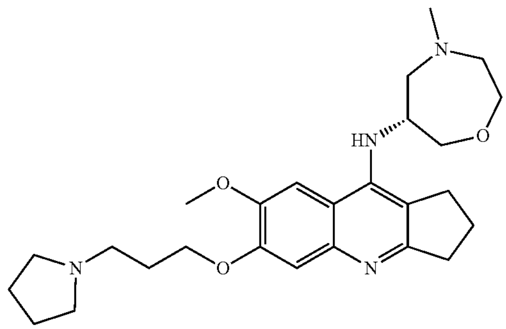 [SMILES: COc1cc2c(N[C@H]3COCCN(C)C3)c3c(nc2cc1OCCCN1CCCC1)CCC3] | (6R)-N-{7-methoxy-6-[3-(pyrrolidin-1-yl)propoxy]-1H,2H,3H-cyclopenta[b]quinolin-9-yl}-4-methyl-1,4-oxazepan-6-amine |
| 315 | 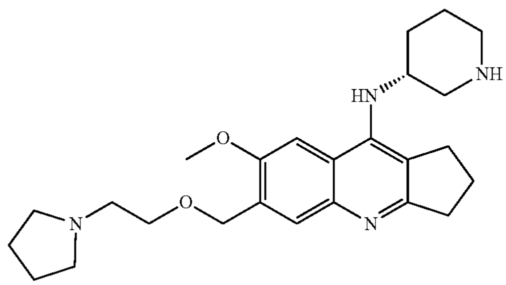 [SMILES: COc1cc2c(N[C@@H]3CCCNC3)c3c(nc2cc1COCCN1CCCC1)CCC3] | (3R)-N-(7-methoxy-6-{[2-(pyrrolidin-1-yl)ethoxy]methyl}-1H,2H,3H-cyclopenta[b]quinolin-9-yl)piperidin-3-amine |
| 316 | 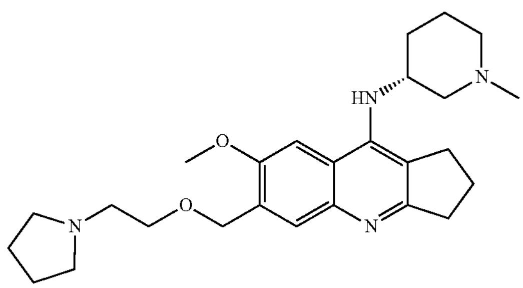 [SMILES: COc1cc2c(N[C@@H]3CCCN(C)C3)c3c(nc2cc1COCCN1CCCC1)CCC3] | (3R)-N-(7-methoxy-6-{[2-(pyrrolidin-1-yl)ethoxy]methyl}-1H,2H,3H-cyclopenta[b]quinolin-9-yl)-1-methylpiperidin-3-amine |
| 317 | 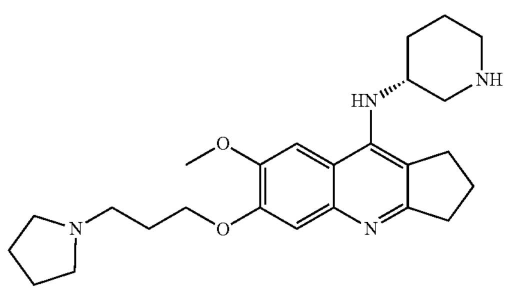 [SMILES: COc1cc2c(N[C@@H]3CCCNC3)c3c(nc2cc1OCCCN1CCCC1)CCC3] | (3R)-N-{7-methoxy-6-[3-(pyrrolidin-1-yl)propoxy]-1H,2H,3H-cyclopenta[b]quinolin-9-yl}piperidin-3-amine |
| 318 | 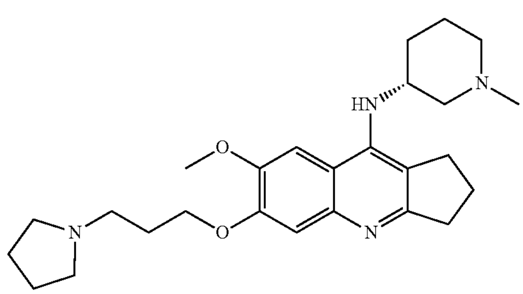 [SMILES: COc1cc2c(N[C@@H]3CCCN(C)C3)c3c(nc2cc1OCCCN1CCCC1)CCC3] | (3R)-N-{7-methoxy-6-[3-(pyrrolidin-1-yl)propoxy]-1H,2H,3H-cyclopenta[b]quinolin-9-yl}-1-methylpiperidin-3-amine |

TABLE 2-continued

| No. | Structure | IUPAC Name |
|---|---|---|
| 319 | 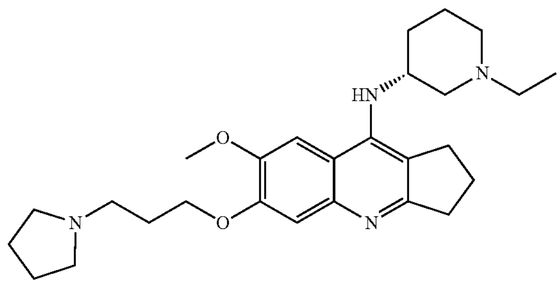 [SMILES: CCN1CCC[C@@H](Nc2c3c(nc4cc(OCCCN5CCCC5)c(OC)cc24)CCC3)C1] | (3R)-1-ethyl-N-{7-methoxy-6-[3-(pyrrolidin-1-yl)propoxy]-1H,2H,3H-cyclopenta[b]quinolin-9-yl}piperidin-3-amine |
| 320 | 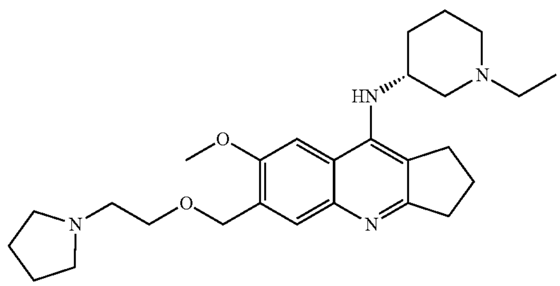 [SMILES: CCN1CCC[C@@H](Nc2c3c(nc4cc(COCCN5CCCC5)c(OC)cc24)CCC3)C1] | (3R)-1-ethyl-N-(7-methoxy-6-{[2-(pyrrolidin-1-yl)ethoxy]methyl}-1H,2H,3H-cyclopenta[b]quinolin-9-yl)piperidin-3-amine |
| 321 | 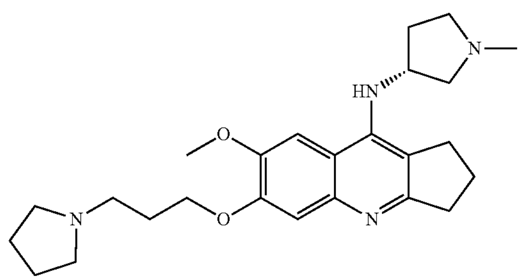 [SMILES: COc1cc2c(N[C@@H]3CCN(C)C3)c3c(nc2cc1OCCCN1CCCC1)CCC3] | (3R)-N-{7-methoxy-6-[3-(pyrrolidin-1-yl)propoxy]-1H,2H,3H-cyclopenta[b]quinolin-9-yl}-1-methylpyrrolidin-3-amine |
| 322 | 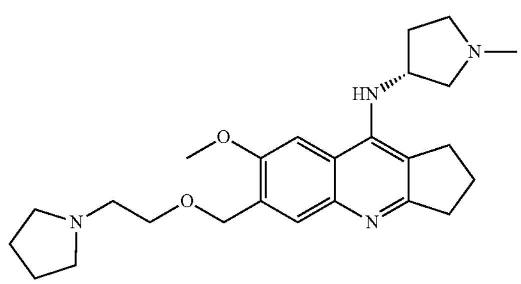 [SMILES: COc1cc2c(N[C@@H]3CCN(C)C3)c3c(nc2cc1COCCN1CCCC1)CCC3] | (3R)-N-(7-methoxy-6-{[2-(pyrrolidin-1-yl)ethoxy]methyl}-1H,2H,3H-cyclopenta[b]quinolin-9-yl)-1-methylpyrrolidin-3-amine |
| 323 | 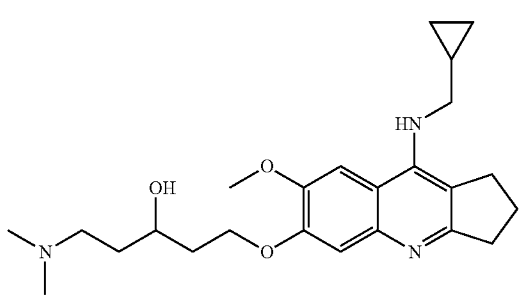 [SMILES: COc1cc2c(NCC3CC3)c3c(nc2cc1OCCC(O)CCN(C)C)CCC3] | 1-((9-((cyclopropylmethyl)amino)-7-methoxy-2,3-dihydro-1H-cyclopenta[b]quinolin-6-yl)oxy)-5-(dimethylamino)pentan-3-ol |

General Synthetic Scheme

Compounds of this disclosure can be made by the methods depicted in the reaction schemes shown below.

The starting materials and reagents used in preparing these compounds are either available from commercial suppliers such as Sigma-Aldrich Chemical Co., (Milwaukee, Wis.), Acros Organics, Bachem (Torrance, Calif.), Oakwood Chemicals, Matrix Chemicals, or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). Generic schemes 1-4 are merely illustrative of some methods by which the compounds of this disclosure, and pharmaceutically acceptable salts thereof, can be synthesized, and various modifications to these schemes can be made and will be suggested to one skilled in the art reading this disclosure. The starting materials, the intermediates, and the final products of the reaction(s) may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 200° C., such as from about 0° C. to about 125° C. and further such as at about room (or ambient) temperature, e.g., about 20° C. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Compounds of the present disclosure such as in compounds of Formula (I), and pharmaceutically acceptable salts thereof, where A can be CH or N; $R^1$ can be hydroxy, alkoxy (for example, a $C_1$-$C_6$ alkoxy, such as methoxy, ethoxy, isopropoxy, n-propoxy, n-butoxy, isobutoxy, sec-butoxy, t-butoxy, pentoxy (straight chained or branched) or hexoxy (straight chained or branched)) or haloalkoxy (for example, a $C_1$-$C_6$ haloalkoxy, such as halomethoxy, haloethoxy, halo-n-propoxy, haloisopropoxy, halo-n-butoxy, halo-sec-butoxy, halo-isobutoxy, halo-t-butoxy, halo-pentoxy (straight-chained or branched) or halo-hexoxy (straight-chained or branched)); $R^2$ can be $-(CH_2)_{0-1}$-O-Alk-$R^{2A}$ or cycloalkoxy (for example, a $C_3$-$C_8$ cycloalkoxy such as cyclopropyl, cyclobutyl, cyclopentyl, cyclohexyl, cycloheptyl, or cyclooctyl) (optionally substituted with heterocyclylalkyl, for example, the heterocyclyl group of the heterocyclylalkyl can be a 3 to 6 membered monocyclic nitrogen containing heterocyclyl and the alkyl group of the heterocyclylalkyl can be a $C_1$-$C_3$ alkyl); X, $X^1$ and $X^2$, are each as defined herein, and can be prepared as illustrated and described in Scheme 1 below.

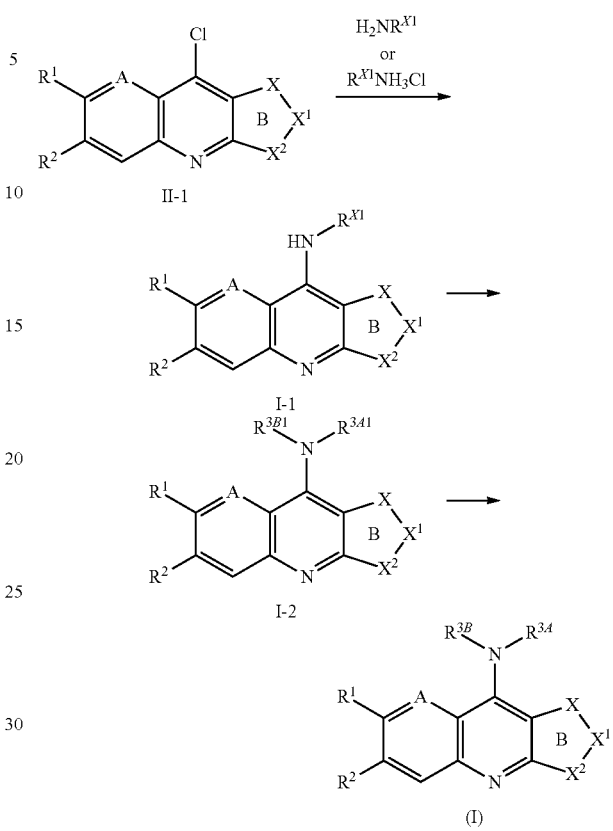

Scheme 1

Reacting compounds II-1 where A can be CH or N; $R^1$ can be hydroxy, alkoxy or haloalkoxy, each as defined herein; $R^2$ can be $-(CH_2)_{0-1}$-O-Alk-$R^{2A}$ or cycloalkoxy (optionally substituted with heterocyclylalkyl) each as defined herein; X, $X^1$ and $X^2$ are each as defined herein, with appropriate commercially available amines H2NR$^{x1}$, or the corresponding HCl salts, under conditions well known in the art, such as Buchwald coupling condition using catalysts such as BrettPhos Pd G1, methyl t-butyl ether adduct, provides compounds I-1. Some compounds I-1 are compounds of Formula (I). Some compounds I-1 are further converted into compounds of I-2 by methods well known in the art, including, such as TFA mediated removal of the Boc group from NR$^{X1}$, or palladium catalyzed hydrogenative cleavage of benzyl group from oxygen and/or nitrogen atom(s) within NR$^{X1}$. Some compounds of I-2 are compounds of Formula (I). Some compounds of I-2 are converted to compounds of Formula (I) by methods well known in the art, including, such as N-alkylation with appropriate halides or tosylates, reductive aminations with appropriate aldehydes or ketones, or Buchwald coupling with appropriate aryl halides or triflates. The halides, tosylates, aldehydes, ketones, aryl halides or aryl triflates are either available from commercial resources, or easily accessible by synthetic methods well known in the art.

Some compounds of formula of II-1 where A can be CH or N; $R^1$ can be hydroxy, alkoxy or haloalkoxy, each as defined herein; $R^2$ can be $-(CH_2)_{0-1}$-O-Alk-$R^{2A}$ or cycloalkoxy (optionally substituted with heterocyclylalkyl), each as defined herein; X, $X^1$ and $X^2$ are each as defined herein, can be prepared as illustrated and described in Scheme 2 below.

Scheme 2

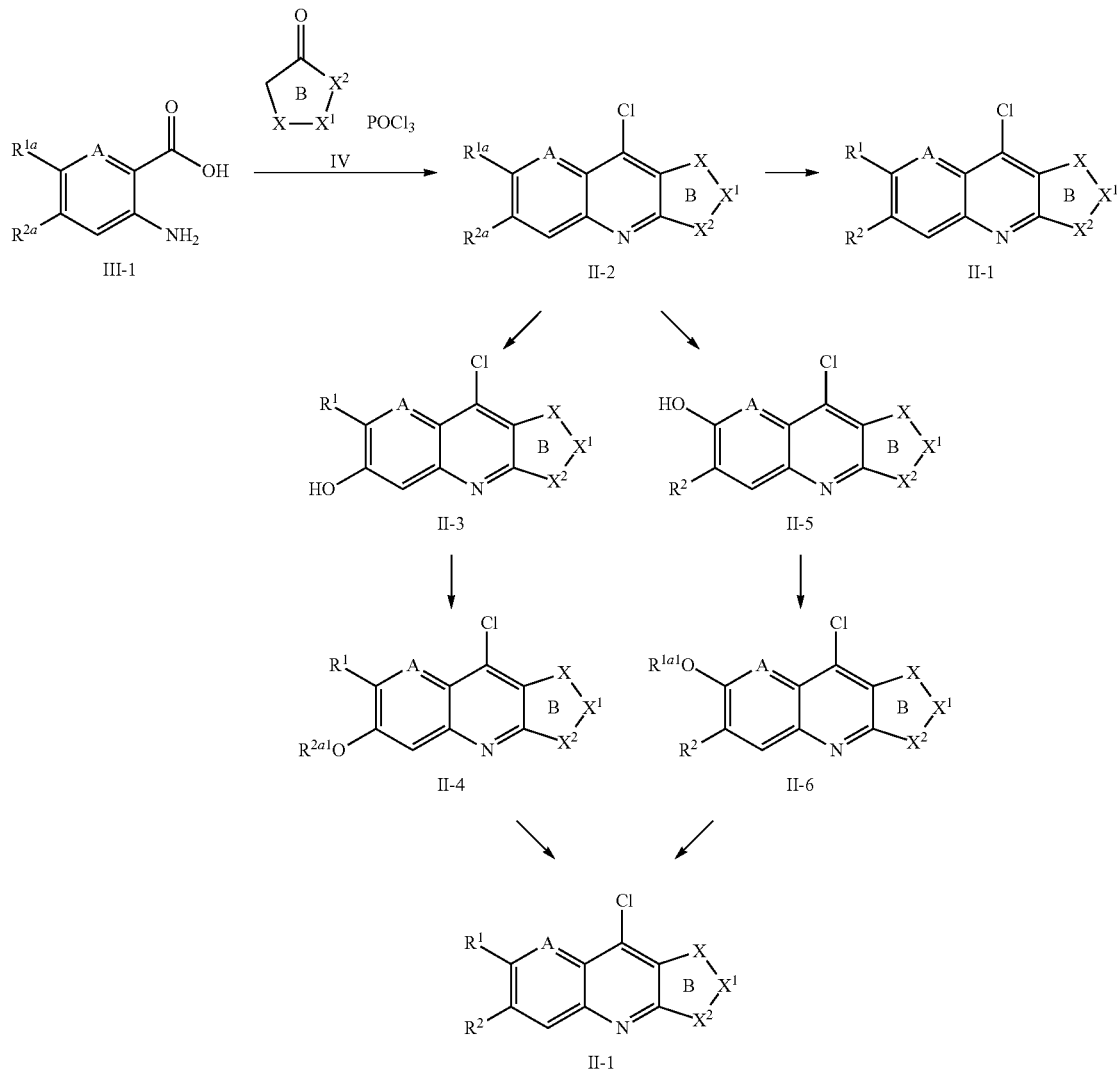

Reaction of amino carboxylate compounds of formula of III-1 where A can be CH; $R^{1a}$ can be hydroxy, alkoxy or haloalkoxy, each as defined herein; $R^{2a}$ can be halo, hydroxyl, —$(CH_2)_{0-1}$—O-Alk-$R^{2A}$ or cycloalkoxy (optionally substituted with heterocyclylalkyl), each as defined herein; with an appropriate cyclic ketones IV (X, $X^1$ and $X^2$ are each as defined in the herein), in the presence of $POCl_3$ provides compounds II-2. Some of I1-2 are compounds of Formula II-1. Some compounds of II-2 are converted to compounds of Formula II-1 after chemical transformations of either or both the $R^{1a}$ and $R^{2a}$ groups by methods well known in the art. Some compounds of II-2 can be converted to hydroxy compounds II-3 by method well known in the art, including, for example $AlCl_3$ mediated de-alkylation of oxygen atom within $R^{2a}$ groups. Compounds II-3 can be converted to compounds of formula of II-4 via methods well known in the art, including, O-alkylation with appropriate halides (for example, $R^{2a1}$Br, $R^{2a1}$Cl, or $R^{2a1}$I), or di-halides (for example, I$(CH_2)_3$Cl), tosylates (for example, $R^{2a1}$OTs) or Mitsunobu reactions with appropriate alcohols $R^{2a1}$OH. Some compounds of II-4 are compounds of formula of II-1. Some compounds of II-4 can be further converted to compounds of formula II-1 after appropriate chemical transformations via methods well known in the art. Some compounds of II-2 can be converted to hydroxy compounds II-5 by methods well known in the art, including, for example $AlCl_3$ mediated de-alkylation of oxygen atom within $R^{1a}$ groups. Some compounds of II-5 are compounds in formula II-1. Some compounds of II-5 can be converted to compounds of formula II-6 via methods well known in the art, including, for example, O-alkylation with appropriate halides (for example, $R^{1a1}$Br, $R^{1a1}$Cl, or $R^{1a1}$I) or tosylate (for example, $R^{1a1}$OTs), or Mitsunobu reactions with appropriate alcohols $R^{1a1}$OH. Compounds of formula II-5 can also be converted to compounds of formula II-6 ($R^{1a1}$=$OCHF_2$) by reaction with commercially available diethyl bromo(difluoro)methyl-phosphonate in the presence of a base, such as KOH. Some compounds of II-6 are compounds of formula of II-1. Some compounds of II-6 can be further converted to compounds of formula II-1 after appropriate chemical transformations via methods well known in the art. Some compounds of formula III-1 (for example, 2-amino-4,5-dimethoxybenzoic acid) are commercially available. Some compounds of formula III-1 (for example, 2-amino-4-methoxy-5-(trifluoromethoxy)benzoic acid) can be prepared from commercial available materials by methods well known in the art. Some compounds of formula IV such as cyclopentanone, cyclohexanone, cycloheptanone, 3,3-dimethylcyclopentan-1-one, spiro[3.4]octan-6-one and bicyclo[3.2.1]octan-6-one are commercially available. Some compounds of formula IV can be made by methods well know in the art. Compounds $R^{2a1}Br$, $R^{2a1}Cl$, $R^{2a1}I$, $R^{2a1}OTs$, $R^{1a1}Br$, $R^{1a1}Cl$, $R^{1a1}I$, $R^{1a1}OTs$, $R^{2a1}OH$ and $R^{1a1}OH$ are either commercially available or can be prepared by methods well known in the art.

Some compounds of formula of II-1 where A can be CH or N; $R^1$ can be hydroxy, alkoxy or haloalkoxy, each as defined herein; $R^2$ can be —$(CH_2)$—O-Alk-$R^{2A}$, each as defined herein; X, $X^1$ and $X^2$ are each as defined herein, can be prepared as illustrated and described in Scheme 3 below.

subjected to reactions with appropriate cyclic ketone IV in the presence of $POCl_3$ to provide compounds of formula II-7. Some compounds of II-7 are compounds of formula of II-1. Some compounds of II-7 was converted to compounds of formula II-1 via appropriate chemical transformations well-known in the art.

Some compounds of formula of II-1 where A can be CH or N; $R^1$ can be hydroxy, alkoxy or haloalkoxy, each as defined herein; $R^{2a}$ can be halo, hydroxyl, —$(CH_2)_{0-1}$—O-Alk-$R^{2A}$ or cycloalkoxy (optionally substituted with heterocyclylalkyl), each as defined herein; X, $X^1$ and $X^2$ are each as defined herein, can be prepared as illustrated and described in Scheme 4 below.

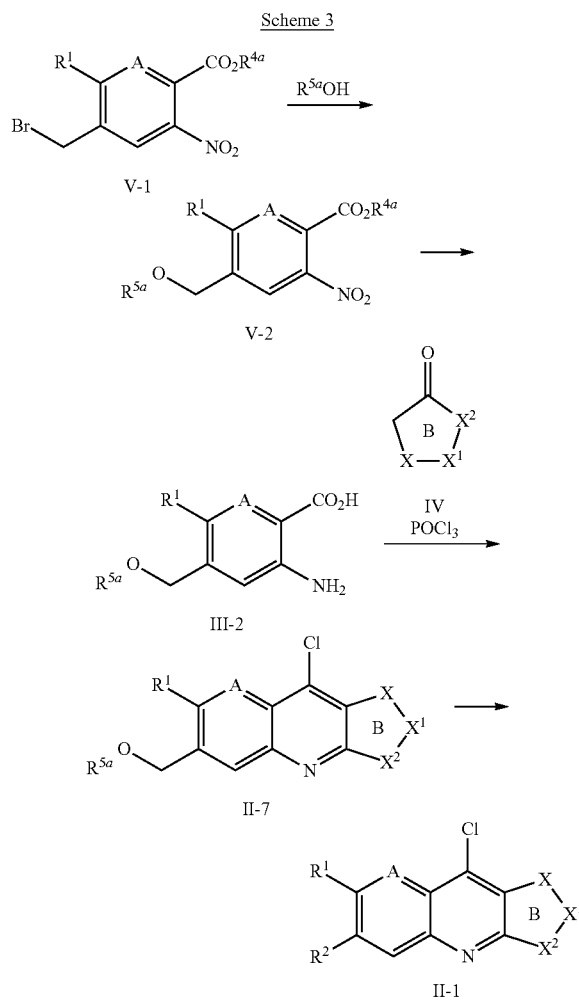

Scheme 3

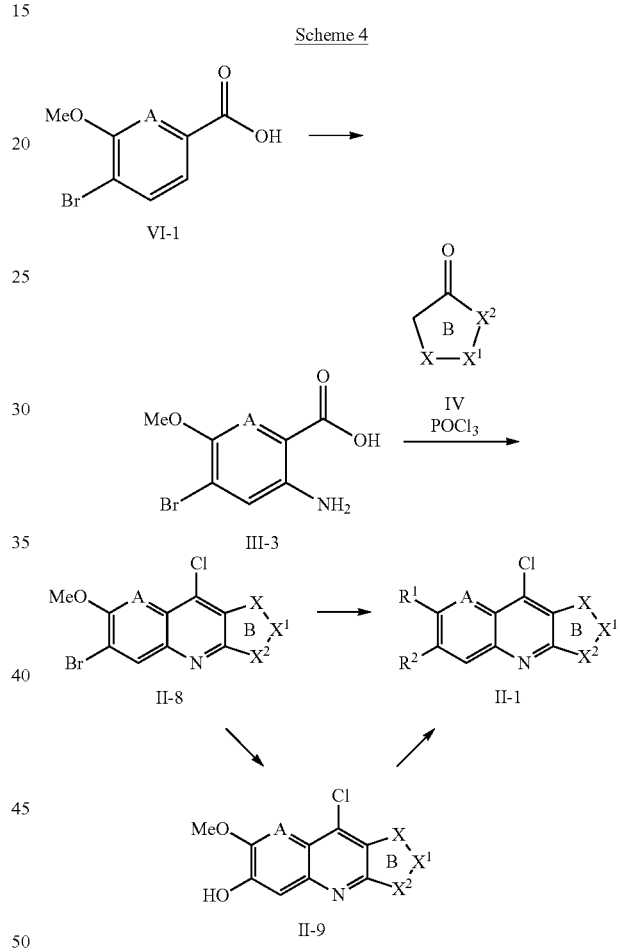

Scheme 4

Reacting commercially available compounds of formula V-1 (for example when $R^1$=OMe, $R^{4a}$=Me) with alcohol $R^{5a}OH$ in the presence of base, such as NaH, provides compounds of formula V-2. V-2 can be converted into amino-carboxylate compounds of formula III-2 by methods well known in the art, including, for example, saponification of V-2, followed by treatment with either $SnCl_2$ or iron dust in the presence of $NH_4Cl$. Compounds III-2 can be further Nitration of 5-bromo-6-methoxypyridine-2-carboxylic acid VI-1 followed by reduction of the resulting product by methods well known in the art, including treatment with $SnCl_2$, or treatment with iron in the presence of $NH_4Cl$, provides the amino-carboxylate compounds of formula III-3. Compounds of formula III-3 can be converted to compounds of formula II-8 upon reaction with appropriate cyclic ketones IV in the presence of $POCl_3$. Reacting compounds of formula II-8 with 4,4,5,5-tetramethyl-2-(propan-2-yloxy)-1,3,2-dioxaborolane in the presence of "BuLi, followed by reaction of the resulting product with hydrogen peroxide leads to formation of compounds of formula II-9, which after chemical transformations well known in the art, including, for example, O-alkylation, or Mitsunobu reaction with appropriate reagents, provides compounds of formula of II-1 ($R^1$=MeO; $R^2$=alkoxy, for example, methoxy, ethoxy, n-propoxy, or isopropoxy, and others as described herein). Some compounds II-8 can also be converted to compounds II-1 via metal catalyzed coupling reactions well known in the arts, including, for example, Suzuki reactions, followed with or without further chemical transformations of the resulting product by methods well known in the art.

Testing

The G9a inhibitory activity of the compounds of the present disclosure can be tested using the in vitro assay described in Biological Examples 1 below.

Administration and Pharmaceutical Composition

In general, the compounds of this disclosure will be administered in a therapeutically effective amount by any of the accepted modes of administration for agents that serve similar utilities. Therapeutically effective amounts of compounds this disclosure may range from about 0.01 to about 500 mg per kg subject body weight per day, which can be administered in single or multiple doses. A suitable dosage level may be from about 0.1 to about 250 mg/kg per day or about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions can be provided in the form of tablets containing about 1.0 to about 1000 milligrams of the active ingredient, particularly about 1, 5, 10, 15, 20, 25, 50, 75, 100, 150, 200, 250, 300, 400, 500, 600, 750, 800, 900, or 1000 milligrams of the active ingredient. The actual amount of the compound of this disclosure, i.e., the active ingredient, will depend upon numerous factors such as the severity of the disease to be treated, the age and relative health of the subject, the potency of the compound being utilized, the route and form of administration, and other factors.

In general, compounds of this disclosure will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules, including enteric coated or delayed release tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a cross-linked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of this disclosure in combination with at least one pharmaceutically acceptable excipient. Acceptable excipients are non-toxic, aid administration, and do not adversely affect the therapeutic benefit of the compound of this disclosure. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose and glycols.

Compressed gases may be used to disperse a compound of this disclosure in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt. %) basis, from about 0.01-99.99 wt. % of a compound of this disclosure based on the total formulation, with the balance being one or more suitable pharmaceutical excipients. For example, the compound is present at a level of about 1-80 wt. %.

The compounds of this disclosure may be used in combination with one or more other drugs in the treatment of diseases or conditions for which compounds of this disclosure or the other drugs may have utility. Such other drug(s) may be administered, by a route and in an amount commonly used therefore, contemporaneously or sequentially with a compound of the present disclosure. When a compound of this disclosure is used contemporaneously with one or more other drugs, a pharmaceutical composition in unit dosage form containing such other drugs and the compound of the present disclosure is preferred. However, the combination therapy may also include therapies in which the compound of this disclosure and one or more other drugs are administered on different overlapping schedules. It is also contemplated that when used in combination with one or more other active ingredients, the compounds of the present disclosure and the other active ingredients may be used in lower doses than when each is used singly.

Accordingly, the pharmaceutical compositions of the present disclosure also include those that contain one or more other drugs, in addition to a compound of the present disclosure.

The above combinations include combinations of a compound of this disclosure not only with one other drug, but also with two or more other active drugs. Likewise, a compound of this disclosure may be used in combination with other drugs that are used in the prevention, treatment, control, amelioration, or reduction of risk of the diseases or conditions for which a compound of this disclosure is useful. Such other drugs may be administered, by a route and in an amount commonly used therefore, contemporaneously or sequentially with a compound of the present disclosure. When a compound of this disclosure is used contemporaneously with one or more other drugs, a pharmaceutical composition containing such other drugs in addition to the compound of this disclosure can be used. Accordingly, the pharmaceutical compositions of the present disclosure also include those that also contain one or more other active ingredients, in addition to a compound of this disclosure. The weight ratio of the compound of this disclosure to the second active ingredient may be varied and will depend upon the effective dose of each ingredient. Generally, an effective dose of each will be used.

Where the subject in need is suffering from or at risk of suffering from cancer, the subject can be treated with a compound of this disclosure in any combination with one or more other anti-cancer agents and/or anti-cancer therapies. In some embodiments, the anti-cancer therapies can be surgery and/or radiation therapy. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec™) geldanamycin, 17-N-Allylamino-17-Demethoxygeldanamycin (17-AAG), flavopiridol, LY294002, bortezomib, trastuzumab, BAY 11-7082, PKC412, or PD184352, paclitaxel (Taxol™), a well-known anti-cancer drug which acts by enhancing and stabilizing microtubule formation and analogs of Taxol™, such as docetaxel (Taxotere™). Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with a compound of this disclosure include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; antibodies (e.g., rituxan); MET inhibitor such as foretinib, carbozantinib, or crizotinib; VEGFR inhibitor such as sunitinib, sorafenib, regorafinib, lenvatinib, vandetanib, carbozantinib, or axitinib; EGFR inhibitor such as afatinib, brivanib, carbozantinib, erlotinib, gefitinib, neratinib, or lapatinib; PI3K inhibitor such as XL147, XL765, BKM120 (buparlisib), GDC-0941, BYL719, IPI145, BAY80-6946. BEX235 (dactolisib), CAL101 (idelalisib), GSK2636771, or TG100-115; MTOR inhibitor such as rapamycin (sirolimus), temsirolimus, everolimus, XL388, XL765, AZD2013, PF04691502, PKI-587, BEZ235, or GDC0349; MEK inhibitor such as AZD6244, trametinib, PD184352, pimasertinib, GDC-0973, or AZD8330; and proteasome inhibitor such as carfilzomib, MLN9708, delanzomib, or bortezomib.

Other anti-cancer agents that can be employed in combination with a compound of this disclosure include Adriamycin; Dactinomycin; Bleomycin; Vinblastine; Cisplatin; acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or RiI2), interferon alfa-2a; interferon alfa-2b; interferon alfa-n1; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer agents that can be employed in combination with a compound of the disclosure such as 20-epi-analogues of 1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; Bfgf inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+ estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+; diethylstilbestrol; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+ pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; Ru retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a compound of this disclosure include alkylating agents, antimetabolites, natural products, or hormones, e.g., nitrogen mustards (e.g., mechloroethamine, cyclophosphamide, chlorambucil, etc.), alkyl sulfonates (e.g., busulfan, etc.), nitrosoureas (e.g., carmustine, lomusitne, etc.), or triazenes (decarbazine, etc.). Examples of antimetabolites include but are not limited to folic acid analog (e.g., methotrexate), pyrimidine analogs (e.g., cytarabine, etc.), or purine analogs (e.g., mercaptopurine, thioguanine, pentostatin, etc.).

Examples of natural products useful in combination with a compound of this disclosure include but are not limited to vinca alkaloids (e.g., vincristine, etc.), epipodophyllotoxins (e.g., etoposide, etc.), antibiotics (e.g., daunorubicin, doxorubicin, bleomycin, etc.), enzymes (e.g., L-asparaginase, etc.), or biological response modifiers (e.g., interferon alpha, etc.).

Examples of alkylating agents that can be employed in combination a compound of this disclosure include, but are not limited to, nitrogen mustards (e.g., mechloroethamine, cyclophosphamide, chlorambucil, melphalan, etc.), ethylenimine and methylmelamines (e.g., hexamethylmelamine, thiotepa, etc.), alkyl sulfonates (e.g., busulfan, etc.), nitrosoureas (e.g., carmustine, lomusitne, semustine, streptozocin, etc.), or triazenes (decarbazine, etc.). Examples of antimetabolites include, but are not limited to folic acid analog (e.g., methotrexate, etc.), pyrimidine analogs (e.g., fluorouracil, floxuridine, cytarabine, etc.), or purine analogs (e.g., mercaptopurine, thioguanine, pentostatin, etc.).

Examples of hormones and antagonists useful in combination a compound of this disclosure include, but are not limited to, adrenocorticosteroids (e.g., prednisone, etc.), progestins (e.g., hydroxyprogesterone caproate, megestrol acetate and medroxyprogesterone acetate, etc.), estrogens (e.g., diethylstilbestrol and ethinyl estradiol, etc.), antiestrogen (e.g., tamoxifen, etc.), androgens (e.g., testosterone propionate, fluoxymesterone, etc.), antiandrogen (e.g., flutamide, etc.) and gonadotropin releasing hormone analog (e.g., leuprolide, etc.). Other agents that can be used in the methods and compositions described herein for the treatment or prevention of cancer include platinum coordination complexes (e.g., cisplatin, carboblatin, etc.), anthracenedione (e.g., mitoxantrone, etc.), substituted urea (e.g., hydroxyurea, etc.), methyl hydrazine derivative (e.g., procarbazine, etc.) and adrenocortical suppressant (e.g., mitotane, aminoglutethimide, etc.).

Examples of anti-cancer agents which act by arresting cells in the G2-M phases due to stabilized microtubules and which can be used in combination with an irreversible Btk inhibitor compound include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8 and Spongistatin 9), Cemadotin hydrochloride (also known as LU-103793 and NSC-D-669356), Epothilones (such as Epothilone A, Epothilone B, Epothilone C (also known as desoxyepothilone A or dEpoA)), Epothilone D (also referred to as KOS-862, dEpoB and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone, Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes) and SSR-250411 (Sanofi).

SYNTHETIC EXAMPLES

The following preparations of compounds of Formula (I) (Examples) and intermediates (References) are given to enable those skilled in the art to more clearly understand and to practice the present disclosure. They should not be considered as limiting the scope of the disclosure, but merely as being illustrative and representative thereof.

Common intermediates that had been made for the syntheses of the described examples are listed in Table B below:

TABLE B

| Intermediate | IUPAC | LCMS found |
|---|---|---|
| Intermediate 1 | 1-[3-({9-chloro-7-methoxy-1H,2H,3H-cyclopenta[b]quinolin-6-yl}oxy)propyl]pyrrolidine | 361.2 |

TABLE B-continued

| Intermediate | IUPAC | LCMS found |
|---|---|---|
| 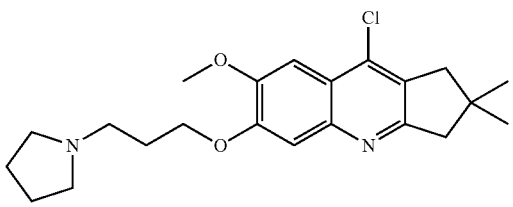<br>Intermediate 2 | 1-[3-({9-chloro-7-methoxy-2,2-dimethyl-1H,2H,3H-cyclopenta[b]quinolin-6-yl}oxy)propyl]pyrrolidine | 389.1 |
| 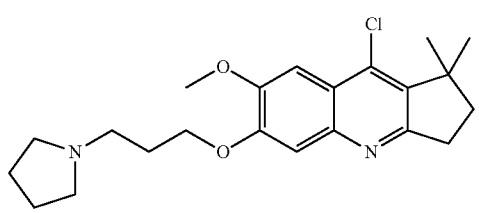<br>Intermediate 3 | 1-[3-({9-chloro-7-methoxy-1,1-dimethyl-1H,2H,3H-cyclopenta[b]quinolin-6-yl}oxy)propyl]pyrrolidine | 389.1 |
| 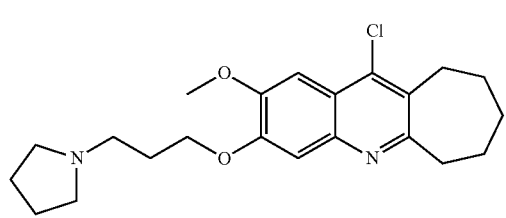<br>Intermediate 4 | 1-[3-({11-chloro-2-methoxy-6H,7H,8H,9H,10H-cyclohepta[b]quinolin-3-yl}oxy)propyl]pyrrolidine | 389.2 |
| 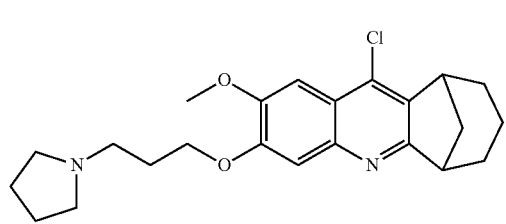<br>Intermediate 5 | 10-chloro-7-methoxy-6-[3-(pyrrolidin-1-yl)propoxy]-3-azatetracyclo[10.3.1.0$^{2,11}$.0$^{4,9}$]hexadeca-2,4,6,8,10-pentaene | 401.3 |
| 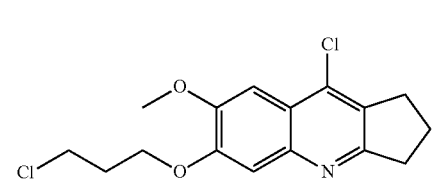<br>Intermediate 6 | 9-chloro-6-(3-chloropropoxy)-7-methoxy-1H,2H,3H-cyclopenta[b]quinoline | 326.0 |
| 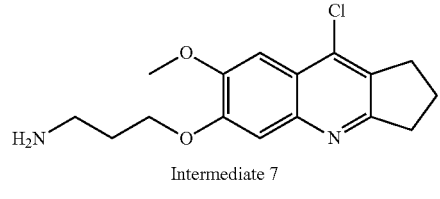 [SMILES: COc1cc2c(Cl)c3c(nc2cc1OCCCN)CCC3]<br>Intermediate 7 | 3-({9-chloro-7-methoxy-1H,2H,3H-cyclopenta[b]quinolin-6-yl}oxy)propan-1-amine | 307.1 |

TABLE B-continued

| Intermediate | IUPAC | LCMS found |
|---|---|---|
| 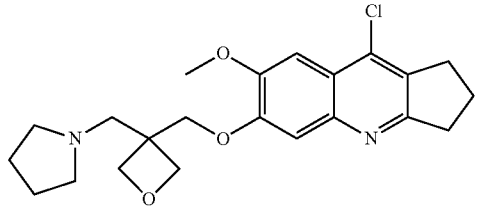<br>Intermediate 8 | 1-({3-[({9-chloro-7-methoxy-1H,2H,3H-cyclopenta[b]quinolin-6-yl}oxy)methyl]oxetan-3-yl}methyl)pyrrolidine | 403.2 |
| 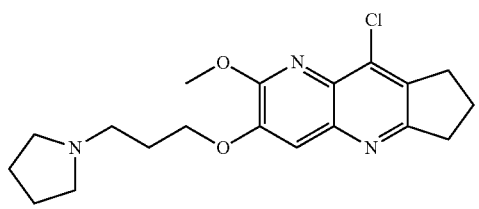<br>Intermediate 9 | 1-[3-({9-chloro-2-methoxy-6H,7H,8H-cyclopenta[b]1,5-naphthyridin-3-yl}oxy)propyl]pyrrolidine | 362.0 |
| 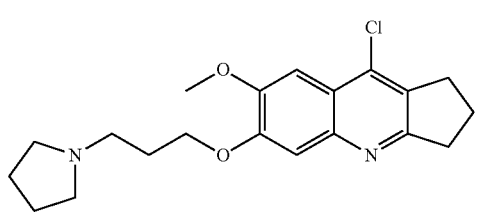<br>Intermediate 10 | 1-[2-({9-chloro-7-methoxy-1H,2H,3H-cyclopenta[b]quinolin-6-yl}methoxy)ethyl]pyrrolidine | 361.1 |
| 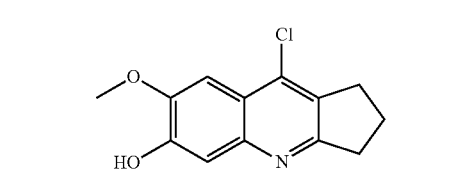<br>Intermediate 11 | 9-chloro-7-methoxy-1H,2H,3H-cyclopenta[b]quinolin-6-ol | 250.0 |
| 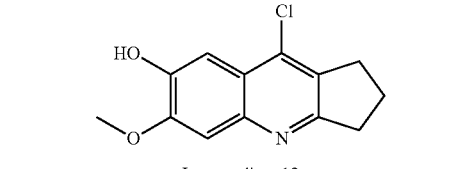<br>Intermediate 12 | 9-chloro-6-methoxy-1H,2H,3H-cyclopenta[b]quinolin-7-ol | 250.0 |
| 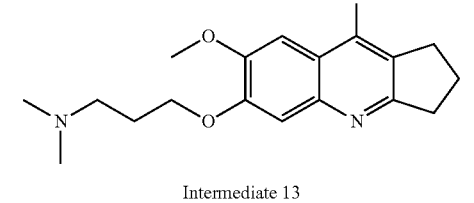<br>Intermediate 13 | [3-({9-chloro-7-methoxy-1H,2H,3H-cyclopenta[b]quinolin-6-yl}oxy)propyl]dimethylamine | 335.2 |
| 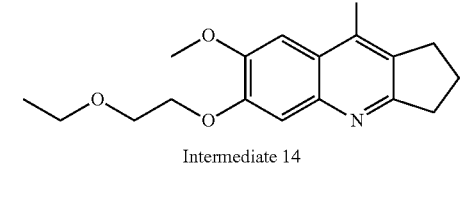<br>Intermediate 14 | 9-chloro-6-(2-ethoxyethoxy)-7-methoxy-1H,2H,3H-cyclopenta[b]quinoline | 322.1 |

TABLE B-continued

| Intermediate | IUPAC | LCMS found |
|---|---|---|
| 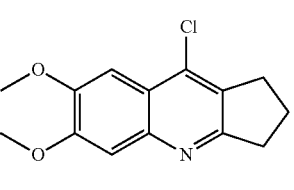 Intermediate 15 | 1-[(2R)-3-({9-chloro-7-methoxy-1H,2H,3H-cyclopenta[b]quinolin-6-yl}oxy)-2-methylpropyl]pyrrolidine | 375.2 |
| 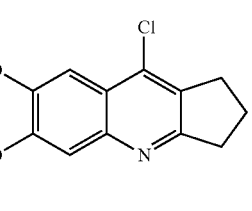 Intermediate 16 | 3-[({9-chloro-7-methoxy-1H,2H,3H-cyclopenta[b]quinolin-6-yl}oxy)methyl]pyridine | 341.2 |
| 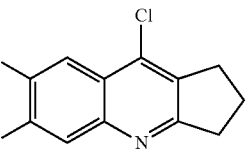 Intermediate 17 | 9-chloro-7-methoxy-6-propoxy-1H,2H,3H-cyclopenta[b]quinoline | 292.1 |
| 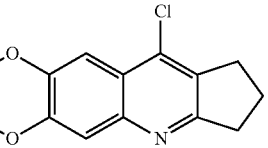 Intermediate 18 | 9-chloro-7-methoxy-6-(3-methoxypropoxy)-1H,2H,3H-cyclopenta[b]quinoline | 322.1 |
| 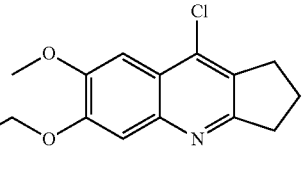 Intermediate 19 | {2-[2-({9-chloro-7-methoxy-1H,2H,3H-cyclopenta[b]quinolin-6-yl}oxy)ethoxy]ethyl}dimethylamine | 365.1 |
| 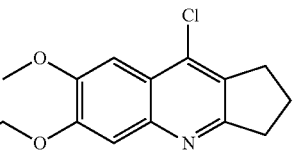 Intermediate 20 | 2-[2-({9-chloro-7-methoxy-1H,2H,3H-cyclopenta[b]quinolin-6-yl}oxy)ethoxy]ethan-1-ol | 338.1 |

TABLE B-continued

| Intermediate | | IUPAC | LCMS found |
|---|---|---|---|
| 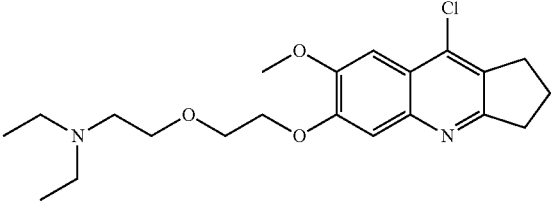 Intermediate 21 | | {2-[2-({9-chloro-7-methoxy-1H,2H,3H-cyclopenta[b]quinolin-6-yl}oxy)ethoxy]ethyl}diethylamine | 393.3 |
| 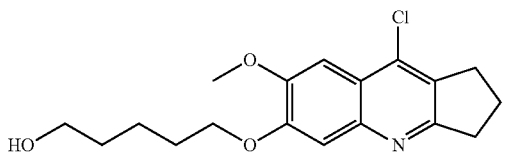 Intermediate 22 | | 5-({9-chloro-7-methoxy-1H,2H,3H-cyclopenta[b]quinolin-6-yl}oxy)pentan-1-ol | 335.9 |
| 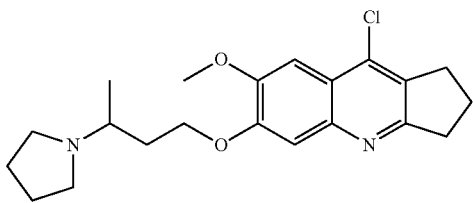 Intermediate 23 | | 1-[4-({9-chloro-7-methoxy-1H,2H,3H-cyclopenta[b]quinolin-6-yl}oxy)butan-2-yl]pyrrolidine | 375.1 |
| 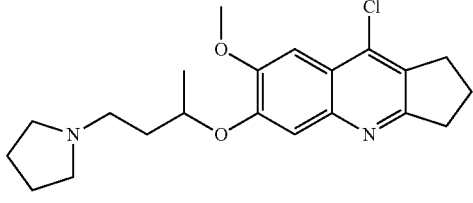 Intermediate 24 | | 1-[3-({9-chloro-7-methoxy-1H,2H,3H-cyclopenta[b]quinolin-6-yl}oxy)butyl]pyrrolidine | 375.1 |
| 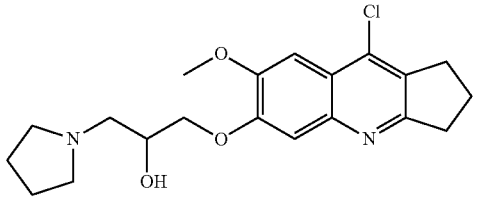 Intermediate 25 | | 1-({9-chloro-7-methoxy-1H,2H,3H-cyclopenta[b]quinolin-6-yl}oxy)-3-(pyrrolidin-1-yl)propan-2-ol | 376.7 |
| 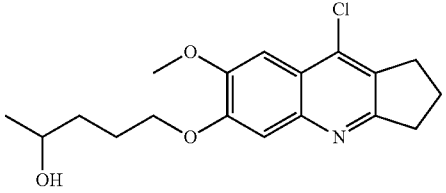 Intermediate 26 | | 5-({9-chloro-7-methoxy-1H,2H,3H-cyclopenta[b]quinolin-6-yl}oxy)pentan-2-ol | 335.8 |

TABLE B-continued

| Intermediate | | IUPAC | LCMS found |
|---|---|---|---|
| 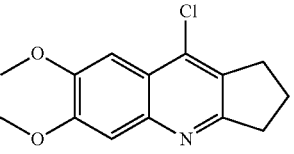<br>Intermediate 27 | | (3R)-1-[3-({9-chloro-7-methoxy-1H,2H,3H-cyclopenta[b]quinolin-6-yl}oxy)propyl]-3-methoxypyrrolidine | 390.8 |
| 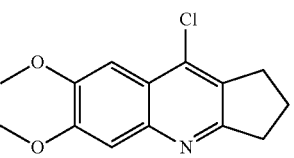<br>Intermediate 28 | | (3S)-1-[3-({9-chloro-7-methoxy-1H,2H,3H-cyclopenta[b]quinolin-6-yl}oxy)propyl]-3-methoxypyrrolidine | 390.8 |
| 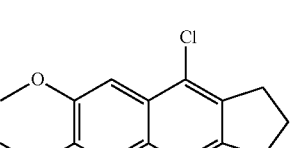<br>Intermediate 29 | | 3-[3-({9-chloro-7-methoxy-1H,2H,3H-cyclopenta[b]quinolin-6-yl}oxy)propyl]-3-azabicyclo[3.1.1]heptane | 387.1 |
| 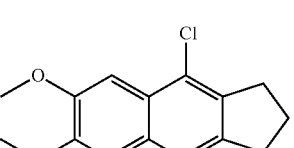<br>Intermediate 30 | | 7-[3-({9-chloro-7-methoxy-1H,2H,3H-cyclopenta[b]quinolin-6-yl}oxy)propyl]-7-azabicyclo[2.2.1]heptane | 387.2 |
| 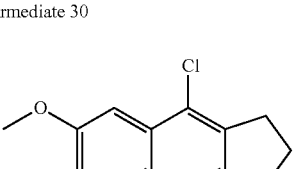<br>Intermediate 31 | | 8-[3-({9-chloro-7-methoxy-1H,2H,3H-cyclopenta[b]quinolin-6-yl}oxy)propyl]-8-azabicyclo[3.2.1]octane | 401.2 |
| 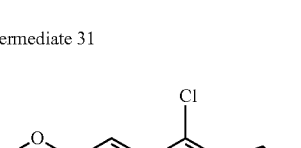<br>Intermediate 32 | | (3S)-1-[3-({9-chloro-7-methoxy-1H,2H,3H-cyclopenta[b]quinolin-6-yl}oxy)propyl]-3-fluoropyrrolidine | 379.1 |

TABLE B-continued

| Intermediate | | IUPAC | LCMS found |
|---|---|---|---|
| 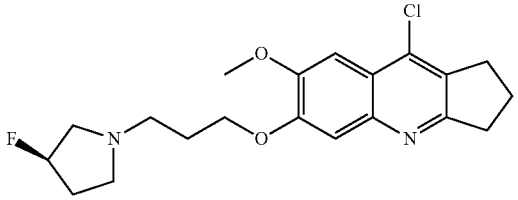<br>Intermediate 33 | | (3R)-1-[3-({9-chloro-7-methoxy-1H,2H,3H-cyclopenta[b]quinolin-6-yl}oxy)propyl]-3-fluoropyrrolidine | 379.2 |
| 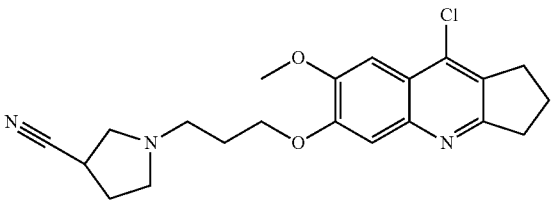<br>Intermediate 34 | | 1-[3-({9-chloro-7-methoxy-1H,2H,3H-cyclopenta[b]quinolin-6-yl}oxy)propyl]pyrrolidine-3-carbonitrile | 386.3 |
| 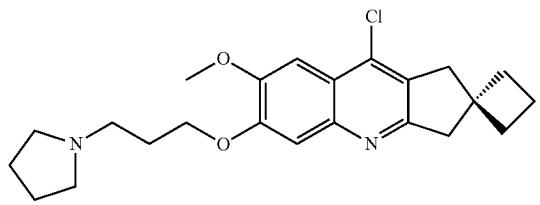<br>Intermediate 35 | | 9'-chloro-7'-methoxy-6'-[3-(pyrrolidin-1-yl)propoxy]-1',3'-dihydrospiro[cyclobutane-1,2'-cyclopenta[b]quinoline] | 400.8 |
| 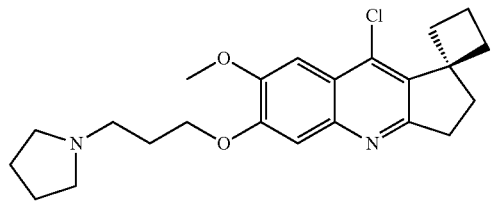<br>Intermediate 36 | | 9'-chloro-7'-methoxy-6'-[3-(pyrrolidin-1-yl)propoxy]-2',3'-dihydrospiro[cyclobutane-1,1'-cyclopenta[b]quinoline] | 400.8 |

Reference 1

Synthesis of 1-[3-({9-chloro-7-methoxy-1H,2H,3H-cyclopenta[b]quinolin-6-yl}oxy)propyl]pyrrolidine ((Intermediate 1)

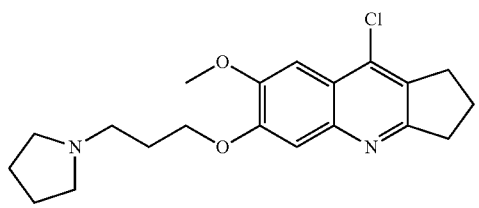 [SMILES: COc1cc2c(Cl)c3c(nc2cc1OCCCN1CCCC1)CCC3]

Step 1

To a 2-L round-bottom flask was added methyl 4-hydroxy-3-methoxybenzoate (100 g, 548.93 mmol, 1.00 eq.), 1-chloro-3-iodopropane (224 g, 1.10 mol, 2.0 eq.), K₂CO₃ (22.7 g, 3.00 eq.) followed by MeCN (1 L). The resulting mixture was allowed to stir at 80° C. for 3 h. The mixture was cooled to rt, the solids were filtered and washed with EtOAc. The filtrate was concentrated under reduced pressure to afford methyl 4-(3-chloropropoxy)-3-methoxybenzoate as a white solid (128 g, 90%).

Step 2

Into a 0° C. solution of methyl 4-(3-chloropropoxy)-3-methoxybenzoate (50.0 g, 193.28 mmol, 1.00 eq.) in acetic anhydride (500 mL) in a 1-L 3-necked round-bottom flask in ice/salt bath was added concentrated HNO₃ (20 mL) dropwise under vigorous stirring. The resulting mixture was allowed to stir in the ice/salt bath till complete consumption of the starting material (about 30 min). The mixture was diluted with 1 L of H₂O/ice and extracted with EtOAc thrice. The combined organic layers were washed with saturated aq. NaHCO₃, brine, and dried over anhydrous Na₂SO₄. Removal of the organic solvents under reduced pressure provided crude methyl 4-(3-chloropropoxy)-5-methoxy-2-nitrobenzoate as a brown oil (60 g).

Step 3

To a rt solution of methyl 4-(3-chloropropoxy)-5-methoxy-2-nitrobenzoate (60.0 g crude, 193.28 mmol, 1.00 eq.) in MeCN (1 L) was added pyrrolidine (41.3 g, 580.70 mmol, 3.00 eq.), NaI (58.2 g, 2.00 eq.), K₂CO₃ (66.9 g, 484.05 mmol, 2.50 eq.) and tetrabutylammonium iodide (3.57 g, 9.67 mmol, 0.05 eq.). The resulting mixture was allowed to stir at 90° C. for 16 h. The solids were filtered and washed with EtOAc. The filtrate was concentrated under reduced pressure to afford methyl 5-methoxy-2-nitro-4-[3-(pyrrolidin-1-yl)propoxy]benzoate as a brown oil (43.2 g, 66% for 2 steps).

Step 4

To a rt solution of methyl 5-methoxy-2-nitro-4-[3-(pyrrolidin-1-yl)propoxy]benzoate (30.0 g, 88.66 mmol, 1.00 eq.) in EtOAc (300 mL) and water (150 mL) was added iron dust (19.9 g, 4.00 eq.) and NH₄OAc (41.0 g, 531.91 mmol, 6.00 eq.). The resulting mixture was allowed to stir in an oil bath at 100° C. for 3 h until the starting material was completely consumed, and then cooled to rt, filtered through a pad of Celite. The filtrate was concentrated under reduced pressure to remove most of the organic solvents. The aqueous phase was back extracted with a mixed solvent of 10% MeOH/CH₂Cl₂ thrice. Removal of the organic solvents under reduced pressure provided methyl 2-amino-5-methoxy-4-[3-(pyrrolidin-1-yl)propoxy]benzoate as a brown crude oil (21.3 g, 78%).

Step 5

To a rt solution of methyl 2-amino-5-methoxy-4-[3-(pyrrolidin-1-yl)propoxy]benzoate (5.00 g; 16.21 mmol; 1.00 eq., made in step 4, reference 1) in a mixture solvent of MeOH/THF/water (1:1:1, 25 mL) was added LiOH (0.58 g; 24.32 mmol; 1.50 eq.). This resulting mixture was allowed to stir at 60° C. for 7 h until the starting material was completely consumed, cooled to rt and treated with AcOH (1.46 g, 24.4 mmol, 1.50 eq.). After removal of solvents under reduced pressure, the residue was left on high reduced pressure overnight, and re-dissolved in 30% ⁱPrOH/CHCl₃. The solid was filtered and washed with MeOH. The organic solutions were combined. Removal of the organic solvents under reduced pressure to provide 2-amino-5-methoxy-4-(3-(pyrrolidin-1-yl)propoxy)benzoic acid as brown syrup (5.5 g).

Step 6

To a mixture of 2-amino-5-methoxy-4-[3-(pyrrolidin-1-yl)propoxy]benzoic acid (5.50 g; 18.69 mmol; 1.00 eq.) and cyclopentanone (1.89 g; 22.42 mmol; 1.20 eq.) was added POCl₃ (15 mL). The resulting mixture was allowed to stir at 100° C. for overnight under N2 atmosphere. The mixture was cooled to rt and then slowly poured into ice/water, and neutralized with 20% aqueous NaOH to pH-12. The resulting mixture was extracted with a mixed solvent of 25% ⁱPrOH/CHCl₃ thrice and the organic layers were combined. After removal of organic solvents under reduced pressure, the residue was purified by chromatography on 40 g silica gel using 0-100% solvent A (Solvent A: 3% NH₄OH/MeOH) in solvent B (Solvent B: 0.1% NH₄OH/10% MeOH/CH₂Cl₂) to provide 9-chloro-7-methoxy-6-(3-(pyrrolidin-1-yl)propoxy)-2,3-dihydro-1H-cyclopenta[b]quinoline as brown solid (1.55 g, 23%). LCMS (ES) [M+1]+ m/z 361.2.

Reference 2

Synthesis of 1-[3-({9-chloro-7-methoxy-2,2-dimethyl-1H,2H,3H-cyclopenta[b]quinolin-6-yl}oxy)propyl]pyrrolidine (Intermediate 2)

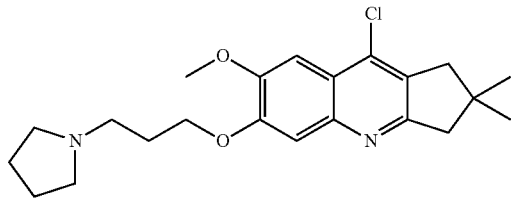 [SMILES: COc1cc2c(Cl)c3c(nc2cc1OCCCN1CCCC1)CC(C)(C)C3]

The title compound was made starting from methyl 4-hydroxy-3-methoxybenzoate following a synthetic sequence as described for Intermediate 1 (reference 1), except that 3,3-dimethylcyclopentan-1-one was used in place of cyclopentanone in step 6. The crude product was purified by chromatography on silica gel using 0-10% solvent A (solvent A: 3% NH₄OH/MeOH) in solvent B (Solvent B: 0.1% NH₄OH/10% MeOH/CH₂Cl₂) to provide the product as a brown solid. LCMS (ES) [M+1]⁺ m/z 389.1.

Reference 3

Synthesis of 1-[3-({9-chloro-7-methoxy-1,1-dimethyl-1H,2H,3H-cyclopenta[b]quinolin-6-yl}oxy)propyl]pyrrolidine (Intermediate 3)

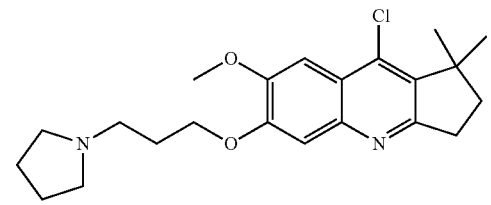 [SMILES: COc1cc2c(Cl)c3c(nc2cc1OCCCN1CCCC1)CCC3(C)C]

The title compound was made starting from methyl 4-hydroxy-3-methoxybenzoate following a synthetic sequence as described for Intermediate 1 (reference 1), except that 3,3-dimethylcyclopentan-1-one was used in place of cyclopentanone in step 6. The crude product was purified by flash chromatography on silica gel using 0-10% solvent A (solvent A: 3% NH₄OH/MeOH) in solvent B (Solvent B: 0.1% NH₄OH/10% MeOH/CH₂Cl₂) to provide the product as a brown solid. LCMS (ES) [M+1]⁺ m/z 389.1.

Reference 4

Synthesis of 1-[3-({11-chloro-2-methoxy-6H,7H,8H,9H,10H-cyclohepta[b]quinolin-3-yl}oxy)propyl]pyrrolidine (Intermediate 4)

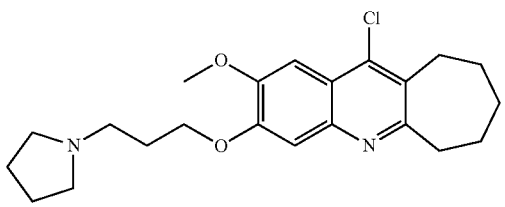 [SMILES: COc1cc2c(Cl)c3c(nc2cc1OCCCN1CCCC1)CCCCC3]

The title compound was made starting from methyl 4-hydroxy-3-methoxybenzoate following a synthetic sequence as described for Intermediate 1 (reference 1, step 6), except that cycloheptanone was used in place of cyclopentanone. The crude product was purified by chromatography on silica gel column using 0-10% solvent A (solvent A: 3% NH$_4$OH/MeOH) in solvent B (Solvent B: 0.1% NH$_4$OH/10% MeOH/CH$_2$Cl$_2$) to provide the product as a brown solid. LCMS (ES) [M+1]$^+$ m/z 389.2.

Reference 5

Synthesis of 10-chloro-7-methoxy-6-[3-(pyrrolidin-1-yl)propoxy]-3-azatetracyclo[10.3.1.0$^{2,11}$.0$^{4,9}$]hexadeca-2,4,6,8,10-pentaene (Intermediate 5)

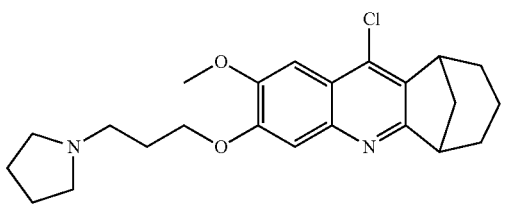 [SMILES: COc1cc2c(Cl)c3c(nc2cc1OCCCN1CCCC1)C1CCCC3C1]

The title compound was made starting from methyl 4-hydroxy-3-methoxybenzoate following a synthetic sequence as described for the synthesis of Intermediate 1 (reference 1), except that bicyclo[3.2.1]octan-6-one was used in place of cyclopentanone in step 6. The crude product was purified by chromatography on silica gel using 0-8% solvent A (solvent A: 3% NH$_4$OH/MeOH) in solvent B (Solvent B: 0.1% NH$_4$OH/10% MeOH/CH$_2$Cl$_2$) to provide the product as a brown solid. LCMS (ES) [M+1]$^+$ m/z 401.3.

Reference 6

Synthesis of 9-chloro-6-(3-chloropropoxy)-7-methoxy-1H,2H,3H-cyclopenta[b]quinoline (Intermediate 6)

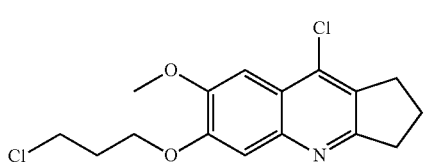 [SMILES: COc1cc2c(Cl)c3c(nc2cc1OCCCCl)CCC3]

A vial containing a mixture of 9-chloro-7-methoxy-1H,2H,3H-cyclopenta[b]quinolin-6-ol (Intermediate 11) (2.0 g; 8.01 mmol; 1.00 eq.), 1-chloro-3-iodopropane (1 965.01 mg; 9.61 mmol; 1.20 eq.) and cesium carbonate (5 741.48 mg; 17.62 mmol; 2.20 eq.) in DMF (10 mL) was sealed and subjected to 90° C. with stir for 45 min. The resulting mixture was cooled to rt, the solids were filtered and washed with EtOAc thrice under filtration. The combined solution was washed with water thrice. After removal of the organic volatiles under reduced pressure, the residue was purified by chromatography on silica gel using 0-100% EtOAc/Hexanes to provide the title product as an off white foam (1.89 g, 72%). LCMS (ES) [M+1]$^+$ m/z 326.0.

Reference 7

Synthesis of 3-({9-chloro-7-methoxy-1H,2H,3H-cyclopenta[b]quinolin-6-yl}oxy)propan-1-amine (Intermediate 7)

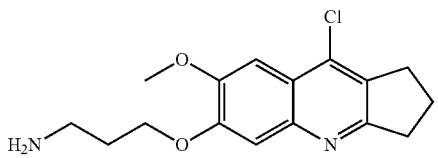 [SMILES: COc1cc2c(Cl)c3c(nc2cc1OCCCN)CCC3]

A mixture of 9-chloro-7-methoxy-1H,2H,3H-cyclopenta[b]quinolin-6-ol (Intermediate 11) (500.00 mg; 2.00 mmol; 1.00 eq.), cesium carbonate (1 957.32 mg; 6.01 mmol; 3.00 eq.) and tert-butyl 3-bromopropylcarbamate (850.00 mg; 3.57 mmol; 1.78 eq.) in MeCN (12 mL) sealed in a vial was allowed to stir at 70° C. for 1 h. The resulting mixture was cooled to rt, and the solid was filtered and washed with 10% MeOH/CH$_2$Cl$_2$ under filtration. The combined filtrates were concentrated under reduced pressure. The remaining residue was re-dissolved in a mixture solvents of TFA/CH$_2$Cl$_2$ (2 mL/5 mL). The mixture was allowed to stir at 50° C. for 30 min, cooled to rt and concentrated under reduced pressure. The residue was treated with sat. aq. NaHCO$_3$, diluted with water and extracted with 20% $^i$PrOH/CHCl$_3$ twice. The organic solutions were combined. After removal of the organic volatiles under reduced pressure, the residue was purified by chromatography on silica gel using 0-10% MeOH/CH$_2$Cl$_2$ (both containing 1% NH$_4$OH) to provide the product as an off white foam (422 mg, 68%). LCMS (ES) [M+1]$^+$ m/z 307.1.

Reference 8

Synthesis of 1-({3-[({9-chloro-7-methoxy-1H,2H,3H-cyclopenta[b]quinolin-6-yl}oxy)methyl]oxetan-3-yl}methyl)pyrrolidine (Intermediate 8)

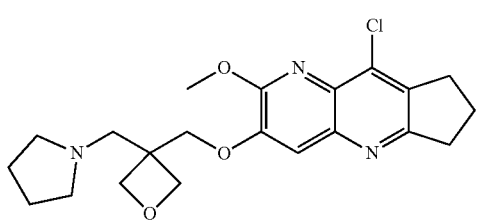 [SMILES: COc1nc2c(Cl)c3c(nc2cc1OCC1(CN2CCCC2)COC1)CCC3]

Step 1

A mixture 9-chloro-7-methoxy-1H,2H,3H-cyclopenta[b]quinolin-6-ol (Intermediate 11) (80.00 mg; 0.32 mmol; 1.00 eq.), 3,3-bis(bromomethyl)oxetane (85.97 mg; 0.35 mmol; 1.10 eq.) and cesium carbonate (313.17 mg; 0.96 mmol; 3.00 eq.) in MeCN (2.5 mL) sealed in a vial was allowed to stir at 70° C. for 30 min. Added additional 3,3-bis(bromomethyl)oxetane (60 mg; 0.25 mmol; 0.78 eq.) was added and the mixture was allowed to stir at 70° C. for additional 2 h. The resulting mixture was cooled to rt, treated with water and extracted with EtOAc thrice. After removal of the organic solvents, the residue was purified by chromatography on silica gel using 0-100% EtOAc/Hexanes to provide {[3-(bromomethyl)oxetan-3-yl]methoxy}-9-chloro-7-methoxy-1H,2H,3H-cyclopenta[b]quinoline (106.0 mg, 81%). LCMS (ES) [M+1]$^+$ m/z 412.1., 414.1.

Step 2

A solution of 6-{[3-(bromomethyl)oxetan-3-yl]methoxy}-9-chloro-7-methoxy-1H,2H,3H-cyclopenta[b]quinoline (106 mg; 0.26 mmol; 1.00 eq.) and pyrrolidine (82.2 mg; 1.17 mmol; 1.50 eq.) in 1,4-dioxane (4.0 mL) sealed in a vial was allowed to stir at 75° C. for 4 h. The resulting solution was cooled to rt. After removal of the organic solvents under reduced pressure, the residue was purified by chromatography on silica gel using 0-10% MeOH/CH$_2$Cl$_2$ (both containing 1% NH$_4$OH) to provide the product as a white solid (84 mg, 81%). LCMS (ES) [M+1]$^+$ m/z 403.2.

Reference 9

Synthesis of 1-[3-({9-chloro-2-methoxy-6H,7H,8H-cyclopenta[13]1,5-naphthyridin-3-yl}oxy)propyl]pyrrolidine (Intermediate 9)

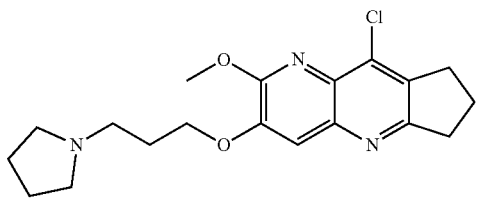 [SMILES: COc1nc2c(Cl)c3c(nc2cc1OCCCN1CCCC1)CCC3]

Step 1

To a solution of 5-bromo-6-methoxypyridine-2-carboxylic acid (500 mg, 2.15 mmol, 1.00 eq.) in sulfuric acid (10 mL) in ice bath was added HNO$_3$ (5 mL) dropwise. The resulting solution was allowed to stir at 60° C. for 16 h. After being cooled to rt, the solution was poured into ice/water (20 mL). The solids were collected by filtration to provide 3-amino-5-bromo-6-methoxypyridine-2-carboxylic acid as a light yellow solid (260 mg, 44%). LCMS (ES) [M−1]$^−$ m/z 275.0.

Step 2

To a mixture of 5-bromo-6-methoxy-3-nitropyridine-2-carboxylic acid (2.6 g, 9.39 mmol, 1.00 eq.) in EtOH (25 mL) and water (25 mL) was added NH$_4$Cl (1.49 g, 28.17 mmol, 3.00 eq.) and Fe (dust) (2.63 g, 46.95 mmol, 5.00 eq.). The resulting mixture was allowed to stir at 70° C. for 3 h. The mixture was basified with 2.0 N aqueous NaOH to pH~10. The precipitate was filtered. The filter cake was washed with MeOH/H$_2$O (V/V=1/1, 2×50 mL). The filtrate was concentrated under vacuum. The residue was redissolved in DMF (20 mL), filtered and subjected to reverse phase preparative HPLC (Prep-C18, 20-45 μM, 120 g, Tianjin Bonna-Agela Technologies; gradient elution of 0% MeCN in water to 5% MeCN in water over a 7 min period, 100% MeCN to 100% MeCN over a 4 min period, where both solvents contain 0.05% FA) to provide 3-amino-5-bromo-6-methoxypyridine-2-carboxylic acid as a light yellow solid (1.0 g, 43%). LCMS (ES) [M−FA−1]$^−$ m/z 245.0.

Step 3

To a solution of 3-amino-5-bromo-6-methoxypyridine-2-carboxylic acid (1.0 g, 4.05 mmol, 1.00 eq.) in POCl$_3$ (30 mL) was added cyclopentanone (680 mg, 8.10 mmol, 2.00 eq.). The resulting solution was allowed to stir at 90° C. for 16 h. The resulting mixture was concentrated under reduced pressure. To the residue was added CH$_2$Cl$_2$ (25 mL) and the mixture was slowly added into ice/water (100 mL) dropwise. The resulting mixture was then basified with 2.0 N aqueous NaOH to pH=10 and extracted with EtOAc thrice. The combined organic layers were dried over anhydrous Na$_2$SO$_4$ and concentrated under reduced pressure. The residue was purified by chromatography on silica gel with EtOAc/petroleum ether (1/2) to provide 3-bromo-9-chloro-2-methoxy-6H, 7H, 8H-cyclopenta[b]1, 5-naphthyridine as a light yellow solid (700 mg, 55%). LCMS (ES) [M+1]$^+$ m/z 315.1.

Step 4

To a solution of 3-bromo-9-chloro-2-methoxy-6H,7H,8H-cyclopenta[b]1,5-naphthyridine (700 mg, 2.23 mmol, 1.00 eq.) and 4,4,5,5-tetramethyl-2-(propan-2-yloxy)-1,3,2-dioxaborolane (1.24 g, 6.69 mmol, 3.00 eq.) in dry THF (15 mL) at −78° C. under N2 atmosphere was added nBuLi (2.7 mL, 2.5 M in hexane, 6.69 mmol, 3.00 eq.) dropwise. The solution was allowed to stir at −78° C. for 1 h before being quenched with H$_2$O (2 mL) followed by addition of H$_2$O$_2$ (30% aq., 2 mL) The resulting mixture was allowed to stir at rt for additional 1 hour. To the solution was added saturated aqueous Na$_2$SO$_3$ (30 mL) and the mixture was allowed to stir at rt for 30 min. The crude mixture was extracted with EtOAc (5×50 mL) The organic layers were combined, dried over anhydrous Na$_2$SO$_4$, and concentrated under reduced pressure. The residue was purified by chromatography on silica gel with EtOAc/petroleum ether (2/1) to provide 9-chloro-2-methoxy-6H, 7H, 8H-cyclopenta[b]1, 5-naphthyridin-3-ol as a light yellow solid (350 mg, 63%). LCMS (ES) [M+1]$^+$ m/z 251.2.

Step 5

To a mixture of 9-chloro-2-methoxy-6H,7H,8H-cyclopenta[b]1,5-naphthyridin-3-ol (350 mg, 1.40 mmol, 1.00 eq.) in MeCN (10 mL) was added 1-(3-chloropropyl)pyrrolidine hydrochloride (258 mg, 1.40 mmol, 1.00 eq.), KI (465 mg, 2.80 mmol, 2.00 eq.) and Cs$_2$CO$_3$ (913 mg, 2.80 mmol, 2.00 eq.). The resulting mixture was allowed to stir at 80° C. for 2 h. The solids were filtered out and the filter cake was washed with MeCN (2×10 mL). The filtrate was concentrated under vacuum. The residue was as purified by chromatography on silica gel with MeOH/CH$_2$Cl$_2$ (1/9) to provide the title compound as a light yellow solid (300 mg, 59%). LCMS (ES) [M+1]$^+$ m/z 362.0.

245

Reference 10

Synthesis of 1-[2-({9-chloro-7-methoxy-1H,2H,3H-cyclopenta[b]quinolin-6-yl}methoxy)ethyl]pyrrolidine (Intermediate 10)

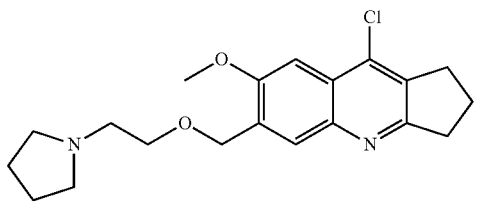 [SMILES: COc1cc2c(Cl)c3c(nc2cc1COCCN1CCCC1)CCC3]

Step 1

Into a suspension of NaH (188.08 mg; 4.70 mmol; 1.30 eq.) in DMF (1.0 mL) in ice bath under N2 was added 2-(1-pyrrolidinyl)ethanol (916.56 mg; 7.96 mmol; 2.20 eq.). The resulting mixture was removed from ice bath and the mixture was allowed to stir at rt for 20 min. The mixture was placed back to ice bath, to the mixture was added a solution of methyl 4-(bromomethyl)-5-methoxy-2-nitrobenzoate (1100.00 mg; 3.62 mmol; 1.00 eq.) in DMF (2.4 mL) The mixture was allowed to warm with the bath to rt and stir for 2 hr. The resulting mixture under N2 atmosphere was treated with saturated aqueous NH₄Cl and water, and extracted with EtOAc thrice. After removal of the organic solvents under reduced pressure, the residue was purified by chromatographs on silica gel with 0-100% EtOAc/Hexanes to provide methyl 5-methoxy-2-nitro-4-{[2-(pyrrolidin-1-yl)ethoxy]methyl}benzoate (942 mg, 77%).

Step 2

To a rt solution of methyl 5-methoxy-2-nitro-4-{[2-(pyrrolidin-1-yl)ethoxy]methyl}benzoate (680.00 mg; 2.01 mmol; 1.00 eq.) in MeOH (8 mL) was added aq. NaOH (1.44 mL; 3.50 mol/L; 5.02 mmol; 2.50 eq.). This solution was allowed to stir at 90° C. for 15 min, cooled to rt, diluted with water and treated with 1.0 N HCl to pH-6. The resulting mixture was extracted with 25% ⁱPrOH/CHCl₃ thrice. The combined organic solutions were washed with water, brine and dried over MgSO₄. After removal of the organic solvents under reduced pressure, the residue was carried to the next step without purification.

Step 3

A mixture of the above residue and SnCl₂ (1441.72 mg; 7.60 mmol) in 1,4-dioxane (12 mL) was allowed stir at 110° C. for 2 hr. The resulting mixture was concentrated under reduced pressure. To the flask with the remaining residue was added celite and MeOH. The mixture was filtered through a small pad of celite, and the celite pad was washed with a mixture of 1% NH₄OH/10% MeOH/89% CH₂Cl₂ multiple times followed by MeOH thrice. All the organic solutions were combined. After removal of the organic solvents under reduced pressure, the residue was purified by chromatographs on silica gel with 1% NH₄OH/10% MeOH/89% CH₂Cl₂ to provide 2-amino-5-methoxy-4-{[2-(pyrrolidin-1-yl)ethoxy]methyl}benzoic acid (321 mg, 54%, 2 steps).

Step 4

The title compound was made starting from 2-amino-5-methoxy-4-{[2-(pyrrolidin-yl)ethoxy]methyl}benzoic acid following a method similar as described for Intermediate 1 (Reference 1, step 6). The crude product was purified by chromatography on silica gel using 0-10% solvent A (solvent A: 3% NH₄OH/MeOH) in solvent B (Solvent B: 0.1% NH₄OH/10% MeOH/CH₂Cl₂) to provide the product as a brown solid. LCMS (ES) [M+1]⁺ m/z 361.1.

Reference 11

Synthesis of 9-chloro-7-methoxy-1H,2H,3H-cyclopenta[b]quinolin-6-ol (Intermediate 11)

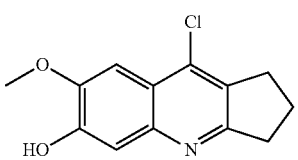 [SMILES: COc1cc2c(Cl)c3c(nc2cc1O)CCC3]

Step 1

Into a 3-L 4-necked round-bottom flask, was placed a mixture of 2-amino-4,5-dimethoxybenzoic acid (98 g, 498 mmol, 1.00 eq.), POCl₃ (3.1 L) and cyclopentanone (46.5 g, 552.7 mmol, 1.10 eq.). The resulting solution was allowed to stir at 110° C. for 16 h. After removal of the volatiles under reduced pressure, the remaining residue was treated with ice/water (1.3 L), basified with 1 N aqueous NaOH to pH=7~8) and extracted with a mixture of CH₂Cl₂/MeOH (V/V=10/1, 5×1.3 L). The combined organic layer were dried over anhydrous Na₂SO₄ and concentrated under vacuum. The residue was purified by silica gel with EtOAc/petroleum ether (1:1) to provide 9-chloro-6,7-dimethoxy-1H,2H,3H-cyclopenta[b]quinolone as a white solid (25.7 g, 24%). LCMS (ES) [M+1]⁺ m/z 264.0.

Step 2

Into a 2-L 4-necked round-bottom flask was placed 9-chloro-6,7-dimethoxy-1H,2H,3H-cyclopenta[b]quinolone (31.6 g, 0.12 mol, 1.00 eq.), CH₂Cl₂ (1.0 L) followed by AlCl₃ (47.88 g, 0.36 mol 3.00 eq.). The resulting solution was allowed to stir at 40° C. for 16 h. This reaction was repeated in this same scale for 4 batches. The resulting mixtures were combined, treated with ice/water (2.0 L) and basified with aqueous NaOH (1.0 N) to pH 7-8. The mixture were combined and directly used in the next step without purification.

Step 3

To the above mixture was added CH₂Cl₂ (2.0 L), Boc₂O (314 g, 1.44 mol, 3.00 eq.) and 4-dimethylaminopyridine (6.1 g, 0.05 mol, 0.10 eq.). The resulting mixture was allowed to stir at rt for 16 h. The organic layer was separated. The water layer was back extracted with a mixture of CH₂Cl₂/MeOH (V/V=10/1, 3×3.0 L). All the organic layers were combined and dried over anhydrous Na₂SO₄. After removal of the organic solvents under reduced pressure, the residue was purified by chromatography on silica gel with EtOAc/petroleum ether (5:1 to 1:1) to provide tert-butyl 9-chloro-7-methoxy-2,3-dihydro-1H-cyclopenta[b]quinolin-6-yl carbonate as white solid (48 g, 20%), LCMS (ES) [M+1]⁺ m/z 350.1; and tert-butyl 9-chloro-6-methoxy-2,3-dihydro-1H-cyclopenta[b]quinolin-7-yl carbonate as a white solid (50 g, 21%), LCMS (ES) [M+1]⁺ m/z 350.1.

Step 4

Into a rt solution of tert-butyl 9-chloro-7-methoxy-2,3-dihydro-1H-cyclopenta[b]quinolin-6-yl carbonate (48.0 g, 0.14 mol, 1.00 eq.) in CH₂Cl₂ (500 mL) was added a saturated HCl solution in dioxane (175 mL) dropwise. The resulting solution was allowed to stir at rt for 16 h. After removal of volatiles under reduced pressure, the residue was triturated with EtOAc (2×200 mL) to provide the title compound as a light brown solid (25.26 g, 74%).

Reference 12

Synthesis of 9-chloro-6-methoxy-1H,2H,3H-cyclopenta[b]quinolin-7-ol (Intermediate 12)

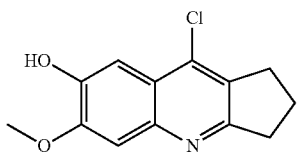 [SMILES: COc1cc2nc3c(c(Cl)c2cc1O)CCC3]

To a solution of tert-butyl 9-chloro-6-methoxy-2,3-dihydro-1H-cyclopenta[b]quinolin-7-yl carbonate (Reference 11, step 3) (1.2 g, 3.43 mmol, 1.00 eq.) in $CH_2Cl_2$ (20 mL) was added a solution of dioxane (10 mL) saturated HCl (gas) dropwise. The resulting solution was stirred for 16 h at rt. After removal of organic volatiles under reduced pressure, the remaining residue was triturated with EtOAc (2×10 mL) to provide the title compound as an off-white solid (769.1 mg, 90%). LCMS (ES) [M-HCl+1]$^+$ m/z 250.0.

Reference 13

Synthesis of [3-({9-chloro-7-methoxy-1H,2H,3H-cyclopenta[b]quinolin-6-yl}oxy)propyl]dimethylamine (Intermediate 13)

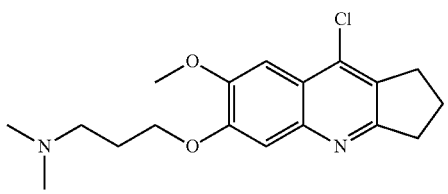 [SMILES: COc1cc2c(Cl)c3c(nc2cc1OCCCN(C)C)CCC3]

A mixture of 9-chloro-7-methoxy-1H,2H,3H-cyclopenta[b]quinolin-6-ol (Intermediate 11) (1.0 g, 4 mmol), N-(3-chloropropyl)-N,N-dimethylamine hydrochloride (696 mg, 4.4 mmol) and $K_2CO_3$ (1.2 g, 8.8 mmol) in DMF (40 ml) was allowed to stir at 100° C. for 3 h. Additional N-(3-chloropropyl)-N,N-dimethylamine hydrochloride (348 mg, 2.2 mmol) and $K_2CO_3$ (0.6 g, 4.4 mmol) were added, and the mixture allowed to continue to stir at 100° C. for 15 h. Another portion of N-(3-chloropropyl)-N,N-dimethylamine hydrochloride (348 mg, 2.2 mmol) and $K_2CO_3$ (0.6 g, 4.4 mmol) were added, and the reaction was allowed to stir at 110° C. for 5 h. The mixture was then cooled to rt and the solution was partitioned into EtOAc (100 ml) and 0.5 M aq. $NaHCO_3$(300 ml). The phases were separated and the aqueous phase was back extracted with EtOAc (2×100 ml). The combined organic phases were then washed with water (100 ml), brine (100 ml), dried over $Na_2SO_4$. After removal of the organic volatiles under reduced pressure, the remaining residue was purified by flash chromatography on silica gel using 0-10% MeOH/$CH_2Cl_2$ to give the title compounds as a tan solid (0.492 g, 37%). LCMS (ES) [M+1]$^+$ m/z 335.2.

Reference 14

Synthesis of {2-[2-({9-chloro-7-methoxy-1H,2H,3H-cyclopenta[b]quinolin-6-yl}oxy)ethoxy]ethyl}dimethylamine (Intermediate 19)

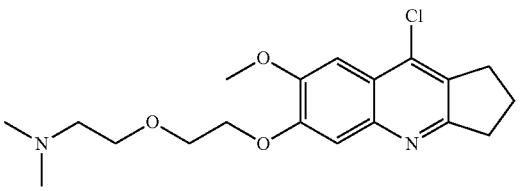 [SMILES: COc1cc2c(Cl)c3c(nc2cc1OCCOCCN(C)C)CCC3]

A mixture of 9-chloro-7-methoxy-1H,2H,3H-cyclopenta[b]quinolin-6-ol (Intermediate 11) (180.00 mg; 0.72 mmol; 1.00 eq.) and (tributylphosphoranylidene)acetonitrile (695.95 mg; 2.88 mmol; 4.00 eq.) in toluene (0.9 mL) was sealed and allowed to stir at 130° C. for 15 min To the mixture was added 2-[2-(dimethylamino)ethoxy]ethan-1-ol (384.06 mg; 2.88 mmol; 4.00 eq.) and the resulting solution was allowed to stir at 130° C. hotplate for 90 min. The mixture was cooled to rt and subjected to chromatography on silica gel using 0-100% solvent A (solvent A: 0.3% $NH_4OH$/10% MeOH/89.7% $CH_2Cl_2$) in $CH_2Cl_2$ to provide the product as a colorless syrup (216 mg, 79%). LCMS (ES) [M+1]$^+$ m/z 365.1.

Reference 15

Synthesis of (3R)-1-[3-({9-chloro-7-methoxy-1H,2H,3H-cyclopenta[b]quinolin-6-yl}oxy)propyl]-3-methoxypyrrolidine (Intermediate 27)

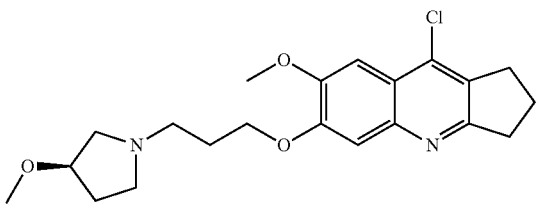 [SMILES: COc1cc2c(Cl)c3c(nc2cc1OCCCN1CC[C@@H](OC)C1)CCC3]

A mixture of (3R)-3-methoxypyrrolidine hydrochloride (101.24 mg; 0.74 mmol; 2.00 eq.), Hunig's base (95.08 mg; 0.74 mmol; 2.00 eq.) in N,N-dimethylformamide (2.40 mL) was allowed to stir at rt for 20 min. To the mixture was added 9-chloro-6-(3-chloropropoxy)-7-methoxy-1H,2H,3H-cyclopenta[b]quinoline (Intermediate 6) (120.00 mg; 0.37 mmol; 1.00 eq.), cesium carbonate (479.41 mg; 1.47 mmol; 4.00 eq.) and KI (30.53 mg; 0.18 mmol; 0.50 eq.) The resulting mixture was heated at 90° C. for 1 hr and the allowed to left at rt for 14 h. The solid was filtered through a small pad of celite. The filtrate was treated with slow addition of water and extracted twice with EtOAc (twice) and 25% $^i$PrOH/$CHCl_3$. The combined organic layers were dried over $MgSO_4$, filtered and concentrated. The remaining residue was purified by chromatography on silica gel using 1% $NH_4OH$/9% MeOH/90% $CH_2Cl_2$ to provide the product as brown solid as off-white solid (90 mg, 63%). LCMS (ES) [M+1]$^+$ m/z 390.8

249

Reference 16

Synthesis of 9'-chloro-7'-methoxy-6'-[3-(pyrrolidin-1-yl)propoxy]-1',3'-dihydrospiro[cyclobutane-1,2'-cyclopenta[b]quinoline](Intermediate 35)

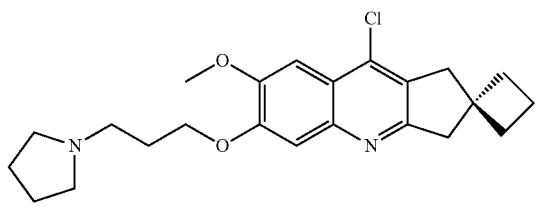

The title compound was made starting from methyl 4-hydroxy-3-methoxybenzoate following a synthetic sequence as described for Intermediate 1 (reference 1), except that spiro[3.4]octan-6-one was used in place of cyclopentanone in step 6. The crude product was purified by chromatography on silica gel using 0-10% solvent A (solvent A: 3% $NH_4OH$/MeOH) in solvent B (Solvent B: 0.1% $NH_4OH$/10% MeOH/$CH_2Cl_2$) to provide the product as a brown solid. LCMS (ES) $[M+1]^+$ m/z 400.8

Reference 17

Synthesis of 9'-chloro-7'-methoxy-6'-[3-(pyrrolidin-1-yl)propoxy]-2',3'-dihydrospiro[cyclobutane-1,1'-cyclopenta[b]quinoline](Intermediate 36)

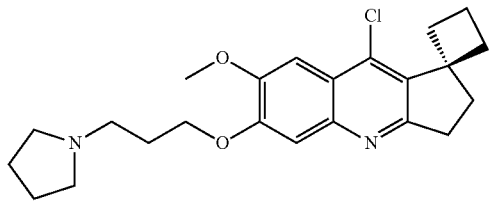

The title compound was made starting from methyl 4-hydroxy-3-methoxybenzoate following a synthetic sequence as described for Intermediate 1 (reference 1), except that spiro[3.4]octan-6-one was used in place of cyclopentanone in step 6. The crude product was purified by chromatography on silica gel using 0-10% solvent A (solvent A: 3% $NH_4OH$/MeOH) in solvent B (Solvent B: 0.1% $NH_4OH$/10% MeOH/$CH_2Cl_2$) to provide the product as a brown solid. LCMS (ES) $[M+1]^+$ m/z 400.8

Intermediates 14, 15, 18 and 20-26 were prepared from Intermediate 11 following a procedure similar to that described for the synthesis of Intermediate 19 in Reference 14. Intermediates 16 and 17 were prepared from Intermediate 11 and the appropriate halides following a procedure similar to that described for the synthesis of Intermediate 13 in Reference 13. Intermediates 28-34 were prepared from Intermediate 6 following a procedure similar as described for the synthesis of Intermediate 27 in Reference 15.

250

Example 1

Synthesis of N-(2-ethoxyethyl)-7-methoxy-6-[3-(pyrrolidin-1-yl)propoxy]-1H,2H,3H-cyclopenta[b]quinolin-9-amine bis(formic acid)

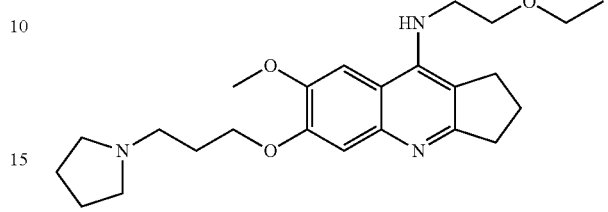

A mixture of 1-[3-({9-chloro-7-methoxy-1H,2H,3H-cyclopenta[b]quinolin-6-yl}oxy)propyl]pyrrolidine (Intermediate 1) (274 mg, 0.76 mmol, 1.00 eq.), 2-ethoxyethan-1-amine (338 mg, 3.8 mmol, 5.0 eq.), t-BuONa (220 mg, 2.28 mmol, 3.00 eq.) in 1, 4-dioxane (4 mL) in a 10 mL microwave reaction vial was purged with N2 for 5 min. To the mixture was added chloro[2-(dicyclohexylphosphino)-3,6-dimethoxy-2',4',6'-triisopropyl-1,1'-biphenyl][2-(2-aminoethyl)phenyl]palladium(II) (BrettPhos Pd G1, Methyl t-Butyl Ether Adduct) (64 mg, 0.08 mmol, 0.1 eq.). The vial was sealed and subjected to a microwave reactor at 115° C. for 1.5 h. The resulting mixture was cooled to rt, treated with water and extracted with 10% MeOH/$CH_2C_2$ thrice. The combined organic layers were concentrated under reduced pressure. The remaining residue was redissolved in DMSO, filtered and subjected to purification on reverse phase preparative HPLC (Prep-C18, 5 µM SunFire column, 19×150 mm, Waters; gradient elution of 5% MeCN in water to 40% MeCN in water over a 20 min period, where both solvents contain 0.1% FA) to provide the title compound as a colorless solid (113 mg, 29%). LCMS (ES) $[M-2FA+1]^+$ m/z 414.2.

Example 2

Synthesis of N-(cyclopropylmethyl)-6-[3-(dimethylamino)propoxy]-7-methoxy-1H,2H,3H-cyclopenta[b]quinolin-9-amine dihydrochloride

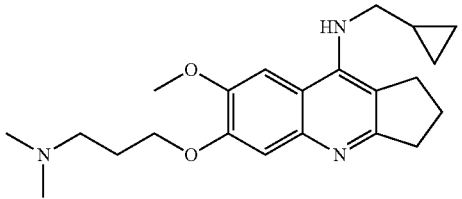 [SMILES: COc1cc2c(NCC3CC3)c3c(nc2cc1OCCCN(C)C)CCC3]

A mixture of [3-({9-chloro-7-methoxy-1H,2H,3H-cyclopenta[b]quinolin-6-yl}oxy)propyl]dimethylamine (Intermediate 13) (80 mg, 0.24 mmol), cyclopropylmethanamine (25.49 mg; 0.36 mmol; 1.50 eq.), t-BuONa (91.84 mg; 0.96 mmol; 4.00 eq.) and chloro[2-(dicyclohexylphosphino)-3,6-dimethoxy-2',4',6'-triisopropyl-1,1'-biphenyl][2-(2-aminoethyl)phenyl]palladium(II) (BrettPhos Pd G1, Methyl t-Butyl Ether Adduct) (19.1 mg; 0.02 mmol; 0.10 eq.) in 1, 4-dioxane (2 mL) in a 10 mL microwave reaction vial was purged with Ar for 5 min. The vial was sealed and subjected to a microwave reactor at 110° C. for 1 h. The resulting mixture was cooled to rt, treated with water and concentrated under reduced pressure. The remaining residue was redissolved in DMSO, filtered and subjected to purification on reverse phase preparative HPLC (Prep-C18, 5 µM SunFire column, 19×150 mm, Waters; gradient elution of 5% MeCN in water to 35% MeCN in water over a 13 min period, where both solvents contain 0.1% HCl) to provide the title compound as a colorless solid (113 mg, 29%). LCMS (ES) [M−2HCl+1]+ m/z 370.4.

Example 3

Synthesis of 6-(3-{3-azabicyclo[3.1.1]heptan-3-yl}propoxy)-N-[(azetidin-3-yl)methyl]-7-methoxy-1H,2H,3H-cyclopenta[b]quinolin-9-amine dihydrochloride

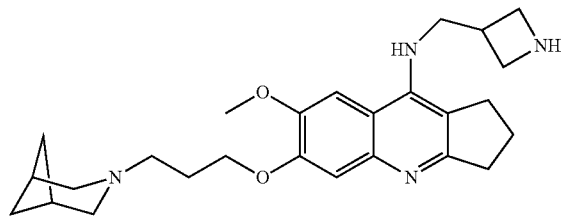 [SMILES: COc1cc2c(NCC3CNC3)c3c(nc2cc1OCCCN1CC2CC(C2)C1)CCC3]

Step 1

Into a solution of 3-[3-({9-chloro-7-methoxy-1H,2H,3H-cyclopenta[b]quinolin-6-yl}oxy)propyl]-3-azabicyclo[3.1.1]heptane (Intermediate 29) (110.00 mg; 0.28 mmol; 1.00 eq.) in 1,4-dioxane (2 ml) was added a solution of tert-butyl 3-(aminomethyl)-1-azetidinecarboxylate (79.43 mg; 0.43 mmol; 1.50 eq.) in dioxane (1 mL) followed by chloro[2-(dicyclohexylphosphino)-3,6-dimethoxy-T,4',6'-triisopropyl-1,1'-biphenyl][2-(2-aminoethyl)phenyl]palladium(II) (BrettPhos Pd G1, Methyl t-Butyl Ether Adduct, 22.71 mg; 0.03 mmol; 0.10 eq.) and ᵗBuONa (54.6 mg; 0.57 mmol; 2.00 eq.). The resulting mixture was allowed to stir at 125° C. for 25 min, cooled to rt and treated with MeCN. The insolubles were filtered, and the filtrate was concentrated under reduced pressure. The residue was subjected to purification on reverse phase preparative HPLC (Prep-C18, 5 µM SunFire column, 19×150 mm, Waters; gradient elution of 5% MeCN in water to 80% MeCN in water over a 13 min period, where both solvents contain 0.1% HCl) to provide tert-butyl 3-({[6-(3-{3-azabicyclo[3.1.1]heptan-3-yl}propoxy)-7-methoxy-1H,2H,3H-cyclopenta[b]quinolin-9-yl]amino}methyl)azetidine-1-carboxylate dihydrochloride as a colorless solid.

Step 2

To a solution of above intermediate in $CH_2Cl_2$ (1 mL) was added trifluoroacetic acid (1 mL) The resulting mixture was allowed to stir at rt for 30 min. After removal of the organic volatiles under reduced pressure, the remaining residue was subjected to purification on reverse phase preparative HPLC (Prep-C18, 5 µM XBridge column, 19×150 mm, Waters; gradient elution of 5% MeCN in water to 60% MeCN in water over a 13 min period, where both solvents contain 0.1% HCl) to provide the title compound as a white solid (7 mg, 6%). LCMS (ES) [M−2HCl+1]+ m/z 437.1.

Example 4

Synthesis of 2-methoxy-N-(propan-2-yl)-3-[3-(pyrrolidin-1-yl)propoxy]-6H, 7H, 8H-cyclopenta[b]1,5-naphthyridin-9-amine, bis (2,2,2-trifluoroacetic acid)

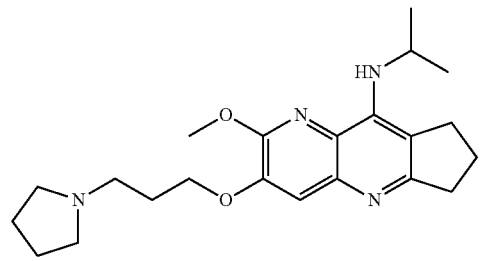

The title compound was made from 1-[3-({9-chloro-2-methoxy-6H,7H,8H-cyclopenta[g]quinolin-3-yl}oxy)propyl]pyrrolidine (Intermediate 9) following a synthetic method similar as described in Example 1, except that propan-2-amine was used in place of 2-ethoxyethan-1-amine. The crude product was subjected to reverse phase preparative HPLC (Prep-C18, 5 µM XBridge column, 19×150 mm, Waters; gradient elution of 10% MeCN in water to 40% MeCN in water over a 6 min period, where both solvents contain 0.05% TFA) to provide the title compound as brown oil (247 mg, 54%). LCMS (ES) [M−2TFA+1]+ m/z 385.3.⁻

Compounds in the remaining entries of Table 1 were made from the corresponding intermediates, as exemplified by Intermediates 1-36 in Table B, and the appropriate amines or appropriate amine hydrochloride salts, following procedures well known in the art, as exemplified by either Example 1, 2, 3 or 4. The final compounds were collected as either free base, or in salt form, for example, hydrochloride, formate or trifluoroacetate salts.

BIOLOGICAL EXAMPLES

Example 1

Determination of G9a Enzymatic Activity Assay

The G9a AlphaLISA assay was used to detect the methyl modifications of a biotinylated histone H3 peptide by the compounds. These modifications are done by the histone methyl transferase activity of the G9a enzyme. The assay consists of reading a chemiluminescent signal at 615 nm; this signal is generated by a laser excitation at 680 nm that transfers a reactive singlet oxygen between the donor beads and acceptor beads. Donor beads are streptavidin conjugated and bind to the biotin on the peptide. Acceptor beads are conjugated with an antibody that recognizes the specific G9a methyl mark on the peptide. If there is a methyl mark on the peptide, the acceptor beads will bind to the peptide. Upon binding, the acceptor beads will be in close proximity (<200 nm) of the donor beads and when the donor beads are excited, the transfer of the oxygen can occur and a strong signal will be generated. If there is no methyl mark, the interaction between beads will not occur and signal will be at background levels.

For the assay, the following buffer was used to set up reactions: 50 mM Tris-HCl pH9, 50 mM NaCl, 0.01% Tween-20 and 1 mM DTT (added fresh prior to starting the reactions). The assay is set up by adding a final concentration of 0.15 nM G9a, 15 uM S-adenosyl-methionine and 100 nM biotinylated histone 3 peptide (1-21). The reaction is incubated at rt for 1 hour and subsequently quenched by the addition of the acceptor beads (anti-H3k9me2 AlphaLISA acceptor beads, PerkinElmer #AL117) at a final concentration of 20 ug/mL. The acceptor beads are incubated for 1 hour. After 1 hour, the donor beads are added at a final concentration of 20 ug/mL (Alpha Streptavidin donor beads, PerkinElmer #6760002). Donor beads are incubated for 0.5 hours. Both donor and acceptor beads are resuspended in AlphaLISA 5X Epigenetics Buffer 1 Kit (PerkinElmer #AL008) prior to addition to the reaction. All manipulations and incubations with the donor and acceptor beads are done in subdued light. Signal is detected in an EnVision plate reader in Alpha mode. See *ACS Med Chem Lett.* 2014; 5(2):205-9.

Percent inhibition was calculated for each compound dilution and the concentration that produced 50% inhibition was calculated. This value is presented as the $pIC_{50}$, which is the negative log of the $IC_{50}$ value in molar. The $pIC_{50}$ values for a representative number of compounds of the disclosure are provided in Table C below.

TABLE C

| No | $pIC_{50}$ |
| --- | --- |
| 1 | 6.8 |
| 2 | 6.8 |
| 3 | 8.04 |
| 4 | 8.21 |
| 5 | 5 |
| 6 | 7.42 |
| 7 | 7.51 |
| 8 | 7.29 |
| 9 | 7.92 |
| 10 | 8.2 |
| 11 | 7.76 |
| 12 | 8.08 |
| 13 | 7.5 |
| 14 | 7.58 |
| 15 | 7.65 |
| 16 | 7.43 |
| 17 | 7.71 |
| 18 | 7.66 |
| 19 | 8.1 |
| 20 | 7.14 |
| 21 | 7.08 |
| 22 | 6.76 |
| 23 | 6.33 |
| 24 | 7.62 |
| 25 | 7.81 |
| 26 | 7.95 |
| 27 | 7.9 |
| 28 | 8 |
| 29 | 8.22 |
| 30 | 7.45 |
| 31 | 6.96 |
| 32 | 6.97 |
| 33 | 6.84 |
| 34 | 7.54 |
| 35 | 7.2 |
| 36 | 7.71 |
| 37 | 6.97 |
| 38 | 6.67 |
| 39 | 7.24 |
| 40 | 7.39 |

TABLE C-continued

| No | $pIC_{50}$ |
| --- | --- |
| 41 | 7.47 |
| 42 | 7.01 |
| 43 | 7.4 |
| 44 | 6.78 |
| 45 | 7.76 |
| 46 | 5.51 |
| 47 | 5.87 |
| 48 | 6.22 |
| 49 | 6.19 |
| 50 | 6.11 |
| 51 | 5 |
| 52 | 5 |
| 53 | 5 |
| 54 | 7.07 |
| 55 | 6.09 |
| 56 | 5.98 |
| 57 | 5.83 |
| 58 | 5.56 |
| 59 | 5 |
| 60 | 5 |
| 61 | 6.27 |
| 62 | 6.03 |
| 63 | 7.74 |
| 64 | 6.9 |
| 65 | 7.14 |
| 66 | 6.36 |
| 67 | 8.87 |
| 68 | 5.81 |
| 69 | 5.57 |
| 70 | 8.31 |
| 71 | 7.39 |
| 72 | 5.71 |
| 73 | 8.84 |
| 74 | 8.08 |
| 75 | 7.28 |
| 76 | 8.19 |
| 77 | 5 |

FORMULATION EXAMPLES

The following are representative pharmaceutical formulations containing a compound of the present disclosure.

Tablet Formulation

The following ingredients are mixed intimately and pressed into single scored tablets.

| Ingredient | Quantity per tablet (mg) |
| --- | --- |
| Compound of this disclosure, or a pharmaceutically acceptable salt thereof | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per tablet (mg) |
| --- | --- |
| Compound of this disclosure, or a pharmaceutically acceptable salt thereof | 200 |
| lactose spray dried | 148 |
| magnesium stearate | 2 |

Injectable Formulation

Compound of the disclosure (e.g., compound 1) in 2% HPMC, 1% Tween 80 in DI water, pH 2.2 with MSA, q.s. to at least 20 mg/mL.

Inhalation Composition

To prepare a pharmaceutical composition for inhalation delivery, 20 mg of a compound disclosed herein is mixed with 50 mg of anhydrous citric acid and 100 mL of 0.9% NaCl (aq). The mixture is incorporated into an inhalation delivery unit, such as a nebulizer, which is suitable for inhalation administration.

Topical Gel Composition

To prepare a pharmaceutical topical gel composition, 100 mg of a compound disclosed herein is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Ophthalmic Solution Composition

To prepare a pharmaceutical ophthalmic solution composition, 100 mg of a compound disclosed herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Nasal Spray Solution

To prepare a pharmaceutical nasal spray solution, 10 g of a compound disclosed herein is mixed with 30 mL of a 0.05M phosphate buffer solution (pH 4.4). The solution is placed in a nasal administrator designed to deliver 100 μL of spray for each application.

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed:

1. A compound of Formula (I)

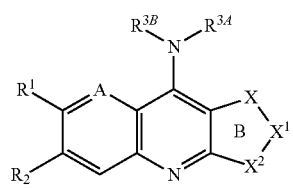

or a pharmaceutically acceptable salt thereof, wherein:

A is CH or N;

$R^1$ is hydroxy, alkoxy or haloalkoxy;

$R^2$ is —$(CH_2)_{0-1}$—O—Alk—$R^{2A}$ or cycloalkoxy, wherein said cycloalkoxy is optionally substituted with heterocyclylalkyl;

Alk is an alkylene wherein one, two or three carbon atoms of the alkylene chain are optionally and independently replaced by $NR^4$ or O, and the alkylene chain is optionally substituted with one or two substituents independently selected from hydroxy, alkoxy, halogen and heterocyclylalkyl;

$R^4$ is hydrogen or alkyl;

$R^{2A}$ is (a) heterocyclyl, optionally substituted with one or more $R^B$, independently selected from hydroxy, alkyl, alkoxy, halogen, cyano, heterocyclylalkyl, haloalkyl and haloalkoxy, (b) spiroheterocycloamino, optionally substituted with one or more $R^c$, wherein $R^c$ is alkyl, (c) heteroaryl, optionally substituted with one or more $R^D$, independently selected from alkyl, alkoxy, halogen and hydroxy, (d) cycloalkyl, optionally substituted with one or more $R^E$, independently selected from hydroxy and heterocyclylalkyl, (e) aryl, optionally substituted with one or more $R^F$, independently selected from hydroxy, halogen, alkoxy and alkyl, (f) sulfamido, (g) alkylcarbonyl, (h) N-sulfonamido, S-sulfonamido, optionally substituted with one or two alkyl groups, (j) aminocarbonyl, (k) alkylamino, (l) haloalkyl, (m) alkoxy, (n) amino, or (o) hydroxy;

$R^{3A}$ is (a) alkyl, optionally substituted with one or more $R^G$, independently selected from alkoxy, hydroxy and cyano, (b) heterocyclyl, optionally substituted with one or more $R^H$, independently selected from alkyl, aryl, and heteroaryl, wherein said aryl and heteroaryl are optionally substituted with one or more halogens, (c) cycloalkylalkyl, (d) heteroaralkyl, (e) heterocyclylalkyl, or (f) cycloalkyl, optionally substituted with cyano;

$R^{3B}$ is hydrogen, alkyl or —(C=O)$NH_2$;

X is $(CR^{4A}R^{4B})_m$, $NR^{4C}$, O or

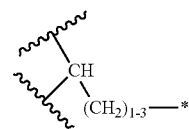

wherein "*" indicates a point of attachment to another carbon atom in Ring B;

$X^1$ is $CR^{5A}R^{5B}$, $NR^{5c}$ or O;

$X^2$ is $(CR^{6A}R^{6B})_n$, $NR^{6C}$ or O;

wherein, X and $X^1$ cannot each be oxygen or nitrogen;

m is 1, 2 or 3;

n is 1, 2 or 3;

wherein the sum of m+n is 2, 3, 4 or 5;

each $R_{4A}$, $R^{4B}$, $R^{4C}$, $R^{5A}$, $R^{5B}$, $R^{5C}$, $R^{6A}$, $R^{6B}$, and $R^{6C}$ is independently hydrogen or alkyl;

provided that:
i. when X is

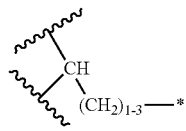

then:
at least one of $X^1$ and $X^2$ is $CR^{5A}R^{5B}$ or $(CR^{6A}R^{6B})_n$, respectively, and one of $R^{5A}$, $R^{5B}$, $R^{6A}$ and $R^{6B}$ is replaced by a bond to the point of attachment of

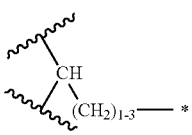

indicated by "*", such that Ring B is a 7- to 11-membered bridged ring system;

ii when $R^1$ is methoxy; $R^2$ is

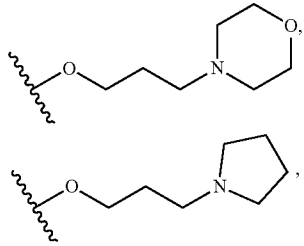

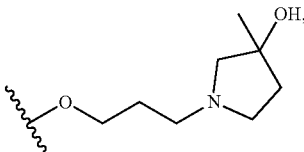

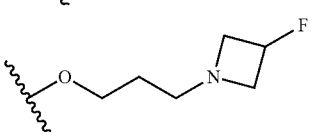

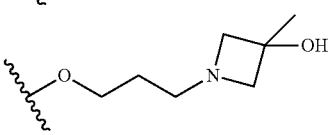

$R^{3A}$ is an unsubstituted $C_1$-$C_6$ alkyl; and $R_{3B}$ is hydrogen; then:
(a1) at least one of X, $X^1$ and $X^2$ is not $(CR^{4A}R^{4B})_m$, $CR^{5A}R^{5B}$ and $(CR^{6A}R^{6B})_n$, respectively;
(b1) the sum of m+n is 4 or 5;
(c1) A is N;
(d1) at least one of $R^{4A}$, $R^{4B}$, $R^{4C}$, $R^{5A}$, $R^{5B}$, $R^{5C}$, $R^{6A}$, $R^{6B}$ and $R^{6C}$ is independently alkyl;

or
(e1) any two, any three, or all four of said (a1), (b1), (c1) and (d1) apply;

iii when $R^1$ is methoxy; $R^2$ is

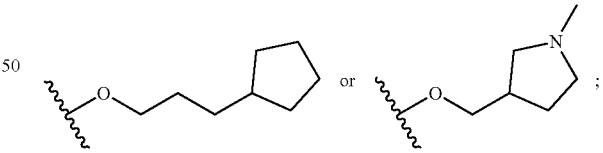

$R^{3A}$ is

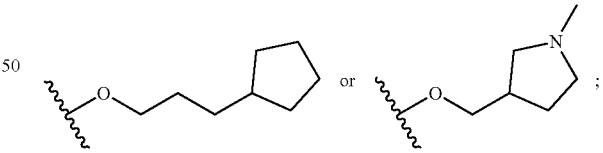

and $R^{3B}$ is hydrogen; then:
(f1) at least one of X, $X^1$ and $X^2$ is not $(CR^{4A}R^{4B})_m$, $CR^{5A}R^{5B}$ and $(CR^{6A}R^{6B})_n$, respectively;
(g1) the sum of m+n is 4 or 5;
(h1) A is N;
(i1) at least one of $R^{4A}$, $R^{4B}$, $R^{4C}$, $R^{5A}$, $R^{5B}$, $R^{5C}$, $R^{6A}$, $R^{6B}$ and $R^{6C}$ is independently alkyl;

or
(j1) any two, any three, or all four of said (f1), (g1), (h1) and (i1) apply; and iv when $R^1$ is methoxy; $R^{3A}$ is an unsubstituted cyclopropylmethyl, an unsubstituted cyclopropylethyl, an unsubstituted cyclobutylmethyl, an unsubstituted cyclobutylethyl, an unsubstituted cyclopentylethyl, an unsubstituted cyclohexylmethyl, or an unsubstituted cyclohexylethyl; and $R_{3B}$ is hydrogen; then:

$R^2$ is not

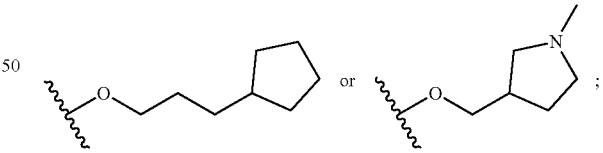

v when $R^1$ is methoxy; $R^2$ is

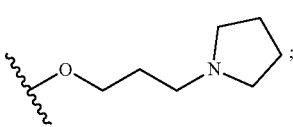

Ring B is

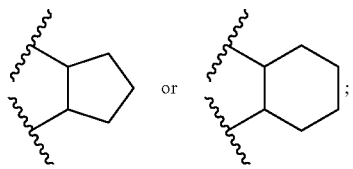 [SMILES: *C1CCCC1* ; *C1CCCCC1*]

$R_{3B}$ is hydrogen; and A is CH; then:
- (k1) $R^{3A}$ is not a 4- to 6-membered unsubstituted heterocyclyl group having 1 oxygen and 0 nitrogen atoms;
- (l1) $R^{3A}$ is not a 4- to 6-membered heterocyclyl group having 1 oxygen and 0 nitrogen atoms and substituted with one or two $C_1$-$C_3$ alkyl groups;
- (m1) $R^{3A}$ is not unsubstituted or N—$C_1$-$C_6$ alkyl-substituted 2-pyrrolidinone;
- (n1) $R^{3A}$ is not unsubstituted or N—$C_1$-$C_6$ alkyl-substituted 2-piperidone;
- (o1) $R^{3A}$ is not N—$C_1$-$C_6$ alkyl-substituted 4-piperidine;

or
- (p1) any two, any three, any four, or all five of said (k1), (l1), (m1), (n1) and (o1) apply;

vi when $R^1$ is methoxy; $R^2$ is

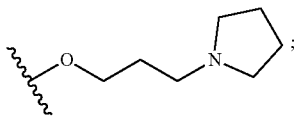 [SMILES: *OCCCN1CCCC1]

$R^{3B}$ is hydrogen; A is CH; and Ring B is

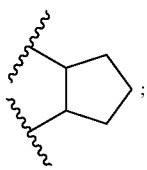 [SMILES: *C1CCCC1*]

then:
$R^{3A}$ is not pyridinylmethyl;

vii when $R^1$ is methoxy; $R^2$ is

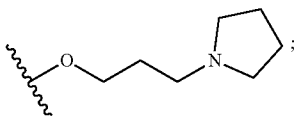 [SMILES: *OCCCN1CCCC1]

$R^{3A}$ is a $C_1$-$C_6$ alkyl, mono-substituted with hydroxy or

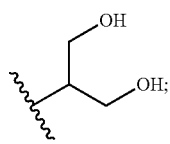 [SMILES: *C(CO)CO]

$R_{3B}$ is hydrogen; and A is CH; then:
- (q1) at least one of X, $X^1$ and $X^2$ is not $(CR^{4A}R^{4B})_m$, $CR^{5A}R^{5B}$ and $(CR^{6A}R^{6B})_n$, respectively;
- (r1) the sum of m+n is 4 or 5;
- (s1) at least one of $R^{4A}$, $R^{4B}$, $R^{4C}$, $R^{5A}$, $R^{5B}$, $R^{5C}$, $R^{6A}R^{6B}$ and $R^6$ is independently alkyl;

or
- (t1) any two, or all three of said (q1), (r1) and (s1) apply;

viii when $R^1$ is methoxy; $R^2$ is

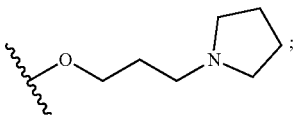 [SMILES: *OCCCN1CCCC1]

$R^{3B}$ is hydrogen; A is CH; and Ring B is

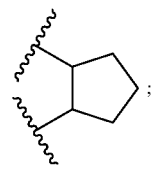 [SMILES: *C1CCCC1*]

then:
$R^{3A}$ is not selected from: 3-oxetanylmethyl, 3-azetidylmethyl, 3-(N-methylcarbamoyl)-azetidylmethyl, 3-(N-methylcarbamoyl)-azetidylethyl and

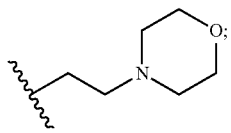 [SMILES: *CCN1CCOCC1]

ix. when $R^1$ is methoxy; $R^2$ is

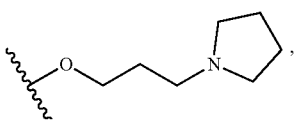

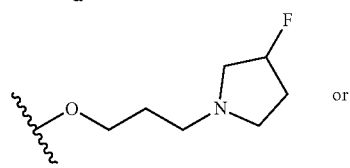

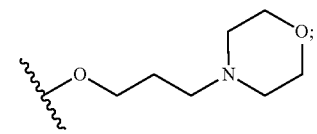

$R^{3A}$ is an unsubstituted $C_3$-$C_6$ cycloalkyl; and $R^{3B}$ is hydrogen; then:

A is N; and x the compound of Formula (I) is not selected from:

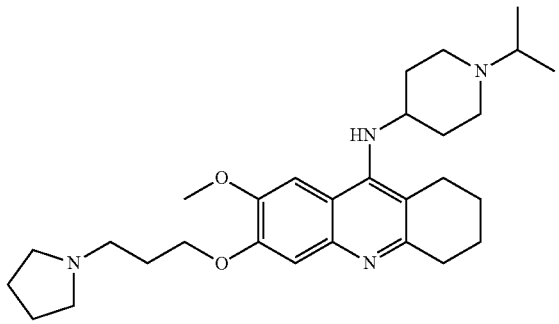

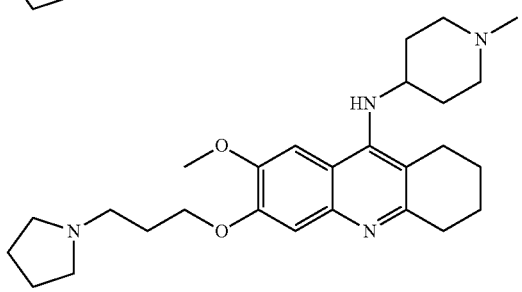
and

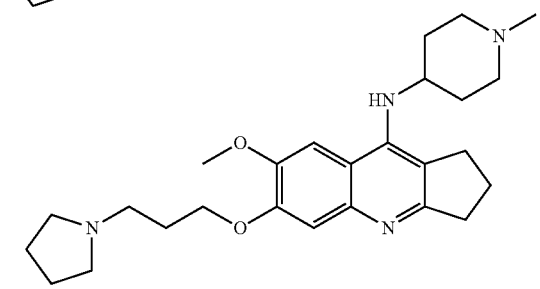

2. The compound of claim 1, wherein A is CH.
3. The compound of claim 1, wherein $R^{3B}$ is hydrogen.
4. The compound of claim 1, wherein X is $(CR^{4A}R^{4B})_m$.
5. The compound of claim 4, wherein m is 1.
6. The compound of claim 4, wherein $R^{4A}$ and $R^{4B}$ are each methyl.
7. The compound of claim 4, wherein m is 2.
8. The compound of claim 4, wherein $R^{4A}$ and $R^{4B}$ are each hydrogen.
9. The compound of claim 1, wherein:
(i) X is

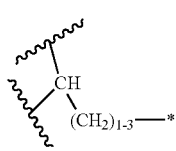

wherein "*" represents the point of attachment to another carbon atom in Ring B,
(ii) at least one of $X^1$ and $X^2$ is $CR^{5A}R^{5B}$ or $(CR^{6A}R^{6B})_n$, respectively, and
(iii) one of $R^{5A}$, $R^{5B}$, $R^{6A}$ and $R^{6B}$ is replaced by a bond to "*", such that
(iv) Ring B is a 7- to 11-membered bridged ring system.

10. The compound of claim 1, wherein $X^1$ is $CR^{5A}R^{5B}$.
11. The compound of claim 10, wherein $R^{5A}$ and $R^{5B}$ are each methyl.
12. The compound of claim 10, wherein $R^{5A}$ and $R^{5B}$ are each hydrogen.
13. The compound of claim 1, wherein $X^2$ is $(CR^{6A}R^{6B})_n$.
14. The compound of claim 13, wherein n is 1.
15. The compound of claim 13, wherein $R^{6A}$ and $R^{6B}$ are each hydrogen.
16. The compound of claim 1, wherein $R^1$ is alkoxy.
17. The compound of claim 16, wherein $R^1$ is —$OCH_3$.
18. The compound of claim 1, wherein $R^1$ is hydroxy.
19. The compound of claim 1, wherein $R^1$ is haloalkoxy.
20. The compound of claim 1, wherein $R^2$ is —O—Alk—$R_2A$.
21. The compound of claim 20, wherein Alk is

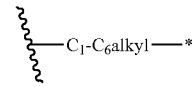

wherein "*" represents the point of attachment of $R^{2A}$; wherein the alkylene chain is optionally substituted with one or two substituents independently selected from hydroxy, alkoxy, halogen and heterocyclylalkyl; and wherein the $C_1$-$C_6$ alkyl is straight-chained or branched.

22. The compound of claim 1, wherein Alk is

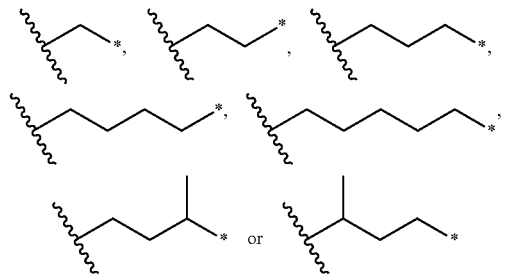

wherein "*" represents the point of attachment of $R^{2A}$; and wherein the alkylene chain is optionally substituted with one or two substituents independently selected from hydroxy, alkoxy, halogen and heterocyclylalkyl.

23. The compound of claim 1, wherein Alk is

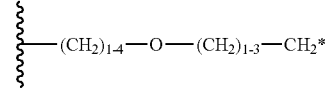

wherein "*" represents the point of attachment of $R^{2A}$.

24. The compound of claim 1, wherein Alk is

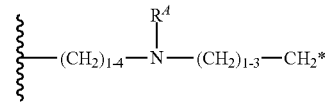

wherein "*" represents the point of attachment of $R^{2A}$; and wherein $R^A$ is hydrogen or a $C_1$-$C_3$ alkyl.

25. The compound of claim 1, wherein Alk is

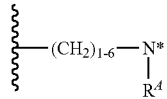

wherein "*" represents the point of attachment of $R^{2A}$;
wherein $R^A$ is hydrogen or a $C_1$-$C_6$ alkyl;
and wherein the alkylene chain is optionally substituted with one or two substituents independently selected from hydroxy, alkoxy, halogen and heterocyclylalkyl.

26. The compound of claim 1, wherein $R^{2A}$ is heterocyclyl, wherein said heterocyclyl is optionally substituted with one or more $R^B$, wherein each $R^B$ is independently selected from hydroxy, alkyl, alkoxy, halogen, cyano, heterocyclylalkyl, haloalkyl and haloalkoxy.

27. The compound of claim 26, wherein $R^{2A}$ is

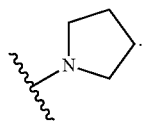

28. The compound of claim 1, wherein $R^{2A}$ is sulfamido.
29. The compound of claim 1, wherein $R^{2A}$ is acetyl bonded to a nitrogen atom in Alk.
30. The compound of claim 1, wherein $R^{2A}$ is N-sulfonamido.
31. The compound of claim 1, wherein $R^{2A}$ is alkylamino.
32. The compound of claim 1, wherein $R^{2A}$ is haloalkyl.
33. The compound of claim 1, wherein $R^{2A}$ is alkoxy.
34. The compound of claim 1, wherein $R^{2A}$ is amino.
35. The compound of claim 1, wherein $R^{2A}$ is a 5- or 6-membered heteroaryl, wherein said 5- or 6-membered heteroaryl is optionally substituted with one or two $R^D$, wherein each $R^D$ is independently selected from alkyl, alkoxy, halogen and hydroxy.
36. The compound of claim 1, wherein $R^{3A}$ is alkyl, wherein said alkyl is optionally substituted with one or more $R^G$, wherein each $R^G$ is independently selected from alkoxy, hydroxy and cyano.
37. The compound of claim 1, wherein $R^{3A}$ is heterocyclyl or heteroaryl, wherein said heterocyclyl is optionally substituted with one or more $R^H$, wherein each $R^H$ is independently selected from alkyl, aryl, and heteroaryl, wherein said heteroaryl and aryl are optionally substituted with one or more halogens.
38. The compound of claim 1, wherein $R^{3A}$ is cycloalkylalkyl.
39. The compound of claim 1, wherein $R^{3A}$ is heteroaralkyl.
40. The compound of claim 1, wherein $R^{3A}$ is heterocyclylalkyl.
41. The compound of claim 1, wherein the compound is selected from the group consisting of

| No | Structure |
|---|---|
| 1 | 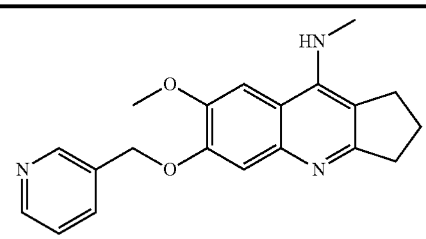 |
| 2 | 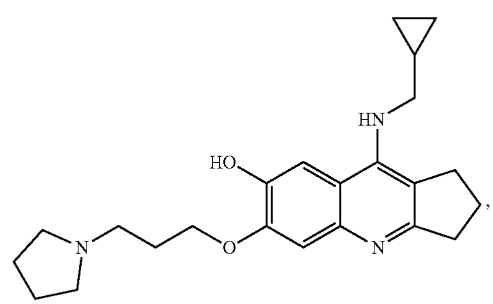 [SMILES: Oc1cc2c(NCC3CC3)c3c(nc2cc1OCCCN1CCCC1)CCC3] |
| 3 | 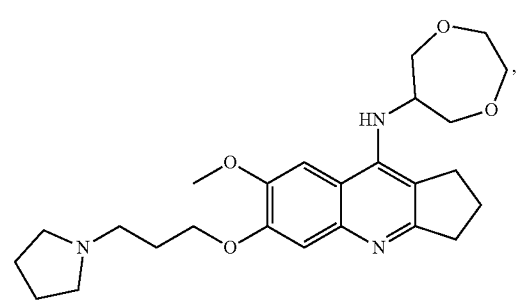 [SMILES: COc1cc2c(NC3COCCOC3)c3c(nc2cc1OCCCN1CCCC1)CCC3] |

| No | Structure |
|---|---|
| 4 | 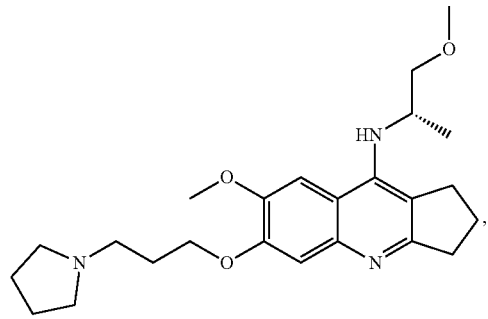 [SMILES: COC[C@H](C)Nc1c2c(nc3cc(OCCCN4CCCC4)c(OC)cc13)CCC2] |
| 5 | 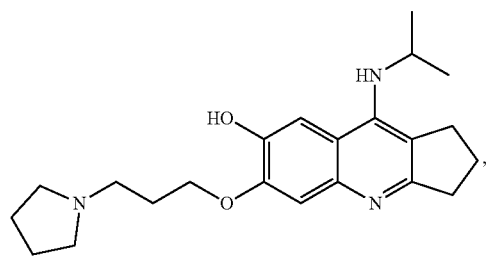 [SMILES: CC(C)Nc1c2c(nc3cc(OCCCN4CCCC4)c(O)cc13)CCC2] |
| 6 | 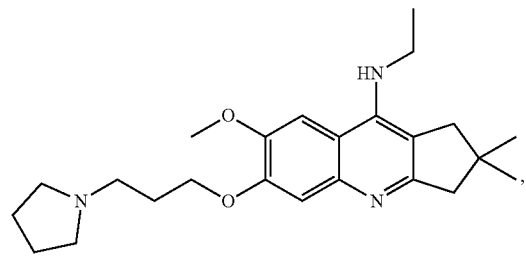 [SMILES: CCNc1c2c(nc3cc(OCCCN4CCCC4)c(OC)cc13)CC(C)(C)C2] |
| 7 | 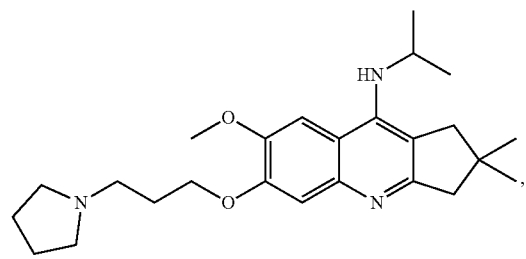 [SMILES: COc1cc2c(NC(C)C)c3c(nc2cc1OCCCN1CCCC1)CC(C)(C)C3] |
| 8 | 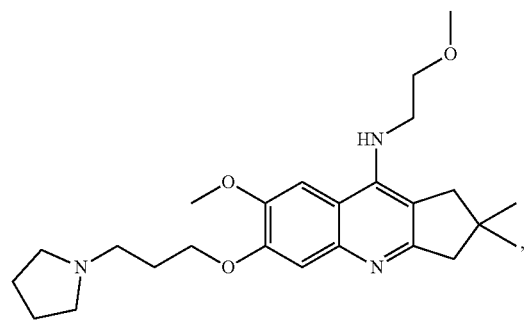 [SMILES: COCCNc1c2c(nc3cc(OCCCN4CCCC4)c(OC)cc13)CC(C)(C)C2] |

| No | Structure |
|---|---|
| 9 | 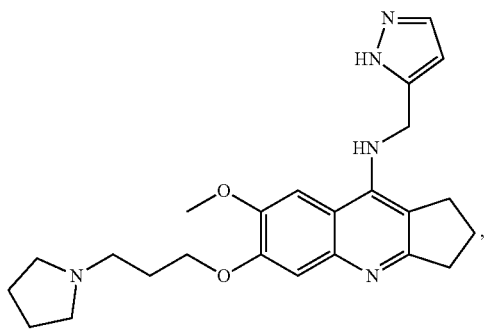 [SMILES: COc1cc2c(NCc3ccn[nH]3)c3c(nc2cc1OCCCN1CCCC1)CCC3] |
| 10 | 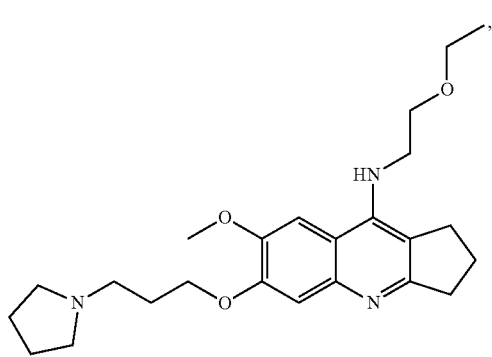 [SMILES: CCOCCNc1c2c(nc3cc(OCCCN4CCCC4)c(OC)cc13)CCC2] |
| 11 | 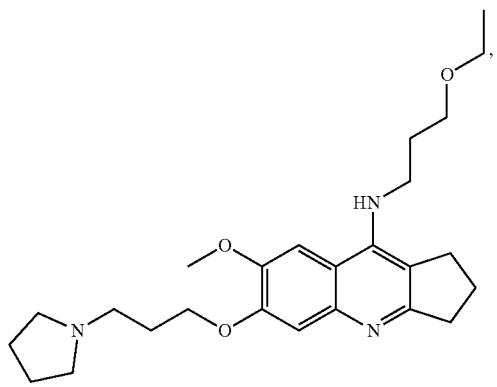 [SMILES: CCOCCCNc1c2c(nc3cc(OCCCN4CCCC4)c(OC)cc13)CCC2] |
| 12 | 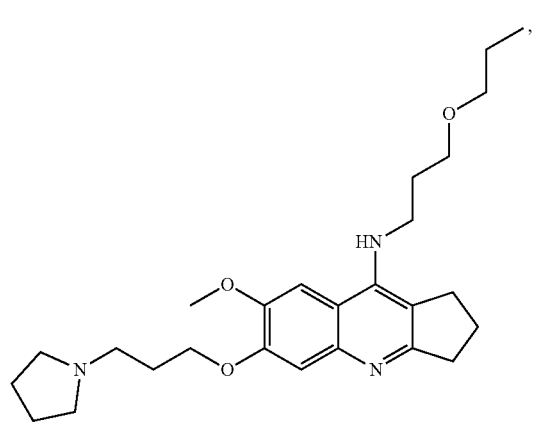 [SMILES: CCCOCCCNc1c2c(nc3cc(OCCCN4CCCC4)c(OC)cc13)CCC2] |

| No | Structure |
|---|---|
| 13 | 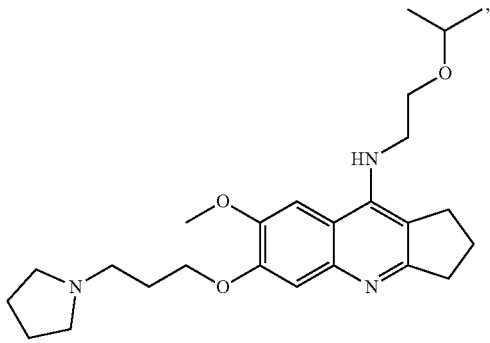 [SMILES: COc1cc2c(NCCOC(C)C)c3c(nc2cc1OCCCN1CCCC1)CCC3] |
| 14 | 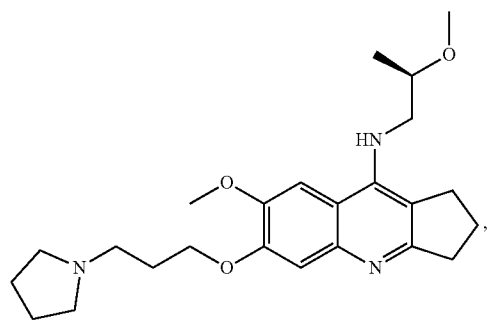 [SMILES: COc1cc2c(NC[C@@H](C)OC)c3c(nc2cc1OCCCN1CCCC1)CCC3] |
| 15 | 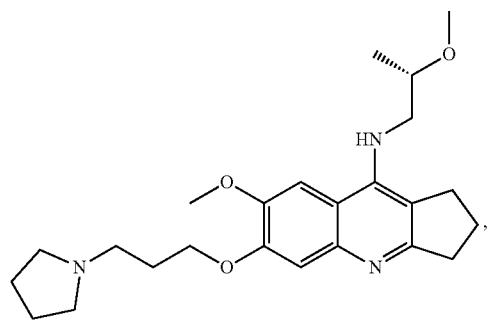 [SMILES: COc1cc2c(NC[C@H](C)OC)c3c(nc2cc1OCCCN1CCCC1)CCC3] |
| 16 | 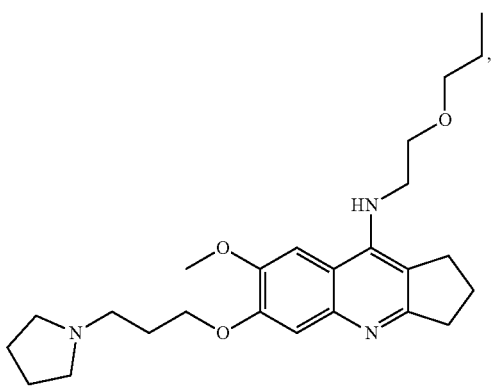 [SMILES: CCCOCCNc1c2c(nc3cc(OCCCN4CCCC4)c(OC)cc13)CCC2] |

-continued
| No | Structure |
|---|---|
| 17 | 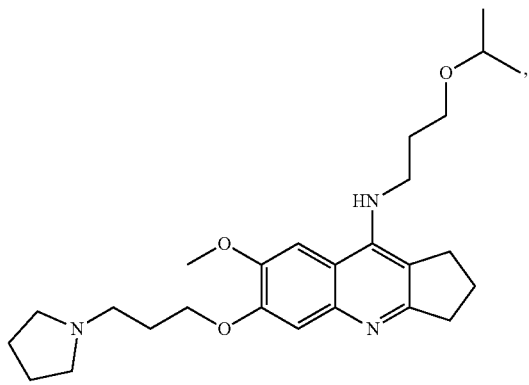 [SMILES: COc1cc2c(NCCCOC(C)C)c3c(nc2cc1OCCCN1CCCC1)CCC3] |
| 18 | 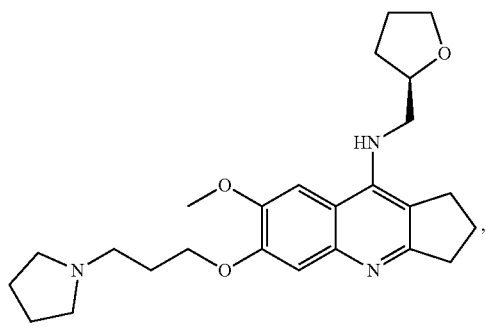 [SMILES: COc1cc2c(NC[C@H]3CCCO3)c3c(nc2cc1OCCCN1CCCC1)CCC3] |
| 19 | 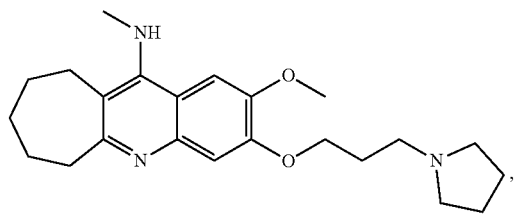 [SMILES: CNc1c2c(nc3cc(OCCCN4CCCC4)c(OC)cc13)CCCCC2] |
| 20 | 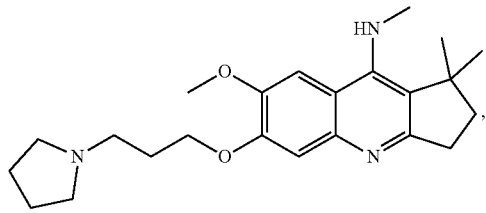 [SMILES: CNc1c2c(nc3cc(OCCCN4CCCC4)c(OC)cc13)CCC2(C)C] |
| 21 | 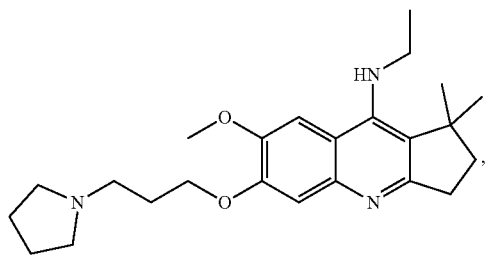 [SMILES: CCNc1c2c(nc3cc(OCCCN4CCCC4)c(OC)cc13)CCC2(C)C] |

| No | Structure |
|---|---|
| 22 | 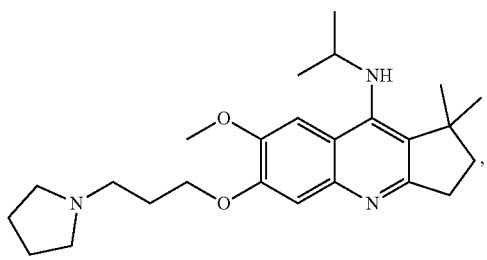 [SMILES: COc1cc2c(NC(C)C)c3c(nc2cc1OCCCN1CCCC1)CCC3(C)C] |
| 23 | 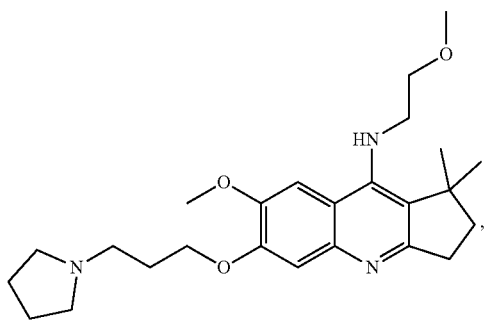 [SMILES: COCCNc1c2c(nc3cc(OCCCN4CCCC4)c(OC)cc13)CCC2(C)C] |
| 24 | 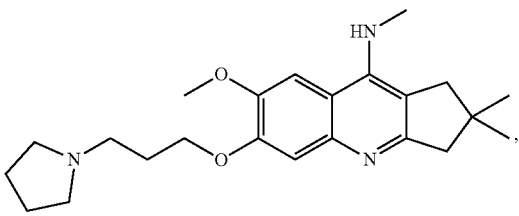 [SMILES: CNc1c2c(nc3cc(OCCCN4CCCC4)c(OC)cc13)CC(C)(C)C2] |
| 25 | 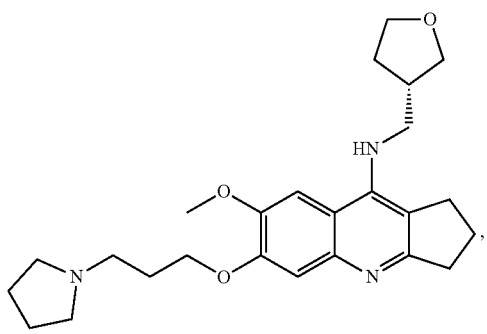 [SMILES: COc1cc2c(NC[C@@H]3CCOC3)c3c(nc2cc1OCCCN1CCCC1)CCC3] |
| 26 | 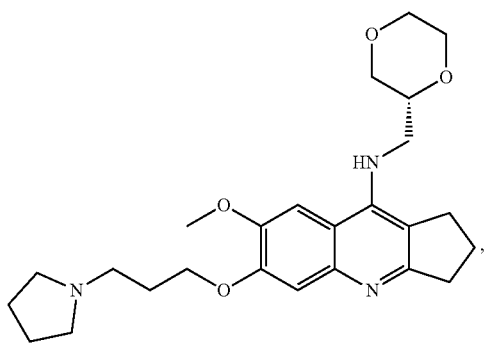 [SMILES: COc1cc2c(NC[C@@H]3COCCO3)c3c(nc2cc1OCCCN1CCCC1)CCC3] |

| No | Structure |
|---|---|
| 27 | 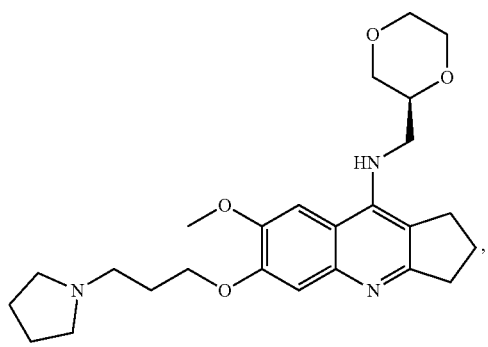 [SMILES: COc1cc2c(NC[C@H]3COCCO3)c3c(nc2cc1OCCCN1CCCC1)CCC3] |
| 28 | 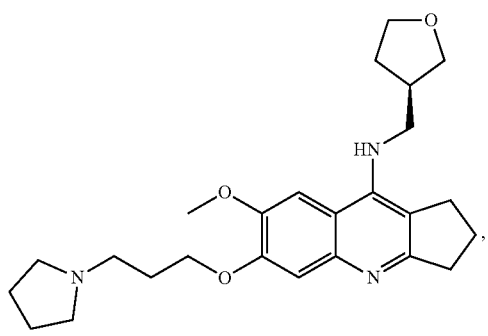 [SMILES: COc1cc2c(NC[C@H]3CCOC3)c3c(nc2cc1OCCCN1CCCC1)CCC3] |
| 29 | 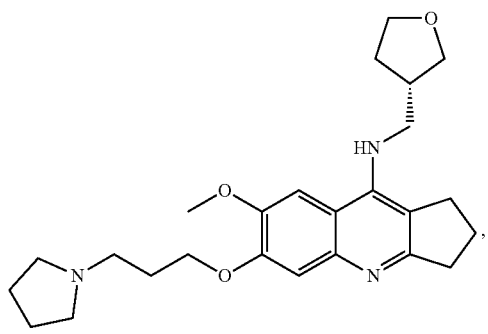 [SMILES: COc1cc2c(NC[C@@H]3CCOC3)c3c(nc2cc1OCCCN1CCCC1)CCC3] |
| 30 | 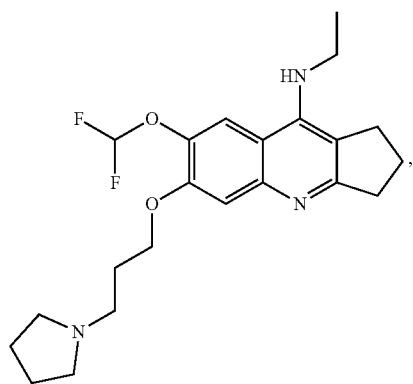 [SMILES: CCNc1c2c(nc3cc(OCCCN4CCCC4)c(OC(F)F)cc13)CCC2] |

| No | Structure |
|---|---|
| 31 | 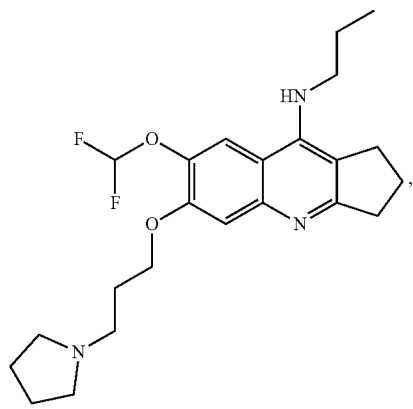 [SMILES: CCCNc1c2c(nc3cc(OCCCN4CCCC4)c(OC(F)F)cc13)CCC2] |
| 32 | 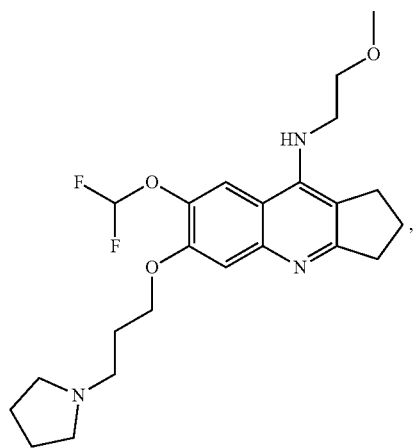 [SMILES: COCCNc1c2c(nc3cc(OCCCN4CCCC4)c(OC(F)F)cc13)CCC2] |
| 33 | 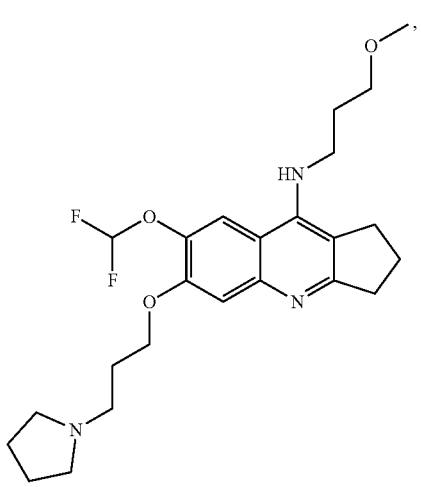 [SMILES: COCCCNc1c2c(nc3cc(OCCCN4CCCC4)c(OC(F)F)cc13)CCC2] |

| No | Structure |
|---|---|
| 34 | (structure) |
| 35 | (structure) |
| 36 | (structure) |
| 37 | (structure) |
| 38 | (structure) |

| No | Structure |
|---|---|
| 39 | 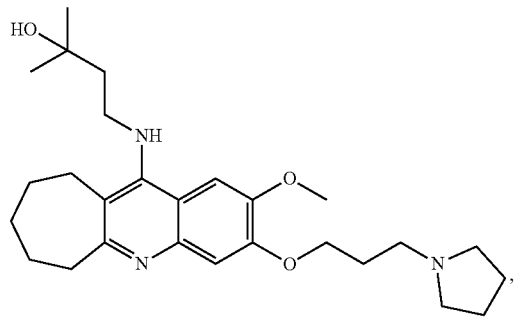 [SMILES: COc1cc2c(NCCC(C)(C)O)c3c(nc2cc1OCCCN1CCCC1)CCCCC3] |
| 40 | 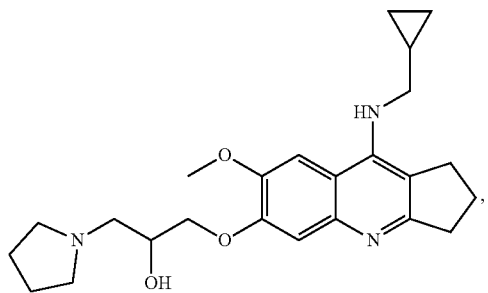 [SMILES: COc1cc2c(NCC3CC3)c3c(nc2cc1OCC(O)CN1CCCC1)CCC3] |
| 41 | 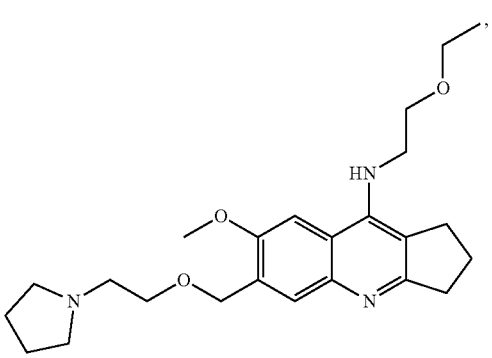 [SMILES: CCOCCNc1c2c(nc3cc(COCCN4CCCC4)c(OC)cc13)CCC2] |
| 42 | 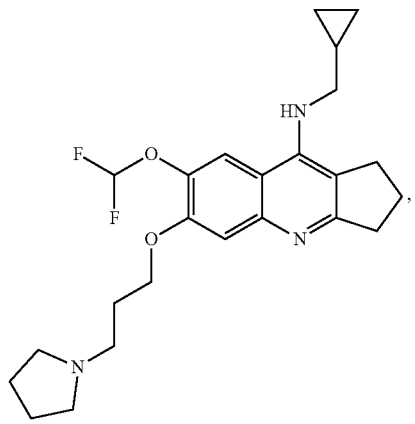 [SMILES: FC(F)Oc1cc2c(NCC3CC3)c3c(nc2cc1OCCCN1CCCC1)CCC3] |

US 11,584,734 B2
283                                                                 284
-continued
| No | Structure |
|----|-----------|
| 43 | 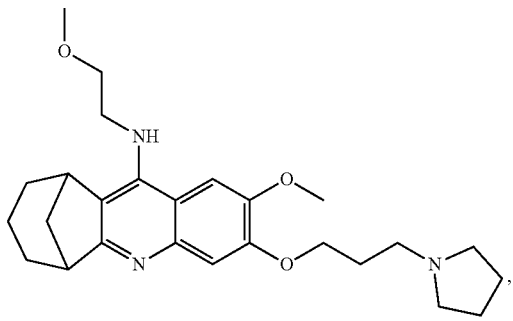 [SMILES: COCCNc1c2c(nc3cc(OCCCN4CCCC4)c(OC)cc13)C1CCCC2C1] |
| 44 | 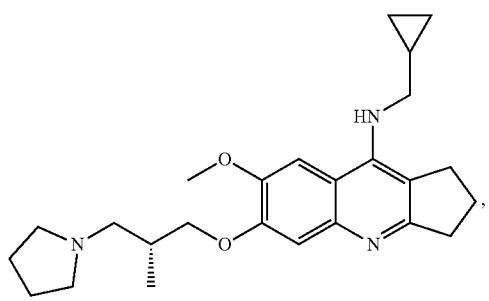 |
| 45 | 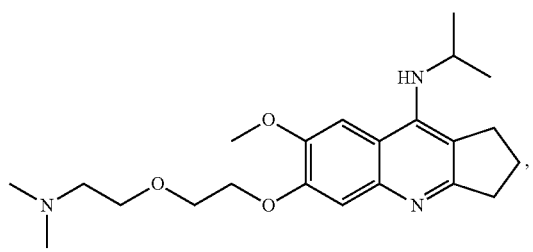 [SMILES: COc1cc2c(NC(C)C)c3c(nc2cc1OCCOCCN(C)C)CCC3] |
| 46 | 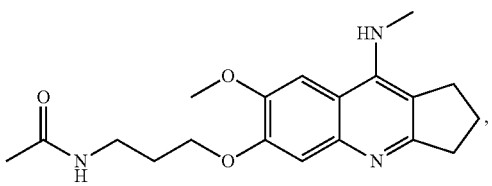 [SMILES: CNc1c2c(nc3cc(OCCCNC(C)=O)c(OC)cc13)CCC2] |
| 47 | 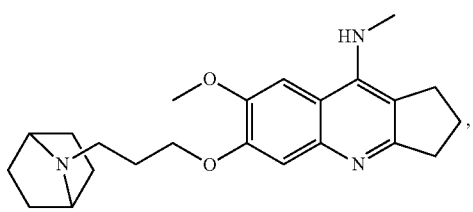 [SMILES: CNc1c2c(nc3cc(OCCCN4C5CCC4CC5)c(OC)cc13)CCC2] |

| No | Structure |
|---|---|
| 48 | 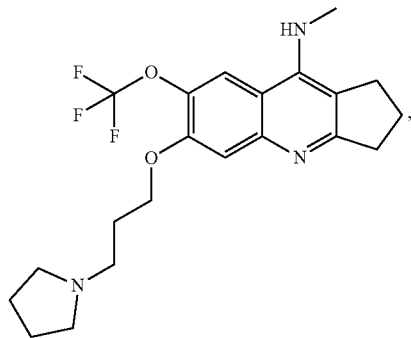 [SMILES: CNc1c2c(nc3cc(OCCCN4CCCC4)c(OC(F)(F)F)cc13)CCC2] |
| 49 | 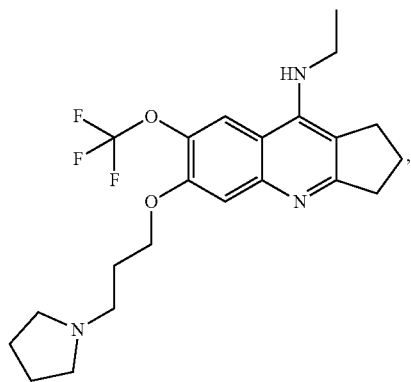 [SMILES: CCNc1c2c(nc3cc(OCCCN4CCCC4)c(OC(F)(F)F)cc13)CCC2] |
| 50 | 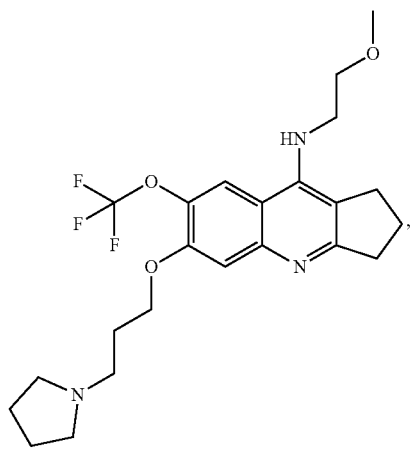 [SMILES: COCCNc1c2c(nc3cc(OCCCN4CCCC4)c(OC(F)(F)F)cc13)CCC2] |
| 51 | 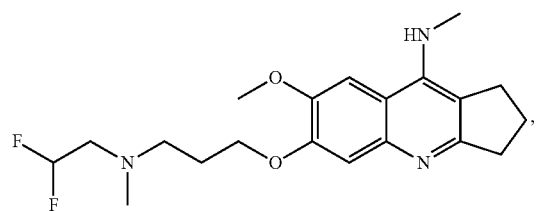 [SMILES: CNc1c2c(nc3cc(OCCCN(C)CC(F)F)c(OC)cc13)CCC2] |

-continued

| No | Structure |
|---|---|
| 52 | *(structure)* |
| 53 | *(structure)* |
| 54 | *(structure)* |
| 55 | *(structure)* |
| 56 | *(structure)* |

-continued

| No | Structure |
|---|---|
| 57 | 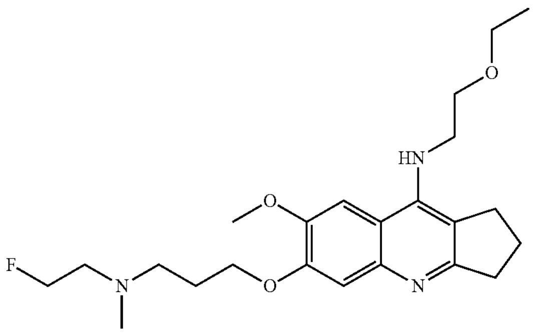 |
| 58 | 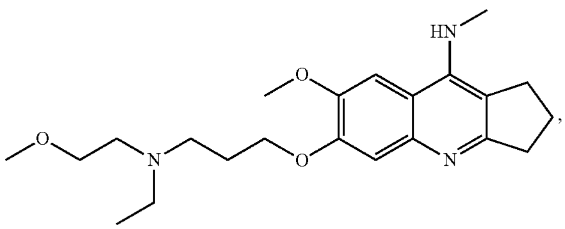 [SMILES: CCN(CCCOc1cc2nc3c(c(NC)c2cc1OC)CCC3)CCOC] |
| 59 | 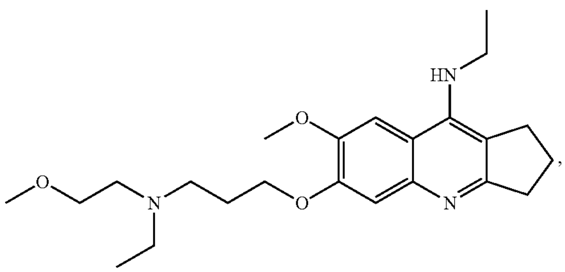 [SMILES: CCNc1c2c(nc3cc(OCCCN(CC)CCOC)c(OC)cc13)CCC2] |
| 60 | 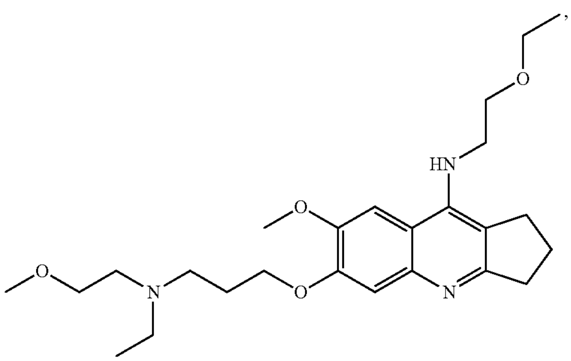 [SMILES: CCOCCNc1c2c(nc3cc(OCCCN(CC)CCOC)c(OC)cc13)CCC2] |
| 61 | 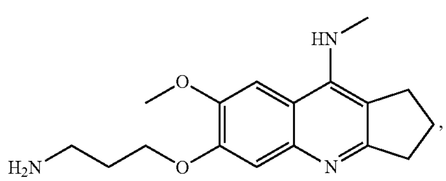 [SMILES: CNc1c2c(nc3cc(OCCCN)c(OC)cc13)CCC2] |
| 62 | 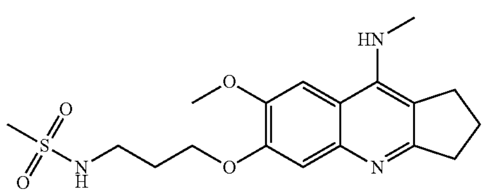 |

| No | Structure |
|---|---|
| 63 | 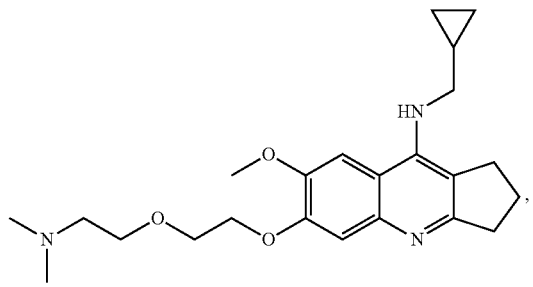 [SMILES: COc1cc2c(NCC3CC3)c3c(nc2cc1OCCOCCN(C)C)CCC3] |
| 64 | 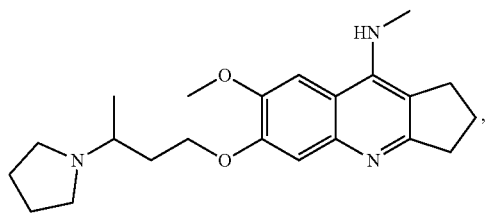 [SMILES: CNc1c2c(nc3cc(OCCC(C)N4CCCC4)c(OC)cc13)CCC2] |
| 65 | 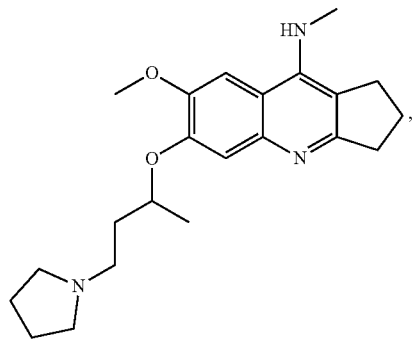 [SMILES: CNc1c2c(nc3cc(OC(C)CCN4CCCC4)c(OC)cc13)CCC2] |
| 66 | 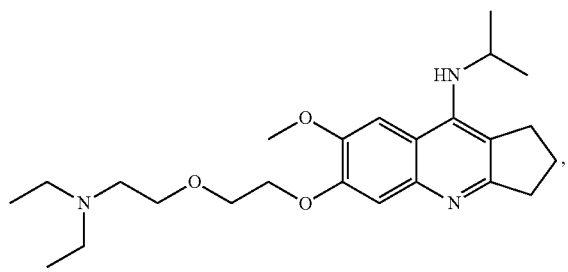 [SMILES: CCN(CC)CCOCCOc1cc2nc3c(c(NC(C)C)c2cc1OC)CCC3] |
| 67 | 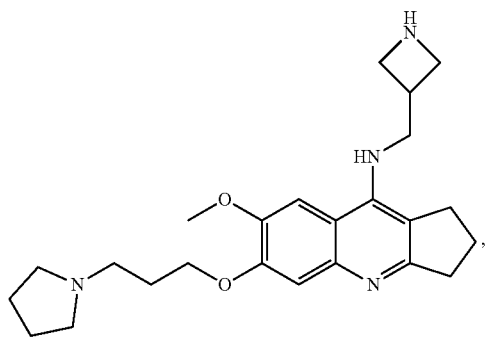 [SMILES: COc1cc2c(NCC3CNC3)c3c(nc2cc1OCCCN1CCCC1)CCC3] |

| No | Structure |
|---|---|
| 68 | 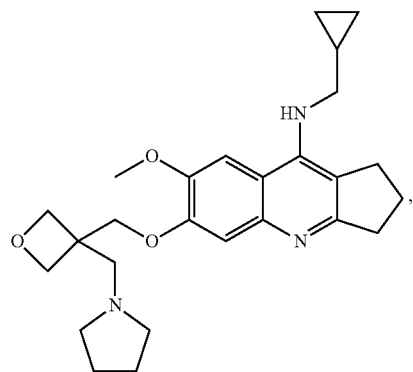 [SMILES: COc1cc2c(NCC3CC3)c3c(nc2cc1OCC1(CN2CCCC2)COC1)CCC3] |
| 69 | 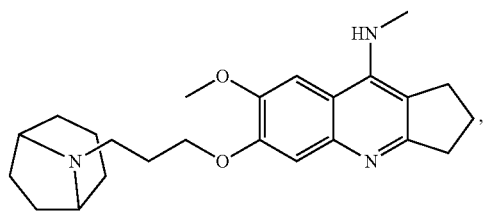 [SMILES: CNc1c2c(nc3cc(OCCCN4C5CCCC4CC5)c(OC)cc13)CCC2] |
| 70 | 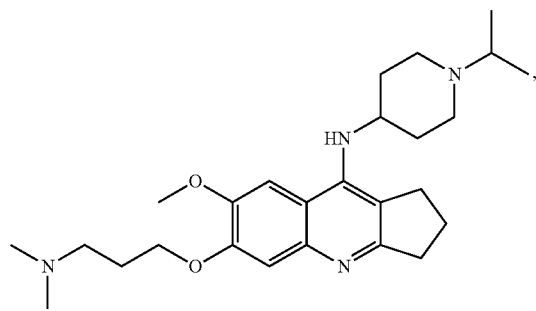 [SMILES: COc1cc2c(NC3CCN(C(C)C)CC3)c3c(nc2cc1OCCCN(C)C)CCC3] |
| 71 | 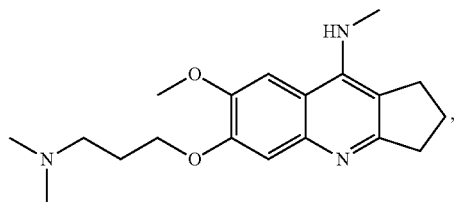 [SMILES: CNc1c2c(nc3cc(OCCCN(C)C)c(OC)cc13)CCC2] |
| 72 | 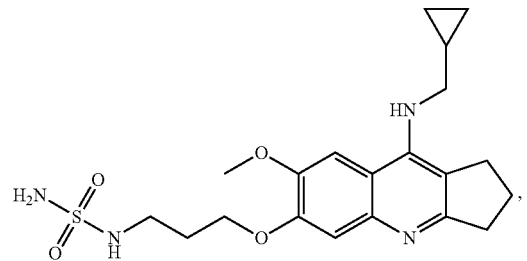 [SMILES: COc1cc2c(NCC3CC3)c3c(nc2cc1OCCCNS(N)(=O)=O)CCC3] |

| No | Structure |
|---|---|
| 73 | 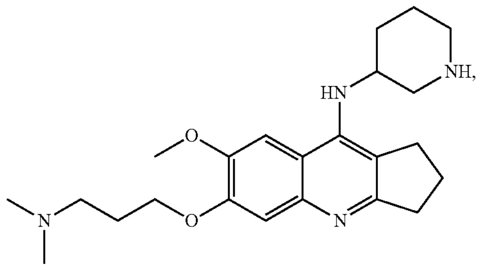 [SMILES: COc1cc2c(NC3CCCNC3)c3c(nc2cc1OCCCN(C)C)CCC3] |
| 74 | 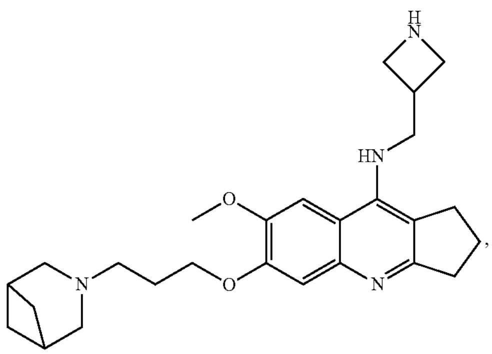 [SMILES: COc1cc2c(NCC3CNC3)c3c(nc2cc1OCCCN1CC2CC(C2)C1)CCC3] |
| 75 | 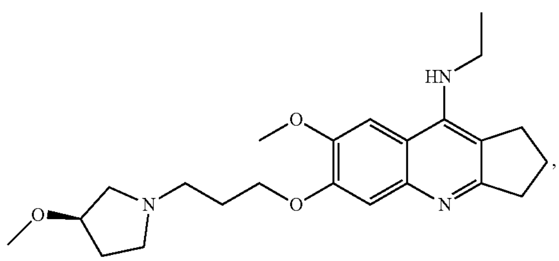 [SMILES: CCNc1c2c(nc3cc(OCCCN4CC[C@@H](OC)C4)c(OC)cc13)CCC2] |
| 76 | 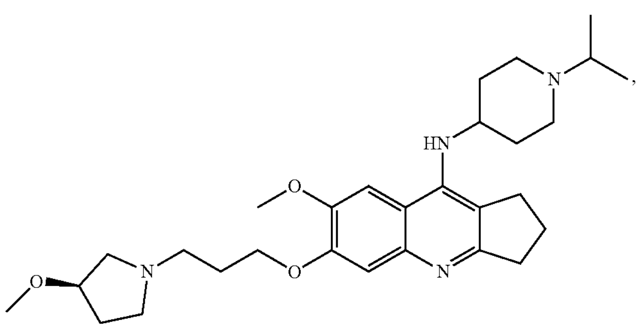 |
| 77 | | or a pharmaceutically acceptable salt thereof.
42. The compound of claim 1, wherein the compound is selected from the group consisting of

| No. | Structure |
|---|---|
| 78 | 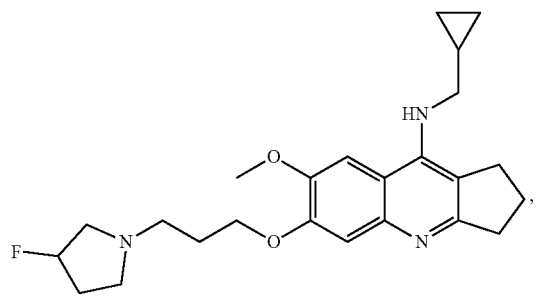 [SMILES: COc1cc2c(NCC3CC3)c3c(nc2cc1OCCCN1CCC(F)C1)CCC3] |
| 79 | 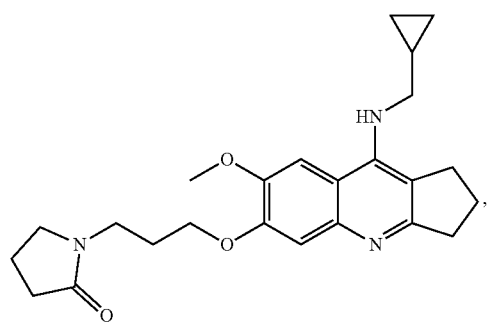 [SMILES: COc1cc2c(NCC3CC3)c3c(nc2cc1OCCCN1CCCC1=O)CCC3] |
| 80 | 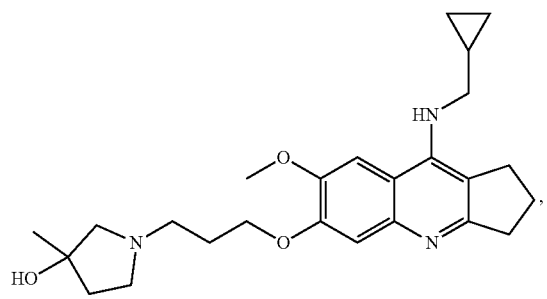 [SMILES: COc1cc2c(NCC3CC3)c3c(nc2cc1OCCCN1CCC(C)(O)C1)CCC3] |
| 81 | 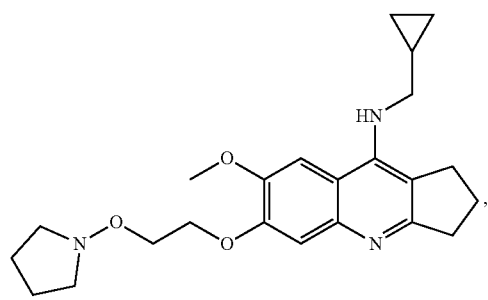 [SMILES: COc1cc2c(NCC3CC3)c3c(nc2cc1OCCON1CCCC1)CCC3] |
| 82 | 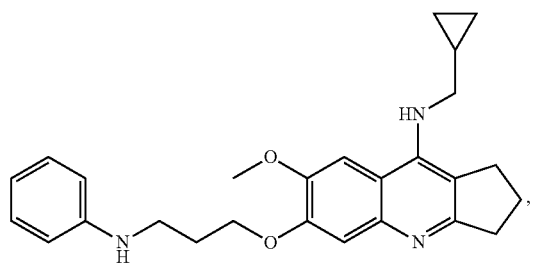 [SMILES: COc1cc2c(NCC3CC3)c3c(nc2cc1OCCCNc1ccccc1)CCC3] |

| No. | Structure |
|---|---|
| 83 | 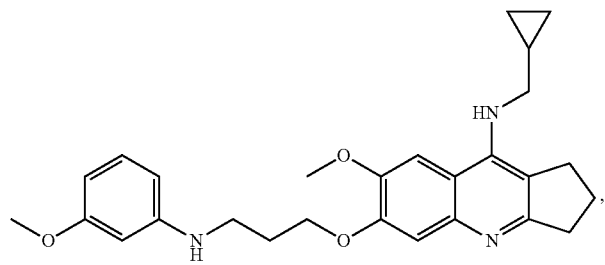 [SMILES: COc1cccc(NCCCOc2cc3nc4c(c(NCC5CC5)c3cc2OC)CCC4)c1] |
| 84 | 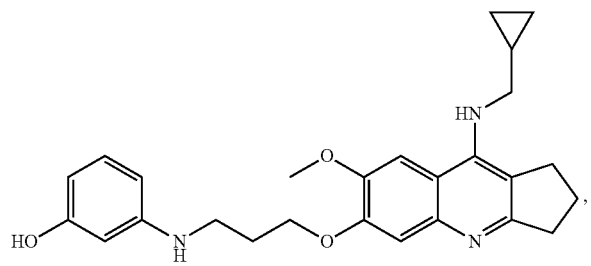 [SMILES: COc1cc2c(NCC3CC3)c3c(nc2cc1OCCCNc1cccc(O)c1)CCC3] |
| 85 | 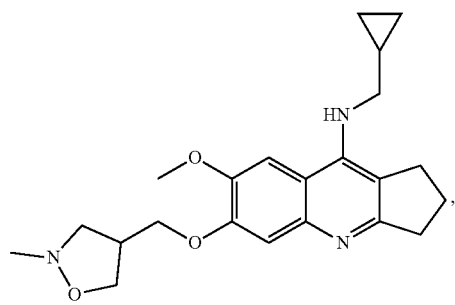 [SMILES: COc1cc2c(NCC3CC3)c3c(nc2cc1OCC1CON(C)C1)CCC3] |
| 86 | 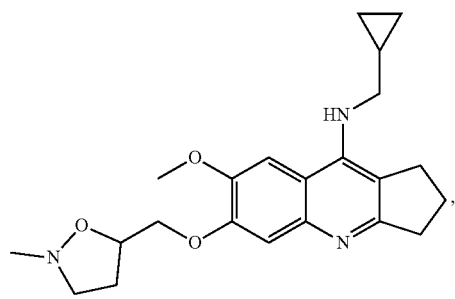 [SMILES: COc1cc2c(NCC3CC3)c3c(nc2cc1OCC1CCN(C)O1)CCC3] |
| 87 | 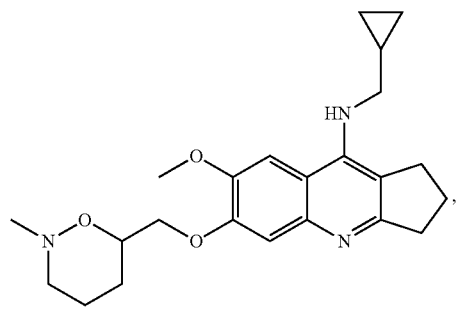 [SMILES: COc1cc2c(NCC3CC3)c3c(nc2cc1OCC1CCCN(C)O1)CCC3] |

| No. | Structure |
|---|---|
| 88 | 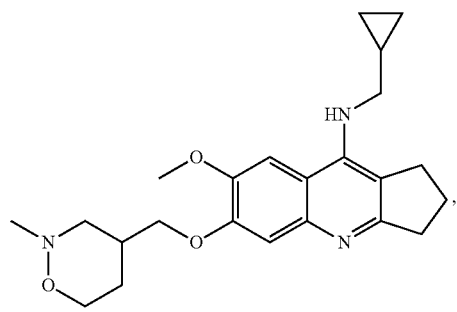 [SMILES: COc1cc2c(NCC3CC3)c3c(nc2cc1OCC1CCON(C)C1)CCC3] |
| 89 | 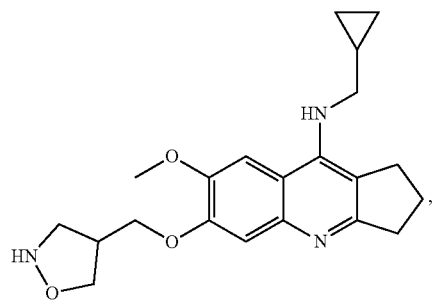 [SMILES: COc1cc2c(NCC3CC3)c3c(nc2cc1OCC1CNOC1)CCC3] |
| 90 | 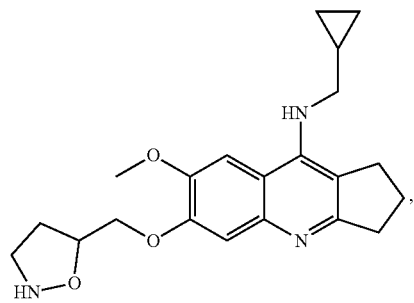 [SMILES: COc1cc2c(NCC3CC3)c3c(nc2cc1OCC1CCNO1)CCC3] |
| 91 | 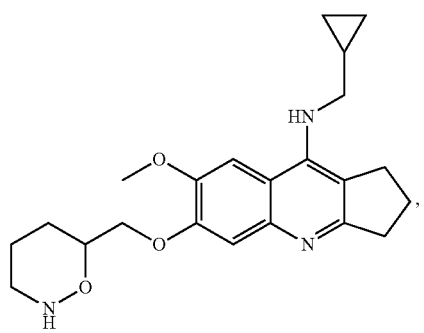 [SMILES: COc1cc2c(NCC3CC3)c3c(nc2cc1OCC1CCCNO1)CCC3] |
| 92 | 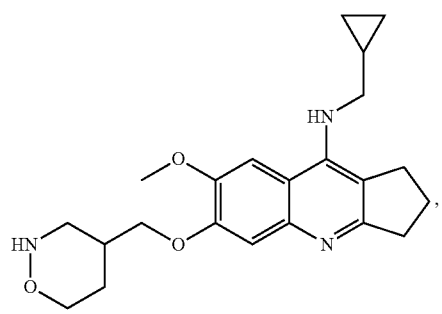 [SMILES: COc1cc2c(NCC3CC3)c3c(nc2cc1OCC1CCONC1)CCC3] |

| No. | Structure |
|---|---|
| 93 | 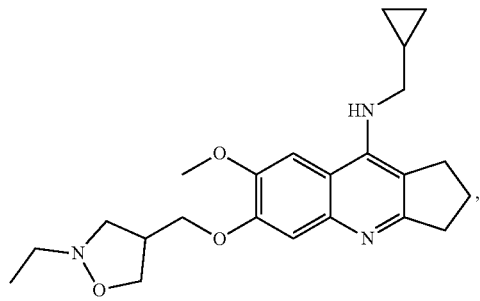 [SMILES: CCN1CC(COc2cc3nc4c(c(NCC5CC5)c3cc2OC)CCC4)CO1] |
| 94 | 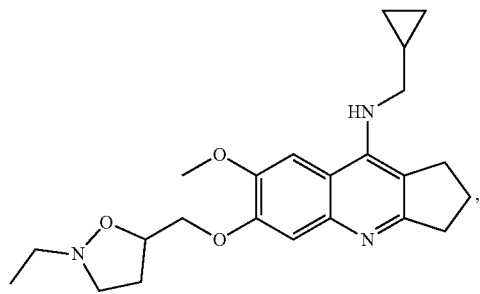 [SMILES: CCN1CCC(COc2cc3nc4c(c(NCC5CC5)c3cc2OC)CCC4)O1] |
| 95 | 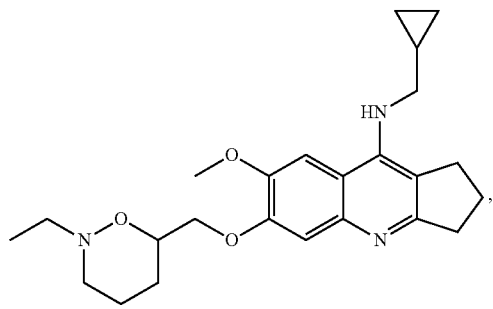 [SMILES: CCN1CCCC(COc2cc3nc4c(c(NCC5CC5)c3cc2OC)CCC4)O1] |
| 96 | 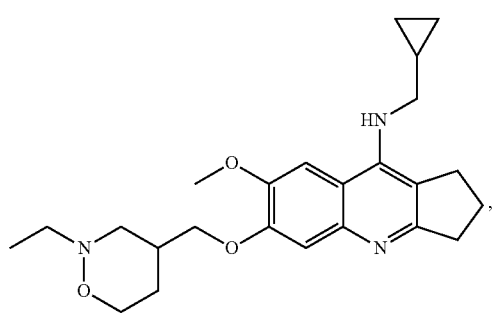 [SMILES: CCN1CC(COc2cc3nc4c(c(NCC5CC5)c3cc2OC)CCC4)CCO1] |
| 97 | 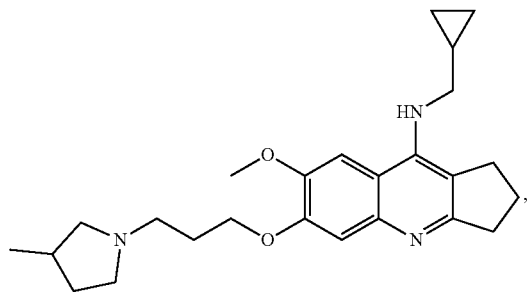 [SMILES: COc1cc2c(NCC3CC3)c3c(nc2cc1OCCCN1CCC(C)C1)CCC3] |

-continued
| No. | Structure |
|---|---|
| 98 | 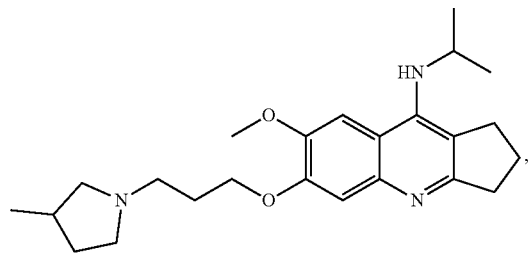 [SMILES: COc1cc2c(NC(C)C)c3c(nc2cc1OCCCN1CCC(C)C1)CCC3] |
| 99 | 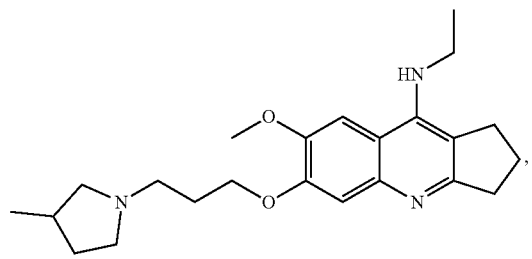 [SMILES: CCNc1c2c(nc3cc(OCCCN4CCC(C)C4)c(OC)cc13)CCC2] |
| 100 | 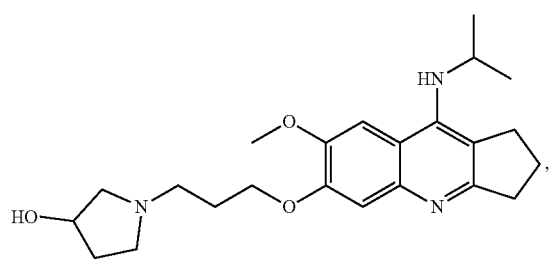 [SMILES: COc1cc2c(NC(C)C)c3c(nc2cc1OCCCN1CCC(O)C1)CCC3] |
| 101 | 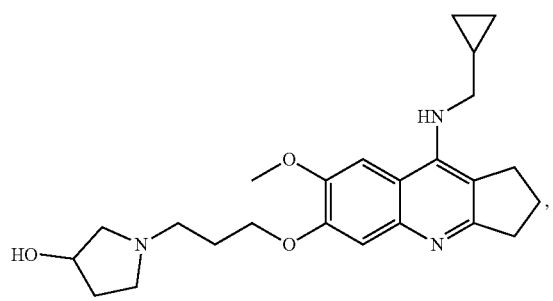 [SMILES: COc1cc2c(NCC3CC3)c3c(nc2cc1OCCCN1CCC(O)C1)CCC3] |
| 102 | 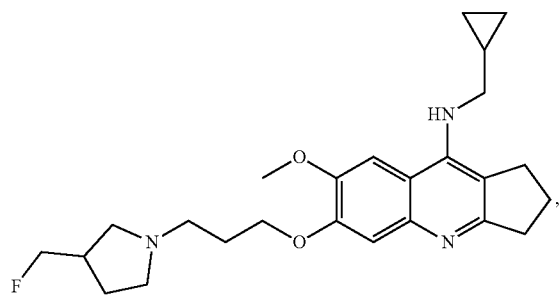 [SMILES: COc1cc2c(NCC3CC3)c3c(nc2cc1OCCCN1CCC(CF)C1)CCC3] |

| No. | Structure |
|---|---|
| 103 | 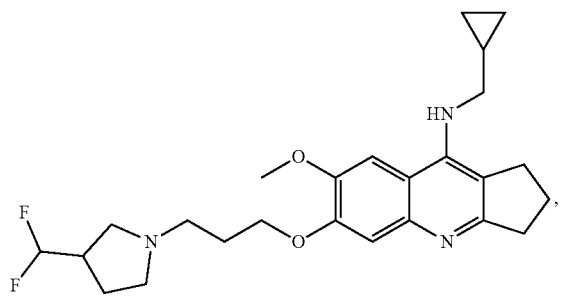 [SMILES: COc1cc2c(NCC3CC3)c3c(nc2cc1OCCCN1CCC(C(F)F)C1)CCC3] |
| 104 | 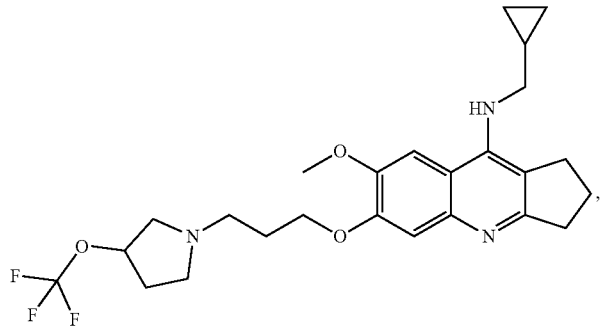 [SMILES: COc1cc2c(NCC3CC3)c3c(nc2cc1OCCCN1CCC(OC(F)(F)F)C1)CCC3] |
| 105 | 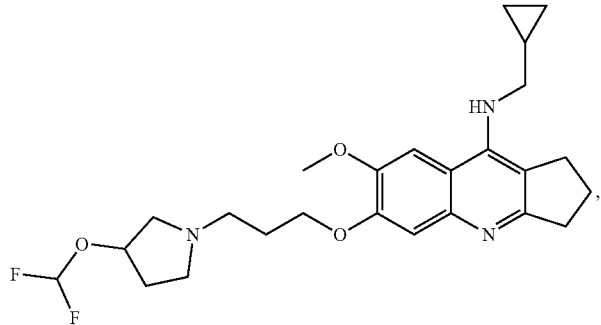 |
| 106 | 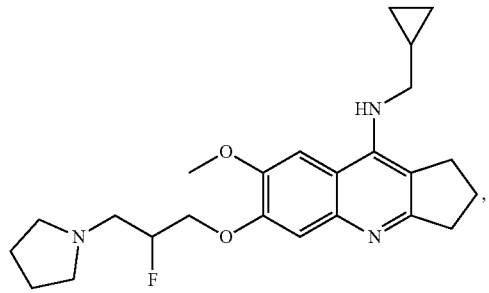 [SMILES: COc1cc2c(NCC3CC3)c3c(nc2cc1OCC(F)CN1CCCC1)CCC3] |
| 107 | 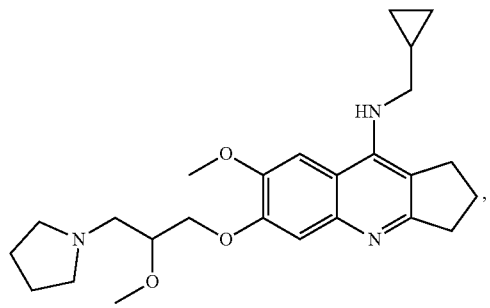 [SMILES: COc1cc2c(NCC3CC3)c3c(nc2cc1OCC(CN1CCCC1)OC)CCC3] |

| No. | Structure |
|---|---|
| 108 | 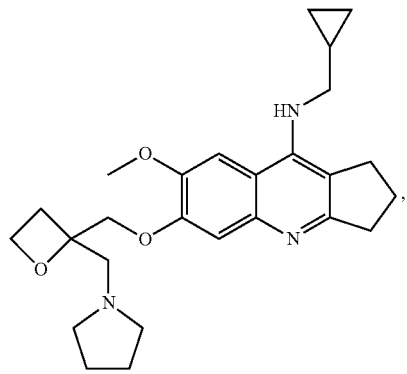 [SMILES: COc1cc2c(NCC3CC3)c3c(nc2cc1OCC1(CN2CCCC2)CCO1)CCC3] |
| 109 | 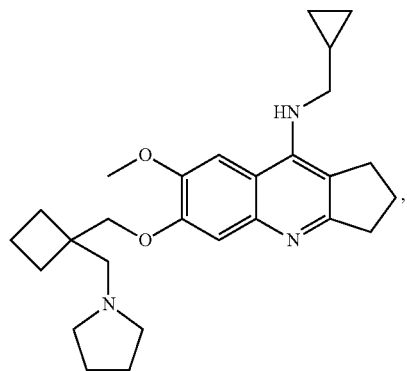 [SMILES: COc1cc2c(NCC3CC3)c3c(nc2cc1OCC1(CN2CCCC2)CCC1)CCC3] |
| 110 | 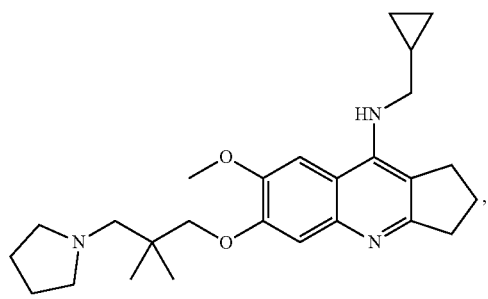 [SMILES: COc1cc2c(NCC3CC3)c3c(nc2cc1OCC(C)(C)CN1CCCC1)CCC3] |
| 111 | 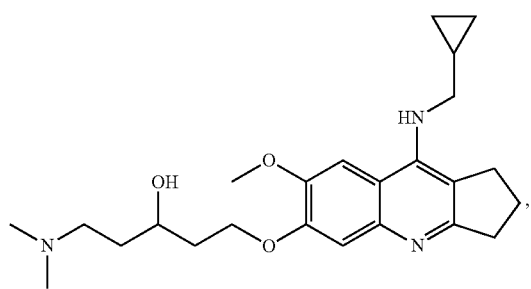 [SMILES: COc1cc2c(NCC3CC3)c3c(nc2cc1OCCC(O)CCN(C)C)CCC3] |

| No. | Structure |
|---|---|
| 112 | 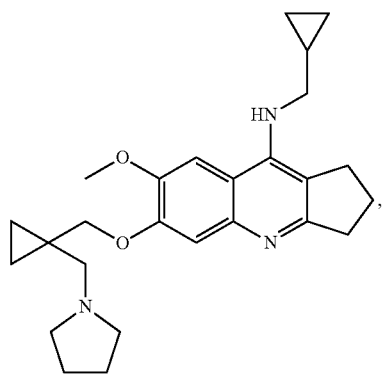 [SMILES: COc1cc2c(NCC3CC3)c3c(nc2cc1OCC1(CN2CCCC2)CC1)CCC3] |
| 113 | 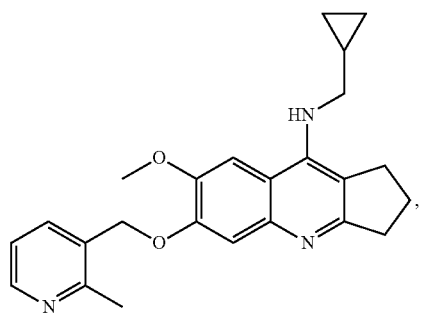 [SMILES: COc1cc2c(NCC3CC3)c3c(nc2cc1OCc1cccnc1C)CCC3] |
| 114 | 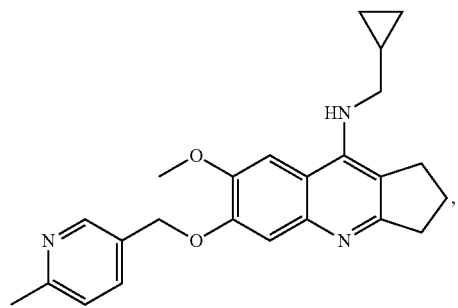 [SMILES: COc1cc2c(NCC3CC3)c3c(nc2cc1OCc1ccc(C)nc1)CCC3] |
| 115 | 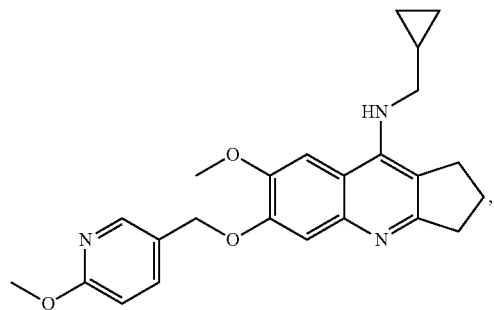 [SMILES: COc1ccc(COc2cc3nc4c(c(NCC5CC5)c3cc2OC)CCC4)cn1] |

-continued
| No. | Structure |
|---|---|
| 116 | 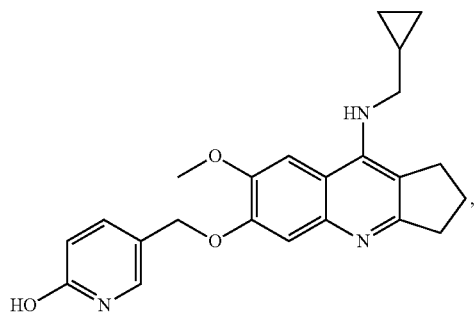 [SMILES: COc1cc2c(NCC3CC3)c3c(nc2cc1OCc1ccc(O)nc1)CCC3] |
| 117 | 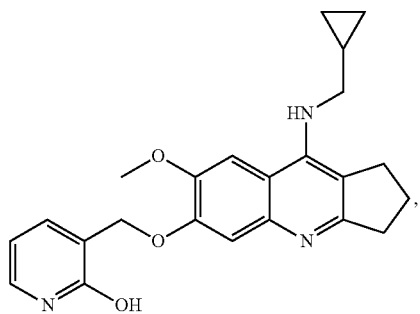 [SMILES: COc1cc2c(NCC3CC3)c3c(nc2cc1OCc1cccnc1O)CCC3] |
| 118 | 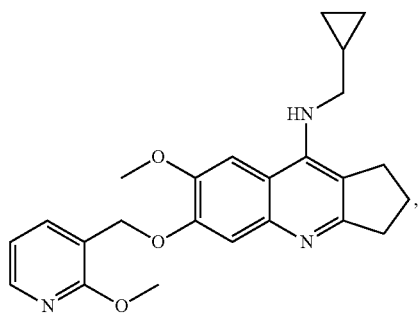 [SMILES: COc1cc2c(NCC3CC3)c3c(nc2cc1OCc1cccnc1OC)CCC3] |
| 119 | 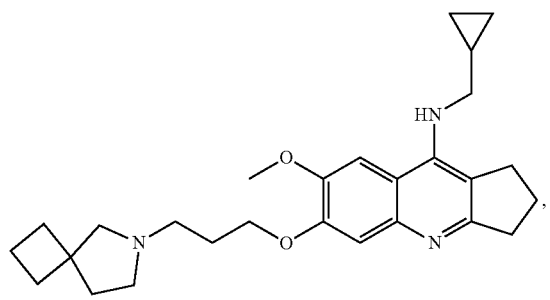 [SMILES: COc1cc2c(NCC3CC3)c3c(nc2cc1OCCCN1CCC2(CCC2)C1)CCC3] |
| 120 | 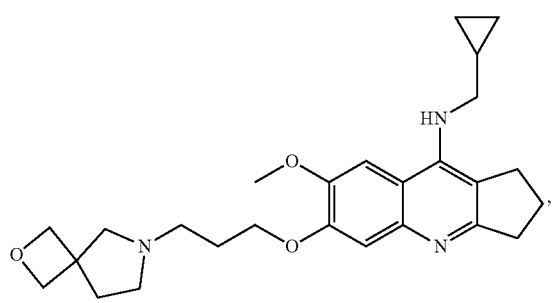 [SMILES: COc1cc2c(NCC3CC3)c3c(nc2cc1OCCCN1CCC2(COC2)C1)CCC3] |

| No. | Structure |
|---|---|
| 121 | 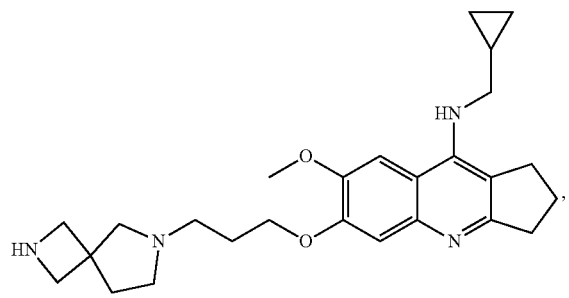 [SMILES: COc1cc2c(NCC3CC3)c3c(nc2cc1OCCCN1CCC2(CNC2)C1)CCC3] |
| 122 | 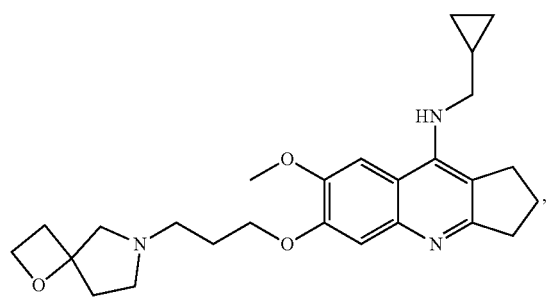 |
| 123 | 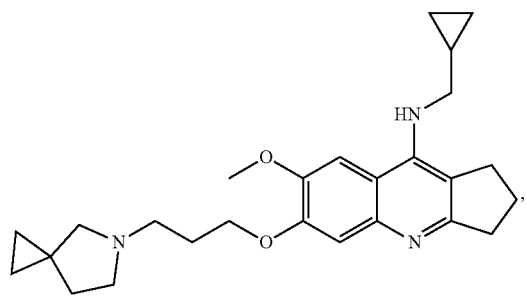 [SMILES: COc1cc2c(NCC3CC3)c3c(nc2cc1OCCCN1CCC2(CC2)C1)CCC3] |
| 124 | 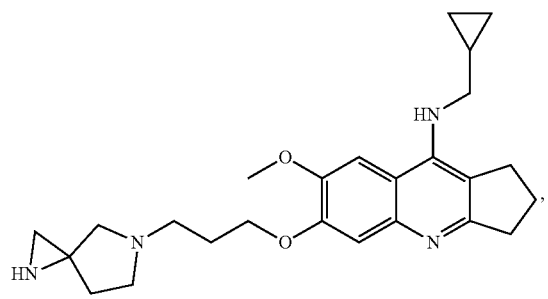 |
| 125 | 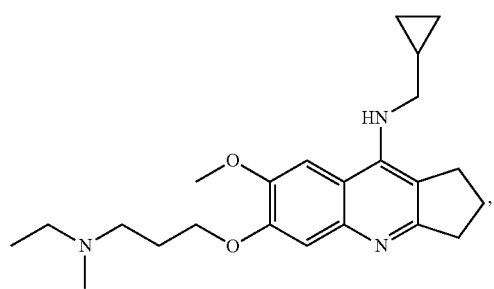 [SMILES: CCN(C)CCCOc1cc2nc3c(c(NCC4CC4)c2cc1OC)CCC3] |

| No. | Structure |
|---|---|
| 126 | 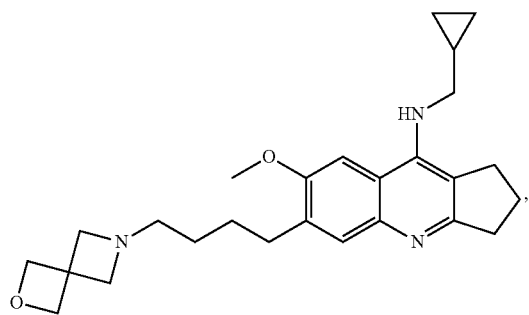 [SMILES: COc1cc2c(NCC3CC3)c3c(nc2cc1CCCCN1CC2(COC2)C1)CCC3] |
| 127 | 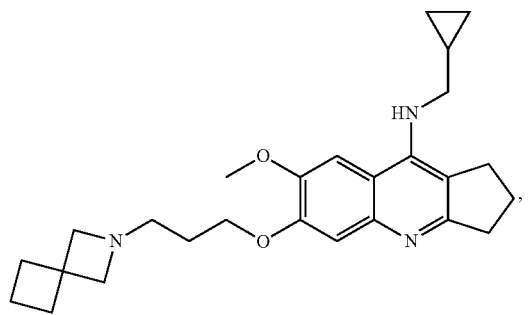 [SMILES: COc1cc2c(NCC3CC3)c3c(nc2cc1OCCCN1CC2(CCC2)C1)CCC3] |
| 128 | 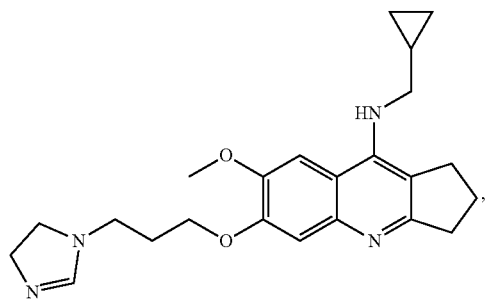 [SMILES: COc1cc2c(NCC3CC3)c3c(nc2cc1OCCCN1C=NCC1)CCC3] |
| 129 | 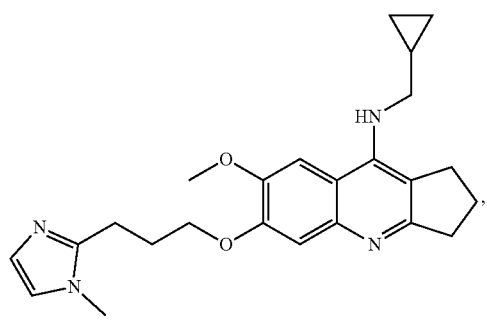 [SMILES: COc1cc2c(NCC3CC3)c3c(nc2cc1OCCCc1nccn1C)CCC3] |
| 130 | 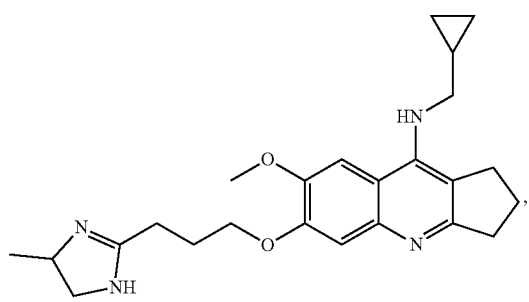 [SMILES: COc1cc2c(NCC3CC3)c3c(nc2cc1OCCCC1=NC(C)CN1)CCC3] |

| No. | Structure |
|---|---|
| 131 | 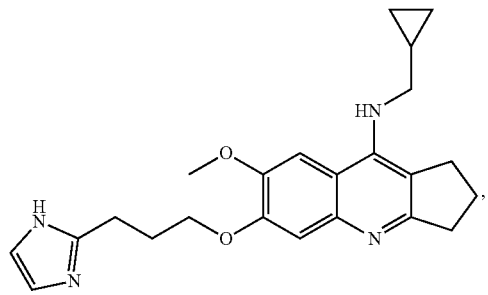 [SMILES: COc1cc2c(NCC3CC3)c3c(nc2cc1OCCCc1ncc[nH]1)CCC3] |
| 132 | 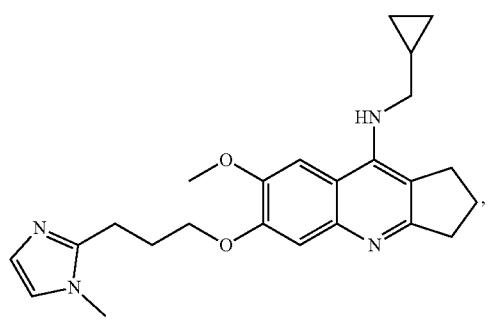 [SMILES: COc1cc2c(NCC3CC3)c3c(nc2cc1OCCCc1nccn1C)CCC3] |
| 133 | 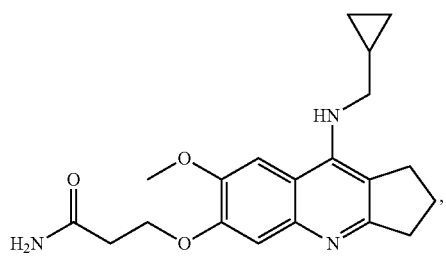 [SMILES: COc1cc2c(NCC3CC3)c3c(nc2cc1OCCC(N)=O)CCC3] |
| 134 | 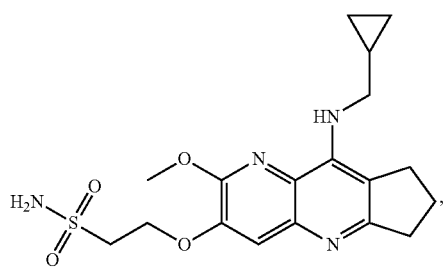 [SMILES: COc1nc2c(NCC3CC3)c3c(nc2cc1OCCS(N)(=O)=O)CCC3] |
| 135 | 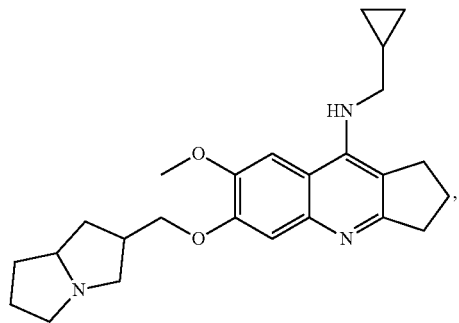 [SMILES: COc1cc2c(NCC3CC3)c3c(nc2cc1OCC1CC2CCCN2C1)CCC3] |

| No. | Structure |
|---|---|
| 136 | 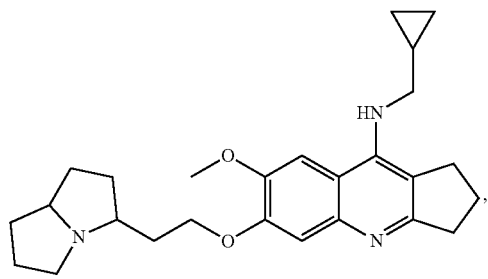 [SMILES: COc1cc2c(NCC3CC3)c3c(nc2cc1OCCC1CCC2CCCN21)CCC3] |
| 137 | 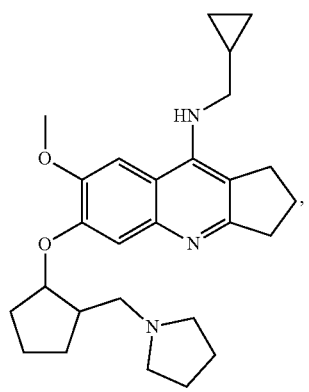 [SMILES: COc1cc2c(NCC3CC3)c3c(nc2cc1OC1CCCC1CN1CCCC1)CCC3] |
| 138 | 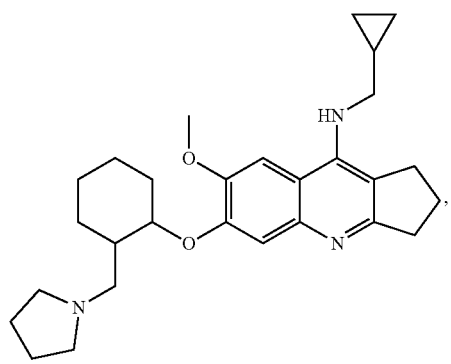 [SMILES: COc1cc2c(NCC3CC3)c3c(nc2cc1OC1CCCCC1CN1CCCC1)CCC3] |
| 139 | 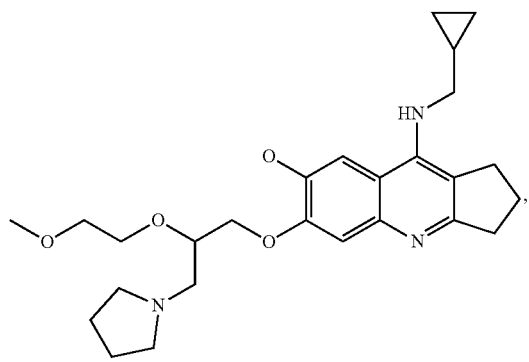 [SMILES: COCCOC(COc1cc2nc3c(c(NCC4CC4)c2cc1O)CCC3)CN1CCCC1] |

| No. | Structure |
|---|---|
| 140 | 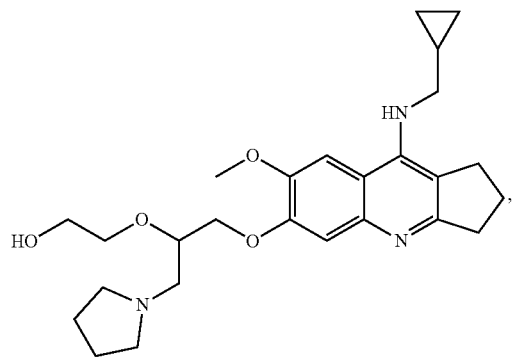 [SMILES: COc1cc2c(NCC3CC3)c3c(nc2cc1OCC(CN1CCCC1)OCCO)CCC3] |
| 141 | 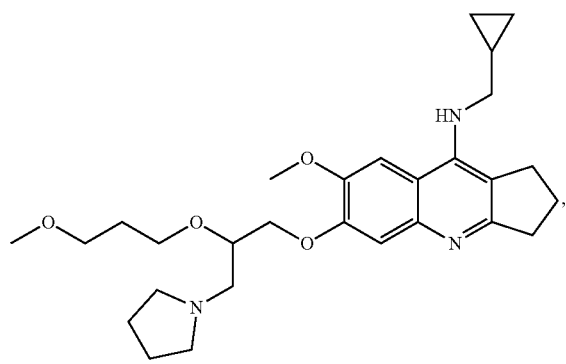 [SMILES: COCCCOC(COc1cc2nc3c(c(NCC4CC4)c2cc1OC)CCC3)CN1CCCC1] |
| 142 | 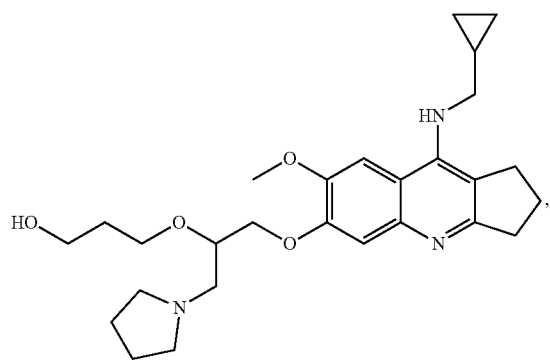 [SMILES: COc1cc2c(NCC3CC3)c3c(nc2cc1OCC(CN1CCCC1)OCCCO)CCC3] |
| 143 | 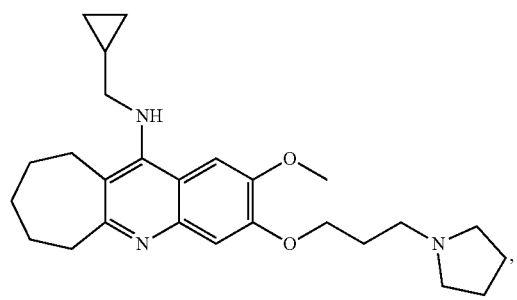 |

| No. | Structure |
|---|---|
| 144 | 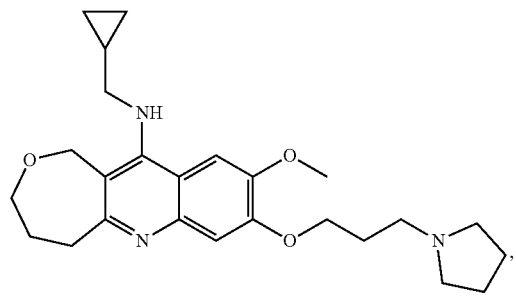 [SMILES: COc1cc2c(NCC3CC3)c3c(nc2cc1OCCCN1CCCC1)CCCCC3] |
| 145 | 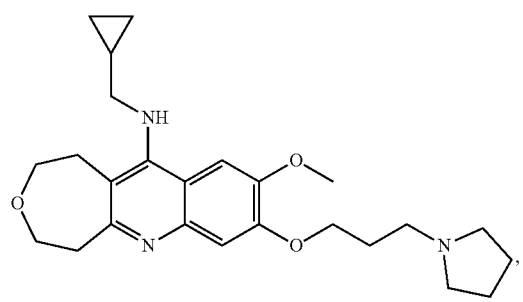 [SMILES: COc1cc2c(NCC3CC3)c3c(nc2cc1OCCCN1CCCC1)CCOCC3] |
| 146 | 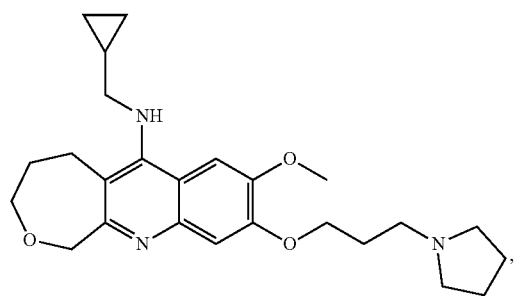 [SMILES: COc1cc2c(NCC3CC3)c3c(nc2cc1OCCCN1CCCC1)COCCC3] |
| 147 | 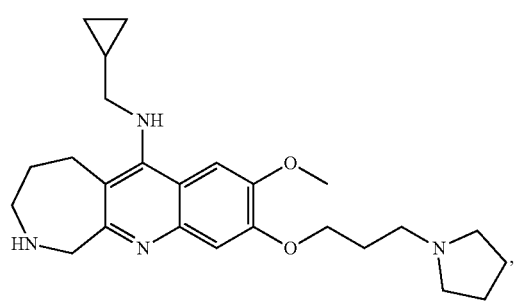 |
| 148 | 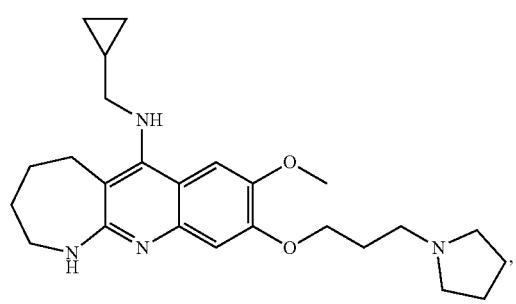 [SMILES: COc1cc2c(NCC3CC3)c3c(nc2cc1OCCCN1CCCC1)NCCCC3] |

| No. | Structure |
|---|---|
| 149 | 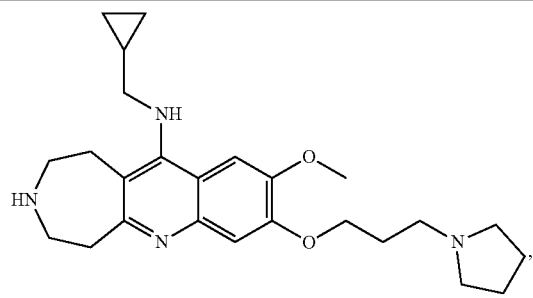 [SMILES: COc1cc2c(NCC3CC3)c3c(nc2cc1OCCCN1CCCC1)CCNCC3] |
| 150 | 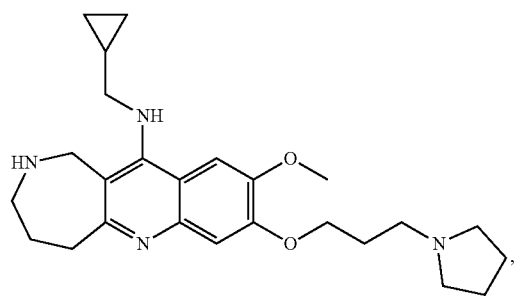 |
| 151 | 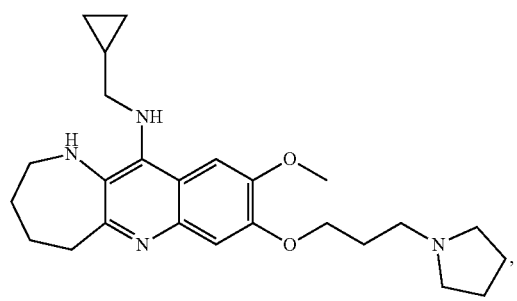 [SMILES: COc1cc2c(NCC3CC3)c3c(nc2cc1OCCCN1CCCC1)CCCCN3] |
| 152 | 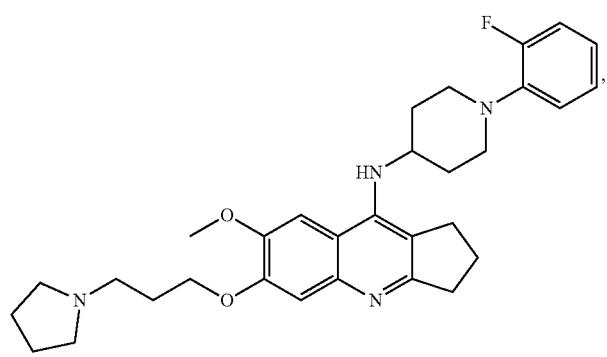 |
| 153 | 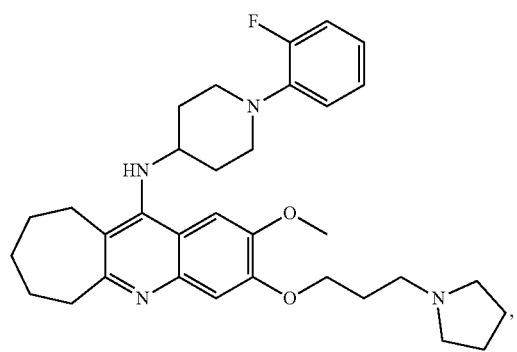 |

| No. | Structure |
|---|---|
| 154 | 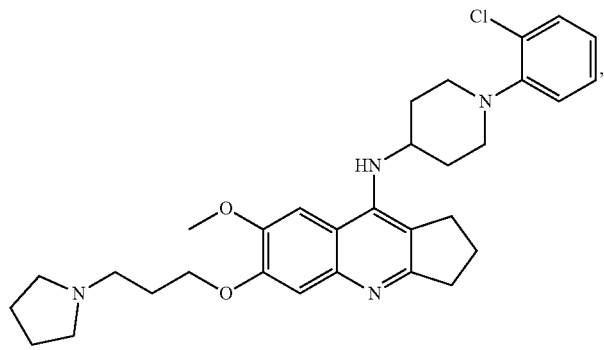 |
| 155 | 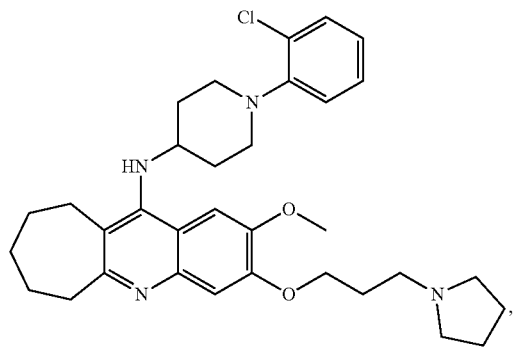 [SMILES: COc1cc2c(NC3CCN(c4ccccc4Cl)CC3)c3c(nc2cc1OCCCN1CCCC1)CCCCC3] |
| 156 | 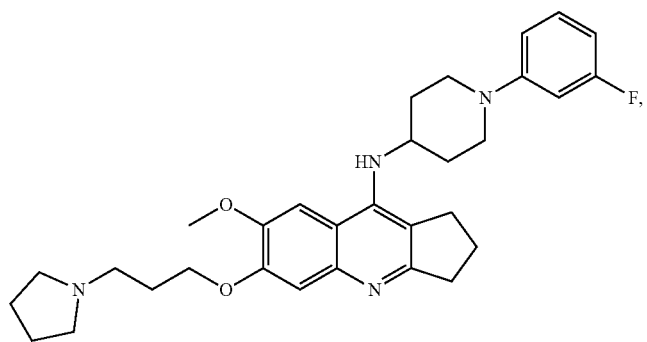 [SMILES: COc1cc2c(NC3CCN(c4cccc(F)c4)CC3)c3c(nc2cc1OCCCN1CCCC1)CCC3] |
| 157 | 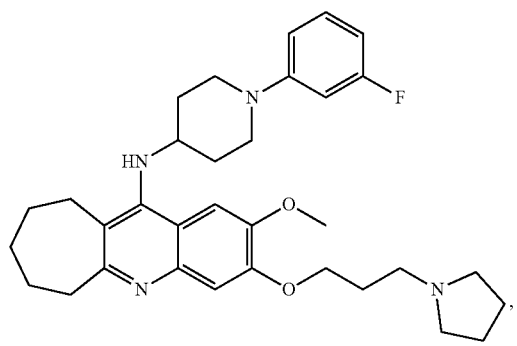 [SMILES: COc1cc2c(NC3CCN(c4cccc(F)c4)CC3)c3c(nc2cc1OCCCN1CCCC1)CCCCC3] |

| No. | Structure |
|---|---|
| 158 | 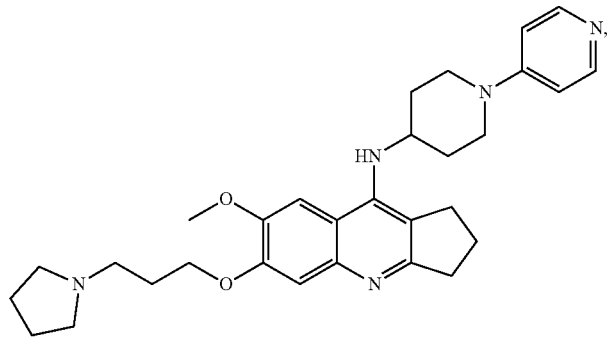 [SMILES: COc1cc2c(NC3CCN(c4ccncc4)CC3)c3c(nc2cc1OCCCN1CCCC1)CCC3] |
| 159 | 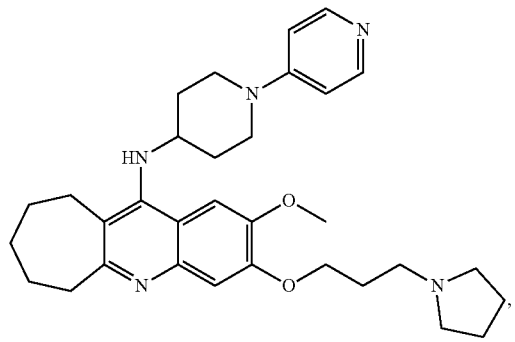 [SMILES: COc1cc2c(NC3CCN(c4ccncc4)CC3)c3c(nc2cc1OCCCN1CCCC1)CCCCC3] |
| 160 | 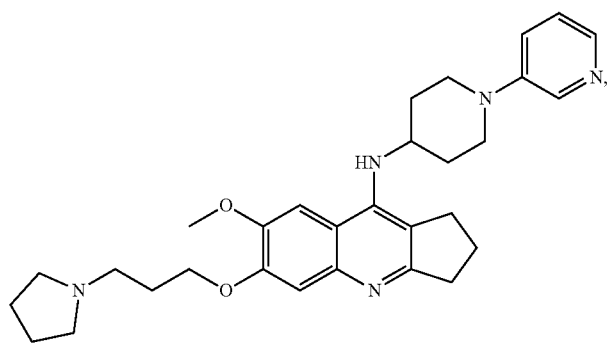 [SMILES: COc1cc2c(NC3CCN(c4cccnc4)CC3)c3c(nc2cc1OCCCN1CCCC1)CCC3] |
| 161 | 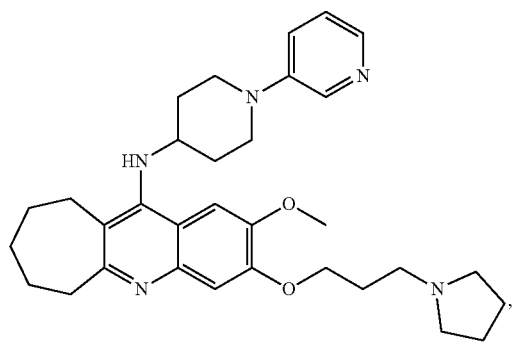 [SMILES: COc1cc2c(NC3CCN(c4cccnc4)CC3)c3c(nc2cc1OCCCN1CCCC1)CCCCC3] |

| No. | Structure |
|---|---|
| 162 | 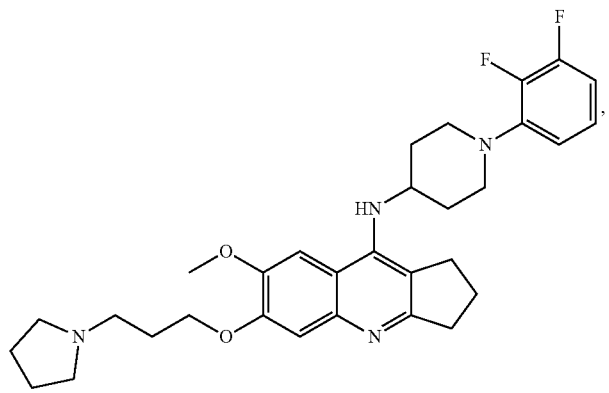 |
| 163 | 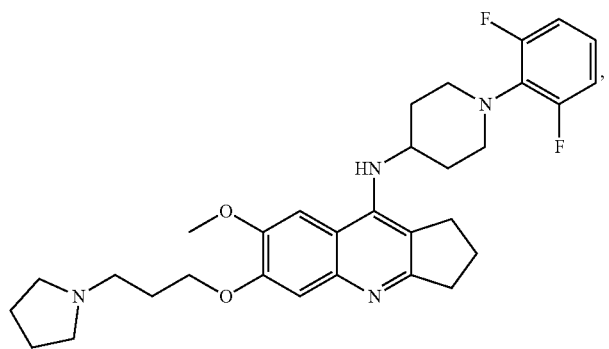 |
| 164 | 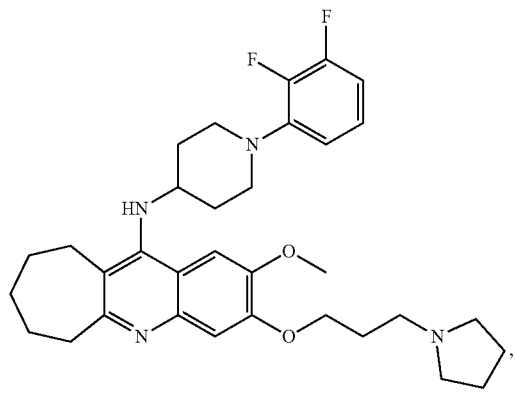 [SMILES: COc1cc2c(NC3CCN(c4cccc(F)c4F)CC3)c3c(nc2cc1OCCCN1CCCC1)CCCCC3] |
| 165 | 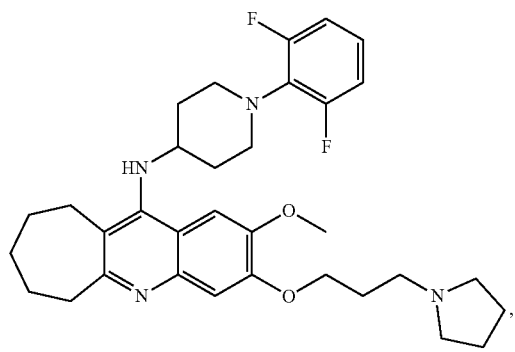 [SMILES: COc1cc2c(NC3CCN(c4c(F)cccc4F)CC3)c3c(nc2cc1OCCCN1CCCC1)CCCCC3] |

| No. | Structure |
|---|---|
| 166 | 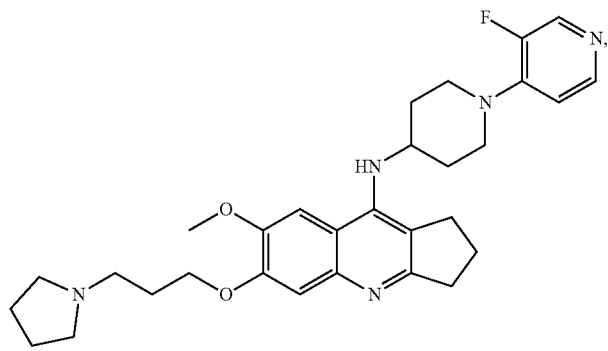 [SMILES: COc1cc2c(NC3CCN(c4ccncc4F)CC3)c3c(nc2cc1OCCCN1CCCC1)CCC3] |
| 167 | 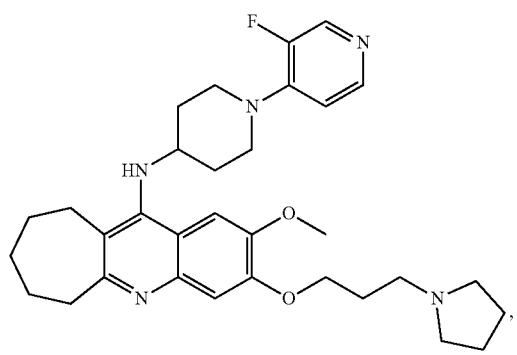 [SMILES: COc1cc2c(NC3CCN(c4ccncc4F)CC3)c3c(nc2cc1OCCCN1CCCC1)CCCCC3] |
| 168 | 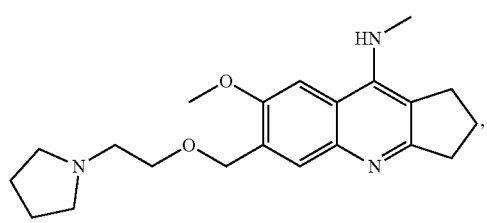 [SMILES: CNc1c2c(nc3cc(COCCN4CCCC4)c(OC)cc13)CCC2] |
| 169 | 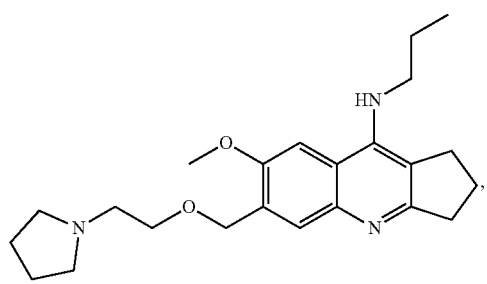 [SMILES: CCCNc1c2c(nc3cc(COCCN4CCCC4)c(OC)cc13)CCC2] |
| 170 | 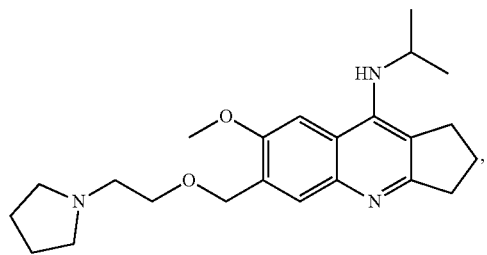 [SMILES: COc1cc2c(NC(C)C)c3c(nc2cc1COCCN1CCCC1)CCC3] |

-continued
| No. | Structure |
|---|---|
| 171 | 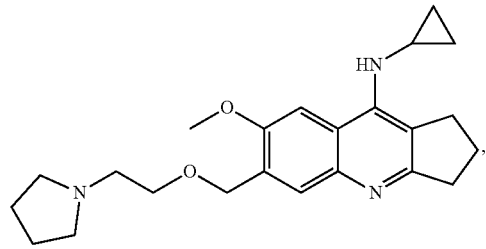 [SMILES: COc1cc2c(NC3CC3)c3c(nc2cc1COCCN1CCCC1)CCC3] |
| 172 | 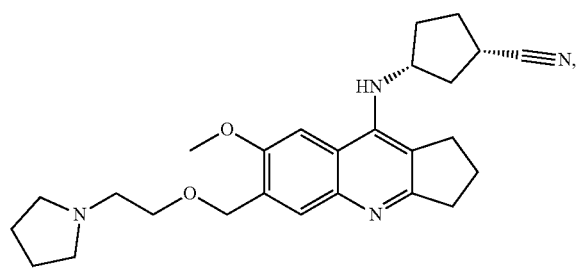 [SMILES: COc1cc2c(N[C@@H]3CC[C@H](C#N)C3)c3c(nc2cc1COCCN1CCCC1)CCC3] |
| 173 | 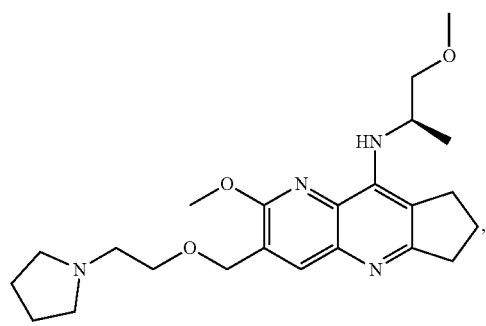 [SMILES: COC[C@@H](C)Nc1c2c(nc3cc(COCCN4CCCC4)c(OC)nc13)CCC2] |
| 174 | 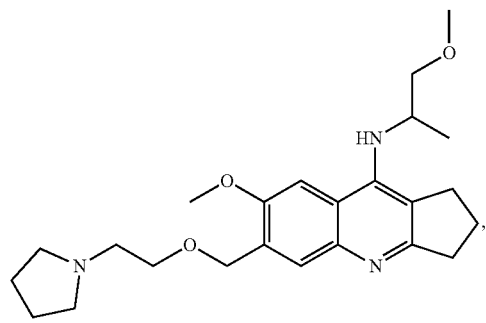 [SMILES: COCC(C)Nc1c2c(nc3cc(COCCN4CCCC4)c(OC)cc13)CCC2] |
| 175 | 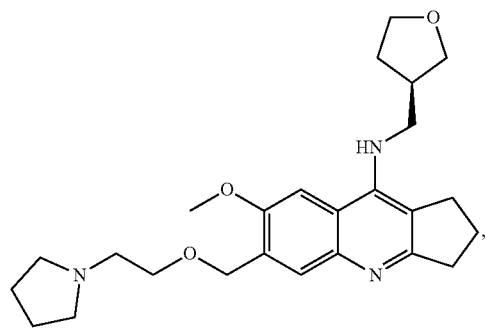 [SMILES: COc1cc2c(NC[C@H]3CCOC3)c3c(nc2cc1COCCN1CCCC1)CCC3] |

| No. | Structure |
|---|---|
| 176 | 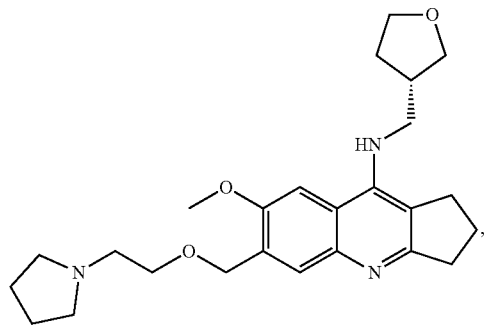 |
| 177 | 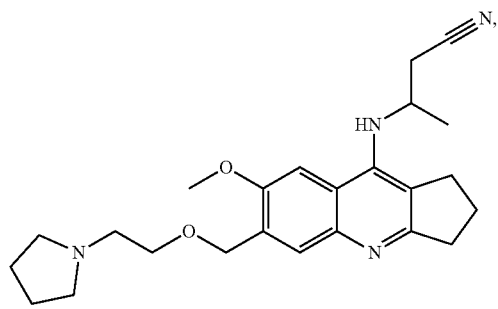 |
| 178 | 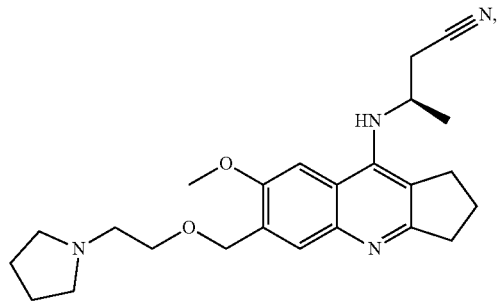 [SMILES: COc1cc2c(N[C@H](C)CC#N)c3c(nc2cc1COCCN1CCCC1)CCC3] |
| 179 | 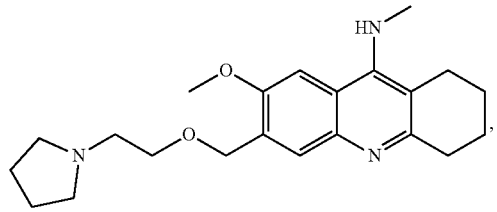 [SMILES: CNc1c2c(nc3cc(COCCN4CCCC4)c(OC)cc13)CCCC2] |
| 180 | 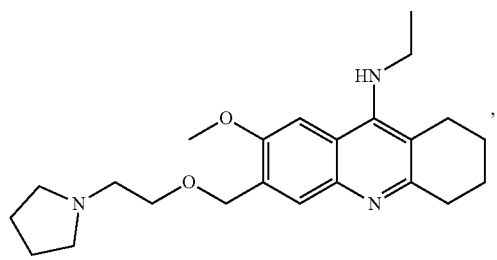 [SMILES: CCNc1c2c(nc3cc(COCCN4CCCC4)c(OC)cc13)CCCC2] |

| No. | Structure |
|---|---|
| 181 | 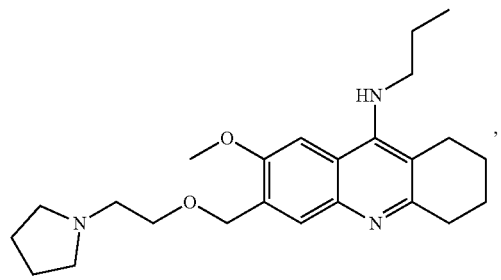 [SMILES: CCCNc1c2c(nc3cc(COCCN4CCCC4)c(OC)cc13)CCCC2] |
| 182 | 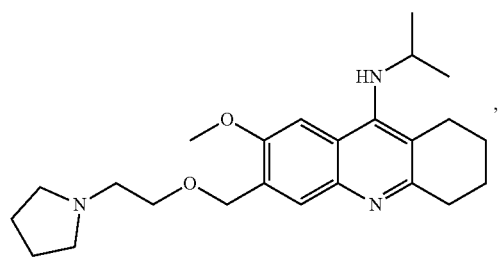 [SMILES: COc1cc2c(NC(C)C)c3c(nc2cc1COCCN1CCCC1)CCCC3] |
| 183 | 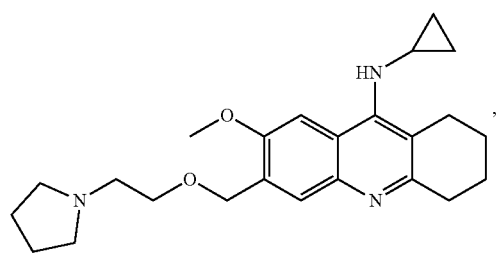 [SMILES: COc1cc2c(NC3CC3)c3c(nc2cc1COCCN1CCCC1)CCCC3] |
| 184 | 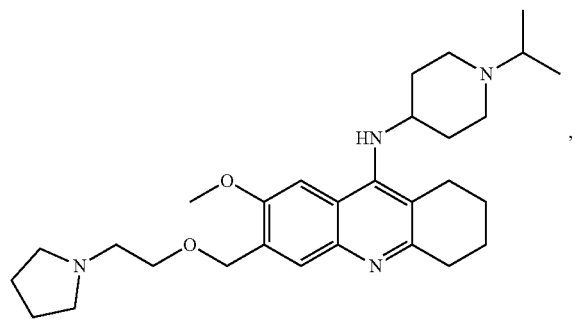 [SMILES: COc1cc2c(NC3CCN(C(C)C)CC3)c3c(nc2cc1COCCN1CCCC1)CCCC3] |
| 185 | 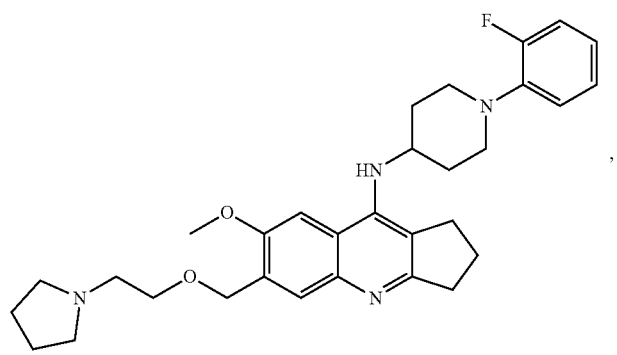 [SMILES: COc1cc2c(NC3CCN(c4ccccc4F)CC3)c3c(nc2cc1COCCN1CCCC1)CCC3] |

| No. | Structure |
|---|---|
| 186 | 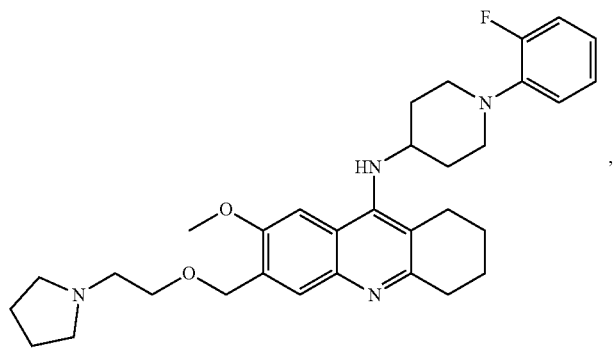 [SMILES: COc1cc2c(NC3CCN(c4ccccc4F)CC3)c3c(nc2cc1COCCN1CCCC1)CCCC3] |
| 187 | 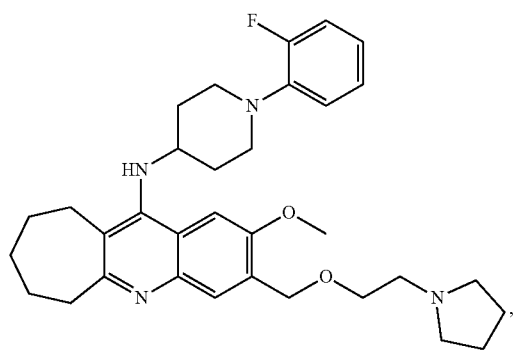 [SMILES: COc1cc2c(NC3CCN(c4ccccc4F)CC3)c3c(nc2cc1COCCN1CCCC1)CCCCC3] |
| 188 | 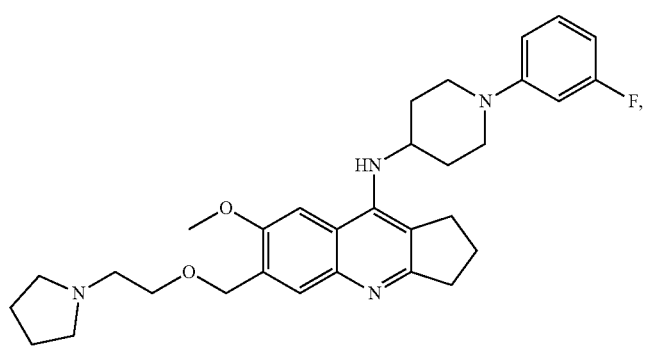 [SMILES: COc1cc2c(NC3CCN(c4cccc(F)c4)CC3)c3c(nc2cc1COCCN1CCCC1)CCC3] |
| 189 | 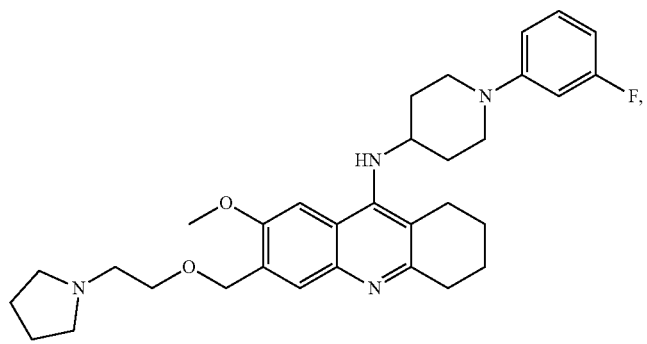 [SMILES: COc1cc2c(NC3CCN(c4cccc(F)c4)CC3)c3c(nc2cc1COCCN1CCCC1)CCCC3] |

-continued
| No. | Structure |
|---|---|
| 190 | 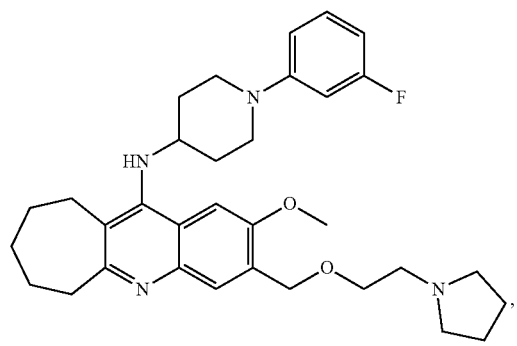 [SMILES: COc1cc2c(NC3CCN(c4cccc(F)c4)CC3)c3c(nc2cc1COCCN1CCCC1)CCCCC3] |
| 191 | 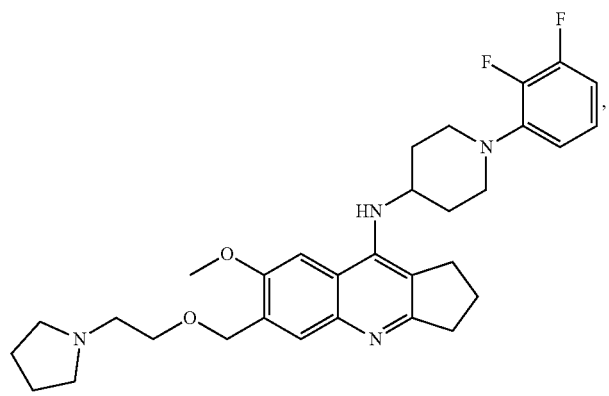 |
| 192 | 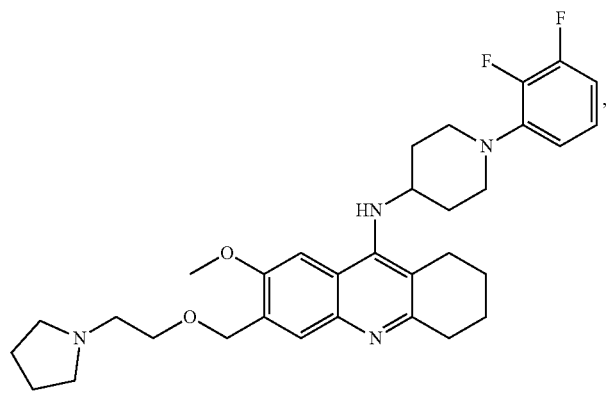 [SMILES: COc1cc2c(NC3CCN(c4cccc(F)c4F)CC3)c3c(nc2cc1COCCN1CCCC1)CCCC3] |
| 193 | 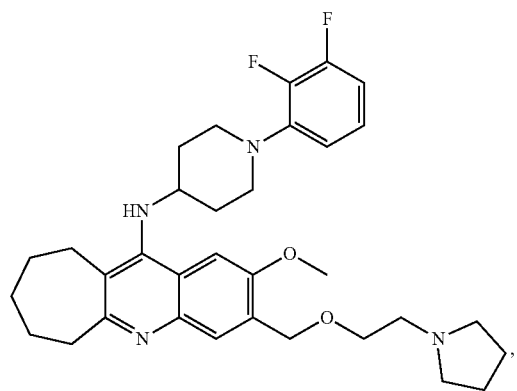 [SMILES: COc1cc2c(NC3CCN(c4cccc(F)c4F)CC3)c3c(nc2cc1COCCN1CCCC1)CCCCC3] |

| No. | Structure |
|---|---|
| 194 | 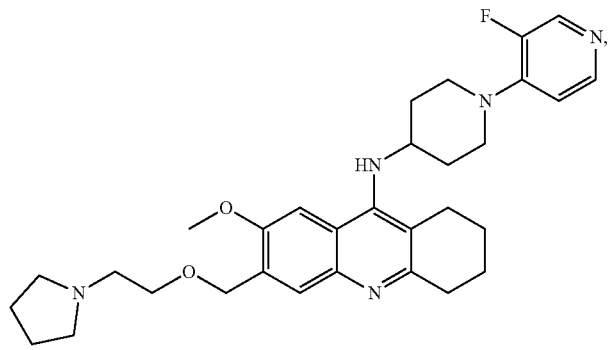 [SMILES: COc1cc2c(NC3CCN(c4ccncc4F)CC3)c3c(nc2cc1COCCN1CCCC1)CCCC3] |
| 195 | 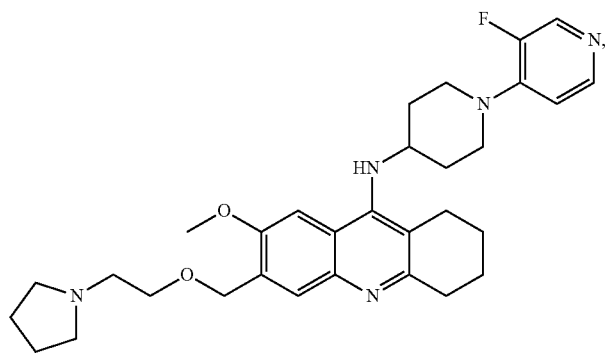 [SMILES: COc1cc2c(NC3CCN(c4ccncc4F)CC3)c3c(nc2cc1COCCN1CCCC1)CCCC3] |
| 196 | 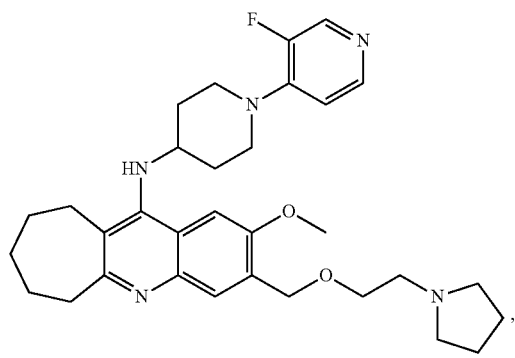 [SMILES: COc1cc2c(NC3CCN(c4ccncc4F)CC3)c3c(nc2cc1COCCN1CCCC1)CCCCC3] |
| 197 | 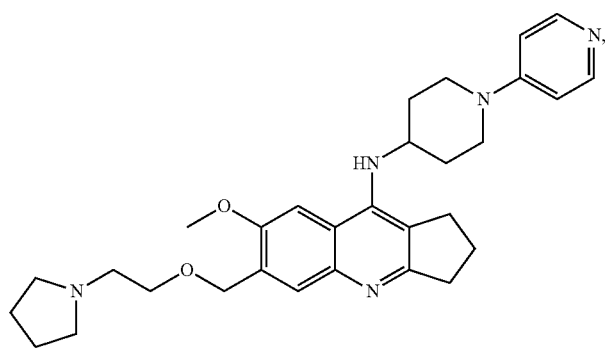 [SMILES: COc1cc2c(NC3CCN(c4ccncc4)CC3)c3c(nc2cc1COCCN1CCCC1)CCC3] |

| No. | Structure |
|---|---|
| 198 | 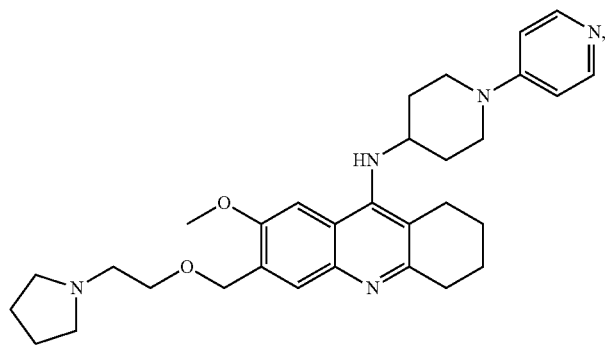 [SMILES: COc1cc2c(NC3CCN(c4ccncc4)CC3)c3c(nc2cc1COCCN1CCCC1)CCCC3] |
| 199 | 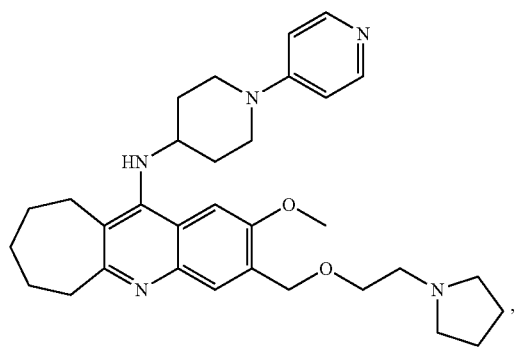 [SMILES: COc1cc2c(NC3CCN(c4ccncc4)CC3)c3c(nc2cc1COCCN1CCCC1)CCCCC3] |
| 200 | 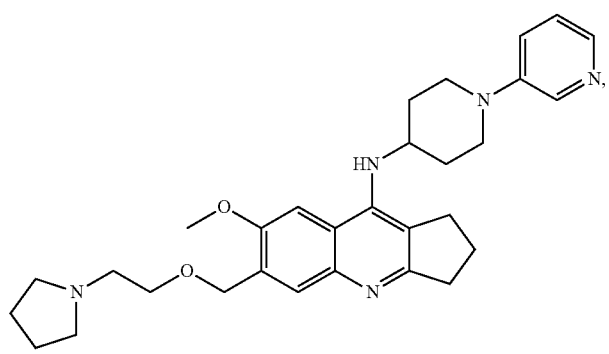 [SMILES: COc1cc2c(NC3CCN(c4cccnc4)CC3)c3c(nc2cc1COCCN1CCCC1)CCC3] |
| 201 | 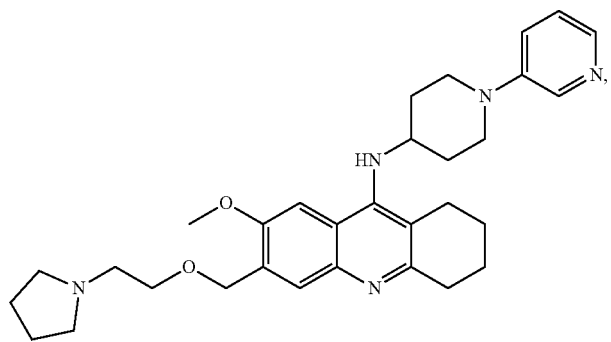 |

| No. | Structure |
|---|---|
| 202 | 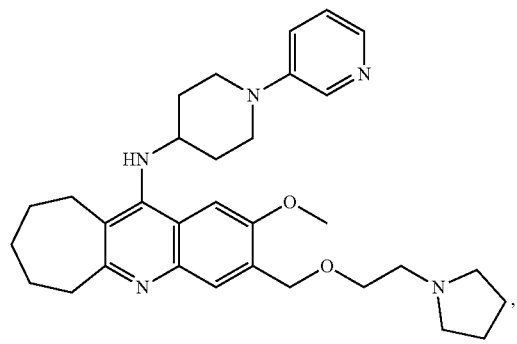 [SMILES: COc1cc2c(NC3CCN(c4cccnc4)CC3)c3c(nc2cc1COCCN1CCCC1)CCCCC3] |
| 203 | 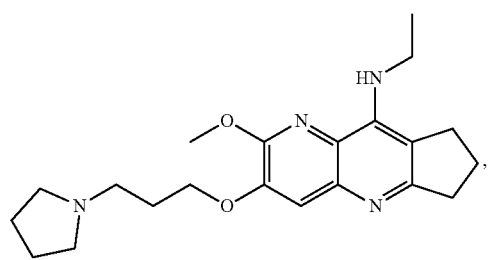 [SMILES: CCNc1c2c(nc3cc(OCCCN4CCCC4)c(OC)nc13)CCC2] |
| 204 | 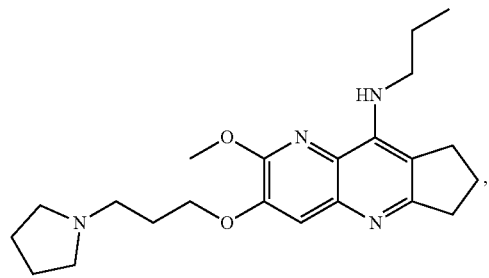 [SMILES: CCCNc1c2c(nc3cc(OCCCN4CCCC4)c(OC)nc13)CCC2] |
| 205 | 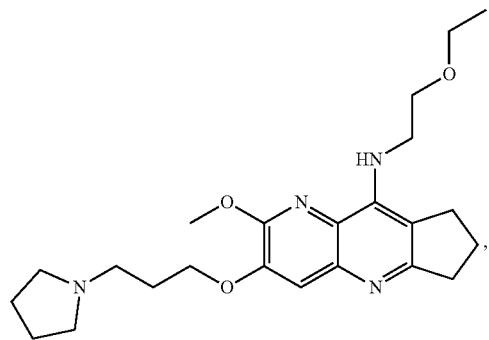 [SMILES: CCOCCNc1c2c(nc3cc(OCCCN4CCCC4)c(OC)nc13)CCC2] |
| 206 | 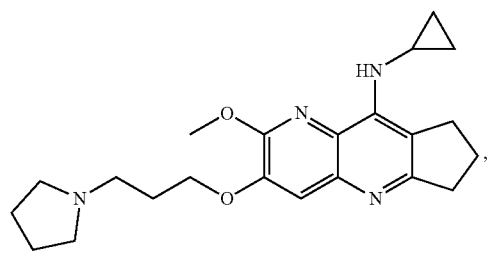 [SMILES: COc1nc2c(NC3CC3)c3c(nc2cc1OCCCN1CCCC1)CCC3] |

| No. | Structure |
|---|---|
| 207 | 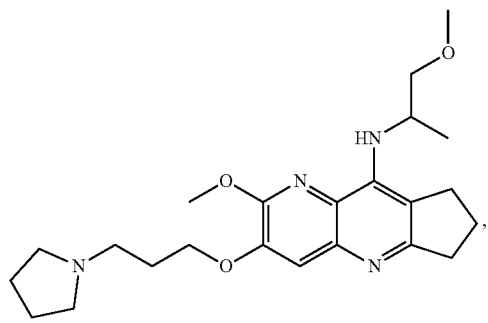 [SMILES: COCC(C)Nc1c2c(nc3cc(OCCCN4CCCC4)c(OC)nc13)CCC2] |
| 208 | 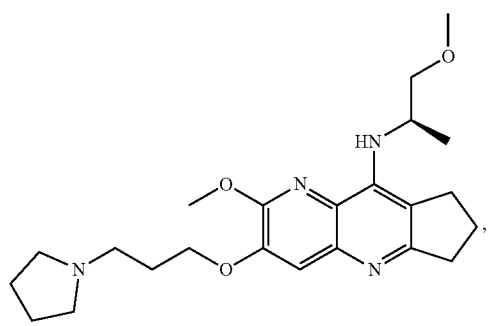 [SMILES: COC[C@@H](C)Nc1c2c(nc3cc(OCCCN4CCCC4)c(OC)nc13)CCC2] |
| 209 | 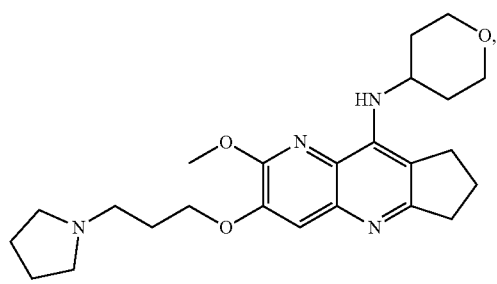 [SMILES: COc1nc2c(NC3CCOCC3)c3c(nc2cc1OCCCN1CCCC1)CCC3] |
| 210 | 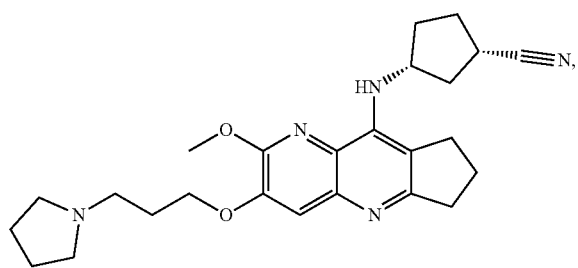 [SMILES: COc1nc2c(N[C@@H]3CC[C@H](C#N)C3)c3c(nc2cc1OCCCN1CCCC1)CCC3] |
| 211 | 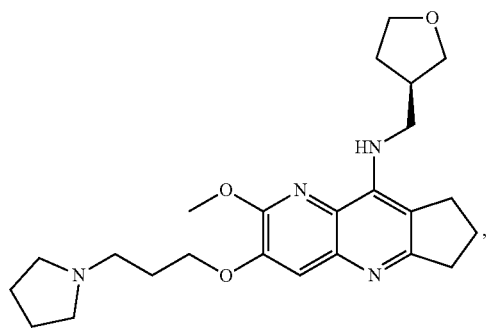 [SMILES: COc1nc2c(NC[C@H]3CCOC3)c3c(nc2cc1OCCCN1CCCC1)CCC3] |

| No. | Structure |
|---|---|
| 212 | 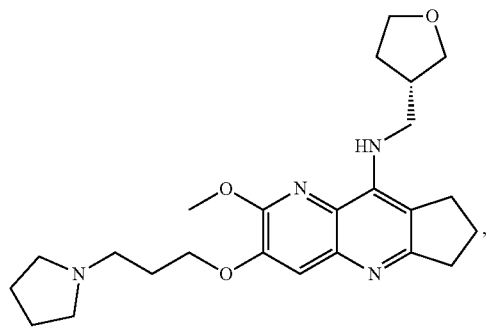 [SMILES: COc1nc2c(NC[C@@H]3CCOC3)c3c(nc2cc1OCCCN1CCCC1)CCC3] |
| 213 | 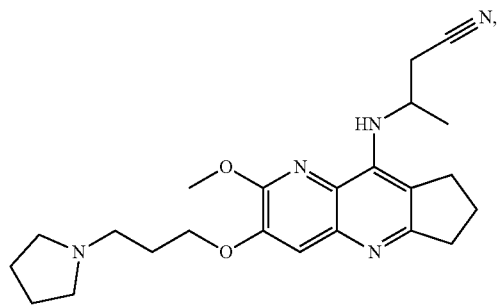 [SMILES: COc1nc2c(NC(C)CC#N)c3c(nc2cc1OCCCN1CCCC1)CCC3] |
| 214 | 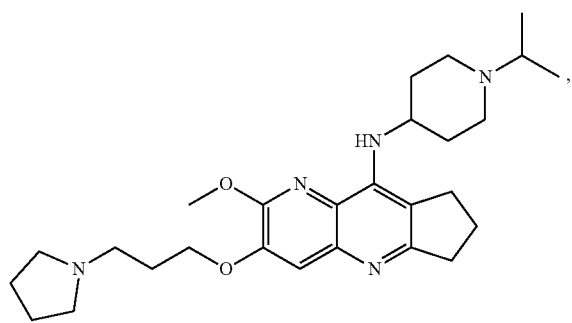 [SMILES: COc1nc2c(NC3CCN(C(C)C)CC3)c3c(nc2cc1OCCCN1CCCC1)CCC3] |
| 215 | 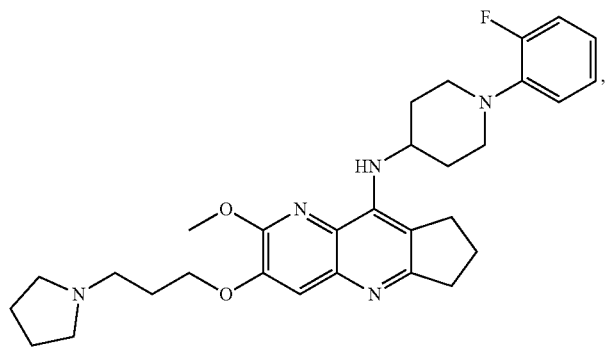 [SMILES: COc1nc2c(NC3CCN(c4ccccc4F)CC3)c3c(nc2cc1OCCCN1CCCC1)CCC3] |

| No. | Structure |
|---|---|
| 216 | 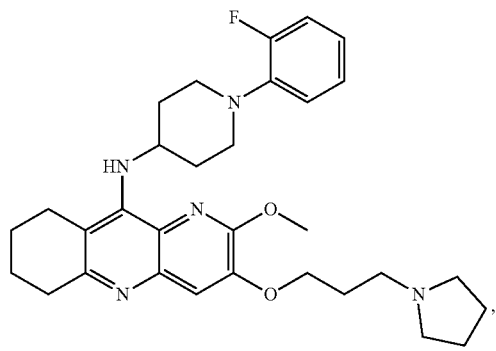 [SMILES: COc1nc2c(NC3CCN(c4ccccc4F)CC3)c3c(nc2cc1OCCCN1CCCC1)CCCC3] |
| 217 | 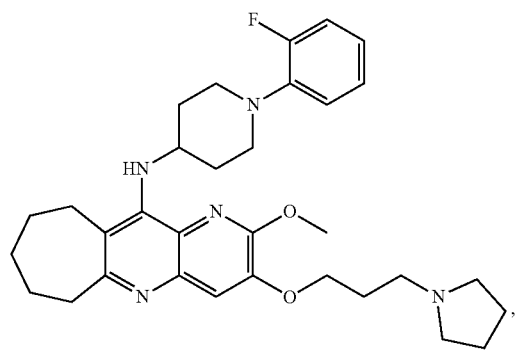 |
| 218 | 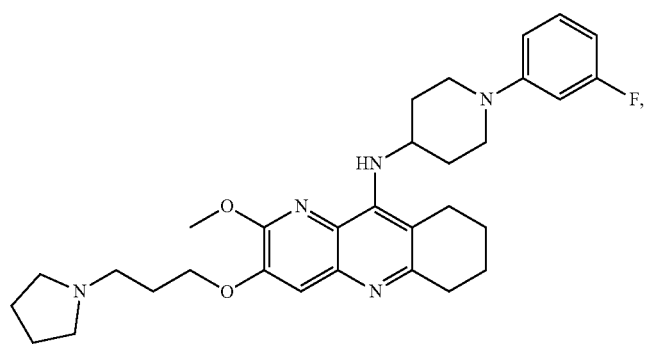 [SMILES: COc1nc2c(NC3CCN(c4cccc(F)c4)CC3)c3c(nc2cc1OCCCN1CCCC1)CCCC3] |
| 219 | 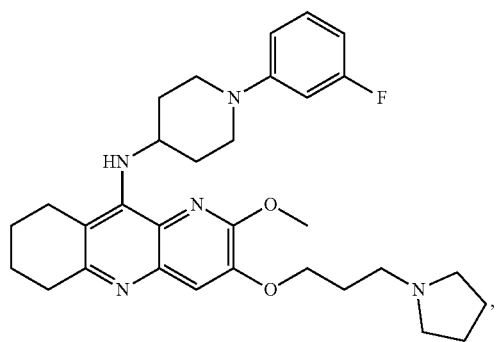 [SMILES: COc1nc2c(NC3CCN(c4cccc(F)c4)CC3)c3c(nc2cc1OCCCN1CCCC1)CCCC3] |

| No. | Structure |
|---|---|
| 220 | 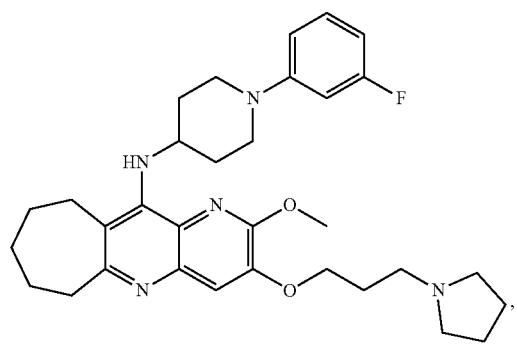 |
| 221 | 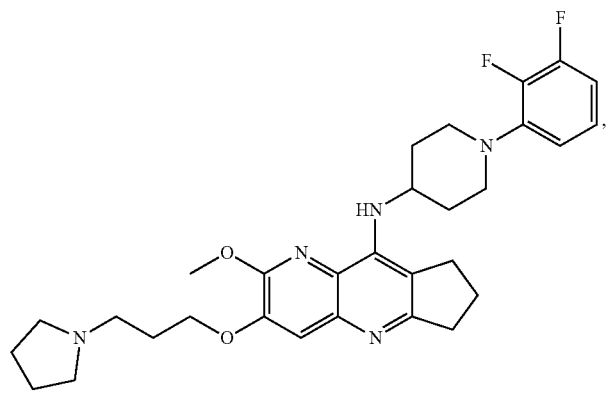 [SMILES: COc1nc2c(NC3CCN(c4cccc(F)c4F)CC3)c3c(nc2cc1OCCCN1CCCC1)CCC3] |
| 222 | 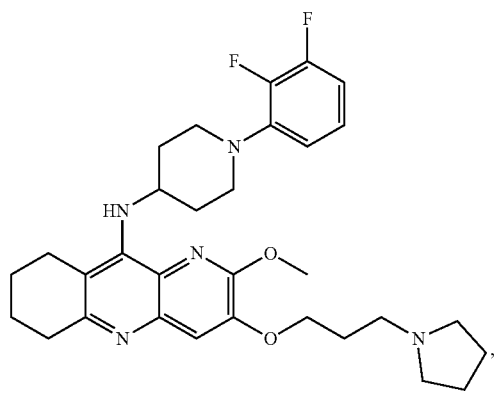 [SMILES: COc1nc2c(NC3CCN(c4cccc(F)c4F)CC3)c3c(nc2cc1OCCCN1CCCC1)CCCC3] |
| 223 | 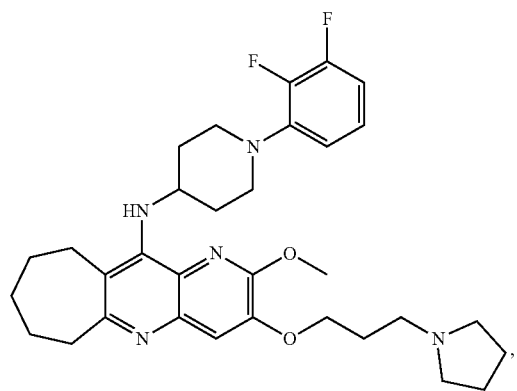 |

| No. | Structure |
|---|---|
| 224 | 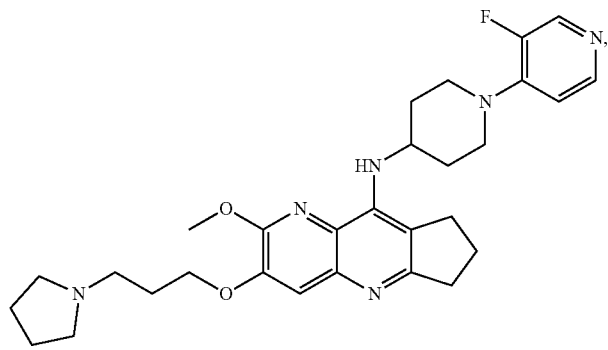 [SMILES: COc1nc2c(NC3CCN(c4ccncc4F)CC3)c3c(nc2cc1OCCCN1CCCC1)CCC3] |
| 225 | 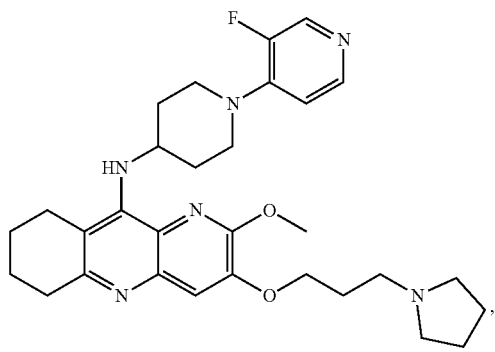 [SMILES: COc1nc2c(NC3CCN(c4ccncc4F)CC3)c3c(nc2cc1OCCCN1CCCC1)CCCC3] |
| 226 | 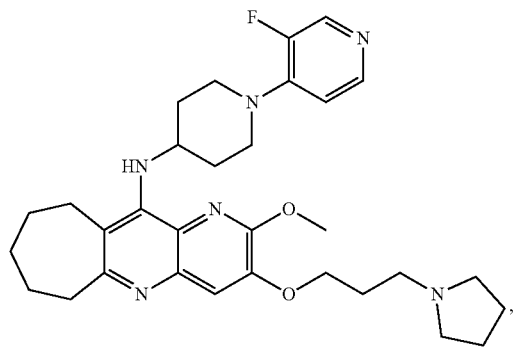 |
| 227 | 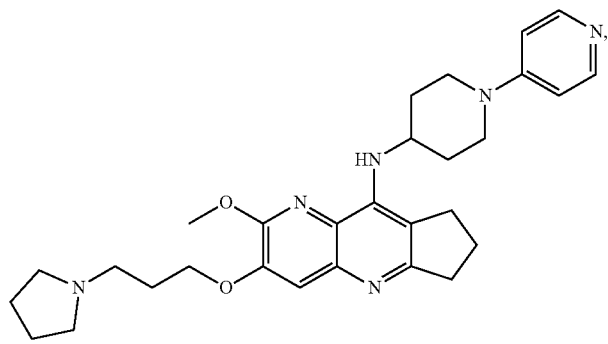 |

| No. | Structure |
|---|---|
| 228 | 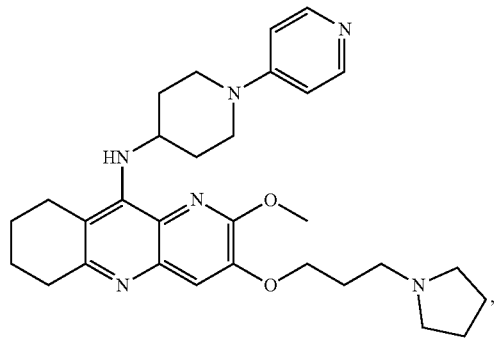 [SMILES: COc1nc2c(NC3CCN(c4ccncc4)CC3)c3c(nc2cc1OCCCN1CCCC1)CCCC3] |
| 229 | 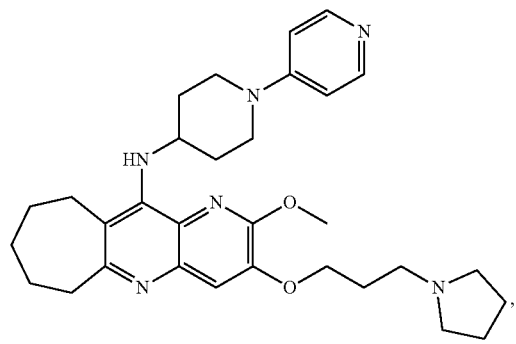 |
| 230 | 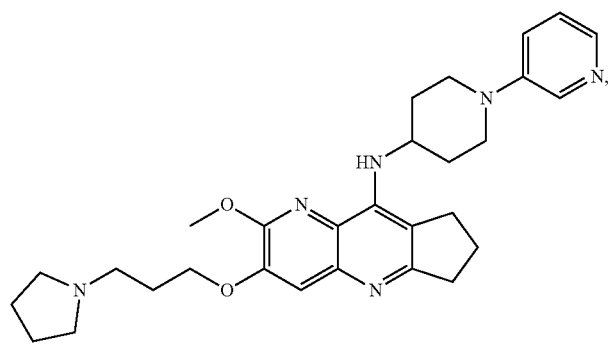 |
| 231 | 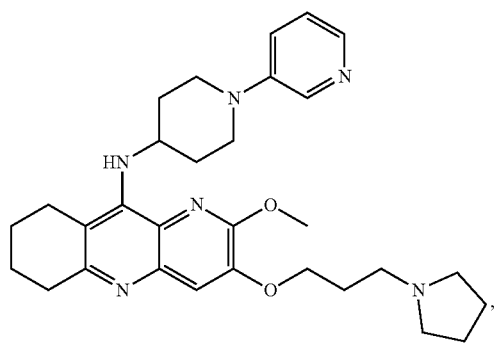 [SMILES: COc1nc2c(NC3CCN(c4cccnc4)CC3)c3c(nc2cc1OCCCN1CCCC1)CCCC3] |

| No. | Structure |
|---|---|
| 232 | 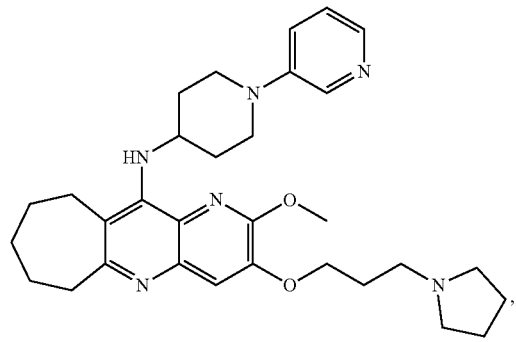 |
| 233 | 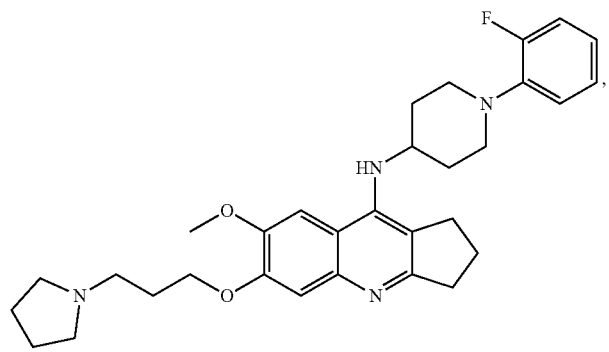 [SMILES: COc1cc2c(NC3CCN(c4ccccc4F)CC3)c3c(nc2cc1OCCCN1CCCC1)CCC3] |
| 234 | 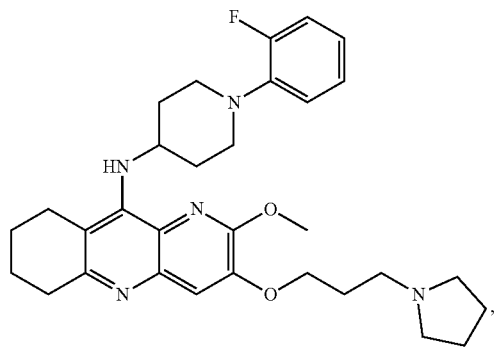 [SMILES: COc1nc2c(NC3CCN(c4ccccc4F)CC3)c3c(nc2cc1OCCCN1CCCC1)CCCC3] |
| 235 | 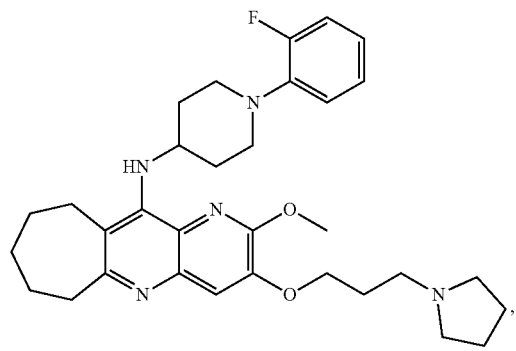 |

| No. | Structure |
|---|---|
| 236 | 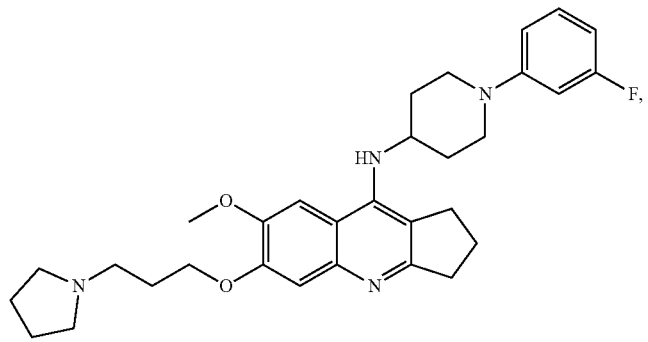 |
| 237 | 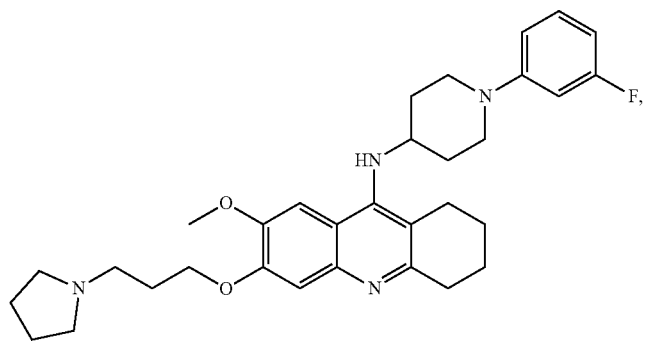 [SMILES: COc1cc2c(NC3CCN(c4cccc(F)c4)CC3)c3c(nc2cc1OCCCN1CCCC1)CCCC3] |
| 238 | 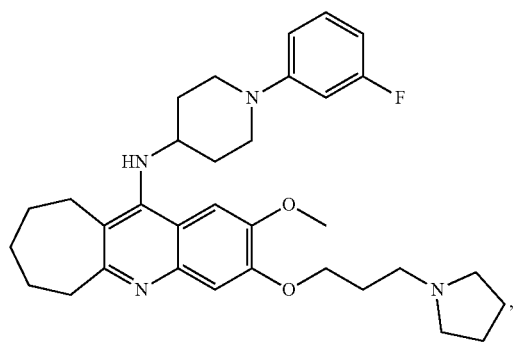 |
| 239 | 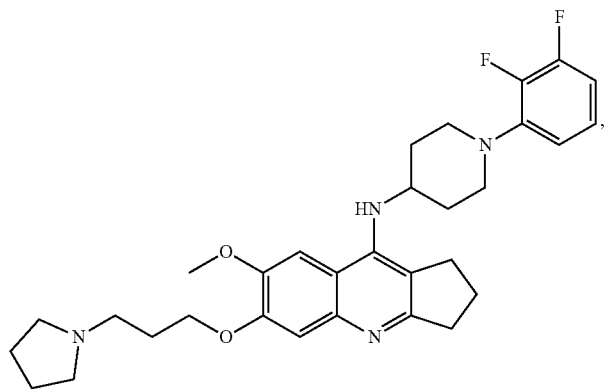 [SMILES: COc1cc2c(NC3CCN(c4cccc(F)c4F)CC3)c3c(nc2cc1OCCCN1CCCC1)CCC3] |

| No. | Structure |
|---|---|
| 240 | 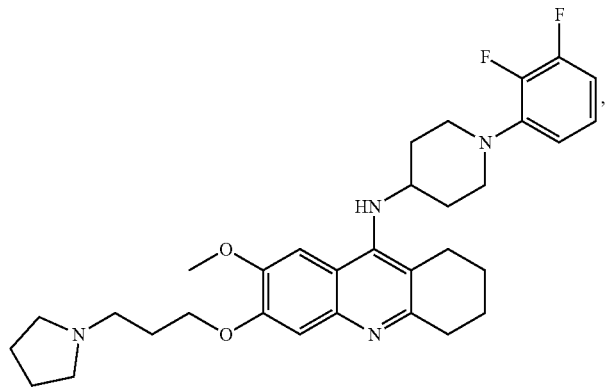 |
| 241 | 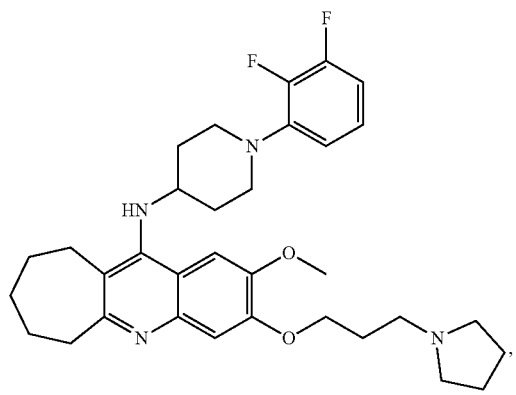 |
| 242 | 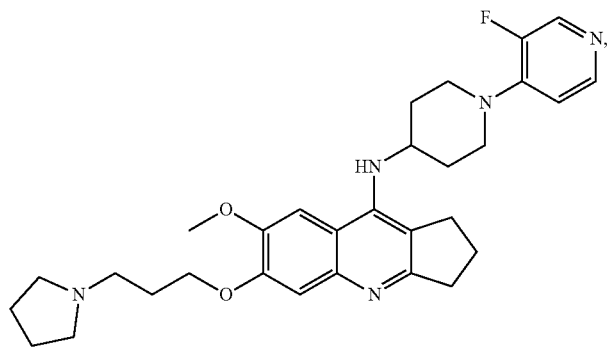 [SMILES: COc1cc2c(NC3CCN(c4ccncc4F)CC3)c3c(nc2cc1OCCCN1CCCC1)CCC3] |
| 243 | 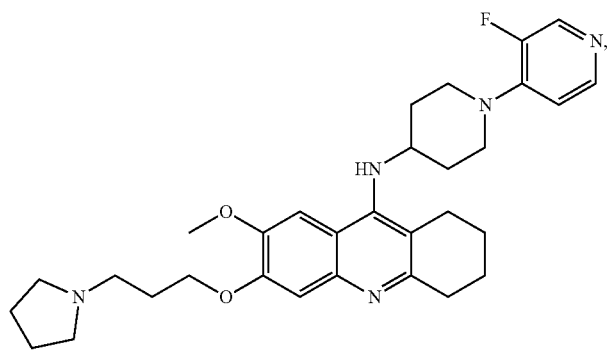 |

-continued
| No. | Structure |
|---|---|
| 244 | 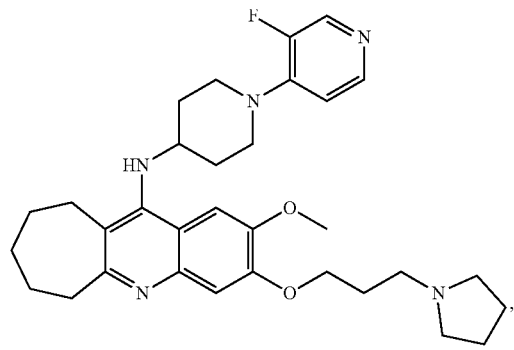 |
| 245 | 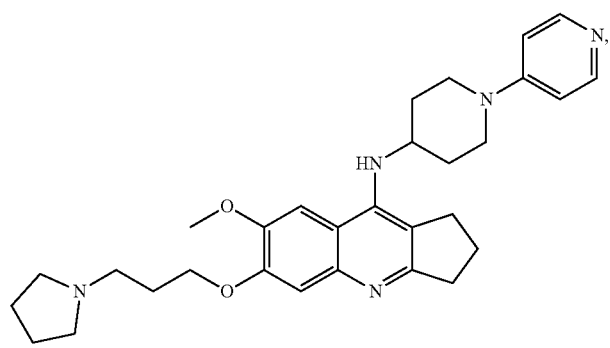 [SMILES: COc1cc2c(NC3CCN(c4ccncc4)CC3)c3c(nc2cc1OCCCN1CCCC1)CCC3] |
| 246 | 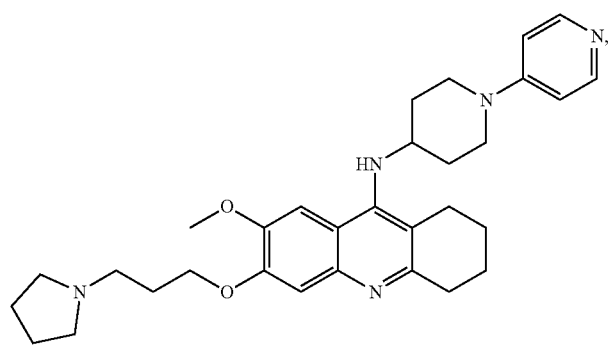 [SMILES: COc1cc2c(NC3CCN(c4ccncc4)CC3)c3c(nc2cc1OCCCN1CCCC1)CCCC3] |
| 247 | 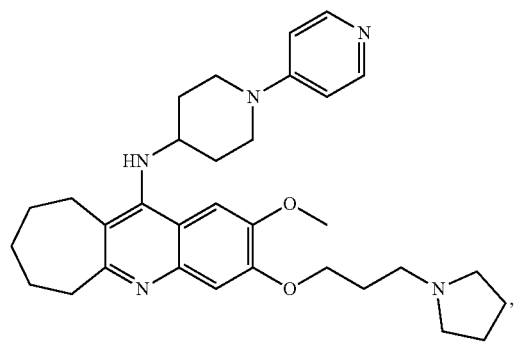 |

| No. | Structure |
|---|---|
| 248 | 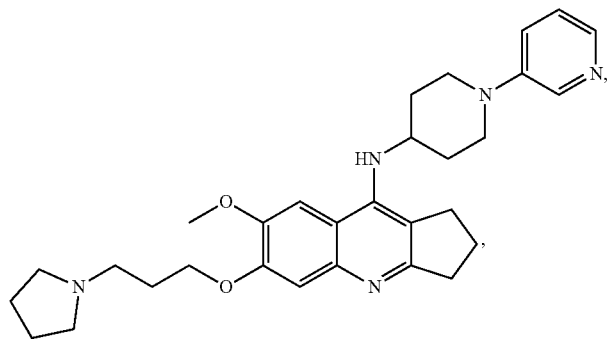 [SMILES: COc1cc2c(NC3CCN(c4cccnc4)CC3)c3c(nc2cc1OCCCN1CCCC1)CCC3] |
| 249 | 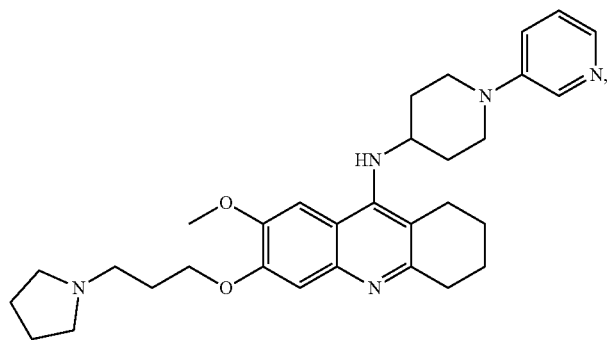 [SMILES: COc1cc2c(NC3CCN(c4cccnc4)CC3)c3c(nc2cc1OCCCN1CCCC1)CCCC3] |
| 250 | 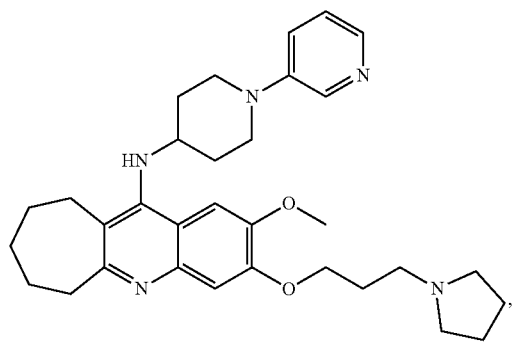 [SMILES: COc1cc2c(NC3CCN(c4cccnc4)CC3)c3c(nc2cc1OCCCN1CCCC1)CCCCC3] |
| 251 | 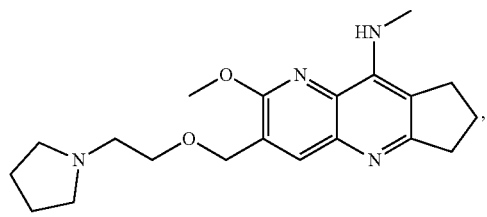 [SMILES: CNc1c2c(nc3cc(COCCN4CCCC4)c(OC)nc13)CCC2] |
| 252 | 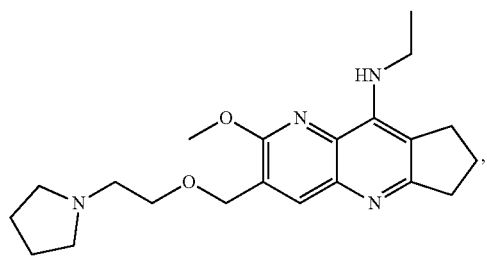 [SMILES: CCNc1c2c(nc3cc(COCCN4CCCC4)c(OC)nc13)CCC2] |

| No. | Structure |
|---|---|
| 253 | 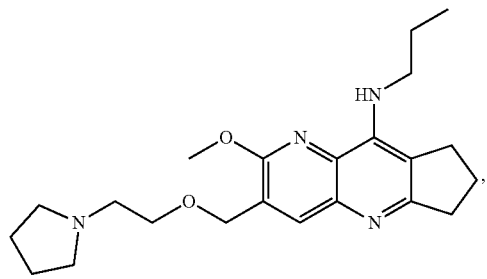 |
| 254 | 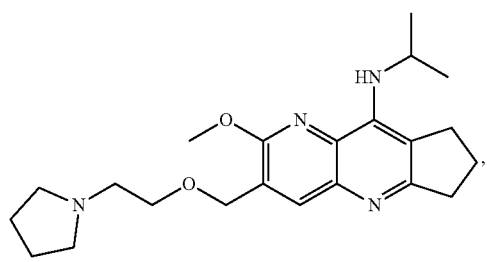 [SMILES: COc1nc2c(NC(C)C)c3c(nc2cc1COCCN1CCCC1)CCC3] |
| 255 | 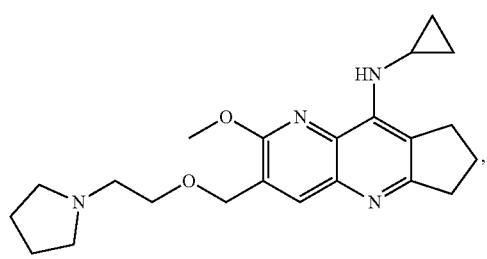 |
| 256 | 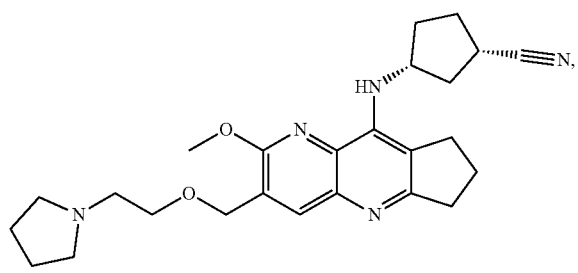 |
| 257 | 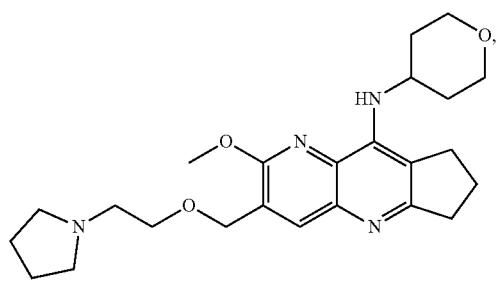 [SMILES: COc1nc2c(NC3CCOCC3)c3c(nc2cc1COCCN1CCCC1)CCC3] |

-continued
| No. | Structure |
|---|---|
| 258 | 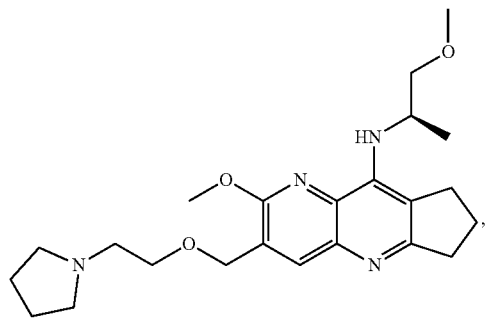 |
| 259 | 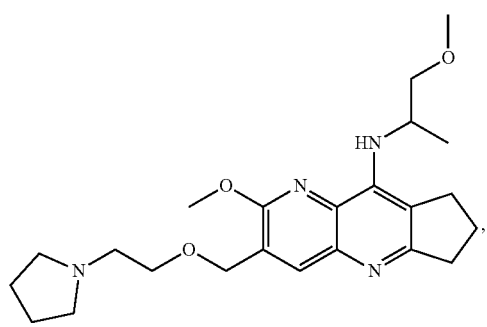 |
| 260 | 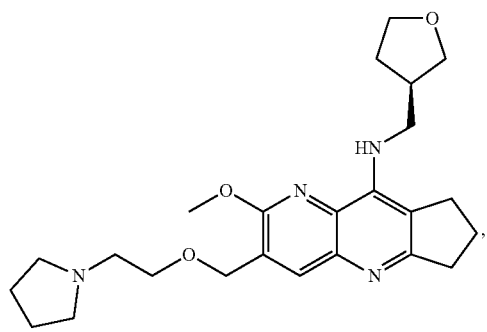 |
| 261 | 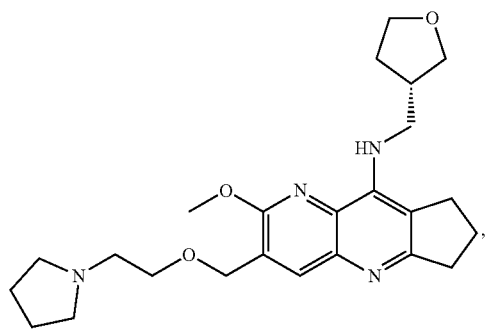 |

| No. | Structure |
|---|---|
| 262 | 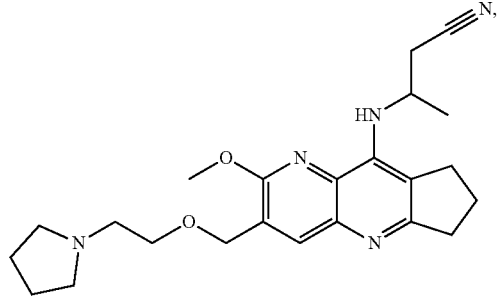 [SMILES: COc1nc2c(NC(C)CC#N)c3c(nc2cc1COCCN1CCCC1)CCC3] |
| 263 | 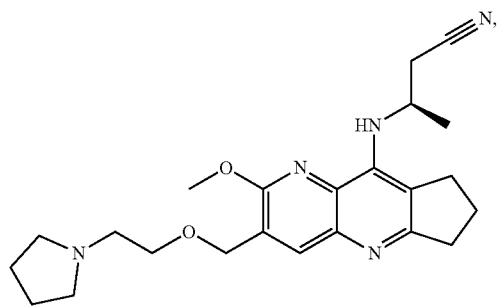 [SMILES: COc1nc2c(N[C@H](C)CC#N)c3c(nc2cc1COCCN1CCCC1)CCC3] |
| 264 | 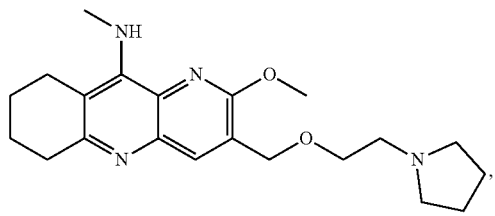 [SMILES: CNc1c2c(nc3cc(COCCN4CCCC4)c(OC)nc13)CCCC2] |
| 265 | 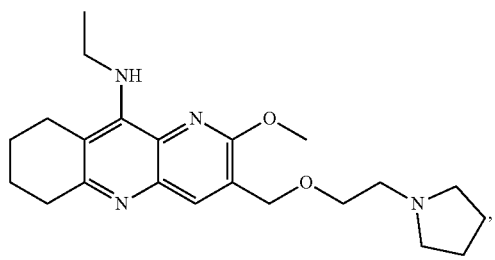 [SMILES: CCNc1c2c(nc3cc(COCCN4CCCC4)c(OC)nc13)CCCC2] |
| 266 | 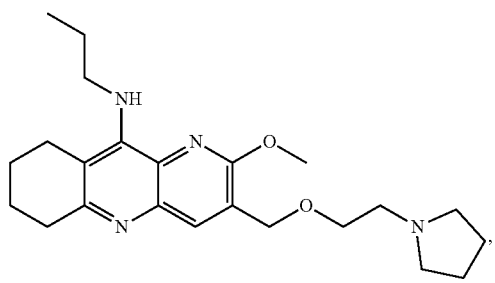 [SMILES: CCCNc1c2c(nc3cc(COCCN4CCCC4)c(OC)nc13)CCCC2] |

| No. | Structure |
|---|---|
| 267 | 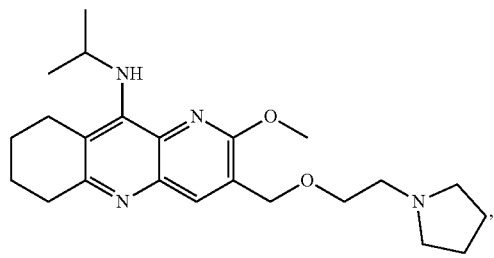 [SMILES: COc1nc2c(NC(C)C)c3c(nc2cc1COCCN1CCCC1)CCCC3] |
| 268 | 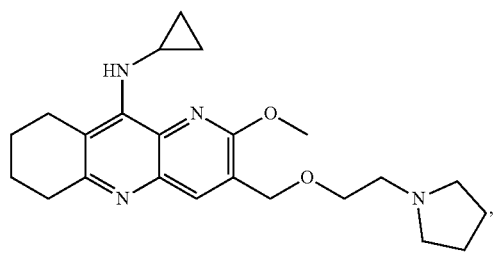 [SMILES: COc1nc2c(NC3CC3)c3c(nc2cc1COCCN1CCCC1)CCCC3] |
| 269 | 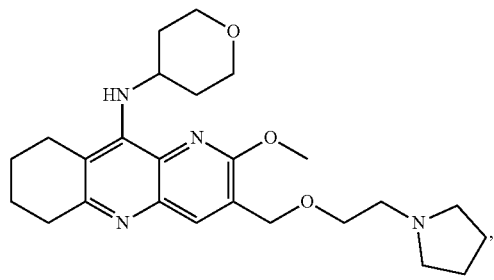 [SMILES: COc1nc2c(NC3CCOCC3)c3c(nc2cc1COCCN1CCCC1)CCCC3] |
| 270 | 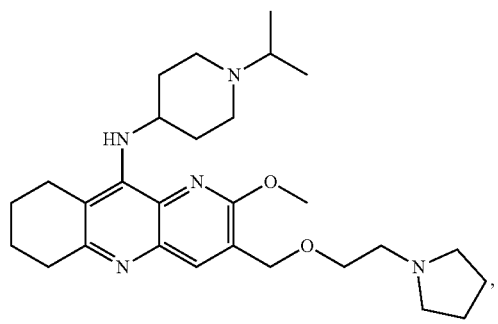 [SMILES: COc1nc2c(NC3CCN(C(C)C)CC3)c3c(nc2cc1COCCN1CCCC1)CCCC3] |
| 271 | 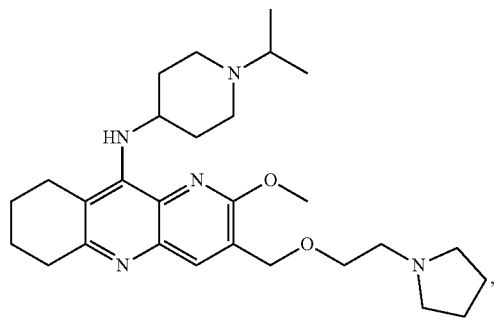 [SMILES: COc1nc2c(NC3CCN(C(C)C)CC3)c3c(nc2cc1COCCN1CCCC1)CCCC3] |

| No. | Structure |
|---|---|
| 272 | 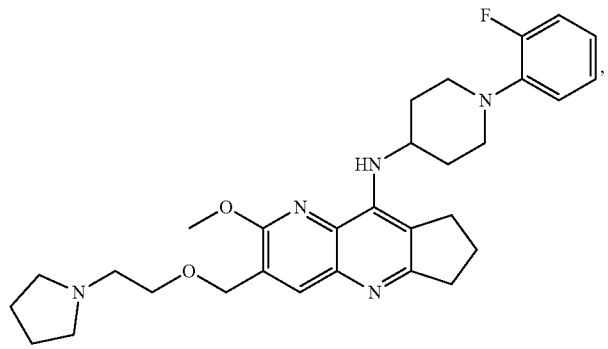 |
| 273 | 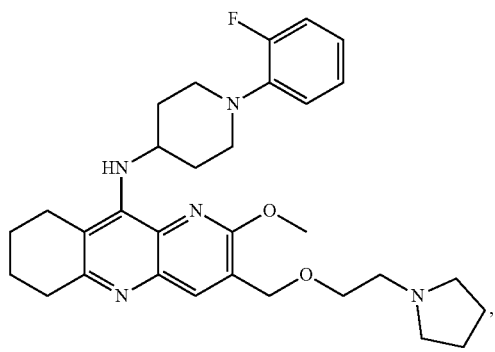 |
| 274 | 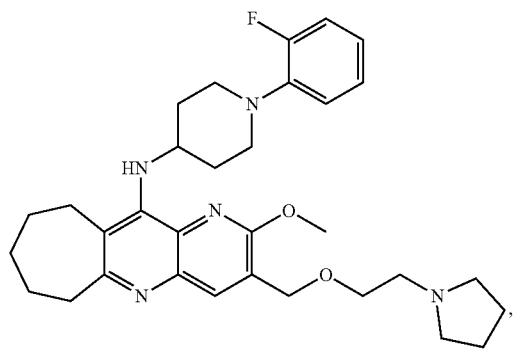 |
| 275 | 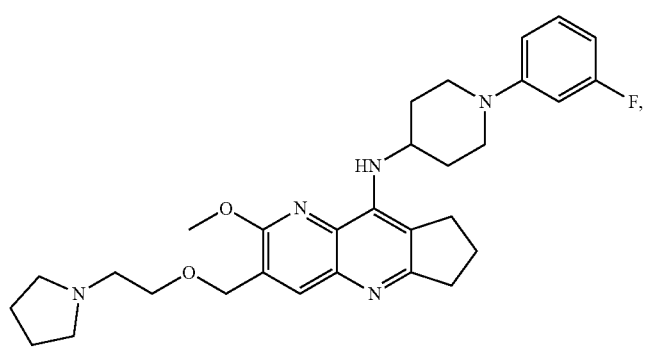 [SMILES: COc1nc2c(NC3CCN(c4cccc(F)c4)CC3)c3c(nc2cc1COCCN1CCCC1)CCC3] |

-continued
| No. | Structure |
|---|---|
| 276 | 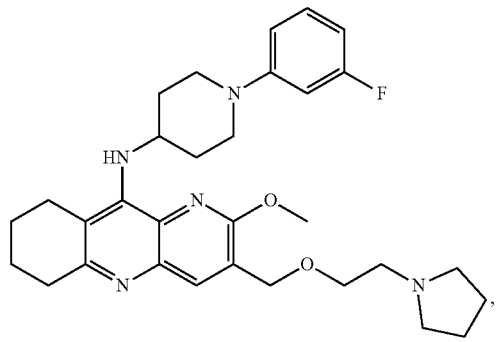 [SMILES: COc1nc2c(NC3CCN(c4cccc(F)c4)CC3)c3c(nc2cc1COCCN1CCCC1)CCCC3] |
| 277 | 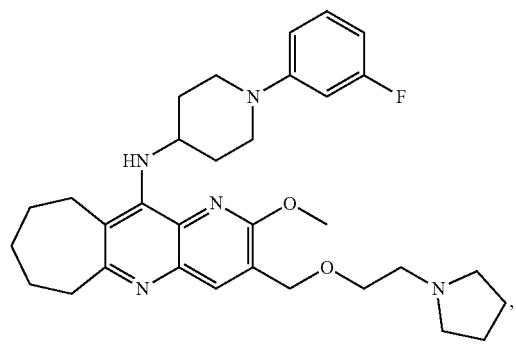 [SMILES: COc1nc2c(NC3CCN(c4cccc(F)c4)CC3)c3c(nc2cc1COCCN1CCCC1)CCCCC3] |
| 278 | 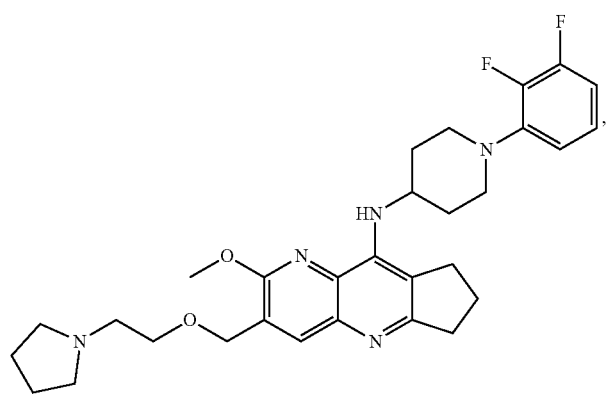 |
| 279 | 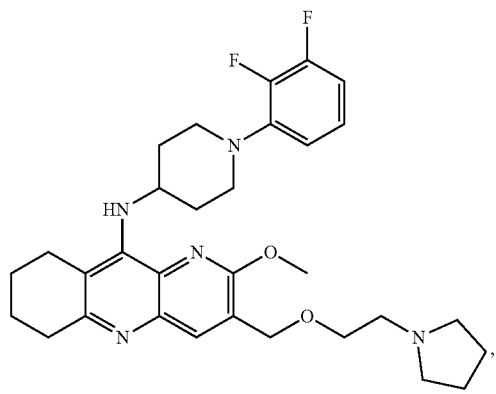 [SMILES: COc1nc2c(NC3CCN(c4cccc(F)c4F)CC3)c3c(nc2cc1COCCN1CCCC1)CCCC3] |

| No. | Structure |
|---|---|
| 280 | 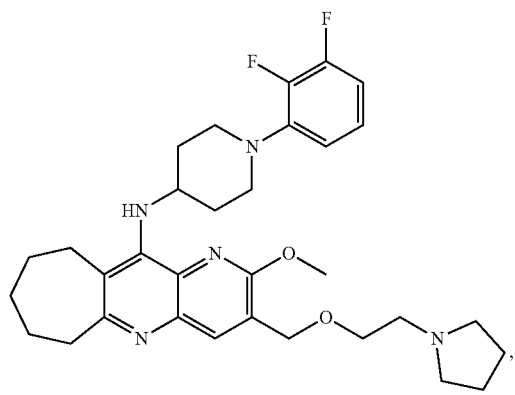 [SMILES: COc1nc2c(NC3CCN(c4cccc(F)c4F)CC3)c3c(nc2cc1COCCN1CCCC1)CCCCC3] |
| 281 | 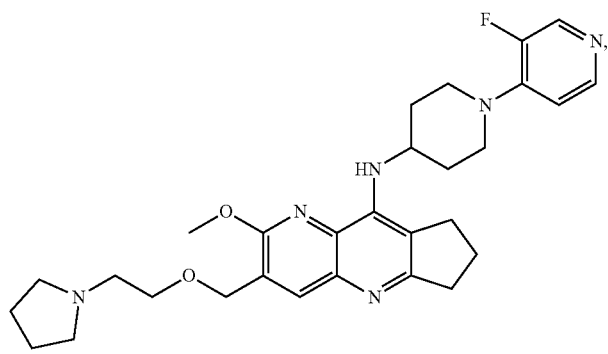 [SMILES: COc1nc2c(NC3CCN(c4ccncc4F)CC3)c3c(nc2cc1COCCN1CCCC1)CCC3] |
| 282 | 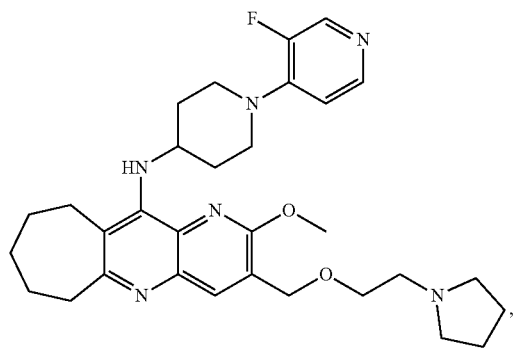 [SMILES: COc1nc2c(NC3CCN(c4ccncc4F)CC3)c3c(nc2cc1COCCN1CCCC1)CCCCC3] |
| 283 | 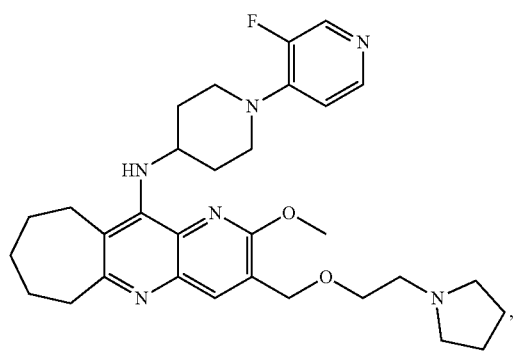 [SMILES: COc1nc2c(NC3CCN(c4ccncc4F)CC3)c3c(nc2cc1COCCN1CCCC1)CCCCC3] |

| No. | Structure |
|---|---|
| 284 | 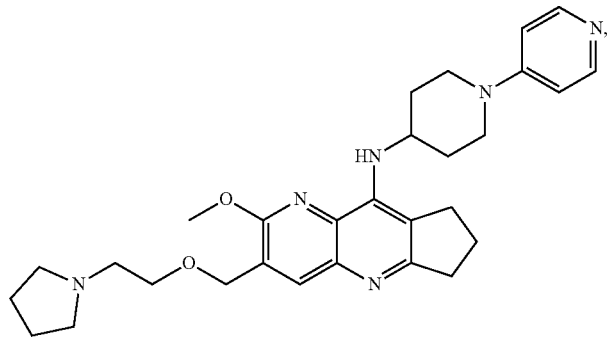 [SMILES: COc1nc2c(NC3CCN(c4ccncc4)CC3)c3c(nc2cc1COCCN1CCCC1)CCC3] |
| 285 | 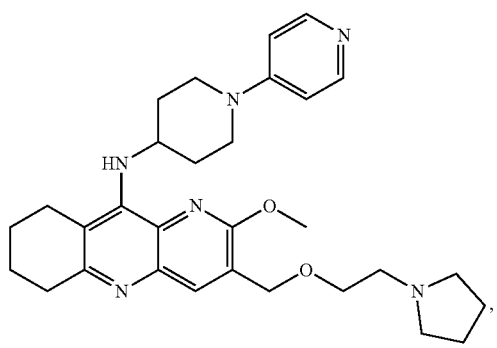 |
| 286 | 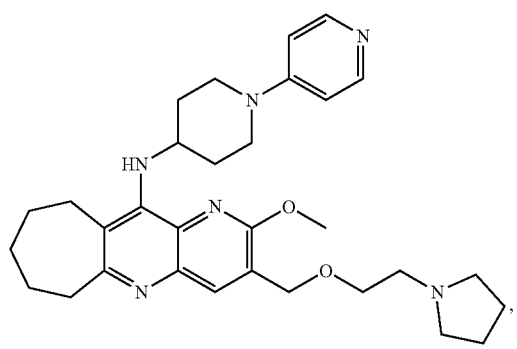 [SMILES: COc1nc2c(NC3CCN(c4ccncc4)CC3)c3c(nc2cc1COCCN1CCCC1)CCCCC3] |
| 287 | 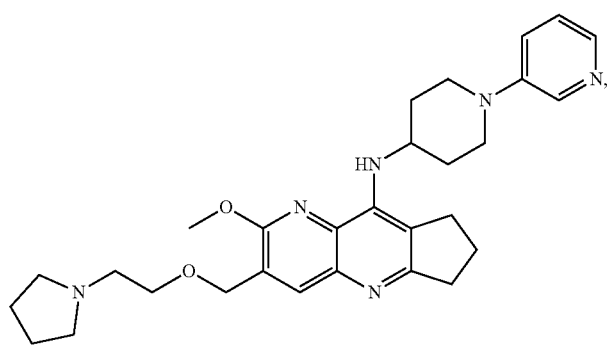 [SMILES: COc1nc2c(NC3CCN(c4cccnc4)CC3)c3c(nc2cc1COCCN1CCCC1)CCC3] |

| No. | Structure |
|---|---|
| 288 | 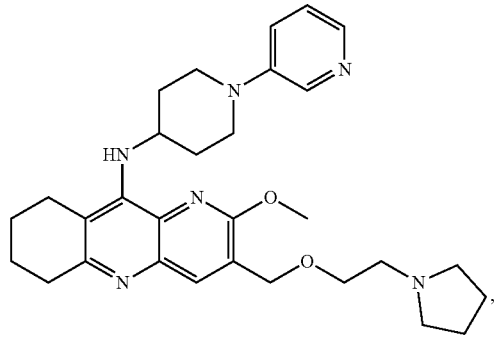 |
| 289 | 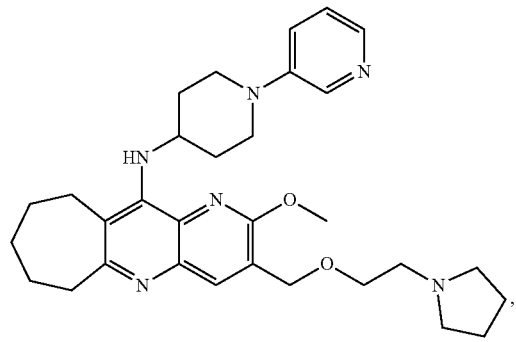 [SMILES: COc1nc2c(NC3CCN(c4cccnc4)CC3)c3c(nc2cc1COCCN1CCCC1)CCCCC3] |
| 290 | 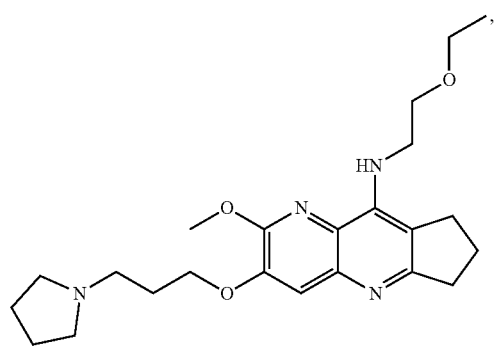 [SMILES: CCOCCNc1c2c(nc3cc(OCCCN4CCCC4)c(OC)nc13)CCC2] |
| 291 | 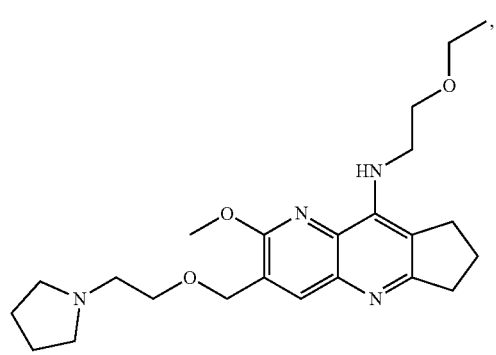 [SMILES: CCOCCNc1c2c(nc3cc(COCCN4CCCC4)c(OC)nc13)CCC2] |

-continued
| No. | Structure |
|---|---|
| 292 | 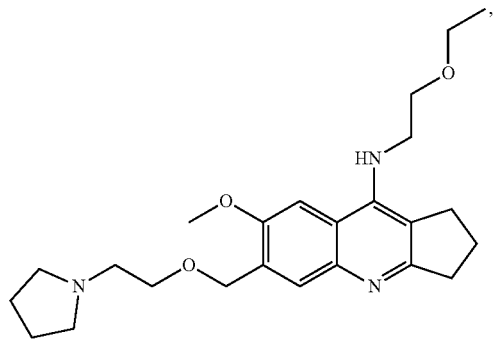 |
| 293 | 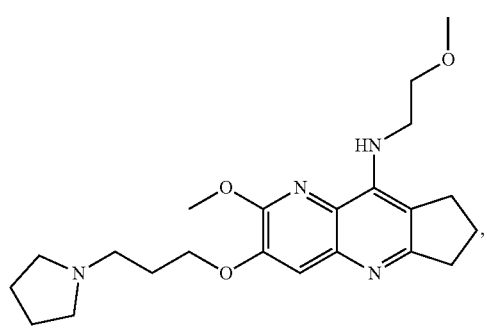 [SMILES: COCCNc1c2c(nc3cc(OCCCN4CCCC4)c(OC)nc13)CCC2] |
| 294 | 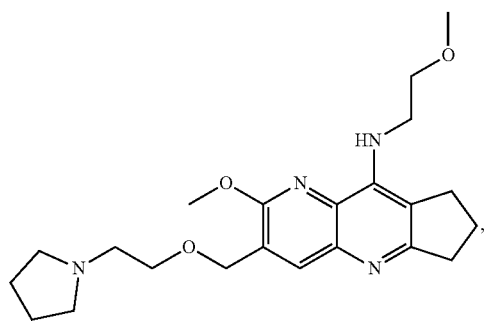 [SMILES: COCCNc1c2c(nc3cc(COCCN4CCCC4)c(OC)nc13)CCC2] |
| 295 | 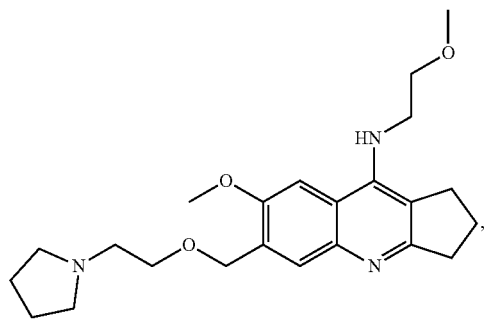 [SMILES: COCCNc1c2c(nc3cc(COCCN4CCCC4)c(OC)cc13)CCC2] |

-continued
| No. | Structure |
|---|---|
| 296 | 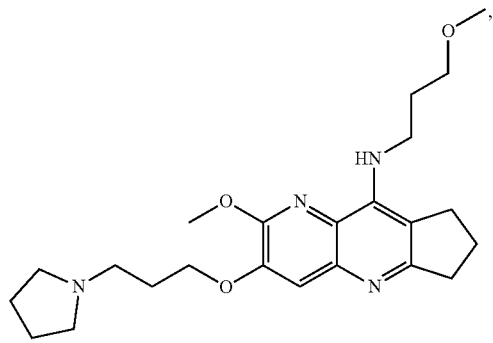 |
| 297 | 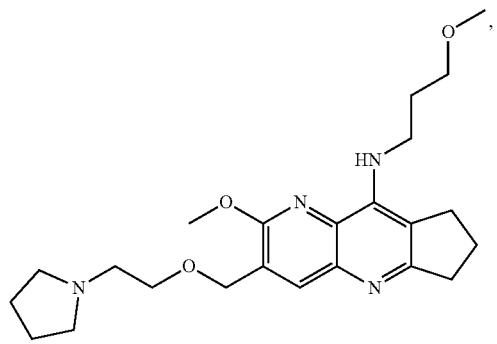 |
| 298 | 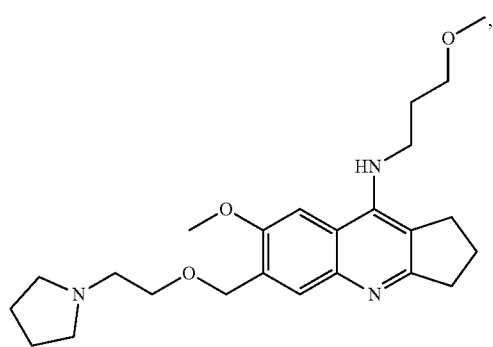 |
| 299 | 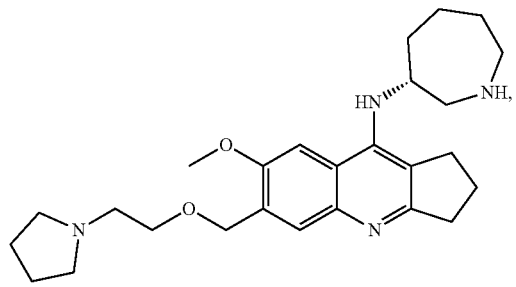 [SMILES: COc1cc2c(N[C@@H]3CCCCNC3)c3c(nc2cc1COCCN1CCCC1)CCC3] |

| No. | Structure |
|---|---|
| 300 | 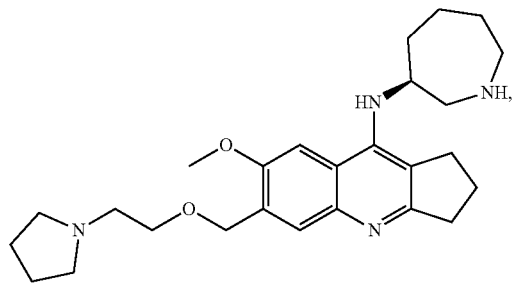 [SMILES: COc1cc2c(N[C@H]3CCCCNC3)c3c(nc2cc1COCCN1CCCC1)CCC3] |
| 301 | 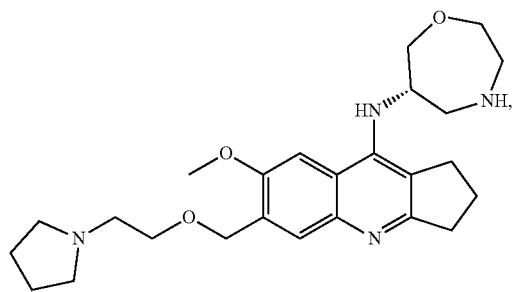 |
| 302 | 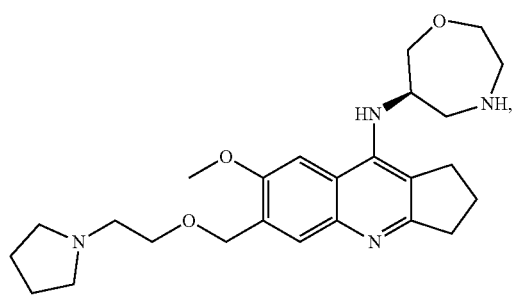 [SMILES: COc1cc2c(N[C@@H]3CNCCOC3)c3c(nc2cc1COCCN1CCCC1)CCC3] |
| 303 | 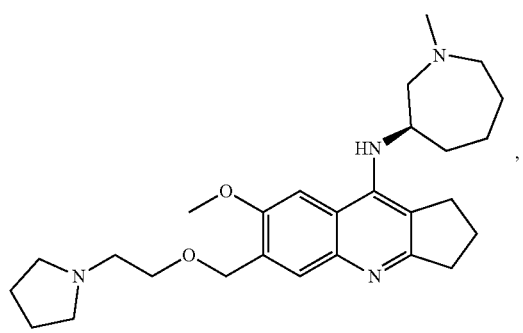 [SMILES: COc1cc2c(N[C@@H]3CCCCN(C)C3)c3c(nc2cc1COCCN1CCCC1)CCC3] |
| 304 | 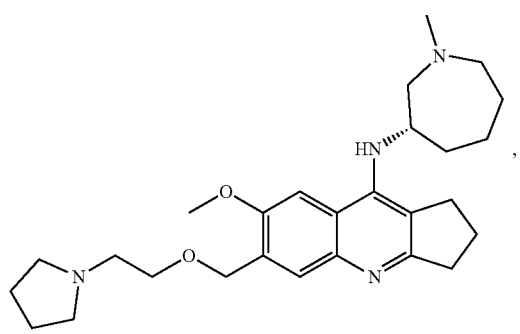 [SMILES: COc1cc2c(N[C@H]3CCCCN(C)C3)c3c(nc2cc1COCCN1CCCC1)CCC3] |

| No. | Structure |
|---|---|
| 305 | 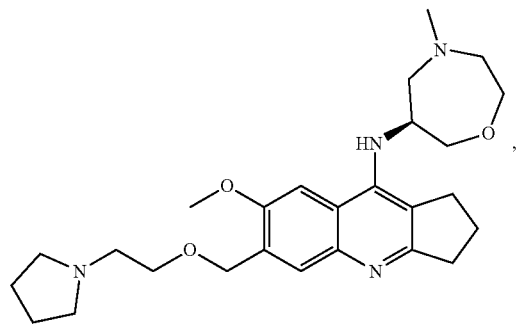 [SMILES: COc1cc2c(N[C@@H]3COCCN(C)C3)c3c(nc2cc1COCCN1CCCC1)CCC3] |
| 306 | 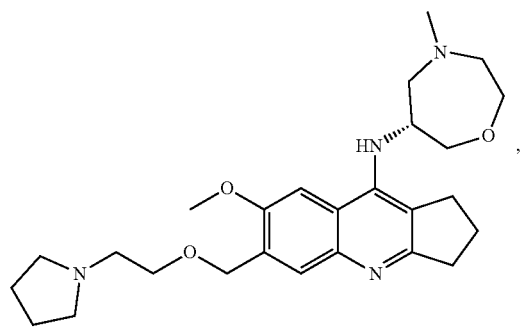 [SMILES: COc1cc2c(N[C@H]3COCCN(C)C3)c3c(nc2cc1COCCN1CCCC1)CCC3] |
| 307 | 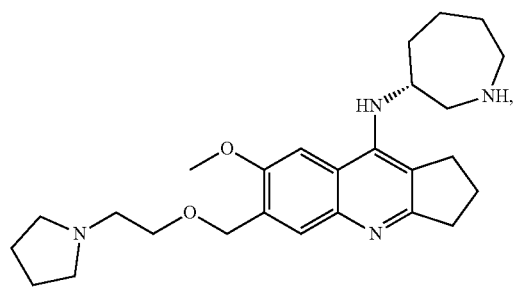 [SMILES: COc1cc2c(N[C@@H]3CCCCNC3)c3c(nc2cc1COCCN1CCCC1)CCC3] |
| 308 | 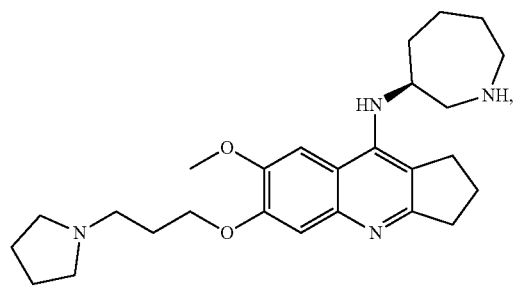 [SMILES: COc1cc2c(N[C@H]3CCCCNC3)c3c(nc2cc1OCCCN1CCCC1)CCC3] |
| 309 | 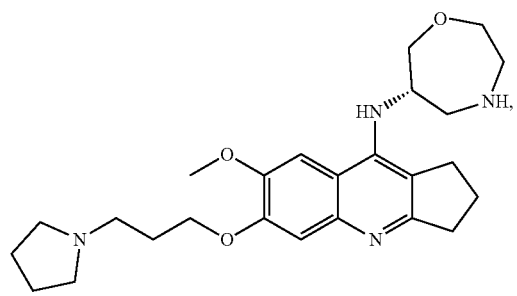 [SMILES: COc1cc2c(N[C@H]3CNCCOC3)c3c(nc2cc1OCCCN1CCCC1)CCC3] |

| No. | Structure |
|---|---|
| 310 | 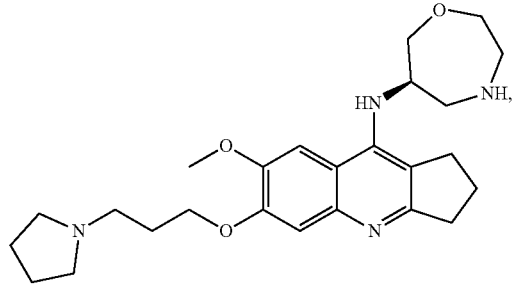 [SMILES: COc1cc2c(N[C@@H]3CNCCOC3)c3c(nc2cc1OCCCN1CCCC1)CCC3] |
| 311 | 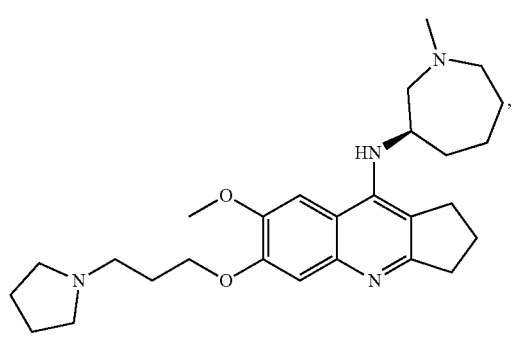 [SMILES: COc1cc2c(N[C@@H]3CCCCN(C)C3)c3c(nc2cc1OCCCN1CCCC1)CCC3] |
| 312 | 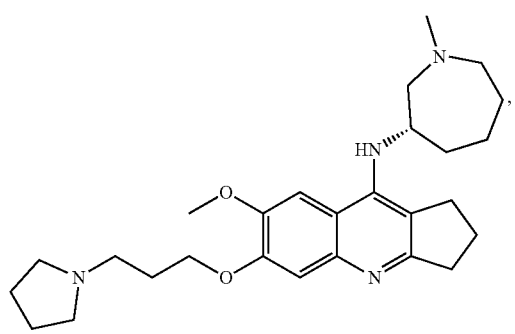 [SMILES: COc1cc2c(N[C@H]3CCCCN(C)C3)c3c(nc2cc1OCCCN1CCCC1)CCC3] |
| 313 | 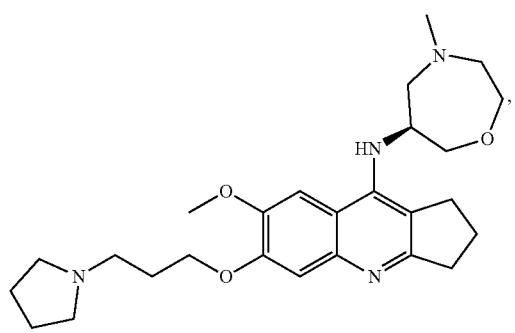 [SMILES: COc1cc2c(N[C@@H]3COCCN(C)C3)c3c(nc2cc1OCCCN1CCCC1)CCC3] |

| No. | Structure |
|---|---|
| 314 | 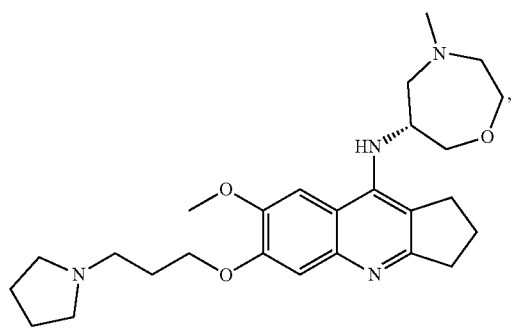 [SMILES: COc1cc2c(N[C@H]3COCCN(C)C3)c3c(nc2cc1OCCCN1CCCC1)CCC3] |
| 315 | 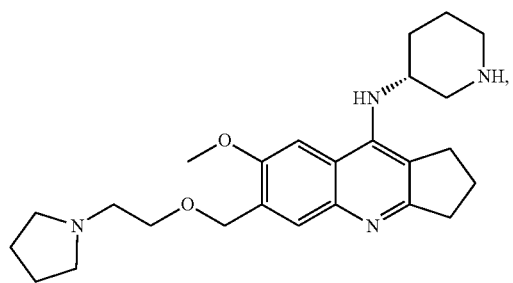 [SMILES: COc1cc2c(N[C@@H]3CCCNC3)c3c(nc2cc1COCCN1CCCC1)CCC3] |
| 316 | 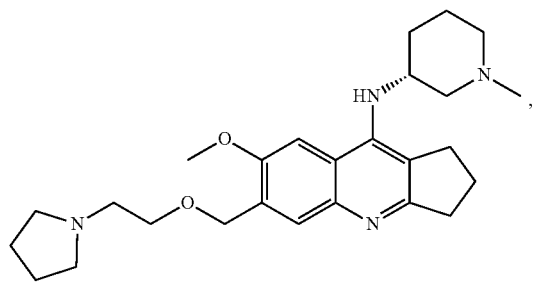 [SMILES: COc1cc2c(N[C@@H]3CCCN(C)C3)c3c(nc2cc1COCCN1CCCC1)CCC3] |
| 317 | 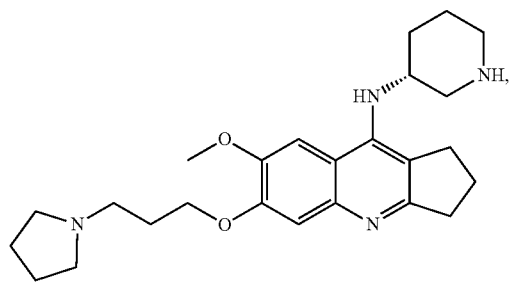 |
| 318 | 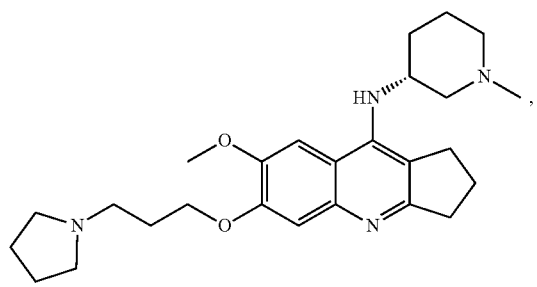 [SMILES: COc1cc2c(N[C@@H]3CCCN(C)C3)c3c(nc2cc1OCCCN1CCCC1)CCC3] |

-continued

| No. | Structure |
|---|---|
| 319 | 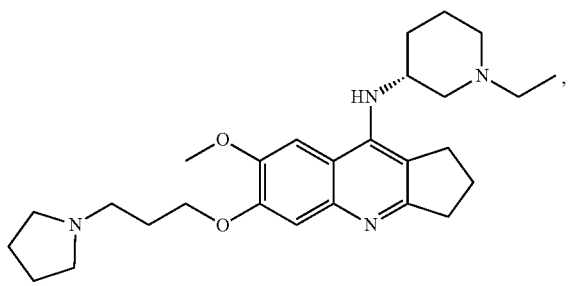 [SMILES: CCN1CCC[C@@H](Nc2c3c(nc4cc(COCCN5CCCC5)c(OC)cc24)CCC3)C1] |
| 320 | 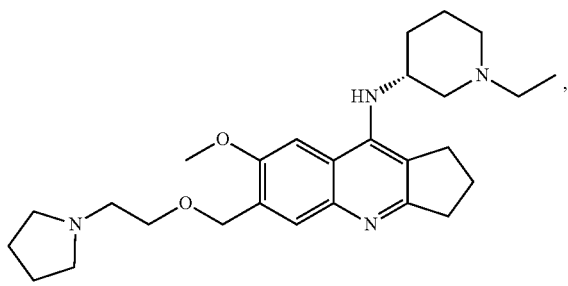 |
| 321 | 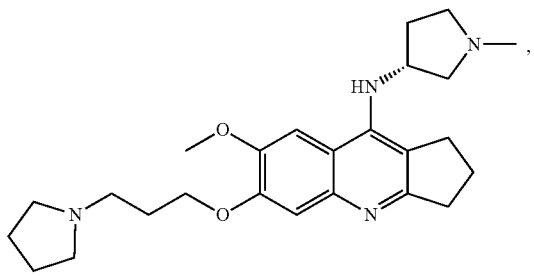 [SMILES: COc1cc2c(N[C@@H]3CCN(C)C3)c3c(nc2cc1OCCCN1CCCC1)CCC3] |
| 322 | 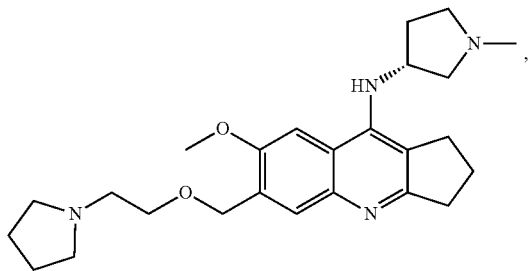 [SMILES: COc1cc2c(N[C@@H]3CCN(C)C3)c3c(nc2cc1COCCN1CCCC1)CCC3] |
| 323 | 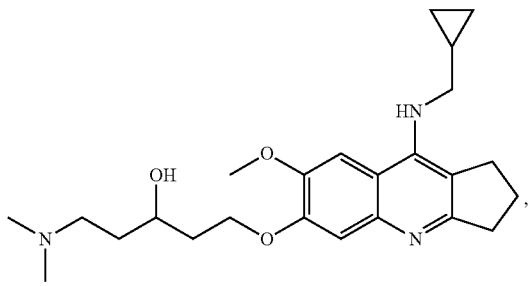 [SMILES: COc1cc2c(NCC3CC3)c3c(nc2cc1OCCC(O)CCN(C)C)CCC3] | or a pharmaceutically acceptable salt thereof.

43. A pharmaceutical composition comprising a compound of claim 1, or a pharmaceutically acceptable salt thereof; and a pharmaceutically acceptable excipient.

44. A method of inhibiting G9a, comprising contacting a cell containing G9a with a therapeutically effective amount of a compound of claim 1, or a pharmaceutically acceptable salt thereof, thereby inhibiting the activity of G9a.

45. A method of ameliorating or treating sickle cell disease or beta-thalassemia, comprising administering a therapeutically effective amount of a compound of claim 1, or a pharmaceutically acceptable salt thereof, or the pharmaceutical composition of claim 43 to a subject in need thereof.

\* \* \* \* \*

UNITED STATES PATENT AND TRADEMARK OFFICE
CERTIFICATE OF CORRECTION

Page 1 of 1

PATENT NO. : 11,584,734 B2
APPLICATION NO. : 16/639047
DATED : February 21, 2023
INVENTOR(S) : Yu et al.

It is certified that error appears in the above-identified patent and that said Letters Patent is hereby corrected as shown below:

In the Claims

Column 256,
Line 25, Claim 1, "S-sulfonamido" should read --(i) S-sulfonamido--.

Signed and Sealed this
Twenty-eighth Day of March, 2023

Katherine Kelly Vidal
*Director of the United States Patent and Trademark Office*